(12) United States Patent
Schrimpf et al.

(10) Patent No.: US 9,983,218 B2
(45) Date of Patent: May 29, 2018

(54) INDOLE AND INDOLINE DERIVATIVES AND METHODS OF USE THEREOF

(71) Applicant: AbbVie Inc., North Chicago, IL (US)

(72) Inventors: Michael R. Schrimpf, Grayslake, IL (US); Chih-hung Lee, Vernon Hills, IL (US); Tao Li, Grayslake, IL (US); Gregory Gfesser, Lindenhurst, IL (US); Kathleen Mortell, Chicago, IL (US); Ramin Faghih, Lake Forest, IL (US); Diana L. Schmidt, Gurnee, IL (US); Kevin Sippy, Antioch, IL (US); William H. Bunnelle, Mundelein, IL (US); Marc Scanio, Lindenhurst, IL (US); Lei Shi, Gurnee, IL (US); Murali Gopalakrishnan, Libertyville, IL (US); Diana L. Donnelly-Roberts, Gurnee, IL (US); Min Hu, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days. days.

(21) Appl. No.: 15/454,313

(22) Filed: Mar. 9, 2017

(65) Prior Publication Data

US 2018/0024144 A1    Jan. 25, 2018

Related U.S. Application Data

(60) Division of application No. 12/727,723, filed on Mar. 19, 2010, now Pat. No. 9,625,475, which is a
(Continued)

(51) Int. Cl.
C07D 471/18 (2006.01)
G01N 33/68 (2006.01)
(Continued)

(52) U.S. Cl.
CPC ....... G01N 33/6896 (2013.01); C07D 471/18 (2013.01); C07D 487/10 (2013.01);
(Continued)

(58) Field of Classification Search
None
See application file for complete search history.

(56) References Cited

U.S. PATENT DOCUMENTS 9,625,475 B2 * 4/2017 Schrimpf ........... G01N 33/6896

* cited by examiner

*Primary Examiner* — Heidi Reese
(74) *Attorney, Agent, or Firm* — Portia Chen

(57) ABSTRACT

The present application relates to indole and indoline derivatives of formula (I), (II), (III), (IV), (V), or (VI)

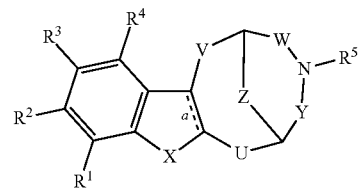

(I)

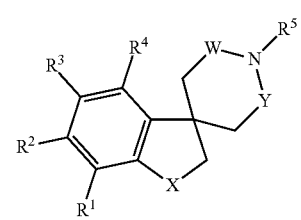

(II)

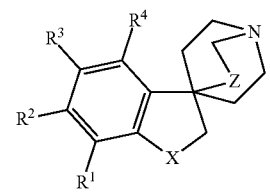

(III)

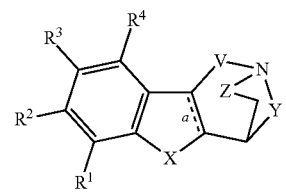

(IV)

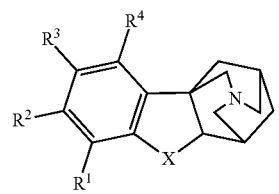

(V)

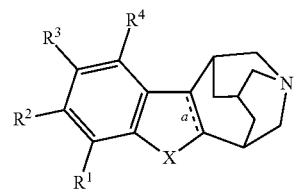

(VI)

wherein a, $R^1$, $R^2$, $R^3$, $R^4$, $R^5$, U, V, W, X, Y, and Z are as defined in the specification. The present application also relates to compositions comprising such compounds, and methods of treating disease conditions using such compounds and compositions, and methods for identifying such compounds.

2 Claims, 6 Drawing Sheets

Related U.S. Application Data continuation-in-part of application No. 12/568,085, filed on Sep. 28, 2009, now Pat. No. 9,063,126.

(60) Provisional application No. 61/225,452, filed on Jul. 14, 2009, provisional application No. 61/101,054, filed on Sep. 29, 2008.

(51) Int. Cl.
*C07D 487/10* (2006.01)
*G01N 33/50* (2006.01)

(52) U.S. Cl.
CPC . *G01N 33/5058* (2013.01); *G01N 2800/2814* (2013.01); *G01N 2800/30* (2013.01)

24-Hour Recall Inhibitory Avoidance in Mouse

Rat Social Recognition

Analgesic Effect Against Neuropathic Pain

INDOLE AND INDOLINE DERIVATIVES AND METHODS OF USE THEREOF

This patent application claims priority to U.S. Provisional Patent Application No. 61/101,054, filed Sep. 29, 2008, and U.S. Provisional Patent Application No. 61/225,452, filed Jul. 14, 2009, the entirety of each application is incorporated herein by reference.

FIELD OF THE INVENTION

The present invention relates to indole and indoline derivatives, compositions comprising these indole and indoline derivatives, methods of preventing or treating disease conditions such as neurodegeneration or neuropsychiatric disorders using such compounds and compositions, and processes for preparing such compounds and compositions.

BACKGROUND OF THE INVENTION

Treatment of dementias of various types, such as but not limited to, Alzheimer's disease (AD), Parkinson's disease, Huntington's disease and other forms, continue to be unmet medical needs. Alzheimer's disease is the most common form of dementia, wherein loss of memory and other intellectual abilities are serious enough to interfere with daily living. Alzheimer's disease is an age-related neurodegenerative disorder characterized by progressive loss of memory accompanied with cholinergic neurodegeneration (Kar, S.; Quirion, R. Amyloid β peptides and central cholinergic neurons: functional interrelationship and relevance to Alzheimer's disease pathology. *Prog. Brain Res.* 2004, 145 (Acetylcholine in the Cerebral Cortex), 261-274.). This disease accounts for over 50% of all progressive cognitive impairment in elderly patients. The prevalence increases with age. Alzheimer's disease is classified by its severity as mild, moderate and severe. The pathological hallmarks of AD include neuronal dysfunction/death, accumulation of senile plaques extracellularly and neurofibrillary tangles (NFTs) intraneuronally. Several hypotheses have been put forth to explain the pathophysiology of this disease, including aberrant β-amyloid (Aβ) metabolism, hyperphosphorylation of cytoskeletal proteins, genetic predisposition such as mutations in genes coding for presenilin-1 and -2 (PS-1 and PS-2) and amyloid precursor protein (APP), apolipoprotein E genotype, oxidative stress, excitotoxicity, inflammation and abnormal cell cycle re-entry. However to date, none of these hypotheses is sufficient to explain the diversity of biochemical and pathological abnormalities in AD.

Two pathological hallmarks of AD are generally recognized: senile plaques composed of β-amyloid peptide 1-42 ($A\beta_{1-42}$) and neurofibrillary tangles (NFTs) formed by abnormal polymerization of microtubule-associated protein tau (Walsh, D. M.; Selkoe, D. J. Deciphering the molecular basis of memory failure in Alzheimer's disease. *Neuron* 2004, 44(1), 181-193.). While the precise cause underlying AD-related memory loss and cognitive changes remains to be fully elucidated, there is evidence indicating that pathological assemblies of $A\beta_{1-42}$ cause diverse forms of AD and that tau plays a role including in mechanisms leading to $A\beta_{1-42}$-induced neurodegeneration. More recent evidence from studies using transgenic animals suggests that tau pathology exacerbates neurodegenerative and cognitive processes in the presence of $A\beta_{1-42}$ (Oddo, S.; Caccamo, A.; et al. Temporal Profile of Amyloid-β (Aβ) Oligomerization in an in Vivo Model of Alzheimer Disease: a link between Aβ and tau pathology. *J. Biol. Chem.* 2006, 281(3), 1599-1604.).

In addition to Aβ and tau, dysregulation of calcium homeostasis also plays an integral role in the pathophysiology of AD (Green, K. N.; LaFerla, F. M. Linking calcium to Aβ and Alzheimer's disease. *Neuron* 2008, 59(2), 190-194.). It is becoming evident that dysregulation of mitochondrial function and resultant altered cellular homeostasis increasingly contributes to the pathology of neurodegenerative diseases such as AD (Moreira, P. I.; Santos, M. S.; et al. Is mitochondrial impairment a common link between Alzheimer's disease and diabetes? A matter under discussion. *Trends Alzheimer's Dis. Res.* 2006, 259-279. Beal, M. F. Mitochondria and neurodegeneration. *Novartis Found. Symp.* 2007, 287 (Mitochondrial Biology), 183-196. Reddy, P. H.; Beal, M. F. Amyloid beta, mitochondrial dysfunction and synaptic damage: implications for cognitive decline in aging and Alzheimer's disease. *Trends Mol. Med.* 2008, 14(2), 45-53.).

Mitochondria play major roles in bioenergetics and cell death/survival signaling of the mammalian cell as they are 'gatekeepers of life and death'. Mitochondrial dysfunction contributes to the pathogenesis of various neurodegenerative diseases with pathophysiological consequences at multiple levels including at the level of calcium-driven excitotoxicity. One of the primary mitochondrial mechanisms is the mitochondrial permeability transition pores (MPTP) that represent a multiprotein complex derived from components of inner and outer mitochondrial membrane. The pores regulate transport of ions and peptides in and out of mitochondria, and their regulation is associated with mechanisms for maintaining cellular calcium homeostasis. A deficit in mitochondria is the earliest feature of neurodegenerative diseases. One general characteristic of aging and neurodegeneration is an increase in the number of neuronal cells undergoing signs of apoptotic degeneration. A key role for this apoptotic process is attributable to the mitochondrial permeability transition pore, which provides transport in and out of mitochondria for both calcium ions and compounds with low molecular weight. It has been proposed that MPTP is a multiprotein complex with the outer membrane fragment including porin (a voltage-dependent ion channel), anti-apoptotic proteins of the Bcl-2 family, and the peripheral benzodiazepine receptor. The inner fragment of MPTP contains an adenine nucleotide translocator and cyclophilin, which may interact with proapoptotic proteins of the Bax family. Inhibition of mitochondrial calcium uptake and/or blocking of MPTP may protect cells against the development of apoptosis in the presence of pathological factors such as excitotoxins and anti-oxidants. Indirect modulation of MPTP via kinase pathways is also known wherein glycogen synthase kinase-3β (GSK3β) mediates convergence of protection signaling to inhibit the mitochondrial MPTP (Juhaszova, M.; Zorov, D. B.; et al. Glycogen synthase kinase-3β mediates convergence of protection signaling to inhibit the mitochondrial permeability transition pore. *J. Clin. Invest.* 2004, 113(11), 1535-1549. Juhaszova, M.; Wang, S.; et al. The identity and regulation of the mitochondrial permeability transition pore: where the known meets the unknown. *Ann. N. Y. Acad. Sci.* 2008, 1123 (Control and Regulation of Transport Phenomena in the Cardiac System), 197-212) and mitochondrial localization during apoptosis (Linseman, D. A.; Butts, B. D.; et al. Glycogen synthase kinase-3β phosphorylates Bax and promotes its mitochondrial localization during neuronal apoptosis. *J. Neurosci.* 2004, 24(44), 9993-10002.). Furthermore, calcium-dependent activation of MPTP in brain mitochondria enhances with age and may play an important role in age related neurodegenerative disorders.

Neuroprotective effects of agents have been linked to various cellular processes including inhibition of mitochondrial MPTPs. For example, the neuroprotective effects of 4-azasteroids parallel the inhibition of the mitochondrial transition pore (Soskic, V.; Klemm, M.; et al. A connection between the mitochondrial permeability transition pore, autophagy, and cerebral amyloidogenesis. *J. Proteome Res.* 2008, 7(6): 2262-2269.). In vivo administration of MPTP inhibitor, 1-(3-chlorophenyl)-3-phenyl-pyrrole-2,5-dione to a mouse model of multiple sclerosis significantly prevented the development of the disease (Pelicci, P., Giorgio, M.; et al. MPTP inhibitors for blockade of degenerative tissue damages. WO 2008067863A2). Compounds such as dimebolin (latrepirdine, 2,3,4,5-tetrahydro-2,8-dimethyl-5-[2-(6-methyl-3-pyridinyl)ethyl]-1H-pyrido[4,3-b]indole) have been shown to improve neuronal function and a role for improved neuronal outgrowth and mitochondrial function has been suggested. Dimebolin has been shown to inhibit neuronal death in models of AD and Huntington's disease, another neurodegenerative disease (Lermontova, N. N.; Lukoyanov, N. V.; et al. Dimebone improves learning in animals with experimental Alzheimer's disease. *Bull. Exp. Biol. Med.* 2000, 129(6), 544-546. Bachurin, S.; Bukatina, E.; et al. Antihistamine agent dimebon as a novel neuroprotector and a cognition enhancer. *Ann. N. Y. Acad. Sci.* 2001, 939 (Neuroprotective Agents), 425-435.). More recently, dimebolin has been shown to possess a clinically beneficial effect in cognition in patients with AD (Burns, A.; Jacoby, R. Dimebon in Alzheimer's disease: old drug for new indication. *Lancet* 2008, 372(9634), 179-80. Doody, R. S.; Gavrilova, S. I.; et al. Effect of dimebon on cognition, activities of daily living, behaviour, and global function in patients with mild-to-moderate Alzheimer's disease: a randomised, double-blind, placebo-controlled study. *Lancet* 2008, 372(9634), 207-215.). Patients with mild-to-moderate Alzheimer's disease administered with 20 mg three times a day (60 mg/day) showed significant improvement in the clinical course of disease, as reflected in improvement over baseline for ADAS-Cog (Alzheimer's disease assessment scale—cognitive subscale). In particular, dimebolin-treated patients demonstrated a significant improvement over placebo in cognition, global function, activities of daily living and behavior. A six-month open-label extension trial of dimebolin produced results similar to those in the preceding 12-month clinical trial (Cummings, J.; Doody, R.; Gavrilova, S.; Sano, M.; Aisen, P.; Seely, L.; Hung, D. 18-month data from an open-label extension of a one-year controlled trial of dimebon in patients with mild-to-moderate Alzheimer's disease. Presented at the International Conference on Alzheimer's Disease (ICAD), Chicago, Ill., USA, July 2008; paper P4-334.). Patients with mild-to-moderate AD who had earlier received the drug for 12 months had preservation of function close to their starting baseline on key symptoms of AD. Patients originally on placebo who received dimebolin in the extension study showed stabilization across all key measures.

Dimebolin has been approved in Russia as a non-selective antihistamine. The drug was sold for many years before selective anti-histaminergic agents were developed. Although dimebolin was initially thought to exert its cognitive enhancing effects through inhibition of butyryl-cholinesterase, acetyl cholinesterase, NMDA receptor or L-type calcium channels (Bachurin, S.; Bukatina, E.; et al. Antihistamine agent dimebon as a novel neuroprotector and a cognition enhancer. *Ann. N. Y. Acad. Sci.* 2001, 939 (Neuroprotective Agents), 425-435. Lermontova, N. N.; Redkozubov, A. E.; et al. Dimebon and tacrine inhibit neurotoxic action of beta-amyloid in culture and block L-type Ca(2+) channels. *Bull. Exp. Biol. Med.* 2001, 132(5), 1079-1083. Grigor'ev, V. V.; Dranyi, O. A.; et al. Comparative Study of Action Mechanisms of Dimebon and Memantine on AMPA- and NMDA-Subtypes Glutamate Receptors in Rat Cerebral Neurons. *Bull. Exp. Biol. Med.* 2003, 136(5): 474-477), its interactions at these targets are weak. More recent data suggest that dimebolin may exert its effects at the level of mitochondria, and that these activities could enhance neuronal function (Hung, D. Dimebon: A phase 3 investigational agent for Alzheimer's disease with a novel mitochondrial mechanism of action. Presented at the International Conference on Alzheimer's Disease, Chicago, Ill., USA, July 2008; paper S4-04-05.). Hung and coworkers (Hung, D. Dimebon: A phase 3 investigational agent for Alzheimer's disease with a novel mitochondrial mechanism of action. Presented at the International Conference on Alzheimer's Disease, Chicago, Ill., USA, July 2008; paper S4-04-05) reported that dimebolin can protect cells from excitotoxic damage and improve neurite outgrowth in neuroblastoma cell lines and primary neurons. From an adverse effect standpoint, in recently reported clinical studies of dimebolin, the most frequent adverse event was dry mouth, which is consistent with the antihistaminic effects of dimebolin (Doody, R. S.; Gavrilova, S. I.; et al. Effect of dimebon on cognition, activities of daily living, behaviour, and global function in patients with mild-to-moderate Alzheimer's disease: a randomised, double-blind, placebo-controlled study. *Lancet* 2008, 372(9634), 207-215.). There is a need in the art to identify and provide novel agents for treating or preventing conditions associated neurodegenerative disorders such as AD, lacking histaminergic (H1) interactions.

As noted earlier, given the likely multiple etiologies of neurodegenerative diseases such as AD, multiple approaches are being pursued as symptomatic approaches or as disease modifying approaches to alter the underlying pathology of the disease (Scatena, R.; Martorana, G. E.; et al. An update on pharmacological approaches to neurodegenerative diseases. *Expert Opin. Invest. Drugs* 2007, 16(1), 59-72.). In particular, the reported benefit of dimebolin in double-blind, placebo-controlled study of patients with mild-to-moderate AD across many cognitive and clinical measures demonstrates the potential of such compounds to prevent or treat a variety of neurodegenerative diseases where an underlying pathology involves deficits in cognitive function. In addition to the need for improved receptor selectivity profile (as for example vs. H1 receptors), one of the current limitations with dimebolin is the dosing regimen necessitating three times per day (t.i.d.) administration in humans. As neuroprotective approaches exemplified by dimebolin continue to be validated as a viable clinical approach, there is a need in the art to identify and provide novel compounds for treating or preventing cognitive deficits associated with AD and other neurodegenerative and neuropsychiatric diseases.

SUMMARY OF THE INVENTION

In one aspect, the present invention relates to compounds of having a formula of (I), (II), (III), (IV), (V), or (VI):

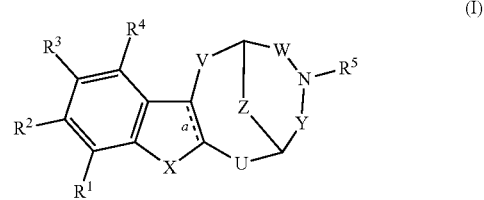

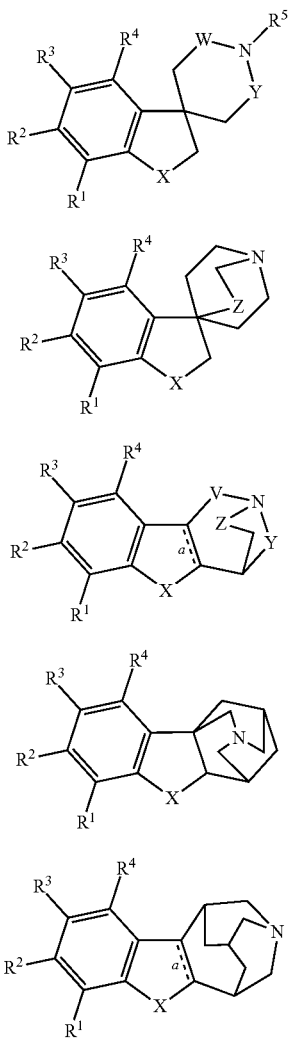

or a pharmaceutically acceptable salt or prodrug thereof, wherein a is a single or double bond;
X is $CHR^6$, $C=CHR^6$, or $NR^6$;
$X^1$ is $CHR^8$ or $NR^8$;
U, V, W, and Y are each independently $—(CH_2)_p—$;
p at each occurrence is independently 0, 1, or 2;
Z is $—(CH_2)_q—$;
q is 1, 2, or 3;
$R^1$, $R^2$, $R^3$, and $R^4$ are each independently hydrogen, alkyl, alkenyl, alkynyl, halogen, cyano, $-G^1$, $—N(R^b)(R^{3a})$, $—N(R^a)C(O)R^{1a}$, $—N(R^a)C(O)O(R^{1a})$, $—N(R^a)C(O)N(R^b)(R^{3a})$, $—OR^{1a}$, $—SR^{1a}$, $—S(O)_2R^{2a}$, or haloalkyl; wherein $R^a$ and $R^b$, at each occurrence, are each independently hydrogen, alkyl, or haloalkyl;

$R^{1a}$ and $R^{3a}$, at each occurrence, are each independently hydrogen, alkyl, haloalkyl, $G^1$, or $—(CR^{6a}R^{7a})_n-G^1$;

$R^{2a}$, at each occurrence, is independently alkyl, haloalkyl, $G^1$, or $—(CR^{6a}R^{7a})_n-G^1$;

n, at each occurrence, is independently 1, 2, 3, 4, or 5;

$R^{6a}$ and $R^{7a}$, at each occurrence, are each independently hydrogen, halogen, alkyl, or haloalkyl;

$G^1$, at each occurrence, is independently aryl, heteroaryl, heterocycle, or cycloalkyl, wherein each $G^1$ is independently unsubstituted or substituted with 1, 2, 3, 4, or 5 substituents selected from the group consisting of alkyl, alkenyl, alkynyl, halogen, cyano, oxo, $—NO_2$, $—OR^{1b}$, $—OC(O)R^{1b}$, $—OC(O)N(R^b)(R^{3b})$, $—SR^{1b}$, $—S(O)_2R^{2b}$, $—S(O)_2N(R^b)(R^{3b})$, $—C(O)R^{1b}$, $—C(O)OR^{1b}$, $—C(O)N(R^b)(R^{3b})$, $—N(R^b)(R^{3b})$, $—N(R^a)C(O)R^{1b}$, $—N(R^a)C(O)O(R^{1b})$, $—N(R^a)C(O)N(R^b)(R^{3b})$, $—(CR^{4b}R^{5b})_m—NO_2$, $—(CR^{4b}R^{5b})_m—OR^{1b}$, $—(CR^{4b}R^{5b})_m—OC(O)R^{1b}$, $—(CR^{4b}R^{5b})_m—OC(O)N(R^b)(R^{3b})$, $—(CR^{4b}R^{5b})_m—SR^{1b}$, $—(CR^{4b}R^{5b})_m—S(O)_2R^{2b}$, $—(CR^{4b}R^{5b})_m—S(O)_2N(R^b)(R^{3b})$, $—(CR^{4b}R^{5b})_m—C(O)R^{1b}$, $—(CR^{4b}R^{5b})_m—C(O)OR^{1b}$, $—(CR^{4b}R^{5b})_m—C(O)N(R^b)(R^{3b})$, $—(CR^{4b}R^{5b})_m—N(R^b)(R^{3b})$, $—(CR^{4b}R^{5b})_m—N(R^a)C(O)R^{1b}$, $—(CR^{4b}R^{5b})_m—N(R^a)C(O)O(R^b)$, $—(CR^{4b}R^{5b})_m—N(R^a)C(O)N(R^b)(R^{3b})$, cyanoalkyl, and haloalkyl;

m, at each occurrence, is independently 1, 2, 3, 4, or 5;

$R^{1b}$ and $R^{3b}$, at each occurrence, are each independently hydrogen, alkoxyalkyl, alkyl, aryl, arylalkyl, haloalkyl, heteroarylalkyl, or heterocyclealkyl;

$R^{2b}$, at each occurrence, is independently alkyl or haloalkyl;

$R^{4b}$ and $R^{5b}$, at each occurrence, are each independently hydrogen, halogen, alkyl, or haloalkyl;

$R^5$ is hydrogen, alkyl, $-G^1$, $—S(O)_2R^{2a}$, $—S(O)_2N(R^b)(R^{3a})$, $—C(O)R^{1a}$, $—C(O)OR^{1a}$, $—C(O)N(R^b)(R^{3a})$, $—(CR^{4a}R^{5a})_m—NO_2$, $—(CR^{4a}R^{5a})_m—OR^{1a}$, $—(CR^{4a}R^{5a})_m—OC(O)R^{1a}$, $—(CR^{4a}R^{5a})_m—OC(O)N(R^b)(R^{3a})$, $—(CR^{4a}R^{5a})_m—SR^{1a}$, $—(CR^{4a}R^{5a})_m—S(O)_2R^{2a}$, $—(CR^{4a}R^{5a})_m—S(O)_2N(R^b)(R^{3a})$, $—(CR^{4a}R^{5a})_m—C(O)R^{1a}$, $—(CR^{4a}R^{5a})_m—C(O)OR^{1a}$, $—(CR^{4a}R^{5a})_m—C(O)N(R^b)(R^{3a})$, $—(CR^{4a}R^{5a})_m—N(R^b)(R^{3a})$, $—(CR^{4a}R^{5a})_m—N(R^a)C(O)R^{1a}$, $—(CR^{4a}R^{5a})_m—N(R^a)C(O)O(R^{1a})$, $—(CR^{4a}R^{5a})_m—N(R^a)C(O)N(R^b)(R^{3a})$, $—(CR^{4a}R^{5a})_m-G^1$, cyanoalkyl, or haloalkyl;

$R^{4a}$ and $R^{5a}$, at each occurrence, are each independently hydrogen, halogen, alkyl, or haloalkyl;

$R^6$ is alkyl, $—S(O)_2R^{2a}$, $—C(O)R^{1a}$, $—C(O)OR^{1a}$, $—C(O)N(R^b)(R^{3a})$, $—(CR^{4a}R^{5a})_m—NO_2$, $—(CR^{4a}R^{5a})_m—OR^{1a}$, $—(CR^{4a}R^{5a})_m—OC(O)R^{1a}$, $—(CR^{4a}R^{5a})_m—OC(O)N(R^b)(R^{3a})$, $—(CR^{4a}R^{5a})_m—SR^{1a}$, $—(CR^{4a}R^{5a})_m—S(O)_2R^{2a}$, $—(CR^{4a}R^{5a})_m—S(O)_2N(R^b)(R^{3a})$, $—(CR^{4a}R^{5a})_m—C(O)R^{1a}$, $—(CR^{4a}R^{5a})_m—C(O)OR^{1a}$, $—(CR^{4a}R^{5a})_m—C(O)N(R^b)(R^{3a})$, $—(CR^{4a}R^{5a})_m—N(R^b)(R^{3a})$, $—(CR^{4a}R^{5a})_m—N(R^a)C(O)R^{1a}$, $—(CR^{4a}R^{5a})_m—N(R^a)C(O)O(R^{1a})$, $—(CR^{4a}R^{5a})_m—N(R^a)C(O)N(R^b)(R^{3a})$, $—(CR^{4a}R^{5a})_m-G^1$, $—(CR^{4a}R^{5a})_m-G^2-G^1$, $—CR^{4a}=CR^{5a}—S(O)_2R^{2a}$, $—CR^{4a}=CR^{5a}—S(O)_2N(R^b)(R^{3a})$, $—CR^{4a}=CR^{5a}—C(O)R^{1a}$, $—CR^{4a}=CR^{5a}—C(O)OR^{1a}$, $—CR^{4a}=CR^{5a}-G^1$, $-G^1$, $-G^2-G^1$, cyanoalkyl, or haloalkyl;

$G^2$ is aryl, heteroaryl, heterocycle, or cycloalkyl unsubstituted or substituted with 1, 2, 3, or 4 substituents selected from the group consisting of alkyl, alkenyl, alkynyl, halogen, cyano, oxo, $—NO_2$, $—OR^{1b}$, $—OC(O)R^{1b}$, $—OC(O)N(R^b)(R^{3b})$, $—SR^{1b}$, $—S(O)_2R^{2b}$, $—S(O)_2N(R^b)(R^{3b})$, $—C(O)R^{1b}$, $—C(O)OR^{1b}$, $—C(O)N(R^b)(R^{3b})$, $—N(R^b)(R^{3b})$, $—N(R^a)C(O)R^{1b}$, $—N(R^a)C(O)O(R^{1b})$, $—N(R^a)C(O)N(R^b)(R^{3b})$, $—(CR^{4b}R^{5b})_m—NO_2$, $—(CR^{4b}R^{5b})_m—OR^{1b}$, $—(CR^{4b}R^{5b})_m—OC(O)R^{1b}$, $—(CR^{4b}R^{5b})_m—OC(O)N(R^b)(R^{3b})$, $—(CR^{4b}R^{5b})_m—SR^{1b}$, $—(CR^{4b}R^{5b})_m—S(O)_2R^{2b}$, $—(CR^{4b}R^{5b})_m—S(O)_2N(R^b)(R^{3b})$, $—(CR^{4b}R^{5b})_m—C(O)R^{1b}$, $—(CR^{4b}R^{5b})_m—C(O)OR^{1b}$, $—(CR^{4b}R^{5b})_m—C(O)N(R^b)(R^{3b})$, $—(CR^{4b}R^{5b})_m—N(R^b)(R^{3b})$, $—(CR^{4b}R^{5b})_m—N(R^a)C(O)R^{1b}$, $—(CR^{4b}R^{5b})_m—N(R^a)C(O)O(R^{1b})$, $—(CR^{4b}R^{5b})_m—N(R^a)C(O)N(R^b)(R^{3b})$, cyanoalkyl, and haloalkyl;

R$^7$ is hydrogen, alkyl, -G$^1$, —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$-G$^1$, cyanoalkyl, or haloalkyl; and R$^8$ is —(CR$^{4a}$R$^{5a}$)$_m$-G$^1$, —(CR$^{4a}$R$^{5a}$)$_m$-G$^2$-G$^1$, or —CR$^{4a}$=CR$^{5a}$-G$^1$;

with the proviso that in a compound of formula (I),
when R$^1$, R$^2$ and R$^4$ are each hydrogen;
R$^3$ is hydrogen or halogen;
U is CH$_2$;
V, W, and Y are each —(CH$_2$)$_p$—, wherein p is 0;
Z is —(CH$_2$)$_q$—, wherein q is 2 or 3;
X is NR$^6$; and
R$^6$ is alkyl, -G$^1$, or —(CR$^{4a}$R$^{5a}$)$_m$-G$^1$, wherein m is 1, R$^{4a}$ and R$^{5a}$ are hydrogen and G$^1$ is phenyl unsubstituted or substituted with alkyl, halogen, hydroxy or —OR$^{1a}$ wherein R$^{1a}$ is alkyl;
R$^5$ is other than hydrogen, alkyl, —(CR$^{4a}$R$^{5a}$)$_m$-G$^1$, —C(O)R$^{1a}$, —(CR$^{4a}$R$^{5a}$)$_m$—OR$^{1a}$, or —(CR$^{4a}$R$^{5a}$)$_m$—C(O)R$^{1a}$ wherein R$^{1a}$ is alkyl, aryl, or heteroaryl, and G$^1$ is aryl or heteroaryl; or with the proviso that in a compound of formula (IV),
when a is a double bond;
V is —(CH$_2$)$_p$—, wherein p is 0;
Y is —(CH$_2$)$_p$—, wherein p is 2;
Z is —(CH$_2$)$_q$—, wherein q is 1; and
X is NR$^6$, then
R$^6$ is other than alkyl, C(O)R$^{1a}$, —(CR$^{4a}$R$^{5a}$)$_m$—OR$^{1a}$, —(CR$^{4a}$R$^{5a}$)$_m$C(O)R$^{1a}$, —(CR$^{4a}$R$^{5a}$)$_m$—N(R$^b$)(R3a), —(CR$^{4a}$R$^{5a}$)$_m$-G$^1$, —CR$^{4a}$=CR$^{5a}$-G$^1$, -G$^1$, cyanoalkyl or haloalkyl.

The present invention further provides processes of making the compounds of the present invention, and intermediates employed in the processes.

In another aspect, the present invention relates to pharmaceutical compositions comprising a therapeutically effective amount of at least one compound(s) having a formula of (I), (II), (III), (IV), (V), or (VI) described above or pharmaceutically acceptable salts thereof, in combination with at least one pharmaceutically acceptable carrier.

In yet another aspect, the present invention relates to a method of preventing or treating a neurodegeneration disorder using a compound of formula (I), (II), (III), (IV), (V), or (VI). Such methods involves administering a therapeutically effective amount of at least one compound of formula (I), (II), (III), (IV), (V) or (VI) to a subject in need of treatment thereof. Examples of neurodegeneration disorders are Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury or any combinations thereof. The above method also further comprises administering a cognitive enhancing drug to the subject. The cognitive enhancing drug can be administered simultaneously or sequentially with the compound of formula (I), (II), (III), (IV), (V), or (VI).

In yet another aspect, the present invention relates to a method of preventing or treating a neuropsychiatric disorder using a compound of formula (I), (II), (III), (IV), (V), or (VI). Such methods involve administering a therapeutically effective amount of at least one compound of formula (I), (II), (III), (IV), (V) or (VI), to a subject in need of treatment thereof. Examples of neuropsychiatric disorders are schizophrenia, cognitive deficits in schizophrenia, attention deficit disorder, attention deficit hyperactivity disorder, bipolar and manic disorders, depression or any combinations thereof. The above method also further comprises administering a cognitive enhancing drug to the subject. The cognitive enhancing drug can be administered simultaneously or sequentially with the compound of formula (I), (II), (III), (IV), (V), or (VI).

In a further aspect, the present invention relates to methods of preventing or treating a pain condition using a compound of formula (I), (II), (III), (IV), (V), or (VI). Such methods include administering a therapeutically effective amount of at least one compound of formula (I), (II), (III), (IV), (V) or (VI), to a subject in need of treatment thereof. Examples of pain conditions includes neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

The present invention can also include use of a compound of formula (I), (II), (III), (IV), (V), or (VI) as neuroprotective agent for the prevention or treatment of a neurological disorder or condition. The method includes administering a therapeutically effective amount of at least one compound of formula (I), (II), (III), (IV), (V) or (VI), to a subject in need of treatment thereof. The neurological disorder or condition can include, but is not limited to, neurodegeneration disorders, neuropsychiatric disorder and pain conditions, brain injuries, stroke and other acute and chronic neuronal injuries or degenerative conditions. The neurological disorder or condition can include, for example, conditions associated, at least in part, with mitochondrial dysfunction and/or neuronal apoptosis in the central nervous system.

In still yet another aspect, the present invention relates to the use of a compound of formula (I), (II), (III), (IV), (V), or (VI) or a pharmaceutically acceptable salt thereof in the manufacture of a medicament for the prevention or treatment of the neurodegeneration disorders described above, alone or in combination with at least one pharmaceutically acceptable carrier.

In still yet another aspect, the present invention relates to a method of identifying one or more target compounds useful for treating a neurodegeneration disorder or a neuropsychiatric disorder. The method comprises the steps of:

a. providing a population of neuronal or neuroblastoma cells or cell lines;

b. adding one or more target compounds to the population of neuronal or neuroblastoma cells or cell lines;

c. determining the neuronal number and neurite outgrowth after the addition of the one or more target compounds; and d. determining whether the one or more target compounds are useful for treating a neurodegeneration disorder or a neuropsychiatric disorder.

In still yet another aspect, the present invention relates to a method of identifying one or more target compounds useful for treating a neurodegeneration disorder or a neuropsychiatric disorder. The method comprises the steps of:

a. providing a population of neuronal or neuroblastoma cells or cell lines;

b. adding one or more target compounds to the population of neuronal or neuroblastoma cells or cell lines;

c. determining mitochondrial membrane potential under serum-deprivation conditions; and d. determining whether the one or more target compounds are useful for treating a neurodegeneration disorder or a neuropsychiatric disorder.

The compounds of formula (I), (II), (III), (IV), (V), or (VI), compositions comprising these compounds, and methods for preventing or treating neurodegenerative or neuropsychiatric disorders by administering these compounds or pharmaceutical compositions are further described herein.

These and other objects of the invention are described in the following paragraphs. These objects should not be deemed to narrow the scope of the invention.

BRIEF DESCRIPTION OF THE FIGURE

In FIG. 2, a 100% response represents the neurite outgrowth of untreated cells. Cells (primary postnatal (P0) cortical cells) treated with $A\beta_{1\text{-}42}$ peptide showed a reduction in neurite outgrowth. Cells pretreated with varying concentrations of the test compound (Example 5) and then subsequently with test compounds and freshly prepared $A\beta_{1\text{-}42}$ peptide showed neurite outgrowth levels similar to or enhanced relative to untreated control cells. The X-axis represents test concentrations, and the Y-axis represents percent effects.

DETAILED DESCRIPTION

Figure 1:
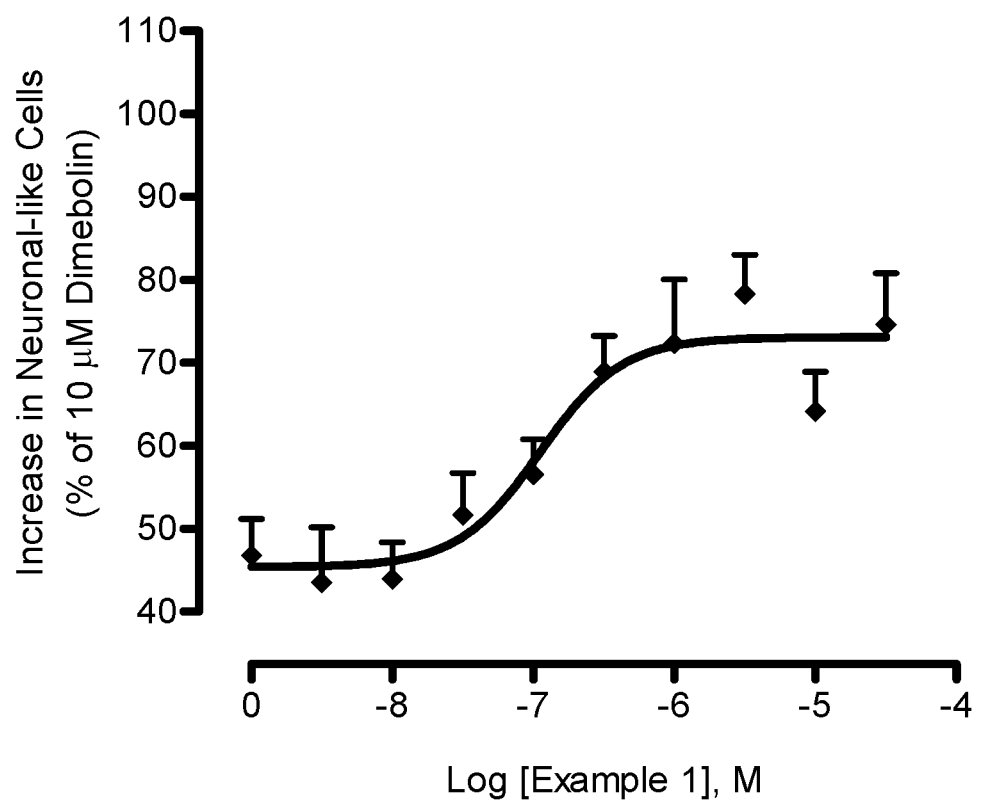
FIG. 1 shows a graphical representation of the concentration-dependent effects of Example 1 on the number of neuron-like cells in nerve growth factor-differentiated PC12 cells. Cells were treated with varying concentrations of the test compound (Example 1). Analysis was conducted 24 hours post-treatment using high-content screen (HCS) microscopy analysis system after staining with β-tubulin and Hoechst 33342. The X-axis represents the test concentrations, and the Y-axis represents percent effects, normalized to 10 μM dimebolin.

In one aspect, the present invention relates to compounds having a formula (I), (II), (III), (IV), (V), and (VI) as shown below:

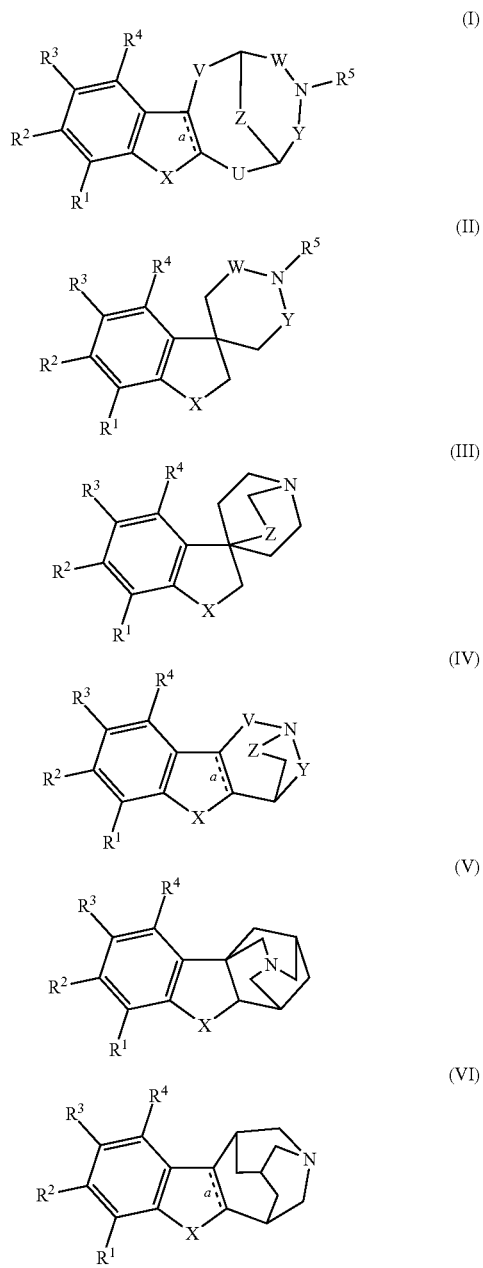

wherein a, $R^1$, $R^2$, $R^3$, $R^4$, $R^5$, U, V, W, X, Y, and Z are as defined above in the Summary of the Invention.

In another aspect, the present invention relates to composition comprising compounds having a formula (I), (II), (III), (IV), (V), and (VI) as described above and at least one pharmaceutically acceptable carrier.

In still yet another aspect, the present invention relates to methods for preventing and treating disease conditions, such as neurodegeneration disorders or neuropsychiatric disorders, using compounds having a formula of formula (I), (II), (III), (IV), (V), and (VI) as described above.

In still yet another aspect, the present invention relates to the use of compounds having a formula (I), (II), (III), (IV), (V), and (VI) in the manufacture of a medicament for the prevention or treatment of the disease conditions, such as neurodegeneration disorders or neuropsychiatric disorders, described above, alone or in combination with at least one pharmaceutically acceptable carrier.

In various embodiments, the present invention provides at least one variable that occurs more than one time in any substituent or in the compound of the present invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double. Representative examples of alkylene include, but are not limited to, —CH=CH— and —CH$_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$] nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "halo" or "halogen" as used herein, means Cl, Br, I, or F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyridazin-3(2H)-onyl, pyridin-2(1H)-onyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, 1,4-benzoxazinyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heterocyclealkyl," as used herein, means a heterocycle group appended to the parent molecular moiety through an alkyl group, as defined herein.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,2-oxazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-b]pyridazinyl, imidazo[1,2-a]pyridinyl, imidazo[1,2-a]pyrimidinyl, indazolyl, indolyl, isoindolyl, isoquinolinyl, naphthyridinyl, pyridoimidazolyl, pyrido[1,2-a]pyrimidin-4-onyl, quinoxalinyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl," as used herein, means a heteroaryl group appended to the parent molecular moiety through an alkyl group, as defined herein.

The term "heteroatom" as used herein, means a nitrogen, oxygen, or sulfur atom.

The term "hydroxyl" or "hydroxy" as used herein, means an —OH group.

The term "oxo" as used herein, means a =O group.

The term "pain", as used herein, is understood to mean nociceptive pain and neuropathic pain, both chronic and acute pain, including but not limited to, osteoarthritis or rheumatoid arthritis pain, ocular pain, pains associated with intestinal inflammation, pains associated with cardiac muscle inflammation, pains associated with multiple sclerosis, pains associated with neuritis, pains associated with carcinomas and sarcomas, pains associated with AIDS, pains associated with chemotherapy, amputation pain, trigeminus neuralgia, headaches, such as migraine cephalalgia, or neuropathic pains, such as post-herpes zoster neuralgia, post-injury pains and post-operative pains.

15

The term "sulfonyl" as used herein, means a —SO$_2$— group.

b. COMPOUNDS

Compounds of the present invention have the formula (I), (II), (III), (IV), (V), or (VI) as described above.

Particular values of variable groups in compounds of formula (I), (II), (III), (IV), (V), or (VI) are as follows. Such values may be used where appropriate with any of the other values, definitions, claims or embodiments defined hereinbefore or hereinafter.

In one embodiment, $R^1$, $R^2$, $R^3$, and $R^4$ are each independently hydrogen, alkyl, alkenyl, alkynyl, halogen, cyano, -$G^1$, —N($R^b$)($R^{3a}$), —N($R^a$)C(O)$R^{1a}$, —N($R^a$)C(O)O($R^{1a}$), —N($R^a$)C(O)N($R^b$)($R^{3a}$), —O$R^{1a}$, —S$R^{1a}$, —S(O)$_2R^{2a}$, or haloalkyl; wherein $R^a$ and $R^b$, at each occurrence, are each independently hydrogen, alkyl, or haloalkyl; $R^{1a}$ and $R^{3a}$, at each occurrence, are each independently hydrogen, alkyl, haloalkyl, $G^1$, or —(C$R^{6a}R^{7a}$)$_n$-$G^1$; $R^{2a}$, at each occurrence, is independently alkyl, haloalkyl, $G^1$, or —(C$R^{6a}R^{7a}$)$_n$-$G^1$; $R^{6a}$ and $R^{7a}$, at each occurrence, are each independently hydrogen, halogen, alkyl, or haloalkyl; n, at each occurrence, is independently 1, 2, 3, 4, or 5; $G^1$ is aryl, heteroaryl, heterocycle, or cycloalkyl, wherein each $G^1$ is independently unsubstituted or substituted with 1, 2, 3, 4, or 5 substituents selected from the group consisting of alkyl, alkenyl, alkynyl, halogen, cyano, oxo, —NO$_2$, —O$R^{1b}$, —OC(O)$R^{1b}$, —OC(O)N($R^b$)($R^{3b}$), —S$R^{1b}$, —S(O)$_2R^{2b}$, —S(O)$_2$N($R^b$)($R^{3b}$), —C(O)$R^{1b}$, —C(O)O$R^{1b}$, —C(O)N($R^b$)($R^{3b}$), —N($R^b$)($R^{3b}$), —N($R^a$)C(O)$R^{1b}$, —N($R^a$)C(O)O($R^{1b}$), —N($R^a$)C(O)N($R^b$)($R^{3b}$), —(C$R^{4b}R^{5b}$)$_m$—NO$_2$, —(C$R^{4b}R^{5b}$)$_m$—O$R^{1b}$, —(C$R^{4b}R^{5b}$)$_m$—OC(O)$R^{1b}$, —(C$R^{4b}R^{5b}$)$_m$—OC(O)N($R^b$)($R^{3b}$), —(C$R^{4b}R^{5b}$)$_m$—S$R^{1b}$, —(C$R^{4b}R^{5b}$)$_m$—S(O)$_2R^{2b}$, —(C$R^{4b}R^{5b}$)$_m$—S(O)$_2$N($R^b$)($R^b$)($R^{3b}$), —(C$R^{4b}R^{5b}$)$_m$—C(O)$R^{1b}$, —(C$R^{4b}R^{5b}$)$_m$—C(O)O$R^{1b}$, —(C$R^{4b}R^{5b}$)$_m$—C(O)N($R^b$)($R^{3b}$), —(C$R^{4b}R^{5b}$)$_m$—N($R^b$)($R^{3b}$), —(C$R^{4b}R^{5b}$)$_m$—N($R^a$)C(O)$R^{1b}$, —(C$R^{4b}R^{5b}$)$_m$—N($R^a$)C(O)O($R^{1b}$), —(C$R^{4b}R^{5b}$)$_m$—N($R^a$)C(O)N($R^b$)($R^{3b}$), cyanoalkyl, and haloalkyl; $R^{1b}$ and $R^{3b}$, at each occurrence, are each independently hydrogen, alkoxyalkyl, alkyl, aryl, arylalkyl, haloalkyl, heteroarylalkyl, or heterocyclealkyl; $R^{2b}$, at each occurrence, is independently alkyl or haloalkyl; $R^{4b}$ and $R^{5b}$, at each occurrence, are each independently hydrogen, halogen, alkyl, or haloalkyl; and m at each occurrence, is independently 1, 2, 3, 4, or 5.

In another embodiment, $R^1$, $R^2$, $R^3$, and $R^4$ are each independently hydrogen, alkyl, haloalkyl, halogen, -$G^1$, —O$R^{1a}$, or —SO$_2R^{2a}$.

In another embodiment, $R^1$, $R^2$, $R^3$, and $R^4$ are each independently hydrogen, alkyl, haloalkyl, halogen, alkoxy, haloalkoxy, cyclopropyl, alkylsulfonyl, pyridyl, pyrazolyl, or aryl optionally substituted with halogen or haloalkyl.

In a further embodiment, $R^1$, $R^2$, and $R^4$ are hydrogen, and $R^3$ is alkyl.

In a further embodiment, $R^1$, $R^2$, and $R^4$ are hydrogen, and $R^3$ is halogen.

In a further embodiment, $R^1$, $R^2$, and $R^4$ are hydrogen, and $R^3$ is fluorine.

In a further embodiment, $R^1$, $R^2$, $R^3$ and $R^4$ are each hydrogen.

In one embodiment, $R^5$ is hydrogen, alkyl, -$G^1$, —S(O)$_2R^{2a}$, —S(O)$_2$N($R^b$)($R^{3a}$), —C(O)$R^{1a}$, —C(O)O$R^{1a}$, —C(O)N($R^b$)($R^{3a}$), —(C$R^{4a}R^{5a}$)$_m$—NO$_2$, —(C$R^{4a}R^{5a}$)$_m$—O$R^{1a}$, —(C$R^{4a}R^{5a}$)$_m$—OC(O)$R^{1a}$, —(C$R^{4a}R^{5a}$)$_m$—OC(O)N($R^b$)($R^{3a}$), —(C$R^{4a}R^{5a}$)$_m$—S$R^{1a}$, —(C$R^{4a}R^{5a}$)$_m$—S(O)$_2R^{2a}$, —(C$R^{4a}R^{5a}$)$_m$—S(O)$_2$N($R^b$)($R^{3a}$), —(C$R^{4a}R^{5a}$)$_m$—C(O)$R^{1a}$, —(C$R^{4a}R^{5a}$)$_m$—C(O)N($R^b$)($R^b$)($R^{3a}$), (C$R^{4a}R^{5a}$)$_m$—N($R^b$)($R^{3a}$), —(C$R^{4a}R^{5a}$)$_m$—N($R^a$)C(O)$R^{1a}$, —(C$R^{4a}R^{5a}$)$_m$—N($R^a$)C(O)O($R^{1a}$), —(C$R^{4a}R^{5a}$)$_m$—N($R^a$)C(O)N($R^b$)($R^{3a}$), —(C$R^{4a}R^{5a}$)$_m$-$G^1$, cyanoalkyl, or haloalkyl; wherein $R^{1a}$ and $R^{3a}$, at each occurrence, are independently hydrogen, alkyl, haloalkyl, $G^1$, or —(C$R^{6a}R^{7a}$)$_n$-$G^1$; $R^{2a}$, at each occurrence, is independently alkyl, haloalkyl, $G^1$, or —(C$R^{6a}R^{7a}$)$_n$-$G^1$; $R^{4a}$, $R^{5a}$, $R^{6a}$ and $R^{7a}$, at each occurrence, are each independently hydrogen, halogen, alkyl, or haloalkyl; and $R^a$, $R^b$, m, n, and $G^1$ are as disclosed in the Summary of the Invention and the embodiments described herein.

In another embodiment, $R^5$ is hydrogen, alkyl, haloalkyl, —C(O)$R^{1a}$, C(O)$R^{1a}$ or S(O)$_2R^{2a}$.

In an additional embodiment, $R^5$ is hydrogen.

In an additional embodiment, $R^5$ is —C(O)$R^{1a}$, C(O)O$R^{1a}$ or S(O)$_2R^{2a}$.

In a further embodiment, $R^5$ is —C(O)$R^{1a}$, wherein $R^{1a}$ is phenyl optionally substituted with alkyl or halogen.

In a further embodiment, $R^5$ is —C(O)O$R^{1a}$, wherein $R^{1a}$ is alkyl.

In a further embodiment, $R^5$ is S(O)$_2R^{2a}$, wherein $R^{2a}$ is phenyl optionally substituted with alkyl, halogen or haloalkyl.

In a further embodiment, $R^5$ is alkyl or haloalkyl.

In one embodiment, X is CH$R^6$, C=CH$R^6$, or N$R^6$.

In a further embodiment, X is N$R^6$.

In one embodiment, $X^1$ is CH$R^8$, or N$R^8$.

In another embodiment, $X^1$ is CH$R^8$.

In a further embodiment, $X^1$ is N$R^6$.

In one embodiment, $R^6$ is alkyl, —S(O)$_2R^{2a}$, —C(O)$R^{1a}$, —C(O)O$R^{1a}$, —C(O)N($R^b$)($R^{3a}$), —(C$R^{4a}R^{5a}$)$_m$—NO$_2$, —(C$R^{4a}R^{5a}$)$_m$—O$R^{1a}$, —(C$R^{4a}R^{5a}$)$_m$—OC(O)$R^{1a}$, —(C$R^{4a}R^{5a}$)$_m$—OC(O)N($R^b$)($R^{3a}$), —(C$R^{4a}R^{5a}$)$_m$—S$R^{1a}$, —(C$R^{4a}R^{5a}$)$_m$—S(O)$_2R^{2a}$, —(C$R^{4a}R^{5a}$)$_m$—S(O)$_2$N($R^b$)($R^b$)($R^{3a}$), —(C$R^{4a}R^{5a}$)$_m$—C(O)$R^{1a}$, —(C$R^{4a}R^{5a}$)$_m$—C(O)O$R^{1a}$, —(C$R^{4a}R^{5a}$)$_m$—C(O)N($R^b$)($R^b$)($R^{3a}$), (C$R^{4a}R^{5a}$)$_m$—N($R^b$)($R^{3a}$), —(C$R^{4a}R^{5a}$)$_m$—N($R^a$)C(O)$R^{1a}$, —(C$R^{4a}R^{5a}$)$_m$—N($R^a$)C(O)O($R^{1a}$), —(C$R^{4a}R^{5a}$)$_m$—N($R^a$)C(O)N($R^b$)($R^{3a}$), —(C$R^{4a}R^{5a}$)$_m$-$G^1$, —(C$R^{4a}R^{5a}$)$_m$-$G^2$-$G^1$, —C$R^{4a}$=C$R^{5a}$—S(O)$_2R^{2a}$, —C$R^{4a}$=C$R^{5a}$—S(O)$_2$N($R^b$)($R^{3a}$), —C$R^{4a}$=C$R^{5a}$—C(O)$R^{1a}$, —C$R^{4a}$=C$R^{5a}$—C(O)O$R^{1a}$, —C$R^{4a}$=C$R^{5a}$-$G^1$, -$G^1$, -$G^2$-$G^1$; cyanoalkyl, or haloalkyl, wherein $R^a$, $R^{1a}$, $R^{2a}$, $R^{3a}$, $R^{4a}$, $R^{5a}$, $R^b$, m, $G^1$, and $G^2$ are as disclosed in the Summary of the Invention and the embodiments described herein.

In another embodiment, $R^6$ is —(C$R^{4a}R^{5a}$)$_m$-$G^1$, wherein $R^{4a}$ and $R^{5a}$ are each hydrogen; m is 1, 2 or 3; and $G^1$ is as disclosed in the Summary of the Invention and the embodiments described herein.

In another embodiment, $R^6$ is —(C$R^{4a}R^{5a}$)$_m$-$G^1$, wherein $R^{4a}$ and $R^{5a}$ are each hydrogen; m is 1 or 2; and $G^1$ is phenyl, piperidinyl, pyrimidinyl, pyridazinyl, pyrazinyl, pyridazin-3(2H)-one, pyridin-2-yl, pyridin-3-yl, pyridin-4-yl, 1H-benzimidazol-2-yl, quinolin-8-yl, thiazolyl, 1,2-oxazol-5-yl, 1,4,5,6-tetrahydropyrimidin-5-yl, imidazo[1,2-b]pyridazin-2-yl, or imidazo[1,2-a]pyrimidin-2-yl; wherein $G^1$ is independently unsubstituted or substituted with 1, 2, 3, 4, or 5 substituents selected from the group consisting of alkyl, halogen, —N($R^b$)($R^{3b}$), and haloalkyl; $R^b$ is hydrogen or alkyl; and $R^{3b}$ is hydrogen, alkoxyalkyl, alkyl, arylalkyl, heteroarylalkyl, or heterocyclealkyl.

In another embodiment, $R^6$ is —(C$R^{4a}R^{5a}$)$_m$-$G^1$, wherein one of $R^{4a}$ or $R^{5a}$ is alkyl and the others of $R^{4a}$ and $R^{5a}$ are hydrogen; m is 1, 2 or 3; and $G^1$ is optionally substituted phenyl or pyridyl.

In a further embodiment, $R^6$ is —CH$_2$CH$_2$-(6-methylpyridin-3-yl).

In another embodiment, $R^6$ is —CR$^{4a}$=CR$^a$-G$^1$, wherein $R^{4a}$ and $R^{5a}$ are each hydrogen, and G$^1$ is as disclosed in the Summary of the Invention and the embodiments described herein.

In another embodiment, $R^6$ is —CR$^{4a}$=CR$^{5a}$-G$^1$, wherein $R^{4a}$ and $R^{5a}$ are each hydrogen, and G$^1$ is optionally substituted pyridyl or phenyl.

In a further embodiment, $R^6$ is —CH=CH-(6-methylpyridin-3-yl).

In another embodiment, $R^6$ is —(CR$^{4a}$R$^{5a}$)$_m$-G$^2$-G$^1$, wherein $R^{4a}$ and $R^{5a}$ are at each occurrence hydrogen; m is 1; and G$^2$ is oxazolyl, pyridyl, pyrimidinyl, or phenyl; and G$^1$ is oxadiazolyl, pyrrolidinyl, piperidinyl, pyrazolyl, pyridazin-3(2H)-onyl, or phenyl, optionally unsubstituted or substituted with 1, 2, or 3 alkyl, haloalkyl or halogen.

In another embodiment, $R^6$ is -G$^2$-G$^1$, wherein G$^2$ is optionally substituted aryl or optionally substituted heteroaryl, and G$^1$ is as disclosed in the Summary of the Invention and the embodiments described herein.

In a another embodiment, $R^6$ is -G$^2$-G$^1$, wherein G$^2$ is a pyridazinyl and G$^1$ is optionally substituted aryl or optionally substituted heteroaryl.

In a another embodiment, $R^6$ is -G$^2$-G$^1$, wherein G$^2$ is a pyridinyl and G$^1$ is optionally substituted aryl, optionally substituted heteroaryl, or optionally substituted heterocycle.

In a further embodiment, $R^6$ is -G$^2$-G$^1$, wherein G$^2$ is a phenyl, pyridinyl, or pyridazinyl, and G$^1$ is optionally substituted phenyl, pyrazolyl, pyridazin-3(2H)-onyl, morpholinyl, piperazinyl, or imidazolyl.

In a further embodiment, $R^6$ is -G$^2$-G$^1$, wherein G$^2$ is a phenyl and G$^1$ is optionally substituted aryl, optionally substituted heterocycle, or optionally substituted heteroaryl.

In another embodiment, $R^6$ is —C(O)R$^{1a}$, wherein R$^{1a}$ is as disclosed in the Summary of the Invention.

In a further embodiment, $R^6$ is —C(O)R$^{1a}$, wherein R$^{1a}$ is —(CR$^{6a}$R$^{7a}$)$_n$-G$^1$, wherein R$^{6a}$, R$^{7a}$, n and G$^1$ are as disclosed in the Summary of the Invention.

In a further embodiment, $R^6$ is —C(O)R$^{1a}$, wherein R$^{1a}$ is —(CR$^{6a}$R$^{7a}$)$_n$-G$^1$, wherein R$^{6a}$, R$^{7a}$ are each hydrogen, n is 1, and G$^1$ is optionally substituted phenyl.

In another embodiment, $R^6$ is G$^1$, wherein G$^1$ is as disclosed in the Summary of the Invention.

In a further embodiment, $R^6$ is G$^1$, wherein G$^1$ is optionally substituted aryl or heteroaryl.

In a further embodiment, $R^6$ is G$^1$, wherein G$^1$ is optionally substituted quinazolinyl, quinoxalin-2(1H)-onyl, pyrido[1,2-a]pyrimidinyl, pyrimidinyl, pyridyl, tetrahydroisoquinolinyl, quinazolinyl, isoquinolinyl, quinoxalinyl, benzoxazinyl, phenyl, pyrido[1,2-a]pyrimidinyl, quinolinyl, or pyrido[1,2-a]pyrimidin-4-onyl.

In another embodiment, $R^6$ is —(CR$^{4a}$R$^{5a}$)$_m$—OR$^{1a}$, wherein R$^{1a}$, R$^{4a}$, R$^{5a}$, and m are as disclosed in the Summary of the Invention.

In a further embodiment, $R^6$ is —(CR$^{4a}$R$^{5a}$)$_m$—OR$^{1a}$, wherein R$^{4a}$, R$^{5a}$, and m are as disclosed in the Summary of the Invention, and R$^{1a}$ is G$^1$, wherein G$^1$ is as described in the Summary of the Invention.

In another embodiment, $R^6$ is —(CR$^{4a}$R$^{5a}$)$_m$—OR$^{1a}$, wherein R$^{1a}$ is phenyl optionally substituted with alkyl, halogen, or OR$^{1b}$, wherein R$^{1b}$ is alkyl or haloalkyl; R$^{4a}$ and R$^{5a}$ are hydrogen at each occurrence, and m is 1 or 2.

In another embodiment, $R^6$ is —S(O)$_2$R$^{2a}$, wherein R$^{2a}$ is as described in the Summary of the Invention.

In a further embodiment, $R^6$ is —S(O)$_2$R$^{2a}$, wherein R$^{2a}$ is as G$^1$, wherein G$^1$ is as described in the Summary of the Invention.

In a further embodiment, $R^6$ is —S(O)$_2$R$^{2a}$, wherein R$^{2a}$ is as G$^1$, wherein G$^1$ is phenyl, or pyridyl, optionally substituted with alkyl, halogen, or haloalkyl.

In another embodiment, $R^6$ is —(CR$^{4a}$R$^{5a}$)$_m$—C(O)OR$^{1a}$ or —(CR$^{4a}$R$^{5a}$)$_m$—C(O)N(R$^b$)(R$^{3a}$), wherein R$^{1a}$, R$^{3a}$, R$^{4a}$, R$^{5a}$, m, and R$^b$ are as disclosed in the Summary of the Invention.

In a further embodiment, $R^6$ is —(CR$^{4a}$R$^{5a}$)$_m$—C(O)OR$^{1a}$ or —(CR$^{4a}$R$^{5a}$)$_m$—C(O)N(R$^b$)(R$^{3a}$), wherein R$^{1a}$ and R$^{3a}$ are each independently G$^1$, wherein G$^1$ is as described in the Summary of the Invention, and R$^{4a}$, R$^{5a}$, m, and R$^b$ are as disclosed in the Summary of the Invention.

In a further embodiment, $R^6$ is —(CR$^{4a}$R$^{5a}$)$_m$—C(O)OR$^{1a}$, wherein R$^{1a}$ is alkyl; R$^{4a}$ and R$^{5a}$ are hydrogen at each occurrence; and m is 1 or 2.

In a further embodiment, $R^6$ is —(CR$^{4a}$R$^{5a}$)$_m$—C(O)N(R$^b$)(R$^{3a}$), wherein R$^{3a}$ is optionally substituted phenyl; R$^{4a}$ and R$^{5a}$ are hydrogen at each occurrence; m is 1 or 2; and R$^b$ is hydrogen.

In another embodiment, $R^6$ is —(CR$^{4a}$R$^{5a}$)$_m$-G$^2$-G$^1$, wherein R$^{4a}$, R$^{5a}$, m, G$^1$, and G$^2$ are as disclosed in the Summary of the Invention.

In a further embodiment, $R^6$ is —(CR$^{4a}$R$^{5a}$)$_m$-G$^2$-G$^1$, wherein R$^{4a}$, R$^{5a}$, and m are as disclosed in the Summary of the Invention and G$^1$ and G$^2$ are independently optionally substituted aryl or heteroaryl.

In one embodiment, $R^7$ is hydrogen, alkyl, -G$^1$, —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)C(O)O(R$^a$), —(CR$^{4a}$R$^{5a}$)$_m$—N(R$^a$)C(O)N(R$^b$)(R$^{3a}$), —(CR$^{4a}$R$^{5a}$)$_m$-G$^1$, cyanoalkyl, or haloalkyl.

In a further embodiment, $R^7$ is hydrogen, alkyl, or haloalkyl.

In one embodiment, $R^8$ is —(CR$^{4a}$R$^{5a}$)$_m$-G$^1$, —(CR$^{4a}$R$^{5a}$)$_m$-G$^2$-G$^1$, or —CR$^{4a}$=CR$^{5a}$-G$^1$.

In another embodiment, $R^8$ is —(CR$^{4a}$R$^{5a}$)$_m$-G$^1$.

In a further embodiment, $R^8$ is —CR$^{4a}$=CR$^{5a}$-G$^1$.

Compounds of formula (I) can include, but are not limited to, compounds wherein a is a single or double bond. Thus, compounds within formula (I) include compounds having the following formula (Ia) and (Ib) and pharmaceutically acceptable salts thereof:

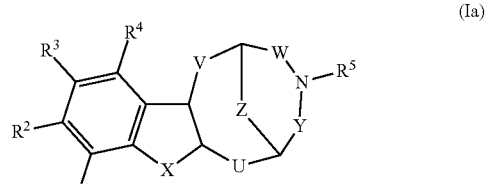

(Ia)

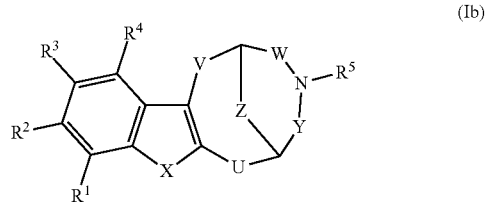

(Ib)

wherein $R^1$, $R^2$, $R^3$, $R^4$, $R^5$, U, V, W, X, Y, and Z are as disclosed in the Summary of the Invention and the embodiments described herein.

Compounds of formula (I) can include, but are not limited to, compounds wherein U is —(CH$_2$)$_p$—, wherein p is 1; V, W, and Y are each —(CH$_2$)$_p$—, wherein p is 0, i.e., a bond; and Z is —(CH$_2$)$_q$—, wherein q is 2.

Compounds of formula (I) can also include, but are not limited to, compounds wherein U is —(CH$_2$)$_p$—, wherein p is 1; V, W, and Y are each —(CH$_2$)$_p$—, wherein p is 0, i.e., a bond; and Z is —(CH$_2$)$_q$—, wherein q is 3.

Compounds of formula (I) can include, but are not limited to, compounds wherein U, V, and W are each —(CH$_2$)$_p$—, wherein p is 0, i.e., a bond; Y is —(CH$_2$)$_p$—, wherein p is 1; and Z is —(CH$_2$)$_q$—, wherein q is 1.

Compounds of formula (I) can include, but are not limited to, compounds wherein U, V, and W are each —(CH$_2$)$_p$—, wherein p is 0, i.e., a bond; Y is —(CH$_2$)$_p$—, wherein p is 1; and Z is —(CH$_2$)$_q$—, wherein q is 2.

Compounds of formula (I) can include, but are not limited to, compounds wherein U, V, and Y are each —(CH$_2$)$_p$—, wherein p is 0, i.e., a bond; W is —(CH$_2$)$_p$—, wherein p is 1; and Z is —(CH$_2$)$_q$—, wherein q is 1.

Compounds of formula (I) can include, but are not limited to, compounds wherein U, V, and Y are each —(CH$_2$)$_p$—, wherein p is 0, i.e., a bond; W is —(CH$_2$)$_p$—, wherein p is 1; and Z is —(CH$_2$)$_q$—, wherein q is 2.

Compounds of formula (I) can include, but are not limited to, compounds wherein U, W, and Y are each —(CH$_2$)$_p$—, wherein p is 0, i.e., a bond; V is —(CH$_2$)$_p$—, wherein p is 1; and Z is —(CH$_2$)$_q$—, wherein q is 2.

Compounds of formula (I) can include, but are not limited to, compounds wherein U, W, and Y are each —(CH$_2$)$_p$—, wherein p is 0, i.e., a bond; V is —(CH$_2$)$_p$—, wherein p is 1; and Z is —(CH$_2$)$_q$—, wherein q is 3.

Compounds of formula (I) can include, but are not limited to, compounds wherein U, V, W, and Y are each —(CH$_2$)$_p$—, wherein p is 0, i.e., a bond; and Z is —(CH$_2$)$_q$—, wherein q is 2.

Compounds of formula (I) can include, but are not limited to, compounds wherein U, V, and W are each —(CH$_2$)$_p$—, wherein p is 0, i.e., a bond; Y is —(CH$_2$)$_p$—, wherein p is 2; and Z is —(CH$_2$)$_q$—, wherein q is 1.

Compounds of formula (I) can include, but are not limited to, compounds wherein V and W are each —(CH$_2$)$_p$—, wherein p is 0, i.e., a bond; and U and Y are each —(CH$_2$)$_p$—, wherein p is 1; and Z is —(CH$_2$)$_q$—, wherein q is 1.

Compounds of formula (I) can include, but are not limited to, compounds wherein U, V, W, and Y are each —(CH$_2$)$_p$—, wherein p is 0, i.e., a bond; and Z is —(CH$_2$)$_q$—, wherein q is 3.

In another embodiment, in compounds of formula (I), wherein $R^1$, $R^2$ and $R^4$ are each hydrogen; $R^3$ is hydrogen or halogen; U is CH$_2$; V, W, and Y are each —(CH$_2$)$_p$—, wherein p is 0, i.e., a bond; Z is —(CH$_2$)$_q$—, wherein q is 2 or 3; X is NR$^6$; and R$^6$ is alkyl, -G$^1$, or —(CR$^{4a}$R$^{5a}$)$_m$-G$^1$, wherein m is 1, R$^{4a}$ and R$^{5a}$ are hydrogen and G$^1$ is phenyl unsubstituted or substituted with alkyl, halogen, hydroxy or —OR$^{1a}$ wherein R$^{1a}$ is alkyl; R$^5$ is other than hydrogen, alkyl, —(CR$^{4a}$R$^{5a}$)$_m$-G$^1$, —C(O)R$^{1a}$, —(CR$^{4a}$R$^{5a}$)$_m$—OR$^{1a}$, or —(CR$^{4a}$R$^{5a}$)$_m$—C(O)R$^{1a}$ wherein R$^{1a}$ is alkyl, aryl, or heteroaryl, and G$^1$ is aryl or heteroaryl.

Compounds of formula (II) can include, but are not limited to, compounds wherein $R^1$, $R^2$, $R^3$, $R^4$, $R^7$, W, $X^1$, and Y are as disclosed in the Summary of the Invention and the embodiments described herein and pharmaceutically acceptable salts thereof.

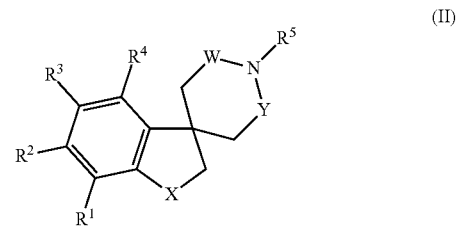

(II)

Compounds of formula (II) can include, but are not limited to, compounds wherein one of W and Y is —(CH$_2$)$_p$—, wherein p is 0, i.e., a bond and the other is —(CH$_2$)$_p$—, wherein p is 1.

Compounds of formula (II) can include, but are not limited to, compounds wherein one of W and Y is —(CH$_2$)$_p$—, wherein p is 0, i.e., a bond and the other is —(CH$_2$)$_p$—, wherein p is 2.

Compounds of formula (III) can include, but are not limited to, compounds wherein $R^1$, $R^2$, $R^3$, $R^4$, X, and Z are as disclosed in the Summary of the Invention and the embodiments described herein and pharmaceutically acceptable salts thereof.

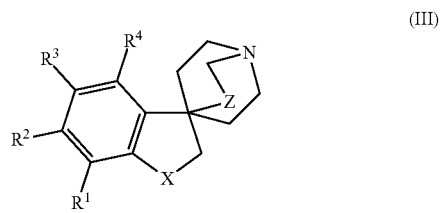

(III)

Compounds of formula (IV) can include, but are not limited to, compounds wherein a is a single or double bond. Thus, compounds within formula (IV) include compounds of the following formula (IVa) and (IVb) and pharmaceutically acceptable salts thereof:

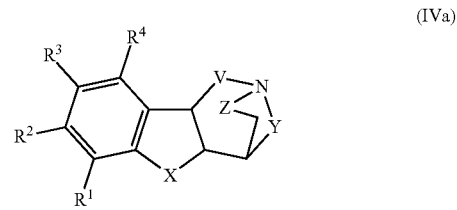

(IVa)

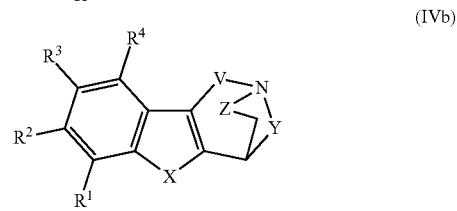

(IVb)

wherein $R^1$, $R^2$, $R^3$, $R^4$, V, X, and Z are as disclosed in the Summary of the Invention and the embodiments described herein.

Compounds of formula (IVa) can include, but are not limited to, compounds wherein V and Y are each —(CH$_2$)$_p$—, wherein p is 1; and Z is —(CH$_2$)$_q$—, wherein q is 1.

Compounds of formula (IVa) can include, but are not limited to, compounds wherein V is —(CH$_2$)$_p$—, wherein p is 1; Y is —(CH$_2$)$_p$—, wherein p is 2; and Z is —(CH$_2$)$_q$—, wherein q is 1.

Compounds of formula (IVa) can include, but are not limited to, compounds wherein V and Y are each —(CH$_2$)$_p$—, wherein p is 1; and Z is —(CH$_2$)$_q$—, wherein q is 2.

Compounds of formula (IVa) can include, but are not limited to, compounds wherein V is —(CH$_2$)$_p$—, wherein p is 0, i.e., a bond; Y is —(CH$_2$)$_p$—, wherein p is 2; and Z is —(CH$_2$)$_q$—, wherein q is 1.

Compounds of formula (IVb) can include, but are not limited to, compounds wherein V, Y, and Z are each CH$_2$.

Compounds of formula (IVb) can include, but are not limited to, compounds wherein V and Y are each —(CH$_2$)$_p$—, wherein p is 1; and Z is —(CH$_2$)$_q$—, wherein q is 2.

In another embodiment, in compounds of formula (IVb), wherein V is —(CH$_2$)$_p$—, wherein p is 0, i.e., a bond; Y is —(CH$_2$)$_p$—, wherein p is 2; and Z is —(CH$_2$)$_q$—, wherein q is 1; R$^6$ is other than alkyl, C(O)R$^{1a}$, —(CR$^{4a}$R$^{5a}$)$_m$—OR$^{1a}$, —(CR$^{4a}$R$^{5a}$)$_m$C(O)R$^{1a}$, —(CR$^{4a}$R$^{5a}$)$_m$—N(R$^b$)(R3a), —(CR$^{4a}$R$^{5a}$)$_m$-G$^1$, —CR$^{4a}$=CR$^{5a}$-G$^1$, -G$^1$, cyanoalkyl or haloalkyl.

Compounds of formula (IVb) can include, but are not limited to, compounds wherein V and Z are each CH$_2$; and Y is CH$_2$CH$_2$.

Compounds of formula (V) can include, but are not limited to, compounds wherein R$^1$, R$^2$, R$^3$, R$^4$, and X are as disclosed in the Summary of the Invention and the embodiments described herein and pharmaceutically acceptable salts thereof.

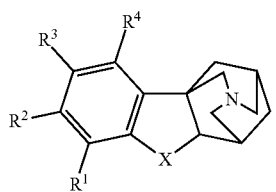
(V)

Compounds of formula (VI) can include, but are not limited to, compounds wherein a is a single or double bond. Thus, compounds within formula (VI) include compounds of the following formula (VIa) and (VIb) and pharmaceutically acceptable salts thereof:

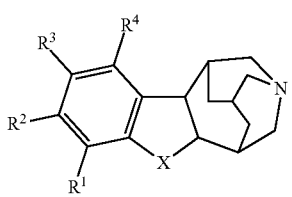
(VIa)

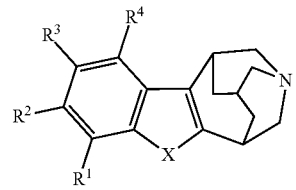
(VIb)

wherein R$^1$, R$^2$, R$^3$, R$^4$, and X are as disclosed in the Summary of the Invention and the embodiments described herein.

Specific embodiments of compounds contemplated as part of the invention include, but are not limited to:
2,11-dimethyl-5-[2-(6-methylpyridin-3-yl)ethyl]-5,6,7,8,9, 10-hexahydro-7,10-epiminocyclohepta[b]indole;
9-methyl-6-[2-(6-methylpyridin-3-yl)ethyl]-3,4,5,6-tetrahydro-1H-2,5-ethanoazepino[4,3-b]indole;
5-[6-(4-iodophenyl)pyridazin-3-yl]-2,11-dimethyl-5,6,7,8, 9,10-hexahydro-7,10-epiminocyclohepta[b]indole;
9-methyl-6-[2-(6-methylpyridin-3-yl)ethyl]-3,4,5,6-tetrahydro-1H-2,5-methanoazepino[4,3-b]indole;
2,8-dimethyl-5-[2-(6-methylpyridin-3-yl)ethyl]-2,3,4,5-tetrahydro-1H-1,4-methanopyrido[4,3-b]indole;
6,10-dimethyl-9-[2-(6-methylpyridin-3-yl)ethyl]-2,3,4,9-tetrahydro-1H-4,1-(epiminomethano)carbazole;
2,6-dimethyl-9-[2-(6-methylpyridin-3-yl)ethyl]-2,3,4,9-tetrahydro-1H-1,4-methano-β-carboline;
6,11-dimethyl-9-[2-(6-methylpyridin-3-yl)ethyl]-2,3,4,9-tetrahydro-1H-1,4-(epiminomethano)carbazole;
2,11-dimethyl-5-[2-(6-methylpyridin-3-yl)ethyl]-5,6,7,8,9, 10-hexahydro-6,9-epiminocyclohepta[b]indole;
2,12-dimethyl-5-[2-(6-methylpyridin-3-yl)ethyl]-6,7,8,9,10, 11-hexahydro-5H-6,10-epiminocycloocta[b]indole;
6,10-dimethyl-9-[2-(6-methylpyridin-3-yl)ethyl]-2,3,4,9-tetrahydro-1H-1,4-epiminocarbazole;
2,9-dimethyl-6-[2-(6-methylpyridin-3-yl)ethyl]-1,2,3,4,5,6-hexahydro-1,5-methanoazepino[4,3-b]indole;
2,9-dimethyl-6-[2-(6-methylpyridin-3-yl)ethyl]-1,2,3,4,5,6-hexahydro-1,4-methanoazepino[4,3-b]indole;
2,11-dimethyl-5-[2-(6-methylpyridin-3-yl)ethyl]-5,6,7,8,9, 10-hexahydro-6,10-epiminocyclohepta[b]indole;
(5aS*,7S*,10R*,10aR*)-2,11-dimethyl-5-[2-(6-methylpyridin-3-yl)ethyl]-5,5a,6,7,8,9,10,10a-octahydro-7,10-epiminocyclohepta[b]indole;
(5aR*,7S*,10R*,10aS*)-2,11-dimethyl-5-[2-(6-methylpyridin-3-yl)ethyl]-5,5a,6,7,8,9,10,10a-octahydro-7,10-epiminocyclohepta[b]indole;
(5aS*,7S*,11R*,11aR*)-2,12-dimethyl-5-[2-(6-methylpyridin-3-yl)ethyl]-5a,6,7,8,9,10,11,11a-octahydro-5H-7,11-epiminocycloocta[b]indole;
(5aR*,7S*,11R*,11aS*)-2,12-dimethyl-5-[2-(6-methylpyridin-3-yl)ethyl]-5a,6,7,8,9,10,11,11a-octahydro-5H-7,11-epiminocycloocta[b]indole;
(5R*,5aS*,10bR*)-9-methyl-6-[2-(6-methylpyridin-3-yl) ethyl]-3,4,5,5a,6,10b-hexahydro-1H-2,5-methanoazepino [4,3-b]indole;
(5R*,5aR*,10bS*)-9-methyl-6-[2-(6-methylpyridin-3-yl) ethyl]-3,4,5,5a,6,10b-hexahydro-1H-2,5-methanoazepino [4,3-b]indole;
(1R*,4R*,4aS*,9bR*)-2,8-dimethyl-5-[2-(6-methylpyridin-3-yl)ethyl]-2,3,4,4a,5,9b-hexahydro-1H-1,4-methanopyrido[4,3-b]indole;

(1R*,4R*,4aR*,9bS*)-2,8-dimethyl-5-[2-(6-methylpyridin-3-yl)ethyl]-2,3,4,4a,5,9b-hexahydro-1H-1,4-methanopyrido[4,3-b]indole;

(1R*,4R*,4aR*,9aS*)-6,10-dimethyl-9-[2-(6-methylpyridin-3-yl)ethyl]-2,3,4,4a,9,9a-hexahydro-1H-4,1-(epiminomethano)carbazole;

(1R*,4R*,4aS*,9aR*)-6,10-dimethyl-9-[2-(6-methylpyridin-3-yl)ethyl]-2,3,4,4a,9,9a-hexahydro-1H-4,1-(epiminomethano)carbazole;

(1S*,4R*,4aS*,9aR*)-2,6-dimethyl-9-[2-(6-methylpyridin-3-yl)ethyl]-2,3,4,4a,9,9a-hexahydro-H-1,4-methano-β-carboline;

(1S*,4R*,4aR*,9aS*)-2,6-dimethyl-9-[2-(6-methylpyridin-3-yl)ethyl]-2,3,4,4a,9,9a-hexahydro-H-1,4-methano-β-carboline;

(1S*,4R*,4aS*,9aR*)-6,11-dimethyl-9-[2-(6-methylpyridin-3-yl)ethyl]-2,3,4,4a,9,9a-hexahydro-1H-1,4-(epiminomethano)carbazole;

(1S*,4R*,4aR*,9aS*)-6,11-dimethyl-9-[2-(6-methylpyridin-3-yl)ethyl]-2,3,4,4a,9,9a-hexahydro-1H-1,4-(epiminomethano)carbazole;

(5aR*,6S*,9R*,10aS*)-2,11-dimethyl-5-[2-(6-methylpyridin-3-yl)ethyl]-5,5a,6,7,8,9,10,10a-octahydro-6,9-epiminocyclohepta[b]indole;

(5S*,6S*,9R*,10aR*)-2,11-dimethyl-5-[2-(6-methylpyridin-3-yl)ethyl]-5,5a,6,7,8,9,10,10a-octahydro-6,9-epiminocyclohepta[b]indole;

(5aR*,6S*,10R*,11S*)-2,12-dimethyl-5-[2-(6-methylpyridin-3-yl)ethyl]-5a,6,7,8,9,10,11,11a-octahydro-5H-6,10-epiminocycloocta[b]indole;

(5S*,6S*,10R*,11aR*)-2,12-dimethyl-5-[2-(6-methylpyridin-3-yl)ethyl]-5a,6,7,8,9,10,11,11a-octahydro-5H-6,10-epiminocycloocta[b]indole;

(1R*,4S*,4aR*,9aR*)-6,10-dimethyl-9-[2-(6-methylpyridin-3-yl)ethyl]-2,3,4,4a,9,9a-hexahydro-1H-1,4-epiminocarbazole;

(1R*,4S*,4aS*,9aS*)-6,10-dimethyl-9-[2-(6-methylpyridin-3-yl)ethyl]-2,3,4,4a,9,9a-hexahydro-1H-1,4-epiminocarbazole;

(1R*,5S*,5aS*,10bR*)-2,9-dimethyl-6-[2-(6-methylpyridin-3-yl)ethyl]-1,2,3,4,5,5a,6,10b-octahydro-1,5-methanoazepino[4,3-b]indole;

(1R*,5S*,5aR*,10bS*)-2,9-dimethyl-6-[2-(6-methylpyridin-3-yl)ethyl]-1,2,3,4,5,5a,6,10b-octahydro-1,5-methanoazepino[4,3-b]indole;

(1R*,4S*,5 S*,10bR*)-2,9-dimethyl-6-[2-(6-methylpyridin-3-yl)ethyl]-1,2,3,4,5,5a,6,10b-octahydro-1, 4-methanoazepino[4,3-b]indole;

(1R*,4S*,5aR*,10bS*)-2,9-dimethyl-6-[2-(6-methylpyridin-3-yl)ethyl]-1,2,3,4,5,5a,6,10b-octahydro-1, 4-methanoazepino[4,3-b]indole;

(5aR*,6R*,10S*,10aR*)-2,11-dimethyl-5-[2-(6-methylpyridin-3-yl)ethyl]-5,5a,6,7,8,9,10,10a-octahydro-6,10-epiminocyclohepta[b]indole;

(5aS*,6R*,10S*,10aS*)-2,11-dimethyl-5-[2-(6-methylpyridin-3-yl)ethyl]-5,5a,6,7,8,9,10,10a-octahydro-6,10-epiminocyclohepta[b]indole;

1',5-dimethyl-1-[2-(6-methylpyridin-3-yl)ethyl]-1,2-dihydrospiro[indole-3,3'-pyrrolidine];

1',5-dimethyl-1-[2-(6-methylpyridin-3-yl)ethyl]-1,2-dihydrospiro[indole-3,3'-piperidine];

2-methyl-5-[2-(6-methylpyridin-3-yl)ethyl]-5,6,7,8,9,10-hexahydro-7,10-epiminocyclohepta[b]indole;

(7S,10R)-2-methyl-5-[2-(6-methylpyridin-3-yl)ethyl]-5,6,7,8,9,10-hexahydro-7,10-epiminocyclohepta[b]indole;

(7R,10S)-2-methyl-5-[2-(6-methylpyridin-3-yl)ethyl]-5,6,7,8,9,10-hexahydro-7,10-epiminocyclohepta[b]indole;

(7R,10S)-2,11-dimethyl-5-[2-(6-methylpyridin-3-yl)ethyl]-5,6,7,8,9,10-hexahydro-7,10-epiminocyclohepta[b]indole;

(7S,10R)-2,11-dimethyl-5-[2-(6-methylpyridin-3-yl)ethyl]-5,6,7,8,9,10-hexahydro-7,10-epiminocyclohepta[b]indole;

5-[2-(6-chloropyridin-3-yl)ethyl]-2,11-dimethyl-5,6,7,8,9,10-hexahydro-7,10-epiminocyclohepta[b]indole;

(7R,10S)-5-[2-(6-chloropyridin-3-yl)ethyl]-2,11-dimethyl-5,6,7,8,9,10-hexahydro-7,10-epiminocyclohepta[b]indole;

(7S,10R)-5-[2-(6-chloropyridin-3-yl)ethyl]-2,11-dimethyl-5,6,7,8,9,10-hexahydro-7,10-epiminocyclohepta[b]indole;

11-ethyl-2-methyl-5-[2-(6-methylpyridin-3-yl)ethyl]-5,6,7,8,9,10-hexahydro-7,10-epiminocyclohepta[b]indole;

11-(2-fluoroethyl)-2-methyl-5-[2-(6-methylpyridin-3-yl)ethyl]-5,6,7,8,9,10-hexahydro-7,10-epiminocyclohepta[b]indole;

2-methyl-5-[2-(6-methylpyridin-3-yl)ethyl]-11-(2,2,2-trifluoroethyl)-5,6,7,8,9,10-hexahydro-7,10-epiminocyclohepta[b]indole;

ethyl (7R,10S)-2-methyl-5-[2-(6-methylpyridin-3-yl)ethyl]-5,6,7,8,9,10-hexahydro-7,10-epiminocyclohepta[b]indole-11-carboxylate;

ethyl (7S,10R)-2-methyl-5-[2-(6-methylpyridin-3-yl)ethyl]-5,6,7,8,9,10-hexahydro-7,10-epiminocyclohepta[b]indole-11-carboxylate;

11-(4-chlorobenzoyl)-2-methyl-5-[2-(6-methylpyridin-3-yl)ethyl]-5,6,7,8,9,10-hexahydro-7,10-epiminocyclohepta[b]indole;

2-methyl-5-[2-(6-methylpyridin-3-yl)ethyl]-11-{[4-(trifluoromethyl)phenyl]sulfonyl}-5,6,7,8,9,10-hexahydro-7,10-epiminocyclohepta[b]indole;

(7R,10S)-2,11-dimethyl-5-[2-(2-methylpyridin-3-yl)ethyl]-5,6,7,8,9,10-hexahydro-7,10-epiminocyclohepta[b]indole;

2,11-dimethyl-5-[(Z)-2-pyridin-3-ylvinyl]-5,6,7,8,9,10-hexahydro-7,10-epiminocyclohepta[b]indole;

(7R,10S)-2,11-dimethyl-5-[(E)-2-pyridin-3-ylvinyl]-5,6,7,8,9,10-hexahydro-7,10-epiminocyclohepta[b]indole;

(7S,10R)-2,11-dimethyl-5-[(E)-2-pyridin-3-ylvinyl]-5,6,7,8,9,10-hexahydro-7,10-epiminocyclohepta[b]indole;

(7S,10R)-2,11-dimethyl-5-[(E)-2-(6-methylpyridin-3-yl)vinyl]-5,6,7,8,9,10-hexahydro-7,10-epiminocyclohepta[b]indole;

(7S,10R)-2,11-dimethyl-5-[(Z)-2-(6-methylpyridin-3-yl)vinyl]-5,6,7,8,9,10-hexahydro-7,10-epiminocyclohepta[b]indole;

(7R,10S)-2-methyl-5-[(Z)-2-(6-methylpyridin-3-yl)vinyl]-5,6,7,8,9,10-hexahydro-7,10-epiminocyclohepta[b]indole;

(7S,10R)-2-methyl-5-[(Z)-2-(6-methylpyridin-3-yl)vinyl]-5,6,7,8,9,10-hexahydro-7,10-epiminocyclohepta[b]indole;

(7S,10R)-2,11-dimethyl-5-(2-pyridin-2-ylethyl)-5,6,7,8,9,10-hexahydro-7,10-epiminocyclohepta[b]indole;

(7S,10R)-5-[2-(5-ethylpyridin-2-yl)ethyl]-2,11-dimethyl-5,6,7,8,9,10-hexahydro-7,10-epiminocyclohepta[b]indole;

(7S,10R)-2,11-dimethyl-5-(2-pyridin-4-ylethyl)-5,6,7,8,9,10-hexahydro-7,10-epiminocyclohepta[b]indole;

2,11-dimethyl-5-(2-pyrimidin-5-ylethyl)-5,6,7,8,9,10-hexahydro-7,10-epiminocyclohepta[b]indole;

(7R,10S)-2,11-dimethyl-5-[2-(2-methylpyrimidin-5-yl)ethyl]-5,6,7,8,9,10-hexahydro-7,10-epiminocyclohepta[b]indole;

(7S,10R)-2,11-dimethyl-5-[2-(2-methylpyrimidin-5-yl)ethyl]-5,6,7,8,9,10-hexahydro-7,10-epiminocyclohepta[b]indole;
(7R,10S)-2,11-dimethyl-5-[2-(6-methylpyridazin-3-yl)ethyl]-5,6,7,8,9,10-hexahydro-7,10-epiminocyclohepta[b]indole;
(7R,10S)-2,11-dimethyl-5-[2-(5-methylpyrazin-2-yl)ethyl]-5,6,7,8,9,10-hexahydro-7,10-epiminocyclohepta[b]indole;
2,11-dimethyl-5-[2-(4-methyl-1,3-thiazol-5-yl)ethyl]-5,6,7,8,9,10-hexahydro-7,10-epiminocyclohepta[b]indole;
2,11-dimethyl-5-(2-phenylethyl)-5,6,7,8,9,10-hexahydro-7,10-epiminocyclohepta[b]indole;
2,11-dimethyl-5-[2-(2-methylphenyl)ethyl]-5,6,7,8,9,10-hexahydro-7,10-epiminocyclohepta[b]indole;
(7R,10S)-2,11-dimethyl-5-[2-(2-methylphenyl)ethyl]-5,6,7,8,9,10-hexahydro-7,10-epiminocyclohepta[b]indole;
(7S,10R)-2,11-dimethyl-5-[2-(2-methylphenyl)ethyl]-5,6,7,8,9,10-hexahydro-7,10-epiminocyclohepta[b]indole;
2,11-dimethyl-5-[2-(4-methylphenyl)ethyl]-5,6,7,8,9,10-hexahydro-7,10-epiminocyclohepta[b]indole;
5-[2-(4-fluorophenyl)ethyl]-2,11-dimethyl-5,6,7,8,9,10-hexahydro-7,10-epiminocyclohepta[b]indole;
5-[2-(3-fluorophenyl)ethyl]-2,11-dimethyl-5,6,7,8,9,10-hexahydro-7,10-epiminocyclohepta[b]indole;
5-[2-(2-fluorophenyl)ethyl]-2,11-dimethyl-5,6,7,8,9,10-hexahydro-7,10-epiminocyclohepta[b]indole;
(7R,10S)-5-[2-(4-chlorophenyl)ethyl]-2,11-dimethyl-5,6,7,8,9,10-hexahydro-7,10-epiminocyclohepta[b]indole;
(7S,10R)-5-[2-(4-chlorophenyl)ethyl]-2,11-dimethyl-5,6,7,8,9,10-hexahydro-7,10-epiminocyclohepta[b]indole;
(7S,10R)-5-[2-(2-chlorophenyl)ethyl]-2,11-dimethyl-5,6,7,8,9,10-hexahydro-7,10-epiminocyclohepta[b]indole;
5-[2-(4-bromophenyl)ethyl]-2,11-dimethyl-5,6,7,8,9,10-hexahydro-7,10-epiminocyclohepta[b]indole;
5-[2-(3-bromophenyl)ethyl]-2,11-dimethyl-5,6,7,8,9,10-hexahydro-7,10-epiminocyclohepta[b]indole;
2,11-dimethyl-5-{2-[4-(trifluoromethyl)phenyl]ethyl}-5,6,7,8,9,10-hexahydro-7,10-epiminocyclohepta[b]indole;
2,11-dimethyl-5-{2-[3-(trifluoromethyl)phenyl]ethyl}-5,6,7,8,9,10-hexahydro-7,10-epiminocyclohepta[b]indole;
(7R,10S)-2,11-dimethyl-5-{2-[3-(trifluoromethyl)phenyl]ethyl}-5,6,7,8,9,10-hexahydro-7,10-epiminocyclohepta[b]indole;
(7S,10R)-2,11-dimethyl-5-{2-[3-(trifluoromethyl)phenyl]ethyl}-5,6,7,8,9,10-hexahydro-7,10-epiminocyclohepta[b]indole;
2,11-dimethyl-5-{2-[2-(trifluoromethyl)phenyl]ethyl}-5,6,7,8,9,10-hexahydro-7,10-epiminocyclohepta[b]indole;
(7R,10S)-2,11-dimethyl-5-{2-[2-(trifluoromethyl)phenyl]ethyl}-5,6,7,8,9,10-hexahydro-7,10-epiminocyclohepta[b]indole;
(7S,10R)-2,11-dimethyl-5-{2-[2-(trifluoromethyl)phenyl]ethyl}-5,6,7,8,9,10-hexahydro-7,10-epiminocyclohepta[b]indole;
5-[2-(4-methoxyphenyl)ethyl]-2,11-dimethyl-5,6,7,8,9,10-hexahydro-7,10-epiminocyclohepta[b]indole;
(7R,10S)-2,11-dimethyl-5-[(E)-2-phenylvinyl]-5,6,7,8,9,10-hexahydro-7,10-epiminocyclohepta[b]indole;
2,11-dimethyl-5-[(E)-2-(4-methylphenyl)vinyl]-5,6,7,8,9,10-hexahydro-7,10-epiminocyclohepta[b]indole;
(7R,10S)-2,11-dimethyl-5-[(E)-2-(4-methylphenyl)vinyl]-5,6,7,8,9,10-hexahydro-7,10-epiminocyclohepta[b]indole;
2,11-dimethyl-5-[(Z)-2-(4-methylphenyl)vinyl]-5,6,7,8,9,10-hexahydro-7,10-epiminocyclohepta[b]indole;
(7R,10S)-2,11-dimethyl-5-[(Z)-2-(4-methylphenyl)vinyl]-5,6,7,8,9,10-hexahydro-7,10-epiminocyclohepta[b]indole;
(7R,10S)-5-[(E)-2-(2,4-dimethylphenyl)vinyl]-2,11-dimethyl-5,6,7,8,9,10-hexahydro-7,10-epiminocyclohepta[b]indole;
5-[(4-chlorophenyl)acetyl]-2,11-dimethyl-5,6,7,8,9,10-hexahydro-7,10-epiminocyclohepta[b]indole;
5-[2-(4-chlorophenyl)propyl]-2,11-dimethyl-5,6,7,8,9,10-hexahydro-7,10-epiminocyclohepta[b]indole;
5-(4-isopropenylphenyl)-2,11-dimethyl-5,6,7,8,9,10-hexahydro-7,10-epiminocyclohepta[b]indole;
2,11-dimethyl-5-(3-phenylpropyl)-5,6,7,8,9,10-hexahydro-7,10-epiminocyclohepta[b]indole;
5-[2-(4-fluorophenoxy)ethyl]-2,11-dimethyl-5,6,7,8,9,10-hexahydro-7,10-epiminocyclohepta[b]indole;
(7S,10R)-5-isoquinolin-7-yl-2,11-dimethyl-5,6,7,8,9,10-hexahydro-7,10-epiminocyclohepta[b]indole;
2,11-dimethyl-5-(phenylsulfonyl)-5,6,7,8,9,10-hexahydro-7,10-epiminocyclohepta[b]indole;
(7R,10S)-2,11-dimethyl-5-[(4-methylphenyl)sulfonyl]-5,6,7,8,9,10-hexahydro-7,10-epiminocyclohepta[b]indole;
(7S,10R)-2,11-dimethyl-5-[(4-methylphenyl)sulfonyl]-5,6,7,8,9,10-hexahydro-7,10-epiminocyclohepta[b]indole;
5-[(4-fluorophenyl)sulfonyl]-2,11-dimethyl-5,6,7,8,9,10-hexahydro-7,10-epiminocyclohepta[b]indole;
5-[(4-chlorophenyl)sulfonyl]-2,11-dimethyl-5,6,7,8,9,10-hexahydro-7,10-epiminocyclohepta[b]indole;
2,11-dimethyl-5-{[4-(trifluoromethyl)phenyl]sulfonyl}-5,6,7,8,9,10-hexahydro-7,10-epiminocyclohepta[b]indole;
5-[(4-methoxyphenyl)sulfonyl]-2,11-dimethyl-5,6,7,8,9,10-hexahydro-7,10-epiminocyclohepta[b]indole;
2,11-dimethyl-5-{[4-(trifluoromethoxy)phenyl]sulfonyl}-5,6,7,8,9,10-hexahydro-7,10-epiminocyclohepta[b]indole;
2,11-dimethyl-5-(pyridin-3-ylsulfonyl)-5,6,7,8,9,10-hexahydro-7,10-epiminocyclohepta[b]indole;
11-methyl-5-[2-(6-methylpyridin-3-yl)ethyl]-5,6,7,8,9,10-hexahydro-7,10-epiminocyclohepta[b]indole;
11-methyl-5-(2-phenylethyl)-5,6,7,8,9,10-hexahydro-7,10-epiminocyclohepta[b]indole;
11-methyl-5-[2-(2-methylphenyl)ethyl]-5,6,7,8,9,10-hexahydro-7,10-epiminocyclohepta[b]indole;
5-[2-(4-chlorophenyl)ethyl]-11-methyl-5,6,7,8,9,10-hexahydro-7,10-epiminocyclohepta[b]indole;
11-methyl-5-[2-(2-methyl-1,4,5,6-tetrahydropyrimidin-5-yl)ethyl]-5,6,7,8,9,10-hexahydro-7,10-epiminocyclohepta[b]indole;
11-methyl-5-{[4-(trifluoromethyl)phenyl]sulfonyl}-5,6,7,8,9,10-hexahydro-7,10-epiminocyclohepta[b]indole;
2-fluoro-11-methyl-5-[2-(4-methylphenyl)ethyl]-5,6,7,8,9,10-hexahydro-7,10-epiminocyclohepta[b]indole;
2-fluoro-5-[2-(4-fluorophenyl)ethyl]-11-methyl-5,6,7,8,9,10-hexahydro-7,10-epiminocyclohepta[b]indole;
2-fluoro-5-[2-(3-fluorophenyl)ethyl]-11-methyl-5,6,7,8,9,10-hexahydro-7,10-epiminocyclohepta[b]indole;
2-bromo-5-[2-(4-chlorophenyl)ethyl]-11-methyl-5,6,7,8,9,10-hexahydro-7,10-epiminocyclohepta[b]indole;
(7R,10S)-2-bromo-5-[2-(4-chlorophenyl)ethyl]-11-methyl-5,6,7,8,9,10-hexahydro-7,10-epiminocyclohepta[b]indole;
(7S,10R)-2-bromo-5-[2-(4-chlorophenyl)ethyl]-11-methyl-5,6,7,8,9,10-hexahydro-7,10-epiminocyclohepta[b]indole;
2-bromo-11-methyl-5-[(4-methylphenyl)sulfonyl]-5,6,7,8,9,10-hexahydro-7,10-epiminocyclohepta[b]indole;
2-methoxy-11-methyl-5-[2-(6-methylpyridin-3-yl)ethyl]-5,6,7,8,9,10-hexahydro-7,10-epiminocyclohepta[b]indole;
(7R,10S)-5-[2-(4-chlorophenyl)ethyl]-2-methoxy-11-methyl-5,6,7,8,9,10-hexahydro-7,10-epiminocyclohepta[b]indole;

(7S,10R)-5-[2-(4-chlorophenyl)ethyl]-2-methoxy-11-methyl-5,6,7,8,9,10-hexahydro-7,10-epiminocyclohepta[b]indole;
(7R,10S)-2-methoxy-11-methyl-5-{2-[3-(trifluoromethyl)phenyl]ethyl}-5,6,7,8,9,10-hexahydro-7,10-epiminocyclohepta[b]indole;
(7S,10R)-2-methoxy-11-methyl-5-{2-[3-(trifluoromethyl)phenyl]ethyl}-5,6,7,8,9,10-hexahydro-7,10-epiminocyclohepta[b]indole;
5-[2-(4-chlorophenyl)ethyl]-4-methoxy-11-methyl-5,6,7,8,9,10-hexahydro-7,10-epiminocyclohepta[b]indole;
5-[2-(4-chlorophenyl)ethyl]-11-methyl-2-(trifluoromethoxy)-5,6,7,8,9,10-hexahydro-7,10-epiminocyclohepta[b]indole;
5-[2-(4-chlorophenyl)ethyl]-11-methyl-2-(trifluoromethyl)-5,6,7,8,9,10-hexahydro-7,10-epiminocyclohepta[b]indole;
2-isopropyl-11-methyl-5-[2-(6-methylpyridin-3-yl)ethyl]-5,6,7,8,9,10-hexahydro-7,10-epiminocyclohepta[b]indole;
(7R,10S)-5-[2-(4-chlorophenyl)ethyl]-2-isopropyl-11-methyl-5,6,7,8,9,10-hexahydro-7,10-epiminocyclohepta[b]indole;
(7S,10R)-5-[2-(4-chlorophenyl)ethyl]-2-isopropyl-11-methyl-5,6,7,8,9,10-hexahydro-7,10-epiminocyclohepta[b]indole;
2-cyclopropyl-11-methyl-5-[(4-methylphenyl)sulfonyl]-5,6,7,8,9,10-hexahydro-7,10-epiminocyclohepta[b]indole;
2-cyclopropyl-11-methyl-5-[2-(6-methylpyridin-3-yl)ethyl]-5,6,7,8,9,10-hexahydro-7,10-epiminocyclohepta[b]indole;
2-tert-butyl-11-methyl-5-[2-(6-methylpyridin-3-yl)ethyl]-5,6,7,8,9,10-hexahydro-7,10-epiminocyclohepta[b]indole;
2-tert-butyl-5-[2-(4-chlorophenyl)ethyl]-11-methyl-5,6,7,8,9,10-hexahydro-7,10-epiminocyclohepta[b]indole;
2-(4-chlorophenyl)-11-methyl-5-[2-(6-methylpyridin-3-yl)ethyl]-5,6,7,8,9,10-hexahydro-7,10-epiminocyclohepta[b]indole;
2-bromo-11-methyl-5-[2-(6-methylpyridin-3-yl)ethyl]-5,6,7,8,9,10-hexahydro-7,10-epiminocyclohepta[b]indole;
2-(4-chlorophenyl)-5-[2-(4-chlorophenyl)ethyl]-11-methyl-5,6,7,8,9,10-hexahydro-7,10-epiminocyclohepta[b]indole;
11-methyl-5-[2-(6-methylpyridin-3-yl)ethyl]-2-[3-(trifluoromethyl)phenyl]-5,6,7,8,9,10-hexahydro-7,10-epiminocyclohepta[b]indole;
5-[2-(4-chlorophenyl)ethyl]-11-methyl-2-[3-(trifluoromethyl)phenyl]-5,6,7,8,9,10-hexahydro-7,10-epiminocyclohepta[b]indole;
11-methyl-5-[2-(6-methylpyridin-3-yl)ethyl]-2-pyridin-3-yl-5,6,7,8,9,10-hexahydro-7,10-epiminocyclohepta[b]indole;
5-[2-(4-chlorophenyl)ethyl]-11-methyl-2-pyridin-3-yl-5,6,7,8,9,10-hexahydro-7,10-epiminocyclohepta[b]indole;
11-methyl-5-[2-(6-methylpyridin-3-yl)ethyl]-2-(1H-pyrazol-4-yl)-5,6,7,8,9,10-hexahydro-7,10-epiminocyclohepta[b]indole;
(5aS,7S,10R,10aR)-2,11-dimethyl-5-[2-(6-methylpyridin-3-yl)ethyl]-5,5a,6,7,8,9,10,10a-octahydro-7,10-epiminocyclohepta[b]indole;
2,12-dimethyl-5-[2-(6-methylpyridin-3-yl)ethyl]-6,7,8,9,10,11-hexahydro-5H-7,11-epiminocycloocta[b]indole;
(7R,11S)-2,12-dimethyl-5-[2-(6-methylpyridin-3-yl)ethyl]-6,7,8,9,10,11-hexahydro-5H-7,11-epiminocycloocta[b]indole;
(7S,11R)-2,12-dimethyl-5-[2-(6-methylpyridin-3-yl)ethyl]-6,7,8,9,10,11-hexahydro-5H-7,11-epiminocycloocta[b]indole;
5-[2-(6-chloropyridin-3-yl)ethyl]-2,12-dimethyl-6,7,8,9,10,11-hexahydro-5H-7,11-epiminocycloocta[b]indole;
(7R,11S)-2-methyl-5-[(Z)-2-(6-methylpyridin-3-yl)vinyl]-6,7,8,9,10,11-hexahydro-5H-7,11-epiminocycloocta[b]indole;
(7S,11R)-2-methyl-5-[(Z)-2-(6-methylpyridin-3-yl)vinyl]-6,7,8,9,10,11-hexahydro-5H-7,11-epiminocycloocta[b]indole;
(7R,11S)-2-methyl-5-[2-(6-methylpyridin-3-yl)ethyl]-6,7,8,9,10,11-hexahydro-5H-7,11-epiminocycloocta[b]indole;
(7S,11R)-2-methyl-5-[2-(6-methylpyridin-3-yl)ethyl]-6,7,8,9,10,11-hexahydro-5H-7,11-epiminocycloocta[b]indole;
2,12-dimethyl-5-[(E)-2-(6-methylpyridin-3-yl)vinyl]-6,7,8,9,10,11-hexahydro-5H-7,11-epiminocycloocta[b]indole;
(7R,11S)-2,12-dimethyl-5-[(Z)-2-(6-methylpyridin-3-yl)vinyl]-6,7,8,9,10,11-hexahydro-5H-7,11-epiminocycloocta[b]indole;
(7S,11R)-2,12-dimethyl-5-[(Z)-2-(6-methylpyridin-3-yl)vinyl]-6,7,8,9,10,11-hexahydro-5H-7,11-epiminocycloocta[b]indole;
(7R,11S)-2-methyl-5-[(E)-2-(6-methylpyridin-3-yl)vinyl]-6,7,8,9,10,11-hexahydro-5H-7,11-epiminocycloocta[b]indole;
(7S,11R)-2-methyl-5-[(E)-2-(6-methylpyridin-3-yl)vinyl]-6,7,8,9,10,11-hexahydro-5H-7,11-epiminocycloocta[b]indole;
(7R,11S)-2-methyl-5-[2-(2-methylphenyl)ethyl]-6,7,8,9,10,11-hexahydro-5H-7,11-epiminocycloocta[b]indole;
(7S,11R)-2-methyl-5-[2-(2-methylphenyl)ethyl]-6,7,8,9,10,11-hexahydro-5H-7,11-epiminocycloocta[b]indole;
(7R,11S)-5-[2-(2,5-dimethylphenyl)ethyl]-2-methyl-6,7,8,9,10,11-hexahydro-5H-7,11-epiminocycloocta[b]indole;
(7S,11R)-5-[2-(2,5-dimethylphenyl)ethyl]-2-methyl-6,7,8,9,10,11-hexahydro-5H-7,11-epiminocycloocta[b]indole;
(7R,11S)-5-[2-(4-chlorophenyl)ethyl]-2-methyl-6,7,8,9,10,11-hexahydro-5H-7,11-epiminocycloocta[b]indole;
(7S,11R)-5-[2-(4-chlorophenyl)ethyl]-2-methyl-6,7,8,9,10,11-hexahydro-5H-7,11-epiminocycloocta[b]indole;
(7R,11S)-2-methyl-5-{2-[3-(trifluoromethyl)phenyl]ethyl}-6,7,8,9,10,11-hexahydro-5H-7,11-epiminocycloocta[b]indole;
2-methyl-5-{(E)-2-[3-(trifluoromethyl)phenyl]vinyl}-6,7,8,9,10,11-hexahydro-5H-7,11-epiminocycloocta[b]indole;
(7S,11R)-2-methyl-5-{2-[3-(trifluoromethyl)phenyl]ethyl}-6,7,8,9,10,11-hexahydro-5H-7,11-epiminocycloocta[b]indole;
12-ethyl-2-methyl-5-{2-[3-(trifluoromethyl)phenyl]ethyl}-6,7,8,9,10,11-hexahydro-5H-7,11-epiminocycloocta[b]indole;
(7R,11S)-2-methyl-5-{(E)-2-[3-(trifluoromethyl)phenyl]vinyl}-6,7,8,9,10,11-hexahydro-5H-7,11-epiminocycloocta[b]indole;
(7S,11R)-2-methyl-5-{(E)-2-[3-(trifluoromethyl)phenyl]vinyl}-6,7,8,9,10,11-hexahydro-5H-7,11-epiminocycloocta[b]indole;
2-methyl-5-{(Z)-2-[3-(trifluoromethyl)phenyl]vinyl}-6,7,8,9,10,11-hexahydro-5H-7,11-epiminocycloocta[b]indole;
5-[2-(6-methylpyridin-3-yl)ethyl]-2-(trifluoromethoxy)-6,7,8,9,10,11-hexahydro-5H-7,11-epiminocycloocta[b]indole;
5-[2-(2-methylphenyl)ethyl]-2-(trifluoromethoxy)-6,7,8,9,10,11-hexahydro-5H-7,11-epiminocycloocta[b]indole;
6-[2-(6-chloropyridin-3-yl)ethyl]-9-methyl-3,4,5,6-tetrahydro-1H-2,5-ethanoazepino[4,3-b]indole;
9-methyl-6-{2-[6-(trifluoromethyl)pyridin-3-yl]ethyl}-3,4,5,6-tetrahydro-1H-2,5-ethanoazepino[4,3-b]indole;

9-methyl-6-[(E)-2-pyridin-3-ylvinyl]-3,4,5,6-tetrahydro-1H-2,5-ethanoazepino[4,3-b]indole;
9-methyl-6-[(Z)-2-pyridin-3-ylvinyl]-3,4,5,6-tetrahydro-1H-2,5-ethanoazepino[4,3-b]indole;
9-methyl-6-[(E)-2-(6-methylpyridin-3-yl)vinyl]-3,4,5,6-tetrahydro-1H-2,5-ethanoazepino[4,3-b]indole;
9-methyl-6-[(Z)-2-(6-methylpyridin-3-yl)vinyl]-3,4,5,6-tetrahydro-1H-2,5-ethanoazepino[4,3-b]indole;
9-methyl-6-[2-(6-methylpyridazin-3-yl)ethyl]-3,4,5,6-tetrahydro-1H-2,5-ethanoazepino[4,3-b]indole;
9-methyl-6-[2-(2-methylphenyl)ethyl]-3,4,5,6-tetrahydro-1H-2,5-ethanoazepino[4,3-b]indole;
6-[2-(2-fluorophenyl)ethyl]-9-methyl-3,4,5,6-tetrahydro-1H-2,5-ethanoazepino[4,3-b]indole;
6-[2-(4-chlorophenyl)ethyl]-9-methyl-3,4,5,6-tetrahydro-1H-2,5-ethanoazepino[4,3-b]indole;
9-methyl-6-{2-[3-(trifluoromethyl)phenyl]ethyl}-3,4,5,6-tetrahydro-1H-2,5-ethanoazepino[4,3-b]indole;
9-methyl-6-[(Z)-2-(4-methylphenyl)vinyl]-3,4,5,6-tetrahydro-1H-2,5-ethanoazepino[4,3-b]indole;
ethyl (9-methyl-1,3,4,5-tetrahydro-6H-2,5-ethanoazepino[4,3-b]indol-6-yl)acetate;
N-(4-chlorophenyl)-2-(9-methyl-1,3,4,5-tetrahydro-6H-2,5-ethanoazepino[4,3-b]indol-6-yl)acetamide;
2-(9-methyl-1,3,4,5-tetrahydro-6H-2,5-ethanoazepino[4,3-b]indol-6-yl)-N-[4-(trifluoromethoxy)phenyl]acetamide;
(5aR*,10bS*)-9-methyl-6-[2-(6-methylpyridin-3-yl)ethyl]-3,4,5,5a,6,10b-hexahydro-1H-2,5-ethanoazepino[4,3-b]indole;
(5aS,10bR)-9-methyl-6-[2-(6-methylpyridin-3-yl)ethyl]-3,4,5,5a,6,10b-hexahydro-1H-2,5-ethanoazepino[4,3-b]indole;
(5aR,10bS)-9-methyl-6-[2-(6-methylpyridin-3-yl)ethyl]-3,4,5,5a,6,10b-hexahydro-1H-2,5-ethanoazepino[4,3-b]indole;
9-fluoro-6-[(E)-2-(6-methylpyridin-3-yl)vinyl]-3,4,5,6-tetrahydro-1H-2,5-ethanoazepino[4,3-b]indole;
9-fluoro-6-[2-(4-fluorophenyl)ethyl]-3,4,5,6-tetrahydro-1H-2,5-ethanoazepino[4,3-b]indole;
6-[(6-chloropyridin-3-yl)methyl]-9-fluoro-3,4,5,6-tetrahydro-1H-2,5-ethanoazepino[4,3-b]indole;
9-fluoro-6-(4-fluorobenzyl)-3,4,5,6-tetrahydro-1H-2,5-ethanoazepino[4,3-b]indole;
6-(4-chlorobenzyl)-9-fluoro-3,4,5,6-tetrahydro-1H-2,5-ethanoazepino[4,3-b]indole;
6-(4-bromobenzyl)-9-fluoro-3,4,5,6-tetrahydro-1H-2,5-ethanoazepino[4,3-b]indole;
9-fluoro-6-[3-(trifluoromethyl)benzyl]-3,4,5,6-tetrahydro-1H-2,5-ethanoazepino[4,3-b]indole;
6-(2,3-difluoro-4-methylbenzyl)-9-fluoro-3,4,5,6-tetrahydro-1H-2,5-ethanoazepino[4,3-b]indole;
9-fluoro-6-[3-fluoro-4-(trifluoromethyl)benzyl]-3,4,5,6-tetrahydro-1H-2,5-ethanoazepino[4,3-b]indole;
9-fluoro-6-[4-(5-methyl-1,2,4-oxadiazol-3-yl)benzyl]-3,4,5,6-tetrahydro-1H-2,5-ethanoazepino[4,3-b]indole;
9-fluoro-6-[(2-methyl-1,3-thiazol-4-yl)methyl]-3,4,5,6-tetrahydro-1H-2,5-ethanoazepino[4,3-b]indole;
9-fluoro-6-[(2-phenyl-1,3-oxazol-4-yl)methyl]-3,4,5,6-tetrahydro-1H-2,5-ethanoazepino[4,3-b]indole;
9-bromo-6-[2-(4-chlorophenyl)ethyl]-3,4,5,6-tetrahydro-1H-2,5-ethanoazepino[4,3-b]indole;
6-[(E)-2-pyridin-3-ylvinyl]-9-(trifluoromethoxy)-3,4,5,6-tetrahydro-1H-2,5-ethanoazepino[4,3-b]indole;
6-[(Z)-2-(6-methylpyridin-3-yl)vinyl]-9-(trifluoromethoxy)-3,4,5,6-tetrahydro-1H-2,5-ethanoazepino[4,3-b]indole;
6-[2-(6-methylpyridin-3-yl)ethyl]-9-(trifluoromethoxy)-3,4,5,6-tetrahydro-1H-2,5-ethanoazepino[4,3-b]indole;
6-[2-(6-methylpiperidin-3-yl)ethyl]-9-(trifluoromethoxy)-3,4,5,6-tetrahydro-1H-2,5-ethanoazepino[4,3-b]indole;
6-[(Z)-2-(6-methylpyridin-3-yl)vinyl]-9-(methylsulfonyl)-3,4,5,6-tetrahydro-1H-2,5-ethanoazepino[4,3-b]indole;
6-[2-(6-methylpyridin-3-yl)ethyl]-9-(methylsulfonyl)-3,4,5,6-tetrahydro-1H-2,5-ethanoazepino[4,3-b]indole;
9-fluoro-6-{[6-(trifluoromethyl)pyridin-3-yl]methyl}-3,4,5,6-tetrahydro-1H-2,5-ethanoazepino[4,3-b]indole;
9-fluoro-6-(pyridin-2-ylmethyl)-3,4,5,6-tetrahydro-1H-2,5-ethanoazepino[4,3-b]indole;
9-fluoro-6-(pyridin-3-ylmethyl)-3,4,5,6-tetrahydro-1H-2,5-ethanoazepino[4,3-b]indole;
9-fluoro-6-(pyridin-4-ylmethyl)-3,4,5,6-tetrahydro-1H-2,5-ethanoazepino[4,3-b]indole;
6-[(pyridin-2-yl)methyl]-3,4,5,6-tetrahydro-1H-2,5-ethanoazepino[4,3-b]indole;
6-(pyridin-3-ylmethyl)-3,4,5,6-tetrahydro-1H-2,5-ethanoazepino[4,3-b]indole;
6-[(pyridin-4-yl)methyl]-3,4,5,6-tetrahydro-1H-2,5-ethanoazepino[4,3-b]indole;
8-[(6-chloropyridin-3-yl)methyl]-11-fluoro-1,4,5,6,7,8-hexahydro-2H-1,5:3,7-dimethanoazonino[5,4-b]indole;
9-fluoro-6-[(2-fluoropyridin-4-yl)methyl]-3,4,5,6-tetrahydro-1H-2,5-ethanoazepino[4,3-b]indole;
11-methyl-8-[2-(6-methylpyridin-3-yl)ethyl]-1,4,5,6,7,8-hexahydro-2H-1,5:3,7-dimethanoazonino[5,4-b]indole;
(1R*,7R*,7aS*,12bR*)-11-methyl-8-[2-(6-methylpyridin-3-yl)ethyl]-1,4,5,6,7,7a,8,12b-octahydro-2H-1,5:3,7-dimethanoazonino[5,4-b]indole;
(1R*,7R*,7aR*,12bS*)-11-methyl-8-[2-(6-methylpyridin-3-yl)ethyl]-1,4,5,6,7,7a,8,12b-octahydro-2H-1,5:3,7-dimethanoazonino[5,4-b]indole;
8-[2-(6-chloropyridin-3-yl)ethyl]-11-methyl-1,4,5,6,7,8-hexahydro-2H-1,5:3,7-dimethanoazonino[5,4-b]indole;
11-methyl-8-[2-(2-methylphenyl)ethyl]-1,4,5,6,7,8-hexahydro-2H-1,5:3,7-dimethanoazonino[5,4-b]indole;
5-[2-(6-chloropyridin-3-yl)ethyl]-2,11-dimethyl-5,6,7,8,9,10-hexahydro-6,10-epiminocyclohepta[b]indole;
(6R,10S)-5-[2-(6-chloropyridin-3-yl)ethyl]-2,11-dimethyl-5,6,7,8,9,10-hexahydro-6,10-epiminocyclohepta[b]indole;
(6S,10R)-5-[2-(6-chloropyridin-3-yl)ethyl]-2,11-dimethyl-5,6,7,8,9,10-hexahydro-6,10-epiminocyclohepta[b]indole;
10-methyl-7-[2-(6-methylpyridin-3-yl)ethyl]-1,3,4,5,6,7-hexahydro-2,6-methanoazocino[4,3-b]indole;
10-methyl-7-[2-(2-methylphenyl)ethyl]-1,3,4,5,6,7-hexahydro-2,6-methanoazocino[4,3-b]indole;
7-[2-(4-chlorophenyl)ethyl]-10-methyl-1,3,4,5,6,7-hexahydro-2,6-methanoazocino[4,3-b]indole;
(4aR*,9bR*)-5-[2-(6-methylpyridin-3-yl)ethyl]-2,3,4,4a,5,9b-hexahydro-1,4-ethanopyrido[3,2-b]indole;
(4aR*,9bR*)-7-methyl-5-[2-(6-methylpyridin-3-yl)ethyl]-2,3,4,4a,5,9b-hexahydro-1,4-ethanopyrido[3,2-b]indole;
(4aR*,9bR*)-8-methyl-5-[2-(6-methylpyridin-3-yl)ethyl]-2,3,4,4a,5,9b-hexahydro-1,4-ethanopyrido[3,2-b]indole;
5-[(4-chlorophenyl)sulfonyl]-8-methyl-2,3,4,5-tetrahydro-1,4-ethanopyrido[3,2-b]indole;
6-isoquinolin-7-yl-9-methyl-3,4,5,6-tetrahydro-1H-2,5-ethanoazepino[4,3-b]indole;
9-methyl-6-quinolin-6-yl-3,4,5,6-tetrahydro-1H-2,5-ethanoazepino[4,3-b]indole;
9-methyl-6-(2-methylquinolin-6-yl)-3,4,5,6-tetrahydro-1H-2,5-ethanoazepino[4,3-b]indole;

9-methyl-6-quinazolin-6-yl-3,4,5,6-tetrahydro-1H-2,5-ethanoazepino[4,3-b]indole;
6-(9-methyl-1,3,4,5-tetrahydro-6H-2,5-ethanoazepino[4,3-b]indol-6-yl)quinazolin-4-ol;
6-(4-methoxyquinazolin-6-yl)-9-methyl-3,4,5,6-tetrahydro-1H-2,5-ethanoazepino[4,3-b]indole;
9-methyl-6-quinolin-2-yl-3,4,5,6-tetrahydro-1H-2,5-ethanoazepino[4,3-b]indole;
9-fluoro-6-isoquinolin-7-yl-3,4,5,6-tetrahydro-1H-2,5-ethanoazepino[4,3-b]indole;
9-fluoro-6-quinolin-2-yl-3,4,5,6-tetrahydro-1H-2,5-ethanoazepino[4,3-b]indole;
9-fluoro-6-[6-(1H-pyrazol-1-yl)pyridin-2-yl]-3,4,5,6-tetrahydro-1H-2,5-ethanoazepino[4,3-b]indole;
9-fluoro-6-quinolin-7-yl-3,4,5,6-tetrahydro-1H-2,5-ethanoazepino[4,3-b]indole;
9-fluoro-6-quinazolin-6-yl-3,4,5,6-tetrahydro-1H-2,5-ethanoazepino[4,3-b]indole;
9-fluoro-6-quinolin-6-yl-3,4,5,6-tetrahydro-1H-2,5-ethanoazepino[4,3-b]indole;
9-fluoro-6-(2-methylquinolin-6-yl)-3,4,5,6-tetrahydro-1H-2,5-ethanoazepino[4,3-b]indole;
6-(4-methoxyquinazolin-6-yl)-3,4,5,6-tetrahydro-1H-2,5-ethanoazepino[4,3-b]indole;
6-(1,3,4,5-tetrahydro-6H-2,5-ethanoazepino[4,3-b]indol-6-yl)quinazolin-4-ol;
6-(2-methylquinolin-6-yl)-3,4,5,6-tetrahydro-1H-2,5-ethanoazepino[4,3-b]indole;
6-quinolin-6-yl-3,4,5,6-tetrahydro-1H-2,5-ethanoazepino[4,3-b]indole;
6-quinolin-7-yl-3,4,5,6-tetrahydro-1H-2,5-ethanoazepino[4,3-b]indole;
6-quinolin-2-yl-3,4,5,6-tetrahydro-1H-2,5-ethanoazepino[4,3-b]indole;
6-[6-(1H-pyrazol-1-yl)pyridin-2-yl]-3,4,5,6-tetrahydro-1H-2,5-ethanoazepino[4,3-b]indole;
6-[4-(4-methylpiperazin-1-yl)phenyl]-3,4,5,6-tetrahydro-1H-2,5-ethanoazepino[4,3-b]indole;
2-[2-(9-fluoro-1,3,4,5-tetrahydro-6H-2,5-ethanoazepino[4,3-b]indol-6-yl)ethyl]pyridazin-3 (2H)-one;
1-[4-(1,3,4,5-tetrahydro-6H-2,5-ethanoazepino[4,3-b]indol-6-yl)phenyl]pyridin-2(1H)-one;
9-fluoro-6-{[6-(2-methylpyrrolidin-1-yl)pyridin-3-yl]methyl}-3,4,5,6-tetrahydro-1H-2,5-ethanoazepino[4,3-b]indole;
9-fluoro-6-{[6-(piperidin-1-yl)pyridin-3-yl]methyl}-3,4,5,6-tetrahydro-1H-2,5-ethanoazepino[4,3-b]indole;
5-[(9-fluoro-1,3,4,5-tetrahydro-6H-2,5-ethanoazepino[4,3-b]indol-6-yl)methyl]-N-isopropyl-N-methylpyridin-2-amine;
N-(1,3-dioxolan-2-ylmethyl)-5-[(9-fluoro-1,3,4,5-tetrahydro-6H-2,5-ethanoazepino[4,3-b]indol-6-yl)methyl]-N-methylpyridin-2-amine;
9-fluoro-6-{[6-(pyrrolidin-1-yl)pyridin-3-yl]methyl}-3,4,5,6-tetrahydro-1H-2,5-ethanoazepino[4,3-b]indole;
5-[(9-fluoro-1,3,4,5-tetrahydro-6H-2,5-ethanoazepino[4,3-b]indol-6-yl)methyl]-N-(2-methoxyethyl)-N-methylpyridin-2-amine;
9-fluoro-6-[(5-fluoropyridin-3-yl)methyl]-3,4,5,6-tetrahydro-1H-2,5-ethanoazepino[4,3-b]indole;
9-fluoro-6-{[6-(1H-pyrazol-1-yl)pyridin-3-yl]methyl}-3,4,5,6-tetrahydro-1H-2,5-ethanoazepino[4,3-b]indole;
2-{5-[(9-fluoro-1,3,4,5-tetrahydro-6H-2,5-ethanoazepino[4,3-b]indol-6-yl)methyl]pyridin-2-yl}pyridazin-3(2H)-one;
9-fluoro-6-[(2-phenylpyrimidin-5-yl)methyl]-3,4,5,6-tetrahydro-1H-2,5-ethanoazepino[4,3-b]indole;
6-(1H-benzimidazol-2-ylmethyl)-9-fluoro-3,4,5,6-tetrahydro-1H-2,5-ethanoazepino[4,3-b]indole;
9-fluoro-6-(quinolin-8-ylmethyl)-3,4,5,6-tetrahydro-1H-2,5-ethanoazepino[4,3-b]indole;
9-fluoro-6-[(3-methyl-1,2-oxazol-5-yl)methyl]-3,4,5,6-tetrahydro-1H-2,5-ethanoazepino[4,3-b]indole;
6-[(6-chloroimidazo[1,2-b]pyridazin-2-yl)methyl]-9-fluoro-3,4,5,6-tetrahydro-1H-2,5-ethanoazepino[4,3-b]indole;
9-fluoro-6-(imidazo[1,2-a]pyrimidin-2-ylmethyl)-3,4,5,6-tetrahydro-1H-2,5-ethanoazepino[4,3-b]indole;
2-{4-[(9-fluoro-1,3,4,5-tetrahydro-6H-2,5-ethanoazepino[4,3-b]indol-6-yl)methyl]phenyl}pyridazin-3(2H)-one;
6-{[6-(trifluoromethyl)pyridin-3-yl]methyl}-3,4,5,6-tetrahydro-1H-2,5-ethanoazepino[4,3-b]indole;
6-[(6-chloroimidazo[1,2-b]pyridazin-2-yl)methyl]-3,4,5,6-tetrahydro-1H-2,5-ethanoazepino[4,3-b]indole;
6'-(9-fluoro-1,3,4,5-tetrahydro-6H-2,5-ethanoazepino[4,3-b]indol-6-yl)-2H-1,2'-bipyridin-2-one;
6-(9-fluoro-1,3,4,5-tetrahydro-6H-2,5-ethanoazepino[4,3-b]indol-6-yl)quinazolin-4-ol;
7-(9-fluoro-1,3,4,5-tetrahydro-6H-2,5-ethanoazepino[4,3-b]indol-6-yl)quinoxalin-2(1H)-one;
7-(9-fluoro-1,3,4,5-tetrahydro-6H-2,5-ethanoazepino[4,3-b]indol-6-yl)-4H-pyrido[1,2-a]pyrimidin-4-one;
2-[6-(9-fluoro-1,3,4,5-tetrahydro-6H-2,5-ethanoazepino[4,3-b]indol-6-yl)pyridin-3-yl]pyridazin-3(2H)-one;
9-fluoro-6-(2-methylpyrimidin-5-yl)-3,4,5,6-tetrahydro-1H-2,5-ethanoazepino[4,3-b]indole;
9-fluoro-6-(pyridin-3-yl)-3,4,5,6-tetrahydro-1H-2,5-ethanoazepino[4,3-b]indole;
6-[6-(morpholin-4-yl)pyridin-2-yl]-3,4,5,6-tetrahydro-1H-2,5-ethanoazepino[4,3-b]indole;
6-(1,3,4,5-tetrahydro-6H-2,5-ethanoazepino[4,3-b]indol-6-yl)nicotinamide;
6-(1,2,3,4-tetrahydroisoquinolin-6-yl)-3,4,5,6-tetrahydro-1H-2,5-ethanoazepino[4,3-b]indole;
6-(2-methyl-1,2,3,4-tetrahydroisoquinolin-6-yl)-3,4,5,6-tetrahydro-1H-2,5-ethanoazepino[4,3-b]indole;
6-(quinazolin-6-yl)-3,4,5,6-tetrahydro-1H-2,5-ethanoazepino[4,3-b]indole;
6-(isoquinolin-7-yl)-3,4,5,6-tetrahydro-1H-2,5-ethanoazepino[4,3-b]indole;
6-(isoquinolin-6-yl)-3,4,5,6-tetrahydro-1H-2,5-ethanoazepino[4,3-b]indole;
6-[4-(1H-imidazol-1-yl)pyridin-2-yl]-3,4,5,6-tetrahydro-1H-2,5-ethanoazepino[4,3-b]indole;
6'-(1,3,4,5-tetrahydro-6H-2,5-ethanoazepino[4,3-b]indol-6-yl)-2H-1,2'-bipyridin-2-one;
7-(1,3,4,5-tetrahydro-6H-2,5-ethanoazepino[4,3-b]indol-6-yl)quinoxalin-2(1H)-one;
7-(1,3,4,5-tetrahydro-6H-2,5-ethanoazepino[4,3-b]indol-6-yl)-2H-1,4-benzoxazin-3(4H)-one;
2-amino-5-(1,3,4,5-tetrahydro-6H-2,5-ethanoazepino[4,3-b]indol-6-yl)benzamide;
7-(1,3,4,5-tetrahydro-6H-2,5-ethanoazepino[4,3-b]indol-6-yl)-4H-pyrido[1,2-a]pyrimidin-4-one;
(7S,10R)-5-(quinolin-6-yl)-5,6,7,8,9,10-hexahydro-7,10-epiminocyclohepta[b]indole;
(7R,10S)-5-(isoquinolin-7-yl)-5,6,7,8,9,10-hexahydro-7,10-epiminocyclohepta[b]indole;
(7S,10R)-5-(isoquinolin-7-yl)-5,6,7,8,9,10-hexahydro-7,10-epiminocyclohepta[b]indole;
(7S,10R)-11-methyl-5-(quinolin-6-yl)-5,6,7,8,9,10-hexahydro-7,10-epiminocyclohepta[b]indole;
(7R,10S)-5-(quinolin-6-yl)-5,6,7,8,9,10-hexahydro-7,10-epiminocyclohepta[b]indole;

7-[(7S,10R)-7,8,9,10-tetrahydro-7,10-epiminocyclohepta[b]indol-5(6H)-yl]-4H-pyrido[1,2-a]pyrimidin-4-one;

7-[(7R,10S)-7,8,9,10-tetrahydro-7,10-epiminocyclohepta[b]indol-5(6H)-yl]-4H-pyrido[1,2-a]pyrimidin-4-one;

6-[(6-chloropyridin-3-yl)methyl]-9-fluoro-1,2,3,4,5,6-hexahydro-1,4-methanoazepino[4,3-b]indole;

(7R,10S)-11-methyl-5-(quinolin-6-yl)-5,6,7,8,9,10-hexahydro-7,10-epiminocyclohepta[b]indole; or 2-[4-(1,3,4,5-tetrahydro-6H-2,5-ethanoazepino[4,3-b]indol-6-yl)phenyl]pyridazin-3(2H)-one.

The present invention also features processes for the preparation of the compounds of the invention. In one embodiment, the present invention provides a process for preparing a compound of formula (VIII) comprising the step of reacting a compound of formula (VII) under alkylation conditions, cross-coupling conditions, or nucleophilic aromatic substitution conditions, wherein $R^6$ is alkyl, $-S(O)_2R^{2a}$, $-(CR^{4a}R^{5a})_m-OR^{1a}$, $-(CR^{4a}R^{5a})_m-G^1$, $-(CR^{4a}R^{5a})_m-G^2-G^1$, $-CR^{4a}=CR^{5a}-G^1$, $-G^1$, or $-G^2-G^1$. Compounds of formula (VIII) are representative of compounds of formula (I). The preparation of compounds of formula (VII) and (VIII) are described in the Examples.

(VII)

(VIII)

In another embodiment, the present invention provides a process for preparing a compound of formula (X) comprising the step of reacting a compound of formula (IX) under alkylation conditions, cross-coupling conditions, or nucleophilic aromatic substitution conditions, wherein $R^6$ is alkyl, $-S(O)_2R^{2a}$, $-(CR^{4a}R^{5a})_m-OR^{1a}$, $-(CR^{4a}R^{5a})_m-G^1$, $-(CR^{4a}R^{5a})_m-G^2-G^1$, $-CR^{4a}=CR^{5a}-G^1$, $-G^1$, or $-G^2-G^1$. Compounds of formula (X) are representative of compounds of formula (IV). Compounds of formula (IX) and (X) are prepared as described in the Examples.

(IX)

(X)

In a another embodiment, the present invention provides a process for preparing a compound of formula (XII) comprising the step of reacting a compound of formula (XI) under alkylation conditions, cross-coupling conditions, or nucleophilic aromatic substitution conditions, wherein $R^6$ is alkyl, $-S(O)_2R^{2a}$, $-(CR^{4a}R^{5a})_m-OR^{1a}$, $-(CR^{4a}R^{5a})_m-G^1$, $-(CR^{4a}R^{5a})_m-G^2-G^1$, $-CR^{4a}=CR^{5a}-G^1$, $-G^1$, or $-G^2-G^1$. Compounds of formula (XII) are representative of compounds of formula (VI). Compounds of formula (XI) and (XII) are prepared as described in the Examples.

(XI)

(XII)

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the compounds of the present invention. The present invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the present invention encompasses any tautomeric or stereoisomeric form, and mixtures thereof, and is not to be limited merely to any one tautomeric or stereoisomeric form utilized within the naming of the compounds or formulae drawings.

Compounds of this invention can exist in an isotopic form containing one or more atoms having an atomic mass or mass number different from the atomic mass or mass number most abundantly found in nature. Isotopes of atoms such as hydrogen, carbon, phosphorous, sulfur fluorine, chlorine, and iodine include, but are not limited to $^2H$, $^3H$, $^{11}C$, $^{14}C$, $^{32}P$, $^{35}S$, $^{18}F$, $^{36}Cl$, and $^{125}I$, respectively. Compounds that contain other isotopes of these and/or other atoms are within the scope of this invention. Compounds containing tritium ($^3H$) and $^{14}C$ radioisotopes are preferred in general for their ease in preparation and detectability for radiolabeled compounds. Isotopically labeled compounds of this invention can be prepared by the general methods well known to persons having ordinary skill in the art. Such Isotopically labeled compounds can be conveniently prepared by carrying out the procedures disclosed in the Examples and Schemes below by substituting a readily available isotopically labeled reagent for a non-isotopically labeled reagent.

c. BIOLOGICAL DATA

To determine the effectiveness of compounds having a formula (I), (II), (III), (IV), (V), or (VI), these compounds can be evaluated in in vitro models of cellular function and in vivo models of pro-cognitive effects.

Abbreviations which have been used in the descriptions of Biological Data that follow are: DMEM for Dulbecco's modified Eagle's medium; DMSO for dimethyl sulfoxide; FBS for fetal bovine serum; FLIPR for fluorometric imaging plate reader; GFAP for glial fibrillary acidic protein; HBSS for Hank's balanced salt solution; i.p. for intraperitoneal; NGF for nerve growth factor; PBS for phosphate buffered saline; TMRE for tetramethylrhodamine ethyl ester perchlorate; and TRITC for tetramethylrhodamine isothiocyanate.

(i) Effects on Neurite Outgrowth in Neurons and Neuronal Cell Lines:

Effects on cellular properties such as neurite outgrowth and neuronal or neuronal-like cell number, etc. can be measured either using rat or human neuronal/neuroblastoma cell lines (e.g., SH-SY5Y, PC12, IMR-32, etc.) or using primary cells (e.g., rat cortical neurons). For example, it has been reported that dimebolin can increase neurite outgrowth in primary rat cortical neurons, comparable to that evoked by Brain Derived Neurotrophic factor (BDNF) (Hung, D. Dimebon: A phase 3 investigational agent for Alzheimer's disease with a novel mitochondrial mechanism of action. Presented at the International Conference on Alzheimer's Disease, Chicago, Ill., USA, July 2008; paper S4-04-05.).

For example, studies were conducted using PC12 cells plated in 96-well plates, treated with or without nerve growth factor (100 ng/mL) for 6 days. Compounds were then added at various concentrations (ranging from 0.1 nM to 30 μM), and incubated for 24 hours. Cells were then fixed and stained by neuron marker β-tubulin (green), and nuclei were stained by Hoechst 33342 (blue). Images were collected using the ImageXpress Micro automatic fluorescent microscopy system (Molecular Devices, Sunnyvale, Calif.) employing a Nikon 10× Plan Fluor objective and Cool Snap HQ CCD camera. The Neurite Outgrowth module in the MetaMorph Imaging software was used to automatically count neuron-like number, and the extent of neurite outgrowth (See, FIG. 1).

In addition to PC12 cells, other cellular model systems may also be used. Rat cortical cells were cultured and prepared for high content microscopy analysis as previously described (Hu, M.; Schurdak, M. E.; et al. High content screen microscopy analysis of $A\beta_{1-42}$-induced neurite outgrowth reduction in rat primary cortical neurons: Neuroprotective effects of α7 neuronal nicotinic acetylcholine receptor ligands. Brain Res. 2007, 1151, 227-235.). Briefly, cortical cell cultures were plated at density of $5\times10^5$ cells/mL onto poly-D-lysine coated 96-well plates and maintained in a cell incubator at 37° C. with 5% $CO_2$. Experiments were performed using 6-7 day-old cortical cell cultures by treating with test compounds. In some experiments, the effect of test compounds on reversing Aβ toxicity were also measured (Hu, M.; Schurdak, M. E.; et al. High content screen microscopy analysis of $A\beta_{1-42}$-induced neurite outgrowth reduction in rat primary cortical neurons: Neuroprotective effects of α7 neuronal nicotinic acetylcholine receptor ligands. Brain Res. 2007, 1151, 227-235.). For assessment of neuroprotective effects, cells were first pretreated with test compounds for about 5 hours. Medium was then replaced with the medium containing freshly prepared about 5 μM $A\beta_{1-42}$ peptide in the absence or presence of the test compounds for 3 days. The untreated group contained the same percentage of vehicle (DMSO) as in the treatment groups. Cells were fixed with approximately 4% paraformaldehyde containing 0.5% Hoechst 33342 for about 15 minutes, followed by three washes using PBS (pH 7.4) and blocked with 10% donkey serum in PBS for 1 hour at room temperature. The cells were then incubated overnight at about 4° C. with mouse anti-tubulin monoclonal antibody (1:100) for staining neurons and rabbit anti-GFAP (1:1000) for staining glia. In the next day, cells were incubated with FITC-labeled anti-mouse and TRITC-labeled anti-rabbit antibodies (1:1000) for about 1 hour at room temperature. After fixing and staining the cells, nuclei (360/400 nm excitation and 465/300 nm emission filters), neuron (475/350 nm excitation and 535/400 nm emission filters) and glial cell (535 nm excitation and 610 nm emission filters) images were collected using the ImageExpress Micro automatic fluorescent microscopy system (Molecular Devices, Sunnyvale, Calif.) employing a Nikon 10× Plan Fluor objective and Cool Snap HQ CCD camera. The Neurite Outgrowth module in the MetaMorph Imaging software was used to automatically count total cell number, number of neuron cells, and the extent of neurite outgrowth.

Figure 2:
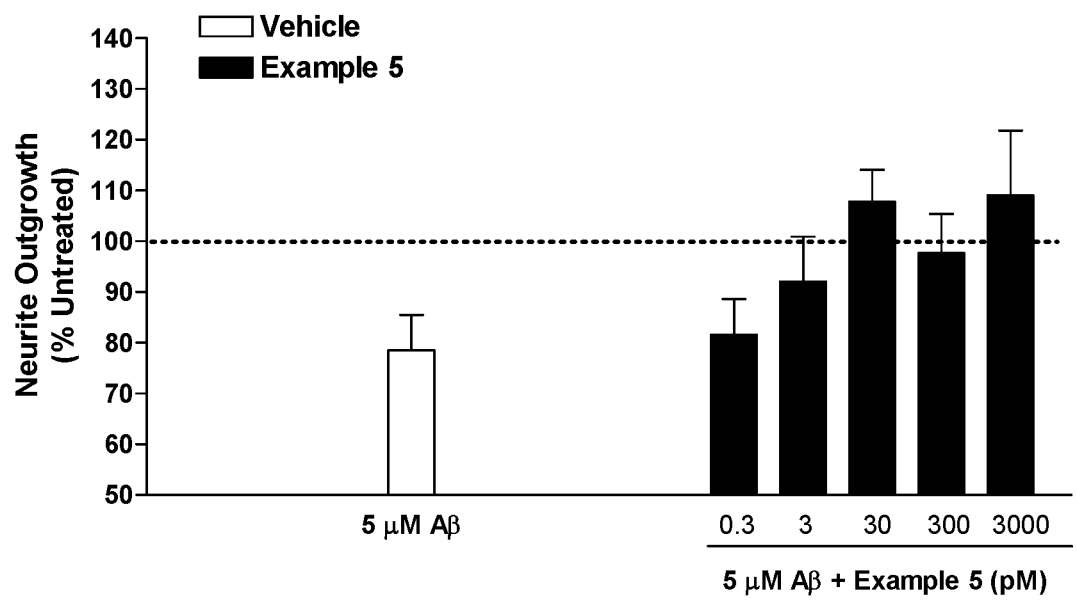
FIG. 2 shows a graphical representation of the concentration-dependent neuroprotective effects of Example 5 on the percent increase of neurite outgrowth.

As shown in FIG. 2, treatment with Example 5 resulted in significant attenuation of the $A\beta_{1-42}$-induced reduction of neurite outgrowth in primary postnatal (P0) cortical cells. In the graph of FIG. 2, 100% response was the response observed for untreated cells. Exposure to $A\beta_{1-42}$ produced a decrease in neurite outgrowth. Treatment of cells with compounds prior to and concomitantly with $A\beta_{1-42}$ gave a neuroprotective effect with neurite outgrowth maintained or enhanced relative to untreated cells.

Table 1 shows the maximum response at the noted test compound concentration relative to 300 nM dimebolin.

TABLE 1

Neurite Outgrowth Assay

| Example | Maximum Effect (of % 300 nM Dimebolin) at Concentration (nM) | Count |
|---|---|---|
| 2 | 117% at 0.03 nM | 2 |
| 5 | 123% at 3000 nM | 3 |
| 6 | 124% at 3 nM | 4 |
| 31 | 96% at 30 nM | 3 |
| 50 | 101% at 30 nM | 3 |
| 133 | 108% at 30 nM | 3 |
| 135 | 126% at 3 nM | 3 |
| 158 | 110% at 30 nM | 3 |
| 165 | 104% at 300 nM | 3 |
| 167 | 92% at 300 nM | 3 |
| 228 | 141% at 300 nM | 1 |
| 229 | 165% at 300 nM | 1 |
| 248 | 109% at 30 nM | 3 |
| 261 | 104% at 30 nM | 2 |
| 262 | 99% at 3 nM | 2 |
| 264 | 110% at 300 nM | 2 |
| 274 | 111% at 300 nM | 2 |
| 277 | 91% at 300 nM | 2 |
| 278 | 96% at 0.003 nM | 3 |
| 279 | 108% at 3 nM | 3 |
| 280 | 107% at 300 nM | 3 |
| 282 | 115% at 30 nM | 3 |

(ii) Effects on $A\beta_{1-42}$ Induced Tau Phosphorylation in PC12 Cells

The effect of test compound(s) on $A\beta_{1-42}$ induced tau phosphorylation can be assessed in a cell line such as PC12 as previously described (Hu, M.; Waring, J. F.; et al. Role of GSK-3$\beta$ activation and $\alpha$7 nAChRs in $A\beta_{1-42}$-induced tau phosphorylation in PC12 cells. *J. Neurochem.* 2008, 106(3), 1371-1377.). Briefly, PC12 cells are plated on poly-D-lysine coated 96-well plates, cultured in Ham's F12K medium supplemented with 15% horse serum, 2.5% FBS, 2 mM L-glutamine, 100 U/mL penicillin and 100 µg/mL streptomycin at 37° C. with 5% CO$_2$ and differentiated with 100 ng/mL NGF for approximately 6 days. Cells are pretreated with test compounds for 30 minutes at about 37° C. The medium is then replaced with that containing freshly prepared $A\beta_{1-42}$ or control peptide in the absence or presence of the test compounds and the cells are incubated at 37° C. for 24 hours. Cells are fixed with 3.7% formaldehyde in PBS (pH 7.4) for about 1 hour at room temperature followed by permeabilization by three washes with 0.1% Triton-X 100 in PBS. The fixed cells are incubated with blocking buffer for about 2 hours at room temperature followed by overnight incubation with primary antibodies AT8 (for phosphorylated tau), anti-human tau (for total Tau), or anti-GSK-3$\beta$. On the next day, cells are washed 3 times with 0.1% Tween-20 in PBS, then incubated with IRDye® 800CW anti-mouse IgG antibodies (1:100) for 1 hour at room temperature for detection of phosphorylated tau (p-tau) or GSK-3$\beta$, or with the Alexa Fluor® 680 anti-rabbit antibodies (1:100) for detection of total tau (t-tau). Cells are then washed three times, and the target signals are simultaneously visualized using Odyssey Infrared Imaging Scanner with the 680-nm fluorophore emitting an image of red color and the 800-nm fluorophore emitting an image of green color. The integrated fluorescence intensities are calculated and analyzed using the Odyssey Infrared Imaging System Application Software version 1.2.15 (Li-Cor Biosciences (Lincoln, Nebr.). The p-tau and t-tau levels are typically presented as the ratio p-tau/t-tau (Hu, M.; Waring, J. F.; et al. Role of GSK-3$\beta$ activation and $\alpha$7 nAChRs in $A\beta_{1-42}$-induced tau phosphorylation in PC12 cells. *J. Neurochem.* 2008, 106(3), 1371-1377.).

(iii) Effects on Mitochondrial Function

The method also involves a high-throughput assay using serum-deprivation conditions involving neuronal cells to screen for compounds that increase or preserve mitochondrial membrane potential. Such compounds can be found to aid in rescuing cells from energy-depletion that occurs in several neurodegenerative states. Mitochondrial-mediated apoptosis occurs in response to a wide range of apoptotic stimuli including p53, c-myc, DNA damage, prooxidants, chemotherapeutic agents, serum starvation and death receptor activation (Lin C-H., Lu Y-Z., Cheng, F-C., Chu L-F. and Hsueh C-M. Bax-regulated mitochondrial-mediated apoptosis is responsible for the in vitro ischemia induced neuronal cell death of Sprague Dawley rat. *Neuroscience Lett.* 2005, 387, 22-27).

Serum deprivation for 16-18 hours initiates the early stages of apoptosis (Chavier D, Lecoeur H, Langonne A, Borgne-Sanchez A, Mariani J., Martinou J-C, Rebouillat D and Jacotot E. Upstream control of apoptosis by caspase-2 in serum-deprived neurons. Apoptosis 10:1243-1259, 2005) and induces stress on a cell before full commitment to cell death. Mitochondria play a critical role in the cell for survival or death due to their regulation of both energy metabolism as well as apoptosis (Sullivan P G, Rabchevsky A G, Waldmeirer P C and Springer J E. Mitochondrial Permeability Transition in CNS Trauma: Cause or Effect of Neuronal Cell Death. *J. Neuroscience Res.* 2005, 79, 231-239). One of the first major events to occur in apoptosis is the breakdown of the membranes of the mitochondria to release cytochrome c, activate caspases, change electron transport and cause a decrease in mitochondrial membrane potential ($\Delta\psi_m$). A change in $\Delta\psi_m$ therefore serves as a measure of mitochondrial function and indicator of cell health.

Thus, this stress inducer, serum deprivation, combined with monitoring changes in the mitochondrial membrane potential in a 96-well format allows for the establishment of an efficient high-throughput screen (HTS) in order to evaluate the ability of compounds to increase mitochondrial membrane potential in the presence of stress and preserve health of the cell. Exemplary procedures for conducting such high-throughput assay are provided below.

Tissue Culture:

SK-N-SH human neuroblastoma cells obtained from American Type Culture Collection (Rockville, Md.) were maintained in the log phase of growth in Minimal Essential Media (MEM), 10% heat inactivated fetal calf serum and 100 units/mL antibiotic-antimycotic (AA). Cells were cultured and maintained in a humidified incubator at 37° C. under 5% CO$_2$ and 95% air. Cells were trypsinized (0.25%) and subcultured every 3 days and used from 15-18 passages.

All cell culture supplies were obtained from Invitrogen (Carlsbad, Calif.).

Serum Deprivation/JC-1 Mitochondrial Membrane Potential (MMP) Assay.

SK-N-SH cells were plated 2-3 days in advance at a concentration of 50,000 cells/well onto collagen coated black-walled 96 well plates (Becton-Dickinson, Bedford, Mass.) in a total volume of 200 µL. On day of experimental treatment, the media containing serum was aspirated from each well and rinsed once with MEM/1% AA without serum. The cells then were incubated overnight in 100 µL of MEM/1% AA (no serum) with and without dimebolin or novel chemical entities overnight for ~18 hours. The following day, JC-1 dye (5,5',6,6'-tetrachloro-1,1',3,3'-tetraethylbenzimidazolcarbocyanide) was diluted 1:10 into MEM media according to the JC-1 Mitochondrial Membrane Potential Assay Kit: (Cayman Chemical Company, Ann Arbor, Mich.) and then 10 µL of the JC-1 dye solution was added to each well. The plates were centrifuged for 5 minutes at 400×g at room temperature followed by 35 minute incubation at 37° C. The plates were washed twice with 200☐ µL of provided Assay Buffer followed an addition of 100 µL of Assay Buffer to each well. The plates were read with an excitation and emission of 560 nM and 595 nM for red fluorescence and with an excitation and emission of 485 nM and 535 nM for green fluorescence to determine the final JC-1 value taking the red to green fluorescence ratio. This assay is based on change in mitochondrial membrane potential (MMP) using this lipophilic cationic dye, JC-1, by monitoring the changes in the ratio of red to green fluorescence as the MMP depolarizes. This change in MMP reflects the health of the cell with healthy, viable cells have a high JC-1 ratio and high MMP whereas apoptotic, unhealthy cells have a low JC-1 ratio or low MMP.

For the ability of compounds to reverse the stress due to serum deprivation and increase the JC-1 ratio, the percent maximal intensity in JC-1 ratio was normalized to that induced by the peak value for 10 µM dimebolin and plotted against the compound concentration to calculate $EC_{50}$ values and to control for plate-to-plate variability. Concentration-response data were analyzed using GraphPad Prism (San Diego, Calif.); the $EC_{50}$ values were derived from a single curve fit to the mean data of n=2-3, in duplicates. Selected data is shown in Table 2.

All compounds were dissolved in dimethyl sulfoxide at 10 mM stock solutions and tested at a concentration that the dimethyl sulfoxide levels never exceeded 1%.

Figure 3:
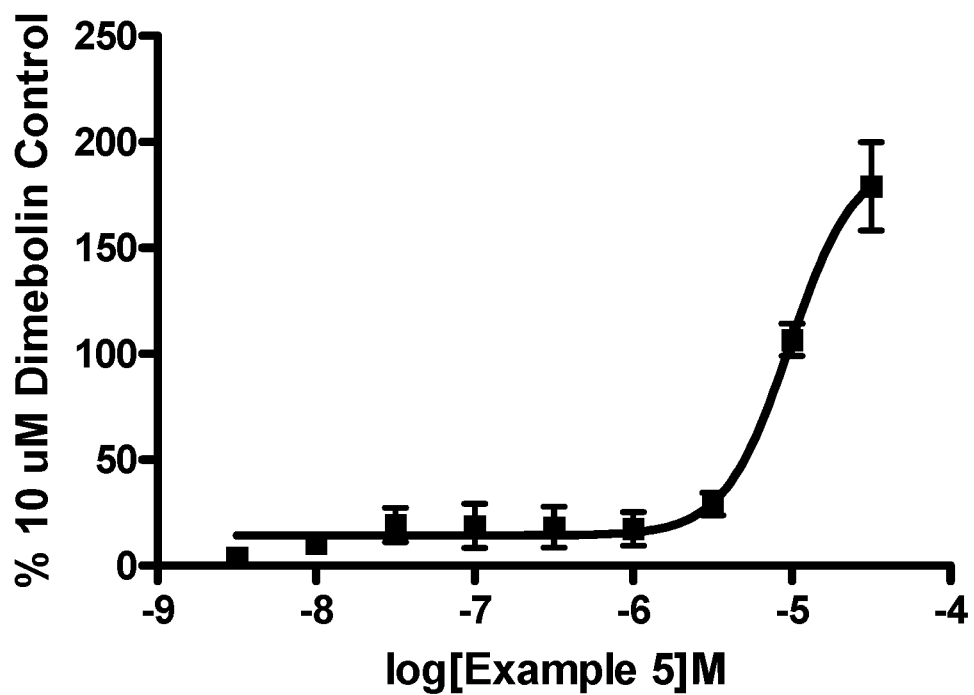
FIG. 3 shows a graphical representation of the concentration-dependent enhancement of mitochondrial function maintenance in the presence of cellular stress. Maintenance of mitochondrial function in the presence of stress prevents the initiation of apoptosis. SK-N-SH cells were treated with varying concentrations of Example 5. Cellular function was determined with a plate reader with an excitation and emission of 560 nM and 595 nM for red fluorescence and with an excitation and emission of 485 nM and 535 nM for green fluorescence to determine the final JC-1 value taking the red to green fluorescence ratio. The X-axis represents the test concentrations, and the Y-axis represents mitochondrial function relative to 10 μM dimebolin (100% response).

As shown in FIG. 3, treatment of SK-N-SH cells with Example 5 maintained mitochondrial function in a dose dependent manner.

TABLE 2

| JC-1 Mitochondrial Membrane Potential (MMP) Assay | | |
| --- | --- | --- |
| Example | $EC_{50}$ (µM) | JC-1 max % |
| 3 | 5.11 | 191 |
| 5 | 12.98 | 209 |
| 6 | 5.79 | 163 |
| 12 | 5.58 | 181 |
| 14 | 4.79 | 110 |
| 16 | 8.38 | 129 |
| 17 | 3.53 | 345 |
| 18 | 3.19 | 307 |
| 23 | 3.32 | 332 |
| 24 | 2.26 | 221 |
| 31 | 6.05 | 97 |
| 32 | 17.32 | 53 |
| 33 | 5.81 | 97 |
| 34 | 18.09 | 175 |
| 35 | 6.71 | 78 |
| 43 | 7.64 | 202 |
| 44 | 3.31 | 291 |
| 50 | 6.45 | 175 |
| 59 | 4.14 | 202 |
| 61 | 4.37 | 211 |
| 67 | 6.49 | 132 |
| 68 | 3.22 | 213 |
| 69 | 4.43 | 161 |
| 77 | 9.22 | 223 |
| 78 | 9.69 | 211 |
| 84 | 6.76 | 173 |
| 87 | 3.33 | 139 |
| 90 | 3.43 | 176 |
| 91 | 6.33 | 129 |
| 93 | 4.81 | 186 |
| 96 | 4.41 | 169 |
| 97 | 5.13 | 164 |
| 98 | 7.26 | 176 |
| 99 | 3.07 | 138 |
| 100 | 3.63 | 140 |
| 103 | 4.17 | 180 |
| 104 | 4.16 | 178 |
| 105 | 3.88 | 129 |
| 106 | 5.73 | 238 |
| 107 | 4.08 | 153 |
| 112 | 3.43 | 101 |
| 113 | 2.99 | 353 |
| 120 | 3.40 | 197 |
| 121 | 3.63 | 129 |
| 122 | 5.29 | 141 |
| 127 | 3.69 | 151 |
| 140 | 3.32 | 194 |
| 146 | 2.84 | 264 |
| 147 | 2.53 | 266 |
| 148 | 3.52 | 99 |
| 150 | 3.60 | 134 |
| 151 | 5.38 | 121 |
| 152 | 3.86 | 156 |
| 154 | 30.00 | 31 |
| 155 | 7.53 | 63 |
| 159 | 2.67 | 240 |
| 160 | 1.61 | 194 |
| 162 | 16.97 | 205 |
| 163 | 4.03 | 140 |
| 164 | 4.95 | 197 |
| 167 | 4.71 | 149 |
| 173 | 6.15 | 120 |
| 174 | 5.48 | 105 |
| 178 | 4.17 | 192 |
| 179 | 5.69 | 116 |
| 181 | 7.89 | 103 |
| 182 | 9.28 | 60 |
| 183 | 8.97 | 172 |
| 184 | 10.70 | 175 |
| 185 | 8.58 | 184 |
| 186 | 14.57 | 93 |
| 187 | 9.37 | 110 |
| 188 | 6.52 | 96 |
| 189 | 11.35 | 107 |
| 190 | 5.06 | 175 |
| 191 | 7.04 | 112 |
| 194 | 2.18 | 321 |
| 196 | 3.91 | 182 |
| 197 | 5.63 | 173 |
| 202 | 3.07 | 239 |
| 203 | 4.53 | 159 |
| 204 | 3.23 | 182 |
| 213 | 5.43 | 177 |
| 215 | 3.34 | 196 |
| 216 | 4.20 | 284 |
| 217 | 2.94 | 182 |
| 219 | 3.07 | 201 |

TABLE 2-continued

JC-1 Mitochondrial Membrane Potential (MMP) Assay

| Example | $EC_{50}$ (µM) | JC-1 max % |
|---|---|---|
| 222 | 4.43 | 215 |
| 223 | 3.84 | 287 |
| 224 | 3.17 | 215 |
| 225 | 2.74 | 209 |
| 226 | 1.68 | 307 |
| 227 | 3.62 | 266 |
| 228 | 1.73 | 263 |
| 229 | 0.70 | 282 |
| 232 | 0.81 | 220 |
| 233 | 0.80 | 250 |
| 234 | 1.27 | 281 |
| 235 | 3.96 | 252 |
| 236 | 1.74 | 268 |
| 237 | 2.48 | 174 |
| 238 | 11.55 | 86.53 |
| 240 | 3.33 | 170 |
| 241 | 7.96 | 156 |
| 242 | 8.12 | 169 |
| 243 | 8.36 | 169 |
| 244 | 5.65 | 226 |
| 245 | 10.02 | 189 |
| 246 | 8.76 | 148 |
| 247 | 4.65 | 192 |
| 248 | 5.24 | 110 |
| 249 | 5.27 | 133 |
| 250 | 8.37 | 77.35 |
| 251 | 4.39 | 193 |
| 252 | 6.2 | 109 |
| 253 | 4.4 | 185 |
| 254 | 8.09 | 57.12 |
| 255 | 5.72 | 171 |
| 256 | 15.47 | 89.6 |
| 257 | 3.6 | 155 |
| 258 | 2.99 | 149 |
| 259 | 3.2 | 126 |
| 260 | 2.91 | 191 |
| 261 | 5.72 | 160 |
| 262 | 8.71 | 182 |
| 263 | 11.01 | 108 |
| 264 | 7.8 | 107 |
| 265 | 1.84 | 264 |
| 266 | 10.74 | 127 |
| 267 | 9.72 | 70.03 |
| 268 | 4.43 | 237 |
| 269 | 0.745 | 204 |
| 270 | 2.81 | 270 |
| 271 | 3.17 | 264 |
| 272 | 3.99 | 149 |
| 273 | 7.48 | 190 |
| 274 | 2.27 | 235 |
| 275 | 3.44 | 130 |
| 276 | 6.65 | 80.55 |
| 277 | 2.4 | 190 |
| 278 | 2.71 | 189 |
| 279 | 5.49 | 209 |
| 280 | 5.25 | 201 |
| 281 | 1.74 | 228 |
| 282 | 3.21 | 228 |
| 283 | 6.02 | 170 |
| 284 | 7.62 | 108 |
| 285 | 9.41 | 149 |
| 286 | 4.41 | 239 |
| 287 | 1.53 | 209 |

(iv) In Vivo Models of Procognitive Effects

A range of animal models capturing diverse cognitive domains may be utilized for assessing procognitive effects of compounds. Examples of these models are provided in Bitner et al., (Bitner, R. S.; Bunnelle, W. H.; et al. Broad-spectrum efficacy across cognitive domains by α7 nicotinic acetylcholine receptor agonism correlates with activation of ERK1/2 and CREB phosphorylation pathways. *J. Neurosci.* 2007, 27(39), 10578-10587.). Various transgenic animal models that are relevant of neurodegenerative diseases of interest may also be utilized to assess effects of test compounds (Goetz, J.; Ittner, L. M. Animal models of Alzheimer's disease and frontotemporal dementia. *Nat. Rev. Neurosci.* 2008, 9(7), 532-544.).

Figure 4:
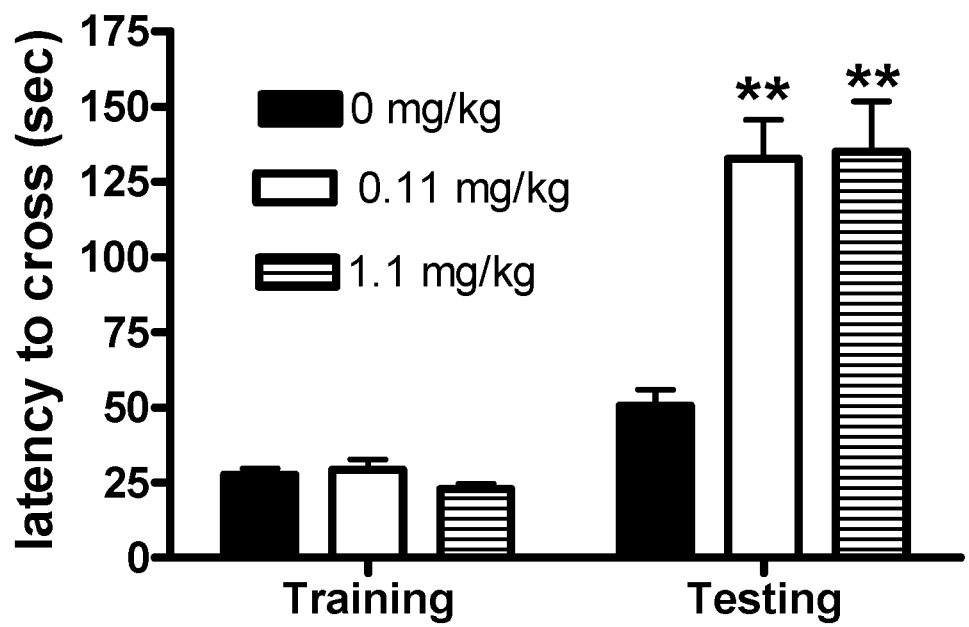
FIG. 4 shows a graphical representation of the concentration-dependent improvement in mouse 24-hour recall inhibitory avoidance scores upon treatment with test compound (Example 5). The X-axis represents the day of exposure to condition, and the Y-axis represents the latency to cross to the punished side.

Inhibitory Avoidance in Mouse: The inhibitory avoidance task involves the uses of a two-compartment step through apparatus (Ugo Basile, Collegeville, Pa.) that measures the animal's ability to remember a brief noxious stimulus (foot shock), and is considered a measure of trial learning, and memory consolidation. Briefly, mice were placed in a lighted compartment of the apparatus where the latency to enter into the preferred dark compartment is recorded. Entry into a dark compartment resulted in the immediate delivery of a mild foot shock (0.2 mA, 1-second duration). Retention testing was conducted 24 hours later with the animal again placed in the lighted compartment where its latency to reenter the dark side of the apparatus was measured (no shock). Increasing retention latency was regarded as an index of memory consolidation (Bitner, R. S.; Bunnelle, W. H.; et al. Broad-spectrum efficacy across cognitive domains by α7 nicotinic acetylcholine receptor agonism correlates with activation of ERK1/2 and CREB phosphorylation pathways. *J. Neurosci.* 2007, 27(39), 10578-10587.). As shown in FIG. 4, the latency to reenter the dark side (punishment side) was significantly increased upon dosing with Example 5 at 0.11 mg/kg and 1.1 mg/kg.

Figure 5:
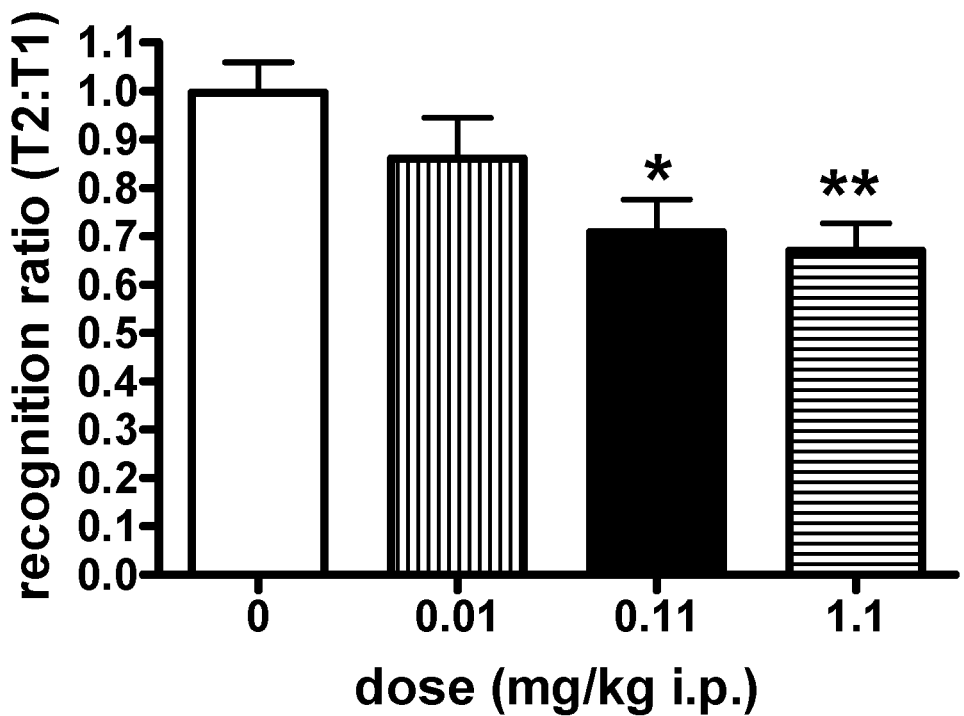
FIG. 5 shows a graphical representation of the concentration-dependent improvement in rat social recognition ratio scores upon treatment with test compound (Example 5). The X-axis represents the test concentrations, and the Y-axis represents the recognition ratio (T2:T1).

Social Recognition in Rat: The social recognition test measures short-term memory on the basis of olfactory cues, and depends on the hippocampus. Adult (350-450 g) rats were allowed to interact with a juvenile (60-80 g) rat for a 5 minute interaction trial (T1) in which the adult exhibits behaviors that included close following, grooming and/or sniffing of the juvenile for as much as 40-50% of the trial duration. The juvenile rat was then removed and the adult rat immediately administered various doses of test compound. A second 5 minute recognition trial (T2) was conducted 120 minutes later where interactive behavior of the adult rat was again monitored. If recognition memory was lost over the 120 minute interval between trials, the interactive behavior would be similar for the two trials; however, if memory was retained, the recognition ratio (T2:T1) would decline, i.e. decreasing T2:T1 ratio was regarded as an index of improved short-term recognition memory (Bitner, R. S.; Bunnelle, W. H.; et al. Broad-spectrum efficacy across cognitive domains by α7 nicotinic acetylcholine receptor agonism correlates with activation of ERK1/2 and CREB phosphorylation pathways. *J. Neurosci.* 2007, 27(39), 10578-10587. Timmermann, D. B.; Groenlien, J. H.; et al. An allosteric modulator of the α7 nicotinic acetylcholine receptor possessing cognition-enhancing properties in vivo. *J. Pharmacol. Exp. Ther.* 2007, 323(1), 294-307.). As shown in FIG. 5, the recognition ratio (T2:T1) declined significantly upon dosing intraperitoneally with Example 5 at 0.11 and 1.1 mg/kg.

Delayed Matching-to-Sample (DMTS) Titration in Monkey: Studies can be conducted in Rhesus monkeys that were initially trained in the DMTS procedure (Buccafusco, J. J.; Terry, A. V.; et al. Profile of nicotinic acetylcholine receptor agonists ABT-594 and A-582941, with differential subtype selectivity, on delayed matching accuracy by young monkeys. *Biochem. Pharmacol.* 2007, 74(8), 1202-1211.). Using a touch-sensitive screen in the animals home-cage, trial initiation consists of presentation of one of three colored stimuli (red, blue, or yellow rectangles) that remain in view (sample stimuli) until touched by subject. Following a delay interval, two choice rectangles are presented, one being the previous sample stimulus, in which correct (matching)

choice-touch to the sample stimuli is food reinforced. For standard DMTS testing, the duration for each delay interval is adjusted for each subject until three levels of performance accuracy were approximated: zero delay (85-100% of trials answered correctly); short delay interval (75-84% correct); medium delay interval (65-74% correct); and long delay interval (55-64% correct). The titration version of the DMTS task used in the present studies requires the animals to perform a 96 trial session that begins with a 0 sec delay interval. If the trial is answered correctly, a 1 second delay interval is presented during the next trial presented. The 1 second incremental progression is maintained until the subject made an incorrect match. The delay interval for the trial after an incorrect match is always decreased by 1 second. After an incorrect match, if the next trial is answered correctly, then the subsequent trial presented a delay interval 1 second longer in duration. Dependent variables include the overall % of trials answered correctly, the number of trials to reach the maximal delay interval attained, and the maximum and average delay interval attained (in seconds). Compounds are administered prior to DMTS testing.

(v) Determination of Analgesic Effect Against Neuropathic Pain

Animals were prepared for testing, by use of a surgical procedure that induces neuropathic pain in one paw. Male Sprague Dawley rats were purchased from Charles River (Portage, Mich.). Prior to surgery, animals were housed in groups and maintained in a temperature-regulated environment. Following nerve ligation surgery, animals were housed in groups, and had access to food and water ad libitum.

The L5 and L6 spinal nerves of anesthetized rats were tightly ligated in a manner described previously (see Kim and Chung, Pain (1992) vol. 50 pp. 355-363). An incision was made on the dorsal portion of the hip and the muscle was blunt-dissected to reveal the spinal processes. The L6 transverse process was removed, and the left side L5 and L6 spinal nerves were tightly ligated with 5.0 braided silk suture. The wound was cleaned, the membrane sewn with 4.0 dissolvable Vicryl suture and the skin closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

Figure 6:
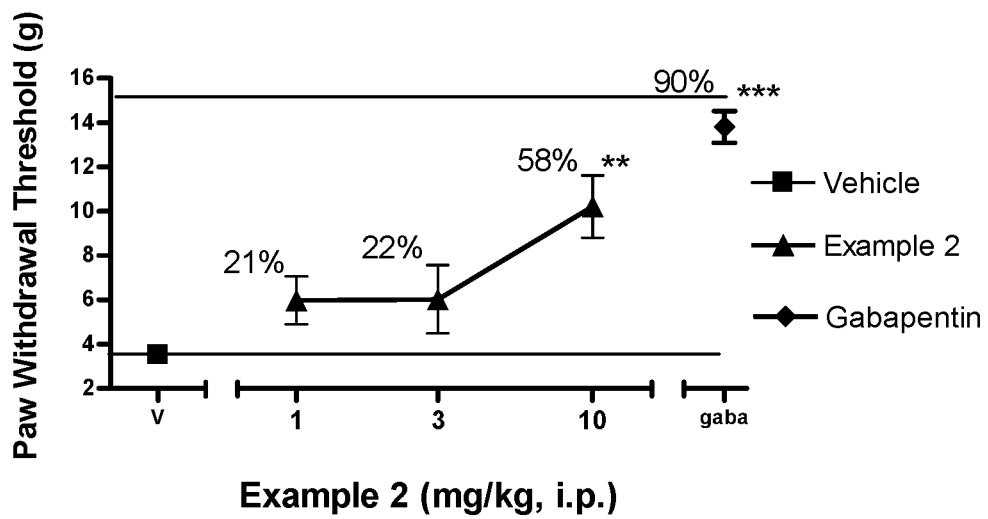
FIG. 6 shows a graphical representation of the concentration-dependent improvement in the treatment of neuropathic pain in rat with test compound (Example 2). The X-axis represents the test concentrations, and the Y-axis represents the pressure applied to elicit a pain response.

For the assessment of neuropathic pain, mechanical allodynia in the affected paw of animals that had undergone spinal nerve ligation was evaluated using testing with von Frey filaments. As described previously by S. R. Chaplan, et al ("Quantitative assessment of tactile allodynia in the rat paw" J. Neurosci. Meth. (1994) vol. 53 pp. 55-63), two weeks following surgery rats were acclimated to a testing box constructed of plexiglass with a wire mesh floor which allowed access to the plantar surface of the animal's hindpaws. Using an Up-Down method (Dixon, Annual Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63), von Frey filaments of increasing stiffness were applied to the plantar surface of the hindpaws and the withdrawal response of the animals was observed; for the surgically affected paw with neuropathic pain (the left side paw) the baseline level of allodynia has a withdrawal threshold of <4 g of pressure. By comparison, for the control paw without allodynia (in this case the right side paw), the typical withdrawal pressure is around 15 g. Representative compounds of the invention, administered intraperitoneally 30 minutes before testing, were able to reduce the symptoms of neuropathic pain and induce a dose-dependent increase in the withdrawal threshold for allodynic (left side) limb, up to a maximum effect of 15 g. The efficacy of the compound in reducing neuropathic pain at different doses was determined by comparing response in the surgery-affected paw versus the response in the control paw. This was expressed as the MPE (maximum potential effect). In this model, the compound of Example 2 (9-methyl-6-[2-(6-methylpyridin-3-yl)ethyl]-3,4,5,6-tetrahydro-1H-2,5-ethanoazepino[4,3-b]indole) was very effective, producing a 58% reduction (p<0.01, *p<0.001 vs. vehicle) in the withdrawal threshold at a dose of 10 mg/kg, administered by intraperitoneal injection as shown in FIG. 6. Example 2 was dosed i.p. (1, 3, and 10 mg/kg, 2 mL/kg) in vehicle (10% dimethyl sulfoxide/HBC). Gabapentin (100 mg/kg, 2.0 mL/kg) was used as an internal control. Test animals were used 2.5 weeks post-surgery. No complicating adverse effects were observed.

(vi) Animal Pharmacokinetics

The pharmacokinetic properties of test compounds were assessed in mouse, rat, dog and monkey to obtain various parameters including clearance (Clp), volume of distribution and bioavailability. For the determination of plasma and brain concentrations of the parent compound, naïve rats or mice can be dosed with the compounds i.p. and sacrificed at various time points post-dosing. For the determination of plasma concentrations, blood was collected into heparinized tubes and then centrifuged, and the separated plasma is frozen at −20° C. until analysis. For analysis, compounds were extracted from the samples via liquid-liquid extraction and quantified by liquid chromatography/mass spectroscopy.

d. METHODS OF USING THE COMPOUNDS

In still yet another embodiment, the present invention provides a method for preventing or treating a disease condition in a subject in need of treatment thereof. The subject in need of treatment thereof can be a mammal, such as, but not limited to, a human.

In one aspect, the disease condition is a neurodegeneration disorder. A neurodegeneration disorder refers to a type of neurological disease marked by the loss of nerve cells in the brain or central nervous system. Examples of neurodegeneration disorders include, but are not limited to, Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury or any combinations thereof.

In another aspect, the disease condition is a neuropsychiatric disorder. A neuropsychiatric disorder is a behavioral or psychological problem associated with a known neurological condition, and typically defined as a cluster of symptoms that co-exist. Examples of neuropsychiatric disorders include, but are not limited to, schizophrenia, cognitive deficits in schizophrenia, attention deficit disorder, attention deficit hyperactivity disorder, bipolar and manic disorders, depression or any combinations thereof.

In a further aspect, the present invention relates to methods of preventing or treating a pain including neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

Cognitive deficits are recognized in various forms of neurodegeneration and neuropsychiatric disorders (such as, but not limited to, dementia, including Alzheimer's disease, (AD) and neuropsychiatric diseases, particularly schizophrenia and bipolar disorders). For example, in AD, current therapies offer modest efficacy, and therefore, there is need for an agent that offers a superior clinical benefit. One such agent, dimebolin, has been shown to inhibit neuronal death in models of neurodegenerative diseases suggestive of modification of disease processes (Lermontova, N. N.; Lukoyanov, N. V.; et al. Dimebon improves learning in animals with experimental Alzheimer's disease. *Bull. Exp. Biol. Med.* 2000, 129(6), 544-546. Bachurin, S.; Bukatina, E.; et al. Antihistamine agent dimebon as a novel neuroprotector and a cognition enhancer. *Ann. N. Y. Acad. Sci.* 2001, 939 (Neuroprotective Agents), 425-435) and more recently, shown to possess beneficial effect in cognition in patients with Alzheimer's disease (Burns, A.; Jacoby, R. Dimebon in Alzheimer's disease: old drug for new indication. *Lancet* 2008, 372(9634), 179-80. Doody, R. S.; Gavrilova, S. I.; et al. Effect of dimebon on cognition, activities of daily living, behaviour, and global function in patients with mild-to-moderate Alzheimer's disease: a randomised, double-blind, placebo-controlled study. *Lancet* 2008, 372(9634), 207-215.). Patients with mild-to-moderate Alzheimer's disease administered with 20 mg three times a day (60 mg/day) showed significant improvement in the clinical course of disease, as reflected in improvement over baseline for ADAS-Cog (Alzheimer's disease assessment scale—cognitive subscale) (Cummings, J.; Doody, R.; Gavrilova, S.; Sano, M.; Aisen, P.; Seely, L.; Hung, D. 18-month data from an open-label extension of a one-year controlled trial of dimebon in patients with mild-to-moderate Alzheimer's disease. Presented at the International Conference on Alzheimer's Disease (ICAD), Chicago, Ill., USA, July 2008; paper P4-334). Patients with mild-to-moderate Alzheimer's disease who had earlier received the drug for 12 months had preservation of function close to their starting baseline on key symptoms of Alzheimer's disease indicated the ability of dimebolin to alter disease progression. Patients originally on placebo who received dimebolin in the extension study showed stabilization across all key measures.

Beneficial effects of agents such as dimebolin have been linked to diverse mechanisms of action including effects at the level of mitochondria. In particular, dimebolin has been reported to improve neuronal function by enhancing neuronal outgrowth and affecting mitochondrial function. For example, Hung and coworkers (Hung, D. Dimebon: A phase 3 investigational agent for Alzheimer's disease with a novel mitochondrial mechanism of action. Presented at the International Conference on Alzheimer's Disease, Chicago, Ill., USA, July 2008; paper S4-04-05) reported that dimebolin can protect cells from excitotoxic damage and improve neurite outgrowth in in vitro model systems. Other mechanisms of action may also contribute to its beneficial effects of compounds with a "dimebolin-like" profile. Indeed, multi-targeted mechanisms have been proposed as viable approaches for treatment of diverse neurodegenerative diseases (Zhang, H.-Y. One-compound-multiple-targets strategy to combat Alzheimer's disease. *FEBS Lett.* 2005, 579, 5260-5264. Youdim, M.; Buccafusco, J. Multi-functional drugs for various CNS targets in the treatment of neurodegenerative disorders. *Trends in Pharm. Sci.* 2005, 26(1), 27-35. Csermely, P.; Agoston, V.; Pongor, S. The efficiency of multi-target drugs: the network approach might help drug design. *Trends in Pharm. Sci.* 2005, 26(4), 178-182. Cavalli, A.; Bolognesi, M. L.; Minarini, A.; Rosini, M.; Tumiatti, V.; Recanatini, M.; Melchiorre, C. Multi-target directed ligands to combat neurodegenerative diseases. *J. Med. Chem.* 2008, 51(3), 347-372.). Dimebolin is also thought to exert its cognitive enhancing effects also through inhibition of butyryl-cholinesterase, acetyl cholinesterase, NMDA receptor or L-type calcium channels (Bachurin, S.; Bukatina, E.; et al. Antihistamine agent dimebon as a novel neuroprotector and a cognition enhancer. *Ann. N. Y. Acad. Sci.* 2001, 939 (Neuroprotective Agents), 425-435. Lermontova, N. N.; Redkozubov, A. E.; et al. Dimebon and tacrine inhibit neurotoxic action of beta-amyloid in culture and block L-type Ca(2+) channels. *Bull. Exp. Biol. Med.* 2001, 132(5), 1079-1083. Grigor'ev, V. V.; Dranyi, O. A.; et al. Comparative Study of Action Mechanisms of Dimebon and Memantine on AMPA- and NMDA-Subtypes Glutamate Receptors in Rat Cerebral Neurons. *Bull. Exp. Biol. Med.* 2003, 136(5): 474-477.). Interactions at the level of select 5HT receptors have also been implicated in the beneficial cognitive of dimebolin-like analogs (Tkachenko, S. Discovery and in vivo evaluation of potent 5-HT6 receptor antagonists for cognition enhancement in treating Alzheimer's disease. Presented at the International Conference on Alzheimer's Disease (ICAD), Chicago, Ill., USA, July 2008; paper P2-478.). Thus, available preclinical and clinical data suggests that compounds exhibiting a "dimebolin-like" profile can be beneficial in treating neurodegenerative diseases such as Alzheimer's disease and other dementias. Therefore, it is believed that the compounds of the present invention exhibit at least one of the mechanisms of action exhibited by dimebolin.

For treating a neurodegenerative or a neuropsychiatric disorder, the method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug. A "cognitive enhancing drug", as defined herein, is a drug that improves impaired human cognitive abilities of the brain (namely, thinking, learning, and memory). Cognitive enhancing drugs work by altering the availability of neurochemicals (e.g., neurotransmitters, enzymes, and hormones), by improving oxygen supply, by stimulating nerve growth, or by inhibiting nerve damage. Examples of cognitive enhancing drugs include a compound that increases the activity of acetylcholine such as, but not limited to, an acetylcholine receptor agonist (e.g., a nicotinic α-7 receptor agonist or allosteric modulator, an α4β2 nicotinic receptor agonist or allosteric modulators), an acetylcholinesterase inhibitor (e.g., donepezil, rivastigmine, and galantamine), a butyrylcholinesterase inhibitor, an N-methyl-D-aspartate (NMDA) receptor antagonist (e.g., memantine), an activity-dependent neuroprotective protein (ADNP) agonist, a serotonin 5-HT1A receptor agonist (e.g., xaliproden), a 5-HT4 receptor agonist, a 5-HT6 receptor antagonist, a serotonin 1A receptor antagonist, a histamine H3 receptor antagonist, a calpain inhibitor, a vascular endothelial growth factor (VEGF) protein or agonist, a trophic growth factor, an anti-apoptotic compound, an AMPA-type glutamate receptor activator, a L-type or N-type calcium channel blocker or modulator, a potassium channel blocker, a hypoxia inducible factor (HIF) activator, a HIF prolyl 4-hydroxylase inhibitor, an anti-inflammatory agent, an inhibitor of amyloid Aβ peptide or amyloid plaque, an inhibitor of tau hyperphosphorylation, a phosphodiesterase 5 inhibitor (e.g., tadalafil, sildenafil), a phosphodiesterase 4 inhibitor, a monoamine oxidase inhibitor, or pharmaceutically acceptable salt thereof. Specific examples of such cognitive enhancing drugs include, but are not limited to, cholinesterase inhibitors such as donepezil (Aricept®), rivastigmine (Exelon®), galanthamine (Reminyl®), N-methyl-D-aspartate antagonists such as memantine (Namenda®). At least one cognitive enhancing drug can be administered simultaneously with the compounds of the present invention or sequentially with the compounds of the present invention (and in any order). Additionally, it is believed that the combinations described herein may have additive or synergistic effects when used in the above-described treatment.

In still yet another embodiment, the present invention relates to a method for preventing (the development of) a disease condition, such as a neurodegeneration disorder or a neuropsychiatric disorder. As used herein, the term "prevent" a disease condition, such as a neurodegenerative disorder or a neuropsychiatric disorder by administration of any of the compounds described herein means that the detectable physical characteristics or symptoms of the disease or condition do not develop following the administration of the compound described herein. Specifically, the method of the present invention comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In still yet another embodiment, the present invention relates to a method for preventing the progression (e.g., worsening) of a disease condition, such as a neurodegeneration disorder or a neuropsychiatric disorder. The method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In the above described methods for preventing the development or progression of a neurodegeneration disorder or a neuropsychiatric disorder one or more biomarkers, diagnostic tests or combination of biomarkers and diagnostic tests known to those skilled the art can be used to determine whether or not (1) a subject is at risk of developing one or more of neurodegeneration disorders or neuropsychiatric disorders; or (2) the neurodegeneration disorders or neuropsychiatric disorders in the subject previously diagnosed with one or more of the aforementioned disorders is progressing (e.g., worsening).

One or more biomarkers, diagnostic tests or combinations of biomarkers and diagnostic tests known in the art can be used to identify subjects who are at risk of developing a neurodegeneration disorder or a neuropsychiatric disorder. Likewise, one or more biomarkers, diagnostic tests or combinations of biomarkers and diagnostic tests known in the art can be used to determine the progression of the disease or condition of subjects who have been identified as suffering from a neurodegeneration disorder or a neuropsychiatric disorder. For example, one or more biological markers, neuroimaging markers or combination of biological or neuroimaging markers (e.g., MRI, etc.) can be used to identify subjects at risk of developing AD or, for those subjects identified as suffering AD, the progression of the disease. Biological markers that can be examined include, but are not limited to, beta-amyloid$_{1-42}$, tau, phosphorylated tau (ptau), plasma Aβ antibodies, α-antichymotrypsin, amyloid precursor protein, APP isoform ratio in platelets, β-secretase (also known as BACE), CD59, 8-hydroxy-deoxyguanine, glutamine synthetase, glial fibrillary acidic protein (GFAP), antibodies to GFAP, interleukin-6-receptor complex, kallikrein, melanotransferrin, neurofilament proteins, nitrotyrosine, oxysterols, sulphatides, synaptic markers, S100β, NPS, plasma signaling proteins, etc., or any combinations thereof (See, Shaw, L., et al., *Nature Reviews* 2007, 6, 295-303. Borroni, B., et al., *Current Med. Chem.* 2007, 14, 1171-1178. Phillips, K., et al., *Nature Reviews* 2006, 5 463-469. Bouwman, F. H., et al., *Neurology* 2007, 69, 1006-1011; Ray, S., et al., *Nature Medicine* 2007, 13(11), 1359-1362. Cummings, J., et al., *Neurology* 2007, 69, 1622-1634.).

Actual dosage levels of active ingredients in the pharmaceutical compositions of the present invention can be varied so as to obtain an amount of the active compound(s) that is effective to achieve the desired therapeutic response for a particular subject (e.g., a mammal, preferably, a human (patient)), compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the present invention can also be administered to a subject as a pharmaceutical composition comprising the compounds of interest in combination with at least one pharmaceutically acceptable carriers. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a subject (namely, a mammal, such as a human) ranges from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. PHARMACEUTICAL COMPOSITIONS

In yet another embodiment, the present invention provides pharmaceutical compositions. The pharmaceutical compositions of the present invention comprise the compounds of the present invention or a pharmaceutically acceptable salt or solvate thereof. The pharmaceutical compositions of the present invention comprise compounds of the present invention that can be formulated together with at least one non-toxic pharmaceutically acceptable carrier.

In yet another embodiment, the present invention provides a pharmaceutical composition comprising compounds of the present invention, or a pharmaceutically acceptable salt thereof, and one or more pharmaceutically acceptable carriers, alone or in combination with one or more compounds that are not the compounds of the present invention. Examples of one or more compounds that can be combined with the compounds of the present invention in pharmaceutical compositions, include, but are not limited to, one or more cognitive enhancing drugs.

The pharmaceutical compositions of this present invention can be administered to a subject (e.g., a mammal, such as a human) orally, rectally, parenterally, intracistemally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of the present invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of the present invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq.). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Esters can be prepared from substrates of formula (I), (II), (III), (IV), (V) or (VI) containing either a hydroxyl group or a carboxy group by general methods known to persons skilled in the art. The typical reactions of these compounds are substitutions replacing one of the heteroatoms by another atom, for example:

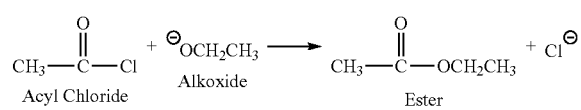

Amides can be prepared from substrates of formula (I), (II), (III), (IV), (V) or (VI) containing either an amino group or a carboxy group in similar fashion. Esters can also react with amines or ammonia to form amides.

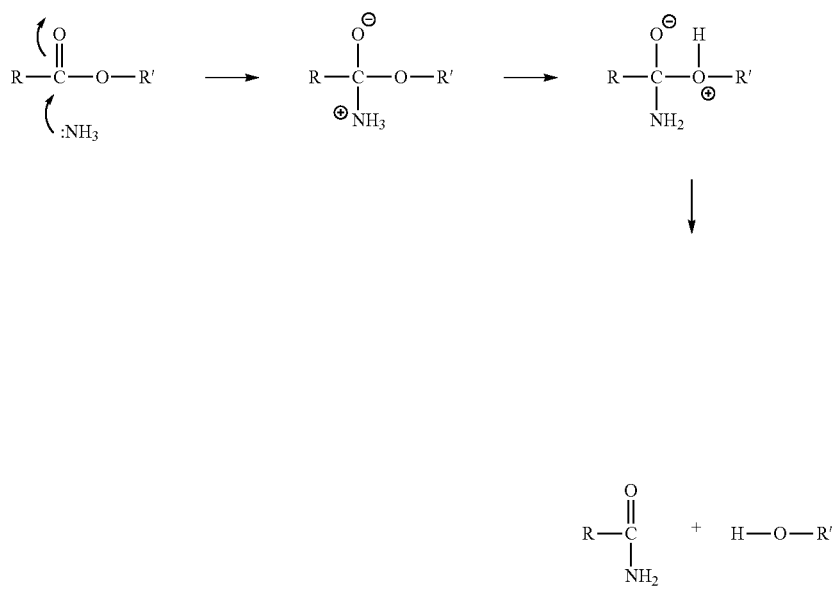

Another way to make amides from compounds of formula (I) is to heat carboxylic acids and amines together.

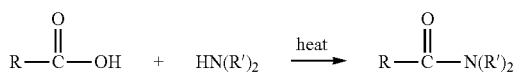

The present invention also contemplates compounds of the present invention formed by synthetic means or formed by in vivo biotransformation of a prodrug.

The compounds of the present invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. SCREENING METHODS

In yet another embodiment, the present invention relates to methods for identifying one or more target compounds that can be used to prevent or treat a neurodegenerative disorder or a neuropsychiatric disorder in a subject in need of treatment thereof. Preferably, the methods of the present invention allow for the identification of one or more target compounds in a high throughput manner.

The method of the present invention involves providing a population of neuronal or neuroblastoma cells or neuronal or neuroblastoma cell lines. Examples of neuronal or neuroblastoma cells or cell lines that can be used in this method include, but are not limited to, PC12, SH-SY5Y, SK-N-SH, IMR-32, or dissociated cells from tissues such as neonatal rat cortex or hippocampus cells. One or more target compounds are added to the population of neuronal or neuroblastoma cells or cell lines. If more then one target compound is being added, the target compounds can all be the same compounds but added in varying concentrations (such as, for example, 0.1 nM to 30 micromolar). Alternatively, the target compounds can all be different compounds. After addition of one or more target compounds to the population of cells or cell lines described above, the cells or cell lines are allowed to incubate for a period from at least one 1 hour to about 72 hours, preferably about 24 hours. The neuronal number and neurite outgrowth can then be determined using routine techniques known in the art. For example, the cells or cell lines can be fixed and then stained using any stain known in the art, such as, for example, β-tubulin (green). The total cell number and the extent of neurite outgrowth can be determined using the Neurite Outgrowth module in the MetaMorph Imaging software (Commercially available from Molecular Devices, Sunnyvale, Calif.). Target compounds that cause an increase in neuronal number and/or neuronal outgrowth are selected for further testing for use in preventing or treating a neurodegenerative or neuropsychiatric disorders.

Method details are described above in the Biological Data section in the description of the Effects on Mitochondrial Function assay.

One advantage of the assay is that after a 16-18 hours stress of serum deprivation, the health of the mitochondria can be measure by a 30 minute step with a fluorescent dye, JC-1. JC-1 measures the change in mitochondria membrane potential by measuring red fluorescence with excitation/emission at 560/595 nM, which is high for healthy cells and green fluorescence with excitation/emission at 485/535 nM), which is low if cells are unhealthy.

Another advantage of the assay is that the assay can measure the effect of mitochondrial function of multiple compounds in either a 1 point concentration or a 9-point dose response curve in a 96-well based format.

g. GENERAL SYNTHESIS

This invention is intended to encompass compounds of the present invention whether prepared by synthetic processes or by metabolic processes. Preparation of the compounds by metabolic processes includes those occurring in the human or animal body (in vivo) or processes occurring in vitro.

Abbreviations which have been used in the descriptions of the Schemes and the Examples that follow are: Ac for acetyl; aq for aqueous; atm for atmosphere; DABCO for diazabicyclo[2.2.2]octane; DMF for N,N-dimethylformamide; Et for ethyl; EtOH for ethanol; HPLC for high pressure liquid chromatography; LC/MS for liquid chromatography/mass spectroscopy; Me for methyl; MeOH for methanol; OAc for acetate; Ph for phenyl; psi for pounds per square inch; TFA for trifluoroacetic acid; THF for tetrahydrofuran; TMS for trimethylsilyl; Ts for p-toluenesulfonyl; TsCl for p-toluenesulfonyl chloride; TsO for p-toluenesulfonate; TsOH for p-toluenesulfonic acid; Xantphos for 9,9-dimethyl-4,5-bis (diphenylphosphino)xanthene.

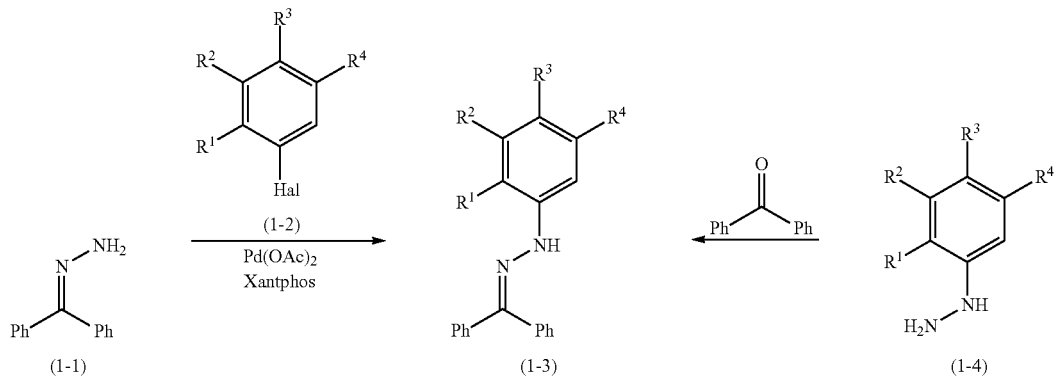

Scheme 1

The compounds of the present invention may be prepared by a variety of processes well known for the preparation of compounds of this class. For example, the compounds of the present invention wherein the groups a, $R^1$, $R^2$, $R^3$, $R^4$, $R^5$, U, V, W, X, Y, and Z, have the meanings as set forth in the Summary of the Invention section unless otherwise noted, can be synthesized as shown in Schemes 1-18.

Compounds of formula (1-3), wherein $R^1$, $R^2$, $R^3$ and $R^4$ are as defined in formulas (I), (II), (III), (IV), (V), and (VI), can be prepared as described in Scheme 1. Benzophenone hydrazone, (1-1), can be reacted with an aryl halide of formula (1-2), wherein Hal is chlorine, bromine, or iodine, in the presence of a palladium/ligand system such as palladium(II) acetate and Xantphos in the presence of a base such as sodium t-butoxide or triethylamine heated in a solvent such as toluene to provide compounds of formula (1-3) (Wagaw, S.; Yang, B. H.; Buchwald, S. L. *J. Am. Chem. Soc.* 1999, 121(44), 10251-10263). Alternatively, aryl hydrazines of formula (1-4) can be reacted with benzophenone in the presence of a catalyst such as ammonium chloride or sulfuric acid in a heated solvent such as water, methanol or ethanol to give compounds of formula (1-3).

Scheme 2

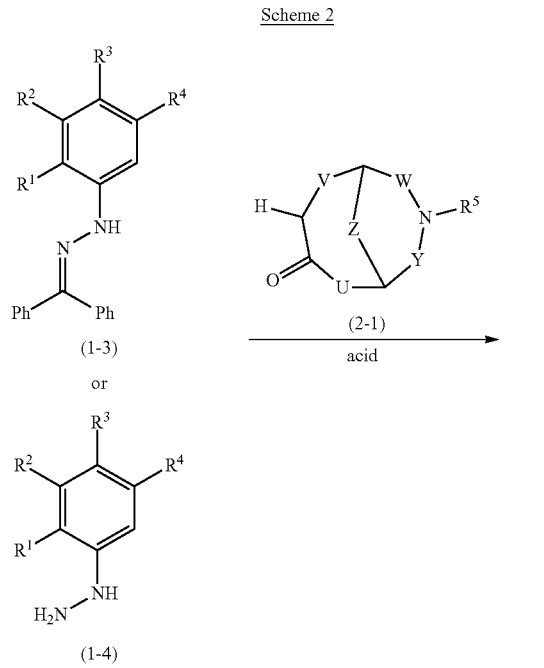

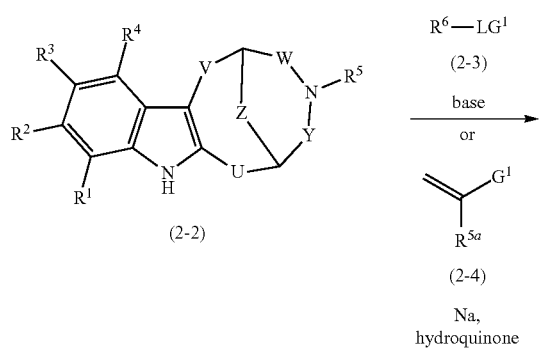

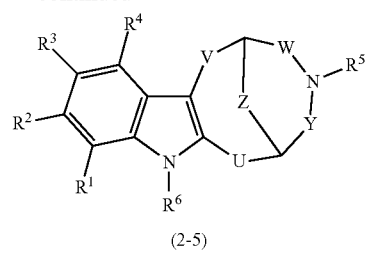

Compounds of formula (2-5), wherein $R^1$, $R^2$, $R^3$, $R^4$, $R^5$, $R^6$, U, V, W, Y, and Z are as defined in formula (I), can be prepared as described in Scheme 2. Compounds of formula (1-3) or (1-4), can be reacted with ketones of formula (2-1) in the presence of an acid under Fischer reaction conditions to give indoles of formula (2-2) (Wagaw, S.; Yang, B. H.; Buchwald, S. L. *J. Am. Chem. Soc.* 1999, 121(44), 10251-10263. Hughes, D. L. Progress in the Fischer Indole Reaction. A Review. *Org. Prep. Proced. Int.* 1993, 25, 607-632. Humphrey, G. R.; Kuethe, J. K. Practical Methodologies for the Synthesis of Indoles. *Chem. Rev.* 2006, 106, 2875-2911.). Compounds of formula (2-2) can be treated with a base such as sodium hydride, sodium amide, lithium diisopropylamide or cesium carbonate and a compound of formula (2-3), wherein $LG^1$ is a suitable leaving group such as chlorine, bromine, iodine, p-toluenesulfonate, or trifluoromethanesulfonate, in solvents such as N,N-dimethylformamide, tetrahydrofuran, toluene, or ether to furnish compounds of formula (2-5) which are representative of compounds of formula (I). Alternatively, compounds of formula (2-2) can be treated with a compound of formula (2-4) in the presence of sodium and hydroquinone in a heated (80-140° C.) solvent such as dimethyl sulfoxide for 24-96 hours to give compounds of formula (2-5) which are representative of compounds of formula (I). Compounds of formula (2-4) can be obtained commercially or synthesized by coupling potassium vinyltrifluoroborate with an aryl or heteroaryl halide in the presence of a catalyst such as palladium(II) chloride, a ligand such as triphenylphosphine, and a base such as cesium carbonate in a solvent such as a mixture of tetrahydrofuran and $H_2O$ heated at 70-90° C.

Scheme 3

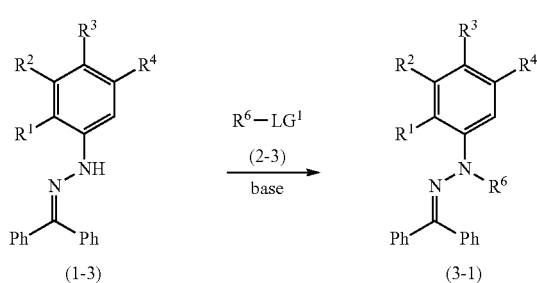

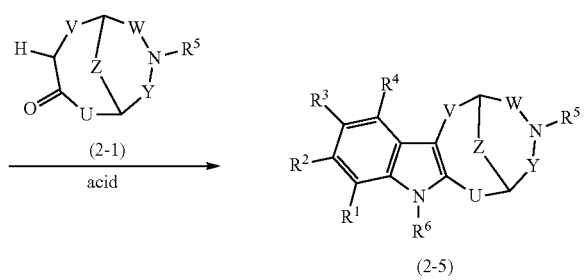

59

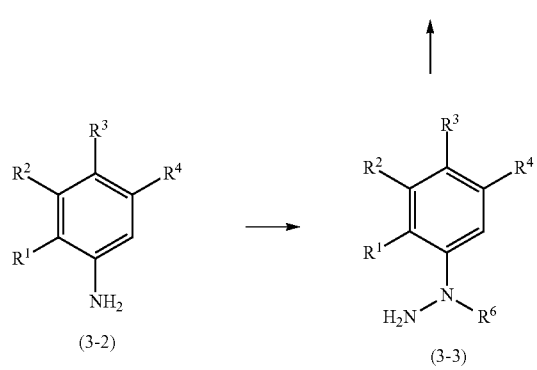

(3-2) → (3-3)

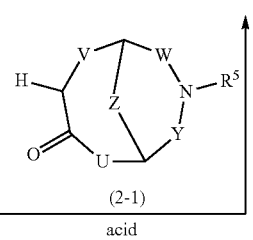

(2-1)

acid

Compounds of formula (2-5), wherein $R^1$, $R^2$, $R^3$, $R^4$, $R^5$, $R^6$, U, V, W, Y, and Z are as defined in formula (I), can be prepared as described in Scheme 3. Hydrazones of formula (1-3) can be alkylated with compounds of formula (2-3) using conditions described in Scheme 2 to supply compounds of formula (3-1) (e.g., Wagaw, S.; Yang, B. H.; Buchwald, S. L. *J. Am. Chem. Soc.* 1999, 44, 10251-10263). Alternatively, compounds of formula (3-1) can be prepared from anilines of formula (3-2). Anilines of formula (3-2) can be transformed to hydrazines of formula (3-3) as described in U.S. Pat. No. 3,409,628. Specifically, anilines of formula (3-2) can be reacted with a vinylheteroaryl or vinylaryl compound in the presence of sodium. Treatment with sodium nitrite and reduction with zinc in acetic acid produces the disubstituted hydrazine (3-3). Subsequently, compounds of formula (3-3) can be transformed to compounds of formula (3-1) using the conditions in Scheme 1 for the conversion of compounds of formula (1-4) to compounds of formula (1-3). Compounds of formula (3-1) can then be reacted with ketones of formula (2-1) under the conditions described in Scheme 2 for the conversion of compounds of formula (1-3) to compounds of formula (2-2) to furnish compounds of formula (2-5) which are representative of compounds of formula (I). Compounds of formula (3-3) can also be directly converted to compounds of formula (2-5) using the conditions previously described for the conversion of compounds of formula (3-1) to compounds of formula (2-5).

60

-continued

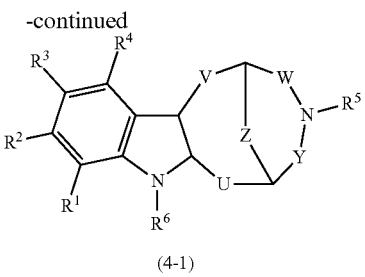

(4-1)

Compounds of formula (4-1), wherein $R^1$, $R^2$, $R^3$, $R^4$, $R^5$, $R^6$, U, V, W, Y, and Z are as defined in formula (I), can be prepared as described in Scheme 4. Compounds of formula (2-5) can be treated with a solution of sodium in liquid ammonia/tetrahydrofuran to supply compounds of formula (4-1). Compounds of formula (2-5) can also be transformed to compounds of formula (4-1) by treatment with borane-tetrahydrofuran complex in a trifluoroacetic acid solution (Berger, J.; Tahbaz, P.; McPhail, A. T.; Onan, K. D. *Tetrahedron Lett.* 1983, 24(24), 2469-2472). Alternatively, compounds of formula (2-5) can be converted to compounds of formula (4-1) by treatment with sodium cyanoborohydride in a mixture of trifluoroacetic acid and methanol. Compounds of formula (4-1) are representative of compounds of formula (I).

Scheme 5

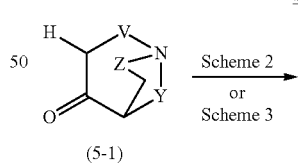

(5-1) → Scheme 2 or Scheme 3

Scheme 4

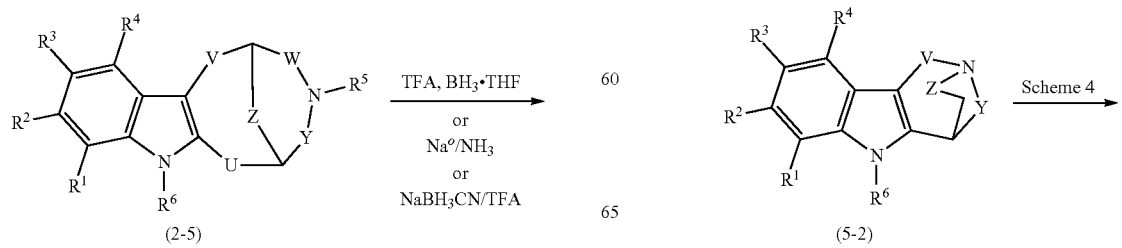

(2-5) → TFA, BH$_3$·THF or Na°/NH$_3$ or NaBH$_3$CN/TFA → (5-2) → Scheme 4

-continued

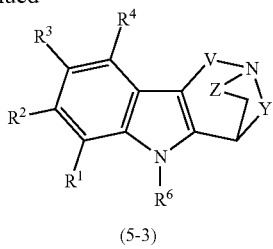

(5-3)

Compounds of formula (5-2) and compounds of formula (5-3), wherein $R^1$, $R^2$, $R^3$, $R^4$, $R^6$, V, Y, and Z are as defined in formula (IV), can be prepared as described in Scheme 5. Compounds of formula (5-1) can be converted to compounds of formula (5-2) with the methodologies described in Scheme 2 or Scheme 3. Subsequently, compounds of formula (5-2) can be transformed to compounds of formula (5-3) under the reduction conditions described in Scheme 4. Compounds of formula (5-2) and (5-3) are representative of compounds of formula (IV).

Scheme 6

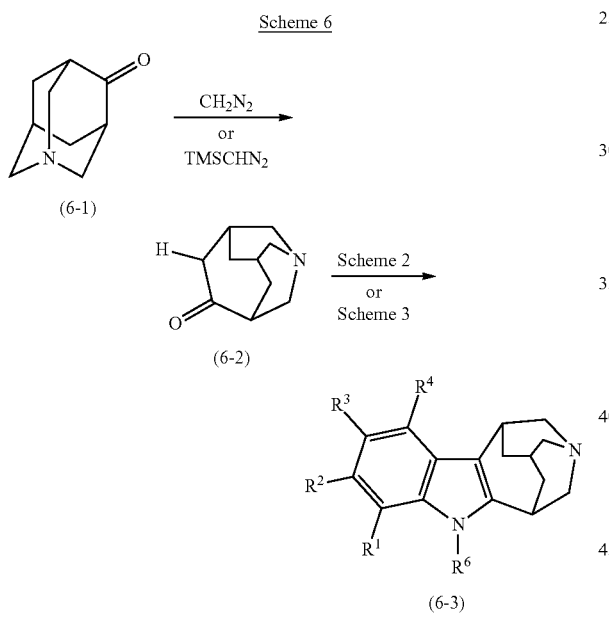

Compounds of formula (6-3) and compounds of formula (6-4), wherein $R^1$, $R^2$, $R^3$, $R^4$, and $R^6$ are as defined in formula (VI), can be prepared as described in Scheme 6. Compounds of formula (6-1) (Becker, D. P.; Flynn, D. L. *Synthesis* 1992, (11), 1080-1082) can be converted to compounds of formula (6-2) by treatment with diazomethane or (trimethylsilyl)diazomethane in a solvent such as tetrahydrofuran or ether (von E. Doering, W.; Virladeanu, L.; Andrews, D. W.; Pagnotta, M. *J. Am. Chem. Soc.* 1985, 107, 428-432). Compounds of formula (6-2) can be converted to compounds of formula (6-3) with the methodologies described in Scheme 2 or Scheme 3. Subsequently, compounds of formula (6-3) can be transformed to compounds of formula (6-4) under the reduction conditions described in Scheme 4. Compounds of formula (6-3) and (6-4) are representative of compounds of formula (VI).

Scheme 7

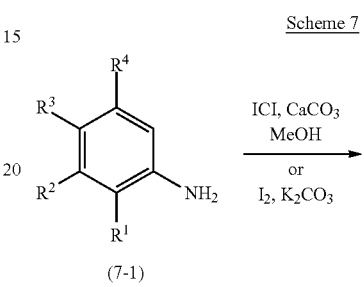

(7-1)

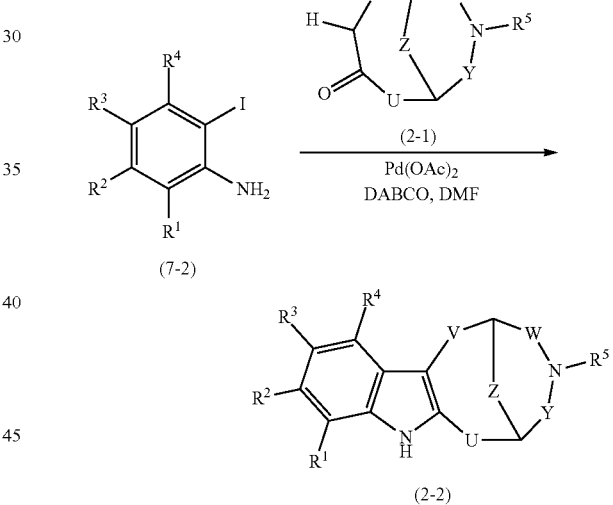

Compounds of formula (2-2) wherein, $R^1$, $R^2$, $R^3$, $R^4$, $R^5$, U, V, W, and Y are as defined in formula (I), can be prepared as described in Scheme 7. Anilines of formula (7-1) can be treated with iodine monochloride in the presence of calcium carbonate in methanol to supply compounds of formula (7-2). Alternatively, an aqueous solution of compounds of formula (7-1) and potassium carbonate or sodium bicarbonate can be treated with iodine to provide compounds of formula (7-2) (Xiao, W.-J.; Alper, H. *J. Org. Chem.* 1999, 64, 9646-9652). Compounds of formula (7-2) can be converted to compounds of formula (2-2) by treatment with compounds of formula (2-1) in the presence of palladium(II) acetate and diazabicyclo[2.2.2]octane (DABCO) in solvent such as methanol (Chen, C.; Lieberman, D. R.; Larsen, R. D.; Verhoeven, T. R.; Reider, P. J. *J. Org. Chem.* 1997, 62, 2676-2677). Compounds of formula (2-2) can then be employed as described in Scheme 2.

Scheme 8

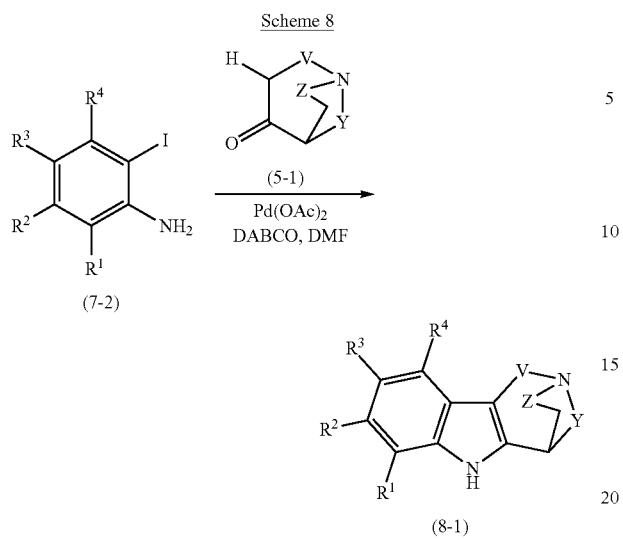

Compounds of formula (8-1) wherein, $R^1$, $R^2$, $R^3$, $R^4$, V, Y, and Z are as defined in formula (IV), can be prepared as described in Scheme 8. Anilines of formula (7-2) can be converted to compounds of formula (8-1) upon treatment with compounds of formula (5-1) under the conditions described in Scheme 7. Compounds of formula (8-1) can then be employed in Scheme 2 substituting for compounds of formula (2-2).

Scheme 9

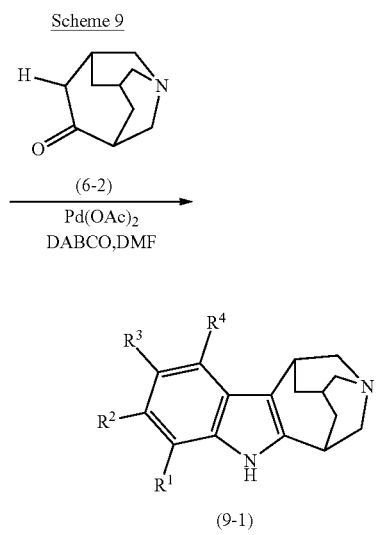

Compounds of formula (9-1) wherein, $R^1$, $R^2$, $R^3$, and $R^4$ are as defined in formula (VI), can be prepared as described in Scheme 9. Anilines of formula (7-2) can be converted to compounds of formula (9-1) upon treatment with compounds of formula (6-2) under the conditions described in Scheme 7. Compounds of formula (9-1) can then be employed in Scheme 2 substituting for compounds of formula (2-2).

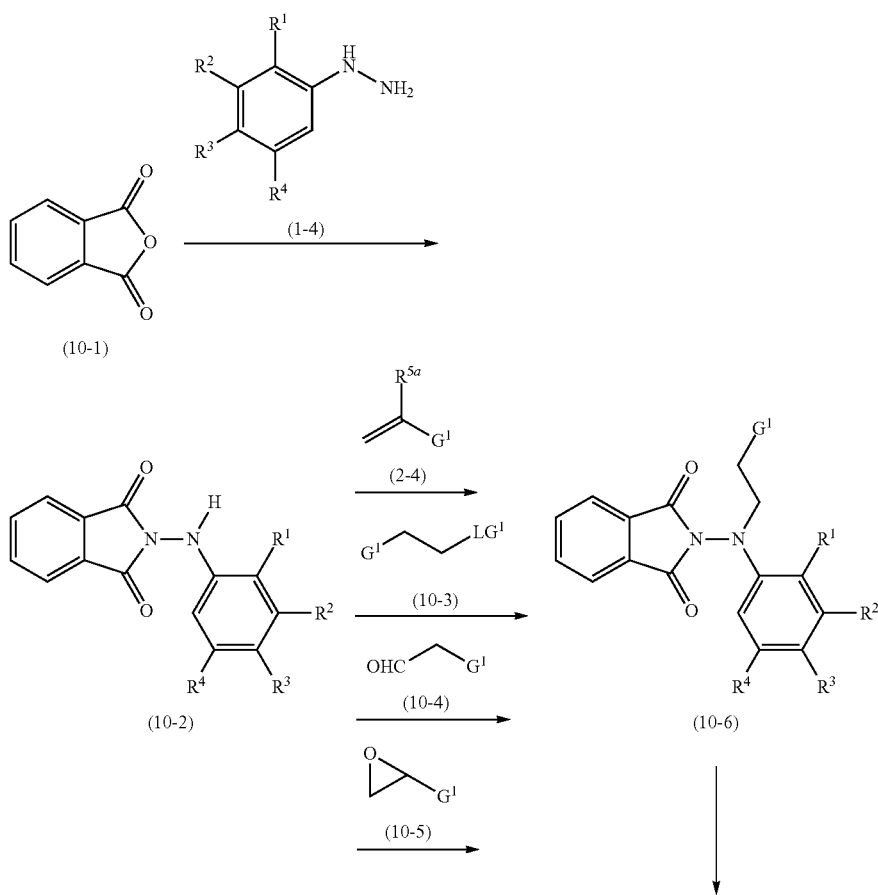

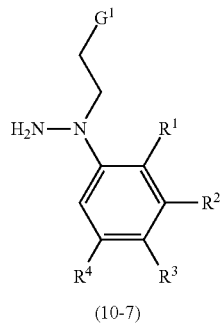

(10-7)

Compounds of formula (10-7), wherein $R^1$, $R^2$, $R^3$ and $R^4$ are as defined in formulas (I), (II), (III), (IV), (V), and (VI), and $G^1$ is defined in the Summary of the Invention, can be prepared as described in Scheme 10. Phthalic anhydride, (10-1), can be reacted with arylhydrazines (1-4) in chloroform, ethanol, acetic acid, or in toluene in the presence of an acid to supply compounds of formula (10-2). Compounds of formula (10-2) can be converted to compounds of formula (10-6) in a variety of ways. For example, compounds of formula (10-2) can be reacted with vinylaryl or vinylheteroaryl groups of formula (2-4) in the presence of sodium optionally in the presence of hydroquinone in solvents such as N,N-dimethylformamide or dimethyl sulfoxide to give compounds of formula (10-6). Compounds of formula (10-2) can also be reacted with compounds of formula (10-3), wherein $LG^1$ is a suitable leaving group such as chlorine, bromine, iodine, p-toluenesulfonate, or trifluoromethanesulfonate, in the presence of a base such as sodium hydride, sodium amide, lithium diisopropylamide or cesium carbonate in solvents such as N,N-dimethylformamide, tetrahydrofuran, toluene, or ether to furnish compounds of formula (10-6). Compounds of formula (10-6) can also be obtained by reacting compounds of formula (10-2) with aldehydes of formula (10-4) under reductive amination conditions such as sodium triacetoxyborohydride in acetic acid or the hydrochloride salt of compounds of formula (10-2) with aldehydes (10-4) in the presence of borane pyridine complex. Compounds of formula (10-2) can also be converted to compounds of formula (10-6) by reacting with compounds of formula (10-5) first in the presence of a base such as sodium hydride or lithium diisopropylamide and subsequently with triethylsilane and trifluoroacetic acid or hydrogen in the presence of palladium. Compounds of formula (10-6) are transformed to compounds of formula (10-7) by treatment with hydrazine hydrate in optionally heated ethanol (Nara, S.; Sakamoto, T.; Miyazawa, E.; Kikugawa, Y. *Synth. Commun.* 2003, 33, 87098). Compounds of formula (10-7) can be used in Schemes 3, 5 or 6 to produce compounds of formulas (I), (IV), or (VI).

Scheme 11

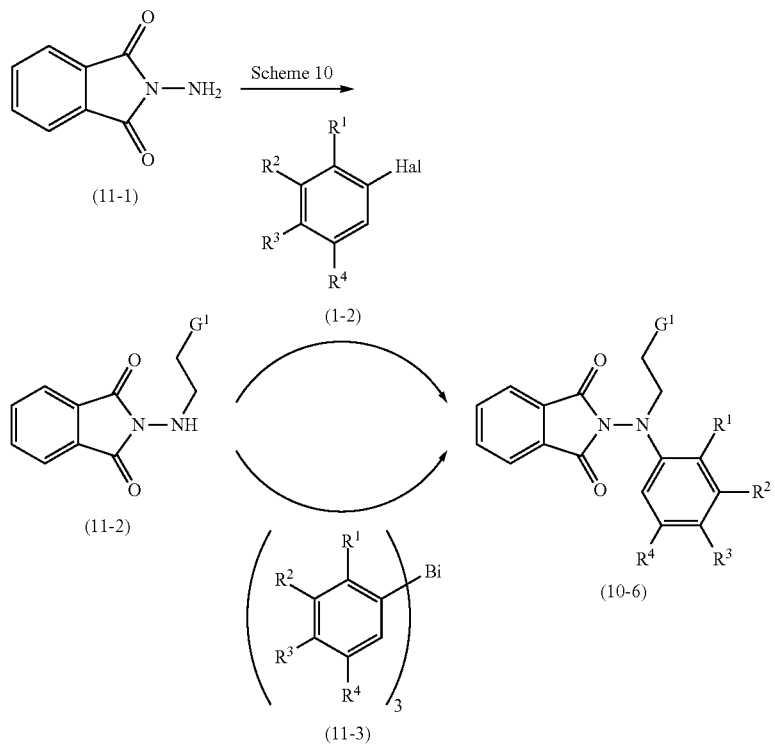

Compounds of formula (10-6), wherein $R^1$, $R^2$, $R^3$ and $R^4$ are as defined in formulas (I), (II), (III), (IV), (V), and (VI), and $G^1$ is defined in the Summary of the Invention, can be prepared as described in Scheme 11. N-Aminophthalimide (11-1) can be reacted under the various alkylating conditions described in Scheme 10 for the conversion of compounds of formula (10-2) to compounds of formula (10-6) to supply compounds of formula (11-2). Compounds of formula (11-2) can be arylated with compounds of formula (1-2) wherein Hal is a halogen limited to iodine or bromine, in the presence of palladium(II) acetate, tri-t-butyl phosphine in the presence of cesium carbonate in heated toluene (Kang, H.-M.; Shin, I.-J.; Kim, H.-Y.; Cho, C.-G. *Org. Lett.* 2006, 8, 2047-2050). Alternatively, compounds of formula (11-2) can be transformed to compounds of formula (10-6) by treatment with compounds of formula (1-2), wherein Hal is limited to iodine, in the presence of copper(II) acetate, cesium carbonate, and 1,10-phenanthroline. Another alternative involves the reaction of compounds of formula (11-2) with compounds of formula (11-3) in the presence of a base such as triethylamine and a catalyst such as copper(II) acetate in optionally heated dichloromethane (Nara, S.; Sakamoto, T.; Miyazawa, E.; Kikugawa, Y. *Synth. Commun.* 2003, 33, 87098). Compounds of formula (10-6) can then be further used as described in Scheme 10.

pounds of formula (2-4), wherein $R^{5a}$ is hydrogen. Alternatively, compounds of formula (2-4), wherein $R^{5a}$ is hydrogen, can be prepared from aryl bromides or heteroaryl bromides of formula (12-2). Accordingly compounds of formula (12-2) are reacted with either potassium vinyltrifluoroborate or triethoxy(vinyl)silane in the presence of a base such as sodium hydroxide and a palladium catalyst such as palladium acetate or phenone oxime-derived palladacycles either conventionally heated or heated in a microwave (Alacid, E.; Najera, C. *J. Org. Chem.* 2008, 73(6), 2315-2322. Gordillo, A.; de Jesus, E.; Lopez-Mardomingo, C. *Chem. Comm.* 2007, 39, 4056-4058.).

Compounds of formula (12-1) can also be converted to compounds of formula (10-4). Once again, esters of formula (12-1) can be first reduced with a reducing agent such as lithium aluminum hydride and then oxidized with a reagent such as manganese(II) oxide to supply the corresponding aldehyde. Subsequent Wittig reaction with (methoxymethyl)triphenylphosphonium chloride and t-butoxide in mixture of glyme and toluene (Kawai, A.; Hara, O.; Hamada, Y.; Shiori, T. *Tetrahedron Lett.* 1988, 29(48), 6331-6334) followed by hydrolysis in aqueous acid provides aldehydes of formula (10-4).

Compounds of formula (10-3) can be prepared from either compounds of formula (2-4) or compounds of formula Scheme 12

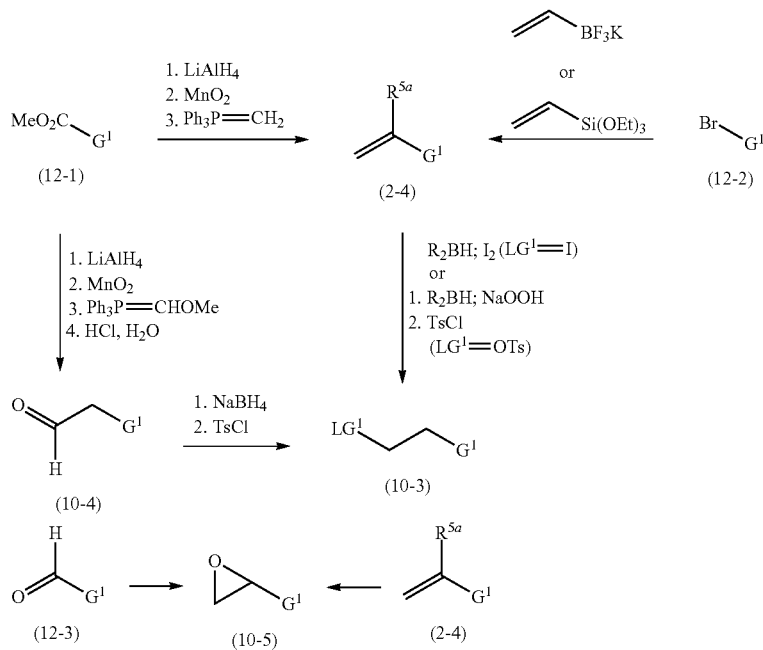

Compounds of formulas (2-4), (10-3), (10-4) and (10-5) that are used in Schemes 10 and 11 can be prepared by one skilled in the art. $G^1$ is as described in the Summary of the Invention and for the methodology described in Scheme 12 is preferentially aryl or heteroaryl. For example, esters of formula (12-1) can be converted to compounds of formula (2-4) in a three step process. To that end, esters of formula (12-1) can be first reduced with a reducing agent such as lithium aluminum hydride and then subsequently oxidized with a reagent such as manganese(II) oxide to supply the corresponding aldehyde. The aldehyde can then be reacted with methylene(triphenyl)phosphorane to furnish com- (10-4). Aldehydes of formula (10-4) can be reacted with a reducing agent such as sodium borohydride to supply the corresponding alcohol. The alcohol can be converted to a leaving group by reaction with a sulfonyl chloride such as p-toluenesulfonyl chloride or methanesulfonyl chloride in the presence of a base such as triethylamine or diisopropylethylamine to furnish compounds of formula (10-3) wherein the leaving group, $LG^1$, is a sulfonate. Compounds of formula (2-4) can also be converted to compounds of formula (10-3). In a one-step process, compounds of formula (2-4) can be reacted with a dialkylborane such as disiamylborane or 9-borabicyclo[3.3.1]nonane (9-BBN) in the presence of iodine to give compounds of formula (10-3), wherein LG$^1$ is iodine. Alternatively, compounds of formula (2-4) can first be converted to the corresponding primary alcohols by hydroboration with a dialkylborane followed by treatment with sodium hydroperoxide. The intermediate alcohols can then be converted to sulfonates of formula (10-3) as previously described giving compounds of formula (10-3), wherein LG$^1$ is p-toluenesulfonate or methanesulfonate.

Compounds of formula (10-5) also can be prepared in more than one way. One option is to convert compounds of formula (12-3) to compounds of formula (10-5) by treatment with trimethylsulfonium iodide in the presence of a base such as tert-butoxide in a solvent such as tert-butanol (Boa, A. N.; Canavan, S. P.; et al. *Bioorg. Med. Chem.* 2005, 13, 1945-1967). As an alternative approach, compounds of formula (2-4) can be converted to the epoxides of formula (10-5) by treatment with m-chloroperoxybenzoic acid in the presence of a base such as sodium bicarbonate in a mixture of water and dichloromethane (Kamabe, M.; Miyazaki, T.; Hashimoto, K.; Shirahama, H. *Heterocycles* 2002, 56(1-2), 105-111).

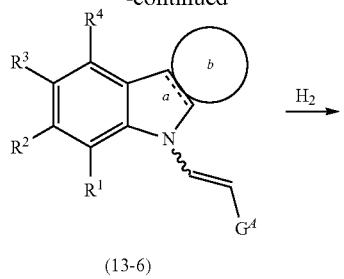

(13-6)

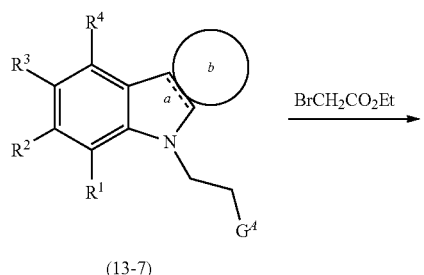

(13-7)

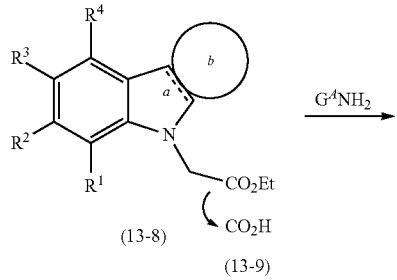

(13-8) (13-9)

Scheme 13

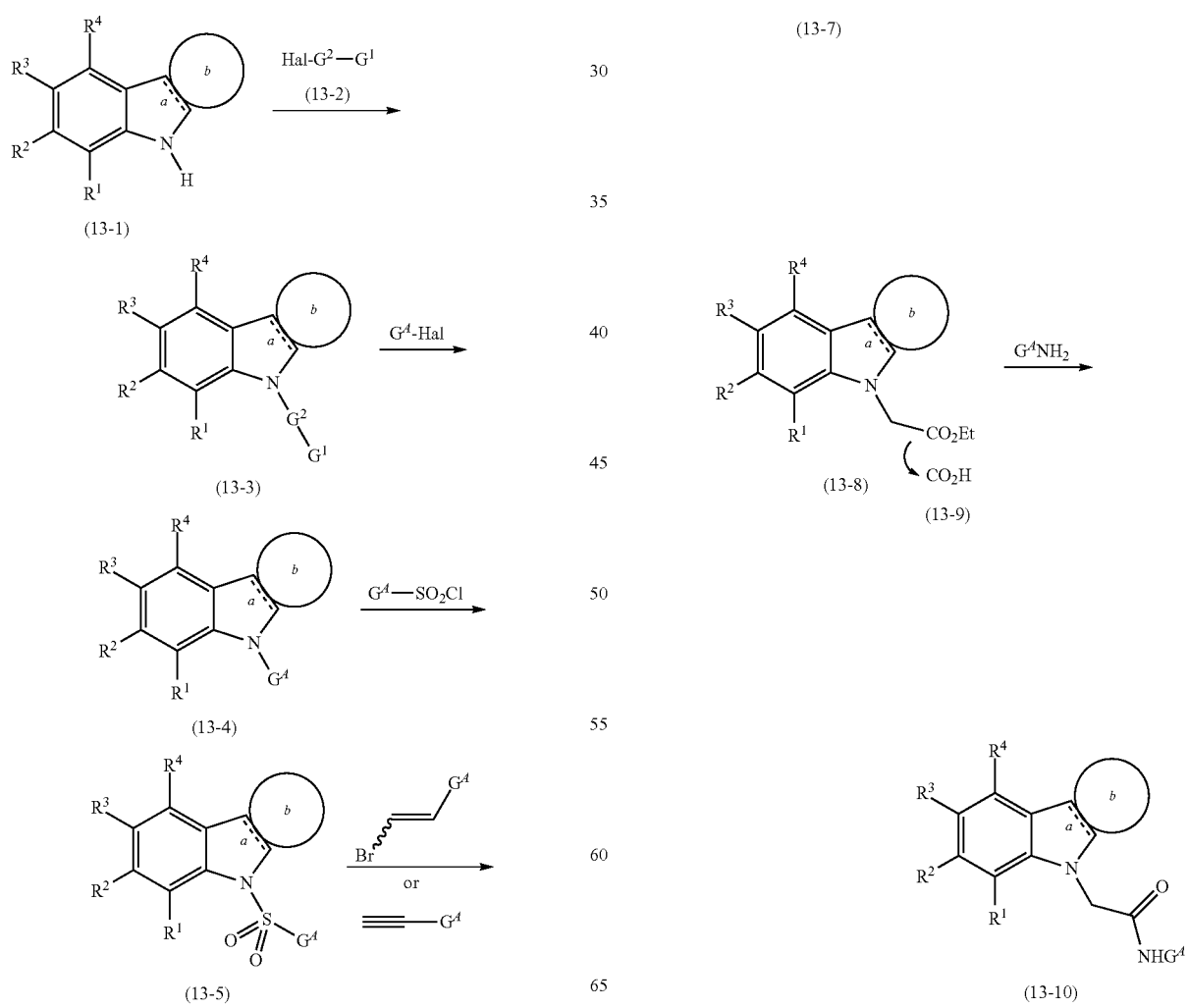

(13-1)

(13-3)

(13-4)

(13-5)

(13-10)

Compounds of formula (13-3), wherein a, $R^1$, $R^2$, $R^3$ and $R^4$ are as defined in formulas (I), (II), (III), (IV), (V), and (VI), $G^1$ is defined in the Summary of the Invention, and b represents the optionally protected bicyclic, tricyclic, or spirocyclic ring systems of compounds of formulas (I), (II), (III), (IV), (V), and (VI), can be prepared as described in Scheme 13. Compounds of formula (13-1) can be treated with compounds of formula (13-2), wherein $G^2$ is pyridazinyl, pyrimidinyl or triazinyl and Hal is chlorine, bromine or iodine, in the presence of a base such as potassium tert-butoxide or sodium hydride in a heated solvent such as N,N-dimethylformamide to provide compounds of formula (13-3). Compounds of formula (13-1) can be reacted with compounds of formula (13-2), wherein Hal is bromine or iodine and $G^2$ is pyridinyl, in the presence of a base such as sodium carbonate, potassium carbonate, potassium phosphate or cesium acetate in the presence of copper and/or copper(I) iodide in a heated solvent such as toluene, dimethyl sulfoxide, chlorobenzene, or nitrobenzene to provide compounds of formula (13-3). Alternatively, compounds of formula (13-1) can be reacted with compounds of formula (13-2) in a palladium-mediated cross-coupling reaction. Accordingly, compounds of formulas (13-1) and (13-2) can be combined in the presence of a catalyst such as bis(tri-t-butylphosphine and a base such as sodium t-butoxide in a heated solvent such as dioxane. The heating may be either conventional or achieved with microwave irradiation.

Compounds of formula (13-4), wherein a, $R^1$, $R^2$, $R^3$ and $R^4$ are as defined in formulas (I), (II), (III), (IV), (V), and (VI), and b represents the optionally protected bicyclic, tricyclic, or spirocyclic ring systems of compounds of formulas (I), (II), (III), (IV), (V), and (VI), can be prepared as described in Scheme 13. Compounds of formula (13-1) can be coupled with compounds of formula $G^A$-Hal, wherein $G^A$ is aryl or heteroaryl and Hal is bromine or iodine, to provide compounds of formula (13-4). The coupling can be accomplished in the presence of a catalyst such as bis(tri-t-butylphosphine)palladium(0) and a base such as sodium tert-butoxide in a solvent such as dioxane with heating to 140-170° C. either conventionally or in a microwave oven to provide compounds of formula (13-4). Alternatively, a nucleophilic aromatic substitution reaction may be carried out on compounds of formula (13-1) when $G^A$ is aryl substituted with one or more electron withdrawing groups such as nitro or cyano and Hal is limited to fluorine. Accordingly, compounds of formula (13-1) an be combined with the arylfluoride in the presence of a base such as sodium hydride in an optionally heated solvent such as N,N-dimethylformamide to give compounds of formula (13-4).

Compounds of formula (13-5), wherein a, $R^1$, $R^2$, $R^3$ and $R^4$ are as defined in formulas (I), (II), (III), (IV), (V), and (VI), and b represents the optionally protected bicyclic, tricyclic, or spirocyclic ring systems of compounds of formulas (I), (II), (III), (IV), (V), and (VI), can be prepared as described in Scheme 13. Compounds of formula (13-1) can be sulfonylated with compounds of formula $G^A SO_2Cl$, wherein $G^A$ is aryl or heteroaryl, in the presence of a base such as potassium tert-butoxide in a solvent such as tetrahydrofuran to provide compounds of formula (13-5).

Compounds of formula (13-6), wherein a, $R^1$, $R^2$, $R^3$ and $R^4$ are as defined in formulas (I), (II), (III), (IV), (V), and (VI), and b represents the optionally protected bicyclic, tricyclic, or spirocyclic ring systems of compounds of formulas (I), (II), (III), (IV), (V), and (VI), can be prepared as described in Scheme 13. Compounds of formula (13-1) can be reacted with Br—CH=CHG$^A$ in the presence of bis(tri-t-butylphosphine)palladium(0) and a base such as potassium tert-butoxide in a solvent such as dioxane with heating to 90-120° C. either conventionally or in a microwave oven to provide compounds of formula (13-6). Alternatively, reaction conditions include n-butyllithium, a catalyst such as bis(dibenzylidene-acetone)palladium, a ligand such as tri-tert-butylphosphine, in a solvent mixture such as 1,2-dimethoxyethane and toluene heated for 12 to 24 hours at 60-80° C. to furnish compounds of formula (13-6). Compounds of formula (13-6) can also be prepared by reacting compounds of formula (13-1) with ≡-$G^A$ in the presence of sodium and hydroquinone in a solvent such as dimethyl sulfoxide heated to 80-120° C. for 12 to 24 hours. Compounds of formula (13-6) can then by reduced in the presence of hydrogen and a catalyst such as $PtO_2$ in an optionally heated solvent such as isopropanol to provide compounds of formula (13-7).

Compounds of formula (13-8), (13-9), and (13-10), wherein a, $R^1$, $R^2$, $R^3$ and $R^4$ are as defined in formulas (I), (II), (III), (IV), (V), and (VI), and b represents the optionally protected bicyclic, tricyclic, or spirocyclic ring systems of compounds of formulas (I), (II), (III), (IV), (V), and (VI), can be prepared as described in Scheme 13. Accordingly, compounds of formula (13-1) can be reacted with ethyl bromoacetate in the presence of a base such as potassium tert-butoxide in a solvent such as tetrahydrofuran at or near ambient temperature over 8 to 24 hours to supply compounds of formula (13-8). Compounds of formula (13-8) can be hydrolyzed to compounds of formula (13-9) in the presence of aqueous sodium hydroxide heated in a solvent such as ethanol. Compounds of formula (13-9) can be coupled with an amine of formula $G^A NH_2$ using amide bond forming conditions well known to one skilled in the art to provide compounds of formula (13-10). One set of amide bond forming conditions include 1-(3-dimethylaminopropyl)-3-ethylcarbodiimide hydrochloride, hydroxybenzotriazole, 4-(dimethylamino)pyridine stirred in dichloromethane for 2 to 24 hours.

In all instances above, when b represents a protected bicyclic, tricyclic, or spirocyclic ring systems of compounds of formulas (I), (II), (III), (IV), (V), and (VI), one skilled in the art will know the appropriate deprotection conditions to reveal the compounds of formulas (I), (II), (III), (IV), (V), and (VI).

Scheme 14
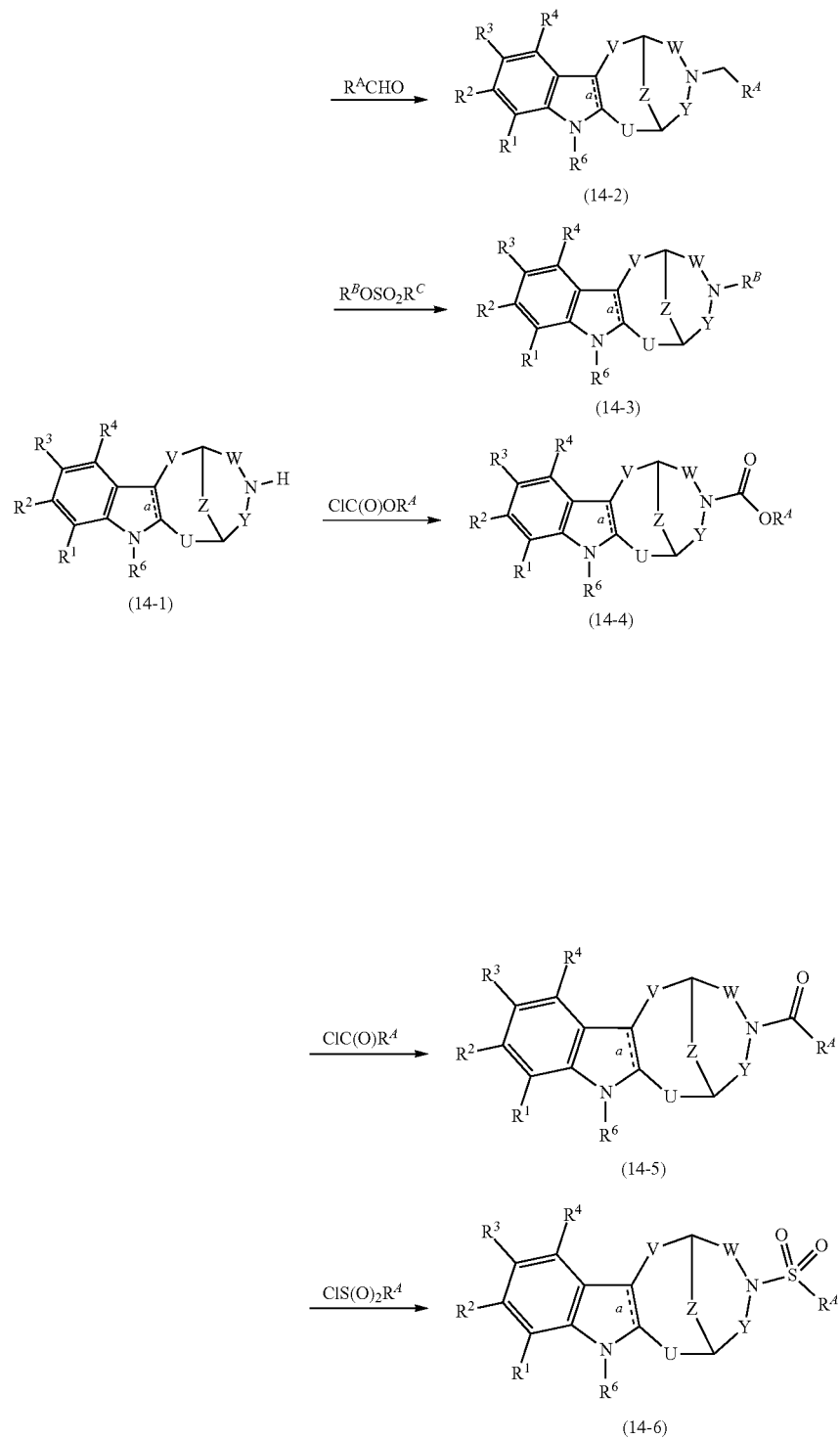

Compounds of formulas (14-2), (14-3), (14-4), (14-5), and (14-6) wherein $R^1$, $R^2$, $R^3$, $R^4$, $R^6$, a, U, V, W, Y, an Z are as defined in formulas (I) can be prepared from compounds of formula (14-1). Compounds of formula (14-1) can be reacted with aldehydes of formula $R^A$CHO under reductive amination conditions to provide compounds of formula (14-2). $R^A$ can be alkyl, arylalkyl, aryl, cycloalkyl, haloalkyl, heteroaryl, heteroarylalkyl, or heterocycle. For example, compounds of formula (14-1) can be treated with aldehydes of formula $R^A$CHO in the presence of sodium cyanoborohydride in the presence of an acid such as acetic acid in methanol to provide compounds of formula (14-2). Compounds of formula (14-1) can be reacted with sulfonates of $R^B$OSO$_2$R$^C$, wherein $R^B$ is alkyl or haloalkyl and $R^C$ is trifluoromethyl or p-tolyl, in the presence of a base such as triethylamine or diisopropylethylamine in a solvent such as N,N-dimethylformamide which can optionally be heated to provide compounds of formula (14-3). Compounds of formula (14-1) can be reacted with ClC(O)OR$^A$ in a solvent such as tetrahydrofuran to provide compounds of formula (14-4). Compounds of formula (14-1) can also be reacted with acid chlorides of formula ClC(O)R$^A$ or sulfonyl chlorides of formula ClSO$_2$R$^A$ in the presence of a base such as triethylamine or diisopropylamine in a solvent such as dichloromethane at or near ambient temperature to provide compounds of formulas (14-5) and (14-6), respectively. Compounds of formulas (14-2), (14-3), (14-4), (14-5), and (14-6) are representative of compounds of formula (I).

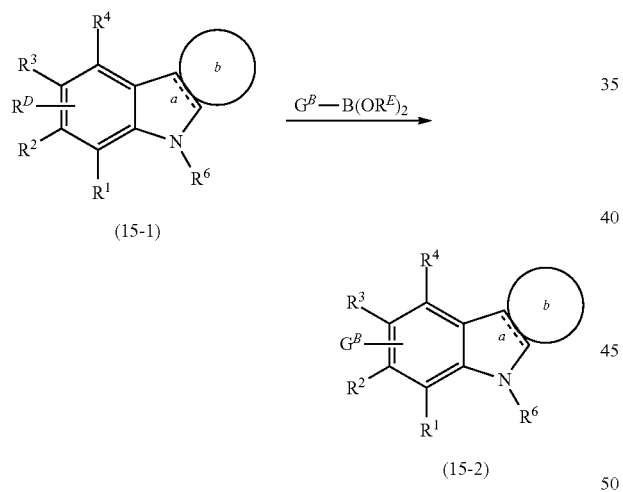

Compounds of formula (15-2), wherein a, $R^1$, $R^2$, $R^3$ and $R^4$ are as defined in formulas (I), (II), (III), (IV), (V), and (VI); and b represents the bicyclic, tricyclic, or spirocyclic ring systems of compounds of formulas (I), (II), (III), (IV), (V), and (VI); can be prepared as described in Scheme 15. Accordingly, compounds of formula (15-2) can be prepared by treating compounds of formula (15-1), wherein $R^D$ is I, Br, Cl or trifluoromethanesulfonate, and wherein one of $R^2$ or $R^3$ is $R^D$, with compounds of formula $G^B$-B(OR$^E$)$_2$, wherein $G^B$ is aryl, heteroaryl or cyclopropyl and $R^E$ is hydrogen, alkyl or joined together with the atoms to which they are attached form a dioxoborolane. The reaction typically requires the use of a base and a catalyst. Examples of bases include but are not limited to potassium carbonate, potassium tert-butoxide, sodium carbonate, potassium phosphate, cesium carbonate, and cesium fluoride. Examples of catalysts include but are not limited to tetrakis(triphenylphosphine)palladium(0), dichloro[1,1'-ferrocenylbis(diphenyl-phosphine)]palladium(II) dichloromethane, bis(dibenzylidene-acetone)palladium, palladium(II) acetate in the presence of a ligand such as tricyclohexylphosphine, and trans-dichlorobis(triphenylphosphine)palladium(II). The reaction may be conducted in a solvent such as but not limited to water, dioxane, 1,2-dimethoxyethane, N,N-dimethylformamide, toluene, ethanol, 2-propanol, tetrahydrofuran and the like or mixtures thereof. The reaction may be conducted at ambient or elevated temperatures.

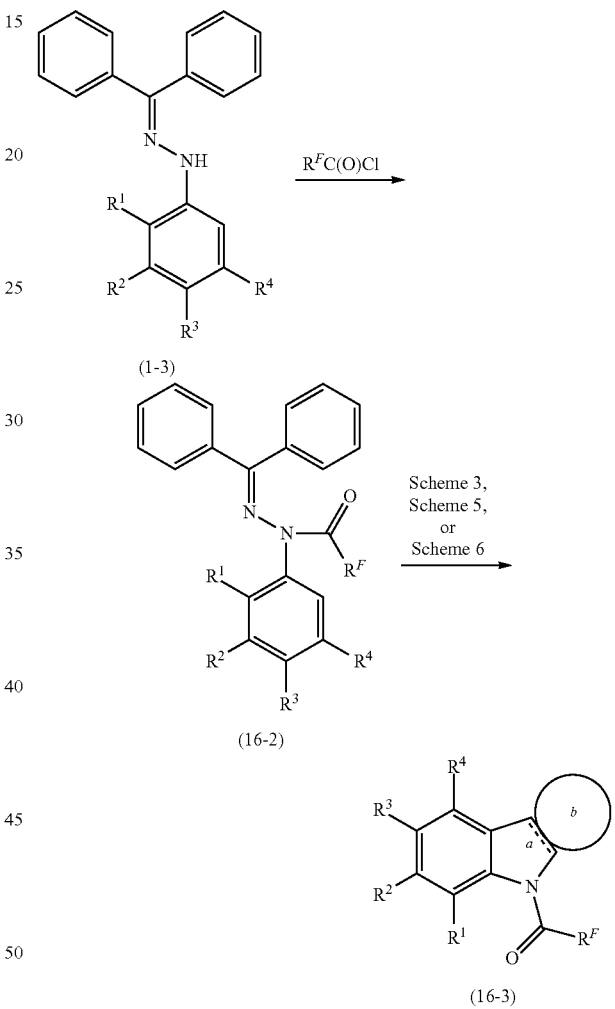

Compounds of formula (16-3), wherein a, $R^1$, $R^2$, $R^3$ and $R^4$ are as defined in formulas (I), (II), (III), (IV), (V), and (VI); and b represents the bicyclic, tricyclic, or spirocyclic ring systems of compounds of formulas (I), (II), (III), (IV), (V), and (VI); can be prepared as described in Scheme 16. Compounds of formula (1-3) can be treated with an acid chloride of formula $R^F$C(O)Cl, wherein $R^F$ is aryl, heteroaryl, arylalkyl, or heteroarylalkyl, in the presence of a base such as triethylamine or diisopropylamine in a base such as N,N-dimethylformamide to provide compounds of formula (16-2). Compounds of formula (16-2) can then be transformed to compounds of formula (16-3) according to the methodology described in Scheme 3, Scheme 5 or Scheme 6.

Scheme 17

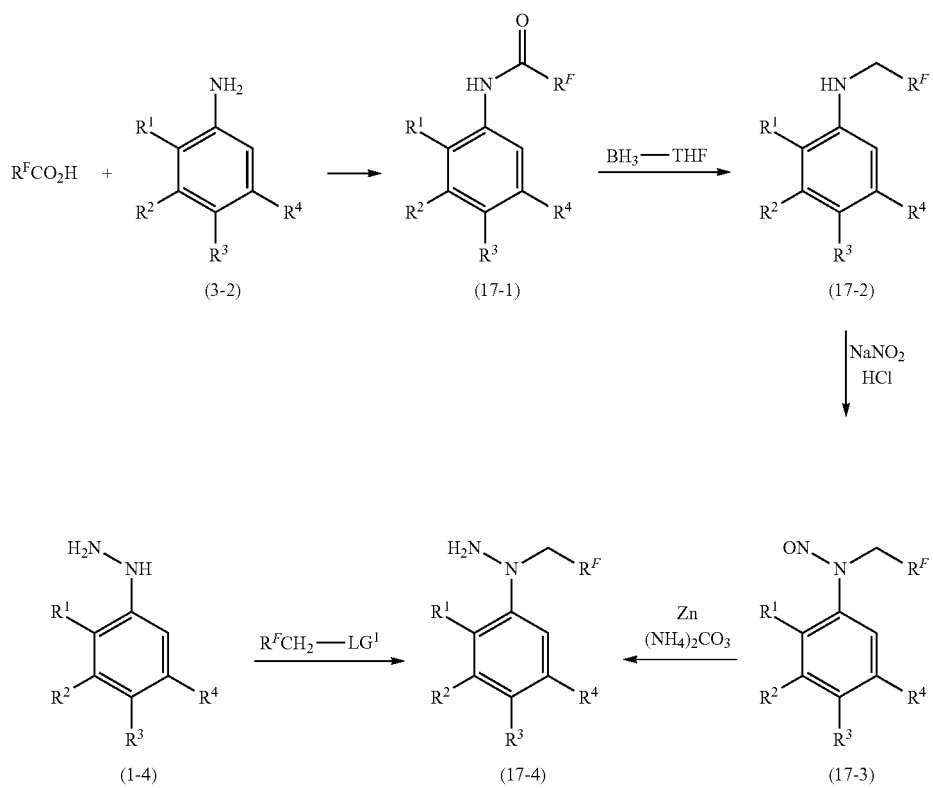

Compounds of formula (17-4) wherein $R^1$, $R^2$, $R^3$ and $R^4$ are as defined in formulas (I), (II), (III), (IV), (V), and (VI), and $R^F$ is aryl, heteroaryl, arylalkyl, or heteroarylalkyl can be prepared as shown in Scheme 17. Carboxylic acids of formula $R^FCO_2H$ can be coupled with anilines of formula (3-2) using standard amide bond forming reaction conditions well known to one skilled in the art to give compounds of formula (17-1). One procedure uses O-(7-azabenzotriazol-1-yl)-N,N,N',N'-tetramethyluronium hexafluorophosphate in the presence of diisopropylethylamine. Compounds of formula (17-1) can be reduced to compounds of formula (17-2) with borane-tetrahydrofuran complex in refluxing tetrahydrofuran. Treatment of compounds of formula (17-2) with sodium nitrite in an acid solution provides compounds of formula (17-3). Compounds of formula (17-3) can be reduced with zinc in the presence of ammonium carbonate to give compounds of formula (17-4). An alternative for the production of compounds of (17-4) involves the alkylation of compounds of formula (1-4) with compounds of formula $R^FCH_2$-$LG^1$, wherein $LG^1$ is a suitable leaving group such as chlorine, bromine, iodine, p-toluenesulfonate, or trifluoromethanesulfonate. Compounds of formula (1-4) can be reacted with compounds of formula $R^FCH_2$-$LG^1$ in the presence of a base such as triethylamine or diisopropylethylamine in a heated solution of ethanol to give compounds of formula (17-4). Alternatively, compounds of formula (1-4) can be reacted with compounds of formula $R^FCH_2$-$LG^1$ in the presence of a base such as sodium amide in a cooled solution of tetrahydrofuran to give compounds of formula (17-4). Compounds of formula (17-4) can be substituted for compounds of formula (3-3) in Scheme 3.

Scheme 18

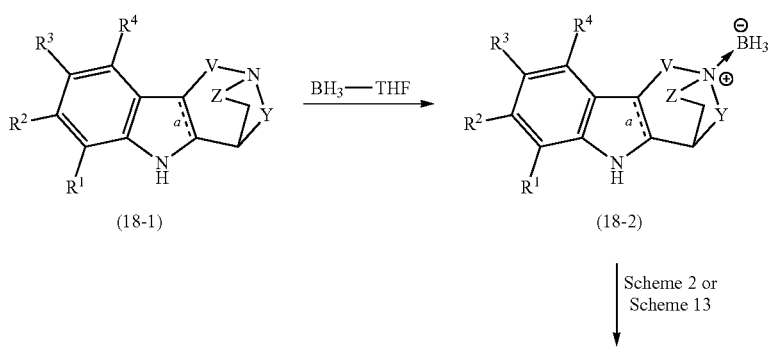

Scheme 2 or Scheme 13

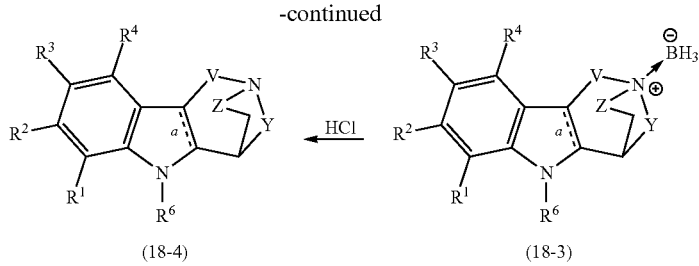

(18-4) ← HCl (18-3)

Compounds of formula (18-4) wherein a, $R^1$, $R^2$, $R^3$, $R^4$ and $R^6$ are as defined in formula (IV) can be prepared as shown in Scheme 18. Compounds of formula (18-1), which can be prepared with the methodologies described in Scheme 2 or Scheme 8, can be reacted with borane-tetrahydrofuran complex in a cooled solution of tetrahydrofuran to furnish the N-borane complex of compounds of formula (18-2). Compounds of formula (18-2) can be converted to compounds of formula (18-3) using the methodologies shown in Scheme 2 or Scheme 13. Compounds of formula (18-3) are transformed to compounds of formula (18-4) with treatment with hydrochloric acid in a solvent such as ethyl acetate. Compounds of formula (18-4) are representative of compounds of formula (IV).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protective Groups in Organic Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

h. EXAMPLES

The compounds and processes of the present invention will be better understood by reference to the following Examples, which are intended as an illustration of and not a limitation upon the scope of the application.

Example 1

2,11-dimethyl-5-[2-(6-methylpyridin-3-yl)ethyl]-5,6,7,8,9,10-hexahydro-7,10-epiminocyclohepta[b]indole Example 1A 2,11-dimethyl-5,6,7,8,9,10-hexahydro-7,10-epiminocyclohepta[b]indole In a 100 mL round-bottomed flask were combined p-tolylhydrazine hydrochloride (1.58 g, 10 mmol; Aldrich), 8-methyl-8-azabicyclo[3.2.1]octan-3-one (1.392 g, 10.00 mmol; Aldrich), and concentrated sulfuric acid (5 mL) in dioxane (50 mL). The reaction mixture was heated to 80° C. for 2.5 hours, then cooled to room temperature. The solvent was decanted, and the residue was dissolved in water (20 mL) and basified with solid potassium carbonate to pH ~12. This solution was extracted with dichloromethane (3×50 mL), and the combined organic phases were dried over magnesium sulfate. After removing the solvent under vacuum, the resulting solid was recrystallized from ether to afford the title compound: $^1$H NMR (300 MHz, CDCl$_3$) δ ppm 2.43 (s, 3H), 2.55 (s, 3H), 2.82 (m, 4H), 3.64 (s, 2H), 6.93 (d, J=7 Hz, 1H), 7.18-7.12 (m, 2H), 7.87 (br s, 1H); MS (DCI/NH$_3$) m/z 201 (M+H)$^+$.

Example 1B 2,11-dimethyl-5-[2-(6-methylpyridin-3-yl)ethyl]-5,6,7,8,9,10-hexahydro-7,10-epiminocyclohepta[b]indole A reaction flask with a septum cap was charged with 30% sodium metal dispersion in paraffin wax (0.14 g, 1.86 mmol; Aldrich) and a solution of 2,11-dimethyl-5,6,7,8,9,10-hexahydro-7,10-epiminocyclohepta[b]indole (0.30 g, 1.33 mmol; Example 1A) in dimethyl sulfoxide (2 mL). The vessel was sealed, flushed with nitrogen, and stirred for 10 minutes. A solution of 2-methyl-5-vinylpyridine (0.24 g, 1.99 mmol; prepared as described in International Publication No. WO 2001017968) and hydroquinone (0.036 g, 0.33 mmol, Aldrich) in anhydrous dimethyl sulfoxide (1.5 mL) was added and the reaction mixture was heated at 100° C. for 72 hours. After cooling the reaction mixture to room temperature, it was poured into water and extracted with ethyl acetate (4×25 mL). The combined organic extracts were washed with brine, concentrated, and purified by preparative HPLC [Waters XBridge™ C18 5 µm OBD column, 30×100 mm, flow rate 40 mL/minute, 5-95% gradient of acetonitrile in buffer (0.1 M aqueous ammonium bicarbonate, adjusted to pH 10 with ammonium hydroxide) over 15 minutes] to afford the title compound: MS (DCI/NH$_3$) m/z 346 (M+H)$^+$.

Example 1C 2,11-dimethyl-5-[2-(6-methylpyridin-3-yl)ethyl]-5,6,7,8,9,10-hexahydro-7,10-epiminocyclohepta[b]indole hydrochloride A solution of the product from Example 1B (0.17 g, 0.49 mmol) in ethyl acetate (4 mL) was treated with a solution of HCl in dioxane (4 M, 0.25 mL, 0.98 mmol; Aldrich), added dropwise. After stirring for 20 minutes, the solid was collected by filtration, rinsed with ethyl acetate, and dried for 10 hours at 75° C. under high vacuum to afford the title compound: $^1$H NMR (300 MHz, methanol-d$_4$) δ ppm 1.72-2.09 (m, 1H), 2.15-2.32 (m, 1H), 2.35-2.48 (m, 3H), 2.45-2.64 (m, 2H), 2.64-2.74 (m, 3H), 2.88-3.08 (m, 3H), 3.22-3.31 (m, 3H), 3.65 (dd, J=17.1, 4.8 Hz, 1H), 4.23-4.58 (m, 3H), 4.97-5.12 (m, 1H), 6.87-7.24 (m, 2H), 7.27-7.43 (m, 1H), 7.75 (t, J=8.9 Hz, 1H), 8.05-8.24 (m, 1H), 8.26-8.42 (m, 1H); MS (DCI/NH$_3$) m/z 346 (M+H)$^+$.

Example 2

9-methyl-6-[2-(6-methylpyridin-3-yl)ethyl]-3,4,5,6-tetrahydro-1H-2,5-ethanoazepino[4,3-b]indole

Example 2A 1-azabicyclo[3.2.2]nonan-4-one

An ice-cooled solution (5° C.) of (trimethylsilyl)diazomethane/hexane (2 N, 30 mL, 60 mmol; Aldrich) under nitrogen was treated dropwise with a solution of quinuclidin-3-one (7500 mg, 60 mmol) in dry tetrahydrofuran (40 mL). Methanol (20 mL) was added, and the yellow solution was warmed to room temperature, stirred for 24 hours, and quenched to colorless by addition of acetic acid. After a few minutes, saturated aqueous sodium carbonate (15 mL) was added. The organic layer was separated, and the aqueous solution was extracted with methylene chloride (3×50 mL). The combined organic layer and extracts were dried over magnesium sulfate, and concentrated in vacuo to give the titled compound. The material was used directly for next step without further purification.

Example 2B 9-methyl-3,4,5,6-tetrahydro-1H-2,5-ethanoazepino[4,3-b]indole

In a 100 mL round-bottomed flask were combined p-tolylhydrazine hydrochloride (1.58 g, 10 mmol; Aldrich), 1-azabicyclo[3.2.2]nonan-4-one (1.392 g, 10.00 mmol; Example 2A), and concentrated sulfuric acid (5 mL) in dioxane (50 mL). The reaction mixture was heated to 80° C. for 2.5 hours, then cooled to room temperature. The solvent was decanted, and the residue was dissolved in water (20 mL) and basified with solid potassium carbonate to pH ~12. This solution was extracted with dichloromethane (3×50 mL), and the combined organic phases were dried over magnesium sulfate. After removing the solvent under vacuum, the resulting solid was further purified by silica gel column chromatography eluting with 20% methanol-dichloromethane to supply the title compound: $^1$H NMR (300 MHz, CDCl$_3$) δ ppm 2.07-1.97 (m, 4H), 2.43 (s, 3H), 2.89 (m, 1H), 3.1 (m, 2H), 3.3 (m, 2H), 4.25 (s, 2H), 6.9 (m, 1H), 7.17 (m, 2H), 76 (br s, 1H); MS (DCI/NH$_3$) m/z 227 (M+H)$^+$.

Example 2C 9-methyl-6-[2-(6-methylpyridin-3-yl)ethyl]-3,4,5,6-tetrahydro-1H-2,5-ethanoazepino[4,3-b]indole A mixture of 9-methyl-3,4,5,6-tetrahydro-1H-2,5-ethanoazepino[4,3-b]indole (226 mg, 1.0 mmol; Example 2B), sodium (46 mg, 2 mmol, 30-35% dispersion is paraffin wax; Aldrich), hydroquinone (0.083 mL, 1.0 mmol; Aldrich) and 2-methyl-5-vinylpyridine (238 mg, 2.0 mmol) in dry dimethyl sulfoxide (10 mL) was purged with nitrogen, then heated to 100° C. with stirring for 72 hours. The mixture was filtered and purified by preparative HPLC (Waters XBridge™ C18 5 µm OBD column, 30×100 mm, flow rate 40 mL/minute, 5-95% gradient of acetonitrile in 0.1% trifluoroacetic acid, over 15 minutes) to afford the title compound as the trifluoroacetic acid salt: $^1$H NMR (300 MHz, methanol-d$_4$) δ ppm 1.94-2.07 (m, 2H), 2.24-2.37 (m, 2H), 2.40 (s, 3H), 2.61 (s, 3H), 3.19 (t, J=6.5 Hz, 2H), 3.35-3.50 (m, 3H), 3.56-3.69 (m, 2H), 4.49 (t, J=6.7 Hz, 2H), 4.70 (s, 2H), 6.98 (d, J=8.3 Hz, 1H), 7.13 (d, J=8.3 Hz, 1H), 7.19 (s, 1H), 7.56 (d, J=8.3 Hz, 1H), 7.90 (dd, J=7.9, 2.0 Hz, 1H), 8.14 (d, J=1.6 Hz, 1H); MS (DCI/NH$_3$) m/z 346 (M+H)$^+$.

Example 3

5-[6-(4-iodophenyl)pyridazin-3-yl]-2,11-dimethyl-5,6,7,8,9,10-hexahydro-7,10-epiminocyclohepta[b]indole A solution of 2,11-dimethyl-5,6,7,8,9,10-hexahydro-7,10-epiminocyclohepta[b]indole (113 mg, 0.499 mmol; Example 1A) and 3-chloro-6-(4-iodophenyl)pyridazine (190 mg, 0.599 mmol, US Patent No. 2005159597) was combined with potassium tert-butoxide (67 mg, 0.599 mmol) in dry N,N-dimethylformamide (8 mL) under a nitrogen atmosphere, and the mixture was heated to 50° C. with stirring for 16 hours. After cooling to room temperature, the mixture was filtered and purified by preparative HPLC (Waters XBridge™ C18 5 μm OBD column, 30×100 mm, flow rate 40 mL/minute, 5-95% gradient of acetonitrile in 0.1% trifluoroacetic acid, over 15 minutes) to afford the title compound as the trifluoroacetic acid salt: $^1$H NMR (300 MHz, methanol-d$_4$) δ ppm 2.02-2.19 (m, 1H), 2.29-2.75 (m, 3H), 2.48 (s, 3H), 3.01 (s, 3H), 3.19 (d, J=18.2 Hz, 1H), 3.68-3.96 (m, 1H), 4.29-4.39 (m, 1H), 5.10-5.24 (m, 1H), 7.17 (d, J=8.7 Hz, 1H), 7.46 (s, 1H), 7.53 (d, J=8.3 Hz, 1H), 7.90-8.00 (m, 4H), 8.05-8.15 (m, 1H), 8.37 (d, J=9.1 Hz, 1H); MS (DCI/NH$_3$) m/z 507 (M+H)$^+$.

Example 4

2-methyl-5-[2-(6-methylpyridin-3-yl)ethyl]-5,6,7,8,9,10-hexahydro-7,10-epiminocyclohepta[b]indole Example 4A 2-methyl-5,6,7,8,9,10-hexahydro-7,10-epiminocyclohepta[b]indole 4-Tolylhydrazine hydrochloride (1.90 g, 12.0 mmol) and tert-butyl 3-oxo-8-azabicyclo[3.2.1]octane-8-carboxylate (2.70 g, 12.0 mmol; Fluka) were heated at 50° C. in anhydrous dioxane (80 mL) for one hour. Sulfuric acid (3.2 mL) was added dropwise, and the resulting mixture was heated at 80° C. overnight. After cooling the mixture to room temperature, the dioxane phase was decanted. The remaining residue was dissolved in methanol (12 mL) and added slowly to a stirred solution of concentrated ammonium hydroxide (30 mL) kept at room temperature with a water bath. The resulting mixture was extracted with ethyl acetate (3×), and the combined organic phases were washed with brine, dried (sodium sulfate), concentrated, and purified by chromatography (silica gel, 0-5% gradient of concentrated aqueous ammonium hydroxide in acetonitrile) to afford the title compound: $^1$H NMR (300 MHz, methanol-d$_4$) δ ppm 1.59-1.72 (m, 1H), 1.93-2.25 (m, 3H), 2.54 (d, J=16 Hz, 1H), 3.25 (dd, J=16 Hz, 4.7, 1H), 3.91-3.99 (m, 1H), 4.49 (d, J=4.8 Hz, 1H), 6.83 (d, J=8.2 Hz, 1H), 7.12 (d, J=8.2 Hz, 1H), 7.19 (s, 1H); MS (ESI) m/z 213 (M+H)$^+$.

Example 4B 2-methyl-5-[2-(6-methylpyridin-3-yl)ethyl]-5,6,7,8,9,10-hexahydro-7,10-epiminocyclohepta[b]indole A suspension of 2-methyl-5,6,7,8,9,10-hexahydro-7,10-epiminocyclohepta[b]indole (170 mg, 0.80 mmol; Example 4A), hydroquinone (9 mg, 0.08 mmol), and ~32% sodium in paraffin (79 mg, 1.1 mmol; Aldrich) in anhydrous dimethyl sulfoxide (800 μL) was sealed in a septum-capped reaction tube. After thoroughly evacuating and purging the vessel with nitrogen, 2-methyl-5-vinylpyridine (143 mg, 1.2 mmol, International Publication No. WO2001/017968) was added, and the reaction was stirred at 100° C. for 48 hours. The thick mixture was cooled to room temperature, poured into water (5 mL), and extracted with ethyl acetate (3×). The combined organic phases were washed with water, filtered through diatomaceous earth, dried (Na$_2$SO$_4$), concentrated, and purified by chromatography on silica (0-5% gradient of concentrated aqueous ammonium hydroxide in acetonitrile). The resulting material was purified further by reverse-phase HPLC [Waters XBridge™ C18 5 μm OBD column, 30×100 mm, flow rate 40 mL/minute, 5-95% gradient of acetonitrile in buffer (0.1 M aqueous ammonium bicarbonate, adjusted to pH 10 with ammonium hydroxide)] to afford the title compound: $^1$H NMR (300 MHz, methanol-d$_4$) δ ppm 1.10-1.26 (m, 1H), 1.84-2.06 (m, 4H), 2.40 (s, 3H), 2.43 (s, 3H), 2.86 (dd, J=16 Hz, 4.6, 1H), 2.97 (ddd, J=14 Hz, 5.4, 5.4, 1H), 3.09 (ddd, J=14 Hz, 9.0, 6, 1H), 3.75-3.86 (m, 1H), 4.14 (ddd, J=15 Hz, 9.0, 5.4, 1H), 4.30 (ddd, J=15 Hz, 6, 5.4, 1H), 4.44 (d, J=4.6 Hz, 1H), 6.90 (d, J=8.3 Hz, 1H), 7.10 (d, J=7.9 Hz, 1H), 7.17 (d, J=8.3 Hz, 1H), 7.20-7.25 (m, 2H), 7.75 (d, J=2.1 Hz, 1H); MS (ESI) m/z 332 (M+H)$^+$.

Example 5

(7S,10R)-2-methyl-5-[2-(6-methylpyridin-3-yl)ethyl]-5,6,7,8,9,10-hexahydro-7,10-epiminocyclohepta[b]indole The individual enantiomers of the mixture of Example 4B were separated by preparative chiral supercritical fluid chromatography (ChiralPak® OD-H 5 μm 21×250 mm column; flow rate 40 mL/minute; gradient of 10-50% CH$_3$OH/CO$_2$ containing 0.1% diethylamine) to afford the free base of the title compound as the second-eluting enantiomer. This material was dissolved in ethyl acetate and treated with 4 M HCl in dioxane (2 equivalents). The resulting precipitate was collected by filtration and dried to afford the title compound as the dihydrochloride salt: $^1$H NMR (300 MHz, methanol-d$_4$) δ ppm 1.51-1.73 (m, 1H), 2.12-2.39 (m, 3H), 2.41 (s, 3H), 2.49-2.68 (m, 4H), 3.01-3.26 (m, 3H), 4.19-4.35 (m, 1H), 4.35-4.52 (m, 2H), 5.14 (s, 1H), 6.98 (d, J=9.8 Hz, 1H), 7.18 (d, J=8.1 Hz, 1H), 7.32 (s, 1H), 7.39-7.52 (m, 1H), 7.66-7.78 (m, 1H), 8.00 (s, 1H); MS (DCI/NH$_3$) m/z 332 (M+H)$^+$. [α]$_D$ −65 (c 0.5, CH$_3$OH).

Example 6

(7R,10S)-2-methyl-5-[2-(6-methylpyridin-3-yl)ethyl]-5,6,7,8,9,10-hexahydro-7,10-epiminocyclohepta[b]indole The individual enantiomers of the mixture of Example 4B were separated by preparative chiral supercritical fluid chromatography (ChiralPak® OD-H 5 μm 21×250 mm column; flow rate 40 mL/minute; gradient of 10-50% CH$_3$OH/CO$_2$ containing 0.1% diethylamine) to afford the free base of the title compound as the first-eluting enantiomer. This material was dissolved in ethyl acetate and treated with 4 M HCl in dioxane (2 equiv). The resulting precipitate was collected by filtration and dried to afford the title compound as the dihydrochloride salt: $^1$H NMR (300 MHz, methanol-d$_4$) δ ppm 1.51-1.73 (m, 1H), 2.12-2.39 (m, 3H), 2.41 (s, 3H), 2.49-2.68 (m, 4H), 3.01-3.26 (m, 3H), 4.19-4.35 (m, 1H), 4.35-4.52 (m, 2H), 5.14 (s, 1H), 6.98 (d, J=9.8 Hz, 1H), 7.18 (d, J=8.1 Hz, 1H), 7.32 (s, 1H), 7.39-7.52 (m, 1H), 7.66-7.78 (m, 1H), 8.00 (s, 1H); MS (DCI/NH$_3$) m/z 332 (M+H)$^+$.

Example 7

(7R,10S)-2,11-dimethyl-5-[2-(6-methylpyridin-3-yl)ethyl]-5,6,7,8,9,10-hexahydro-7,10-epiminocyclohepta[b]indole The individual enantiomers of the mixture of Example 1B were separated by preparative chiral supercritical fluid chromatography (ChiralPak® OD-H 5 μm 21×250 mm column; flow rate 40 mL/minute; gradient of 10-50% $CH_3OH/CO_2$ containing 0.1% diethylamine, 20 minutes) to afford the free base of the title compound as the first-eluting enantiomer (0.104 g, 0.301 mmol). This material was dissolved in warm ethanol (2 mL) and treated with a solution of D-tartaric acid (0.045 g, 0.301 mmol) in warm ethanol (2 mL). Upon cooling, a solid formed, which was collected by filtration to afford the title compound as the D-tartaric acid salt: $^1$H NMR (300 MHz, methanol-$d_4$): δ ppm 1.45 (s, 1H), 2.12 (s, 1H), 2.31-2.53 (m, 7H), 2.73-3.00 (m, 2H), 3.05-3.22 (m, 2H), 4.28-4.57 (m, 3H), 4.82-5.02 (m, 9H), 7.06 (s, 1H), 7.16 (d, J=7.9 Hz, 1H), 7.24-7.46 (m, 3H), 7.71 (s, 1H); MS (DCI/$NH_3$) m/z 346 (M+H)$^+$.

Example 8

(7S,10R)-2,11-dimethyl-5-[2-(6-methylpyridin-3-yl)ethyl]-5,6,7,8,9,10-hexahydro-7,10-epiminocyclohepta[b]indole The individual enantiomers of the mixture of Example 1B were separated by preparative chiral supercritical fluid chromatography (ChiralPak® OD-H 5 μm 21×250 mm column; flow rate 40 mL/minute; gradient of 10-50% $CH_3OH/CO_2$ containing 0.1% diethylamine, 20 minute) to afford the free base of the title compound as the second-eluting enantiomer (0.104 g, 0.301 mmol). This material was dissolved in warm ethyl acetate (2 mL) and ethanol (0.5 mL) and treated with hydrogen chloride/dioxane (4 M; 0.158 ml, 0.632 mmol), added dropwise. Upon cooling, a solid formed which was collected by filtration to afford the title compound as the dihydrochloride salt: $^1$H NMR (500 MHz, pyridine-$d_5$) δ ppm 1.48 (s, 1H), 1.97 (s, 1H), 2.25-2.88 (m, 10H), 2.88-3.15 (m, 3H), 4.23 (s, 3H), 5.08 (d, J=4.9 Hz, 1H), 6.96 (d, J=7.9 Hz, 1H), 7.23 (s, 2H), 7.35 (s, 1H), 7.46 (s, 1H), 7.60 (s, 1H), 8.15 (s, 1H), 8.74 (s, 1H); MS (DCI/$NH_3$) m/z 346 (M+H)$^+$.

Example 9

5-[2-(6-chloropyridin-3-yl)ethyl]-2,11-dimethyl-5,6,7,8,9,10-hexahydro-7,10-epiminocyclohepta[b]indole A reaction tube with a septum cap was charged with 2,11-dimethyl-5,6,7,8,9,10-hexahydro-7,10-epiminocyclohepta[b]indole (0.226 g, 0.999 mmol; Example 1A), sodium (30-35% dispersion in paraffin; 0.095 g, 1.364 mmol; Aldrich), 2-chloro-5-vinylpyridine (0.209 g, 1.498 mmol; *J. Chem. Soc. Chem. Commun.* 1994, 15, 1775), hydroquinone (11 mg, 0.100 mmol; Aldrich), and dimethyl sulfoxide (3 mL), and then sealed. The reaction vessel was evacuated and flushed with nitrogen (10×), then heated to 100° C. for 24 hours. After cooling the mixture to room temperature, it was poured into water, extracted with ethyl acetate (3×), and then purified twice by reverse-phase HPLC [Waters XBridge™ C18 5 μm OBD column, 30×100 mm, flow rate 40 mL/minute, 5-95% gradient over 15 minutes of acetonitrile in buffer (0.1 M aqueous ammonium bicarbonate, adjusted to pH 10 with ammonium hydroxide)] to afford the title compound: $^1$H NMR (300 MHz, CDCl$_3$) δ ppm 1.16-1.31 (m, 1H), 1.72-1.86 (m, 2H), 2.10-2.30 (m, 5H), 2.46 (s, 3H), 2.69 (dd, J=16.3, 4.4 Hz, 1H), 3.04 (ddd, J=25.2, 13.9, 6.5 Hz, 2H), 3.45 (t, J=5.4 Hz, 1H), 4.12 (d, J=4.8 Hz, 1H), 4.19 (t, J=6.7 Hz, 2H), 6.94-7.03 (m, 2H), 7.10 (d, J=7.4 Hz, 1H), 7.17 (d, J=8.3 Hz, 1H), 7.28 (s, 1H), 8.04 (d, J=2.4 Hz, 1H); MS (DCI) m/z 366/368 (M+H)$^+$.

Example 10

(7R,10S)-5-[2-(6-chloropyridin-3-yl)ethyl]-2,11-dimethyl-5,6,7,8,9,10-hexahydro-7,10-epiminocyclohepta[b]indole The individual enantiomers from the mixture of Example 9 (400 mg, 1.09 mmol) were separated by preparative chiral supercritical fluid chromatography (ChiralPak® OD-H 5 μm column, 21×250 mm, 35° C., 10-30% gradient of $CH_3OH$—$CO_2$ containing 0.1% diethylamine) to obtain the title compound as the first eluting peak: $^1$H NMR (300 MHz, CDCl$_3$) δ ppm 1.16-1.31 (m, 1H), 1.72-1.86 (m, 2H), 2.10-2.30 (m, 5H), 2.46 (s, 3H), 2.69 (dd, J=16.3, 4.4 Hz, 1H), 3.04 (ddd, J=25.2, 13.9, 6.5 Hz, 2H), 3.45 (t, J=5.4 Hz, 1H), 4.12 (d, J=4.8 Hz, 1H), 4.19 (t, J=6.7 Hz, 2H), 6.94-7.03 (m, 2H), 7.10 (d, J=7.4 Hz, 1H), 7.17 (d, J=8.3 Hz, 1H), 7.28 (s, 1H), 8.04 (d, J=2.4 Hz, 1H); MS (DCI) m/z 366/368 (M+H)$^+$.

Example 11

(7S,10R)-5-[2-(6-chloropyridin-3-yl)ethyl]-2,11-dimethyl-5,6,7,8,9,10-hexahydro-7,10-epiminocyclohepta[b]indole The individual enantiomers from the mixture of Example 9 (400 mg, 1.09 mmol) were separated by preparative chiral supercritical fluid chromatography (ChiralPak® OD-H 5 μm column, 21×250 mm, 35° C., 10-30% gradient of $CH_3OH$—$CO_2$ containing 0.1% diethylamine) to obtain the title compound as the second eluting peak: $^1$H NMR (300 MHz, CDCl$_3$) δ ppm 1.16-1.31 (m, 1H), 1.72-1.86 (m, 2H), 2.10-2.30 (m, 5H), 2.46 (s, 3H), 2.69 (dd, J=16.3, 4.4 Hz, 1H), 3.04 (ddd, J=25.2, 13.9, 6.5 Hz, 2H), 3.45 (t, J=5.4 Hz, 1H), 4.12 (d, J=4.8 Hz, 1H), 4.19 (t, J=6.7 Hz, 2H), 6.94-7.03 (m, 2H), 7.10 (d, J=7.4 Hz, 1H), 7.17 (d, J=8.3 Hz, 1H), 7.28 (s, 1H), 8.04 (d, J=2.4 Hz, 1H); MS (DCI) m/z 366/368 (M+H)$^+$.

Example 12

11-ethyl-2-methyl-5-[2-(6-methylpyridin-3-yl)ethyl]-5,6,7,8,9,10-hexahydro-7,10-epiminocyclohepta[b]indole A solution of 2-methyl-5-[2-(6-methylpyridin-3-yl)ethyl]-5,6,7,8,9,10-hexahydro-7,10-epiminocyclohepta[b]indole (76 mg, 0.23 mmol; Example 4), acetic acid (34 μL, 0.59 mmol), and acetaldehyde (26 μL, 0.47 mmol) in methanol (1.5 mL) was treated with sodium cyanoborohydride (29 mg, 0.46 mmol), and stirred in a closed vial at room temperature for six days. Additional acetaldehyde (13 μL) and sodium cyanoborohydride (15 mg) were added and the mixture was stirred two more days, after which yet more acetaldehyde (12 μL) and sodium cyanoborohydride (14 mg) were added. After another day, the mixture was concentrated, diluted with ethyl acetate, filtered, and purified by reverse-phase HPLC (C8 column, 10-95% gradient of acetonitrile in aqueous ammonium acetate) to afford the title compound: $^1$H NMR (300 MHz, methanol-$d_4$) δ ppm 1.28 (t, 3H), 1.38-1.53 (m, 1H), 2.11 (m, 1H), 2.29 (m, 3H), 2.43 (s, 3H), 2.44 (s, 3H), 2.86-3.00 (m, 2H), 3.00-3.19 (m, 3 H), 4.06-4.18 (m, 1H), 4.18-4.32 (m, 1H), 4.39 (ddd, J=15 Hz, 6, 6, 1H), 4.99 (d, J=5.0 Hz, 1H), 7.06 (dd, J=8.3 Hz, 1.5, 1H), 7.15 (d, J=8.0 Hz, 1H), 7.29-7.36 (m, 3H), 7.72 (d, J=2.0 Hz, 1H); MS (ESI) m/z 360 (M+H)$^+$.

Example 13

11-(2-fluoroethyl)-2-methyl-5-[2-(6-methylpyridin-3-yl)ethyl]-5,6,7,8,9,10-hexahydro-7,10-epiminocyclohepta[b]indole A solution of 2-methyl-5-[2-(6-methylpyridin-3-yl)ethyl]-5,6,7,8,9,10-hexahydro-7,10-epiminocyclohepta[b]indole (60 mg, 0.18 mmol; Example 4) and diisopropylethylamine (50 μL, 0.29 mmol) in anhydrous N,N-dimethylformamide (500 μL) was treated dropwise with 2-fluoroethyl tosylate (42 μL, 0.24 mmol). The reaction mixture was stirred at room temperature for 1 hour and then heated at 50° C. overnight. After cooling the mixture to room temperature, it was purified by reverse-phase HPLC (C8 column, 10-95% gradient of acetonitrile in aqueous ammonium acetate) to afford the title compound: $^1$H NMR (500 MHz, methanol-d$_4$) δ ppm 1.21 (m, 1H), 1.76 (dd, J=9.4, 9.4, 1H), 1.85 (d, J=16.5, 1H), 2.04-2.23 (m, 2H), 2.40 (s, 3H), 2.42 (s, 3H), 2.55 (dd, J=9.6, 4.3, 1H), 2.60 (m, 1H), 2.64 (dd, J=16.5, 4.3, 1H), 3.07 (m, 2H), 3.52 (m, 1H), 4.23-4.27 (m, 3H), 4.44 (m, 1H), 4.54 (m, 1H), 6.94 (d, J=8.3, 1H), 7.09 (d, J=7.9, 1H), 7.19 (s, 1H), 7.21 (dd, J=7.9, 2.2, 1H), 7.24 (d, J=8.3, 1H), 7.73 (d, J=2.1, 1H); MS (ESI) m/z 378 (M+H)$^+$.

Example 14

2-methyl-5-[2-(6-methylpyridin-3-yl)ethyl]-11-(2,2,2-trifluoroethyl)-5,6,7,8,9,10-hexahydro-7,10-epiminocyclohepta[b]indole A solution of 2-methyl-5-[2-(6-methylpyridin-3-yl)ethyl]-5,6,7,8,9,10-hexahydro-7,10-epiminocyclohepta[b]indole (60 mg, 0.18 mmol; Example 4) and diisopropylethylamine (50 μL, 0.29 mmol) in anhydrous N,N-dimethylformamide (500 μL) was cooled with a water-ice bath and then treated dropwise with 2,2,2-trifluoroethyl triflate (35 μL, 0.24 mmol). After 5 minutes the bath was removed and the reaction mixture was stirred at room temperature for 6.5 hours, then diluted with acetonitrile and purified by reverse phase HPLC (C8 column, 10-95% gradient of acetonitrile in aqueous ammonium acetate) to afford the title compound: $^1$H NMR (300 MHz, methanol-d$_4$) δ ppm 1.12-1.25 (m, 1H), 1.69-1.80 (m, 1H), 1.86 (d, J=17 Hz, 1H), 2.04-2.24 (m, 2H), 2.41 (s, 3H), 2.41 (s, 3H), 2.55 (dd, J=17 Hz, 4.4, 1H), 2.78-2.92 (m, 2H), 3.08 (t, J=6.2 Hz, 2H), 3.47-3.56 (m, 1H), 4.20-4.32 (m, 3H), 6.96 (d, J=8.3 Hz, 1H), 7.08 (d, J=7.9 Hz, 1H), 7.14-7.21 (m, 2H), 7.27 (d, J=8.3 Hz, 1H), 7.75 (d, J=2.1 Hz, 1H); MS (ESI) m/z 414 (M+H)$^+$.

Example 15 ethyl (7R,10S)-2-methyl-5-[2-(6-methylpyridin-3-yl)ethyl]-5,6,7,8,9,10-hexahydro-7,10-epiminocyclohepta[b]indole-11-carboxylate (7R,10S)-2-Methyl-5-[2-(6-methylpyridin-3-yl)ethyl]-5,6,7,8,9,10-hexahydro-7,10-epiminocyclohepta[b]indole (40.8 mg, 0.123 mmol; Example 6) in tetrahydrofuran (3.0 mL) was treated with ethyl carbonochloridate (0.014 ml, 0.148 mmol; Aldrich), added dropwise. After 1 hour, water (5 mL) was added and the aqueous solution was extracted with CH$_2$Cl$_2$. The organic layer was dried over magnesium sulfate, filtered, and concentrated. The resulting material was purified by reverse-phase HPLC [Waters XBridge™ C18 5 μm OBD column, 30×100 mm, flow rate 40 mL/minute, 40-99% gradient of methanol in buffer (0.1 M aqueous ammonium bicarbonate, adjusted to pH 10 with ammonium hydroxide) over 20 minutes] to provide the title compound: $^1$H NMR (300 MHz, CDCl$_3$) δ ppm 1.10-1.38 (m, 5H), 1.81-2.03 (m, 2H), 2.06-2.25 (m, 2H), 2.46 (s, 3H), 2.56 (s, 3H), 3.00 (m, 2H), 3.98-4.26 (m, 4H), 4.57 (dd, J=14.1, 12.5 Hz, 1H), 5.10-5.36 (m, 1H), 6.90-7.08 (m, 2H), 7.16 (d, J=8.7 Hz, 1H), 7.30-7.37 (m, 2H), 8.21 (s, 1H); MS (ESI) m/z 404 (M+H)$^+$.

Example 16 ethyl (7S,10R)-2-methyl-5-[2-(6-methylpyridin-3-yl)ethyl]-5,6,7,8,9,10-hexahydro-7,10-epiminocyclohepta[b]indole-11-carboxylate A solution of (7S,10R)-2-methyl-5-[2-(6-methylpyridin-3-yl)ethyl]-5,6,7,8,9,10-hexahydro-7,10-epiminocyclohepta[b]indole (109 mg, 0.329 mmol; Example 5) in tetrahydrofuran (3.0 mL) was treated with ethyl carbonochloridate (0.31 ml, 0.323 mmol; Aldrich), added dropwise. After 1 hour, water (5 mL) was added and the aqueous solution was extracted with CH$_2$Cl$_2$. The organic layer was dried over MgSO$_4$, filtered, and concentrated. The resulting material was purified by preparative HPLC [Waters XBridge™ C18 5 μm OBD column, 30×100 mm, flow rate 40 mL/minute, 40-99% gradient of methanol in buffer (0.1 M aqueous ammonium bicarbonate, adjusted to pH 10 with ammonium hydroxide) over 20 minutes] to provide the title compound: $^1$H NMR (300 MHz, CDCl$_3$) δ ppm 1.10-1.38 (m, 5H), 1.81-2.03 (m, 2H), 2.06-2.25 (m, 2H), 2.46 (s, 3H), 2.56 (s, 3H), 3.00 (m, J=7.1, 2H), 3.98-4.26 (m, 4H), 4.57 (dd, J=14.1, 12.5 Hz, 1H), 5.10-5.36 (m, 1H), 6.90-7.08 (m, 2H), 7.16 (d, J=8.7 Hz, 1H), 7.30-7.37 (m, 2H), 8.21 (s, 1H); MS (ESI) m/z 404 (M+H)$^+$.

Example 17

11-(4-chlorobenzoyl)-2-methyl-5-[2-(6-methylpyridin-3-yl)ethyl]-5,6,7,8,9,10-hexahydro-7,10-epiminocyclohepta[b]indole A solution of 2-methyl-5-[2-(6-methylpyridin-3-yl)ethyl]-5,6,7,8,9,10-hexahydro-7,10-epiminocyclohepta[b]indole (36 mg, 0.11 mmol; Example 4), 4-chlorobenzoyl chloride (0.015 mL, 0.12 mmol; Aldrich) and triethylamine (0.015 mL, 0.11 mmol; Aldrich) in methylene chloride (5 mL) was stirred at 25° C. for one hour. The reaction mixture was reduced to dryness and the residue was purified by preparative HPLC [Waters XBridge™ RP18 column, 5 μm, 30×100 mm, flow rate 40 mL/minute, 5-95% gradient of acetonitrile in buffer (0.1 M aqueous ammonium bicarbonate, adjusted to pH 10 with ammonium hydroxide)] to afford the title compound: $^1$H NMR (400 MHz, methanol-d$_4$) δ ppm 1.25-1.47 (m, 1H), 1.87-1.99 (m, 1H), 2.09-2.28 (m, 3H), 2.37-2.46 (two m, 6H, amide rotamers), 2.75-2.90 (two dd, J=16.5, 4.3 Hz, 1H, amide rotamers), 3.05-3.13 (m, 2H), 4.20-4.39 (m, 2H), 4.91-5.04 (two m, 1H, amide rotamers), 6.93-7.02 (two s, 1H, amide rotamers), 7.06-7.20 (m, 2H), 7.21-7.51 (m, 6H), 7.74-7.83 (two s, 1H, amide rotamers); MS (APCI) m/z 470 (M+H)$^+$.

Example 18

2-methyl-5-[2-(6-methylpyridin-3-yl)ethyl]-11-{[4-(trifluoromethyl)phenyl]sulfonyl}-5,6,7,8,9,10-hexahydro-7,10-epiminocyclohepta[b]indole A solution of 2-methyl-5-[2-(6-methylpyridin-3-yl)ethyl]-5,6,7,8,9,10-hexahydro-7,10-epiminocyclohepta[b]indole (36 mg, 0.11 mmol; Example 4), 4-trifluoromethylbenzenesulfonyl chloride (29 mg, 0.12 mmol) and triethylamine (0.015 mL, 0.11 mmol) in methylene chloride (5 mL) was stirred at 25° C. for one hour. The reaction mixture was reduced to dryness and the residue was purified by reverse-phase HPLC [Waters XBridge™ RP18 column, 5 m, 30×100 mm, flow rate 40 mL/minute, 5-95% gradient of acetonitrile in buffer (0.1 M aqueous ammonium bicarbonate, adjusted to pH 10 with ammonium hydroxide)] to afford the title compound: $^1$H NMR (300 MHz, methanol-$d_4$) δ ppm 1.12-1.23 (m, 1H), 1.70 (dd, J=16.6, 1.0 Hz, 1H), 1.82-1.96 (m, 1H), 2.05-2.21 (m, 2H), 2.41 (s, 3H), 2.46 (s, 3H), 2.60 (dd, J=16.6, 4.7 Hz, 1H), 2.70-2.81 (m, 1H), 2.85-2.97 (m, 1H), 3.65 (ddd, J=14.7, 9.1, 5.8 Hz, 1H), 3.93 (ddd, J=14.6, 6.1, 4.7 Hz, 1H), 4.38-4.48 (m, 1H), 5.17 (d, J=4.7 Hz, 1H), 6.97 (two d, J=1.4 Hz, 1H, rotamers), 7.04-7.13 (m, 3H), 7.24-7.34 (m, 3H), 7.63-7.71 (m, 3H); MS (APCI) m/z 540 (M+H)$^+$.

Example 19

(7R,10S)-2,11-dimethyl-5-[2-(2-methylpyridin-3-yl)ethyl]-5,6,7,8,9,10-hexahydro-7,10-epiminocyclohepta[b]indole

Example 19A (7R,10S)-2,11-dimethyl-5,6,7,8,9,10-hexahydro-7,10-epiminocyclohepta[b]indole The individual enantiomers of the mixture of Example 1A were separated by preparative chiral HPLC (Chiralpak® AD 50×400 mm column; flow rate 100 mL/minute; 60:20:20:0.2 hexane-ethanol-methanol-diethylamine, 25° C.) to afford the title compound as the second-eluting peak.

Example 19B (7R,10S)-2,11-dimethyl-5-[2-(2-methylpyridin-3-yl)ethyl]-5,6,7,8,9,10-hexahydro-7,10-epiminocyclohepta[b]indole A reaction tube with a septum cap was charged with (7R,10S)-2,11-dimethyl-5,6,7,8,9,10-hexahydro-7,10-epiminocyclohepta[b]indole (200 mg, 0.884 mmol; Example 19A), sodium (30-35% dispersion in paraffin; 122 mg, 1.599 mmol; Aldrich) and hydroquinone (10.0 mg, 0.088 mmol; Aldrich) and dimethyl sulfoxide (1 mL), and the vessel was evacuated and flushed with nitrogen (3×). 2-Methyl-3-vinylpyridine (211 mg, 1.767 mmol; Aldrich) in dimethyl sulfoxide (1.5 mL) was added via a syringe and the vessel was again evacuated and flushed with nitrogen, and then heated at 100° C. for 72 hours. After cooling the reaction mixture, water (5 mL) was added, and the aqueous solution was extracted with CH$_2$Cl$_2$ (3×10 mL). The combined organic extracts were dried over MgSO$_4$, filtered, and concentrated. The resulting material was purified by reverse-phase HPLC [Waters XBridge™ C18 5 μm OBD column, 30×100 mm, flow rate 40 mL/minute, 40-99% gradient of methanol in buffer (0.1 M aqueous ammonium bicarbonate, adjusted to pH 10 with ammonium hydroxide) over 20 minutes] to provide the title compound: $^1$H NMR (300 MHz, methanol-$d_4$) δ ppm 1.11-1.36 (m, 1H), 1.69-1.87 (m, 2H), 2.09 (s, 3H), 2.12-2.30 (m, 5H), 2.40 (s, 3H), 2.70 (dd, J=16.1, 3.9 Hz, 1H), 3.12 (t, J=5.3 Hz, 2H), 3.34-3.46 (m, 1H), 4.12 (d, J=5.1 Hz, 1H), 4.19-4.44 (m, 2H), 6.91 (d, J=9.5 Hz, 1H), 7.04-7.12 (m, 1H), 7.13-7.22 (m, 2H), 7.27 (d, J=7.5 Hz, 1H), 8.17-8.25 (m, 1H); MS (DCI/NH$_3$) m/z 346 (M+H)$^+$.

Example 20

2,11-dimethyl-5-[(Z)-2-pyridin-3-ylvinyl]-5,6,7,8,9,10-hexahydro-7,10-epiminocyclohepta[b]indole A reaction tube with a septum cap was charged with 30% sodium metal dispersion in paraffin wax (0.30 g, 4.0 mmol; Aldrich) and a solution of 2,11-dimethyl-5,6,7,8,9,10-hexahydro-7,10-epiminocyclohepta[b]indole (0.112 g, 0.495 mmol; Example 1A) in dimethyl sulfoxide (2 mL). The vessel was sealed, flushed with nitrogen, and stirred for 10 minutes. A solution of 3-ethynylpyridine (0.206 g, 2.0 mmol; Aldrich) and hydroquinone (0.072 g, 0.66 mmol; Aldrich) in anhydrous dimethyl sulfoxide (1.5 mL) was added and the reaction mixture was heated at 100° C. for 16 hours. After the reaction mixture was cooled to room temperature, it was purified by reverse-phase HPLC [Waters XBridge™ C18 5 μm OBD column, 30×100 mm, flow rate 40 mL/minute, 5-95% gradient over 15 minutes of acetonitrile in buffer (0.1 M aqueous ammonium bicarbonate, adjusted to pH 10 with ammonium hydroxide)] to afford the title compound as the minor alkene isomer: $^1$H NMR (300 MHz, methanol-$d_4$) δ ppm 1.31-1.45 (m, 1H), 1.91 (t, J=9 Hz, 1H), 2.12-2.34 (m, 3H), 2.30 (s, 3H), 2.38 (s, 3H), 2.90 (dd, J=17, 4 Hz, 1H), 3.41-3.48 (m, 1H), 4.20 (d, J=5 Hz, 1H), 6.63 (d, J=8 Hz, 1H), 6.83-6.95 (m, 2H), 7.00 (d, J=8 Hz, 1H), 7.16-7.28 (m, 3H), 8.04 (d, J=2 Hz, 1H), 8.27 (dd, J=5, 2 Hz, 1H); MS (DCI/NH$_3$) m/z 330 (M+H)$^+$.

Example 21

(7R,10S)-2,11-dimethyl-5-[(E)-2-pyridin-3-ylvinyl]-5,6,7,8,9,10-hexahydro-7,10-epiminocyclohepta[b]indole The racemate of the title compound was obtained by reverse-phase HPLC [Waters XBridge™ C18 5 μm OBD column, 30×100 mm, flow rate 40 mL/minute, 5-95% gradient over 15 minutes of acetonitrile in buffer (0.1 M aqueous ammonium bicarbonate, adjusted to pH 10 with ammonium hydroxide)] as the major component from the reaction mixture of Example 20. The individual enantiomers were separated by preparative chiral supercritical fluid chromatography (ChiralPak® OD-H 5 μm column, 21×250 mm, 35° C., 10-50% gradient of CH$_3$OH—CO$_2$ containing 0.1% diethylamine) to afford the title compound as the first-eluting peak: $^1$H NMR (300 MHz, methanol-$d_4$) δ ppm 1.61-1.76 (m, 1H), 1.93 (t, J=9 Hz, 1H), 2.23-2.36 (m, 2H), 2.41 (s, 3H), 2.43 (s, 3H), 2.70 (d, J=17 Hz, 1H), 3.40 (dd, J=17, 4 Hz, 1H), 3.61-3.70 (m, 1H), 4.22 (d, J=5 Hz, 1H), 6.81 (d, J=15 Hz, 1H), 7.06 (dd, J=8, 1 Hz, 1H), 7.28 (s, 1H), 7.41 (dd, J=8, 5 Hz, 1H), 7.63 (d, J=8 Hz, 1H), 7.74 (d, J=15 Hz, 1H), 8.04 (dt, J=8, 2 Hz, 1H), 8.35 (dd, J=5, 2 Hz, 1H), 8.65 (d, J=2 Hz, 1H); MS (DCI/NH$_3$) m/z 330 (M+H)$^+$.

Example 22

(7S,10R)-2,11-dimethyl-5-[(E)-2-pyridin-3-ylvinyl]-5,6,7,8,9,10-hexahydro-7,10-epiminocyclohepta[b]indole The racemate of the title compound was obtained from the mixture of Example 20. The individual enantiomers were separated by preparative chiral supercritical fluid chromatography (ChiralPak® OD-H 5 µm column, 21×250 mm, 35° C., 10-50% gradient of $CH_3OH$—$CO_2$ containing 0.1% diethylamine) to afford the title compound as the second-eluting peak: $^1$H NMR (300 MHz, methanol-$d_4$) δ ppm 1.57-1.75 (m, 1H), 1.93 (t, J=9 Hz, 1H), 2.26-2.37 (m, 2H), 2.41 (s, 3H), 2.43 (s, 3H), 2.70 (d, J=17 Hz, 1H), 3.40 (dd, J=17, 4 Hz, 1H), 3.61-3.69 (m, 1H), 4.22 (d, J=5 Hz, 1H), 6.81 (d, J=15 Hz, 1H), 7.06 (dd, J=8, 1 Hz, 1H), 7.28 (s, 1H), 7.41 (dd, J=8, 5 Hz, 1H), 7.63 (d, J=8 Hz, 1H), 7.74 (d, J=15 Hz, 1H), 8.04 (dt, J=8, 2 Hz, 1H), 8.35 (dd, J=5, 2 Hz, 1H), 8.65 (d, J=2 Hz, 1H); MS (DCI/$NH_3$) m/z 330 (M+H)$^+$.

Example 23

(7S,10R)-2,11-dimethyl-5-[(E)-2-(6-methylpyridin-3-yl)vinyl]-5,6,7,8,9,10-hexahydro-7,10-epiminocyclohepta[b]indole

Example 23A (7S,10R)-2,11-dimethyl-5,6,7,8,9,10-hexahydro-7,10-epiminocyclohepta[b]indole The individual enantiomers of the mixture of Example 1A were separated by preparative chiral HPLC (Chiralpak® AD 50×400 mm column; flow rate 100 mL/minute; 60:20:20:0.2 hexane-ethanol-methanol-diethylamine, 25° C.) to afford the title compound as the first-eluting peak.

Example 23B (E)-2-methyl-5-(2-(4,4,5,5-tetramethyl-1,3,2-dioxaborolan-2-yl)vinyl)pyridine A dry 500-mL round-bottom flask was charged with carbonylchlorohydrido-tris(triphenylphosphine) ruthenium (II) (0.571 g, 0.600 mmol; Aldrich) and dry toluene (80 mL) under nitrogen. After pinacolborane (3.19 ml, 22.00 mmol, Aldrich) and 5-ethynyl-2-methylpyridine (2.343 g, 20 mmol; International Publication No. WO2005090333) were added, the mixture was stirred at room temperature for 16 hours. The reaction mixture was extracted with ether, then the extract was washed with water, dried over $MgSO_4$ and concentrated. The resulting material was purified by flash chromatography (silica gel, hexanes/ethyl acetate, 3:1) to afford the title compound: $^1$H NMR (300 MHz, $CDCl_3$) δ ppm 1.31 (s, 12H), 2.55 (s, 3H), 6.19 (d, J=19 Hz, 1H), 7.13 (d, J=8 Hz, 1H), 7.36 (d, J=18 Hz, 1H), 7.71 (dd, J=8, 2 Hz, 1H), 8.56 (d, J=2 Hz, 1H); MS (DCI/$NH_3$) m/z 246 (M+H)$^+$.

Example 23C 5-(2-bromovinyl)-2-methylpyridine

A solution of (E)-2-methyl-5-(2-(4,4,5,5-tetramethyl-1,3,2-dioxaborolan-2-yl)vinyl)-pyridine (1.0 g, 4.08 mmol; Example 23B) in acetonitrile (10 mL) was treated with N-bromosuccinimide (0.346 mL, 4.08 mmol; Aldrich) and triethylamine (0.625 mL, 4.49 mmol; Aldrich) and stirred at room temperature for 16 hours. Water was added and the mixture was extracted several times with ethyl acetate. The combined organic extracts were concentrated, and the resulting material was purified by flash chromatography (silica gel, hexane/ethyl acetate, 3:1) to afford the title compound as a 1.2:1 Z/E mixture: $^1$H NMR (300 MHz, $CDCl_3$) δ ppm 2.54 (s, 3H), 2.57 (s, 3.6H), 6.52 (d, J=14 Hz, 1.2H), 6.75-6.85 (d, J=14 Hz, 1H), 7.01-7.22 (m, 4.4H), 7.52 (dd, J=8, 2 Hz, 1H), 8.07 (dd, J=8, 2 Hz, 1.2H), 8.43 (d, J=2 Hz, 1H), 8.66 (d, J=2 Hz, 1.2H); MS (DCI/$NH_3$) m/z 198/200 (M+H)$^+$.

Example 23D (7S,10O)-2,11-dimethyl-5-[(E)-2-(6-methylpyridin-3-yl)vinyl]-5,6,7,8,9,10-hexahydro-7,10-epiminocyclohepta[b]indole A 30-mL reaction tube was charged with (7S,10R)-2,11-dimethyl-5,6,7,8,9,10-hexahydro-7,10-epiminocyclohepta[b]indole (453 mg; 2.0 mmol, Example 23A), 5-(2-bromovinyl)-2-methylpyridine (396 mg, 2.00 mmol; Example 23C), bis(tri-t-butylphosphine)palladium(0) (51 mg, 0.10 mmol; Aldrich), sodium t-butoxide (481 mg, 5.00 mmol; Aldrich) and anhydrous dioxane (8 mL). The vessel was flushed with nitrogen, sealed, and heated to 100° C. with stirring for 30 minutes. After cooling the mixture, it was quenched with water and extracted with ethyl acetate. The organic phase was concentrated and purified by reverse-phase HPLC [Waters XBridge™ C18 5 µm OBD column, 30×100 mm, flow rate 40 mL/minute, 5-95% gradient of methanol in buffer (0.1 M aqueous ammonium bicarbonate, adjusted to pH 10 with ammonium hydroxide)] to afford the title compound as the major product: $^1$H NMR (300 MHz, methanol-$d_4$) δ ppm 1.59-1.75 (m, 1H), 1.92 (t, J=9 Hz, 1H), 2.23-2.36 (m, 2H), 2.40 (s, 3H), 2.43 (s, 3H), 2.52 (s, 3H), 2.68 (d, J=17 Hz, 1H), 3.39 (dd, J=17, 4 Hz, 1H), 3.64 (t, J=5 Hz, 1H), 4.22 (d, J=5 Hz, 1H), 6.77 (d, J=15 Hz, 1H), 7.05 (d, J=9 Hz, 1H), 7.25-7.32 (m, 2H), 7.61 (d, J=9 Hz, 1H), 7.68 (d, J=15 Hz, 1H), 7.94 (dd, J=8, 2 Hz, 1H), 8.50 (d, J=2 Hz, 1H); MS (DCI/$NH_3$) m/z 344 (M+H)$^+$.

Example 24

(7S,10R)-2,11-dimethyl-5-[(Z)-2-(6-methylpyridin-3-yl)vinyl]-5,6,7,8,9,10-hexahydro-7,10-epiminocyclohepta[b]indole Purification of the mixture from Example 23D by reverse-phase HPLC [Waters XBridge™ C18 5 µm column, 30×100 mm, flow rate 40 mL/minute, 5-95% gradient over 15 minutes of acetonitrile in buffer (0.1 M aqueous ammonium bicarbonate, adjusted to pH 10 with ammonium hydroxide)] afforded the title compound as the minor product: $^1$H NMR (300 MHz, methanol-$d_4$) δ ppm 1.32-1.45 (m, 1H), 1.87-1.96 (m, 1H), 2.12-2.29 (m, 3H), 2.30 (s, 3H), 2.38 (s, 3H), 2.40 (s, 3H), 2.90 (dd, J=17, 4 Hz, 1H), 3.42-3.49 (m, 1H), 4.20 (d, J=5 Hz, 1H), 6.60 (d, J=8 Hz, 1H), 6.84-6.98 (m, 3H), 7.03-7.16 (m, 2H), 7.25 (s, 1H), 7.92 (d, J=2 Hz, 1H); MS (DCI/$NH_3$) m/z 344 (M+H)$^+$.

Example 25

(7R,10S)-2-methyl-5-[(Z)-2-(6-methylpyridin-3-yl)vinyl]-5,6,7,8,9,10-hexahydro-7,10-epiminocyclohepta[b]indole The coupling of 2-methyl-5,6,7,8,9,10-hexahydro-7,10-epiminocyclohepta[b]indole (212 mg, 1.00 mmol; Example 4A) and 5-ethynyl-2-methylpyridine (586 mg, 5.00 mmol; International Publication No. WO2005090333) was performed as described in Example 20 to afford the racemate of the title compound. The individual enantiomers were separated by preparative chiral supercritical fluid chromatography (ChiralPak® OD-H 5 μm column, 21×250 mm, 35° C., 10-50% gradient of $CH_3OH—CO_2$ containing 0.1% diethylamine) to afford the title compound as the first-eluting peak: $^1$H NMR (300 MHz, methanol-$d_4$) δ ppm 1.37-1.53 (m, 1H), 1.99-2.13 (m, 3H), 2.29-2.36 (m, 1H), 2.38 (s, 3H), 2.41 (s, 3H), 3.01 (dd, J=16, 5 Hz, 1H), 3.90 (t, J=6 Hz, 1H), 4.55 (d, J=4 Hz, 1H), 6.58 (d, J=8 Hz, 1H), 6.80-6.88 (m, 2H), 6.90 (d, J=9 Hz, 1H), 7.01-7.14 (m, 2H), 7.28 (s, 1H), 7.93 (d, J=2 Hz, 1H); MS (DCI/$NH_3$) m/z 330 (M+H)$^+$.

Example 26

(7S,10R)-2-methyl-5-[(Z)-2-(6-methylpyridin-3-yl)vinyl]-5,6,7,8,9,10-hexahydro-7,10-epiminocyclohepta[b]indole The coupling of 2-methyl-5,6,7,8,9,10-hexahydro-7,10-epiminocyclohepta[b]indole (212 mg, 1.00 mmol; Example 4A) and 5-ethynyl-2-methylpyridine (586 mg, 5.00 mmol; WO2005090333) was performed as described in Example 20 to afford the racemate of the title compound. The individual enantiomers were separated by preparative chiral supercritical fluid chromatography (ChiralPak® OD-H 5 μm column, 21×250 mm, 35° C., 10-50% gradient of $CH_3OH—CO_2$ containing 0.1% diethylamine) to afford the title compound as the second-eluting peak: $^1$H NMR (300 MHz, methanol-$d_4$) δ ppm 1.37-1.52 (m, 1H), 1.97-2.15 (m, 3H), 2.32 (d, J=17 Hz, 1H), 2.38 (s, 3H), 2.40 (s, 3H), 3.00 (dd, J=16, 4 Hz, 1H), 3.86-3.91 (m, 1H), 4.53 (d, J=4 Hz, 1H), 6.58 (d, J=9 Hz, 1H), 6.80-6.88 (m, 2H), 6.90 (d, J=8 Hz, 1H), 7.02-7.13 (m, 2H), 7.27 (s, 1H), 7.93 (d, J=2 Hz, 1H); MS (DCI/$NH_3$) m/z 330 (M+H)$^+$.

Example 27

(7S,10R)-2,11-dimethyl-5-(2-pyridin-2-ylethyl)-5,6,7,8,9,10-hexahydro-7,10-epiminocyclohepta[b]indole A reaction tube with a septum cap was charged with (7S,10R)-2,11-dimethyl-5,6,7,8,9,10-hexahydro-7,10-epiminocyclohepta[b]indole (300 mg, 1.33 mmol; Example 23A), sodium (30-35% dispersion in paraffin; 203 mg, 2.65 mmol; Aldrich), hydroquinone (15.0 mg, 0.100 mmol; Aldrich) and dimethyl sulfoxide (1 mL), and the vessel was evacuated and flushed with nitrogen (3×). A solution of 2-vinylpyridine (181 mg, 1.723 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, methanol-$d_4$) δ ppm 1.37 (m, 1H), 1.72 (m, 2H), 1.95 (m, 1H), 2.39 (s, 3H), 2.45 (s, 3H), 2.53 (m, 1H), 2.63 (m, 1H), 2.78 (m, 1H), 3.36 (m, 2H), 3.53 (m, 1H), 4.65 (m, 2H), 7.00 (d, J=2 Hz, 1H), 7.05 (dd, J=2, 8 Hz, 1H), 7.12 (dd, J=2, 8 Hz, 1H), 7.28 (m, 1H), 7.35 (dd, J=2, 8 Hz, 1H), 7.65 (m, 1H), 8.65 (m, 1H); MS (ESI) m/z 332 (M+H)$^+$.

Example 28

(7S,10R)-5-[2-(5-ethylpyridin-2-yl)ethyl]-2,11-dimethyl-5,6,7,8,9,10-hexahydro-7,10-epiminocyclohepta[b]indole A reaction tube with a septum cap was charged with (7S,10R)-2,11-dimethyl-5,6,7,8,9,10-hexahydro-7,10-epiminocyclohepta[b]indole (210 mg, 0.93 mmol; Example 23A), sodium (30-35% dispersion in paraffin; 142 mg, 1.86 mmol; Aldrich), hydroquinone (10.2 mg, 0.090 mmol; Aldrich) and dimethyl sulfoxide (1 mL), and the vessel was evacuated and flushed with nitrogen (3×). A solution of 5-ethyl-2-vinylpyridine (161 mg, 1.206 mmol; 3B Scientific) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, methanol-$d_4$) δ ppm 1.24 (t, J=7.6 Hz, 3H), 1.29 (m, 1H), 1.85 (m, 2H), 2.17 (m, 1H), 2.45 (s, 3H), 2.50 (s, 3H), 2.55 (m, 5H), 3.36 (m, 2H), 3.53 (m, 1H), 4.65 (m, 2H), 6.99 (d, J=2 Hz, 1H), 7.05 (dd, J=8, 8 Hz, 1H), 7.28 (m, 1H), 7.49 (d, J=8 Hz, 1H), 8.11 (dd, J=2, 8 Hz, 1H), 8.45 (d, J=2 Hz, 1H); MS (ESI) m/z 360 (M+H)$^+$.

Example 29

(7S,10R)-2,11-dimethyl-5-(2-pyridin-4-ylethyl)-5,6,7,8,9,10-hexahydro-7,10-epiminocyclohepta[b]indole A reaction tube with a septum cap was charged with (7S,10R)-2,11-dimethyl-5,6,7,8,9,10-hexahydro-7,10-epiminocyclohepta[b]indole (300 mg, 1.33 mmol; Example 23A), sodium (30-35% dispersion in paraffin; 203 mg, 2.65 mmol; Aldrich), hydroquinone (15.0 mg, 0.100 mmol; Aldrich) and dimethyl sulfoxide (1 mL), and the vessel was evacuated and flushed with nitrogen (3×). A solution of 4-vinylpyridine (181 mg, 1.723 mmol; ASDI Products) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.44 (m, 1H), 1.70 (m, 2H), 1.95 (m, 1H), 2.30 (s, 3H), 2.44 (s, 3H), 2.55 (m, 1H), 2.75 (m, 1H), 2.78 (m, 1H), 3.06 (m, 2H), 3.53 (m, 1H), 4.65 (m, 2H), 7.00

(d, J=2 Hz, 1H), 7.05 (dd, J=8 Hz, 1H), 7.18 (dd, J=2, 8 Hz, 1H), 7.49 (d, J=8 Hz, 2H), 8.45 (d, J=8 Hz, 2H); MS (ESI) m/z 332 (M+H)$^+$.

Example 30

2,11-dimethyl-5-(2-pyrimidin-5-ylethyl)-5,6,7,8,9,10-hexahydro-7,10-epiminocyclohepta[b]indole Example 30A 5-vinylpyridmidine A solution of potassium vinyltrifluoroborate (843 mg, 6.29 mmol; Aldrich), palladium(II) chloride (22 mg, 0.124 mmol; Aldrich), triphenylphosphine (99 mg, 0.377 mmol; Aldrich), cesium carbonate (6.15 g, 18.87 mmol; Aldrich), and 5-bromopyrimidine (843 mg, 6.29 mmol; Aldrich) in tetrahydrofuran/H$_2$O (9:1; 10 mL) was heated at 85° C. under a nitrogen atmosphere for 24 hours. The reaction mixture was cooled to room temperature, diluted with water (15 mL), and extracted with dichloromethane (2×25 mL). The combined organic extracts were dried over MgSO$_4$, filtered, concentrated, and the crude material was purified by flash chromatography (silica gel, 5-60% ethyl acetate in hexanes) to afford the title compound: $^1$H NMR (300 MHz, CDCl$_3$) δ ppm 5.52 (d, J=11.1 Hz, 1H), 5.93 (d, J=17.9 Hz, 1H), 6.66 (dd, J=17.5, 11.1 Hz, 1H), 8.76 (s, 2H), 9.10 (s, 1H).

Example 30B 2,11-dimethyl-5-(2-pyrimidin-5-ylethyl)-5,6,7,8,9,10-hexahydro-7,10-epiminocyclohepta[b]indole A reaction tube was charged with 2,11-dimethyl-5,6,7,8,9,10-hexahydro-7,10-epiminocyclohepta[b]indole (150 mg, 0.663 mmol; Example 1A), sodium (30-35% dispersion in paraffin; 91 mg, 1.193 mmol; Aldrich) and hydroquinone (7.30 mg, 0.066 mmol; Aldrich) and then sealed with a septum cap. Dimethyl sulfoxide (1 mL) and 5-vinylpyrimidine (71 mg, 0.663 mmol; Example 30A) were introduced through the septum and the vessel was evacuated and backfilled with nitrogen (~10×). The mixture was heated at 100° C. for 3 days. After cooling, the reaction mixture was filtered and purified by reverse-phase HPLC (Waters XBridge™ C18 5 μm OBD 30×100 mm column, flow rate 40 mL/minute, 5-95% gradient of acetonitrile in 0.1% trifluoroacetic acid over 15 minutes) to afford the title compound as the trifluoroacetic acid salt: $^1$H NMR (300 MHz, CDCl$_3$) δ ppm 2.03 (d, J=2.7 Hz, 1H), 2.21-2.33 (m, 1H), 2.43 (s, 5H), 2.53-2.65 (m, 2H), 2.89-3.09 (m, 6H), 3.49-3.58 (m, 2H), 4.18-4.31 (m, 1H), 6.98 (s, 2H), 7.13-7.40 (m, 4H); MS (DCI/NH$_3$) m/z 333 (M+H)$^+$.

Example 31

(7R,10S)-2,11-dimethyl-5-[2-(2-methylpyrimidin-5-yl)ethyl]-5,6,7,8,9,10-hexahydro-7,10-epiminocyclohepta[b]indole Example 31A 2-methyl-5-vinylpyrimidine A solution of potassium vinyltrifluoroborate (666 mg, 4.97 mmol; Aldrich), palladium(II) chloride (18 mg, 0.099 mmol; Aldrich), triphenylphosphine (78 mg, 0.298 mmol; Aldrich), cesium carbonate (4.86 g, 14.91 mmol; Aldrich), and 2-methyl-5-bromopyrimidine (867 mg, 4.97 mmol; AniChem) in tetrahydrofuran/H$_2$O (9:1; 10 mL) was heated at 85° C. under a nitrogen atmosphere for 24 hours. The reaction mixture was cooled to room temperature, diluted with water (15 mL), and extracted with dichloromethane (2×25 mL). The combined organic extracts were dried over MgSO$_4$, filtered, concentrated, and the crude material was purified by flash chromatography (silica gel, 5-60% ethyl acetate in hexanes) to afford the title compound: $^1$H NMR (300 MHz, CDCl$_3$) δ ppm 2.73 (s, 3H), 5.44 (d, J=11.10 Hz, 1H), 5.86 (d, J=17.85 Hz, 1H), 6.63 (dd, J=17.85, 11.10 Hz, 1H), 8.66 (s, 2H); MS (DCI/NH$_3$) m/z 121 (M+H)$^+$, 138 (M+NH$_4$)$^+$.

Example 31B (7R,10S)-2,11-dimethyl-5-[2-(2-methylpyrimidin-5-yl)ethyl]-5,6,7,8,9,10-hexahydro-7,10-epiminocyclohepta[b]indole A reaction tube was charged with (7R,10S)-2,11-dimethyl-5,6,7,8,9,10-hexahydro-7,10-epiminocyclohepta[b]indole (300 mg, 1.326 mmol; Example 19A), sodium (30-35% dispersion in paraffin; 183 mg, 2.386 mmol; Aldrich) and hydroquinone (14.6 mg, 0.133 mmol; Aldrich) and then sealed with a septum cap. Dimethyl sulfoxide (1 mL) and 2-methyl-5-vinylpyrimidine (319 mg, 2.65 mmol; Example 31A) were introduced through the septum and the vessel was evacuated and backfilled with nitrogen (~10×). The mixture was heated at 100° C. for 72 hours. After cooling, the reaction mixture was diluted with water (5 mL), extracted with dichloromethane (3×10 mL) and concentrated. The crude residue was purified by reverse-phase HPLC [Waters XBridge™ C18 5 μm 30×100 mm column, flow rate 40 mL/minute, 40-99% gradient of methanol in buffer (0.1 M aqueous ammonium bicarbonate, adjusted to pH 10 with ammonium hydroxide) over 20 minutes], and then purified further by reverse-phase HPLC (Waters XBridge™ C18 5 μm OBD 30×100 mm column, flow rate 40 mL/minute, 5-95% gradient of acetonitrile and 0.1% aqueous trifluoroacetic acid) to afford the title compound as the trifluoroacetic acid salt: $^1$H NMR (300 MHz, methanol-d$_4$) δ ppm 1.11-1.35 (m, 1H), 1.73-1.89 (m, 1H), 2.08-2.34 (m, 5H), 2.39 (s, 3H), 2.48-2.69 (m, 4H), 2.86 (dd, J=16.5, 4.6 Hz, 1H), 2.99-3.18 (m, 2H), 3.46 (s, 1H), 4.15 (d, J=4.8 Hz, 1H), 4.18-4.44 (m, 2H), 6.92 (d, J=8.7 Hz, 1H), 7.05-7.29 (m, 2H), 8.05 (s, 2H); MS (ESI) m/z 347 (M+H)$^+$.

Example 32

(7S,10R)-2,11-dimethyl-5-[2-(2-methylpyrimidin-5-yl)ethyl]-5,6,7,8,9,10-hexahydro-7,10-epiminocyclohepta[b]indole A reaction tube with a septum cap was charged with (7S,10R)-2,11-dimethyl-5,6,7,8,9,10-hexahydro-7,10-epiminocyclohepta[b]indole (400 mg, 1.78 mmol; Example 23A), sodium (30-35% dispersion in paraffin; 271 mg, 3.53 mmol; Aldrich), hydroquinone (20.0 mg, 0.133 mmol; Aldrich) and dimethyl sulfoxide (1 mL), and the vessel was evacuated and flushed with nitrogen (3×). A solution of 2-methyl-5-vinylpyrimidine (319 mg, 2.65 mmol; Example 31A) in dimethyl sulfoxide (2 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, methanol-$d_4$) δ ppm 1.28 (m, 1H), 1.70 (m, 2H), 1.95 (m, 1H), 2.21 (s, 3H), 2.39 (s, 3H), 2.44 (s, 3H), 2.48 (m, 1H), 2.75 (m, 1H), 2.78 (m, 1H), 3.06 (m, 2H), 3.53 (m, 1H), 4.65 (m, 2H), 6.95 (dd, J=2, 8 Hz, 1H), 7.15 (dd, J=8, 1H), 7.2 (m, 1H), 8.05 (s, 2H); MS (ESI) m/z 347 (M+H)$^+$.

Example 33

(7R,10S)-2,11-dimethyl-5-[2-(6-methylpyridazin-3-yl)ethyl]-5,6,7,8,9,10-hexahydro-7,10-epiminocyclohepta[b]indole The coupling of (7R,10S)-2,11-dimethyl-5,6,7,8,9,10-hexahydro-7,10-epiminocyclohepta[b]indole (350 mg, 1.55 mmol, Example 19A) and 3-methyl-6-vinylpyridazine (260 mg, 1.93 mmol; *J. Med. Chem.* 2005, 48, 1367-1383) was performed as described in Example 1B to afford the title compound: $^1$H NMR (300 MHz, CDCl$_3$) δ ppm 1.17-1.27 (m, 1H), 1.70-1.84 (m, 1H), 1.95 (d, J=16.3 Hz, 1H), 2.14-2.25 (m, 5H), 2.45 (s, 3H), 2.65 (s, 3H), 2.80 (dd, J=16.6, 4.1 Hz, 1H), 3.35 (t, J=6.8 Hz, 2H), 3.43-3.51 (m, 1H), 4.12 (d, J=5.1 Hz, 1H), 4.46 (t, J=6.4 Hz, 2H), 6.59 (d, J=8.5 Hz, 1H), 6.94-7.04 (m, J=8.5 Hz, 2H), 7.20 (d, J=8.1 Hz, 1H), 7.25 (s, 1H); MS (DCI/NH$_3$) m/z 347 (M+H)$^+$.

Example 34

(7R,10S)-2,11-dimethyl-5-[2-(5-methylpyrazin-2-yl)ethyl]-5,6,7,8,9,10-hexahydro-7,10-epiminocyclohepta[b]indole The coupling of (7R,10S)-2,11-dimethyl-5,6,7,8,9,10-hexahydro-7,10-epiminocyclohepta[b]indole (235 mg, 1.04 mmol; Example 19A) and 2-methyl-5-vinylpyrazine (100 mg, 0.83 mmol; prepared using methodology described in Molander, G. A.; et al. *J. Org. Chem.*, 2006, 71, 9681-9686) was performed as described in Example 1B to afford the title compound: $^1$H NMR (300 MHz, CDCl$_3$) δ ppm 1.23-1.37 (m, 1H), 1.83 (t, J=9.3 Hz, 1H), 1.98 (d, J=15.9 Hz, 1H), 2.15-2.30 (m, 5H), 2.45 (s, 3H), 2.51 (s, 3H), 2.83 (dd, J=16.3, 4.1 Hz, 1H), 3.16 (t, J=6.8 Hz, 2H), 3.49 (d, J=4.7 Hz, 1H), 4.13 (d, J=4.7 Hz, 1H), 4.30-4.41 (m, 2H), 6.92-7.00 (m, 1H), 7.20 (d, J=8.1 Hz, 1H), 7.26 (s, 1H), 7.92 (d, J=1.4 Hz, 1H), 8.41 (s, 1H); MS (DCI/NH$_3$) m/z 347 (M+H)$^+$.

Example 35

2,11-dimethyl-5-[2-(4-methyl-1,3-thiazol-5-yl)ethyl]-5,6,7,8,9,10-hexahydro-7,10-epiminocyclohepta[b]indole A reaction tube was charged with 2,11-dimethyl-5,6,7,8,9,10-hexahydro-7,10-epiminocyclohepta[b]indole (150 mg, 0.663 mmol; Example 1A), sodium (30-35% dispersion in paraffin; 91 mg, 1.193 mmol; Aldrich) and hydroquinone (7.30 mg, 0.066 mmol; Aldrich) and then sealed with a septum cap. Dimethyl sulfoxide (1 mL) and 4-methyl-5-vinylthiazole (83 mg, 0.663 mmol; Aldrich) were introduced through the septum and the vessel was evacuated and backfilled with nitrogen (~10×). The mixture was heated at 100° C. for 3 days. After cooling, the reaction mixture was filtered and purified by reverse-phase HPLC (Waters XBridge™ C18 5 µm OBD 30×100 mm column, flow rate 40 mL/minute, 5-95% gradient of acetonitrile in 0.1% trifluoroacetic acid over 15 minutes) to afford the title compound as the trifluoroacetic acid salt: $^1$H NMR (300 MHz, methanol-$d_4$) δ ppm 1.70 (s, 2H), 1.77 (s, 3H), 2.10-2.31 (m, 2H), 2.43 (s, 5H), 2.65 (s, 2H), 2.90 (s, 3H), 4.04-4.21 (m, 2H), 4.28-4.40 (m, 1H), 4.39-4.53 (m, 1H), 6.92-7.17 (m, 1H), 7.19-7.39 (m, 2H), 8.76 (d, J=4.7 Hz, 1H); MS (DCI/NH$_3$) m/z 352 (M+H)$^+$.

General Procedure A

N-Arylation of Benzophenone Hydrazone

A flame-dried round bottom flask was evacuated, backfilled with nitrogen, and charged with palladium(II) acetate (0.01 equivalents; Aldrich), Xantphos (0.011 equivalents; Aldrich), and toluene (1 mL). The flask was then capped with a septum, and the mixture was stirred at room temperature under nitrogen for approximately 5 minutes. The septum was removed, and benzophenone hydrazone (10.0 equivalents; Aldrich), aryl halide (10.0 equivalents), and sodium tert-butoxide (14.0 equivalents, Aldrich) were added, followed by additional toluene (9 mL). The flask was re-capped, flushed with nitrogen, and the evacuation-backfill cycle was repeated two more times. The reaction mixture was heated at 80° C. overnight, then cooled to room temperature and diluted with ether (15 mL). The resulting heterogeneous mixture was filtered through a pad of silica gel with rinsing with additional ether. The filtrate was concentrated in vacuo to afford the crude product which was carried on to the next step without further purification.

General Procedure B

N-Alkylation of N-Aryl Benzophenone Hydrazone

A solution of an N-aryl benzophenone hydrazone (1.0 equivalent), alkyl halide (1.0-10.0 equivalents), and tetrabutylammonium iodide (0.001 equivalents, Aldrich) in 1:1 dichloromethane/50% aqueous NaOH (0.3 M in hydrazone) was stirred vigorously at 40° C. overnight. After cooling, the reaction mixture was diluted with 15 mL water and extracted with dichloromethane (25 mL). The organic phase was dried over magnesium sulfate, filtered, and concentrated in vacuo to afford the crude product which was carried on to the next step without purification.

General Procedure C

Procedure for Fischer Indolization of N-aryl-N-alkyl Benzophenone Hydrazones

A solution of the crude N-aryl-N-alkyl benzophenone hydrazone in ethanol (5 mL/mmol) was treated with the ketone (1.5 equivalents) and p-toluenesulfonic acid monohydrate (2.0 equivalents), and the solution was heated to reflux until the hydrazone was consumed, as ascertained by LC/MS. The reaction mixture was cooled to room temperature, neutralized with saturated sodium bicarbonate solution, and extracted with ether (2×10 mL). The combined ether extracts were dried over magnesium sulfate and concentrated in vacuo. The resulting material was purified by reverse-phase HPLC (Waters XBridge™ C18 5 μm OBD column, 30×100 mm, flow rate 40 mL/minute, 5-95% gradient of acetonitrile in 0.1% trifluoroacetic acid over 15 minutes) to afford the title compound as the trifluoroacetate salt.

Example 36

2,11-dimethyl-5-(2-phenylethyl)-5,6,7,8,9,10-hexahydro-7,10-epiminocyclohepta[b]indole Example 36A 1-(diphenylmethylene)-2-p-tolylhydrazine General procedure A was used to convert benzophenone hydrazone (6.31 g, 32.3 mmol; Aldrich) and 1-bromo-4-methylbenzene 5.0 g, 29.2 mmol; Aldrich) into the title compound: MS (DCI/NH$_3$) m/z 287 (M+H)$^+$.

Example 36B 2-(diphenylmethylene)-1-phenethyl-1-p-tolylhydrazine

General procedure B was used to convert 1-(diphenylmethylene)-2-p-tolylhydrazine (200 mg, 0.69 mmol; Example 36A) and 2-bromoethylbenzene (210 mg, 0.69 mmol; Aldrich) to the title compound: MS (DCI/NH$_3$) m/z 391 (M+H)$^+$.

Example 36C 2,11-dimethyl-5-(2-phenylethyl)-5,6,7,8,9,10-hexahydro-7,10-epiminocyclohepta[b]indole General procedure C was used to convert 2-(diphenylmethylene)-1-phenethyl-1-p-tolylhydrazine (273 mg, 0.698 mmol; Example 36B) and tropinone (131 mg, 1.05 mmol; Aldrich) to the title compound as the trifluoroacetic acid salt: $^1$H NMR (300 MHz, CDCl$_3$) δ ppm 1.12-1.39 (m, 1H), 1.71-1.98 (m, 2H), 2.05-2.33 (m, 5H), 2.47 (s, 3H), 2.65 (dd, J=16.5, 4.2 Hz, 1H), 2.88-3.20 (m, 2H), 3.32-3.54 (m, 1H), 3.98-4.30 (m, 3H), 6.80-6.91 (m, 2H), 7.04-7.13 (m, 1H), 7.13-7.23 (m, 3H), 7.26-7.33 (m, 1H), 7.39 (dd, J=19.3, 8.5 Hz, 1H); MS (DCI/NH$_3$) m/z 331 (M+H)$^+$.

Example 37

2,11-dimethyl-5-[2-(2-methylphenyl)ethyl]-5,6,7,8,9,10-hexahydro-7,10-epiminocyclohepta[b]indole Example 37A 2-(diphenylmethylene)-1-(2-methylphenethyl)-1-p-tolylhydrazine General procedure B was used to convert 1-(diphenylmethylene)-2-p-tolylhydrazine (200 mg, 0.69 mmol; Example 36A) and 2-methylphenethylbromide (278 mg, 1.4 mmol; Aldrich) to the title compound: MS (DCI/NH$_3$) m/z 404 (M+H)$^+$.

Example 37B 2,11-dimethyl-5-[2-(2-methylphenyl)ethyl]-5,6,7,8,9,10-hexahydro-7,10-epiminocyclohepta[b]indole General procedure C was used to convert 2-(diphenylmethylene)-1-(2-methylphenethyl)-1-p-tolylhydrazine (300 mg, 0.74 mmol; Example 37A) and tropinone (155 mg, 1.1 mmol; Aldrich) to the title compound as the trifluoroacetate salt: $^1$H NMR (300 MHz, CDCl$_3$) δ ppm 1.12-1.39 (m, 1H), 1.71-1.98 (m, 2H), 2.05-2.33 (m, 5H), 2.35 (s, 3H), 2.47 (s, 3H), 2.65 (dd, J=16.5, 4.2 Hz, 1H), 2.88-3.20 (m, 2H), 3.32-3.54 (m, 1H), 3.98-4.30 (m, 3H), 7.04-7.20 (m, 4H), 7.24-7.42 (m, 3H); MS (DCI/NH$_3$) m/z 345 (M+H)$^+$.

Example 38

(7R,10S)-2,11-dimethyl-5-[2-(2-methylphenyl)ethyl]-5,6,7,8,9,10-hexahydro-7,10-epiminocyclohepta[b]indole A reaction tube was charged with (7R,10S)-2,11-dimethyl-5,6,7,8,9,10-hexahydro-7,10-epiminocyclohepta[b]indole (200 mg, 0.884 mmol; Example 19A), sodium (30-35% dispersion in paraffin; 122 mg, 1.591 mmol; Aldrich) and hydroquinone (9.7 mg, 0.088 mmol; Aldrich) and then sealed with a septum cap. Dimethyl sulfoxide (1 mL) and 1-methyl-2-vinylbenzene (209 mg, 1.77 mmol; Aldrich) were introduced through the septum and the vessel was evacuated and backfilled with nitrogen (~10×). The mixture was heated at 100° C. for 72 hours. After cooling, the reaction mixture was filtered and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.12-1.39 (m, 1H), 1.71-1.98 (m, 2H), 2.05-2.33 (m, 5H), 2.35 (s, 3H), 2.47 (s, 3H), 2.65 (dd, J=16.5, 4.2 Hz, 1H), 2.88-3.20 (m, 2H), 3.32-3.54 (m, 1H), 3.98-4.30 (m, 3H), 7.04-7.20 (m, 4H), 7.24-7.42 (m, 3H); MS (DCI/NH$_3$) m/z 345 (M+H)$^+$.

Example 39

(7S,10R)-2,11-dimethyl-5-[2-(2-methylphenyl)ethyl]-5,6,7,8,9,10-hexahydro-7,10-epiminocyclohepta[b]indole A reaction tube with a septum cap was charged with (7S,10R)-2,11-dimethyl-5,6,7,8,9,10-hexahydro-7,10-epiminocyclohepta[b]indole (300 mg, 1.33 mmol; Example 23A), sodium (30-35% dispersion in paraffin; 203 mg, 2.65 mmol; Aldrich), hydroquinone (15.0 mg, 0.100 mmol; Aldrich) and dimethyl sulfoxide (1 mL), and the vessel was evacuated and flushed with nitrogen (3×). A solution of 1-methyl-2-vinylbenzene (204 mg, 1.723 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.25 (m, 1H), 1.73 (m, 2H), 1.91 (m, 1H), 2.25 (s, 3H), 2.35 (s, 3H), 2.42 (s, 3H), 2.48 (m, 1H), 2.75 (m, 1H), 3.15 (m, 2H), 4.06 (m, 1H), 4.26 (m, 2H), 4.80 (m, 1H), 6.65 (d, J=8 Hz, 1H), 6.98 (m, 1H), 7.15 (m, 2H), 7.28 (m, 2H), 7.33 (d, J=8 Hz, 1H); MS (ESI) m/z 345 (M+H)$^+$.

Example 40

2,11-dimethyl-5-[2-(4-methylphenyl)ethyl]-5,6,7,8,9,10-hexahydro-7,10-epiminocyclohepta[b]indole Example 40A 2-(diphenylmethylene)-1-(4-methylphenethyl)-1-p-tolylhydrazine General procedure B was used to convert 1-(diphenylmethylene)-2-p-tolylhydrazine (200 mg, 0.69 mmol; Example 36A) and 4-methylphenethylbromide (278 mg, 1.4 mmol; Aldrich) to the title compound: MS (DCI/NH$_3$) m/z 404 (M+H)$^+$.

Example 40B 2,11-dimethyl-5-[2-(4-methylphenyl)ethyl]-5,6,7,8,9,10-hexahydro-7,10-epiminocyclohepta[b]indole General procedure C was used to convert 2-(diphenylmethylene)-1-(4-methylphenethyl)-1-p-tolylhydrazine (300 mg, 0.74 mmol; Example 40A) and tropinone (155 mg, 1.1 mmol; Aldrich) to the title compound as the trifluoroacetic acid salt: $^1$H NMR (300 MHz, CDCl$_3$) δ ppm 1.12-1.39 (m, 1H), 1.71-1.98 (m, 2H), 2.05-2.33 (m, 5H), 2.35 (s, 3H), 2.47 (s, 3H), 2.65 (dd, J=16.5, 4.2 Hz, 1H), 2.88-3.20 (m, 2H), 3.32-3.54 (m, 1H), 3.98-4.30 (m, 3H), 6.70 (t, J=7.7 Hz, 1H), 6.99 (t, J=7.9 Hz, 1H), 7.06-7.17 (m, 3H), 7.26-7.45 (m, 2H); MS (DCI/NH$_3$) m/z 345 (M+H)$^+$.

Example 41

5-[2-(4-fluorophenyl)ethyl]-2,11-dimethyl-5,6,7,8,9,10-hexahydro-7,10-epiminocyclohepta[b]indole Example 41A 2-(diphenylmethylene)-1-(4-fluorophenethyl)-1-p-tolylhydrazine General procedure B was used to convert 1-(diphenylmethylene)-2-p-tolylhydrazine (200 mg, 0.69 mmol; Example 36A) and 4-fluorophenethylbromide (1.38 g, 6.8 mmol; Aldrich) to the title compound: MS (DCI/NH$_3$) m/z 409 (M+H)$^+$.

Example 41B

5-[2-(4-fluorophenyl)ethyl]-2,11-dimethyl-5,6,7,8,9,10-hexahydro-7,10-epiminocyclohepta[b]indole General procedure C was used to convert 2-(diphenylmethylene)-1-(4-fluorophenethyl)-1-p-tolylhydrazine (300 mg, 0.734 mmol; Example 41A) and tropinone (153 mg, 1.1 mmol; Aldrich) to the title compound as the trifluoroacetic acid salt: $^1$H NMR (300 MHz, CDCl$_3$) δ ppm 1.14-1.35 (m, 1H), 1.68-1.88 (m, 2H), 2.10-2.29 (m, 5H), 2.46 (s, 3H), 2.66 (dd, J=16.3, 4.4 Hz, 1H), 2.89-3.11 (m, 2H), 3.36-3.54 (m, 1H), 4.07-4.24 (m, 3H), 6.84-6.88 (m, 2H), 6.90 (s, 2H), 6.98 (dd, J=8.1, 1.4 Hz, 1H), 7.21 (d, J=8.1 Hz, 1H), 7.27 (s, 1H); MS (DCI/NH$_3$) m/z 349 (M+H)$^+$.

Example 42

5-[2-(3-fluorophenyl)ethyl]-2,11-dimethyl-5,6,7,8,9,10-hexahydro-7,10-epiminocyclohepta[b]indole Example 42A 2-(diphenylmethylene)-1-(3-fluorophenethyl)-1-p-tolylhydrazine General procedure B was used to convert 1-(diphenylmethylene)-2-p-tolylhydrazine (200 mg, 0.69 mmol; Example 36A) and 3-fluorophenethylbromide (1.38 g, 6.7 mmol; Aldrich) to the title compound: MS (DCI/NH$_3$) m/z 409 (M+H)$^+$.

Example 42B

5-[2-(3-fluorophenyl)ethyl]-2,11-dimethyl-5,6,7,8,9,10-hexahydro-7,10-epiminocyclohepta[b]indole General procedure C was used to convert 2-(diphenylmethylene)-1-(3-fluorophenethyl)-1-p-tolylhydrazine (300 mg, 0.734 mmol; Example 42A) and tropinone (153 mg, 1.1 mmol; Aldrich) to the title compound as the trifluoroacetic acid salt: $^1$H NMR (300 MHz, CDCl$_3$) δ ppm 1.17-1.39 (m, 1H), 1.71-1.93 (m, 2H), 2.11-2.31 (m, 5H), 2.41-2.55 (m, 3H), 2.58-2.75 (m, 1H), 2.89-3.15 (m, 2H), 3.35-3.52 (m, 1H), 4.08-4.30 (m, 3H), 6.58-6.67 (m, 1H), 6.69-6.77 (m, 1H), 6.84-6.95 (m, 1H), 6.95-7.04 (m, 1H), 7.12-7.24 (m, 2H), 7.25-7.31 (m, 1H); MS (DCI/NH$_3$) m/z 349 (M+H)$^+$.

Example 43

5-[2-(2-fluorophenyl)ethyl]-2,11-dimethyl-5,6,7,8,9,10-hexahydro-7,10-epiminocyclohepta[b]indole A reaction tube was charged with 2,11-dimethyl-5,6,7,8,9,10-hexahydro-7,10-epiminocyclohepta[b]indole (200 mg, 0.884 mmol; Example 1A), sodium (30-35% dispersion in paraffin; 122 mg, 1.591 mmol; Aldrich) and hydroquinone (9.7 mg, 0.088 mmol; Aldrich) and then sealed with a septum cap. A solution of 1-fluoro-2-vinylbenzene (162 mg, 1.326 mmol; Aldrich) in dimethyl sulfoxide (1 mL) was introduced through the septum and the vessel was evacuated and backfilled with nitrogen (~10×). The mixture was heated at 100° C. for 72 hours. After cooling, the reaction mixture was diluted with water (5 mL), extracted with dichloromethane, and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.39-1.56 (m, 1H), 1.92-2.15 (m, 4H), 2.29 (d, J=16.3 Hz, 2H), 2.39-2.93 (m, 5H), 3.13 (t, J=6.3 Hz, 2H), 4.09 (s, 1H), 4.15-4.39 (m, 2H), 4.82 (s, 1H), 6.61-6.70 (m, 1H), 6.84-6.95 (m, 1H), 6.98-7.08 (m, 1H), 7.09-7.23 (m, 3H), 7.31 (d, J=8.5 Hz, 1H); MS (ESI) m/z 349 (M+H)+.

Example 44

(7R,10S)-5-[2-(4-chlorophenyl)ethyl]-2,11-dimethyl-5,6,7,8,9,10-hexahydro-7,10-epiminocyclohepta[b]indole A reaction tube was charged with (7R,10S)-2,11-dimethyl-5,6,7,8,9,10-hexahydro-7,10-epiminocyclohepta[b]indole (200 mg, 0.884 mmol; Example 19A), sodium (30-35% dispersion in paraffin; 122 mg, 1.591 mmol; Aldrich) and hydroquinone (9.7 mg, 0.088 mmol; Aldrich) and then sealed with a septum cap. A solution of 1-chloro-4-vinylbenzene (245 mg, 1.767 mmol; Aldrich) in dimethyl sulfoxide (1 mL) was introduced through the septum and the vessel was evacuated and backfilled with nitrogen (~10×). The mixture was heated at 100° C. for 72 hours. After cooling, the reaction mixture the reaction mixture was diluted with water (5 mL), extracted with dichloromethane, and purified by reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, methanol-$d_4$) δ ppm 1.30-1.54 (m, 1H), 2.03-2.21 (m, 2H), 2.47-2.48 (m, 3H), 2.52-2.62 (m, 3H), 2.83-2.91 (m, 2H), 3.04-3.19 (m, 2H), 3.96-4.22 (m, 2H), 4.26-4.39 (m, 1H), 4.38-4.52 (m, 1H), 4.89-5.01 (m, 1H), 6.84 (t, J=8.7 Hz, 2H), 7.00-7.13 (m, 2H), 7.13-7.23 (m, 2H), 7.30 (s, 1H); MS (ESI) m/z 365 (M+H)+.

Example 45

(7S,10R)-5-[2-(4-chlorophenyl)ethyl]-2,11-dimethyl-5,6,7,8,9,10-hexahydro-7,10-epiminocyclohepta[b]indole A reaction tube with a septum cap was charged with (7S,10R)-2,11-dimethyl-5,6,7,8,9,10-hexahydro-7,10-epiminocyclohepta[b]indole (300 mg, 1.33 mmol; Example 23A), sodium (30-35% dispersion in paraffin; 203 mg, 2.65 mmol; Aldrich), hydroquinone (15.0 mg, 0.100 mmol; Aldrich) and dimethyl sulfoxide (1 mL), and the vessel was evacuated and flushed with nitrogen (3×). A solution of 1-chloro-4-vinylbenzene (239 mg, 1.723 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ 1.40 (m, 1H), 2.10 (m, 3H), 2.25 (s, 3H), 2.42 (s, 3H), 2.48 (m, 1H), 2.75 (m, 1H), 3.15 (m, 2H), 4.14 (m, 1H), 4.23 (m, 2H), 4.85 (m, 1H), 6.25 (d, J=2 Hz, 1H), 6.99 (d, J=8 Hz, 1H), 7.05 (m, 2H), 7.33 (d, J=8 Hz, 2H); MS (ESI) m/z 365 (M+H)+.

Example 46

(7S,10R)-5-[2-(2-chlorophenyl)ethyl]-2,11-dimethyl-5,6,7,8,9,10-hexahydro-7,10-epiminocyclohepta[b]indole A reaction tube with a septum cap was charged with (7S,10R)-2,11-dimethyl-5,6,7,8,9,10-hexahydro-7,10-epiminocyclohepta[b]indole (300 mg, 1.33 mmol; Example 23A), sodium (30-35% dispersion in paraffin; 203 mg, 2.65 mmol; Aldrich), hydroquinone (15.0 mg, 0.100 mmol; Aldrich) and dimethyl sulfoxide (1 mL), and the vessel was evacuated and flushed with nitrogen (3×). A solution of 1-chloro-2-vinylbenzene (239 mg, 1.723 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ 1.42 (m, 1H), 2.10 (m, 3H), 2.25 (s, 3H), 2.42 (s, 3H), 2.48 (m, 1H), 2.75 (m, 1H), 3.15 (m, 2H), 4.15 (m, 1H), 4.34 (m, 2H), 4.89 (m, 1H), 6.60 (dd, J=2, 8 Hz, 1H), 6.99 (m, 1H), 7.15 (m, 3H), 7.33 (m, 2H); MS (ESI) m/z 365 (M+H)+.

Example 47

5-[2-(4-bromophenyl)ethyl]-2,11-dimethyl-5,6,7,8,9,10-hexahydro-7,10-epiminocyclohepta[b]indole A reaction tube with a septum cap was charged with 2,11-dimethyl-5,6,7,8,9,10-hexahydro-7,10-epiminocyclohepta[b]indole (250 mg, 1.105 mmol; Example 1A), sodium (30-35% dispersion in paraffin; 170 mg, 2.21 mmol; Aldrich), hydroquinone (12.0 mg, 0.11 mmol; Aldrich) and dimethyl sulfoxide (1 mL), and the vessel was evacuated and flushed with nitrogen (3×). A solution of 1-bromo-4-vinylbenzene (303 mg, 1.657 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.40 (m, 1H), 2.10 (m, 3H), 2.27 (s, 3H), 2.42 (s, 3H), 2.48 (m, 1H), 2.75 (m, 1H), 3.15 (m, 2H), 4.15 (m, 1H), 4.23 (m, 2H), 4.90 (m, 1H), 6.65 (d, J=8 Hz, 1H), 7.15 (m, 1H), 7.35 (m, 5H); MS (ESI) m/z 410 (M+H)+.

Example 48

5-[2-(3-bromophenyl)ethyl]-2,11-dimethyl-5,6,7,8,9,10-hexahydro-7,10-epiminocyclohepta[b]indole A reaction tube with a septum cap was charged with 2,11-dimethyl-5,6,7,8,9,10-hexahydro-7,10-epiminocyclohepta[b]indole (300 mg, 1.33 mmol; Example 1A), sodium (30-35% dispersion in paraffin; 203 mg, 2.65 mmol; Aldrich), hydroquinone (15.0 mg, 0.100 mmol; Aldrich) and dimethyl sulfoxide (1 mL), and the vessel was evacuated and flushed with nitrogen (3×). A solution of 1-bromo-3-vinylbenzene (303 mg, 1.66 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.46 (m, 1H), 2.10 (m, 3H), 2.25 (s, 3H), 2.42 (s, 3H), 2.48 (m, 1H), 2.75 (m, 1H), 3.15 (m, 2H), 4.13 (m, 1H), 4.23 (m, 2H), 4.89 (m, 1H), 6.55 (d, J=2 Hz, 1H), 7.15 (m, 3H), 7.35 (m, 3H); MS (ESI) m/z 410 (M+H)$^+$.

Example 49

2,11-dimethyl-5-{2-[4-(trifluoromethyl)phenyl]ethyl}-5,6,7,8,9,10-hexahydro-7,10-epiminocyclohepta[b]indole A reaction tube with a septum cap was charged with 2,11-dimethyl-5,6,7,8,9,10-hexahydro-7,10-epiminocyclohepta[b]indole (250 mg, 1.1 mmol; Example 1A), sodium (30-35% dispersion in paraffin; 169 mg, 2.21 mmol; Aldrich), hydroquinone (15.0 mg, 0.100 mmol; Aldrich) and dimethyl sulfoxide (1 mL), and the vessel was evacuated and flushed with nitrogen (3×). A solution of 1-(trifluoromethyl)-4-vinylbenzene (285 mg, 1.66 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.37 (m, 1H), 2.05 (m, 3H), 2.25 (s, 3H), 2.42 (s, 3H), 2.55 (m, 1H), 2.88 (m, 1H), 3.19 (m, 2H), 4.11 (m, 1H), 4.29 (m, 2H), 4.86 (m 1H), 6.95 (d, J=8 Hz, 2H), 7.15 (m, 1H), 7.35 (m, 2H), 7.45 (d, J=8 Hz, 2H); MS (ESI) m/z 399 (M+H)$^+$.

Example 50

2,11-dimethyl-5-{2-[3-(trifluoromethyl)phenyl]ethyl}-5,6,7,8,9,10-hexahydro-7,10-epiminocyclohepta[b]indole A reaction tube with a septum cap was charged with 2,11-dimethyl-5,6,7,8,9,10-hexahydro-7,10-epiminocyclohepta[b]indole (250 mg, 1.1 mmol; Example 1A), sodium (30-35% dispersion in paraffin; 169 mg, 2.21 mmol; Aldrich), hydroquinone (15.0 mg, 0.100 mmol; Aldrich) and dimethyl sulfoxide (1 mL), and the vessel was evacuated and flushed with nitrogen (3×). A solution of 1-(trifluoromethyl)-3-vinylbenzene (285 mg, 1.66 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.38 (m, 1H), 2.05 (m, 3H), 2.25 (s, 3H), 2.42 (s, 3H), 2.55 (m, 1H), 2.88 (m, 1H), 3.18 (m, 2H), 4.11 (m, 1H), 4.29 (m, 2H), 4.85 (m, 1H), 7.02 (d, J=8 Hz, 1H), 7.15 (m, 2H), 7.30 (m, 3H), 7.47 (d, J=8 Hz, 1H); MS (ESI) m/z 399 (M+H)$^+$.

Example 51

(7R,10S)-2,11-dimethyl-5-{2-[3-(trifluoromethyl)phenyl]ethyl}-5,6,7,8,9,10-hexahydro-7,10-epiminocyclohepta[b]indole A reaction tube was charged with (7R,10S)-2,11-dimethyl-5,6,7,8,9,10-hexahydro-7,10-epiminocyclohepta[b]indole (200 mg, 0.884 mmol; Example 19A), sodium (30-35% dispersion in paraffin; 122 mg, 1.591 mmol; Aldrich) and hydroquinone (9.7 mg, 0.088 mmol; Aldrich) and then sealed with a septum cap. A solution of 1-trifluoromethyl-3-vinylbenzene (304 mg, 1.767 mmol; Aldrich) in dimethyl sulfoxide (1 mL) was introduced through the septum and the vessel was evacuated and backfilled with nitrogen (~10×). The mixture was heated at 100° C. for 72 hours. After cooling, the reaction mixture the reaction mixture was diluted with water (5 mL), extracted with dichloromethane, and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, methanol-d$_4$) δ ppm 1.30-1.54 (m, 1H), 2.03-2.21 (m, 2H), 2.47-2.48 (m, 3H), 2.52-2.62 (m, 3H), 2.83-2.91 (m, 2H), 3.04-3.19 (m, 2H), 3.96-4.22 (m, 2H), 4.26-4.39 (m, 1H), 4.38-4.52 (m, 1H), 4.89-5.01 (m, 1H), 7.02-7.11 (m, 1H), 7.18 (dd, J=18.5, 8.0 Hz, 2H), 7.27-7.33 (m, 1H), 7.34-7.44 (m, 1H), 7.45-7.58 (m, 2H); MS (ESI) m/z 399 (M+H)$^+$.

Example 52

(7S,10R)-2,11-dimethyl-5-{2-[3-(trifluoromethyl)phenyl]ethyl}-5,6,7,8,9,10-hexahydro-7,10-epiminocyclohepta[b]indole A reaction tube with a septum cap was charged with (7S,10R)-2,11-dimethyl-5,6,7,8,9,10-hexahydro-7,10-epiminocyclohepta[b]indole (250 mg, 1.1 mmol; Example 23A), sodium (30-35% dispersion in paraffin; 169 mg, 2.21 mmol; Aldrich), hydroquinone (15.0 mg, 0.100 mmol; Aldrich) and dimethyl sulfoxide (1 mL), and the vessel was evacuated and flushed with nitrogen (3×). A solution of 1-(trifluoromethyl)-3-vinylbenzene (285 mg, 1.66 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.38 (m, 1H), 2.05 (m, 3H), 2.25 (s, 3H), 2.42 (s, 3H), 2.55 (m, 1H), 2.88 (m, 1H), 3.18 (m, 2H), 4.11 (m, 1H), 4.29 (m, 2H), 4.85 (m, 1H), 7.02 (d, J=8 Hz, 1H), 7.15 (m, 2H), 7.30 (m, 3H), 7.47 (d, J=8 Hz, 1H); MS (ESI) m/z 399 (M+H)$^+$.

Example 53

2,11-dimethyl-5-{2-[2-(trifluoromethyl)phenyl]ethyl}-5,6,7,8,9,10-hexahydro-7,10-epiminocyclohepta[b]indole A reaction tube with a septum cap was charged with 2,11-dimethyl-5,6,7,8,9,10-hexahydro-7,10-epiminocyclohepta[b]indole (250 mg, 1.1 mmol; Example 1A), sodium (30-35% dispersion in paraffin; 169 mg, 2.21 mmol; Aldrich), hydroquinone (15.0 mg, 0.100 mmol; Aldrich) and dimethyl sulfoxide (1 mL), and the vessel was evacuated and flushed with nitrogen (3×). A solution of 1-(trifluoromethyl)-2-vinylbenzene (285 mg, 1.66 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.38 (m, 1H), 2.05 (m, 3H), 2.25 (s, 3H), 2.42 (s, 3H), 2.55 (m, 1H), 2.69 (m, 1H), 3.28 (m, 2H), 4.14 (m, 1H), 4.29 (m, 2H), 4.90 (m, 1H), 6.66 (d, J=8 Hz, 1H), 7.15 (dd, J=2, 8 Hz, 1H), 7.30 (m, 4H), 7.70 (d, J=8 Hz, 1H); MS (ESI) m/z 399 (M+H)$^+$.

Example 54

(7R,10S)-2,11-dimethyl-5-{2-[2-(trifluoromethyl)phenyl]ethyl}-5,6,7,8,9,10-hexahydro-7,10-epiminocyclohepta[b]indole A reaction tube was charged with (7R,10S)-2,11-dimethyl-5,6,7,8,9,10-hexahydro-7,10-epiminocyclohepta[b]indole (200 mg, 0.884 mmol; Example 19A), sodium (30-35% dispersion in paraffin; 122 mg, 1.591 mmol; Aldrich) and hydroquinone (9.7 mg, 0.088 mmol; Aldrich) and then sealed with a septum cap. A solution of 1-trifluoromethyl-2-vinylbenzene (304 mg, 1.767 mmol; Aldrich) in dimethyl sulfoxide (1 mL) was introduced through the septum and the vessel was evacuated and backfilled with nitrogen (~10×). The mixture was heated at 100° C. for 72 hours. After cooling, the reaction mixture was diluted with water (5 mL), extracted with dichloromethane, and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.38 (m, 1H), 2.05 (m, 3H), 2.25 (s, 3H), 2.42 (s, 3H), 2.55 (m, 1H), 2.69 (m, 1H), 3.29 (m, 2H), 4.16 (m, 1H), 4.29 (m, 2H), 4.92 (m, 1H), 6.66 (d, J=8 Hz, 1H), 7.15 (dd, J=2, 8 Hz, 1H), 7.30 (m, 4H), 7.70 (d, J=8 Hz, 1H); MS (ESI) m/z 399 (M+H)$^+$.

Example 55

(7S,10R)-2,11-dimethyl-5-{2-[2-(trifluoromethyl)phenyl]ethyl}-5,6,7,8,9,10-hexahydro-7,10-epiminocyclohepta[b]indole A reaction tube with a septum cap was charged with (7S,10R)-2,11-dimethyl-5,6,7,8,9,10-hexahydro-7,10-epiminocyclohepta[b]indole (250 mg, 1.1 mmol; Example 23A), sodium (30-35% dispersion in paraffin; 169 mg, 2.21 mmol; Aldrich), hydroquinone (15.0 mg, 0.100 mmol; Aldrich) and dimethyl sulfoxide (1 mL), and the vessel was evacuated and flushed with nitrogen (3×). A solution of 1-(trifluoromethyl)-2-vinylbenzene (285 mg, 1.66 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.38 (m, 1H), 2.05 (m, 3H), 2.25 (s, 3H), 2.42 (s, 3H), 2.55 (m, 1H), 2.69 (m, 1H), 3.29 (m, 2H), 4.16 (m, 1H), 4.29 (m, 2H), 4.92 (m, 1H), 6.66 (d, J=8 Hz, 1H), 7.15 (dd, J=2, 8 Hz, 1H), 7.30 (m, 4H), 7.70 (d, J=8 Hz, 1H); MS (ESI) m/z 399 (M+H)$^+$.

Example 56

5-[2-(4-methoxyphenyl)ethyl]-2,11-dimethyl-5,6,7,8,9,10-hexahydro-7,10-epiminocyclohepta[b]indole A reaction tube was charged with 2,11-dimethyl-5,6,7,8,9,10-hexahydro-7,10-epiminocyclohepta[b]indole (200 mg, 0.884 mmol; Example 1A), sodium (30-35% dispersion in paraffin; 122 mg, 1.591 mmol; Aldrich) and hydroquinone (9.7 mg, 0.088 mmol; Aldrich) and then sealed with a septum cap. A solution of 1-methoxy-4-vinylbenzene (178 mg, 1.326 mmol; Aldrich) in dimethyl sulfoxide (1 mL) was introduced through the septum and the vessel was evacuated and backfilled with nitrogen (~10×). The mixture was heated at 100° C. for 72 hours. After cooling, the reaction mixture was diluted with water (5 mL), extracted with dichloromethane, and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.38 (m, 1H), 2.05 (m, 3H), 2.25 (s, 3H), 2.42 (s, 3H), 2.55 (m, 1H), 2.69 (m, 1H), 3.29 (m, 2H), 4.16 (m, 1H), 4.29 (m, 2H), 4.92 (m, 1H), 6.73-6.82 (m, 1H), 7.13 (d, J=8.7 Hz, 1H), 7.17-7.27 (m, 4H), 7.33 (d, J=7.9 Hz, 1H); MS (ESI) m/z 361 (M+H)⁺.

Example 57

(7R,10S)-2,11-dimethyl-5-[(E)-2-phenylvinyl]-5,6,7,8,9,10-hexahydro-7,10-epiminocyclohepta[b]indole A solution of (7R,10S)-2,11-dimethyl-5,6,7,8,9,10-hexahydro-7,10-epiminocyclohepta[b]indole (314 mg, 1.387 mmol; Example 19A) in toluene/1,2-dimethoxyethane (6 mL, 5/1) under nitrogen atmosphere was treated with n-butyllithium (2 M in cyclohexane; 694 µL, 1.387 mmol; Aldrich) at room temperature. After stirring the mixture for 30 minutes, bis(dibenzylidene-acetone)palladium (63.8 mg, 0.111 mmol; Aldrich), tri-tert-butylphosphine (1 M in toluene; 222 µL, 0.222 mmol; Aldrich) and (E)-(2-bromovinyl)benzene (179 µL, 1.389 mmol; ARVI Products) were added. The flask was purged with nitrogen again and heated at 70° C. for 18 hours. After cooling, the reaction mixture was filtered through a pad of diatomaceous earth and the volatiles were evaporated. The residue was purified by flash chromatography (24 g silica gel, CH₃OH-10% concentrated NH₄OH) to afford the title compound: ¹H NMR (300 MHz, methanol-d₄) δ ppm 1.33 (d, J=10.2 Hz, 1H), 1.68 (m, 1H), 1.93 (t, J=9.3 Hz, 1H), 2.29 (m, 1H), 2.41 (s, 3H), 2.42 (s, 3H), 2.67 (d, J=16 Hz, 1H), 3.34 (m, 1H), 3.65 (bs, 1H), 4.23 (d, J=4 Hz, 1H), 6.79 (d, J=14.7 Hz, 1H), 7.04 (dd, J=1.4, 8 Hz, 1H), 7.21 (m, 1H), 7.26 (s, 1H), 7.34 (m, 2H), 7.50 (m, 2H), 7.57 (m, 2H); MS (ESI) m/z 329 (M+H)⁺.

Example 58

2,11-dimethyl-5-[(E)-2-(4-methylphenyl)vinyl]-5,6,7,8,9,10-hexahydro-7,10-epiminocyclohepta[b]indole The coupling of 2,11-dimethyl-5,6,7,8,9,10-hexahydro-7,10-epiminocyclohepta[b]indole (112 mg, 0.495 mmol, Example 1A) and 1-ethynyl-4-methylbenzene (232 mg, 2.0 mmol; Aldrich) was performed as described in Example 20 to afford the title compound as the minor isomer: ¹H NMR (300 MHz, methanol-d₄) δ ppm 1.60-1.71 (m, 1H), 1.87-1.96 (m, 1H), 2.21-2.32 (m, 2H), 2.33 (s, 3H), 2.40 (s, 3H), 2.42 (s, 3H), 2.65 (d, J=16 Hz, 1H), 3.34-3.43 (m, 1H), 3.60-3.67 (m, 1H), 4.22 (d, J=4 Hz, 1H), 6.75 (d, J=15 Hz, 1H), 7.03 (dd, J=8, 1 Hz, 1H), 7.16 (d, J=8 Hz, 2H), 7.26 (s, 1H), 7.38 (d, J=8 Hz, 2H), 7.49-7.56 (m, 2H); MS (DCI/NH₃) m/z 343=(M+H)⁺.

Example 59

(7R,10S)-2,11-dimethyl-5-[(E)-2-(4-methylphenyl)vinyl]-5,6,7,8,9,10-hexahydro-7,10-epiminocyclohepta[b]indole A reaction tube with a septum cap was charged with (7R,10S)-2,11-dimethyl-5,6,7,8,9,10-hexahydro-7,10-epiminocyclohepta[b]indole (200 mg, 0.884 mmol; Example 19A), cesium fluoride (175 mg, 1.149 mmol; Aldrich), hydroquinone (9.7 mg, 0.088 mmol; Aldrich) and 1-ethynyl-4-methylbenzene (123 mg, 1.060 mmol; Aldrich) and the vessel was evacuated and flushed with nitrogen. Dimethyl sulfoxide (2 mL) was added and the vessel was again evacuated and flushed with nitrogen, and then heated at 135° C. for 72 hours. After the mixture was cooled to room temperature, it was filtered, concentrated, and the resulting material was purified by reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: ¹H NMR (300 MHz, methanol-d₄) δ ppm 1.60 (m, 1H), 1.87 (m, 1H), 2.21 (m, 2H), 2.30 (s, 3H), 2.42 (s, 3H), 2.42 (s, 3H), 2.65 (d, J=15.5 Hz, 1H), 3.39 (m, 1H), 3.63 (m, 1H), 4.20 (d, J=3.5 Hz, 1H), 6.75 (d, J=15.5 Hz, 1H), 7.03 (dd, J=1, 8 Hz, 1H), 7.15 (d, J=8 Hz, 2H), 7.28 (s, 1H), 7.40 (d, J=8 Hz, 2H), 7.52 (m, 2H); MS (ESI) m/z 343 (M+H)⁺.

Example 60

2,11-dimethyl-5-[(Z)-2-(4-methylphenyl)vinyl]-5,6,7,8,9,10-hexahydro-7,10-epiminocyclohepta[b]indole The coupling of 2,11-dimethyl-5,6,7,8,9,10-hexahydro-7,10-epiminocyclohepta[b]indole (112 mg, 0.495 mmol, Example 1A) and 1-ethynyl-4-methylbenzene (232 mg, 2.0 mmol; Aldrich) was performed as described in Example 20. Additional purification by reverse-phase HPLC (Waters XBridge™ C18 5 µm OBD 30×100 mm column, flow rate 40 mL/minute, 5-95% gradient of acetonitrile in 0.1% trifluoroacetic acid over 15 minutes) afforded the title compound as the trifluoroacetic acid salt as the major isomer: ¹H NMR (300 MHz, pyridine-d₅) δ ppm 1.45-1.56 (m, 1H), 2.02-2.14 (m, 4H), 2.34-2.48 (m, 5H), 2.66 (ddd, J=18, 12, 6 Hz, 1H), 2.74 (s, 3H), 2.98 (br. s, 1H), 4.14 (dd, J=7, 5 Hz, 1H), 5.11 (d, J=5 Hz, 1H), 6.65 (d, J=9 Hz, 1H), 6.73 (d, J=9 Hz, 1H), 6.87 (d, J=8 Hz, 2H), 6.93 (d, J=8 Hz, 2H), 7.10 (d, J=8 Hz, 1H), 7.29 (d, J=8 Hz, 1H), 7.36 (s, 1H); MS (DCI/NH₃) m/z 343 (M+H)⁺.

Example 61

(7R,10S)-2,11-dimethyl-5-[(Z)-2-(4-methylphenyl)vinyl]-5,6,7,8,9,10-hexahydro-7,10-epiminocyclohepta[b]indole A portion of the racemic mixture from Example 60 (60 mg, 0.175 mmol) was purified further by preparative chiral supercritical fluid chromatography (ChiralPak® OD-H 5 µm column, 21×250 mm, 35° C., 10-50% gradient of CH₃OH—CO₂ containing 0.1% diethylamine, over 20 minutes) to afford the title compound as the first-eluting enantiomer: ¹H NMR (300 MHz, methanol-d₄) δ ppm 1.27-1.40 (m, 1H), 1.83-1.93 (m, 1H), 2.04-2.35 (m, 3H), 2.23 (s, 3H), 2.28 (s, 3H), 2.41 (s, 3H), 2.80 (dd, J=17, 5 Hz, 1H), 3.35-3.41 (m, 1H), 4.19 (d, J=5 Hz, 1H), 6.57 (d, J=8 Hz, 1H), 6.74 (d, J=8 Hz, 3H), 6.89 (dd, J=8, 1 Hz, 1H), 6.94 (d, J=8 Hz, 2H), 7.06 (d, J=8 Hz, 1H), 7.24 (s, 1H); MS (DCI/NH₃) m/z 343 (M+H)⁺.

Example 62

(7R,10S)-5-[(E)-2-(2,4-dimethylphenyl)vinyl]-2,11-dimethyl-5,6,7,8,9,10-hexahydro-7,10-epiminocyclohepta[b]indole A reaction tube was charged with (7R,10S)-2,11-dimethyl-5,6,7,8,9,10-hexahydro-7,10-epiminocyclohepta[b]indole (200 mg, 0.884 mmol; Example 19A), sodium (30-35% dispersion in paraffin; 122 mg, 1.591 mmol; Aldrich) and hydroquinone (9.7 mg, 0.088 mmol; Aldrich) and then sealed with a septum cap. A solution of 1-ethynyl-2,4- dimethylbenzene (230 mg, 1.767 mmol; Aldrich) in dimethyl sulfoxide (1 mL) was introduced through the septum and the vessel was evacuated and backfilled with nitrogen (~10×). The mixture was heated at 100° C. for 72 hours. After cooling, the reaction mixture the reaction mixture was diluted with water (5 mL), extracted with dichloromethane, and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, methanol-$d_4$) δ ppm 1.60 (m, 1H), 1.87 (m, 1H), 2.21 (m, 2H), 2.30 (s, 3H), 2.42 (s, 3H), 2.42-2.48 (m, 8H), 2.65 (d, J=15.5 Hz, 1H), 3.39 (m, 1H), 3.63 (m, 1H), 4.20 (d, J=3.5 Hz, 1H), 7.06-7.17 (m, 2H), 7.31-7.42 (m, 2H), 7.45-7.53 (m, 1H), 7.54-7.64 (m, 1H); MS (ESI) m/z 356 (M+H)$^+$.

Example 63

5-[(4-chlorophenyl)acetyl]-2,11-dimethyl-5,6,7,8,9,10-hexahydro-7,10-epiminocyclohepta[b]indole Example 63A 2-(4-chlorophenyl)-N'-(diphenylmethylene)-N-p-tolylacetohydrazide To an ice-chilled solution of 1-(diphenylmethylene)-2-p-tolylhydrazine (270 mg, 0.94 mmol; Example 36A) and N,N-diisopropyl-N-ethylamine (120 mg, 0.94 mmol; Aldrich) in N,N-dimethylformamide (2.0 mL) was added 2-(4-chlorophenyl)acetyl chloride (178 mg, 0.94 mmol; Alfa Aesar). After 10 minutes the ice bath was removed and the reaction mixture was stirred at room temperature overnight (18 hours). The reaction mixture was diluted with water (10 mL) and extracted with dichloromethane (2×20 mL). The combined organic extracts were dried over magnesium sulfate, filtered, and concentrated in vacuo to afford the crude product, which was carried on to the next step without further purification: LC/MS m/z 439 (M+H)$^+$.

Example 63 B

5-[(4-chlorophenyl)acetyl]-2,11-dimethyl-5,6,7,8,9,10-hexahydro-7,10-epiminocyclohepta[b]indole General procedure C was used to convert 2-(4-chlorophenyl)-N'-(diphenylmethylene)-N-p-tolylacetohydrazide (400 mg, 0.91 mmol; Example 63A) and tropinone (190 mg, 1.4 mmol; Aldrich) into the title compound as the trifluoroacetic acid salt: MS (DCI/NH$_3$) m/z 395.8 (M+NH$_4$)$^+$.

Example 64

5-[2-(4-chlorophenyl)propyl]-2,11-dimethyl-5,6,7,8,9,10-hexahydro-7,10-epiminocyclohepta[b]indole A reaction tube with a septum cap was charged with 2,11-dimethyl-5,6,7,8,9,10-hexahydro-7,10-epiminocyclohepta[b]indole (250 mg, 1.1 mmol; Example 1A), sodium (30-35% dispersion in paraffin; 169 mg, 2.21 mmol; Aldrich), hydroquinone (15.0 mg, 0.100 mmol; Aldrich) and dimethyl sulfoxide (1 mL), and the vessel was evacuated and flushed with nitrogen (3×). A solution of 1-chloro-4-(prop-1-en-2-yl)benzene (253 mg, 1.66 mmol; Aldrich) in dimethyl sulfoxide (1.5 mL) was added via a syringe and the vessel was again evacuated and flushed with nitrogen, and then heated at 100° C. for 72 hours. After the mixture was cooled to room temperature, brine (2 mL) was added and the mixture was stirred for few minutes. Ethyl acetate (4 mL) was added and mixture was stirred for several minutes at 40° C. The organic phase was separated, concentrated, and the resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.38 (m, 1H), 1.41 (d, J=7.5 Hz, 3H), 2.05 (m, 3H), 2.25 (s, 3H), 2.42 (s, 3H), 2.55 (m, 1H), 2.69 (m, 1H), 3.29 (m, 1H), 4.16 (m, 1H), 4.29 (m, 2H), 4.87 (m 1H), 6.82 (m, 3H), 7.18 (m, 3H), 7.30 (d, J=8 Hz, 1H); MS (ESI) m/z 379 (M+H)$^+$.

Example 65

5-(4-isopropenylphenyl)-2,11-dimethyl-5,6,7,8,9,10-hexahydro-7,10-epiminocyclohepta[b]indole A reaction tube was charged with 2,11-dimethyl-5,6,7,8,9,10-hexahydro-7,10-epiminocyclohepta[b]indole (200 mg, 0.884 mmol; Example 1A), sodium (30-35% dispersion in paraffin; 122 mg, 1.591 mmol; Aldrich) and hydroquinone (9.7 mg, 0.088 mmol; Aldrich) and then sealed with a septum cap. A solution of 1-fluoro-4-(prop-1-en-2-yl)benzene (180 mg, 1.326 mmol; Aldrich) in dimethyl sulfoxide (1 mL) was introduced through the septum and the vessel was evacuated and backfilled with nitrogen (~10×). The mixture was heated at 100° C. for 72 hours. After cooling, the reaction mixture was diluted with water (5 mL), extracted with dichloromethane, and purified by reverse-phase HPLC (Phenomenex® Luna® C8(2) 5 min 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.78-1.98 (m, 1H), 2.22 (s, 3H), 2.48 (s, 3H), 2.57-2.78 (m, 4H), 2.83 (s, 3H), 3.28 (d, J=4.4 Hz, 1H), 4.30 (s, 1H), 5.01 (s, 1H), 5.21 (s, 1H), 5.44 (s, 1H), 7.06 (d, J=9.5 Hz, 1H), 7.15-7.21 (m, 1H), 7.22-7.34 (m, 3H), 7.57-7.67 (m, 2H); MS (ESI) m/z 343 (M+H).

Example 66

2,11-dimethyl-5-(3-phenylpropyl)-5,6,7,8,9,10-hexahydro-7,10-epiminocyclohepta[b]indole A flask containing tetrahydrofuran (2.0 mL) was charged with sodium amide (0.014 g, 0.331 mmol; Alfa Aesar), chilled to 0° C., and treated with 2,11-dimethyl-5,6,7,8,9,10-hexahydro-7,10-epiminocyclohepta[b]indole (50 mg, 0.220 mmol; Example 1A), added in portions. After 5 minutes, the ice bath was removed and stirring was continued for 1 hour. The solution was chilled again in an ice bath and (3-bromopropyl)benzene (44 mg, 0.221 mmol; Aldrich) was added dropwise. After 10 minutes, the ice bath was removed and stirring was continued for 1.5 hours. The reaction mixture was then diluted with water (10 mL) and extracted with dichloromethane (2×15 mL). The combined organic extracts were dried over magnesium sulfate, filtered, concentrated in vacuo, and the resulting residue was purified by reverse-phase HPLC (Waters XBridge™ C18 5 μm OBD column, 30×100 mm, flow rate 40 mL/minute, 5-95% gradient of acetonitrile in 0.1% trifluoroacetic acid, over 15 minutes) to afford the title compound as the trifluoroacetate salt: ¹H NMR (300 MHz, CDCl$_3$) δ ppm 1.00 (d, J=14.6 Hz, 1H), 1.28-1.52 (m, 2H), 1.61 (s, 1H), 1.93-2.15 (m, 5H), 2.52-2.82 (m, 5H), 2.95 (d, J=3.7 Hz, 1H), 3.18 (dd, J=17.6, 4.4 Hz, 1H), 3.90-4.16 (m, 2H), 4.35 (s, 1H), 4.97 (s, 1H), 6.98-7.18 (m, 5H), 7.29-7.36 (m, 3H); MS (DCI/NH$_3$) m/z 345 (M+H)$^+$.

Example 67

5-[2-(4-fluorophenoxy)ethyl]-2,11-dimethyl-5,6,7,8, 9,10-hexahydro-7,10-epiminocyclohepta[b]indole A flask containing tetrahydrofuran (5.0 mL) was charged with sodium amide (109 mg, 2.65 mmol; Alfa Aesar), chilled to 0° C., and treated with 2,11-dimethyl-5,6,7,8,9,10-hexahydro-7,10-epiminocyclohepta[b]indole (300 mg, 1.326 mmol; Example 1A), added in portions. After 5 minutes, the ice bath was removed and the mixture was heated to 60° C. for 15 minutes. The solution was cooled to room temperature and 1-(2-bromoethoxy)-4-fluorobenzene (348 mg, 1.591 mmol; Aldrich) was added slowly. The reaction mixture was stirred overnight at room temperature, then diluted with water (5 mL) and extracted with dichloromethane (2×10 mL). The combined organic extracts were dried over magnesium sulfate, filtered, concentrated in vacuo, and the resulting residue was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: ¹H NMR (300 MHz, methanol-d$_4$) δ ppm 1.79-2.07 (m, 1H), 2.12-2.30 (m, 1H), 2.34-2.50 (m, 4H), 2.50-2.66 (m, 1H), 2.93 (s, 3H), 3.02-3.20 (m, 1H), 3.66 (d, J=17.1 Hz, 1H), 4.13-4.37 (m, 3H), 4.42-4.58 (m, 2H), 4.93-5.12 (m, 1H), 6.61-6.84 (m, 2H), 6.81-7.01 (m, 2H), 7.01-7.14 (m, 1H), 7.31 (s, 1H), 7.34-7.43 (m, 1H); MS (ESI) m/z 365 (M+H)$^+$.

Example 68

(7S,10R)-5-isoquinolin-7-yl-2,11-dimethyl-5,6,7,8,9, 10-hexahydro-7,10-epiminocyclohepta[b]indole A 30-mL microwave reaction tube was charged with (7S,10R)-2,11-dimethyl-5,6,7,8,9,10-hexahydro-7,10-epiminocyclohepta[b]indole (453 mg, 2.0 mmol; Example 23A), 7-bromoisoquinoline (624 mg, 3.00 mmol; Frontier), bis(tri-t-butylphosphine)palladium(0) (51.1 mg, 0.100 mmol; Aldrich) and anhydrous dioxane (8 mL). The vessel was flushed with nitrogen and sodium tert-butoxide (481 mg, 5.00 mmol; Aldrich) was added. After purging the reaction mixture with nitrogen again, it was sealed and heated to 180° C. (Biotage Personal Chemistry, maximum 300 W) with stirring for 30 minutes. The mixture was cooled and quenched with water, and then extracted with ethyl acetate. The organic phase was concentrated and purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: ¹H NMR (300 MHz, methanol-d$_4$) δ ppm 1.61-1.73 (m, 1H), 1.94-2.04 (m, 1H), 2.23-2.43 (m, 3H), 2.43 (s, 3H), 2.45 (s, 3H), 3.21-3.30 (m, 1H), 3.57-3.63 (m, 1H), 4.30 (d, J=5 Hz, 1H), 6.96 (d, J=8 Hz, 1H), 7.18 (d, J=8 Hz, 1H), 7.33 (s, 1H), 7.84 (dd, J=9, 2 Hz, 1H), 7.92 (d, J=6 Hz, 1H), 8.10-8.18 (m, 2H), 8.50 (d, J=6 Hz, 1H), 9.32 (s, 1H); MS (DCI/NH$_3$) m/z 354 (M+H)$^+$.

Example 69

2,11-dimethyl-5-(phenylsulfonyl)-5,6,7,8,9,10-hexahydro-7,10-epiminocyclohepta[b]indole A solution of 2,11-dimethyl-5,6,7,8,9,10-hexahydro-7,10-epiminocyclohepta[b]indole (230.8 mg, 1.020 mmol; Example 1A) in tetrahydrofuran (5 mL) was treated with potassium tert-butoxide (1 M in tetrahydrofuran; 1.6 mL, 1.6 mmol; Aldrich), and the reaction was stirred for 30 minutes at ambient temperature. Benzenesulfonyl chloride (291.9 mg, 1.653 mmol; Aldrich) was added and the reaction was stirred for 4 hours. The mixture was diluted with water (35 mL) and 1 M NaOH (5 mL) and extracted with dichloromethane (2×35 mL). The combined organic layers were dried over sodium sulfate, filtered, concentrated, and the residue was purified by reverse-phase HPLC (Phenomenex® Luna® Combi-HTS™ C8(2) 5 μm 100 Å 30×75 mm column, gradient of 10-95% acetonitrile in 0.1% trifluoroacetic acid, flow rate 50 mL/minute) to afford the title compound as the trifluoroacetic acid salt: ¹H NMR (300 MHz, methanol-d$_4$) δ ppm 1.92-1.98 (m, 1H), 2.20-2.27 (m, 1H), 2.41 (s, 3H), 2.57-2.62 (s, 1H), 2.76 (br s, 1H), 2.94 (s, 3H), 3.37-3.44 (m, 1H), 3.72-3.78 (m, 1H), 4.31-4.35 (m, 1H), 4.99-5.00 (m, 1H), 7.22 (d, J=8.7 Hz, 1H), 7.32 (s, 1H), 7.51-7.56 (m, 2H), 7.63-7.68 (m, 1H), 7.88-7.91 (m, 2H), 7.98 (d, J=8.7 Hz, 1H); MS (DCI/NH$_3$) m/z 367 (M+H)$^+$. Anal. Calcd. for C$_{21}$H$_{22}$N$_2$O$_2$S.1.15 TFA: C, 56.24; H, 4.69; N, 5.63. Found: C, 56.19; H, 4.70; N, 5.66.

Example 70

(7R,10S)-2,11-dimethyl-5-[(4-methylphenyl)sulfonyl]-5,6,7,8,9,10-hexahydro-7,10-epiminocyclohepta [b]indole The reaction of (7R,10S)-2,11-dimethyl-5,6,7,8,9,10-hexahydro-7,10-epiminocyclohepta[b]indole (253.0 mg, 1.118 mmol; Example 19A) and p-toluenesulfonyl chloride (284.1 mg, 490 mmol; Aldrich) was performed as described in Example 69 except that the crude material was purified by flash chromatography (silica gel, CH$_2$Cl$_2$/CH$_3$OH 10:1) to afford the title compound: ¹H NMR (300 MHz, methanol-d$_4$) δ ppm 1.49-1.54 (m, 1H), 1.76-1.82 (m, 1H), 2.20-2.28 (m, 5H), 2.33 (s, 3H), 2.38 (s, 3H), 2.79 (d, J=17.9 Hz, 1H), 3.34-3.39 (m, 1H), 3.54-3.58 (m, 1H), 4.09 (d, J=4.8 Hz, 1H), 7.09 (d, J=8.7 Hz, 1H), 7.20 (s, 1H), 7.25-7.28 (m, 2H), 7.63-7.65 (m, 2H), 7.93 (d, J=8.3 Hz, 1H); MS (DCI/NH$_3$) m/z 381 (M+H)$^+$. Anal. Calcd. for C$_{22}$H$_{24}$N$_2$O$_2$S: C, 69.44; H, 6.36; N, 7.36. Found: C, 69.22; H, 6.52; N, 7.27.

Example 71

(7S,10R)-2,11-dimethyl-5-[(4-methylphenyl)sulfonyl]-5,6,7,8,9,10-hexahydro-7,10-epiminocyclohepta [b]indole The reaction of (7S,10R)-2,11-dimethyl-5,6,7,8,9,10-hexahydro-7,10-epiminocyclohepta[b]indole (196.1 mg, 0.866 mmol; Example 23A) and p-toluenesulfonyl chloride (199.5 mg, 1.046 mmol, Aldrich) was performed as described in Example 69 except that the crude material was purified by flash chromatography (silica gel, CH$_2$Cl$_2$/CH$_3$OH 10:1) to afford the title compound: ¹H NMR (300 MHz, methanol-d$_4$) δ ppm 1.49-1.54 (m, 1H), 1.76-1.82 (m, 1H), 2.20-2.28 (m, 5H), 2.33 (s, 3H), 2.38 (s, 3H), 2.79 (d, J=17.9 Hz, 1H), 3.34-3.39 (m, 1H), 3.54-3.58 (m, 1H), 4.09

(d, J=4.8 Hz, 1H), 7.09 (d, J=8.7 Hz, 1H), 7.20 (s, 1H), 7.25-7.28 (m, 2H), 7.63-7.65 (m, 2H), 7.93 (d, J=8.8 Hz, 1H); MS (DCI/NH$_3$) m/z 381 (M+H)$^+$

Example 72

5-[(4-fluorophenyl)sulfonyl]-2,11-dimethyl-5,6,7,8,9,10-hexahydro-7,10-epiminocyclohepta[b]indole The reaction of 2,11-dimethyl-5,6,7,8,9,10-hexahydro-7,10-epiminocyclohepta[b]indole (198.4 mg, 0.887 mmol; Example 1A) and 4-fluorobenzenesulfonyl chloride (243.2 mg, 1.250 mmol, Aldrich) was performed as described in Example 69 except that it was purified by preparative HPLC (Phenomenex® Luna® Combi-HTS™ C8(2) 5 µm 100 Å AXIA™ 30×75 mm column, gradient of 10-100% acetonitrile in 0.1% trifluoroacetic acid, flow rate 50 mL/minute) to afford the title compound as the trifluoroacetic acid salt: $^1$H NMR (300 MHz, methanol-d$_4$) δ ppm 1.95-2.01 (m, 1H), 2.21-2.28 (m, 1H), 2.41 (s, 3H), 2.55-2.63 (m, 2H), 3.34-3.43 (m, 4H), 3.71-3.79 (m, 1H), 4.32-4.34 (m, 1H), 4.99-5.05 (m, 1H), 7.21-7.33 (m, 4H), 7.95-8.01 (m, 3H); MS (DCI/NH$_3$) m/z 385 (M+H)$^+$. Anal. Calcd. for C$_{21}$H$_{21}$FN$_2$O$_2$S.1.1 TFA: C, 54.65; H, 4.37; N, 5.49; F, 16.02. Found: C, 54.45; H, 4.31; N, 5.49; F, 15.94.

Example 73

5-[(4-chlorophenyl)sulfonyl]-2,11-dimethyl-5,6,7,8,9,10-hexahydro-7,10-epiminocyclohepta[b]indole The reaction of 2,11-dimethyl-5,6,7,8,9,10-hexahydro-7,10-epiminocyclohepta[b]indole (114.1 mg, 0.504 mmol; Example 1A) and 4-chlorobenzenesulfonyl chloride (152.7 mg, 0.723 mmol, Aldrich) was performed as described in Example 69 except that the crude material was purified by flash chromatography (silica gel, CH$_2$Cl$_2$/CH$_3$OH 10:1) to afford the title compound: $^1$H NMR (300 MHz, methanol-d$_4$) δ ppm 1.49-1.56 (m, 1H), 1.78-1.81 (m, 1H), 2.22-2.32 (m, 5H), 2.39 (s, 3H), 2.79 (d, J=17.5 Hz, 1H), 3.34-3.39 (m, 1H), 3.53-3.59 (m, 1H), 4.10 (d, J=5.2 Hz, 1H), 7.12 (d, J=8.3 Hz, 1H), 7.22 (s, 1H), 7.46-7.51 (m, 2H), 7.73-7.78 (m, 2H), 7.93 (d, J=8.7 Hz, 1H); MS (DCI/NH$_3$) m/z 401 (M+H)$^+$. Anal. Calcd. for C$_{21}$H$_{21}$ClN$_2$O$_2$S.0.4 H$_2$O: C, 61.80; H, 5.38; N, 6.86. Found: C, 61.51; H, 5.02; N, 6.70.

Example 74

2,11-dimethyl-5-{[4-(trifluoromethyl)phenyl]sulfonyl}-5,6,7,8,9,10-hexahydro-7,10-epiminocyclohepta[b]indole The reaction of 2,11-dimethyl-5,6,7,8,9,10-hexahydro-7,10-epiminocyclohepta[b]indole (232.1 mg, 1.026 mmol; Example 1A) and (trifluoromethyl)benzenesulfonyl chloride (367.9 mg, 1.504 mmol, Aldrich) was performed as described in Example 69 except that the crude material was purified by flash chromatography (silica gel, CH$_2$Cl$_2$/CH$_3$OH 10:1) to afford the title compound: $^1$H NMR (300 MHz, methanol-d$_4$) δ ppm 1.64-1.70 (m, 1H), 1.90-1.94 (m, 1H), 2.22-2.35 (m, 2H), 2.40 (s, 3H), 2.47 (s, 3H), 2.98 (d, J=18.2 Hz, 1H), 3.43-3.53 (m, 1H), 3.78-3.52 (m, 1H), 4.35-4.37 (m, 1H), 7.17 (d, J=8.7 Hz, 1H), 7.26 (s, 1H), 7.73 (d, J=8.3 Hz, 1H), 7.80-7.83 (m, 2H), 7.95-8.01 (m, 2H); MS (DCI/NH$_3$) m/z 435 (M+H)$^+$.

Example 75

5-[(4-methoxyphenyl)sulfonyl]-2,11-dimethyl-5,6,7,8,9,10-hexahydro-7,10-epiminocyclohepta[b]indole The reaction of 2,11-dimethyl-5,6,7,8,9,10-hexahydro-7,10-epiminocyclohepta[b]indole (219.2 mg, 0.969 mmol; Example 1A) and 4-methoxybenzenesulfonyl chloride (278.5 mg, 1.348 mmol, Aldrich) was performed as described in Example 69 except that the crude material was purified by flash chromatography (silica gel, CH$_2$Cl$_2$/CH$_3$OH 10:1) to afford the title compound: $^1$H NMR (300 MHz, methanol-d$_4$) δ ppm 1.50-1.55 (m, 1H), 1.77-1.83 (m, 1H), 2.20-2.28 (m, 5H), 2.38 (s, 3H), 2.78 (d, J=18.2 Hz, 1H), 3.34-3.39 (m, 1H), 3.55-3.58 (m, 1H), 3.79 (s, 3H), 4.09 (d, J=4.8 Hz, 1H), 6.93-6.98 (m, 2H), 7.10 (d, J=8.7 Hz, 1H), 7.20 (s, 1H), 7.68-7.74 (m, 2H), 7.94 (d, J=8.3 Hz, 1H); MS (DCI/NH$_3$) m/z 397 (M+H)$^+$. Anal. Calcd. for C$_{22}$H$_{24}$N$_2$O$_3$S.0.55 H$_2$O: C, 65.02; H, 6.23; N, 6.89. Found: C, 65.15; H, 6.18; N, 6.73.

Example 76

2,11-dimethyl-5-{[4-(trifluoromethoxy)phenyl]sulfonyl}-5,6,7,8,9,10-hexahydro-7,10-epiminocyclohepta[b]indole The reaction of 2,11-dimethyl-5,6,7,8,9,10-hexahydro-7,10-epiminocyclohepta[b]indole (235.2 mg, 1.039 mmol; Example 1A) and 4-(trifluoromethoxy)benzenesulfonyl chloride (399.9 mg, 1.534 mmol, Aldrich) was performed as described in Example 69 except that the crude material was purified by flash chromatography (silica gel, CH$_2$Cl$_2$/CH$_3$OH 10:1) to afford the title compound: $^1$H NMR (300 MHz, methanol-d$_4$) δ ppm 1.46-1.56 (m, 1H), 1.77-1.87 (m, 1H), 2.18-2.31 (m, 5H), 2.39 (s, 3H), 2.79 (d, J=18.2 Hz, 1H), 3.34-3.39 (m, 1H), 3.56-3.59 (m, 1H), 4.10 (d, J=4.8 Hz, 1H), 7.13 (d, J=8.3 Hz, 1H), 7.23 (s, 1H), 7.36-7.39 (m, 2H), 7.86-7.91 (m, 2H), 7.95 (d, J=8.7 Hz, 1H); MS (DCI/NH$_3$) m/z 451 (M+H)$^+$. Anal. Calcd. for C$_{22}$H$_{21}$F$_3$N$_2$O$_3$S: C, 58.66; H, 4.70; N, 6.22; F, 12.65. Found: C, 58.77; H, 4.76; N, 6.18; F, 12.66.

Example 77

2,11-dimethyl-5-(pyridin-3-ylsulfonyl)-5,6,7,8,9,10-hexahydro-7,10-epiminocyclohepta[b]indole The reaction of 2,11-dimethyl-5,6,7,8,9,10-hexahydro-7,10-epiminocyclohepta[b]indole (216.6 mg, 0.857 mmol; Example 1A) and pyridine-3-sulfonyl chloride (290.2 mg, 1.634 mmol, Astatech) was performed as described in Example 69 except that the crude material was purified by flash chromatography (silica gel, CH$_2$Cl$_2$/CH$_3$OH 10:1) to afford the title compound: $^1$H NMR (300 MHz, methanol-d$_4$) δ ppm 1.52-1.58 (m, 1H), 1.77-1.83 (m, 1H), 2.24-2.30 (m, 5H), 2.39 (s, 3H), 2.82 (d, J=18.0 Hz, 1H), 3.34-3.42 (m, 1H), 3.53-3.62 (m, 1H), 4.11 (d, J=5.1 Hz, 1H), 7.15 (d, J=8.2 Hz, 1H), 7.23 (s, 1H), 7.50 (ddd, J=8.2, 5.0, 0.7 Hz, 1H), 7.94 (d, J=8.5 Hz, 1H), 8.16 (ddd, J=8.2, 2.5, 1.5 Hz, 1H), 8.71 (dd, J=4.8, 1.4 Hz, 1H), 8.91 (dd, J=2.4, 0.7 Hz, 1H); MS (DCI/NH$_3$) m/z 368 (M+H)$^+$. Anal. Calcd. for C$_{20}$H$_{21}$N$_3$O$_2$S.0.4 H$_2$O: C, 64.11; H, 5.86; N, 11.22. Found: C, 63.74; H, 5.48; N, 11.03.

Example 78

11-methyl-5-[2-(6-methylpyridin-3-yl)ethyl]-5,6,7,8,9,10-hexahydro-7,10-epiminocyclohepta[b]indole

Example 78A 11-methyl-5,6,7,8,9,10-hexahydro-7,10-epiminocyclohepta[b]indole A mixture of phenylhydrazine hydrochloride (2.89 g, 19.99 mmol; Aldrich) and tropinone (2.78 g, 19.99 mmol; Aldrich) in ethanol (15 mL) was heated at reflux for 3 hours. The resulting solution was cooled to room temperature and the volatiles were removed under vacuum. The residue was taken up in 7% (w/w) $H_2SO_4$/dioxane (42 g) and heated at 60° C. under nitrogen for 14 hours. The mixture was cooled to room temperature and concentrated under vacuum. The residue was dissolved in water (25 mL) and the solution was made basic (pH >9) by addition of 25% NaOH (20 mL). The resulting mixture was extracted with $CH_2Cl_2$ (2×25 mL) and the extract was concentrated to residue which was purified by flash chromatography (120 g silica eluted with $CH_2Cl_2$—$CH_3OH$-14.8 M aqueous $NH_4OH$, 90:10:1) followed by crystallization from ethyl acetate to provide the title compound: $^1$H NMR (300 MHz, methanol-$d_4$) δ ppm 1.56-1.72 (m, 1H), 1.89 (t, J=9.3 Hz, 1H), 2.20-2.34 (m, 2H), 2.36 (s, 3H), 2.46 (d, J=16.7 Hz, 1H), 3.25 (dd, J=16.7, 4.8 Hz, 1H), 3.55 (t, J=5.4 Hz, 1H), 4.20 (d, J=5.2 Hz, 1H), 6.90-7.05 (m, 2H), 7.25 (d, J=7.1 Hz, 1H), 7.38 (d, J=7.1 Hz, 1H); MS (DCI) m/z 213 (M+H)$^+$.

Example 78B 11-methyl-5-[2-(6-methylpyridin-3-yl)ethyl]-5,6,7,8,9,10-hexahydro-7,10-epiminocyclohepta[b]indole The product of Example 78A (150 mg, 0.707 mmol) and sodium dispersion in paraffin (30%, 120 mg, 1.566 mmol; Aldrich) were weighed into a 20 mL glass vial with stir bar and septum cap. Dimethyl sulfoxide (2 mL) was added, and the mixture was stirred at room temperature under nitrogen for 20 minutes. A solution of hydroquinone (22 mg, 0.20 mmol; Aldrich) and 2-methyl-5-vinylpyridine (166 mg, 1.39 mmol; International Publication No. WO2001/017968) in dimethyl sulfoxide (0.5 mL) was added, and the mixture was heated at 100° C. under nitrogen for 14 hours. The mixture was cooled to room temperature, diluted with water (40 mL) and extracted with dichloromethane (3×20 mL), then with ethyl acetate (2×20 mL). The combined organic phase was concentrated under vacuum, and the residue was passed through a column of silica gel with dichloromethane (150 mL), then $CH_2Cl_2$—$CH_3OH$-14.8 M aqueous $NH_4OH$, (90:10:1). The product was further purified by reverse-phase HPLC [Waters XBridge™ C18 5 µm OBD 30×100 mm column, flow rate 40 mL/minute, 20-95% gradient of acetonitrile in buffer (0.1 M aqueous ammonium bicarbonate, adjusted to pH 10 with ammonium hydroxide) over 20 minutes] to provide the title compound (120 mg). This material was taken up in ethanol (5 mL) and a solution of HCl in dioxane (4 M, 0.4 mL) was added. Ethyl acetate (10 mL) was added, and the mixture was heated to boiling for 2 minutes, then cooled to room temperature, and finally placed in the freezer to complete precipitation. The precipitate was collected by filtration and dried under vacuum to provide the title compound as the dihydrochloride salt: $^1$H NMR (300 MHz, methanol-$d_4$) δ ppm 1.11-1.23 (m, 1H), 1.74-1.83 (m, 1H), 1.90 (dd, J=16.6, 1.0 Hz, 1H), 2.05-2.27 (m, 2H), 2.19 (s, 3H), 2.41 (s, 3H), 2.77 (dd, J=16.6, 4.4 Hz, 1H), 2.99-3.17 (m, 2H), 3.35-3.44 (m, 1H), 4.14 (d, J=5.1 Hz, 1H), 4.19-4.40 (m, 2H), 7.01 (td, J=7.4, 1.2 Hz, 1H), 7.06-7.14 (m, 2H), 7.24 (dd, J=8.0, 2.2 Hz, 1H), 7.34 (d, J=8.1 Hz, 1H), 7.40 (d, J=7.8 Hz, 1H), 7.76 (d, J=2.0 Hz, 1H); MS (DCI) m/z 332 (M+H)$^+$. Anal. Calc. for $C_{22}H_{25}N_3 \cdot 2HCl \cdot 1.2H_2O$): C, 62.03; H, 6.96; N, 9.86. Found: C, 62.09; H, 7.13; N, 9.84.

Example 79

11-methyl-5-(2-phenylethyl)-5,6,7,8,9,10-hexahydro-7,10-epiminocyclohepta[b]indole

Example 79A 1-(diphenylmethylene)-2-phenylhydrazine

General procedure A was used to convert benzophenone hydrazone (3.42 g, 20 mmol; Aldrich) and 1-bromobenzene (3.14 g, 20 mmol; Aldrich) to the title compound: MS (DCI/NH$_3$) m/z 273 (M+H)$^+$.

Example 79B 2-(diphenylmethylene)-1-phenethyl-1-phenylhydrazine

General procedure B was used to convert 1-(diphenylmethylene)-2-phenylhydrazine (200 mg, 0.735 mmol; Example 79A) and (2-bromoethyl)benzene (1.29 g, 6.9 mmol; Aldrich) to the title compound: MS (DCI/NH$_3$) m/z 391 (M+H)$^+$.

Example 79C 11-dimethyl-5-(2-phenylethyl)-5,6,7,8,9,10-hexahydro-7,10-epiminocyclohepta[b]indole General procedure C was used to convert 2-(diphenylmethylene)-1-phenethyl-1-phenylhydrazine (276 mg, 1.3 mmol; Example 79B) and tropinone (153 mg, 1.1 mmol; Aldrich) to the title compound as the trifluoroacetic acid salt: $^1$H NMR (300 MHz, CDCl$_3$) δ ppm 0.89-1.12 (m, 1H), 1.30-1.52 (m, 2H), 1.63 (s, 1H), 1.97-2.18 (m, 2H), 2.29-2.65 (m, 5H), 4.08 (s, 1H), 4.17-4.41 (m, 2H), 4.89 (d, J=3.6 Hz, 1H), 6.82 (dd, J=7.1, 2.4 Hz, 2H), 7.14-7.23 (m, 4H), 7.32 (t, J=7.1 Hz, 1H), 7.47 (t, J=8.3 Hz, 2H); MS (DCI/NH$_3$) m/z 317 (M+H)$^+$.

Example 80

11-methyl-5-[2-(2-methylphenyl)ethyl]-5,6,7,8,9,10-hexahydro-7,10-epiminocyclohepta[b]indole trifluoroacetate

Example 80A 2-(diphenylmethylene)-1-(2-methylphenethyl)-1-phenylhydrazine

General procedure B was used to convert 1-(diphenylmethylene)-2-phenylhydrazine (200 mg, 0.943 mmol; Example 79A) and 1-(2-bromoethyl)-2-methylbenzene (1.46 g, 7.37 mmol; Aldrich) into the title compound: MS (DCI/NH$_3$) m/z 391 (M+H)$^+$.

Example 80B 11-methyl-5-[2-(2-methylphenyl)ethyl]-5,6,7,8,9,10-hexahydro-7,10-epiminocyclohepta[b]indole trifluoroacetate General procedure C was used to convert 2-(diphenylmethylene)-1-(2-methylphenethyl)-1-phenylhydrazine (276 mg, 0.707 mmol; Example 80A) and tropinone (148 mg, 1.1 mmol; Aldrich) into the title compound as the trifluoroacetic acid salt: $^1$H NMR (300 MHz, CDCl$_3$) δ ppm 1.00 (d, J=14.6 Hz, 1H), 1.28-1.52 (m, 2H), 1.61 (s, 1H), 1.93-2.15 (m, 5H), 2.27-2.63 (m, 4H), 3.04-3.27 (m, 2H), 4.08 (s, 1H), 4.17-4.45 (m, 2H), 4.90 (s, 1H), 6.66 (d, J=7.5 Hz, 1H), 6.93-7.04 (m, 1H), 7.05-7.22 (m, 3H), 7.28-7.38 (m, 1H), 7.47 (dd, J=7.1, 5.4 Hz, 2H); MS (DCI/NH$_3$) m/z 331 (M+H)$^+$.

Example 81

5-[2-(4-chlorophenyl)ethyl]-11-methyl-5,6,7,8,9,10-hexahydro-7,10-epiminocyclohepta[b]indole The product of Example 78A (150 mg, 0.707 mmol) and sodium dispersion in paraffin (30%, 120 mg, 1.57 mmol; Aldrich) were weighed into a 20 mL glass vial with stir bar and septum cap. Dimethyl sulfoxide (2 mL) was added, and the mixture was stirred at room temperature under nitrogen for 20 minutes. A solution of hydroquinone (22 mg, 0.20 mmol; Aldrich) and p-chlorostyrene (199 mg, 1.44 mmol; Aldrich) in dimethyl sulfoxide (0.5 mL) was added, and the mixture was heated at 100° C. under nitrogen for 39 hours. The mixture was cooled to room temperature, diluted with water (40 mL) and saturated brine (10 mL) and extracted with dichloromethane (4×20 mL). The combined organic phase was concentrated under vacuum, and the residue was passed through a column of silica gel with dichloromethane (100 mL), then CH$_2$Cl$_2$—CH$_3$OH-14.8 M aqueous NH$_4$OH, 90:10:1) to provide the crude title compound. The product was further purified by reverse-phase HPLC [Waters XBridge™ C18 5 µm OBD 30×100 mm column, flow rate 40 mL/minute, 30-95% gradient of acetonitrile in buffer (0.1 M aqueous ammonium bicarbonate, adjusted to pH 10 with ammonium hydroxide) over 18 minutes] to provide the title compound: $^1$H NMR (300 MHz, methanol-d$_4$) δ ppm 1.17-1.30 (m, 1H), 1.73-1.83 (m, 1H), 1.88 (dd, J=16.4, 1.2 Hz, 1H), 2.04-2.29 (m, 2H), 2.20 (s, 3H), 2.73 (dd, J=16.8, 4.2 Hz, 1H), 2.95-3.14 (m, 2H), 3.40 (dd, J=7.1, 4.4 Hz, 1H), 4.15 (d, J=5.4 Hz, 1H), 4.22 (ddd, J=14.3, 8.1, 6.1 Hz, 1H), 4.32 (dt, J=14.7, 6.1 Hz, 1H), 6.78-6.85 (m, 2H), 7.02 (ddd, J=7.9, 7.0, 1.0 Hz, 1H), 7.07-7.14 (m, 1H), 7.12-7.16 (m, 2H), 7.37 (dd, J=8.1, 1.0 Hz, 1H), 7.40 (dd, J=7.8, 1.0 Hz, 1H); MS (DCI) m/z 351/353 (M+H)$^+$.

Example 82

11-methyl-5-[2-(2-methyl-1,4,5,6-tetrahydropyrimidin-5-yl)ethyl]-5,6,7,8,9,10-hexahydro-7,10-epiminocyclohepta[b]indole

Example 82A

2-Methyl-5-((trimethylsilyl)ethynyl)pyrimidine

Isopropyl acetate (30 mL) was added to a mixture of 5-bromo-2-methylpyrimidine (3 g, 17.3 mmol), copper(I) iodide (0.066 g, 0.35 mmol) and bis(triphenylphosphine)palladium (II) dichloride (0.243 g, 0.35 mmol) in a 100 mL 3-neck flask equipped with a condenser. The resulting solution was sparged with a stream of nitrogen for 15 minutes and kept under nitrogen during further manipulations. Trimethylsilylacetylene (3.12 mL, 22.5 mmol) and diisopropylamine (4.90 mL, 34.7 mmol) were added successively to the reaction solution, and the mixture was stirred at room temperature for 30 minutes. The dark mixture was heated at 60° C. for 15 hours, then cooled to room temperature, diluted with isopropyl acetate (15 mL) and filtered through diatomaceous earth. The filtrate was washed successively with saturated aqueous NaHCO$_3$ (2×25 mL), 10% aqueous Na$_2$S$_2$O$_3$ (20 mL) and brine, then dried (MgSO$_4$) and concentrated under vacuum. The dark residue was purified by flash chromatography on silica gel (hexanes-ethyl acetate, gradient from 100:0-70:30) to provide the title compound: $^1$H NMR (300 MHz, CDCl$_3$) δ ppm 0.27 (s, 9H), 2.74 (s, 3H), 8.68 (s, 2H).

Example 82B

5-Ethynyl-2-methylpyrimidine

A solution of the product of example 82A (2.05 g, 10.8 mmol) in methanol (30 mL) was stirred with potassium carbonate (1.49 g, 10.8 mmol) at room temperature. After 2 hours, the reaction mixture was filtered, and the filtrate was concentrated under vacuum to provide the title compound suitable for use in the next step: $^1$H NMR (300 MHz, methanol-d$_4$) δ ppm 2.69 (s, 3H), 3.34 (s, 1H), 8.75 (s, 2H); MS (ESI) m/z 119 (M+H)$^+$.

Example 82C 11-methyl-5-[2-(2-methylpyrimidin-5-yl)vinyl]-5,6,7,8,9,10-hexahydro-7,10-epiminocyclohepta[b]indole The product of Example 78A (178 mg, 0.838 mmol) and sodium dispersion in paraffin (30%, 129 mg, 1.68 mmol; Aldrich) were weighed into a 20 mL glass vial with stir bar and septum cap. Dimethyl sulfoxide (3 mL) was added, and the mixture was stirred at room temperature under nitrogen for 20 minutes. A mixture of hydroquinone (28 mg, 0.26 mmol; Aldrich) and 5-ethynyl-2-methylpyrimidine from Example 82B (121 mg, 1.024 mmol) in dimethyl sulfoxide (1.0 mL) was added, and the reaction was heated at 100° C. under nitrogen for 64 hours. The mixture was cooled to room temperature, diluted with water (40 mL) and extracted with dichloromethane (4×40 mL), then ethyl acetate (2×40 mL). The combined organic phase was concentrated under vacuum, and the residue was passed through a column of silica gel with dichloromethane (200 mL), then CH$_2$Cl$_2$—CH$_3$OH-14.8 M aqueous NH$_4$OH, 90:10:1) to provide the crude title compound. This was further purified by reverse-phase HPLC [Waters XBridge™ C18 5 µm OBD 30×100 mm column, flow rate 40 mL/minute, 20-95% gradient of acetonitrile in buffer (0.1 M aqueous ammonium bicarbonate, adjusted to pH 10 with ammonium hydroxide) over 18 minutes] to provide the title compound: $^1$H NMR (300 MHz, methanol-d$_4$) δ ppm 1.59-1.73 (m, 1H), 1.93 (t, J=9.3 Hz, 1H), 2.24-2.36 (m, 2H), 2.41 (s, 3H), 2.68 (s, 3H), 2.73 (dd, J=17.0, 1.0 Hz, 1H), 3.42 (dd, J=17.0, 4.4 Hz, 1H), 3.59-3.72 (m, 1H), 4.25 (d, J=4.7 Hz, 1H), 6.77 (d, J=14.9 Hz, 1 H), 7.15 (td, J=7.5, 1.0 Hz, 1H), 7.24 (td, J=7.6, 1.4 Hz, 1H), 7.48 (d, J=7.5 Hz, 1H), 7.78 (d, J=8.1 Hz, 1H), 7.85 (d, J=14.9 Hz, 1H), 8.87 (s, 2H).

Example 82D 11-methyl-5-[2-(2-methyl-1,4,5,6-tetrahydropyrimidin-5-yl)ethyl]-5,6,7,8,9,10-hexahydro-7,10-epiminocyclohepta[b]indole A solution of the product of Example 82C (9 mg, 0.027 mmol) in methanol (10 mL) was treated with $PtO_2$ (10 mg). The reaction flask was evacuated and purged with nitrogen (4 cycles), then with hydrogen (5 cycles), and the suspension was stirred at room temperature under hydrogen (1 atm) for 40 hours. The flask was evacuated and purged with nitrogen (5 cycles) and the mixture was filtered through a pad of diatomaceous earth with methanol (5 mL) rinse. The filtrate was concentrated under vacuum and the residue was taken up in ethyl acetate (1 mL). A solution of p-toluenesulfonic acid monohydrate (5.5 mg, 0.029 mmol) in ethyl acetate (0.5 mL) was added, and the mixture was stirred for 30 minutes, then concentrated under vacuum. The residual solid was triturated with ethyl acetate (0.2 mL) and dried under vacuum to provide the title compound as the p-toluenesulfonate salt: $^1$H NMR (300 MHz, methanol-$d_4$) δ ppm 1.72-1.87 (m, 2H), 1.97-2.09 (m, 2H), 2.14 (s, 2H), 2.15 (s, 1H), 2.19-2.31 (m, 1H), 2.35 (s, 3H), 2.41-2.71 (m, 2H), 2.81 (s, 1H), 2.96 (s, 2H), 2.99-3.15 (m, 3H), 3.37-3.53 (m, 2H), 3.57-3.69 (m, 4H), 4.15-4.29 (m, 2H), 4.29-4.38 (m, J=4.8 Hz, 1H), 5.02-5.13 (m, 1H), 7.08-7.26 (m, 4H), 7.45 (t, J=7.7 Hz, 1H), 7.53 (d, J=7.9 Hz, 1H), 7.64 (d, J=8.3 Hz, 2H); MS (DCI) m/z 337 (M+H)$^+$.

Example 83

11-methyl-5-{[4-(trifluoromethyl)phenyl]sulfonyl}-5,6,7,8,9,10-hexahydro-7,10-epiminocyclohepta[b]indole The reaction of 11-methyl-5,6,7,8,9,10-hexahydro-7,10-epiminocyclohepta[b]indole (215.2 mg, 1.014 mmol; Example 78A) and 4-(trifluoromethyl)benzenesulfonyl chloride (349.2 mg, 1.430 mmol, Aldrich) was performed as described in Example 69 except that the crude material was purified by flash chromatography (silica gel, $CH_2Cl_2$/$CH_3OH$ 10:1) to afford the title compound: $^1$H NMR (300 MHz, methanol-$d_4$) δ ppm 1.53-1.60 (m, 1H), 1.80-1.89 (m, 1H), 2.20-2.30 (m, 5H), 2.84 (dd, J=18.0, 1.0 Hz, 1H), 3.39 (dd, J=18.1, 4.2 Hz, 1H), 3.58-3.62 (m, 1H), 4.14 (d, J=4.8 Hz, 1H), 7.23-7.34 (m, 2H), 7.43-7.45 (m, 1H), 7.79-7.82 (m, 2H), 7.98-8.00 (m, 2H), 8.08-8.10 (m, 1H); MS (DCI/$NH_3$) m/z 421 (M+H)$^+$. Anal. Calcd. for $C_{21}H_{19}F_3N_2O_2S$: C, 59.99; H, 4.55; N, 6.66. Found: C, 59.87; H, 4.67; N, 6.68.

Example 84

2-fluoro-11-methyl-5-[2-(4-methylphenyl)ethyl]-5,6,7,8,9,10-hexahydro-7,10-epiminocyclohepta[b]indole Example 84A 1-(diphenylmethylene)-2-(4-fluorophenyl)hydrazine General procedure A was used to convert benzophenone hydrazone (1.962 g, 10.0 mmol; Aldrich) and 1-bromo-4-fluorobenzene (1.75 g, 10.0 mmol; source) to the title compound. MS (DCI/$NH_3$) m/z 291 (M+H)$^+$.

Example 84B 2-(diphenylmethylene)-1-(4-methylphenethyl)-1-(4-fluorophenyl)hydrazine General procedure B was used to convert 1-(diphenylmethylene)-2-(4-fluorophenyl)-hydrazine (200 mg, 0.689 mmol; Example 84A) and 4-methylphenethylbromide (274 mg, 1.37 mmol; Aldrich) to the title compound: MS (DCI/$NH_3$) 409 m/z (M+H)$^+$.

Example 84C 2-fluoro-11-methyl-5-[2-(4-methylphenyl)ethyl]-5,6,7,8,9,10-hexahydro-7,10-epiminocyclohepta[b]indole trifluoroacetate General procedure C was used to convert 2-(diphenylmethylene)-1-(4-methylphenethyl)-1-(4-fluorophenyl)hydrazine (300 mg, 0.734 mmol; Example 84B) and tropinone (153 mg, 1.102 mmol; Aldrich) to the title compound as the trifluoroacetic acid salt: $^1$H NMR (300 MHz, methanol-$d_4$) δ ppm 1.12-1.39 (m, 1H) 1.71-1.98 (m, 2H) 2.05-2.33 (m, 5H) 2.47 (s, 3H) 2.65 (dd, J=16.46, 4.16 Hz, 1H) 2.88-3.20 (m, 2H) 3.32-3.54 (m, 1H) 3.98-4.30 (m, 3H) 6.71 (d, J=8.1 Hz, 2H), 6.94-7.03 (m, 2H), 7.08 (s, 1H), 7.21 (d, J=2.4 Hz, 1H), 7.46 (dd, J=9.0, 3.9 Hz, 1H); MS (DCI/$NH_3$) m/z 349 (M+H)$^+$.

Example 85

2-fluoro-5-[2-(4-fluorophenyl)ethyl]-11-methyl-5,6,7,8,9,10-hexahydro-7,10-epiminocyclohepta[b]indole Example 85A 1-(4-fluorophenethyl)-1-(4-fluorophenyl)hydrazine A flask containing tetrahydrofuran (6.0 mL; Aldrich) was charged with sodium amide (0.488 g, 11.89 mmol; Acros) and chilled to 0° C. (4-Fluorophenyl)hydrazine (1.0 g, 7.9 mmol; Aldrich) was added in portions. After 5 minutes the solid had completely dissolved. The ice bath was removed and stirring was continued for 1 hour. The solution was chilled again in an ice bath and 1-(2-bromoethyl)-4-fluorobenzene (1.731 ml, 8.72 mmol; Aldrich) was added dropwise. After 10 minutes the ice bath was removed and stirring was continued for 1.5 hours. The mixture was poured into water (5 mL). The tetrahydrofuran was removed under reduce pressure and the residue was diluted with water (20 mL). The aqueous layer was extracted with diisopropyl ether (2×25 mL) and the combined organic extracts were dried over magnesium sulfate, filtered, and concentrated in vacuo to afford the title product which was carried on without further purification: MS (DCI/$NH_3$) m/z 248.9 (M+H)$^+$.

Example 85B 2-fluoro-5-[2-(4-fluorophenyl)ethyl]-11-methyl-5,6,7,8,9,10-hexahydro-7,10-epiminocyclohepta[b]indole General procedure C was used to convert 1-(4-fluorophenethyl)-1-(4-fluorophenyl)-hydrazine (276 mg, 1.1 mmol; Example 85A) and tropinone (232 mg, 1.7 mmol; Aldrich) into the title compound as the trifluoroacetic acid salt: $^1$H NMR (300 MHz, CDCl$_3$) δ ppm 1.79-2.15 (m, 2H), 2.41-2.69 (m, 5H), 3.08 (t, J=6.2 Hz, 2H), 4.11 (s, 1H), 4.18-4.36 (m, 2H), 4.80 (d, J=4.8 Hz, 1H), 6.73-6.83 (m, 2H), 6.84-6.94 (m, 2H), 6.99-7.17 (m, 2H), 7.32 (dd, J=8.9, 4.2 Hz, 1H); MS (DCI/NH$_3$) m/z 353 (M+H)$^+$.

Example 86

2-fluoro-5-[2-(3-fluorophenyl)ethyl]-11-methyl-5,6,7,8,9,10-hexahydro-7,10-epiminocyclohepta[b]indole

Example 86A 2-(diphenylmethylene)-1-(3-fluorophenethyl)-1-(4-fluorophenyl)hydrazine General procedure B was used to convert 1-(diphenylmethylene)-2-(4-fluorophenyl)-hydrazine (200 mg, 0.69 mmol; Example 84A) and 1-(2-bromoethyl)-3-fluorobenzene (280 mg, 1.37 mmol; Aldrich) into the title compound: MS (DCI/NH$_3$) 413 m/z (M+H)$^+$.

Example 86B 2-fluoro-5-[2-(3-fluorophenyl)ethyl]-11-methyl-5,6,7,8,9,10-hexahydro-7,10-epiminocyclohepta[b]indole General procedure C was used to convert 2-(diphenylmethylene)-1-(3-fluorophenethyl)-1-(4-fluorophenyl)hydrazine (300 mg, 0.727 mmol; Example 86A) and tropinone (152 mg, 1.091 mmol; Aldrich) into the title compound as the trifluoroacetic acid salt. $^1$H NMR (300 MHz, CDCl$_3$) δ ppm 1.02-1.55 (m, 2H), 1.79-2.15 (m, 2H), 2.41-2.69 (m, 5H), 3.08 (t, J=6.2 Hz, 2H), 4.11 (s, 1H), 4.18-4.36 (m, 2H), 4.80 (d, J=4.8 Hz, 1H), 6.52-6.64 (m, 1H), 6.68-6.79 (m, 1H), 6.88-7.07 (m, 3H), 7.23 (dd, J=9.5, 2.4 Hz, 2H).

Example 87

2-bromo-5-[2-(4-chlorophenyl)ethyl]-11-methyl-5,6,7,8,9,10-hexahydro-7,10-epiminocyclohepta[b]indole

Example 87A 2-bromo-11-methyl-5,6,7,8,9,10-hexahydro-7,10-epiminocyclohepta[b]indole A mixture of 4-bromophenylhydrazine hydrochloride (4.87 g, 21.8 mmol; Aldrich) and tropinone (3.03 g, 21.8 mmol; Aldrich) in 1 M HCl-acetic acid (50 mL) was stirred at 20° C. for 1 hour, then warmed to 60° C. for 8.5 hours and cooled to room temperature. The reaction mixture was concentrated under vacuum and the residue was purified by flash chromatography (silica gel, eluted with CH$_2$Cl$_2$—CH$_3$OH-14.8 M aqueous NH$_4$OH (90:10:1)) to provide the title compound: $^1$H NMR (300 MHz, methanol-d$_4$) δ ppm 1.54-1.71 (m, 1H), 1.88 (t, J=9.2 Hz, 1H), 2.19-2.33 (m, 2H), 2.36 (s, 3H), 2.46 (d, J=16.6 Hz, 1H), 3.24 (d, J=16.8, 4.6 Hz, 1H), 3.50-3.60 (m, 1H), 4.17 (d, J=5.1 Hz, 1H), 7.09 (dd, J=8.5, 1.7 Hz, 1H), 7.17 (d, J=8.5 Hz, 1H), 7.52 (d, J=1.7 Hz, 1H); MS (DCI) m/z 291/293 (MH$^+$).

Example 87B 2-bromo-5-[2-(4-chlorophenyl)ethyl]-11-methyl-5,6,7,8,9,10-hexahydro-7,10-epiminocyclohepta[b]indole 2-Bromo-11-methyl-5,6,7,8,9,10-hexahydro-7,10-epiminocyclohepta[b]indole (228 mg, 0.783 mmol; Example 87A) and sodium dispersion in paraffin (30%, 168 mg, 2.19 mmol; Aldrich) were weighed into a 20 mL glass vial with stir bar and septum cap. Dimethyl sulfoxide (2.5 mL) was added, and the mixture was stirred at room temperature under nitrogen for 30 minutes. A solution of hydroquinone (52 mg, 0.48 mmol; Aldrich) and 4-chlorostyrene (213 mg, 1.54 mmol; Aldrich) in dimethyl sulfoxide (2 mL) was added, and the reaction was heated at 105° C. under nitrogen for 87 hours. The mixture was cooled to room temperature, diluted with water (100 mL) and extracted with chloroform (3×50 mL). The combined organic phases were washed with brine (30 mL) and concentrated under vacuum. The residue was purified by flash chromatography (silica gel, eluted with CHCl$_3$—CH$_3$OH-14.8 M aqueous NH$_4$OH, 100:0:0-90:10:1) to provide the crude title compound. This was further purified by reverse-phase HPLC [Waters XBridge™ C18 5 μm OBD 30×100 mm column, flow rate 40 mL/minute, 40-99% gradient of methanol in buffer (0.1 M aqueous ammonium bicarbonate, adjusted to pH 10 with ammonium hydroxide) over 20 minutes] to provide the title compound: $^1$H NMR (300 MHz, methanol-d$_4$) δ ppm 1.16-1.30 (m, 1H), 1.78 (t, J=9.3 Hz, 1H), 1.90 (d, J=17.0 Hz, 1H), 2.04-2.30 (m, 2H), 2.22 (s, 3H), 2.74 (dd, J=17.0, 4.1 Hz, 1H), 2.96-3.11 (m, 2H), 3.43 (dd, J=6.4, 4.7 Hz, 1H), 4.15 (d, J=5.1 Hz, 1H), 4.17-4.37 (m, 2H), 6.77-6.86 (m, 2H), 7.12-7.16 (m, 2H), 7.19 (dd, J=8.6, 1.9 Hz, 1H), 7.30 (d, J=8.5 Hz, 1H), 7.55 (d, J=2.0 Hz, 1H); MS (DCI) m/z 429/431/433 (M+H)$^+$.

Example 88

(7R,10S)-2-bromo-5-[2-(4-chlorophenyl)ethyl]-11-methyl-5,6,7,8,9,10-hexahydro-7,10-epiminocyclohepta[b]indole The individual enantiomers from the racemic mixture of Example 87B were separated by preparative chiral supercritical fluid chromatography (ChiralPak® OD-H 5 μm column, 21×250 mm, 35° C., 10-50% gradient of CH$_3$OH—CO$_2$ containing 0.1% diethylamine, flow rate 40 mL/minute) to obtain the title compound as the first eluting enantiomer: $^1$H NMR (300 MHz, methanol-d$_4$) δ ppm 1.14-1.28 (m, 1H), 1.72-1.81 (m, 1H), 1.89 (d, J=16.7 Hz, 1H), 2.07-2.26 (m, 2H), 2.19 (s, 3H), 2.73 (dd, J=16.5, 4.2 Hz, 1H), 2.97-3.12 (m, 2H), 3.36-3.44 (m, 1H), 4.11 (d, J=5.2 Hz, 1H), 4.22 (ddd, J=14.7, 7.5, 5.9 Hz, 1H), 4.31 (dt, J=14.7, 5.9 Hz, 1H), 6.82 (d, J=8.7 Hz, 2H), 7.15 (d, J=8.7 Hz, 2H), 7.18 (dd, J=8.7, 1.6 Hz, 1H), 7.30 (d, J=8.7 Hz, 1H), 7.55 (d, J=1.6 Hz, 1H).

Example 89

(7S,10R)-2-bromo-5-[2-(4-chlorophenyl)ethyl]-11-methyl-5,6,7,8,9,10-hexahydro-7,10-epiminocyclohepta[b]indole The individual enantiomers from the racemic mixture of Example 87B were separated by preparative chiral supercritical fluid chromatography (ChiralPak® OD-H 5 μm column, 21×250 mm, 35° C., 10-50% gradient of CH$_3$OH—CO$_2$ containing 0.1% diethylamine, flow rate 40 mL/minute) to obtain the title compound as the second-eluting enantiomer: $^1$H NMR (300 MHz, methanol-d$_4$) δ ppm 1.16-1.27 (m, 1H), 1.76 (t, J=9.3 Hz, 1H), 1.89 (d, J=16.6 Hz, 1H), 2.05-2.25 (m, 2H), 2.19 (s, 3H), 2.73 (dd, J=16.8, 3.6 Hz, 1H), 2.99-3.10 (m, 2H), 3.36-3.43 (m, 1H), 4.11 (d, J=4.7 Hz, 1H), 4.17-4.35 (m, 2H), 6.82 (d, J=8.1 Hz, 2H), 7.15 (d, J=8.5 Hz, 2H), 7.16-7.21 (m, J=8.5, 2.0 Hz, 1H), 7.29 (d, J=8.5 Hz, 1H), 7.54 (d, J=1.7 Hz, 1H).

Example 90

2-bromo-11-methyl-5-[(4-methylphenyl)sulfonyl]-5,6,7,8,9,10-hexahydro-7,10-epiminocyclohepta[b]indole The reaction of 2-bromo-11-methyl-5,6,7,8,9,10-hexahydro-7,10-epiminocyclohepta[b]indole (320.5 mg, 1.101 mmol; Example 87A) and p-toluenesulfonyl chloride (221.8 mg, 1.163 mmol, Aldrich) was performed as described in Example 69 except that the crude material was purified by flash chromatography (silica gel, CH$_2$Cl$_2$/CH$_3$OH 10:1) to afford the title compound: $^1$H NMR (300 MHz, methanol-d$_4$) δ ppm 1.49-1.54 (m, 1H), 1.77-1.83 (m, 1H), 2.19-2.28 (m, 5H), 2.35 (s, 3H), 2.82 (d, J=18.2 Hz, 1H), 3.35-3.41 (m, 1H), 3.54-3.59 (m, 1H), 4.11 (d, J=4.8 Hz, 1H), 7.30-7.32 (m, 2H), 7.39 (dd, J=8.9, 1.8 Hz, 1H), 7.60 (d, J=2.0 Hz, 1H), 7.67-7.70 (m, 2H), 8.00 (d, J=8.7 Hz, 1H); MS (DCI/NH$_3$) m/z 445 (M+H)$^+$.

Example 91

2-methoxy-11-methyl-5-[2-(6-methylpyridin-3-yl)ethyl]-5,6,7,8,9,10-hexahydro-7,10-epiminocyclohepta[b]indole Example 91A 2-methoxy-11-methyl-5,6,7,8,9,10-hexahydro-7,10-epiminocyclohepta[b]indole A suspension of (4-methoxyphenyl)hydrazine hydrochloride (875 mg, 5.0 mmol, Aldrich), tropinone (696 mg, 5.0 mmol; Aldrich), and 4 M HCl-dioxane (2.5 mL, 10.0 mmol; Aldrich) in ethanol (10 mL) was heated to 80° C. for 16 hours. After cooling to room temperature, the reaction mixture was concentrated, basified with 5 N NaOH (aqueous), and then extracted with ethyl acetate (3×50 mL). The combined organic phases were concentrated and the residue was purified by reverse-phase HPLC [Waters XBridge™ RP18 column, 5 μm, 30×100 mm, flow rate 40 mL/minute, 20-95% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.67-1.81 (m, 1H), 1.99 (t, J=9 Hz, 1H), 2.25-2.43 (m, 2H), 2.50 (s, 3H), 2.57 (d, J=17 Hz, 1H), 3.26-3.34 (m, 1H), 3.68-3.76 (m, 1H), 3.80 (s, 3H), 4.39 (d, J=4 Hz, 1H), 6.70 (dd, J=9, 2 Hz, 1H), 6.93 (d, J=2 Hz, 1H), 7.16 (d, J=9 Hz, 1H); MS (DCI/NH$_3$) m/z 243 (M+H)$^+$.

Example 91B 2-methoxy-11-methyl-5-[2-(6-methylpyridin-3-yl)ethyl]-5,6,7,8,9,10-hexahydro-7,10-epiminocyclohepta[b]indole The coupling of 2-methoxy-11-methyl-5,6,7,8,9,10-hexahydro-7,10-epiminocyclohepta[b]indole (100 mg, 0.413 mmol; Example 91A) and 2-methyl-5-vinylpyridine (98 mg, 0.825 mmol; IBScreen) was performed as described in Example 1B to afford the title compound: $^1$H NMR (300 MHz, methanol-d$_4$) δ ppm 1.11-1.24 (m, 1H), 1.73-1.83 (m, 1H), 1.87 (d, J=16 Hz, 1H), 2.04-2.28 (m, 2H), 2.18 (s, 3H), 2.41 (s, 3H), 2.74 (dd, J=17, 4 Hz, 1H), 2.97-3.15 (m, 2H), 3.35-3.41 (m, 1H), 3.81 (s, 3H), 4.11 (d, J=5 Hz, 1H), 4.15-4.36 (m, 2H), 6.75 (dd, J=9, 2 Hz, 1H), 6.92 (d, J=2 Hz, 1H), 7.09 (d, J=8 Hz, 1H), 7.20-7.28 (m, 2H), 7.75 (d, J=2 Hz, 1H); MS (DCI/NH$_3$) m/z 362 (M+H)$^+$.

Example 92

(7R,10S)-5-[2-(4-chlorophenyl)ethyl]-2-methoxy-11-methyl-5,6,7,8,9,10-hexahydro-7,10-epiminocyclohepta[b]indole The coupling of 2-methoxy-11-methyl-5,6,7,8,9,10-hexahydro-7,10-epiminocyclohepta[b]indole (122 mg, 0.503 mmol; Example 91A) and 1-chloro-4-vinylbenzene (140 mg, 1.00 mmol, Aldrich) was performed as described in Example 1B to afford the title compound as a racemic mixture. Individual enantiomers were obtained by preparative chiral supercritical fluid chromatography (ChiralPak® OD-H 5 μm column, 21×250 mm, 35° C., 10-50% gradient of CH$_3$OH—CO$_2$ containing 0.1% diethylamine, flow rate 40 mL/minute) to afford the title compound as the first-eluting enantiomer: $^1$H NMR (300 MHz, methanol-d$_4$) δ ppm 1.18-1.30 (m, 1H), 1.74-1.90 (m, 2H), 2.05-2.31 (m, 2H), 2.22 (s, 3H), 2.72 (dd, J=16, 4 Hz, 1H), 2.96-3.10 (m, 2H), 3.38-3.45 (m, 1H), 3.82 (s, 3H), 4.13-4.34 (m, 3H), 6.77 (dd, J=9, 2 Hz, 1H), 6.82 (d, J=8 Hz, 2H), 6.93 (d, J=2 Hz, 1H), 7.14 (d, J=8 Hz, 2H), 7.26 (d, J=9 Hz, 1H); MS (DCI/NH$_3$) m/z 381/383 (M+H)$^+$.

Example 93

(7S,10R)-5-[2-(4-chlorophenyl)ethyl]-2-methoxy-11-methyl-5,6,7,8,9,10-hexahydro-7,10-epiminocyclohepta[b]indole Purification of the racemic mixture from Example 92 by preparative chiral supercritical fluid chromatography (ChiralPak® OD-H 5 μm column, 21×250 mm, 35° C., 10-50% gradient of CH$_3$OH—CO$_2$ containing 0.1% diethylamine, flow rate 40 mL/minute) afforded the title compound as the second-eluting enantiomer: $^1$H NMR (300 MHz, methanol-d$_4$) δ ppm 1.18-1.29 (m, 1H), 1.74-1.90 (m, 2H), 2.05-2.29 (m, 2H), 2.21 (s, 3H), 2.71 (dd, J=16, 4 Hz, 1H), 2.94-3.12 (m, 2H), 3.37-3.43 (m, 1H), 3.82 (s, 3H), 4.12-4.33 (m, 3H), 6.76 (dd, J=9, 2 Hz, 1H), 6.82 (d, J=8 Hz, 2H), 6.93 (d, J=2 Hz, 1H), 7.14 (d, J=8 Hz, 2H), 7.26 (d, J=9 Hz, 1H); MS (DCI/NH$_3$) m/z 381/383 (M+H)$^+$.

Example 94

(7R,10S)-2-methoxy-11-methyl-5-{2-[3-(trifluoromethyl)phenyl]ethyl}-5,6,7,8,9,10-hexahydro-7,10-epiminocyclohepta[b]indole The coupling of 2-methoxy-11-methyl-5,6,7,8,9,10-hexahydro-7,10-epiminocyclohepta[b]indole (122 mg, 0.503 mmol; Example 91A) and 1-(trifluoromethyl)-3-vinylbenzene (172 mg, 1.00 mmol, Aldrich) was performed as described in Example 1B to afford the title compound as a racemic mixture. Individual enantiomers were obtained by preparative chiral supercritical fluid chromatography (ChiralPak® OD-H 5 µm column, 21×250 mm, 35° C., 10-50% gradient of CH$_3$OH—CO$_2$ containing 0.1% diethylamine, flow rate 40 mL/minute) to afford the title compound as the first-eluting enantiomer: $^1$H NMR (300 MHz, methanol-d$_4$) δ ppm 1.10-1.23 (m, 1H), 1.70-1.81 (m, 1H), 1.88 (d, J=17 Hz, 1H), 2.05-2.26 (m, 2H), 2.17 (s, 3H), 2.75 (dd, J=17, 4 Hz, 1H), 3.05-3.21 (m, 2H), 3.34-3.40 (m, 1H), 3.81 (s, 3H), 4.10 (d, J=5 Hz, 1H), 4.18-4.38 (m, 2H), 6.74 (dd, J=9, 2 Hz, 1H), 6.92 (d, J=2 Hz, 1H), 7.11 (d, J=7 Hz, 1H), 7.15 (s, 1H), 7.23 (d, J=9 Hz, 1H), 7.33 (t, J=8 Hz, 1H), 7.41-7.47 (m, 1H); MS (DCI/NH$_3$) m/z 415 (M+H)$^+$.

Example 95

(7S,10R)-2-methoxy-11-methyl-5-{2-[3-(trifluoromethyl)phenyl]ethyl}-5,6,7,8,9,10-hexahydro-7,10-epiminocyclohepta[b]indole Purification of the racemic mixture from Example 94 by preparative chiral supercritical fluid chromatography (ChiralPak® OD-H 5 µm column, 21×250 mm, 35° C., 10-50% gradient of CH$_3$OH—CO$_2$ containing 0.1% diethylamine, flow rate 40 mL/minute) afforded the title compound as the second-eluting enantiomer: $^1$H NMR (300 MHz, methanol-d$_4$) δ ppm 1.11-1.23 (m, 1H), 1.72-1.82 (m, 1H), 1.89 (d, J=17 Hz, 1H), 2.04-2.27 (m, 2H), 2.18 (s, 3H), 2.76 (dd, J=16, 4 Hz, 1H), 3.05-3.21 (m, 2H), 3.35-3.42 (m, 1H), 3.81 (s, 3H), 4.12 (d, J=5 Hz, 1H), 4.19-4.39 (m, 2H), 6.75 (dd, J=9, 2 Hz, 1H), 6.92 (d, J=2 Hz, 1H), 7.12 (d, J=8 Hz, 1H), 7.15 (s, 1H), 7.23 (d, J=9 Hz, 1H), 7.34 (t, J=8 Hz, 1H), 7.41-7.47 (m, 1H); MS (DCI/NH$_3$) m/z 415 (M+H)$^+$.

Example 96

5-[2-(4-chlorophenyl)ethyl]-4-methoxy-11-methyl-5,6,7,8,9,10-hexahydro-7,10-epiminocyclohepta[b]indole Example 96A 4-methoxy-6,7,8,9,10,11-hexahydro-5H-7,11-epiminocycloocta[b]indole A suspension of (2-methoxyphenyl)hydrazine hydrochloride (875 mg, 5.0 mmol; TCI-US), tropinone (696 mg, 5.0 mmol; Aldrich), and 4M HCl-dioxane (2.5 mL, 10.0 mmol; Aldrich) in ethanol (10 mL) was heated to 80° C. for 16 hours. After cooling to room temperature, the reaction mixture was concentrated, basified with 5 N NaOH (aqueous), and then extracted with ethyl acetate (3×50 mL). The combined organic phase was concentrated and the residue was purified by reverse-phase HPLC [Waters XBridge™ RP18 column, 5 µm, 30×100 mm, flow rate 40 mL/minute, 20-95% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.62-1.80 (m, 1H), 1.97 (t, J=9 Hz, 1H), 2.24-2.38 (m, 2H), 2.47 (s, 3H), 2.57 (d, J=17 Hz, 1H), 3.25-3.36 (m, 1H), 3.65-3.73 (m, 1H), 3.92 (s, 3H), 4.34 (d, J=4 Hz, 1H), 6.59 (d, J=8 Hz, 1H), 6.87-6.95 (m, 1H), 6.97-7.04 (m, 1H); MS (DCI/NH$_3$) m/z 243 (M+H)$^+$.

Example 96B

5-[2-(4-chlorophenyl)ethyl]-4-methoxy-11-methyl-5,6,7,8,9,10-hexahydro-7,10-epiminocyclohepta[b]indole The coupling of 4-methoxy-6,7,8,9,10,11-hexahydro-5H-7,11-epiminocycloocta[b]indole (49 mg, 2.0 mmol, Example 96A) and 1-chloro-4-vinylbenzene (40 mg, 0.289 mmol, Aldrich) was performed as described in Example 1B to afford the title compound: $^1$H NMR (300 MHz, methanol-d$_4$, with NaOD added) δ ppm 1.11-1.23 (m, 1H), 1.69-1.79 (m, 1H), 1.85 (d, J=17 Hz, 1H), 2.07-2.27 (m, 5H), 2.73 (dd, J=16, 4 Hz, 1H), 2.93-3.10 (m, 2H), 3.96 (s, 3H), 4.05 (d, J=5 Hz, 1H), 4.26-4.39 (m, 1H), 4.44-4.55 (m, 1H), 6.66 (dd, J=7, 1 Hz, 1H), 6.82 (d, J=8 Hz, 2H), 6.90-7.03 (m, 2H), 7.14 (d, J=8 Hz, 2H); MS (DCI/NH$_3$) m/z 381/383 (M+H)$^+$.

Example 97

5-[2-(4-chlorophenyl)ethyl]-1-methyl-2-(trifluoromethoxy)-5,6,7,8,9,10-hexahydro-7,10-epiminocyclohepta[b]indole Example 97A 11-methyl-2-trifluoromethoxy-5,6,7,8,9,10-hexahydro-7,10-epiminocyclohepta[b]indole A solution of 4-(trifluoromethoxy)phenylhydrazine hydrochloride (1062 mg, 5.0 mmol; Maybridge), tropinone (696 mg, 5.0 mmol; Aldrich), and concentrated sulfuric acid (2.0 mL; J. T Baker) in dioxane (30 mL) was heated to 80° C. for 16 hours. After cooling to room temperature, the reaction mixture was concentrated, basified with 5 N NaOH (aqueous), and then extracted with ethyl acetate (3×50 mL). The combined organic phase was concentrated and the residue was purified by reverse-phase HPLC [Waters XBridge™ RP18 column, 5 µm, 30×100 mm, flow rate 40 mL/minute, 20-95% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.58-1.73 (m, 1H), 1.90 (t, J=9 Hz, 1H), 2.25-2.34 (m, 2H), 2.37 (s, 3H), 2.48 (dd, J=17, 1 Hz, 1H), 3.21-3.28 (m, 1H), 3.53-3.60 (m, 1H), 4.20 (d, J=5 Hz, 1H), 6.91 (dt, J=9, 1 Hz, 1H), 7.24-7.31 (m, 2H); MS (DCI/NH$_3$) m/z 297 (M+H)$^+$.

Example 97B

5-[2-(4-chlorophenyl)ethyl]-11-methyl-2-(trifluoromethoxy)-5,6,7,8,9,10-hexahydro-7,10-epiminocyclohepta[b]indole The coupling of 11-methyl-2-trifluoromethoxy-5,6,7,8,9,10-hexahydro-7,10-epiminocyclohepta[b]indole (50 mg, 0.169 mmol; Example 97A) and 1-chloro-4-vinylbenzene (45 mg, 0.339 mmol; Aldrich) was performed as described in Example 1B to afford the title compound: $^1$H NMR (300 MHz, methanol-d$_4$) δ ppm 1.21-1.32 (m, 1H), 1.73-1.83 (m, 1H), 1.90 (d, J=17 Hz, 1H), 2.07-2.30 (m, 2H), 2.21 (s, 3H), 2.74 (dd, J=17, 4 Hz, 1H), 2.98-3.13 (m, 2H), 3.38-3.44 (m, 1H), 4.14 (d, J=5 Hz, 1H), 4.20-4.41 (m, 2H), 6.84 (d, J=8 Hz, 2H), 7.00 (d, J=8 Hz, 1H), 7.15 (d, J=8 Hz, 2H), 7.30 (s, 1H), 7.40 (d, J=9 Hz, 1H); MS (DCI/NH$_3$) m/z 435/437 (M+H)$^+$.

Example 98

5-[2-(4-chlorophenyl)ethyl]-11-methyl-2-(trifluoromethyl)-5,6,7,8,9,10-hexahydro-7,10-epiminocyclohepta[b]indole Example 98A 11-methyl-2-(trifluoromethyl)-5,6,7,8,9,10-hexahydro-7,10-epiminocyclohepta[b]indole A solution of 4-(trifluoromethyl)phenyl)hydrazine (1.5 g, 8.52 mmol; Aldrich) and tropinone (1.19 g, 8.52 mmol) in 7% sulfuric acid in dioxane (50 mL) was heated to 100° C. overnight. Water (100 mL) was added and the solution was basified (to ~pH 12) by the addition of 4 M aqueous NaOH. The aqueous solution was extracted with dichloromethane (3×75 mL) and the combined extracts were concentrated in vacuo and purified by flash chromatography (40 g silica gel, 0-100% $CH_2Cl_2/CH_3OH/14.8$ M aqueous $NH_4OH$ (78:20:2) in $CH_2Cl_2$ over 25 minutes) to afford the title compound. $^1H$ NMR (300 MHz, methanol-$d_4$) δ ppm 1.93-2.15 (m, 1H), 2.22-2.38 (m, 1H), 2.54-2.72 (m, 2H), 2.93-3.14 (m, 2H), 3.37 (s, 3H), 4.33 (s, 1H), 5.04-5.23 (m, 1H), 7.34-7.46 (m, 1H), 7.46-7.61 (m, 1H), 7.88 (s, 1H); MS (ESI)$^+$ m/z 281 (M+H)$^+$.

Example 98B

5-[2-(4-chlorophenyl)ethyl]-11-methyl-2-(trifluoromethyl)-5,6,7,8,9,10-hexahydro-7,10-epiminocyclohepta[b]indole A reaction tube was charged with 11-methyl-2-(trifluoromethyl)-5,6,7,8,9,10-hexahydro-7,10-epiminocyclohepta[b]indole (280 mg, 0.999 mmol; Example 98A), sodium (30-35% dispersion in paraffin; 91 mg, 1.193 mmol; Aldrich) and hydroquinone (11.00 mg, 0.100 mmol; Aldrich) and then sealed with a septum cap. Dimethyl sulfoxide (1 mL) and 1-chloro-4-vinylbenzene (277 mg, 1.998 mmol; Aldrich) were introduced through the septum and the vessel was evacuated and backfilled with nitrogen (~10×). The mixture was heated at 100° C. for 72 hours. After cooling, the reaction mixture was diluted with water (5 mL), extracted with dichloromethane, concentrated, and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1H$ NMR (300 MHz, methanol-$d_4$) δ ppm 1.30-1.60 (m, 1H), 1.96-2.16 (m, 1H), 2.26 (d, J=17.6 Hz, 1H), 2.30-2.53 (m, 2H), 2.65 (s, 4H), 2.94-3.20 (m, 3H), 3.98 (s, 1H), 4.32 (d, J=22.0 Hz, 1H), 4.40-4.62 (m, 1H), 6.74-6.98 (m, 2H), 7.19 (d, J=8.5 Hz, 2H), 7.46 (d, J=6.8 Hz, 1H), 7.62 (d, J=8.5 Hz, 1H), 7.86 (s, 1H); MS (ESI) m/z 419 (M+H)$^+$.

Example 99

2-isopropyl-11-methyl-5-[2-(6-methylpyridin-3-yl)ethyl]-5,6,7,8,9,10-hexahydro-7,10-epiminocyclohepta[b]indole Example 99A 2-isopropyl-11-methyl-5,6,7,8,9,10-hexahydro-7,10-epiminocyclohepta[b]indole A solution of (4-isopropylphenyl)hydrazine hydrochloride (930 mg, 5.0 mmol; Aldrich), tropinone (696 mg, 5.0 mmol; Aldrich), and 4 M HCl-dioxane (2.5 mL, 10.0 mmol; Aldrich) in ethanol (10 mL) was heated to 80° C. for 16 hours. After cooling to room temperature, the reaction mixture was concentrated, basified with 5 N NaOH (aqueous), and then extracted with ethyl acetate (3×50 mL). The combined organic phases were concentrated and the residue was purified by reverse-phase HPLC [Waters XBridge™ RP18 column, 5 μm, 30×100 mm, flow rate 40 mL/minute, 20-95% gradient of methanol in buffer (0.1 M aqueous ammonium bicarbonate, adjusted to pH 10 with ammonium hydroxide)] to afford the title compound: $^1H$ NMR (300 MHz, methanol-$d_4$) δ ppm 1.26 (s, 3H), 1.28 (s, 3H), 1.57-1.71 (m, 1H), 1.90 (t, J=10 Hz, 1H), 2.22-2.35 (m, 2H), 2.37 (s, 3H), 2.45 (d, J=15 Hz, 1H), 2.89-3.00 (m, 1H), 3.24 (dd, J=17, 4 Hz, 1H), 3.54 (t, J=5 Hz, 1H), 4.20 (d, J=5 Hz, 1H), 6.92 (dd, J=9, 1 Hz, 1H), 7.17 (d, J=9 Hz, 1H), 7.22 (s, 1H); MS (DCI/$NH_3$) m/z 255 (M+H)$^+$.

Example 99B 2-isopropyl-11-methyl-5-[2-(6-methylpyridin-3-yl)ethyl]-5,6,7,8,9,10-hexahydro-7,10-epiminocyclohepta[b]indole The coupling of 2-isopropyl-11-methyl-5,6,7,8,9,10-hexahydro-7,10-epiminocyclohepta[b]indole (85 mg, 0.334 mmol; Example 99A) and 2-methyl-5-vinylpyridine (80 mg, 0.668 mmol; IBScreen) was performed as described in Example 1B to afford the title compound: $^1H$ NMR (500 MHz, pyridine-$d_5$) δ ppm 1.35 (d, J=7 Hz, 6H), 1.41-1.50 (m, 1H), 1.98 (t, J=11 Hz, 1H), 2.28 (d, J=17 Hz, 1H), 2.36-2.43 (m, 1H), 2.44 (s, 3H), 2.55-2.77 (m, 4H), 2.99 (t, J=7 Hz, 2H), 3.03-3.12 (m, 1H), 4.16-4.25 (m, 3H), 5.10 (d, J=5 Hz, 1H), 6.92 (d, J=8 Hz, 1H), 7.09 (d, J=6 Hz, 1H), 7.29 (d, J=8 Hz, 1H), 7.50 (d, J=8 Hz, 1H), 7.53 (s, 1H), 8.16 (s, 1H); MS (DCI/$NH_3$) m/z 374 (M+H)$^+$.

Example 100

(7R,10S)-5-[2-(4-chlorophenyl)ethyl]-2-isopropyl-11-methyl-5,6,7,8,9,10-hexahydro-7,10-epiminocyclohepta[b]indole The coupling of 2-isopropyl-11-methyl-5,6,7,8,9,10-hexahydro-7,10-epiminocyclohepta[b]indole (127 mg, 0.499 mmol; Example 99A) and 1-chloro-4-vinylbenzene (138 mg, 0.999 mmol, Aldrich) was performed as described in Example 1B to afford the title compound as a racemic mixture. Individual enantiomers were obtained by preparative chiral supercritical fluid chromatography (ChiralPak® OD-H 5 μm column, 21×250 mm, 35° C., 10-50% gradient of $CH_3OH$—$CO_2$ containing 0.1% diethylamine, flow rate 40 mL/minute) to afford the title compound as the first-eluting enantiomer: $^1H$ NMR (300 MHz, methanol-$d_4$) δ ppm 1.18-1.28 (m, 1H), 1.30 (d, J=7 Hz, 6H), 1.74-1.88 (m, 2H), 2.05-2.28 (m, 2H), 2.20 (s, 3H), 2.70 (dd, J=16, 4 Hz, 1H), 2.92-3.12 (m, 3H), 3.36-3.42 (m, 1H), 4.13-4.33 (m, 3H), 6.82 (d, J=8 Hz, 2H), 7.02 (dd, J=8, 2 Hz, 1H), 7.14 (d, J=8 Hz, 2H), 7.25 (d, J=2 Hz, 1H), 7.29 (d, J=8 Hz, 1H); MS (DCI/$NH_3$) m/z 393 (M+H)$^+$.

Example 101

(7S,10R)-5-[2-(4-chlorophenyl)ethyl]-2-isopropyl-11-methyl-5,6,7,8,9,10-hexahydro-7,10-epiminocyclohepta[b]indole Purification of the racemic mixture from Example 100 by preparative chiral supercritical fluid chromatography (ChiralPak® OD-H 5 μm column, 21×250 mm, 35° C., 10-50% gradient of $CH_3OH$—$CO_2$ containing 0.1% diethylamine, flow rate 40 mL/minute) afforded the title compound as the second-eluting enantiomer: $^1H$ NMR (300 MHz, methanol-$d_4$) δ ppm 1.17-1.28 (m, 1H), 1.30 (d, J=7 Hz, 6H), 1.74-1.88 (m, 2H), 2.04-2.28 (m, 2H), 2.19 (s, 3H), 2.69 (dd, J=16, 4 Hz, 1H), 2.92-3.12 (m, 3H), 3.35-3.39 (m, 1H), 4.10-4.34 (m, 3H), 6.82 (d, J=8 Hz, 2H), 7.02 (dd, J=8, 2 Hz,

Example 102

2-cyclopropyl-11-methyl-5-[(4-methylphenyl)sulfonyl]-5,6,7,8,9,10-hexahydro-7,10-epiminocyclohepta[b]indole A solution of 2-bromo-11-methyl-5-[(4-methylphenyl)sulfonyl]-5,6,7,8,9,10-hexahydro-7,10-epiminocyclohepta[b]indole (340.0 mg, 0.763 mmol; Example 90) in toluene (8 mL) and water (0.4 mL) was treated with cyclopropylboronic acid (91.7 mg, 1.068 mmol; Aldrich), potassium phosphate (530.9 mg, 2.74 mmol), tricyclohexylphosphine (25.3 mg, 0.090 mmol; Aldrich) and palladium(II) acetate (11.0 mg, 0.049 mmol; Aldrich). The reaction was purged with nitrogen for 15 minutes, and then heated to 100° C. for 18 hours. The resulting mixture was diluted with water (35 mL) and extracted with dichloromethane (3×35 mL). The combined organic layers were dried over sodium sulfate, filtered and concentrated, and the residue was purified by silica gel chromatography ($CH_2Cl_2/CH_3OH$ 10:1) to afford the title compound: $^1$H NMR (300 MHz, methanol-$d_4$) δ ppm 0.65-0.70 (m, 2H), 0.91-0.97 (m, 2H), 1.49-1.54 (m, 1H), 1.76-1.82 (m, 1H), 1.93-2.01 (m, 1H), 2.20-2.28 (m, 5H), 2.33 (s, 3H), 2.78 (d, J=17.9 Hz, 1H), 3.34-3.38 (m, 1H), 3.54-3.59 (m, 1H), 4.10 (d, J=4.8 Hz, 1H), 7.01 (dd, J=8.7, 1.6 Hz, 1H), 7.11 (d, J=1.2 Hz, 1H), 7.26-7.28 (m, 2H), 7.62-7.65 (m, 2H), 7.93 (d, J=8.7 Hz, 1H); MS (DCI/NH$_3$) m/z 407 (M+H)$^+$.

Example 103

2-cyclopropyl-11-methyl-5-[2-(6-methylpyridin-3-yl)ethyl]-5,6,7,8,9,10-hexahydro-7,10-epiminocyclohepta[b]indole

Example 103A 2-cyclopropyl-11-methyl-5,6,7,8,9,10-hexahydro-7,10-epiminocyclohepta[b]indole A solution of 2-cyclopropyl-11-methyl-5-[(4-methylphenyl)sulfonyl]-5,6,7,8,9,10-hexahydro-7,10-epiminocyclohepta[b]indole (271.2 mg, 0.667 mmol; Example 102) in methanol (5 mL) was treated with potassium hydroxide (473.6 mg, 7.34 mmol). The reaction mixture was heated to reflux for 19 hours, then diluted with water (35 mL) and extracted with dichloromethane (3×35 mL). The combined organic layers were washed with brine (25 mL), dried over sodium sulfate, filtered and concentrated in vacuo to afford the title compound: $^1$H NMR (300 MHz, methanol-$d_4$) δ ppm 0.60-0.65 (m, 2H), 0.84-0.91 (m, 2H), 1.59-1.69 (m, 1H), 1.86-2.00 (m, 2H), 2.26-2.48 (m, 6H), 3.20-3.27 (m, 1H), 3.54-3.56 (m, 1H), 4.19 (d, J=4.8 Hz, 1H), 6.79 (dd, J=8.3, 1.6 Hz, 1H), 7.10-7.15 (m, 2H); MS (DCI/NH$_3$) m/z 253 (M+H)$^+$.

Example 103B 2-cyclopropyl-11-methyl-5-[2-(6-methylpyridin-3-yl)ethyl]-5,6,7,8,9,10-hexahydro-7,10-epiminocyclohepta[b]indole A solution of 2-cyclopropyl-11-methyl-5,6,7,8,9,10-hexahydro-7,10-epiminocyclohepta[b]indole (66.0 mg, 0.262 mmol; Example 103A) in dimethyl sulfoxide (2 mL) was treated with 2-methyl-5-vinylpyridine (91.8 mg, 0.770 mmol; International Publication No. WO2001/017968), hydroquinone (8.8 mg, 0.080 mmol; Aldrich) and sodium dispersion in paraffin (30%; 31.9 mg, 0.416 mmol; Aldrich). The reaction was purged with nitrogen and heated to 110° C. for 19 hours under nitrogen. The mixture was diluted with methanol (10 mL), filtered, concentrated in vacuo, and purified by reverse-phase HPLC [Waters XBridge™ RP18 column, 5 μm, 30×100 mm, flow rate 40 mL/minute, 20-95% gradient of methanol in buffer (0.1 M aqueous ammonium bicarbonate, adjusted to pH 10 with ammonium hydroxide)] to afford the title compound: $^1$H NMR (300 MHz, methanol-$d_4$) δ ppm 0.62-0.66 (m, 2H), 0.85-0.94 (m, 2H), 1.15-1.21 (m, 1H), 1.75-1.90 (m, 2H), 1.96-2.00 (m, 1H), 2.16-2.23 (m, 4H), 2.41 (s, 3H), 2.62-2.42 (m, 2H), 3.00-3.09 (m, 2H), 3.37-3.39 (m, 1H), 4.12 (d, J=4.8 Hz, 1H), 4.23-4.33 (m, 2H), 6.88 (dd, J=8.5, 1.7 Hz, 1H), 7.08-7.13 (m, 2H), 7.20-7.25 (m, 2H), 7.74 (d, J=2.0 Hz, 1H); MS (DCI/NH$_3$) m/z 372 (M+H)$^+$.

Example 104

2-tert-butyl-11-methyl-5-[2-(6-methylpyridin-3-yl)ethyl]-5,6,7,8,9,10-hexahydro-7,10-epiminocyclohepta[b]indole

Example 104A 2-tert-butyl-11-methyl-5,6,7,8,9,10-hexahydro-7,10-epiminocyclohepta[b]indole A suspension of (4-tert-butylphenyl)hydrazine hydrochloride (1000 mg, 5.0 mmol; Aldrich), tropinone (696 mg, 5.0 mmol; Aldrich), and 4 M HCl-dioxane (2.5 mL, 10.0 mmol; Aldrich) in ethanol (10 mL) was heated to 80° C. for 16 hours. After cooling to room temperature, the reaction mixture was concentrated, basified with 5 N NaOH (aqueous), and then extracted with ethyl acetate (3×50 mL). The combined organic phase was concentrated and the residue was purified by reverse-phase HPLC [Waters XBridge™ RP18 column, 5 m, 30×100 mm, flow rate 40 mL/minute, 20-95% gradient of methanol in buffer (0.1 M aqueous ammonium bicarbonate, adjusted to pH 10 with ammonium hydroxide)] to afford the title compound: $^1$H NMR (300 MHz, methanol-$d_4$) δ ppm 1.36 (s, 9H), 1.61-1.74 (m, 1H), 1.93 (t, J=9 Hz, 1H), 2.25-2.36 (m, 2H), 2.41 (s, 3H), 2.48 (d, J=17 Hz, 1H), 3.21-3.29 (m, 1H), 3.56-3.63 (m, 1H), 4.26 (d, J=4 Hz, 1H), 7.10-7.15 (m, 1H), 7.16-7.21 (m, 1H), 7.38 (d, J=1 Hz, 1H); MS (DCI/NH$_3$) m/z 269 (M+H)$^+$.

Example 104B 2-tert-butyl-11-methyl-5-[2-(6-methylpyridin-3-yl)ethyl]-5,6,7,8,9,10-hexahydro-7,10-epiminocyclohepta[b]indole The coupling of 2-tert-butyl-11-methyl-5,6,7,8,9,10-hexahydro-7,10-epiminocyclohepta[b]indole (62 mg, 0.522 mmol, Example 104A) and 2-methyl-5-vinylpyridine (80 mg, 0.668 mmol, IBScreen) was performed according to the procedure described in Example 1B to afford the title compound: $^1$H NMR (500 MHz, pyridine-$d_5$) δ ppm 1.12-1.24 (m, 1H), 1.37 (s, 9H), 1.76-1.92 (m, 2H), 2.05-2.28 (m, 2H), 2.19 (s, 3H), 2.41 (s, 3H), 2.74 (dd, J=16, 4 Hz, 1H), 2.98-3.14 (m, 2H), 3.39 (dd, J=7, 4 Hz, 1H), 4.15 (d, J=5 Hz, 1H), 4.17-4.37 (m, 2H), 7.10 (d, J=8 Hz, 1H), 7.18-7.29 (m, 3H), 7.40 (d, J=1 Hz, 1H), 7.73 (d, J=2 Hz, 1H); MS (DCI/NH$_3$) m/z 388 (M+H)$^+$.

Example 105

2-tert-butyl-5-[2-(4-chlorophenyl)ethyl]-11-methyl-5,6,7,8,9,10-hexahydro-7,10-epiminocyclohepta[b]indole The coupling of 2-tert-butyl-11-methyl-5,6,7,8,9,10-hexahydro-7,10-epiminocyclohepta[b]indole (134 mg, 0.499 mmol, Example 104A) and 1-chloro-4-vinylbenzene (138 mg, 0.999 mmol, Aldrich) was performed according to the procedure described in Example 1B to afford the title compound: $^1$H NMR (300 MHz, methanol-d$_4$) δ ppm 1.39-1.44 (m, 1H), 1.45 (s, 9H), 1.97 (t, J=11 Hz, 1H), 2.26 (d, J=17 Hz, 1H), 2.35-2.44 (m, 1H), 2.52-2.61 (m, 1H), 2.64 (s, 3H), 2.93-3.04 (m, 2H), 4.14-4.18 (m, 1H), 4.21 (t, J=7 Hz, 2H), 5.12 (d, J=5 Hz, 1H), 6.84 (d, J=8 Hz, 2H), 7.17 (d, J=8 Hz, 2H), 7.51 (s, 2H), 7.76 (s, 1H); MS (DCI/NH$_3$) m/z 407 (M+H)$^+$.

Example 106

2-(4-chlorophenyl)-11-methyl-5-[2-(6-methylpyridin-3-yl)ethyl]-5,6,7,8,9,10-hexahydro-7,10-epiminocyclohepta[b]indole Example 106A 2-bromo-11-methyl-5-[2-(6-methylpyridin-3-yl)ethyl]-5,6,7,8,9,10-hexahydro-7,10-epiminocyclohepta[b]indole A suspension of sodium (76 mg, 0.99 mmol, 30% dispersion in paraffin wax, Aldrich), 2-bromo-11-methyl-5,6,7,8,9,10-hexahydro-7,10-epiminocyclohepta[b]indole (160 mg, 0.55 mmol; Example 87A) and 2-methyl-5-vinylpyridine (118 mg, 0.99 mmol; International Publication No. WO2001/017968) in dimethyl sulfoxide (2.5 mL) was degassed with nitrogen several times. The reaction mixture was stirred at 110° C. for 18 hours. The residue was diluted with aqueous sodium carbonate (1.0 M, 60 mL) and extracted with chloroform-isopropanol (4:1, 2×30 mL). The combined organic extracts were dried (sodium sulfate), concentrated under vacuum, and the residue was purified by preparative HPLC [Waters XBridge™ RP18 column, 5 µm, 30×100 mm, flow rate 40 mL/minute, 15-95% gradient of acetonitrile in buffer (0.1 M aqueous ammonium bicarbonate, adjusted to pH 10 with ammonium hydroxide)] to afford the title compound: $^1$H NMR (500 MHz, methanol-d$_4$) δ ppm 1.11-1.24 (m, 1H), 1.74-1.81 (m, 1H), 1.89-1.96 (m, 1H), 2.10-2.31 (m, 2H), 2.19 (s, 3H), 2.42-2.43 (s, 3H), 2.78 (dd, J=16.6, 3.2 Hz, 1H), 3.00-3.13 (m, 2H), 4.09-4.14 (m, 1H), 4.20-4.29 (m, 1H), 4.34 (dt, J=14.7, 5.9 Hz, 1H), 7.08-7.13 (m, 1H), 7.15-7.20 (m, 2H), 7.22-7.28 (m, 2H), 7.51-7.56 (m, 1H), 7.76 (d, J=1.8 Hz, 1H); MS (APCI) m/z 410/412 (M+H)$^+$.

Example 106B 2-(4-chlorophenyl)-11-methyl-5-[2-(6-methylpyridin-3-yl)ethyl]-5,6,7,8,9,10-hexahydro-7,10-epiminocyclohepta[b]indole A suspension of the product of Example 106A (22 mg, 0.054 mmol), 4-chlorophenylboronic acid (9.2 mg, 0.059 mmol; Aldrich), dichlorobis(triphenylphosphine)palladium (II) (1.9 mg, 2.7 µmol; Aldrich)) and 1.0 M aqueous sodium carbonate (0.54 mL, 0.13 mmol) in 2-propanol (1.5 mL) was purged with nitrogen and stirred at 100° C. for one hour. The reaction mixture was cooled and filtered through a glass microfiber frit, rinsing with 2-propanol (70% aqueous solution). The resulting mixture was purified by preparative HPLC [Waters XBridge™ RP18 column, 5 µm, 30×100 mm, flow rate 40 mL/minute, 30-99% gradient of methanol in buffer (0.1 M aqueous ammonium bicarbonate, adjusted to pH 10 with ammonium hydroxide)] to afford the title compound: $^1$H NMR (500 MHz, methanol-d$_4$) δ ppm 1.20 (ddd, J=13.0, 9.2, 6.6 Hz, 1H), 1.78-1.86 (m, 1H), 1.91 (d, J=16.5 Hz, 1H), 2.09-2.27 (m, 2H), 2.20 (s, 3H), 2.41 (s, 3H), 2.78 (dd, J=16.5, 3.7 Hz, 1H), 3.04-3.19 (m, 2H), 3.41 (dd, J=7.3, 4.6 Hz, 1H), 4.20 (d, J=5.5 Hz, 1H), 4.25-4.32 (m, 1H), 4.34-4.42 (m, 1H), 7.11 (d, J=7.9 Hz, 1H), 7.27 (dd, J=7.9, 2.1 Hz, 1H), 7.34-7.45 (m, 4H), 7.58-7.65 (m, 3H), 7.78 (d, J=1.8 Hz, 1H); MS (APCI) m/z 442 (M+H)$^+$.

Example 107

2-(4-chlorophenyl)-5-[2-(4-chlorophenyl)ethyl]-11-methyl-5,6,7,8,9,10-hexahydro-7,10-epiminocyclohepta[b]indole The coupling of the product of Example 87B (30 mg, 0.070 mmol) and 4-chlorophenylboronic acid (12 mg, 0.077 mmol; Aldrich) was performed according to the procedure described in Example 106B to provide the title compound: $^1$H NMR (500 MHz, methanol-d$_4$) δ ppm 1.20-1.30 (m, 1H), 1.77-1.84 (m, 1H), 1.88 (d, J=16.8 Hz, 1H), 2.09-2.17 (m, 1H), 2.21 (s, 3H), 2.21-2.28 (m, 1H), 2.74 (dd, J=16.8, 3.7 Hz, 1H), 2.99-3.15 (m, 2H), 3.37-3.42 (m, J=7.3, 4.3 Hz, 1H), 4.20 (d, J=5.5 Hz, 1H), 4.22-4.29 (m, J=14.3, 8.2, 5.8 Hz, 1H), 4.30-4.38 (m, J=14.6, 6.0, 6.0 Hz, 1H), 6.85 (d, J=8.5 Hz, 2H), 7.15 (d, J=8.2 Hz, 2H), 7.35-7.48 (m, 4H), 7.60-7.66 (m, 3H); MS (DCI/NH$_3$) m/z 461 (M+H)$^+$.

Example 108

11-methyl-5-[2-(6-methylpyridin-3-yl)ethyl]-2-[3-(trifluoromethyl)phenyl]-5,6,7,8,9,10-hexahydro-7,10-epiminocyclohepta[b]indole Example 108A 11-methyl-2-[3-(trifluoromethyl)phenyl]-5,6,7,8,9,10-hexahydro-7,10-epiminocyclohepta[b]indole The coupling of 2-bromo-11-methyl-5,6,7,8,9,10-hexahydro-7,10-epiminocyclohepta[b]indole (90 mg, 0.31 mmol; Example 87A) and 3-(trifluoromethyl)phenylboronic acid (65 mg, 0.34 mmol; Aldrich) was performed according to the procedure described in Example 106B to afford the title compound: $^1$H NMR (500 MHz, methanol-d$_4$) δ ppm 1.62-1.73 (m, 1H), 1.93-1.99 (m, 1H), 2.27-2.37 (m, 2H), 2.40 (s, 3H), 2.50 (d, J=16.8 Hz, 1H), 3.24-3.35 (m, 1H), 3.57-3.61 (m, 1H), 4.32 (d, J=4.9 Hz, 1H), 7.31-7.35 (m, 1H), 7.36-7.39 (m, 1H), 7.52-7.62 (m, 2H), 7.68 (d, J=1.2 Hz, 1H), 7.86-7.91 (m, 2H); MS (APCI) m/z 357 (M+H)$^+$.

Example 108B 11-methyl-5-[2-(6-methylpyridin-3-yl)ethyl]-2-[3-(trifluoromethyl)phenyl]-5,6,7,8,9,10-hexahydro-7,10-epiminocyclohepta[b]indole The coupling of 11-methyl-2-[3-(trifluoromethyl)phenyl]-5,6,7,8,9,10-hexahydro-7,10-epiminocyclohepta[b]indole (40 mg, 0.11 mmol; Example 108A) and 2-methyl-5-vinylpyridine (24 mg, 0.20 mmol; International Publication No. WO2001/017968) was performed as described in Example 106A to afford the title compound: $^1$H NMR (500 MHz, methanol-d$_4$) δ ppm 1.23 (ddd, J=13.2, 9.1, 6.7 Hz, 1H), 1.81-1.91 (m, 1H), 1.96 (d, J=16.5 Hz, 1H), 2.11-2.22 (m, 1H), 2.22-2.30 (m, 1H), 2.25 (s, 3H), 2.42 (s, 3H), 2.82 (dd, J=16.2, 2.7 Hz, 1H), 3.05-3.18 (m, 2H), 3.47 (dd, J=6.9, 4.4 Hz, 1H), 4.25-4.33 (m, 2H), 4.35-4.44 (m, 1H), 7.12 (d, J=7.9 Hz, 1H), 7.29 (dd, J=7.9, 2.1 Hz, 1H), 7.39-7.48 (m, 2H), 7.55-7.64 (m, 2H), 7.71 (d, J=1.5 Hz, 1H), 7.78 (d, J=1.8 Hz, 1H), 7.87-7.93 (m, 2H); MS (APCI) m/z 476 (M+H)$^+$.

Example 109

5-[2-(4-chlorophenyl)ethyl]-11-methyl-2-[3-(trifluoromethyl)phenyl]-5,6,7,8,9,10-hexahydro-7,10-epiminocyclohepta[b]indole The coupling of 2-bromo-5-[2-(4-chlorophenyl)ethyl]-11-methyl-5,6,7,8,9,10-hexahydro-7,10-epiminocyclohepta[b]indole (30 mg, 0.07 mmol; Example 87B) and 3-(trifluoromethyl)phenylboronic acid (15 mg, 0.08 mmol; Aldrich) was performed according to the procedure described in Example 106B to afford the title compound: $^1$H NMR (500 MHz, methanol-d$_4$) δ ppm 1.21-1.29 (m, 1H), 1.78-1.85 (m, 1H), 1.88 (d, J=16.5 Hz, 1H), 2.09-2.17 (m, 1H), 2.19-2.28 (m, 1H), 2.21 (s, 3H), 2.74 (dd, J=16.2, 3.4 Hz, 1H), 3.02-3.15 (m, 2H), 3.40 (dd, J=7.3, 4.6 Hz, 1H), 4.22 (d, J=5.2 Hz, 1H), 4.24-4.31 (m, 1H), 4.32-4.39 (m, 1H), 6.83-6.88 (m, 2H), 7.14-7.17 (m, 2H), 7.38-7.44 (m, 1H), 7.47-7.51 (m, 1H), 7.54-7.64 (m, 2H), 7.70 (d, J=1.5 Hz, 1H), 7.88-7.94 (m, 2H); MS (DCI/NH$_3$) m/z 495 (M+H)$^+$.

Example 110

11-methyl-5-[2-(6-methylpyridin-3-yl)ethyl]-2-pyridin-3-yl-5,6,7,8,9,10-hexahydro-7,10-epiminocyclohepta[b]indole The coupling of 2-bromo-11-methyl-5-[2-(6-methylpyridin-3-yl)ethyl]-5,6,7,8,9,10-hexahydro-7,10-epiminocyclohepta[b]indole (14.2 mg, 0.035 mmol; Example 106A) and pyridine-3-boronic acid (4.7 mg, 0.038 mmol; Aldrich) was performed according to the procedure described in Example 106B to provide the title compound: $^1$H NMR (500 MHz, methanol-d$_4$) δ ppm 1.21 (ddd, J=13.0, 9.1, 6.6 Hz, 1H), 1.79-1.88 (m, 1H), 1.94 (d, J=16.5 Hz, 1H), 2.10-2.19 (m, 1H), 2.19-2.29 (m, 1H), 2.21 (s, 3H), 2.42 (s, 3H), 2.80 (dd, J=16.3, 3.8 Hz, 1H), 3.05-3.19 (m, 2H), 3.42 (dd, J=7.3, 4.6 Hz, 1H), 4.24 (d, J=5.2 Hz, 1H), 4.26-4.34 (m, 1H), 4.35-4.44 (m, 1H), 7.12 (d, J=7.9 Hz, 1H), 7.29 (dd, J=7.9, 2.1 Hz, 1H), 7.39-7.43 (m, 1H), 7.46-7.52 (m, 2H), 7.72-7.80 (m, 2H), 8.12 (ddd, J=8.1, 2.0, 1.8 Hz, 1H), 8.45 (dd, J=4.9, 1.5 Hz, 1H), 8.83 (d, J=2.1 Hz, 1H); MS (APCI) m/z 409 (M+H)$^+$.

Example 111

5-[2-(4-chlorophenyl)ethyl]-11-methyl-2-pyridin-3-yl-5,6,7,8,9,10-hexahydro-7,10-epiminocyclohepta[b]indole The coupling of 2-bromo-5-[2-(4-chlorophenyl)ethyl]-11-methyl-5,6,7,8,9,10-hexahydro-7,10-epiminocyclohepta[b]indole (30 mg, 0.07 mmol; Example 87B) and pyridine-3-boronic acid (9.4 mg, 0.077 mmol; Aldrich) was performed according to the procedure described in Example 106B to provide the title compound: $^1$H NMR (500 MHz, methanol-d$_4$) δ ppm 1.25 (ddd, J=13.1, 9.0, 6.6 Hz, 1H), 1.75-1.85 (m, 1H), 1.89 (d, J=16.5 Hz, 1H), 2.10-2.18 (m, 1H), 2.19-2.28 (m, 1H), 2.21 (s, 3H), 2.75 (dd, J=16.6, 3.5 Hz, 1H), 3.02-3.15 (m, 2H), 3.40 (dd, J=7.2, 4.7 Hz, 1H), 4.22 (d, J=5.2 Hz, 1H), 4.24-4.31 (m, 1H), 4.32-4.41 (m, 1H), 6.85 (d, J=8.2 Hz, 2H), 7.15 (d, J=8.2 Hz, 2H), 7.38-7.44 (m, 1H), 7.48-7.52 (m, 2H), 7.72 (d, J=1.5 Hz, 1H), 8.13 (dt, J=7.9, 1.8 Hz, 1H), 8.45 (dd, J=4.7, 1.4 Hz, 1H), 8.83 (d, J=1.8 Hz, 1H); MS (DCI/NH$_3$) m/z 428 (M+H)$^+$.

Example 112

11-methyl-5-[2-(6-methylpyridin-3-yl)ethyl]-2-(1H-pyrazol-4-yl)-5,6,7,8,9,10-hexahydro-7,10-epiminocyclohepta[b]indole Example 112A 11-methyl-5-[2-(6-methylpyridin-3-yl)ethyl]-2-(1-trityl-1H-pyrazol-4-yl)-5,6,7,8,9,10-hexahydro-7,10-epiminocyclohepta[b]indole The coupling of 2-bromo-11-methyl-5-[2-(6-methylpyridin-3-yl)ethyl]-5,6,7,8,9,10-hexahydro-7,10-epiminocyclohepta[b]indole (33 mg, 0.08 mmol; Example 106A) and 4-(4,4,5,5-tetramethyl-1,3,2-dioxaborolan-2-yl)-1-trityl-1H-pyrazole (39 mg, 0.09 mmol; as prepared in Japan Patent No. 200523207) was performed according to the procedure described in Example 106B to provide the title compound: $^1$H NMR (500 MHz, methanol-d$_4$) δ ppm 1.16 (ddd, J=13.0, 9.3, 6.1 Hz, 1H), 1.73-1.82 (m, 1H), 1.89 (d, J=16.8 Hz, 1H), 2.06-2.15 (m, 1H), 2.16-2.23 (m, 1H), 2.17 (s, 3H), 2.40 (s, 3H), 2.75 (dd, J=16.3, 3.5 Hz, 1H), 3.00-3.13 (m, 2H), 3.38 (dd, J=6.9, 4.7 Hz, 1H), 4.14 (d, J=5.5 Hz, 1H), 4.18-4.27 (m, 1H), 4.28-4.37 (m, 1H), 7.07-7.13 (m, 2H), 7.18-7.23 (m, 6H), 7.29-7.33 (m, 3H), 7.33-7.38 (m, 8H), 7.50 (d, J=1.2 Hz, 1H), 7.68 (s, 1H), 7.75 (d, J=1.8 Hz, 1H), 7.94 (s, 1H); MS (APCI) m/z 640 (M+H)$^+$.

Example 112B 11-methyl-5-[2-(6-methylpyridin-3-yl)ethyl]-2-(1H-pyrazol-4-yl)-5,6,7,8,9,10-hexahydro-7,10-epiminocyclohepta[b]indole A solution of 11-methyl-5-[2-(6-methylpyridin-3-yl)ethyl]-2-(1-trityl-1H-pyrazol-4-yl)-5,6,7,8,9,10-hexahydro-7,10-epiminocyclohepta[b]indole (25 mg, 0.039 mmol; Example 112A) in a solvent mixture of methanol (1.0 mL) and methylene chloride (1.0 mL) at 0° C. was treated with trifluoroacetic acid (2.0 mL) and the mixture was allowed to warm to ambient temperature. After stirring for 3 hours, the reaction mixture was concentrated under vacuum and the residue was dissolved in dimethyl sulfoxide (2.0 mL) and purified by reverse-phase HPLC [Waters XBridge™ RP18 column, 5 μm, 30×100 mm, flow rate 40 mL/minute, 35-99% gradient of methanol in buffer (0.1 M aqueous ammonium bicarbonate, adjusted to pH 10 with ammonium hydroxide)] to afford the title compound: $^1$H NMR (500 MHz, methanol-d$_4$) δ ppm 1.18 (ddd, J=12.6, 9.1, 6.7 Hz, 1H), 1.77-1.84 (m, 1H), 1.89 (d, J=16.5 Hz, 1H), 2.08-2.16 (m, 1H), 2.19 (s, 3H), 2.19-2.26 (m, 1H), 2.41 (s, 3H), 2.76 (dd, J=16.8, 3.1 Hz, 1H), 3.02-3.16 (m, 2H), 3.39 (dd, J=7.0, 4.3 Hz, 1H), 4.17 (d, J=5.2 Hz, 1H), 4.20-4.29 (m, 1H), 4.30-4.38 (m, 1H), 7.10 (d, J=7.9 Hz, 1H), 7.25 (dd, J=7.9, 2.1 Hz, 1H), 7.34 (s, 2H), 7.61 (s, 1H), 7.78 (d, J=1.8 Hz, 1H), 7.91 (s, 2H); MS (APCI) m/z 398 (M+H)$^+$.

Example 113

(5aS,7S,10R,10aR)-2,11-dimethyl-5-[2-(6-methyl-pyridin-3-yl)ethyl]-5,5a,6,7,8,9,10,10a-octahydro-7,10-epiminocyclohepta[b]indole A solution of (7S,10R)-2,11-dimethyl-5-[2-(6-methyl-pyridin-3-yl)ethyl]-5,6,7,8,9,10-hexahydro-7,10-epimino-cyclohepta[b]indole (274 mg, 0.79 mmol, Example 8) in trifluoroacetic acid (5 mL) was chilled to −15° C. (ice/salt bath) under nitrogen. A solution of sodium cyanotrihydroborate (199 mg, 3.17 mmol; Aldrich) in methanol (2 mL) was added dropwise (~15 minute, gas formation!), and then the reaction was allowed to warm slowly to room temperature. After 2 hours at room temperature, methanol (10 mL) was added and the mixture was concentrated in vacuo. The residue was diluted with dichloromethane (50 mL) and washed with saturated aqueous solution of sodium bicarbonate (30 mL), followed by brine (30 mL), and dried over magnesium sulfate and concentrated. The resulting material was purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, methanol-d$_4$) δ ppm 1.67 (m, 1H), 1.86 (m, 1H), 2.08 (m, 1H), 2.25 (s, 3H), 2.42 (m, 3H), 2.72 (s, 3H), 2.83 (s, 3H), 3.04 (m, 3H), 3.30 (m, 2H), 3.54 (m, 1H), 3.85 (m, 2H), 6.62 (d, J=8 Hz, 1H), 7.00 (m, 2H), 7.85 (d, J=8 Hz, 1H), 8.43 (dd, J=2, 8 Hz, 1H), 8.65 (s, 1H); MS (ESI) m/z 348 (M+H)$^+$.

Example 114

2,12-dimethyl-5-[2-(6-methylpyridin-3-yl)ethyl]-6,7,8,9,10,11-hexahydro-5H-7,11-epiminocyclooocta[b]indole Example 114A 2,12-dimethyl-6,7,8,9,10,11-hexahydro-5H-7,11-epiminocyclooocta[b]indole In a 100 mL round-bottom flask were combined p-tolyl-hydrazine hydrochloride (1.58 g, 10 mmol; Aldrich), pseudopelletierine hydrochloride (2.0 g, 10.5 mmol; Acros), and concentrated sulfuric acid (5 mL) in dioxane (50 mL). The reaction mixture was heated to 80° C. for 2.5 hours, then cooled to room temperature. The solvent was decanted, and the residue was dissolved in water (20 mL) and basified with solid potassium carbonate to pH ~12. This solution was extracted with dichloromethane (3×50 mL), and the combined organic phases were dried over magnesium sulfate. After removing the solvent under vacuum, the resulting solid was recrystallized from ether to afford the title compound: $^1$H NMR (300 MHz, methanol-d$_4$) δ ppm 1.21-1.41 (m, 2H), 1.60-1.71 (m, 2H), 1.90-2.08 (m, 2H), 2.35 (s, 3H), 2.38 (s, 3H), 2.42-2.52 (m, 1H), 3.16-3.27 (m, 2H), 4.09 (t, J=3 Hz, 1H), 6.86 (dd, J=8, 1 Hz, 1H), 7.10 (s, 1H), 7.17 (d, J=8 Hz, 1H); MS (DCI/NH$_3$) m/z 241 (M+H)$^+$.

Example 114B 2,12-dimethyl-5-[2-(6-methylpyridin-3-yl)ethyl]-6,7,8,9,10,11-hexahydro-5H-7,11-epiminocyclooocta[b]indole A reaction flask with a septum cap was charged with 30% sodium metal dispersion in paraffin wax (0.30 g, 4.0 mmol; Aldrich) and a solution of 2,12-dimethyl-6,7,8,9,10,11-hexahydro-5H-7,11-epiminocyclooocta[b]indole (0.48 g, 2.0 mmol; Example 114A) in dimethyl sulfoxide (4 mL). The vessel was sealed, flushed with nitrogen, and stirred for 10 minutes. A solution of 2-methyl-5-vinylpyridine (0.238 g, 2.0 mmol; prepared as described in International Publication No. WO 2001017968) and hydroquinone (0.072 g, 0.66 mmol; Aldrich) in anhydrous dimethyl sulfoxide (1.5 mL) was added and the reaction was heated at 100° C. for 72 hours. After cooling the mixture to room temperature, it was poured into water and extracted with ethyl acetate (4×25 mL). The combined organic extracts were washed with brine, concentrated, and purified by reverse-phase HPLC [Waters XBridge™ C18 5 μm OBD column, 30×100 mm, flow rate 40 mL/minute, 5-95% gradient of acetonitrile in buffer (0.1 M aqueous ammonium bicarbonate, adjusted to pH 10 with ammonium hydroxide) over 15 minutes] to afford the title compound: $^1$H NMR (300 MHz, methanol-d$_4$) δ ppm 0.82-1.00 (m, 1H), 1.17-1.30 (m, 1H), 1.32-1.42 (m, 1H), 1.55-1.64 (m, 1H), 1.78-1.99 (m, 3H), 2.15 (s, 3H), 2.40 (s, 6H), 2.66 (dd, J=17, 7 Hz, 1H), 3.06-3.15 (m, 3H), 4.03 (t, J=3 Hz, 1H), 4.30-4.37 (m, 2H), 6.95 (dd, J=8, 1 Hz, 1H), 7.08-7.14 (m, 2H), 7.26 (d, J=8 Hz, 1H), 7.32 (dd, J=8, 2 Hz, 1H), 7.82 (d, J=2 Hz, 1H); MS (DCI/NH$_3$) m/z 360 (M+H)$^+$.

Example 115

(7R,11S)-2,12-dimethyl-5-[2-(6-methylpyridin-3-yl)ethyl]-6,7,8,9,10,11-hexahydro-5H-7,11-epiminocyclooocta[b]indole Purification of the racemic mixture from Example 114B (60 mg) by preparative chiral supercritical fluid chromatography (ChiralPak® OD-H 5 μm column, 21×250 mm, 35° C., 10-50% gradient of CH$_3$OH—CO$_2$ containing 0.1% diethylamine, flow rate 40 mL/minute) afforded the title compound as the first-eluting enantiomer: $^1$H NMR (300 MHz, CDCl$_3$) δ ppm 0.82-1.01 (m, 1H), 1.16-1.28 (m, 1H), 1.31-1.41 (m, 1H), 1.54-1.65 (m, 1H), 1.77-1.98 (m, 3H), 2.15 (s, 3H), 2.40 (s, 6H), 2.65 (dd, J=17, 7 Hz, 1H), 3.06-3.15 (m, 3H), 4.03 (t, J=3 Hz, 1H), 4.30-4.37 (m, 2H), 6.95 (dd, J=8, 1 Hz, 1H), 7.08-7.15 (m, 2 H), 7.26 (d, J=8 Hz, 1H), 7.33 (dd, J=8, 2 Hz, 1H), 7.82 (d, J=2 Hz, 1H); MS (DCI/NH$_3$) m/z 360 (M+H)$^+$.

Example 116

(7S,11R)-2,12-dimethyl-5-[2-(6-methylpyridin-3-yl)ethyl]-6,7,8,9,10,11-hexahydro-5H-7,11-epiminocyclooocta[b]indole Purification of the racemic mixture from Example 114B (60 mg) by preparative chiral supercritical fluid chromatography (ChiralPak® OD-H 5 μm column, 21×250 mm, 35° C., 10-50% gradient of CH$_3$OH—CO$_2$ containing 0.1% diethylamine, flow rate 40 mL/minute) afforded the title compound as the second-eluting enantiomer: $^1$H NMR (300 MHz, CDCl$_3$) δ ppm 0.82-1.00 (m, 1H), 1.17-1.28 (m, 1H), 1.32-1.41 (m, 1H), 1.55-1.65 (m, 1H), 1.77-1.99 (m, 3H), 2.15 (s, 3H), 2.40 (s, 6H), 2.65 (dd, J=17, 7 Hz, 1H), 3.05-3.15 (m, 3H), 4.03 (t, J=3 Hz, 1H), 4.30-4.37 (m, 2H), 6.95 (dd, J=8, 1 Hz, 1H), 7.09-7.14 (m, 2H), 7.26 (d, J=8 Hz, 1H), 7.33 (dd, J=8, 2 Hz, 1H), 7.82 (d, J=2 Hz, 1H); MS (DCI/NH$_3$) m/z 360 (M+H)$^+$.

Example 117

5-[2-(6-chloropyridin-3-yl)ethyl]-2,12-dimethyl-6,7,8,9,10,11-hexahydro-5H-7,11-epiminocycloocta[b]indole

Example 117A 2-(6-chloropyridin-3-yl)-N-p-tolylacetamide

In a 500 mL round-bottom flask were combined 2-(6-chloropyridin-3-yl)acetic acid (10.3 g, 60.0 mmol; Oakwood), p-toluidine (6.43 g, 60.0 mmol; Aldrich) and N,N-diisopropylethylamine (34.3 mL, 198 mmol; Aldrich) in tetrahydrofuran (220 mL). The mixture was stirred at room temperature for 1 hour, and then O-(7-azabenzotriazol-1-yl)-N,N,N',N'-tetramethyluronium hexafluorophosphate (HATU; 25.1 g, 66.0 mmol; Aldrich) was added. After 16 hours, the reaction was concentrated, the residue dissolved in ethyl acetate (500 mL) and washed with water (50 mL). The organic phase was concentrated and purified by flash chromatography (silica gel, hexanes/ethyl acetate, 2:1) to afford the title compound: $^1$H NMR (300 MHz, methanol-d$_4$) δ ppm 2.28 (s, 3H), 3.71 (s, 2H), 7.11 (d, J=8 Hz, 2H), 7.37-7.46 (m, 3H), 7.81 (dd, J=8, 3 Hz, 1H), 8.33 (d, J=2 Hz, 1H); MS (DCI/NH$_3$) m/z 261 (M+H)$^+$.

Example 117B

N-(2-(6-chloropyridin-3-yl)ethyl)-4-methylaniline

A 500 mL reaction flask containing 2-(6-chloropyridin-3-yl)-N-p-tolylacetamide (12 g, 46 mmol; Example 117A) in tetrahydrofuran (200 mL) was treated with 1 M borane-tetrahydrofuran (100 mL, 100 mmol; Aldrich) and then heated to reflux with stirring for 16 hours. After cooling the reaction mixture to room temperature, it was quenched with ethanol, concentrated and purified by flash chromatography (silica gel, hexanes/ethyl acetate, 2:1) to afford the title compound: $^1$H NMR (300 MHz, methanol-d$_4$) δ ppm 2.19 (s, 3H), 2.89 (t, J=7 Hz, 2H), 3.35 (t, J=7 Hz, 2H), 6.56 (d, J=8 Hz, 2H), 6.93 (d, J=8 Hz, 2H), 7.37 (d, J=8 Hz, 1H), 7.70 (dd, J=8, 2 Hz, 1H), 8.21 (d, J=2 Hz, 1H); MS (DCI/NH$_3$) m/z 247 (M+H)$^+$.

Example 117C

N-(2-(6-chloropyridin-3-yl)ethyl)-N-p-tolylnitrous amide

A 250 mL reaction flask was charged with N-(2-(6-chloropyridin-3-yl)ethyl)-4-methylaniline (5 g, 20.3 mmol; Example 117B) in 1 N aqueous HCl (22 mL) and ethanol (20 mL). The mixture was stirred at room temperature until complete dissolution was obtained (~2 hours). The reaction then was cooled in an ice bath and a solution of sodium nitrite (1.55 g, 22.47 mmol; Aldrich) in water (10 mL) was added dropwise with stirring. After the addition was complete, the reaction mixture was allowed to warm briefly to room temperature, then it was cooled again in an ice bath before filtering. The filter cake was washed with water several times and then dried to afford the title compound: $^1$H NMR (300 MHz, methanol-d$_4$) δ ppm 2.38 (s, 3H), 2.88 (t, J=7 Hz, 1H), 4.34 (t, J=7 Hz 2H), 7.25-7.39 (m, 5H), 7.63 (dd, J=8, 2 Hz, 1H), 8.11 (d, J=2 Hz, 1H); MS (DCI/NH$_3$) m/z 276 (M+H)$^+$.

Example 117D 2-chloro-5-(2-(1-p-tolylhydrazinyl)ethyl)pyridine

A 250 mL flask was charged with N-(2-(6-chloropyridin-3-yl)ethyl)-N-p-tolylnitrous amide (5.2 g, 18.9 mmol; Example 117C) and ammonium carbonate (3.62 g, 37.7 mmol; Aldrich) in acetonitrile (10 mL) and water (30 mL). The mixture was cooled in an ice bath and zinc dust (1.63 g, 24.5 mmol; Aldrich) was added very slowly over 2 hours. After stirring for an additional 1 hour, the reaction was filtered to remove the solid material. The filtrate was concentrated and extracted with ethyl acetate. The organic extracts were then purified by flash chromatography (silica gel, hexane/ethyl acetate, 2:1) to afford the title compound: $^1$H NMR (300 MHz, methanol-d$_4$) δ ppm 2.22 (s, 3H), 2.89-2.99 (m, 2H), 3.52-3.60 (m, 2H), 6.81-6.90 (m, 2H), 6.98-7.04 (m, 2H), 7.36 (d, J=8 Hz, 1H), 7.74 (dd, J=8, 3 Hz, 1H), 8.25 (d, J=2 Hz, 1H); MS (DCI/NH$_3$) m/z 262 (M+H)$^+$.

Example 117E 2,12-Dimethyl-5-[2-(6-chloropyridin-3-yl)ethyl]-6,7,8,9,10,11-hexahydro-5H-7,11-epiminocycloocta[b]indole In a 25 mL round-bottomed flask were combined 2-chloro-5-(2-(1-p-tolylhydrazinyl)-ethyl)pyridine (50 mg, 0.19 mmol; Example 117D), pseudopelletierine hydrochloride (40 g, 0.21 mmol; Acros), and concentrated sulfuric acid (31 μL) in dioxane (8 mL). The reaction mixture was heated to 80° C. for 6 hours, then cooled to room temperature. The solvent was removed under vacuum and residue was purified by reverse-phase HPLC [Waters XBridge™ C18 5 μm OBD column, 30×100 mm, flow rate 40 mL/minute, 5-95% gradient of acetonitrile in buffer (0.1% trifluoroacetic acid) over 15 minutes] to afford the title compound as the bistrifluoroacetic acid salt: $^1$H NMR (300 MHz, methanol-d$_4$) δ ppm 0.94-1.13 (m, 1H), 1.39-1.51 (m, 1H), 1.71-1.80 (m, 1H), 1.91-2.17 (m, 3H), 2.43 (s, 3H), 2.50 (d, J=18 Hz, 1H), 2.66 (s, 3H), 2.96 (dd, J=18, 7 Hz, 1H), 3.14-3.23 (m, 2H), 3.83 (t, J=5 Hz, 1H), 4.41 (t, J=6 Hz, 2H), 4.90 (d, J=2 Hz, 1H), 7.09 (d, J=8 Hz, 1H), 7.24 (s, 1H), 7.32 (d, J=8 Hz, 1H), 7.37 (d, J=8 Hz, 1H), 7.50 (dd, J=8, 2 Hz, 1H), 7.77 (d, J=2 Hz, 1H); MS (DCI/NH$_3$) m/z 380 (M+H)$^+$.

Example 118

(7R,11S)-2-methyl-5-[(Z)-2-(6-methylpyridin-3-yl)vinyl]-6,7,8,9,10,11-hexahydro-5H-7,11-epiminocycloocta[b]indole

Example 118A 2-methyl-6,7,8,9,10,11-hexahydro-5H-7,11-epiminocycloocta[b]indole In a 100 mL round-bottom flask were combined p-tolylhydrazine hydrochloride (1.80 g, 11.4 mmol; Alfa Aesar), 9-azabicyclo[3.3.1]nonan-3-one hydrochloride (2.0 g, 11.4 mmol; Accela ChemBio), and concentrated sulfuric acid (5 mL) in dioxane (50 mL). The reaction mixture was heated to 80° C. for 2.5 hours, then cooled to room temperature. The solvent was decanted, and the residue was dissolved in water (20 mL) and basified with solid potassium carbonate to pH ~12. This solution was extracted with dichloromethane (3×50 mL), and the combined organic phases were dried over magnesium sulfate. After removing the solvent under vacuum, the residue was purified by silica gel chromatography ($CH_2Cl_2/CH_3OH$, 3:1) to afford the title compound: $^1H$ NMR (300 MHz, $CDCl_3$) δ ppm 1.39-1.50 (m, 2H), 1.75 (d, J=14 Hz, 2H), 1.91-2.07 (m, 2H), 2.38 (s, 3H), 2.72 (d, J=17 Hz, 1H), 3.27-3.39 (m, 1H), 3.70 (t, J=5 Hz, 1H), 4.55 (t, J=3 Hz, 1H), 6.88 (dd, J=8, 1 Hz, 1H), 7.14 (s, 1H), 7.18 (d, J=8 Hz, 1H); MS (DCI/$NH_3$) m/z 227 (M+H)$^+$.

Example 118B (7R,11S)-2-methyl-5-[(Z)-2-(6-methylpyridin-3-yl)vinyl]-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (227 mg, 1.0 mmol; Example 118A) and 5-ethynyl-2-methylpyridine (235 mg, 2.0 mmol; prepared as described in International Publication No. WO2005090333) was performed according to the procedure described in Example 20 to give both (E)- and (Z)-isomers. Individual enantiomers of the (Z)-isomer were obtained by preparative chiral supercritical fluid chromatography (ChiralPak® OD-H 5 μm column, 21×250 mm, 35° C., 10-50% gradient of $CH_3OH$—$CO_2$ containing 0.1% diethylamine, 20 minutes) to afford the title compound as the first-eluting enantiomer: $^1H$ NMR (300 MHz, methanol-$d_4$) δ ppm 1.33-1.48 (m, 2H), 1.49-1.58 (m, 1H), 1.68-1.78 (m, 1H), 1.83-2.07 (m, 2H), 2.37 (s, 3H), 2.40 (s, 3H), 2.46 (d, J=18 Hz, 1H), 3.06 (dd, J=17, 7 Hz, 1H), 3.54-3.61 (m, 1H), 4.48 (t, J=3 Hz, 1H), 6.64 (d, J=8 Hz, 1H), 6.81-6.91 (m, 2H), 6.97 (d, J=8 Hz, 1H), 7.06 (d, J=8 Hz, 1H), 7.18-7.25 (m, 2H), 8.00 (d, J=2 Hz, 1H); MS (DCI/$NH_3$) m/z 344 (M+H)$^+$.

Example 119

(7S,11R)-2-methyl-5-[(Z)-2-(6-methylpyridin-3-yl)vinyl]-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (227 mg, 1.0 mmol; Example 118A) and 5-ethynyl-2-methylpyridine (235 mg, 2.0 mmol; prepared as described in International Publication No. WO2005090333) was performed according to the procedure described in Example 20 to give both (E)- and (Z)-isomers. Individual enantiomers of the (Z)-isomer were obtained by preparative chiral supercritical fluid chromatography (ChiralPak® OD-H 5 μm column, 21×250 mm, 35° C., 10-50% gradient of $CH_3OH$—$CO_2$ containing 0.1% diethylamine, 20 minutes) to afford the title compound as the second-eluting enantiomer: $^1H$ NMR (300 MHz, methanol-$d_4$) δ ppm 1.33-1.50 (m, 2H), 1.54 (dd, J=14, 2 Hz, 1H), 1.74 (dd, J=13, 2 Hz, 1H), 1.85-2.07 (m, 2H), 2.37 (s, 3H), 2.40 (s, 3H), 2.47 (d, J=18 Hz, 1H), 3.07 (dd, J=18, 7 Hz, 1H), 3.59 (t, J=5 Hz, 1H), 4.50 (t, J=3 Hz, 1H), 6.65 (d, J=9 Hz, 1H), 6.81-6.92 (m, 2H), 6.97 (d, J=8 Hz, 1H), 7.06 (d, J=8 Hz, 1H), 7.16-7.26 (m, 2H), 7.99 (d, J=2 Hz, 1H); MS (DCI/$NH_3$) m/z 344 (M+H)$^+$.

Example 120

(7R,11S)-2-methyl-5-[2-(6-methylpyridin-3-yl)ethyl]-6,7,8,9,10,11-hexahydro-5H-7,11-epiminocycloocta[b]indole A suspension of 2-methyl-5-[(Z)-2-(6-methylpyridin-3-yl)vinyl]-6,7,8,9,10,11-hexahydro-5H-7,11-epiminocycloocta[b]indole (750 mg, 2.18 mmol; from Example 118B) and platinum(IV) oxide (105 mg, 0.462 mmol; Aldrich) in 2-propanol (30 mL) was heated to 65° C. under hydrogen balloon atmosphere (1 atm) for 16 hours, then cooled to room temperature. The catalyst and solvent were removed, and the residue was purified by preparative chiral supercritical fluid chromatography (ChiralPak® OD-H 5 μm column, 21×250 mm, 35° C., 10-50% gradient of $CH_3OH$—$CO_2$ containing 0.1% diethylamine, flow rate 40 mL/minute, 20 minutes) to afford the title compound as the first-eluting enantiomer: $^1H$ NMR (300 MHz, $CDCl_3$) δ ppm 0.96-1.14 (m, J=18, 18, 9, 5 Hz, 1H), 1.25-1.40 (m, 2H), 1.60 (dd, J=13, 2 Hz, 1H), 1.75-1.96 (m, 2H), 2.03 (d, J=17 Hz, 1H), 2.39 (s, 3H), 2.42 (s, 3H), 2.87 (dd, J=17, 7 Hz, 1H), 3.00-3.21 (m, 2H), 3.43 (t, J=6 Hz, 1H), 4.20-4.42 (m, 3H), 6.92 (dd, J=8, 1 Hz, 1H), 7.09-7.15 (m, 2H), 7.20 (d, J=8 Hz, 1H), 7.36 (dd, J=8, 2 Hz, 1H), 7.88 (d, J=2 Hz, 1H); MS (DCI/$NH_3$) m/z 346 (M+H)$^+$.

Example 121

(7S,11R)-2-methyl-5-[2-(6-methylpyridin-3-yl)ethyl]-6,7,8,9,10,11-hexahydro-5H-7,11-epiminocycloocta[b]indole Purification of the racemic mixture from Example 120 by preparative chiral supercritical fluid chromatography (ChiralPak® OD-H 5 μm column, 21×250 mm, 35° C., 10-50% gradient of $CH_3OH$—$CO_2$ containing 0.1% diethylamine, flow rate 40 mL/minute, 20 minutes) afforded the title compound as the second-eluting enantiomer: $^1H$ NMR (300 MHz, $CDCl_3$) δ ppm 0.96-1.15 (m, J=18, 18, 9, 4 Hz, 1H), 1.25-1.40 (m, 2H), 1.61 (dd, J=13, 2 Hz, 1H), 1.75-1.95 (m, 2H), 2.03 (d, J=17 Hz, 1H), 2.39 (s, 3H), 2.42 (s, 3H), 2.87 (dd, J=17, 8 Hz, 1H), 2.99-3.21 (m, 2H), 3.44 (t, J=5 Hz, 1H), 4.20-4.42 (m, 3H), 6.92 (dd, J=8, 1 Hz, 1H), 7.08-7.15 (m, 2H), 7.21 (d, J=8 Hz, 1H), 7.36 (dd, J=8, 2 Hz, 1H), 7.88 (d, J=2 Hz, 1H); MS (DCI/$NH_3$) m/z 346 (M+H)$^+$.

Example 122

2,12-dimethyl-5-[(E)-2-(6-methylpyridin-3-yl)vinyl]-6,7,8,9,10,11-hexahydro-5H-7,11-epiminocycloocta[b]indole The coupling of 2,12-dimethyl-6,7,8,9,10,11-hexahydro-5H-7,11-epiminocycloocta[b]indole (110 mg, 0.458 mmol; Example 114A) and 5-ethynyl-2-methylpyridine (107 mg, 0.915 mmol; prepared as described in International Publication No. WO2005090333) was performed according to the procedure described in Example 20 to give the title compound as the minor of two alkene isomers: $^1H$ NMR (300 MHz, methanol-$d_4$) δ ppm 1.30-1.53 (m, 2H), 1.73-1.88 (m, 2H), 1.97-2.17 (m, 2H), 2.43 (s, 3H), 2.53 (s, 3H), 2.55 (s, 3H), 2.88 (d, J=18 Hz, 1H), 3.40-3.51 (m, 1H), 3.56 (br. s, 1H), 4.41 (s, 1H), 6.88 (d, J=15 Hz, 1H), 7.10 (dd, J=8, 1 Hz, 1H), 7.24 (s, 1H), 7.30 (d, J=8 Hz, 1H), 7.67 (d, J=8 Hz, 1H), 7.74 (d, J=15 Hz, 1H), 7.97 (dd, J=8, 2 Hz, 1H), 8.53 (d, J=2 Hz, 1H); MS (DCI/NH$_3$) m/z 358 (M+H)$^+$.

Example 123

(7R,11S)-2,12-dimethyl-5-[(Z)-2-(6-methylpyridin-3-yl)vinyl]-6,7,8,9,10,11-hexahydro-5H-7,11-epiminocycloocta[b]indole The coupling of 2,12-dimethyl-6,7,8,9,10,11-hexahydro-5H-7,11-epiminocycloocta[b]indole (110 mg, 0.458 mmol; Example 114A) and 5-ethynyl-2-methylpyridine (107 mg, 0.915 mmol; prepared as described in International Publication No. WO2005090333) was performed according to the procedure described in Example 20 to give the racemic mixture of the title compound as the major of two alkene isomers. The individual enantiomers from the racemic mixture of the major alkene isomer were separated by preparative chiral supercritical fluid chromatography (ChiralPak® OD-H 5 μm column, 21×250 mm, 35° C., 10-50% gradient of CH$_3$OH—CO$_2$ containing 0.1% diethylamine) to afford the title compound as the first-eluting enantiomer: $^1$H NMR (300 MHz, methanol-d$_4$) δ ppm 1.18-1.30 (m, 1H), 1.30-1.41 (m, 1H), 1.48 (dd, J=13, 2 Hz, 1H), 1.69 (dd, J=13, 2 Hz, 1H), 1.83-2.09 (m, 2H), 2.26 (d, J=17 Hz, 1H), 2.28 (s, 3H), 2.38 (s, 3H), 2.39 (s, 3H), 2.89 (dd, J=18, 7 Hz, 1H), 3.17 (t, J=5 Hz, 1H), 4.13 (s, 1H), 6.64 (d, J=9 Hz, 1H), 6.84-6.90 (m, 1H), 6.92-7.01 (m, 2H), 7.03-7.09 (m, 1H), 7.15-7.22 (m, 2H), 7.96 (d, J=2 Hz, 1H); MS (DCI/NH$_3$) m/z 358 (M+H)$^+$.

Example 124

(7S,11R)-2,12-dimethyl-5-[(Z)-2-(6-methylpyridin-3-yl)vinyl]-6,7,8,9,10,11-hexahydro-5H-7,11-epiminocycloocta[b]indole The coupling of 2,12-dimethyl-6,7,8,9,10,11-hexahydro-5H-7,11-epiminocycloocta[b]indole (110 mg, 0.458 mmol; Example 114A) and 5-ethynyl-2-methylpyridine (107 mg, 0.915 mmol; prepared as described in International Publication No. WO2005090333) was performed according to the procedure described in Example 20 to give the racemic mixture of the title compound as the major of two alkene isomers. The individual enantiomers from this racemic mixture were separated by preparative chiral supercritical fluid chromatography (ChiralPak® OD-H 5 μm column, 21×250 mm, 35° C., 10-50% gradient of CH$_3$OH—CO$_2$ containing 0.1% diethylamine) to afford the title compound as the second-eluting enantiomer: $^1$H NMR (300 MHz, methanol-d$_4$) δ ppm 1.18-1.41 (m, 2H), 1.48 (dd, J=13, 2 Hz, 1H), 1.65-1.75 (m, 1H), 1.83-2.08 (m, 2H), 2.26 (d, J=17 Hz, 1H), 2.28 (s, 3 H), 2.38 (s, 3H), 2.39 (s, 3H), 2.90 (dd, J=18, 7 Hz, 1H), 3.17 (t, J=5 Hz, 1H), 4.13 (s, 1H), 6.64 (d, J=8 Hz, 1H), 6.84-6.91 (m, 1H), 6.92-7.10 (m, 3H), 7.15-7.23 (m, 2H), 7.96 (d, J=2 Hz, 1H); MS (DCI/NH$_3$) m/z 358 (M+H)$^+$.

Example 125

(7R,11S)-2-methyl-5-[(E)-2-(6-methylpyridin-3-yl)vinyl]-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (227 mg, 1.00 mmol; Example 118A) and 5-ethynyl-2-methylpyridine (235 mg, 2.0 mmol; prepared as described in International Publication No. WO2005090333) was performed according to the procedure described in Example 20 to produce both (E) and (Z) isomers of the title compound. Individual enantiomers of the (E) isomer were obtained by preparative chiral supercritical fluid chromatography (ChiralPak® OD-H 5 μm column, 21×250 mm, 35° C., 10-50% gradient of CH$_3$OH—CO$_2$ containing 0.1% diethylamine) to afford the title compound as the first-eluting enantiomer: $^1$H NMR (300 MHz, methanol-d$_4$) δ ppm 1.35-1.54 (m, 2H), 1.66-1.81 (m, 2H), 1.89-2.07 (m, 2H), 2.42 (s, 3H), 2.53 (s, 3H), 2.84 (d, J=17 Hz, 1H), 3.33-3.45 (m, 1H), 3.69 (t, J=6 Hz, 1H), 4.43 (s, 1H), 6.83 (d, J=15 Hz, 1H), 7.06 (d, J=8 Hz, 1H), 7.22 (s, 1H), 7.29 (d, J=8 Hz, 1H), 7.64 (d, J=8 Hz, 1H), 7.73 (d, J=15 Hz, 1H), 7.95 (dd, J=8, 2 Hz, 1H), 8.51 (d, J=2 Hz, 1H); MS (DCI/NH$_3$) m/z 344 (M+H)$^+$.

Example 126

(7S,11R)-2-methyl-5-[(E)-2-(6-methylpyridin-3-yl)vinyl]-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (227 mg, 1.00 mmol; Example 118A) and 5-ethynyl-2-methylpyridine (235 mg, 2.0 mmol; prepared as described in International Publication No. WO2005090333) was performed according to the procedure described in Example 20 to produce both (E)- and (Z)-isomers of the title compound. Individual enantiomers of the (E)-isomer were obtained by preparative chiral super critical fluid chromatography (ChiralPak® OD-H 5 μm column, 21×250 mm, 35° C., 10-50% gradient of CH$_3$OH—CO$_2$ containing 0.1% diethylamine) to afford the title compound as the second-eluting enantiomer: $^1$H NMR (300 MHz, methanol-d$_4$) δ ppm 1.38-1.63 (m, 2H), 1.83-1.96 (m, 2H), 1.98-2.18 (m, 2H), 2.44 (s, 3H), 2.54 (s, 3H), 3.10 (d, J=18 Hz, 1H), 3.55 (dd, J=18, 7 Hz, 1H), 4.01 (t, J=5 Hz, 1H), 4.83 (s, 1H), 6.89 (d, J=15 Hz, 1H), 7.13 (dd, J=8, 1 Hz, 1H), 7.31 (d, J=9 Hz, 2H), 7.68 (d, J=8 Hz, 1H), 7.73 (d, J=15 Hz, 1H), 7.97 (dd, J=8, 2 Hz, 1H), 8.54 (d, J=2 Hz, 1H); MS (DCI/NH$_3$) m/z 344 (M+H)$^+$.

Example 127

(7R,11S)-2-methyl-5-[2-(2-methylphenyl)ethyl]-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (110 mg, 0.486 mmol; Example 118A) and 1-methyl-2-vinylbenzene (115 mg, 0.972 mmol; Aldrich) was performed according to the procedure described in Example 114B to provide title compound as a racemic mixture. Individual enantiomers were obtained by preparative chiral supercritical fluid chromatography (ChiralPak® OD-H 5 μm column, 21×250 mm, 35° C., 10-50% gradient of CH$_3$OH—CO$_2$ containing 0.1% diethylamine, 20 minutes) to afford the title compound as the first-eluting enantiomer: $^1$H NMR (300 MHz, methanol-d$_4$) δ ppm 1.13-1.33 (m, 3H), 1.60-1.96 (m, 4H), 2.00 (s, 3H), 2.40 (s, 3H), 2.79 (dd, J=17, 7 Hz, 1H), 2.98-3.08 (m, 1H), 3.16 (ddd, J=14, 9, 6 Hz, 1H), 3.36-3.43 (m, 1H), 4.20 (ddd, J=15, 9, 5 Hz, 1H), 4.32-4.42 (m, 2H), 6.90-6.98 (m, 2H), 6.99-7.11 (m, 3H), 7.14 (s, 1H), 7.27 (d, J=8 Hz, 1H); MS (DCI/NH$_3$) m/z 345 (M+H)$^+$.

Example 128

(7S,11R)-2-methyl-5-[2-(2-methylphenyl)ethyl]-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (110 mg, 0.486 mmol; Example 118A) and 1-methyl-2-vinylbenzene (115 mg, 0.972 mmol; Aldrich) was performed according to the procedure described in Example 114B to afford the title compound as a racemic mixture. Individual enantiomers were obtained by preparative chiral supercritical fluid chromatography (ChiralPak® OD-H 5 μm column, 21×250 mm, 35° C., 10-50% gradient of $CH_3OH$—$CO_2$ containing 0.1% diethylamine, 20 minutes) to afford the title compound as the second-eluting enantiomer: $^1H$ NMR (300 MHz, methanol-$d_4$) δ ppm 1.10-1.34 (m, 3H), 1.59-1.96 (m, 4H), 2.00 (s, 3H), 2.40 (s, 3H), 2.79 (dd, J=17, 7 Hz, 1H), 2.97-3.09 (m, 1H), 3.11-3.22 (m, 1H), 3.37-3.43 (m, 1H), 4.20 (ddd, J=14, 9, 5 Hz, 1H), 4.31-4.42 (m, 2H), 6.90-6.97 (m, 2H), 6.99-7.11 (m, 3H), 7.14 (s, 1H), 7.27 (d, J=8 Hz, 1H); MS (DCI/$NH_3$) m/z 345 (M+H)$^+$.

Example 129

(7R,11S)-5-[2-(2,5-dimethylphenyl)ethyl]-2-methyl-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (110 mg, 0.486 mmol; Example 118A) and 1,4-dimethyl-2-vinylbenzene (129 mg, 0.972 mmol; Aldrich) was performed according to the procedure described in Example 114B to afford the title compound as a racemic mixture. Individual enantiomers were obtained by preparative chiral supercritical fluid chromatography (ChiralPak® OD-H 5 μm column, 21×250 mm, 35° C., 10-50% gradient of $CH_3OH$—$CO_2$ containing 0.1% diethylamine, 20 minutes) to afford the title compound as the first-eluting enantiomer: $^1H$ NMR (300 MHz, methanol-$d_4$) δ ppm 1.07-1.35 (m, 3H), 1.60-1.96 (m, 4H), 1.99 (s, 3H), 2.15 (s, 3H), 2.41 (s, 3H), 2.82 (dd, J=17, 7 Hz, 1H), 2.94-3.16 (m, 2H), 3.38-3.45 (m, 1H), 4.19 (ddd, J=15, 9, 5 Hz, 1H), 4.30-4.41 (m, 2H), 6.69 (s, 1H), 6.84-6.99 (m, 3H), 7.14 (s, 1H), 7.27 (d, J=8 Hz, 1H); MS (DCI/$NH_3$) m/z 359 (M+H)$^+$.

Example 130

(7S,11R)-5-[2-(2,5-dimethylphenyl)ethyl]-2-methyl-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (110 mg, 0.486 mmol; Example 118A) and 1,4-dimethyl-2-vinylbenzene (129 mg, 0.972 mmol; Aldrich) was performed according to the procedure described in Example 114B to afford the title compound as a racemic mixture. Individual enantiomers were obtained by preparative chiral supercritical fluid chromatography (ChiralPak® OD-H 5 μm column, 21×250 mm, 35° C., 10-50% gradient of $CH_3OH$—$CO_2$ containing 0.1% diethylamine, 20 minutes) to afford the title compound as the second-eluting enantiomer: $^1H$ NMR (300 MHz, methanol-$d_4$) δ ppm 1.07-1.32 (m, 3H), 1.62 (dd, J=13, 2 Hz, 1H), 1.70-1.95 (m, 3H), 2.00 (s, 3H), 2.15 (s, 3H), 2.40 (s, 3H), 2.79 (dd, J=17, 7 Hz, 1H), 2.94-3.16 (m, 2H), 3.34-3.40 (m, 1H), 4.19 (ddd, J=14, 9, 5 Hz, 1H), 4.28-4.39 (m, 2H), 6.69 (s, 1H), 6.85-6.97 (m, 3H), 7.13 (s, 1H), 7.26 (d, J=8 Hz, 1H); MS (DCI/$NH_3$) m/z 359 (M+H)$^+$.

Example 131

(7R,11S)-5-[2-(4-chlorophenyl)ethyl]-2-methyl-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (226 mg, 1.0 mmol; Example 118A) and 1-chloro-4-vinylbenzene (277 mg, 1.99 mmol; Aldrich) was performed according to the procedure described in Example 114B to afford the title compound as a racemic mixture. Individual enantiomers were obtained by preparative chiral supercritical fluid chromatography (ChiralPak® OD-H 5 μm column, 21×250 mm, 35° C., 10-50% gradient of $CH_3OH$—$CO_2$ containing 0.1% diethylamine, 20 minutes) to afford the title compound as the first-eluting enantiomer: $^1H$ NMR (300 MHz, methanol-$d_4$) δ ppm 1.03-1.17 (m, 1H), 1.28-1.43 (m, 2H), 1.65 (d, J=13 Hz, 1H), 1.76-1.94 (m, 2H), 1.98 (d, J=17 Hz, 1H), 2.40 (s, 3H), 2.90 (dd, J=17, 8 Hz, 1H), 2.97-3.15 (m, 2H), 3.47-3.54 (m, 1H), 4.15-4.27 (m, 1H), 4.31-4.44 (m, 2H), 6.93-6.99 (m, 2H), 7.15 (s, 1H), 7.18 (d, J=8 Hz, 2H), 7.26 (d, J=8 Hz, 1H); MS (DCI/$NH_3$) m/z 365 367 (M+H)$^+$.

Example 132

(7S,11R)-5-[2-(4-chlorophenyl)ethyl]-2-methyl-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (226 mg, 1.0 mmol; Example 118A) and 1-chloro-4-vinylbenzene (277 mg, 1.99 mmol; Aldrich) was performed according to the procedure described in Example 114B to afford the title compound as a racemic mixture. Individual enantiomers were obtained by preparative chiral supercritical fluid chromatography (ChiralPak® OD-H 5 μm column, 21×250 mm, 35° C., 10-50% gradient of $CH_3OH$—$CO_2$ containing 0.1% diethylamine, 20 minute) to afford the title compound as the second-eluting enantiomer: $^1H$ NMR (300 MHz, methanol-$d_4$) δ ppm 1.04-1.20 (m, 1H), 1.29-1.44 (m, 2H), 1.66 (dd, J=13, 2 Hz, 1H), 1.78-2.04 (m, 3H), 2.40 (s, 3H), 2.92 (dd, J=17, 7 Hz, 1H), 2.98-3.17 (m, 2H), 3.50-3.57 (m, 1H), 4.21 (ddd, J=15, 9, 6 Hz, 1H), 4.32-4.42 (m, 1H), 4.43-4.47 (m, 1H), 6.92-7.00 (m, 3H), 7.14-7.21 (m, 3H), 7.27 (d, J=8 Hz, 1H); MS (DCI/$NH_3$) m/z 365 367 (M+H)$^+$.

Example 133

(7R,11S)-2-methyl-5-{2-[3-(trifluoromethyl)phenyl]ethyl}-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (110 mg, 0.486 mmol; Example 118A) and 1-(trifluoromethyl)-3-vinylbenzene (167 mg, 1.00 mmol; Aldrich) was performed according to the procedure described in Example 114B to afford the title compound as a racemic mixture. Individual enantiomers were obtained by preparative chiral supercritical fluid chromatography (ChiralPak® OD-H 5 μm column, 21×250 mm, 35° C., 10-50% gradient of $CH_3OH$—$CO_2$ containing 0.1% diethylamine, 20 minutes) to afford the title compound as the first-eluting enantiomer: $^1$H NMR (300 MHz, methanol-$d_4$) δ ppm 0.97-1.14 (m, 1H), 1.23-1.43 (m, 2H), 1.62 (dd, J=13, 2 Hz, 1H), 1.75-1.97 (m, 2H), 2.09 (d, J=17 Hz, 1H), 2.40 (s, 3H), 2.90 (dd, J=17, 7 Hz, 1H), 3.10-3.25 (m, 2H), 3.49 (t, J=5 Hz, 1H), 4.27-4.42 (m, 3H), 6.93 (dd, J=8, 1 Hz, 1H), 7.14 (s, 1H), 7.18-7.24 (m, 2H), 7.29 (s, 1H), 7.35 (t, J=8 Hz, 1H), 7.42-7.48 (m, 1H); MS (DCI/$NH_3$) m/z 399 (M+H)$^+$.

Example 134

2-methyl-5-{(E)-2-[3-(trifluoromethyl)phenyl]vinyl}-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (1132 mg, 5.0 mmol; Example 118A) and 1-ethynyl-3-(trifluoromethyl)benzene (1701 mg, 10.0 mmol; Aldrich) was performed according to the procedure described in Example 20 to afford the title compound as the major isomeric product: $^1$H NMR (300 MHz, methanol-$d_4$) δ ppm 1.34-1.54 (m, 2H), 1.67-1.80 (m, 2H), 1.89-2.07 (m, 2H), 2.42 (s, 3H), 2.84 (d, J=17 Hz, 1H), 3.34-3.45 (m, 1H), 3.68 (t, J=5 Hz, 1H), 4.41 (t, J=3 Hz, 1H), 6.91 (d, J=15 Hz, 1H), 7.06 (dd, J=8, 1 Hz, 1H), 7.22 (s, 1H), 7.46-7.57 (m, 2H), 7.65 (d, J=8 Hz, 1H), 7.72-7.84 (m, 3H); MS (DCI/$NH_3$) m/z 397 (M+H)$^+$.

Example 135

(7S,11R)-2-methyl-5-{2-[3-(trifluoromethyl)phenyl]ethyl}-6,7,8,9,10,11-hexahydro-5H-7,11-epiminocycloocta[b]indole In a 100 mL round-bottomed flask were combined 2-methyl-5-{(E)-2-[3-(trifluoromethyl)phenyl]vinyl}-6,7,8,9,10,11-hexahydro-5H-7,11-epiminocycloocta[b]indole (300 mg, 0.757 mmol; Example 134), 10% palladium on carbon (35 mg; Aldrich) in ethanol (30 mL). The reaction mixture was heated to 40° C. under a hydrogen balloon atmosphere for 16 hours, then cooled to room temperature. The catalyst and solvent were removed, and the residue was purified by reverse-phase HPLC [Waters XBridge™ C18 5 μm OBD column, 30×100 mm, flow rate 40 mL/minute, 5-95% gradient of acetonitrile in buffer (0.1% trifluoroacetic acid) over 15 minutes] to afford the title compound as a racemic mixture. This material was purified further by preparative chiral supercritical fluid chromatography (ChiralPak® OD-H 5 μm column, 21×250 mm, 35° C., 10-50% gradient of $CH_3OH$—$CO_2$ containing 0.1% diethylamine, 20 minutes) to afford the title compound: $^1$H NMR (300 MHz, $CDCl_3$) δ ppm 0.97-1.17 (m, 1H), 1.22-1.42 (m, 2H), 1.61 (dd, J=13, 2 Hz, 1H), 1.74-1.95 (m, 2H), 2.06 (d, J=17 Hz, 1H), 2.40 (s, 3H), 2.87 (dd, J=17, 7 Hz, 1H), 3.10-3.23 (m, 2H), 3.44 (t, J=6 Hz, 1H), 4.25-4.44 (m, 3H), 6.93 (d, J=8 Hz, 1H), 7.13 (s, 1H), 7.17-7.23 (m, 2H), 7.29 (s, 1H), 7.35 (t, J=8 Hz, 1H), 7.42-7.48 (m, 1H); MS (DCI/$NH_3$) m/z 399 (M+H)$^+$.

Example 136

12-ethyl-2-methyl-5-{2-[3-(trifluoromethyl)phenyl]ethyl}-6,7,8,9,10,11-hexahydro-5H-7,11-epiminocycloocta[b]indole In a 100 mL round-bottom flask were combined 2-methyl-5-{(E)-2-[3-(trifluoromethyl)phenyl]vinyl}-6,7,8,9,10,11-hexahydro-5H-7,11-epiminocycloocta[b]indole (300 mg, 0.757 mmol; Example 134) and 10% palladium on carbon (35 mg; Aldrich) in ethanol (30 mL). The reaction mixture was heated to 40° C. under a hydrogen balloon atmosphere for 16 hours, then cooled to room temperature. The catalyst and solvent were removed, and the residue was purified by reverse-phase HPLC [Waters XBridge™ C18 5 μm OBD column, 30×100 mm, flow rate 40 mL/minute, 5-95% gradient of acetonitrile in buffer (0.1% trifluoroacetic acid) over 15 minutes] to afford the title compound as a byproduct as the trifluoroacetic acid salt: $^1$H NMR (300 MHz, $CDCl_3$) δ ppm 0.90-1.08 (m, 4H), 1.18-1.30 (m, 1H), 1.39 (ddd, J=13, 4, 2 Hz, 1H), 1.59 (dd, J=13, 2 Hz, 1H), 1.77-1.99 (m, 3H), 2.18-2.33 (m, 2H), 2.40 (s, 3H), 2.55 (dd, J=17, 7 Hz, 1H), 3.14-3.26 (m, 3H), 4.16 (t, J=3 Hz, 1H), 4.27-4.45 (m, 2H), 6.94 (dd, J=8, 1 Hz, 1H), 7.08-7.16 (m, 2H), 7.23-7.28 (m, 2H), 7.31 (t, J=8 Hz, 1H), 7.40-7.45 (m, 1H); MS (DCI/$NH_3$) m/z 427 (M+H)$^+$.

Example 137

(7R,11S)-2-methyl-5-{(E)-2-[3-(trifluoromethyl)phenyl]vinyl}-6,7,8,9,10,11-hexahydro-5H-7,11-epiminocycloocta[b]indole Purification of the racemic mixture from Example 134 by preparative chiral supercritical fluid chromatography (ChiralPak® OD-H 5 μm column, 21×250 mm, 35° C., 10-50% gradient of $CH_3OH$—$CO_2$ containing 0.1% diethylamine, flow rate 40 mL/minute, 20 minutes) afforded the title compound as the first-eluting enantiomer: $^1$H NMR (300 MHz, methanol-$d_4$) δ ppm 1.37-1.56 (m, 2H), 1.70-1.83 (m, 2H), 1.90-2.09 (m, 2H), 2.42 (s, 3H), 2.89 (d, J=17 Hz, 1H), 3.41 (dd, J=18, 7 Hz, 1H), 3.73 (t, J=5 Hz, 1H), 4.49 (t, J=3 Hz, 1H), 6.92 (d, J=15 Hz, 1H), 7.07 (dd, J=8, 1 Hz, 1H), 7.23 (s, 1H), 7.47-7.58 (m, 2H), 7.66 (d, J=8 Hz, 1H), 7.76 (d, J=15 Hz, 1H), 7.79-7.84 (m, 2H); MS (DCI/$NH_3$) m/z 397 (M+H)$^+$.

Example 138

(7S,11R)-2-methyl-5-{(E)-2-[3-(trifluoromethyl)phenyl]vinyl}-6,7,8,9,10,11-hexahydro-5H-7,11-epiminocycloocta[b]indole Purification of the racemic mixture from Example 134 by preparative chiral supercritical fluid chromatography (ChiralPak® OD-H 5 μm column, 21×250 mm, 35° C., 10-50% gradient of $CH_3OH$—$CO_2$ containing 0.1% diethylamine, flow rate 40 mL/minute, 20 minutes) afforded the title compound as the second-eluting enantiomer: $^1$H NMR (300 MHz, methanol-$d_4$) δ ppm 1.38-1.56 (m, 2H), 1.72-1.83 (m, 2H), 1.91-2.09 (m, 2H), 2.43 (s, 3H), 2.90 (d, J=17 Hz, 1H), 3.42 (dd, J=17, 7 Hz, 1H), 3.75 (t, J=5 Hz, 1H), 4.51 (s, 1H), 6.92 (d, J=15 Hz, 1H), 7.08 (dd, J=8, 1 Hz, 1H), 7.23 (s, 1H), 7.48-7.58 (m, 2H), 7.66 (d, J=8 Hz, 1H), 7.76 (d, J=15 Hz, 1H), 7.79-7.85 (m, 2H); MS (DCI/$NH_3$) m/z 397 (M+H)$^+$.

Example 139

2-methyl-5-{(Z)-2-[3-(trifluoromethyl)phenyl]vinyl}-6,7,8,9,10,11-hexahydro-5H-7,11-epiminocycloocta[b]indole The coupling of 2-methyl-6,7,8,9,10,11-hexahydro-5H-7,11-epiminocycloocta[b]indole (1132 mg, 5.0 mmol; Example 118A) and 1-ethynyl-3-(trifluoromethyl)benzene (1701 mg, 10.0 mmol; Aldrich) was performed according to the procedure described in Example 20 to afford the title compound as the minor isomeric product: $^1$H NMR (300 MHz, methanol-d$_4$) δ ppm 1.26-1.44 (m, J=27, 14, 4, 4 Hz, 1H), 1.46-1.58 (m, 1H), 1.67 (dd, J=15, 2 Hz, 1H), 1.86-2.18 (m, 3H), 2.40 (s, 3H), 2.68 (d, J=18 Hz, 1H), 3.24-3.31 (m, 1H), 4.01 (t, J=6 Hz, 1H), 5.04 (t, J=3 Hz, 1H), 6.84 (d, J=9 Hz, 1H), 6.92-7.03 (m, 3H), 7.18-7.24 (m, 2H), 7.29-7.39 (m, 2H), 7.44-7.50 (m, 1H); MS (DCI/NH$_3$) m/z 397 (M+H)$^+$.

Example 140

5-[2-(6-methylpyridin-3-yl)ethyl]-2-(trifluoromethoxy)-6,7,8,9,10,11-hexahydro-5H-7,11-epiminocycloocta[b]indole Example 140A 2-trifluoromethoxy-6,7,8,9,10,11-hexahydro-5H-7,11-epiminocycloocta[b]indole In a 30 mL microwave reaction tube were combined 4-(trifluoromethoxy)phenylhydrazine hydrochloride (1062 mg, 5.0 mmol; Maybridge), 9-azabicyclo[3.3.1]nonan-3-one hydrochloride (878 mg, 5.0 mmol; Accela ChemBio), and 1 N HCl in acetic acid (15 mL, 15 mmol; Aldrich). The reaction mixture was microwaved at 150° C. (Biotage Personal Chemistry, maximum 300 W) for 15 minutes, then cooled to room temperature. The solvent was removed, and the residue was dissolved in water (20 mL) and basified with solid potassium carbonate to ~pH 12. This solution was extracted with dichloromethane (3×50 mL), and the combined organic phases were dried over magnesium sulfate. After removing the solvent under vacuum, the residue was purified by flash chromatography (silica gel, CH$_2$Cl$_2$/CH$_3$OH, 3:1) to afford the title compound: $^1$H NMR (300 MHz, CDCl$_3$) δ ppm 1.33-1.52 (m, 2H), 1.64-1.78 (m, 2H), 1.89-2.06 (m, 2H), 2.68 (d, J=17 Hz, 1H), 3.25-3.34 (m, 1H), 3.62 (t, J=5 Hz, 1H), 4.43 (t, J=3 Hz, 1H), 6.93 (ddd, J=9, 2, 1 Hz, 1H), 7.22 (d, J=1 Hz, 1H), 7.31 (d, J=9 Hz, 1H); MS (DCI/NH$_3$) m/z 297 (M+H)$^+$.

Example 140B

5-[2-(6-methylpyridin-3-yl)ethyl]-2-(trifluoromethoxy)-6,7,8,9,10,11-hexahydro-5H-7,11-epiminocycloocta[b]indole The coupling of 2-trifluoromethoxy-6,7,8,9,10,11-hexahydro-5H-7,11-epiminocycloocta[b]indole (148 mg, 0.500 mmol; Example 140A) and 2-methyl-5-vinylpyridine (119 mg, 1.00 mmol; IBScreen) was performed according to the procedure described in Example 114B to afford the title compound: $^1$H NMR (500 MHz, pyridine-d$_5$) δ ppm 1.09-1.22 (m, 1H), 1.29-1.39 (m, J=7, 7 Hz, 1H), 1.46 (d, J=14 Hz, 1H), 1.75 (d, J=14 Hz, 1H), 2.26-2.44 (m, 3H), 2.48 (s, 3H), 2.95-3.04 (m, 1H), 3.05-3.13 (m, 1H), 3.47 (dd, J=18, 7 Hz, 1H), 4.22-4.31 (m, 1H), 4.34-4.43 (m, 2H), 5.29 (s, 1H), 6.99 (d, J=8 Hz, 1H), 7.23-7.31 (m, 2H), 7.51 (d, J=9 Hz, 1H), 7.60 (s, 1H), 8.37 (d, J=2 Hz, 1H); MS (DCI/NH$_3$) m/z 416 (M+H)$^+$.

Example 141

5-[2-(2-methylphenyl)ethyl]-2-(trifluoromethoxy)-6,7,8,9,10,11-hexahydro-5H-7,11-epiminocycloocta[b]indole The coupling of 2-trifluoromethoxy-6,7,8,9,10,11-hexahydro-5H-7,11-epiminocycloocta[b]indole (148 mg, 0.500 mmol; Example 140A) and 1-methyl-2-vinylbenzene (118 mg, 1.00 mmol; Aldrich) was performed according to the procedure described in Example 114B to afford the title compound: $^1$H NMR (500 MHz, pyridine-d$_5$) δ ppm 1.09-1.21 (m, 1H), 1.29-1.43 (m, 2H), 1.80 (d, J=13 Hz, 1H), 2.02-2.10 (m, 4H), 2.27 (tt, J=14, 5 Hz, 1H), 2.41 (tt, J=14, 4 Hz, 1H), 3.00 (dt, J=14, 5 Hz, 1H), 3.05-3.14 (m, 1H), 3.35 (dd, J=18, 7 Hz, 1H), 4.21 (ddd, J=15, 9, 6 Hz, 1H), 4.28-4.33 (m, 1H), 4.37 (ddd, J=15, 5, 5 Hz, 1H), 5.29 (s, 1H), 6.92 (d, J=7 Hz, 1H), 7.06 (t, J=7 Hz, 1H), 7.09-7.12 (m, 1H), 7.15 (t, J=7 Hz, 1H), 7.30 (d, J=10 Hz, 1H), 7.54 (d, J=9 Hz, 1H), 7.63 (s, 1H); MS (DCI/NH$_3$) m/z 415 (M+H)$^+$.

Example 142

6-[2-(6-chloropyridin-3-yl)ethyl]-9-methyl-3,4,5,6-tetrahydro-1H-2,5-ethanoazepino[4,3-b]indole In a 50 mL round-bottom flask were combined 2-chloro-5-(2-(1-p-tolylhydrazinyl)-ethyl)pyridine (0.272 g, 1.039 mmol; Example 117D), and 1-azabicyclo[3.2.2]nonan-4-one (0.188 g, 1.351 mmol; Example 2A) in dioxane (5 mL). After 10 minutes of warming to 50° C., the suspension cleared. Concentrated sulfuric acid (0.277 mL, 5.20 mmol) was added and the mixture was heated at 80° C. After 1.5 hours, the mixture was cooled and concentrated to about 3 mL. The residue was dissolved in water (75 mL), basified with concentrated sodium hydroxide (30 mmol), extracted with chloroform (4×25 mL), dried over magnesium sulfate, and concentrated. The residue was purified by reverse-phase HPLC [Waters XBridge™ C18 5 μm OBD column, 30×100 mm, flow rate 40 mL/minute, 5-95% gradient of acetonitrile in buffer (0.1 M aqueous ammonium bicarbonate, adjusted to pH 10 with ammonium hydroxide) over 15 minutes] to give the title compound: $^1$H NMR (300 MHz, methanol-d$_4$) δ ppm 1.63 (dddd, J=14.3, 9.3, 5.2, 2.4 Hz, 2H), 1.95 (ddt, J=13.6, 9.2, 5.2 Hz, 2H), 2.39 (s, 3H), 2.95 (m, 1H), 3.00 (m, 2H), 3.06 (t, J=6.4 Hz, 2H), 3.19 (ddd, J=14.1, 9.0, 5.2 Hz, 2H), 4.22 (s, 2H), 4.38 (t, J=6.4 Hz, 2H), 6.92 (dd, J=8.5, 1.4 Hz, 1H), 7.11 (br s, 1H), 7.12 (d, J=8.5 Hz, 1H), 7.25 (d, J=8.1 Hz, 1H), 7.36 (dd, J=8.3, 2.4 Hz, 1H), 7.79 (d, J=2.0 Hz, 1H); MS (DCI/NH$_3$) m/z 366 (M+H)$^+$.

Example 143

9-methyl-6-{2-[6-(trifluoromethyl)pyridin-3-yl]ethyl}-3,4,5,6-tetrahydro-1H-2,5-ethanoazepino[4,3-b]indole Example 143A 2-trifluoromethyl-5-ethenylpyridine Potassium vinyltrifluoroborate (362 mg, 2.7 mmol; Aldrich), 5-bromo-2-trifluoromethylpyridine (539 mg, 2.38 mmol; Aldrich) and triphenylphosphine (37.7 mg, 0.144 mmol) were added at room temperature to a solution of cesium carbonate (2.16 g, 6.63 mmol) in water (2 mL). Tetrahydrofuran (18 mL) was added, and the reaction flask was evacuated and purged with nitrogen (3 cycles). Palladium(II) chloride (9.2 mg, 0.052 mmol) was added, and the reaction flask was again evacuated and purged with nitrogen (3 cycles), then heated under nitrogen at 75-80° C. for 22 hours. The mixture was cooled to room temperature and the aqueous layer was separated and extracted with ethyl ether (2×5 mL). The combined organic phase was concentrated by distillation through a Vigreaux column at atmospheric pressure to a volume of approximately 2 mL, and the residue was purified by flash chromatography (40 g silica, eluted with hexanes-ethyl acetate, 100:0-90:10). The product-containing fractions were combined and concentrated by distillation through a Vigreaux column at atmospheric pressure to a volume of approximately 2 mL, then distilled bulb-to-bulb (air bath 80-90° C./10-20 torr) to provide the title compound: $^1$H NMR (300 MHz, methanol-$d_4$) δ ppm 5.56 (d, J=10.9 Hz, 1H), 6.08 (d, J=17.6 Hz, 1H), 6.86 (dd, J=17.8, 11.0 Hz, 1H), 7.77 (d, J=8.1 Hz, 1H), 8.11 (dd, J=8.3, 2.2 Hz, 1H), 8.74 (d, J=1.7 Hz, 1H).

Example 143B 9-methyl-6-{2-[6-(trifluoromethyl)pyridin-3-yl]ethyl}-3,4,5,6-tetrahydro-1H-2,5-ethanoazepino[4,3-b]indole Sodium dispersion in paraffin (30%, 46 mg, 0.60 mmol; Aldrich) was combined with 9-methyl-3,4,5,6-tetrahydro-1H-2,5-ethanoazepino[4,3-b]indole (100 mg, 0.442 mmol; Example 2B) in a 20 mL vial with stir bar and septum cap. Dimethyl sulfoxide (2.5 mL) was added, and the vial was evacuated and purged with nitrogen (10 cycles). The mixture was stirred at room temperature for 10 minutes, and a solution of the product of Example 143A (115 mg, 0.663 mmol) and hydroquinone (12 mg, 0.110 mmol) in dimethyl sulfoxide (0.5 mL) was added. The vial was evacuated and purged with nitrogen (5 cycles) and the mixture was stirred with heating at 115° C. for 39 hours. The dark brown mixture was cooled to room temperature, applied directly to a column of silica gel and eluted with chloroform, followed by CHCl$_3$—CH$_3$OH-14.8 M aqueous NH$_4$OH (90:10:1). The product-containing fractions were combined and concentrated under vacuum, and the residue was purified by HPLC [Waters XBridge™ C18 5 μm OBD column, 30×100 mm, flow rate 40 mL/minute, 20-90% gradient of acetonitrile in buffer (0.1 M aqueous ammonium bicarbonate, adjusted to pH 10 with ammonium hydroxide) over 20 minutes] to provide the title compound: $^1$H NMR (300 MHz, methanol-$d_4$) δ ppm 1.46-1.64 (m, 2H), 1.79-1.98 (m, 2H), 2.38 (s, 3H), 2.84-3.01 (m, 3H), 3.05-3.22 (m, 4H), 4.16 (s, 2H), 4.42 (t, J=6.27 Hz, 2H), 6.89 (dd, J=8.48, 1.02 Hz, 1H), 7.09 (d, J=7.80 Hz, 1H), 7.10 (d, J=0.68 Hz, 1H), 7.54 (dd, J=8.10, 1.70 Hz, 1H), 7.59 (d, J=8.10 Hz, 1H), 8.12 (s, 1H); MS (ESI) m/z 400 (MH)$^+$.

Example 144

9-methyl-6-[(E)-2-pyridin-3-ylvinyl]-3,4,5,6-tetrahydro-1H-2,5-ethanoazepino[4,3-b]indole bistrifluoroacetate The coupling of 9-methyl-3,4,5,6-tetrahydro-1H-2,5-ethanoazepino[4,3-b]indole (113 mg, 0.50 mmol; Example 2B) and 3-ethynylpyridine (0.206 g, 2.0 mmol; Aldrich) was performed according to the procedure described in Example 20 to afford a mixture of two isomers. Fractions containing the E-isomer were repurified by reverse-phase HPLC (Waters XBridge™ C18 5 μm OBD column, 30×100 mm, flow rate 40 mL/minute, 5-95% gradient of acetonitrile in 0.1% trifluoroacetic acid over 15 minutes) to afford the title compound as the trifluoroacetic acid salt: $^1$H NMR (300 MHz, methanol-$d_4$) δ ppm 2.25-2.50 (m, 4H), 2.45 (s, 3H), 3.49-3.62 (m, 2H), 3.64-3.82 (m, 3H), 4.78 (s, 2H), 7.00 (d, J=15 Hz, 1H), 7.17 (d, J=8 Hz, 1H), 7.28 (s, 1H), 7.69-7.80 (m, 2H), 7.98 (d, J=15 Hz, 1H), 8.50 (d, J=8 Hz, 1H), 8.56 (d, J=5 Hz, 1H), 8.90 (s, 1H); MS (DCI/NH$_3$) m/z 330 (M+H)$^+$.

Example 145

9-methyl-6-[(Z)-2-pyridin-3-ylvinyl]-3,4,5,6-tetrahydro-1H-2,5-ethanoazepino[4,3-b]indole The coupling of 9-methyl-3,4,5,6-tetrahydro-1H-2,5-ethanoazepino[4,3-b]indole (113 mg, 0.50 mmol; Example 2B) and 3-ethynylpyridine (0.206 g, 2.0 mmol; Aldrich) was performed according to the procedure described in Example 20 to afford the title compound as one of two isomers: $^1$H NMR (300 MHz, methanol-$d_4$) δ ppm 1.62-1.76 (m, 2H), 1.81-1.96 (m, 2H), 2.38 (s, 3H), 2.92-3.08 (m, 3H), 3.09-3.22 (m, 2H), 4.21 (s, 2H), 6.75 (d, J=8 Hz, 1H), 6.84-7.03 (m, 3H), 7.14-7.30 (m, 3H), 8.02 (d, J=2 Hz, 1H), 8.26 (dd, J=5, 2 Hz, 1H); MS (DCI/NH$_3$) m/z 330 (M+H)$^+$.

Example 146

9-methyl-6-[(E)-2-(6-methylpyridin-3-yl)vinyl]-3,4,5,6-tetrahydro-1H-2,5-ethanoazepino[4,3-b]indole The coupling of 9-methyl-3,4,5,6-tetrahydro-1H-2,5-ethanoazepino[4,3-b]indole (453 mg, 2.0 mmol; Example 2B) and 5-ethynyl-2-methylpyridine (937 mg, 8.0 mmol; prepared as described in International Publication No. WO2005090333) was performed according to the procedure described in Example 20 to afford the title compound as the minor isomer: $^1$H NMR (300 MHz, methanol-$d_4$) δ ppm 2.05-2.19 (m, 4H), 2.41 (s, 3H), 2.53 (s, 3H), 3.00-3.14 (m, 2H), 3.17-3.28 (m, 2H), 3.39-3.47 (m, 1H), 4.22 (s, 2H), 6.74 (d, J=15 Hz, 1H), 7.03 (dd, J=8, 2 Hz, 1H), 7.12-7.19 (m, 1H), 7.29 (d, J=8 Hz, 1H), 7.54 (d, J=8 Hz, 1H), 7.69 (d, J=14 Hz, 1H), 7.95 (dd, J=8, 2 Hz, 1H), 8.51 (d, J=2 Hz, 1H); MS (DCI/NH$_3$) m/z 344 (M+H)$^+$.

Example 147

9-methyl-6-[(Z)-2-(6-methylpyridin-3-yl)vinyl]-3,4,5,6-tetrahydro-1H-2,5-ethanoazepino[4,3-b]indole The coupling of 9-methyl-3,4,5,6-tetrahydro-1H-2,5-ethanoazepino[4,3-b]indole (453 mg, 2.0 mmol; Example 2B) and 5-ethynyl-2-methylpyridine (937 mg, 8.0 mmol; prepared as described in International Publication No. WO2005090333) was performed according to the procedure described in Example 20 to afford the title compound as the major isomeric product: $^1$H NMR (300 MHz, methanol-$d_4$) δ ppm 1.65-1.79 (m, 2H), 1.83-1.97 (m, 2H), 2.38 (s, 3H), 2.39 (s, 3H), 2.94-3.08 (m, 3H), 3.10-3.23 (m, 2H), 4.23 (s, 2H), 6.72 (d, J=8 Hz, 1H), 6.84-6.98 (m, 3H), 7.03-7.18 (m, 3H), 7.88 (d, J=2 Hz, 1H); MS (DCI/NH$_3$) m/z 344 (M+H)$^+$.

Example 148

9-methyl-6-[2-(6-methylpyridazin-3-yl)ethyl]-3,4,5,6-tetrahydro-1H-2,5-ethanoazepino[4,3-b]indole Example 148A 3-bromo-6-methylpyridazine 6-Methylpyridazin-3(2H)-one (2.5 g, 22.70 mmol, Alfa) and phosphorus oxybromide (16.27 g, 56.8 mmol, Aldrich)

were heated at 90° C. under a nitrogen atmosphere for 1.5 hours. After cooling, the mixture was poured onto ice (100 g), neutralized with sodium bicarbonate, and the aqueous phase was extracted with CH₂Cl₂ (3×30 mL). The combined organic phase was washed with 5% NaHCO₃, brine, dried (Na₂SO₄) and concentrated. The residue was dissolved in hot ethyl acetate and washed through a plug of silica gel, eluting with ethyl acetate and concentrated. MS (DCI/NH₃) m/z 172 (M+H)⁺, 190 (M+NH₄)⁺.

Example 148B 3-methyl-6-vinylpyridazine

Potassium vinyltrifluoroborate (1.71 g, 12.7 mmol, Aldrich), 3-bromo-6-methylpyridazine (1.95 g, 11.3 mmol, Example 148A) and triphenylphosphine (0.18 g, 0.67 mmol) were added at room temperature to a solution of Cs₂CO₃ (10.1 g, 31.0 mmol) in water (9.5 mL). Tetrahydrofuran (85 mL) was added, and the reaction flask was evacuated and purged with nitrogen (3 cycles). PdCl₂ (50 mg, 0.28 mmol, Arcos) was added, and the reaction flask was again evacuated and purged with nitrogen (3 cycles), then heated under nitrogen at 75-80° C. for 22 hours. The mixture was cooled to room temperature and the aqueous layer was separated and extracted with ethyl ether (3×50 mL). The combined organic phase was concentrated to a volume of approximately 5 mL, and the residue was purified by flash chromatography (80 g silica, eluted with hexanes-ethyl acetate, 100:0-90:10): ¹H NMR (300 MHz, methanol-d₄) δ ppm 2.71 (s, 3H) 5.63 (d, J=11.2 Hz, 1H) 6.18 (d, J=18.3 Hz, 1H) 7.04 (dd, J=17.8, 11.0 Hz, 1H) 7.23-7.34 (m, J=8.8 Hz, 1H) 7.49 (d, J=8.8 Hz, 1H).

Example 148C 9-methyl-6-[2-(6-methylpyridazin-3-yl)ethyl]-3,4,5,6-tetrahydro-1H-2,5-ethanoazepino[4,3-b]indole Under nitrogen, 9-methyl-3,4,5,6-tetrahydro-1H-2,5-ethanoazepino[4,3-b]indole (260 mg, 1.15 mmol, Example 2B), was coupled with 3-methyl-6-vinylpyridazine (280 mg, 1.86 mmol, Example 148B) according to the procedure described in Example 1B to give the title compound: ¹H NMR (300 MHz, CDCl₃) δ ppm 1.65-1.76 (m, 2H) 1.85-1.95 (m, 2H) 2.43 (s, 3H) 2.67 (s, 3H) 2.96-3.09 (m, 3H) 3.17-3.25 (m, 2H) 3.30 (t, J=7.1 Hz, 2H) 4.23 (s, 2H) 4.55 (t, J=7.1 Hz, 2H) 6.82 (d, J=8.5 Hz, 1H) 6.96 (dd, J=8.3, 1.2 Hz, 1H) 7.11 (dd, J=17.1, 8.4 Hz, 2H) 7.16 (s, 1H); MS (DCI/NH₃) m/z 347 (M+H)⁺.

Example 149

9-methyl-6-[2-(2-methylphenyl)ethyl]-3,4,5,6-tetrahydro-1H-2,5-ethanoazepino[4,3-b]indole A solution of 9-methyl-3,4,5,6-tetrahydro-1H-2,5-ethanoazepino[4,3-b]indole (1.2 g, 5.3 mmol; Example 2B) and in trifluoroacetic acid (20 mL) was cooled to −30° C. A solution of sodium cyanoborohydride (1.75 g, 26.5 mmol; Aldrich) in methanol (6.5 mL) was added dropwise over a period of 30 minutes. The reaction mixture was allowed to slowly warm to ambient temperature over a period of 30 minutes, then diluted with methanol (2×30 mL) and concentrated under vacuum. The residue was purified by preparative HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)] to afford the indoline. A portion of this material (68 mg, 0.30 mmol), sodium (37 mg, 0.48 mmol; 30% dispersion in paraffin wax, Aldrich) and 2-methyl-5-vinylpyridine (56 mg, 0.48 mmol; prepared as described in International Publication No. WO2001017968) were processed as described in Example 106A and purified by preparative HPLC [Waters XBridge™ RP18 column, 5 μm, 30×100 mm, flow rate 40 mL/minute, 5-95% gradient of acetonitrile in 0.1% aqueous trifluoroacetic acid] to provide a trifluoroacetic acid salt. This was exposed in the air at ambient temperature for 7 days and further purified by preparative HPLC [Waters XBridge™ RP18 column, 5 μm, 30×100 mm, flow rate 40 mL/minute, 35-99% gradient of methanol in buffer (0.1 M aqueous ammonium bicarbonate, adjusted to pH 10 with ammonium hydroxide)] to afford the title compound: ¹H NMR (300 MHz, methanol-d₄) δ ppm 1.45-1.63 (m, 2H), 1.71-1.90 (m, 2H), 2.02 (s, 3H), 2.39 (s, 3H), 2.79-2.95 (m, 3H), 2.99-3.15 (m, 4H), 4.13 (s, 2H), 4.30 (t, J=6.6 Hz, 2H), 6.84-6.94 (m, 2H), 6.97-7.06 (m, 3H), 7.07-7.11 (m, 1H), 7.14-7.19 (m, J=8.5 Hz, 1H); MS (APCI) m/z 345 (M+H)⁺.

Example 150

6-[2-(2-fluorophenyl)ethyl]-9-methyl-3,4,5,6-tetrahydro-1H-2,5-ethanoazepino[4,3-b]indole The coupling of 9-methyl-3,4,5,6-tetrahydro-1H-2,5-ethanoazepino[4,3-b]indole (158 mg, 0.70 mmol; Example 2B) and 1-fluoro-2-vinylbenzene (171 mg, 1.40 mmol; Aldrich) was performed according to the procedure described in Example 114B to afford the title compound: ¹H NMR (300 MHz, methanol-d₄) δ ppm 1.63-1.76 (m, 2H), 1.87-2.01 (m, 2H), 2.39 (s, 3H), 2.88-3.22 (m, 7H), 4.16 (s, 2H), 4.33 (t, J=7 Hz, 2H), 6.86-7.26 (m, 7H); MS (DCI/NH₃) m/z 349 (M+H)⁺.

Example 151

6-[2-(4-chlorophenyl)ethyl]-9-methyl-3,4,5,6-tetrahydro-1H-2,5-ethanoazepino[4,3-b]indole The coupling of 9-methyl-3,4,5,6-tetrahydro-1H-2,5-ethanoazepino[4,3-b]indole (226 mg, 1.0 mmol; Example 2B) and 1-chloro-4-vinylbenzene (277 mg, 2.0 mmol; Aldrich) was performed according to the procedure described in Example 114B to afford the title compound: ¹H NMR (300 MHz, methanol-d₄) δ ppm 1.52-1.66 (m, 2H), 1.80-1.95 (m, 2H), 2.39 (s, 3H), 2.85-3.03 (m, 5H), 3.05-3.19 (m, 2H), 4.15 (s, 2H), 4.32 (t, J=7 Hz, 2H), 6.82-6.96 (m, 3H), 7.06-7.22 (m, 4H); MS (DCI/NH₃) m/z 365 (M+H)⁺.

Example 152

9-methyl-6-{2-[3-(trifluoromethyl)phenyl]ethyl}-3,4,5,6-tetrahydro-1H-2,5-ethanoazepino[4,3-b]indole The coupling of 9-methyl-3,4,5,6-tetrahydro-1H-2,5-ethanoazepino[4,3-b]indole (226 mg, 1.0 mmol; Example 2B) and 1-(trifluoromethyl)-3-vinylbenzene (344 mg, 2.0 mmol; Aldrich) was performed according to the procedure described in Example 114B to afford the title compound: ¹H NMR (300 MHz, methanol-d₄) δ ppm 1.45-1.55 (m, 2H), 1.78-1.88 (m, 2H), 2.39 (s, 3H), 2.84-2.93 (m, 3H), 3.04-3.13 (m, 4H), 4.13 (s, 2H), 4.37 (t, J=6 Hz, 2H), 6.91 (d, J=8

Hz, 1H), 7.09 (s, 1H), 7.11-7.16 (m, 3H), 7.33 (t, J=8 Hz, 1H), 7.42 (d, J=8 Hz, 1H); MS (DCI/NH$_3$) m/z 399 (M+H)$^+$.

Example 153

9-methyl-6-[(Z)-2-(4-methylphenyl)vinyl]-3,4,5,6-tetrahydro-1H-2,5-ethanoazepino[4,3-b]indole The coupling of 9-methyl-3,4,5,6-tetrahydro-1H-2,5-ethanoazepino[4,3-b]indole (113 mg, 0.50 mmol; Example 2B) and 1-ethynyl-4-methylbenzene (232 mg, 2.0 mmol; Aldrich) was performed according to the procedure described in Example 20. The product was repurified by reverse-phase HPLC (Waters XBridge™ C18 5 μm OBD column, 30×100 mm, flow rate 40 mL/minute, 5-95% gradient of acetonitrile in 0.1% trifluoroacetic acid over 15 minutes) to afford the title compound as a trifluoroacetate salt: $^1$H NMR (300 MHz, methanol-d$_4$) δ ppm 1.66-1.80 (m, 2H), 1.98-2.12 (m, 2H), 2.22 (s, 3H), 2.43 (s, 3H), 3.16-3.23 (m, 1H), 3.35-3.45 (m, 2H), 3.47-3.60 (m, 2H), 4.73 (s, 2H), 6.72 (d, J=8 Hz, 2H), 6.76-6.84 (m, 2H), 6.97 (d, J=8 Hz, 2H), 7.03 (d, J=9 Hz, 1H), 7.18 (d, J=8 Hz, 1H), 7.25-7.27 (m, 1H); MS (DCI/NH$_3$) m/z 343 (M+H)$^+$.

A-Example 154 ethyl (9-methyl-1,3,4,5-tetrahydro-6H-2,5-ethano-azepino[4,3-b]indol-6-yl)acetate Example 154A 9-methyl-3,4,5,6-tetrahydro-1H-2,5-ethanoazepino[4,3-b]indole N-borane complex A suspension of 9-methyl-3,4,5,6-tetrahydro-1H-2,5-ethanoazepino[4,3-b]indole (903.4 mg, 3.99 mmol; Example 2B) in tetrahydrofuran (20 mL) was treated with 1 M BH$_3$ in tetrahydrofuran (5 mL, 5 mmol; Aldrich), which was added portionwise over 10 minutes. After 3 hours, the reaction mixture was concentrated in vacuo and purified by silica gel chromatography (eluting with CH$_2$Cl$_2$) to afford the title compound: $^1$H NMR (300 MHz, CDCl$_3$) δ ppm 2.06-2.22 (m, 4H), 2.43 (s, 3H), 3.00-3.04 (m, 1H), 3.23-3.33 (m, 2H), 3.42-3.52 (m, 2H), 4.41 (s, 2H), 7.00 (dd, J=8.1, 1.7 Hz, 1H), 7.17 (d, J=1.6 Hz, 1H), 7.21 (d, J=8.5 Hz, 1H), 7.72 (br s, 1H); MS (DCI/NH$_3$) m/z 256 (M+NH$_3$—H)$^+$.

Example 154B ethyl (9-methyl-1,3,4,5-tetrahydro-6H-2,5-ethano-azepino[4,3-b]indol-6-yl)acetate N-borane complex A solution of 9-methyl-3,4,5,6-tetrahydro-1H-2,5-ethanoazepino[4,3-b]indole N-borane complex (357.4 mg, 1.49 mmol; Example 154A) in tetrahydrofuran (5 mL) was treated with potassium tert-butoxide (195.0 mg, 1.74 mmol; Aldrich) and the reaction was stirred at ambient temperature for 15 minutes. Ethyl bromoacetate (368.4 mg, 2.21 mmol; Aldrich) was then added and stirring was continued overnight (16 hours). The mixture was diluted with water (45 mL) and 1 M aqueous NaOH (5 mL) and extracted with dichloromethane (2×50 mL). The combined organic layers were dried over magnesium sulfate, filtered and concentrated in vacuo. The resulting material was purified by silica gel chromatography (eluting with dichloromethane). to afford the title compound: $^1$H NMR (300 MHz, CDCl$_3$) δ ppm 1.25 (t, J=7.1 Hz, 3H) 2.06-2.20 (m, 4H), 2.43 (s, 3H), 3.04-3.07 (m, 1H), 3.27-3.34 (m, 2H), 3.40-3.50 (m, 2H), 4.18 (q, J=7.1 Hz, 2H), 4.42 (s, 2H), 7.46 (s, 2H), 7.25 (dd, J=8.5, 1.0 Hz, 1H), 7.11 (d, J=8.2 Hz, 1H), 7.18-7.19 (m, 1H); MS (DCI/NH$_3$) m/z 342 (M+NH$_3$—H)$^+$.

Example 154C ethyl (9-methyl-1,3,4,5-tetrahydro-6H-2,5-ethano-azepino[4,3-b]indol-6-yl)acetate A solution of ethyl (9-methyl-1,3,4,5-tetrahydro-6H-2,5-ethanoazepino[4,3-b]indol-6-yl)acetate N-borane complex (100.7 mg, 0.31 mmol; Example 154B) in acetone (3 mL) was treated with 3 M aqueous hydrochloric acid (1 mL, 3 mmol) and the reaction was stirred at ambient temperature for 1 hour. The mixture was concentrated in vacuo, dissolved in methanol, stirred for 30 minutes, then concentrated again. The resulting material was triturated with methanol/ether and isolated by filtration. The solid was washed with additional ether to afford the title compound as the hydrochloride salt: $^1$H NMR (300 MHz, methanol-d$_4$) δ ppm 1.26 (t, J=7.1 Hz, 3H) 2.30-2.37 (m, 4H), 2.42 (s, 3H), 3.35-3.39 (m, 1H), 3.46-3.55 (m, 2H), 3.61-3.70 (m, 2H), 4.20 (q, J=7.1 Hz, 2H), 4.73 (s, 2H), 5.03 (s, 2H), 7.02-7.05 (m, 1H), 7.21-7.23 (m, 2H); MS (DCI/NH$_3$) m/z 313 (M+H)$^+$. Anal. Calcd. for C$_{19}$H$_{24}$N$_2$O$_2$.HCl: C, 65.41; H, 7.22; N, 8.03; Cl, 10.16. Found: C, 65.17; H, 7.22; N, 8.03; Cl, 10.03.

Example 155

N-(4-chlorophenyl)-2-(9-methyl-1,3,4,5-tetrahydro-6H-2,5-ethanoazepino[4,3-b]indol-6-yl)acetamide Example 155A (9-methyl-1,3,4,5-tetrahydro-6H-2,5-ethanoazepino[4,3-b]indol-6-yl)acetic acid N-borane complex A suspension of ethyl (9-methyl-1,3,4,5-tetrahydro-6H-2,5-ethanoazepino[4,3-b]indol-6-yl)acetate N-borane complex (187.2 mg, 0.57 mmol; Example 154B) in ethanol (3 mL) and 1 M aqueous sodium hydroxide (3 mL) was heated to 60° C. for 1 hour. The reaction was diluted with water (30 mL), acidified with 1 M HCl (4 mL), and extracted with dichloromethane (2×30 mL). The combined organic layers were dried over sodium sulfate, filtered and concentrated in vacuo to afford the title compound: $^1$H NMR (300 MHz, CDCl$_3$) δ ppm 2.02-2.19 (m, 4H), 2.43 (s, 3H), 3.02-3.06 (m, 1H), 3.23-3.32 (m, 2H), 3.40-3.49 (m, 2H), 4.42 (s, 2H), 4.82 (s, 2H), 7.03 (d, J=8.5 Hz, 1H), 7.09 (d, J=8.1 Hz, 1H), 7.19 (s, 1H); MS (DCI/NH$_3$) m/z 314 (M+NH$_3$—H)$^+$.

Example 155B

N-(4-chlorophenyl)-2-(9-methyl-1,3,4,5-tetrahydro-6H-2,5-ethanoazepino[4,3-b]indol-6-yl)acetamide N-borane complex A solution of (9-methyl-1,3,4,5-tetrahydro-6H-2,5-ethanoazepino[4,3-b]indol-6-yl)acetic acid N-borane complex (80.5 mg, 0.27 mmol; Example 155A) in dichloromethane (3 mL) was treated with 4-chloroaniline (90.7 mg, 0.71 mmol; Aldrich), 1-hydroxybenzotriazole hydrate (HOBt; 50.0 mg, 0.33 mmol; Aldrich), 4-dimethylaminopyridine (DMAP; 12.2 mg, 0.10 mmol; Aldrich) and N-(3-dimethyl-aminopropyl-N'-ethylcarbodimide hydrochloride (EDCI;

81.2 mg, 0.42 mmol; Aldrich). After stirring for 6 hours, the reaction mixture was concentrated in vacuo and the residue was purified by preparative HPLC [Waters Nova-Pak® HR C18 6 μm 60 Å Prep-Pak® cartridge column (40×100 mm) using a gradient of 10-100% acetonitrile in 10 mM aqueous ammonium acetate over 12 minutes at a flow rate of 70 mL/minute] to provide the title compound: $^1$H NMR (300 MHz, methanol-$d_4$) δ ppm 2.12-2.23 (m, 4H), 2.40 (s, 3H), 3.19-3.45 (m, 5H), 4.36 (s, 2H), 4.96 (s, 2H), 6.98 (d, J=8.3 Hz, 1H), 7.14 (s, 1H), 7.20 (d, J=8.3 Hz, 1H), 7.27-7.32 (m, 2H), 7.51-7.55 (m, 2H); MS (DCI/NH$_3$) m/z 423 (M+NH$_3$—H)$^+$.

Example 155C

N-(4-chlorophenyl)-2-(9-methyl-1,3,4,5-tetrahydro-6H-2,5-ethanoazepino[4,3-b]indol-6-yl)acetamide The product of Example 155B (48.4 mg, 0.12 mmol) was treated with 3 M HCl (aqueous) in acetone as described in Example 154C to afford the title compound as the hydrochloride salt: $^1$H NMR (300 MHz, methanol-$d_4$) δ ppm 2.32-2.37 (m, 4H), 2.42 (s, 3H), 3.41-3.44 (m, 1H), 3.50-3.56 (m, 2H), 3.60-3.70 (m, 2H), 4.74 (s, 2H), 5.05 (s, 2H), 7.05 (dd, J=8.5, 1.0 Hz, 1H), 7.21-7.23 (m, 1H), 7.25-7.33 (m, 3H), 7.53-7.58 (m, 2H); MS (DCI/NH$_3$) m/z 394 (M+H)$^+$. Anal. Calcd. for $C_{23}H_{24}ClN_3O\cdot HCl\cdot 0.1\ H_2O$: C, 63.92; H, 5.88; N, 9.72. Found: C, 63.75; H, 5.65; N, 9.71.

Example 156

2-(9-methyl-1,3,4,5-tetrahydro-6H-2,5-ethanoazepino[4,3-b]indol-6-yl)-N-[4-(trifluoromethoxy)phenyl]acetamide Example 156A 2-(9-methyl-1,3,4,5-tetrahydro-6H-2,5-ethanoazepino[4,3-b]indol-6-yl)-N-[4-(trifluoromethoxy)phenyl]acetamide N-borane complex The coupling of (9-methyl-1,3,4,5-tetrahydro-6H-2,5-ethanoazepino[4,3-b]indol-6-yl)acetic acid N-borane complex (75.8 mg, 0.25 mmol; Example 155A) and 4-trifluoromethoxyaniline (142.0 mg, 0.802 mmol, Aldrich) was performed as described in Example 155B to afford the title compound: $^1$H NMR (300 MHz, methanol-$d_4$) δ ppm 2.09-2.23 (m, 4H), 2.40 (s, 3H), 3.19-3.45 (m, 5H), 4.36 (s, 2H), 4.98 (s, 2H), 6.96-7.00 (m, 1H), 7.14 (s, 1H), 7.19-7.23 (m, 3H), 7.61-7.65 (m, 2H); MS (DCI/NH$_3$) m/z 473 (M+NH$_3$—H)$^+$.

Example 156B 2-(9-methyl-1,3,4,5-tetrahydro-6H-2,5-ethanoazepino[4,3-b]indol-6-yl)-N-[4-(trifluoromethoxy)phenyl]acetamide The product of Example 156A (44.2 mg, 0.10 mmol) was treated with 3 M HCl (aqueous) in acetone as described in Example 154C to afford the title compound as the hydrochloride salt: $^1$H NMR (300 MHz, methanol-$d_4$) δ ppm 2.32-2.37 (m, 4H), 2.42 (s, 3H), 3.41-3.44 (m, 1H), 3.50-3.57 (m, 2H), 3.60-3.67 (m, 2H), 4.74 (s, 2H), 5.06 (s, 2H), 7.05 (dd, J=8.5, 1.7 Hz, 1H), 7.21-7.29 (m, 4H), 7.62-7.97 (m, 2H); MS (DCI/NH$_3$) m/z 444 (M+H)$^+$. Anal. Calcd. for $C_{24}H_{24}F_3N_3O_2\cdot HCl\cdot 0.65\ H_2O$: C, 58.63; H, 5.39; N, 8.55. Found: C, 58.56; H, 5.24; N, 8.50.

Example 157

(5aR*,10bS*)-9-methyl-3,4,5,5a,6,10b-hexahydro-1H-2,5-ethanoazepino[4,3-b]indole A solution of 9-methyl-3,4,5,6-tetrahydro-1H-2,5-ethanoazepino[4,3-b]indole (1.2 g, 5.3 mmol; Example 2B) in trifluoroacetic acid (20 mL) was cooled to −30° C. A solution of sodium cyanoborohydride (1.75 g, 26.5 mmol; Aldrich) in methanol (6.5 mL) was added dropwise over a period of 30 minutes. The reaction mixture was allowed to slowly warm to ambient temperature over a period of 30 minutes, then diluted with methanol (60 mL) and concentrated under vacuum. The residue was purified by preparative HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (400 MHz, methanol-$d_4$) δ ppm 1.54-1.75 (m, 1H), 1.89-2.04 (m, 2H), 2.20 (s, 3H), 2.41-2.58 (m, 1H), 2.89-2.99 (m, 2H), 2.99-3.13 (m, 2H), 3.21-3.41 (m, 3H), 3.54-3.63 (m, 1H), 4.12 (dd, J=8.7, 5.0 Hz, 1H), 6.52 (d, J=7.6 Hz, 1H), 6.81 (d, J=7.9 Hz, 1H), 6.83 (s, 1H); MS (+DCI) m/z 229 (M+H)$^+$.

Example 158

(5aR*,10bS*)-9-methyl-6-[2-(6-methylpyridin-3-yl)ethyl]-3,4,5,5a,6,10b-hexahydro-1H-2,5-ethanoazepino[4,3-b]indole 9-Methyl-6-[2-(6-methylpyridin-3-yl)ethyl]-3,4,5,6-tetrahydro-1H-2,5-ethanoazepino[4,3-b]indole (210 mg, 0.61 mmol; Example 2) was processed as described in Example 157 to provide the title compound: $^1$H NMR (300 MHz, methanol-$d_4$) δ ppm 1.43-1.63 (m, 1H), 1.78-2.06 (m, 2H), 2.19 (s, 3H), 2.25-2.44 (m, 2H), 2.48 (s, 3H), 2.67 (dd, J=13.9, 11.5 Hz, 1H), 2.73-2.91 (m, 4H), 2.93-3.09 (m, 1H), 3.12-3.27 (m, 3H), 3.35-3.48 (m, 1H), 3.49-3.59 (m, 1H), 3.85 (dd, J=8.7, 5.2 Hz, 1H), 6.41 (d, J=7.9 Hz, 1H), 6.79 (s, 1H), 6.85 (d, J=8.3 Hz, 1H), 7.23 (d, J=7.9 Hz, 1H), 7.64 (dd, J=7.9, 2.0 Hz, 1H), 8.27 (d, J=2.0 Hz, 1H); MS (APCI) m/z 348 (M+H)$^+$.

Example 159

(5aS,10bR)-9-methyl-6-[2-(6-methylpyridin-3-yl)ethyl]-3,4,5,5a,6,10b-hexahydro-1H-2,5-ethanoazepino[4,3-b]indole Individual enantiomers of the racemic mixture of Example 158 (150 mg, 0.43 mmol) were separated by preparative chiral supercritical fluid chromatography (ChiralPak® OD-H 5 μm column, 21×250 mm, 35° C., 10-50% gradient of CH$_3$OH—CO$_2$ containing 0.1% diethylamine, flow rate 40 mL/minute) to afford the title compound as the first-eluting enantiomer: $^1$H NMR (500 MHz, methanol-$d_4$) δ ppm 1.46-1.56 (m, 1H), 1.81-1.90 (m, 1H), 1.90-1.99 (m, 1H), 2.19 (s, 3H), 2.25-2.41 (m, 2H), 2.48 (s, 3H), 2.62 (dd, J=14.0, 11.6 Hz, 1H), 2.71-2.87 (m, 4H), 2.90-3.04 (m, 1H), 3.10-3.22 (m, 3H), 3.35-3.44 (m, 1H), 3.45-3.53 (m, 1H), 3.82 (dd, J=8.5, 5.2 Hz, 1H), 6.39 (d, J=7.9 Hz, 1H), 6.78 (s, 1H), 6.84 (d, J=7.6 Hz, 1H), 7.22 (d, J=7.9 Hz, 1H), 7.62 (dd, J=7.9, 2.1 Hz, 1H), 8.26 (d, J=2.1 Hz, 1H); MS (APCI) m/z 348 (M+H)+.

Example 160

(5aR,10bS)-9-methyl-6-[2-(6-methylpyridin-3-yl) ethyl]-3,4,5,5a,6,10b-hexahydro-1H-2,5-ethanoazepino[4,3-b]indole Individual enantiomers of the racemic mixture of Example 158 (150 mg, 0.43 mmol) were separated by preparative chiral supercritical fluid chromatography (ChiralPak® OD-H 5 μm column, 21×250 mm, 35° C., 10-50% gradient of $CH_3OH$—$CO_2$ containing 0.1% diethylamine, flow rate 40 mL/minute) to afford the title compound as the second-eluting enantiomer: $^1$H NMR (500 MHz, methanol-$d_4$) δ ppm 1.43-1.58 (m, 1H), 1.78-1.90 (m, 1H), 1.90-2.00 (m, 1H), 2.19 (s, 3H), 2.25-2.41 (m, 2H), 2.48 (s, 3H), 2.63 (dd, J=14.0, 11.6 Hz, 1H), 2.72-2.87 (m, 4H), 2.89-3.04 (m, 1H), 3.11-3.22 (m, 3H), 3.36-3.44 (m, 1H), 3.45-3.53 (m, 1H), 3.83 (dd, J=8.5, 5.2 Hz, 1H), 6.40 (d, J=7.9 Hz, 1H), 6.78 (s, 1H), 6.84 (d, J=7.6 Hz, 1H), 7.22 (d, J=7.9 Hz, 1H), 7.63 (dd, J=8.1, 2.3 Hz, 1H), 8.26 (s, 1H); MS (APCI) m/z 348 (M+H)+.

Example 161

9-fluoro-3,4,5,6-tetrahydro-1H-2,5-ethanoazepino[4,3-b]indole

A mixture of (4-fluorophenyl)hydrazine hydrochloride (10.67 g, 65.6 mmol; Aldrich) and 1-azabicyclo[3.2.2] nonan-4-one (9.13 g, 65.6 mmol; Example 2A) in 100 mL of 7% sulfuric acid in dioxane was heated to 100° C. for 30 hours. The reaction mixture was basified (~pH 11) by the addition of 50% aqueous sodium hydroxide then stirred in an ice-bath for 30 minutes. The resulting solid was collected by filtration, washed sequentially with water, hexanes and ether (3×30 mL), and dried to afford the title compound: $^1$H NMR (300 MHz, methanol-$d_4$) δ ppm 2.06 (m, 4H), 3.03 (m, 3H), 3.23 (m, 2H), 3.65 (s, 1H), 4.18 (s, 2H), 6.77 (ddd, J=2.6, 8.8, 9.6 Hz, 1H), 6.94 (dd, J=2.8, 9.6 Hz, 1H), 7.20 (dd, J=4.0, 8.8 Hz, 1H); MS (ESI) m/z 231 (M+H)+.

Example 162

9-fluoro-6-[(E)-2-(6-methylpyridin-3-yl)vinyl]-3,4,5,6-tetrahydro-1H-2,5-ethanoazepino[4,3-b]indole A solution of 9-fluoro-3,4,5,6-tetrahydro-1H-2,5-ethanoazepino[4,3-b]indole (100 mg, 0.434 mmol; Example 161) in a mixture of toluene (4 mL) and 1,2-dimethoxyethane (1 mL) was degassed with nitrogen. n-Butyllithium (2 M in cyclohexane; 217 mL, 0.434 mmol; Aldrich) was added at room temperature and the mixture stirred for 30 minutes. Bis(dibenzylidene-acetone)palladium (19.98 mg, 0.035 mmol; Aldrich), tri-tert-butylphosphine (1 M in toluene; 0.069 mL, 0.069 mmol; Aldrich) and (E)-5-(2-bromovinyl)-2-methylpyridine (86 mg, 0.434 mmol; Example 23C) were added. The reaction mixture was heated at 70° C. for 18 hours. After cooling, the mixture was filtered through a pad of diatomaceous earth and concentrated in vacuo, and the residue was purified by flash chromatography (silica gel, Isco SF15-24, using a of chloroform/methanol/concentrated $NH_4OH$, 90/9/1) to afford the title compound: $^1$H NMR (300 MHz, methanol-$d_4$) δ 2.20 (m, 4H), 2.55 (s, 3H), 3.23 (m, 4H), 3.52 (m, 1H), 4.39 (s, 2H), 6.82 (d, J=14.5 Hz, 1H), 6.97 (td, J=2.5, 9.0 Hz, 1H), 7.10 (dd, J=2.5, 9.0 Hz, 1H), 7.32 (d, J=8 Hz, 1H), 7.64 (dd, J=4.0, 9.0 Hz, 1H), 7.72 (d, J=14.5 Hz, 1H), 7.99 (dd, J=2.3, 8.0 Hz, 1H), 8.55 (d, J=2.1 Hz, 1H); MS (ESI) m/z 348 (M+H)+.

Example 163

9-fluoro-6-[2-(4-fluorophenyl)ethyl]-3,4,5,6-tetrahydro-1H-2,5-ethanoazepino[4,3-b]indole General procedure C was used to convert 1-(4-fluorophenethyl)-1-(4-fluorophenyl)-hydrazine (276 mg, 1.1 mmol; Example 85A) and 1-azabicyclo[3.2.2]nonan-4-one (144 mg, 1.1 mmol; Example 2A) into the title compound as the trifluoroacetic acid salt: $^1$H NMR (300 MHz, CDCl$_3$) δ ppm 1.60-1.77 (m, 2H) 1.96-2.15 (m, 2H) 2.92 (s, 1H) 3.05 (t, J=6.54 Hz, 2H) 3.24 (d, J=28.16 Hz, 2H), 3.51-3.74 (m, 2H) 4.31 (t, J=6.35 Hz, 2H) 4.57 (s, 2H) 6.81-6.89 (m, 2H) 6.89-6.95 (m, 2H) 6.99-7.07 (m, 2H) 7.21-7.34 (m, 1H); MS (DCI/NH$_3$) m/z 353 (M+H)+.

Example 164

6-[(6-chloropyridin-3-yl)methyl]-9-fluoro-3,4,5,6-tetrahydro-1H-2,5-ethanoazepino[4,3-b]indole Example 164A 9-fluoro-3,4,5,6-tetrahydro-1H-2,5-ethanoazepino[4,3-b]indole N-borane complex A solution of 9-fluoro-3,4,5,6-tetrahydro-1H-2,5-ethanoazepino[4,3-b]indole (3.5 g, 15.2 mmol; Example 161) in tetrahydrofuran (30 mL) was chilled in an ice bath under a dry nitrogen atmosphere and then borane tetrahydrofuran complex (1.0 M; 16.7 mL, 16.7 mmol; Aldrich) was added slowly. After the addition was complete, the ice bath was removed and the reaction mixture was allowed to warm to room temperature and stir for 3 hours. The volatile components were removed under vacuum and the residue was purified by flash chromatography (silica gel, 100% dichloromethane) to afford the title compound: $^1$H NMR (400 MHz, CDCl$_3$) δ ppm 2.04-2.35 (m, 4H), 3.06 (s, 1H), 3.21-3.39 (m, 2H), 3.41-3.58 (m, 2H), 4.38 (s, 2H), 6.86-6.95 (m, 1H), 7.01 (dd, J=9.2, 2.4 Hz, 1H), 7.23 (dd, J=8.9, 4.3 Hz, 1H), 7.85 (brs, 1H); MS (ESI–) m/z 243 (M–H)−.

Example 164B

6-[(6-chloropyridin-3-yl)methyl]-9-fluoro-3,4,5,6-tetrahydro-1H-2,5-ethanoazepino[4,3-b]indole N-borane complex To a solution of 9-fluoro-3,4,5,6-tetrahydro-1H-2,5-ethanoazepino[4,3-b]indole N-borane complex (452 mg, 1.85 mmol; Example 164A) in tetrahydrofuran (5.0 mL) was added sodium amide (120 mg, 3.09 mmol; Aldrich) in portions. After 30 minutes, 2-chloro-5-(chloromethyl)pyridine (250 mg, 1.5 mmol; Aldrich) was added and the solution was heated to 55° C. overnight. The reaction was cooled to room temperature, quenched with water (5.0 mL), and then extracted with dichloromethane (2×10 mL). The combined organic extracts were dried over magnesium sulfate, filtered, and concentrated under reduced pressure: $^1$H NMR (300 MHz, CDCl$_3$) δ ppm 1.73-2.00 (m, 4H), 2.01-2.25 (m, 3H), 3.07 (s, 1H), 3.28 (d, J=7.1 Hz, 2H), 3.35-3.57 (m, 2H), 4.41 (s, 2H), 5.31 (s, 2H), 6.89-7.01 (m, 1H), 7.03-7.17 (m, 3H), 7.22 (s, 1H), 8.14 (d, J=2.4 Hz, 1H); MS (ESI−) m/z 368 (M−H)⁻.

Example 164C

6-[(6-chloropyridin-3-yl)methyl]-9-fluoro-3,4,5,6-tetrahydro-1H-2,5-ethanoazepino[4,3-b]indole A solution of 6-[(6-chloropyridin-3-yl)methyl]-9-fluoro-3,4,5,6-tetrahydro-1H-2,5-ethanoazepino[4,3-b]indole N-borane complex (420 mg, 1.18 mmol; Example 164B) in ethyl acetate (5.0 mL) was treated with HCl (4 M in dioxane; 2 mL, 65.8 mmol; Aldrich) and the mixture was stirred at room temperature overnight. The reaction mixture was concentrated in vacuo, and the residue was dissolved in water (5 mL) and then basified (pH 10) with 4 M aqueous sodium hydroxide. The mixture was concentrated in vacuo and the resulting material was purified by flash chromatography [12 g silica gel, 0-100% gradient of CH₃OH-14.8 M-NH₄OH (aq) (10:1) in CH₂Cl₂] to afford the title compound: ¹H NMR (300 MHz, CDCl₃) δ ppm 1.80-2.08 (m, 4H), 2.98-3.16 (m, 2H), 3.17-3.37 (m, 2H), 3.49 (s, 1H), 4.26 (s, 2H), 5.28 (s, 2H), 6.84-6.95 (m, 1H), 7.02-7.16 (m, 3H), 7.19-7.25 (m, 1H), 8.16 (s, 1H); MS (ESI)⁺ m/z 356 (M+H)⁺.

Example 164D

6-[(6-chloropyridin-3-yl)methyl]-9-fluoro-3,4,5,6-tetrahydro-1H-2,5-ethanoazepino[4,3-b]indole tartrate The salt was prepared by dissolving the starting material from Example 164C (275. mg, 0.775 mmol) in ethyl acetate (5.0 mL) and ethanol (1.0 mL) then adding (2S,3S)-2,3-dihydroxysuccinic acid (128 mg, 0.852 mmol, dissolved in a minimal amount of methanol) slowly and stirring rapidly over night. The material precipitated to give a white solid. The solid was collected by filtration and dried under vacuum to give the titled compound: ¹H NMR (300 MHz, methanol-d₄) δ ppm 1.97-2.13 (m, 2H) 2.19-2.37 (m, 2H) 3.38-3.51 (m, 3H) 3.51-3.69 (m, 2H) 4.41 (s, 2H) 4.70 (s, 2H) 5.54 (s, 2H) 6.89-7.05 (m, 1H) 7.18 (dd, J=9.32, 2.58 Hz, 1H) 7.32-7.50 (m, 3H) 8.05 (s, 1H); MS (DCI/NH₃) m/z 356 (M+H)⁺. Anal. Calcd. for C₂₀H₁₉ClFN₃·C₄H₆O₆: C, 56.98; H, 4.97; 8.31. Found: C, 56.71; H, 4.88; N, 8.20.

Example 165

9-fluoro-6-(4-fluorobenzyl)-3,4,5,6-tetrahydro-1H-2,5-ethanoazepino[4,3-b]indole Example 165A 1-(4-fluorobenzyl)-1-(4-fluorophenyl)hydrazine A flask containing tetrahydrofuran (2.0 mL) was charged with sodium amide (89 mg, 4.61 mmol; Aldrich) and chilled to 0° C. (4-Fluorophenyl)hydrazine hydrochloride (500 mg, 3.08 mmol; Aldrich) was added in portions. After 5 minutes the solid had completely dissolved and the ice bath was removed. Stirring was continued for 1 hour, then the solution was chilled again in an ice bath and 1-(bromomethyl)-4-fluorobenzene (0.416 mL, 3.38 mmol; Aldrich) was added dropwise. After 30 minutes the ice bath was removed and the reaction was heated to 50° C. overnight. The mixture was diluted with water (5 mL), extracted with dichloromethane (2×10 mL) and the combined organic extracts were dried over magnesium sulfate, filtered, and concentrated in vacuo to afford the title product which was carried on without further purification: LC/MS (DCI/NH₃) m/z 218 (M+H-NH₃)⁺.

Example 165B 9-fluoro-6-(4-fluorobenzyl)-3,4,5,6-tetrahydro-1H-2,5-ethanoazepino[4,3-b]indole A solution of 1-(4-fluorobenzyl)-1-(4-fluorophenyl)hydrazine (500 mg, 2.13 mmol; Example 165A) and 1-azabicyclo[3.2.2]nonan-4-one (446 mg, 3.2 mmol; Example 2A) in 7% sulfuric acid in dioxane (10 mL) was heated at 80° C. overnight. Water (20 mL) was added and the solution was basified (~pH 10) by the addition of 4 M NaOH. The aqueous solution was extracted with dichloromethane (2×10 mL) and the combined extracts were concentrated in vacuo and purified by reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: ¹H NMR (300 MHz, CDCl₃) δ ppm 1.80-2.16 (m, 4H), 2.94 (s, 1H), 3.08-3.24 (m, 2H), 3.27-3.45 (m, 2H), 4.38 (s, 2H), 5.24 (s, 2H), 6.85-7.02 (m, 5H), 7.06 (dd, J=9.5, 2.4 Hz, 1H), 7.15 (dd, J=8.7, 4.4 Hz, 1H); MS (ESI)⁺ m/z 339 (M+H)⁺.

Example 166

6-(4-chlorobenzyl)-9-fluoro-3,4,5,6-tetrahydro-1H-2,5-ethanoazepino[4,3-b]indole Example 166A 1-(4-chlorobenzyl)-1-(4-fluorophenyl)hydrazine A flask containing tetrahydrofuran (2.0 mL) was charged with sodium amide (202 mg, 4.92 mmol; Aldrich) and chilled to 0° C. (4-Fluorophenyl)hydrazine hydrochloride (400 mg, 2.46 mmol; Aldrich) was added in portions. After 5 minutes the solid had completely dissolved and the ice bath was removed. Stirring was continued for 1 hour, then the solution was chilled again in an ice bath and 1-(bromomethyl)-4-chlorobenzene (556 mg, 2.7 mmol; Aldrich) was added dropwise. After 30 minutes, the ice bath was removed and the reaction was heated to 50° C. overnight. The mixture was diluted with water (5 mL) and extracted with dichloromethane (2×10 mL). The combined organic extracts were dried over magnesium sulfate, filtered, and concentrated in vacuo to afford the title product which was carried on without further purification: LC/MS (DCI/NH₃) m/z 234 (M+H-NH₃)⁺.

Example 166B 6-(4-chlorobenzyl)-9-fluoro-3,4,5,6-tetrahydro-1H-2,5-ethanoazepino[4,3-b]indole A solution of 1-(4-chlorobenzyl)-1-(4-fluorophenyl)hydrazine (500 mg, 1.99 mmol; Example 166A) and 1-azabicyclo[3.2.2]nonan-4-one (416 mg, 2.99 mmol; Example 2A) in 7% sulfuric acid in dioxane (10 mL) was heated at 80° C. overnight. Water (20 mL) was added and the solution was basified (~pH 10) by the addition of 4 M aqueous NaOH.

Example 167

6-(4-bromobenzyl)-9-fluoro-3,4,5,6-tetrahydro-1H-2,5-ethanoazepino[4,3-b]indole

Example 167A 1-(4-bromobenzyl)-1-(4-fluorophenyl)hydrazine

A flask containing tetrahydrofuran (2.0 mL) was charged with sodium amide (253 mg, 6.15 mmol; Aldrich) and chilled to 0° C. (4-Fluorophenyl)hydrazine hydrochloride (500 mg, 3.08 mmol; Aldrich) was added in portions. After 5 minutes the solid had completely dissolved and the ice bath was removed. Stirring was continued for 1 hour, then the solution was chilled again in an ice bath and 1-(bromomethyl)-4-bromobenzene (845 mg, 3.38 mmol; Aldrich) was added dropwise. After 30 minutes the ice bath was removed and the reaction was heated to 50° C. overnight. The mixture was diluted with water (5 mL) and extracted with dichloromethane (2×10 mL). The combined organic extracts were dried over magnesium sulfate, filtered, and concentrated in vacuo to afford the title product which was carried on without further purification: LC/MS (DCI/NH$_3$) m/z 279 (M+H-NH$_3$)$^+$.

Example 167B 6-(4-bromobenzyl)-9-fluoro-3,4,5,6-tetrahydro-1H-2,5-ethanoazepino[4,3-b]indole A solution of 1-(4-bromobenzyl)-1-(4-fluorophenyl)hydrazine (500 mg, 1.69 mmol; Example 167A) and 1-azabicyclo[3.2.2]nonan-4-one (354 mg, 2.54 mmol; Example 2A) in 7% sulfuric acid in dioxane (10 mL) was heated at 80° C. overnight. Water (20 mL) was added and the solution was basified (~pH 10) by the addition of 4 M aqueous NaOH. The aqueous solution was extracted with dichloromethane (2×10 mL) and the combined extracts were concentrated in vacuo and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (500 MHz, CDCl$_3$) δ ppm 1.76-2.00 (m, 4H), 2.94 (s, 1H), 3.01-3.14 (m, 2H), 3.18-3.30 (m, 2H), 4.26 (s, 2H), 5.25 (s, 2H), 6.81 (d, J=8.5 Hz, 2H), 6.85-6.95 (m, 1H), 7.06 (dd, J=9.2, 2.4 Hz, 1H), 7.12 (dd, J=8.8, 4.1 Hz, 1H), 7.40 (d, J=8.5 Hz, 2H); MS (ESI)$^+$ m/z 398.9 (M+H)$^+$.

Example 168

9-fluoro-6-[3-(trifluoromethyl)benzyl]-3,4,5,6-tetrahydro-1H-2,5-ethanoazepino[4,3-b]indole

Example 168A

1-[(3-trifluoromethyl)benzyl]-1-(4-fluorophenyl)hydrazine

A flask containing tetrahydrofuran (2.0 mL) was charged with sodium amide (189 mg, 4.61 mmol; Aldrich) and chilled to 0° C. (4-Fluorophenyl)hydrazine hydrochloride (500 mg, 3.08 mmol; Aldrich) was added in portions. After 5 minutes, the solid had completely dissolved and the ice bath was removed. Stirring was continued for 1 hour, then the solution was chilled again in an ice bath and 1-(bromomethyl)-3-trifluorobenzene (517 mg, 3.38 mmol; Aldrich) was added dropwise. After 30 minutes, the ice bath was removed and the reaction was heated to 50° C. overnight. The mixture was diluted with water (5 mL) and extracted with dichloromethane (2×10 mL). The combined organic extracts were dried over magnesium sulfate, filtered, and concentrated in vacuo to afford the title product which was carried on without further purification: MS (ESI+) m/z 265 (M+H-NH$_3$)$^+$.

Example 168B 9-fluoro-6-[3-(trifluoromethyl)benzyl]-3,4,5,6-tetrahydro-1H-2,5-ethanoazepino[4,3-b]indole A solution of 1-[(3-trifluoromethyl)benzyl]-1-(4-fluorophenyl)hydrazine (500 mg, 1.76 mmol; Example 168A) and 1-azabicyclo[3.2.2]nonan-4-one (364 mg, 2.64 mmol; Example 2A) in 7% sulfuric acid in dioxane (10 mL) was heated at 80° C. overnight. Water (20 mL) was added and the solution was basified (~pH 10) by the addition of 4 M aqueous NaOH. The aqueous solution was extracted with dichloromethane (2×10 mL) and the combined extracts were concentrated in vacuo and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (500 MHz, CDCl$_3$) δ ppm 1.76-2.00 (m, 4H), 2.94 (s, 1H), 3.01-3.14 (m, 2H), 3.18-3.30 (m, 2H), 4.26 (s, 2H), 5.25 (s, 2H), 6.86-6.96 (m, 1H), 7.01-7.16 (m, 3H), 7.30 (s, 1H), 7.39 (t, J=7.8 Hz, 1H), 7.52 (d, J=7.8 Hz, 1H); MS (ESI)$^+$ m/z 389 (M+H)$^+$.

Example 169

6-(2,3-difluoro-4-methylbenzyl)-9-fluoro-3,4,5,6-tetrahydro-1H-2,5-ethanoazepino[4,3-b]indole

Example 169A 1-(2,3-difluoro-4-methylbenzyl)-1-(4-fluorophenyl)hydrazine

A flask containing tetrahydrofuran (2.0 mL) was charged with sodium amide (152 mg, 3.69 mmol; Aldrich) and chilled to 0° C. (4-Fluorophenyl)hydrazine hydrochloride (400 mg, 2.64 mmol; Aldrich) was added in portions. After 5 minutes, the solid had completely dissolved and the ice bath was removed. Stirring was continued for 1 hour, then (The aqueous solution was extracted with dichloromethane (2×10 mL) and the combined extracts were concentrated in vacuo and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (500 MHz, CDCl$_3$) δ ppm 1.76-2.00 (m, 4H), 2.94 (s, 1H), 3.01-3.14 (m, 2H), 3.18-3.30 (m, 2H), 4.26 (s, 2H), 5.25 (s, 2H), 6.80-6.93 (m, 3H), 7.01-7.15 (m, 2H), 7.24 (d, J=8.2 Hz, 2H); MS (DCI/NH$_3$) m/z 355 (M+H)$^+$.)

the solution was chilled again in an ice bath and 1-(bromomethyl)-2,3-difluoro-4-methylbenzene (598 mg, 2.72 mmol; Aldrich) was added dropwise. After 30 minutes, the ice bath was removed and the reaction was heated to 50° C. overnight. The mixture was diluted with water (5 mL) and extracted with dichloromethane (2×10 mL). The combined organic extracts were dried over magnesium sulfate, filtered, and concentrated in vacuo to afford the title product which was carried on without further purification: LC/MS (DCI/NH$_3$) m/z 250 (M+H-NH$_3$)$^+$.

Example 169B 6-(2,3-difluoro-4-methylbenzyl)-9-fluoro-3,4,5,6-tetrahydro-1H-2,5-ethanoazepino[4,3-b]indole A solution of 1-(2,3-difluoro-4-methylbenzyl)-1-(4-fluorophenyl)hydrazine (500 mg, 1.65 mmol; Example 169A) and 1-azabicyclo[3.2.2]nonan-4-one (392 mg, 2.82 mmol; Example 2A) in 7% sulfuric acid in dioxane (10 mL) was heated at 80° C. overnight. Water (20 mL) was added and the solution was basified (~pH 10) by the addition of 4 M aqueous NaOH. The aqueous solution was extracted with dichloromethane (2×10 mL) and the combined extracts were concentrated in vacuo and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.82-2.08 (m, 4H), 2.28 (s, 3H), 2.95-3.17 (m, 3H), 3.18-3.38 (m, 2H), 4.28 (s, 2H), 5.30 (s, 2H), 6.16 (t, J=7.1 Hz, 1H), 6.74 (t, J=7.0 Hz, 1H), 6.83-6.92 (m, 1H), 7.06 (dd, J=9.5, 2.4 Hz, 1H), 7.12 (dd, J=9.0, 4.2 Hz, 1H); MS (DCI/NH$_3$) m/z 371 (M+H)$^+$.

Example 170

9-fluoro-6-[3-fluoro-4-(trifluoromethyl)benzyl]-3,4,5,6-tetrahydro-1H-2,5-ethanoazepino[4,3-b]indole Example 170A 1-(3-fluoro-4-trifluoromethylbenzyl)-1-(4-fluorophenyl)hydrazine A flask containing tetrahydrofuran (2.0 mL) was charged with sodium amide (152 mg, 3.69 mmol; Aldrich) and chilled to 0° C. (4-Fluorophenyl)hydrazine hydrochloride (400 mg, 3.17 mmol; Aldrich) was added in portions. After 5 minutes, the solid had completely dissolved and the ice bath was removed. Stirring was continued for 1 hour, then the solution was chilled again in an ice bath and 4-(bromomethyl)-2-fluoro-1-(trifluoromethyl)benzene (598 mg, 2.33 mmol; Alfa Aesar) was added dropwise. After 30 minutes, the ice bath was removed and the reaction was heated to 50° C. overnight. The mixture was diluted with water (5 mL) and extracted with dichloromethane (2×10 mL). The combined organic extracts were dried over magnesium sulfate, filtered, and concentrated in vacuo to afford the title product which was carried on without further purification: LC/MS (DCI/NH$_3$) m/z 250 (M+H-NH$_3$)$^+$.

Example 170B 9-fluoro-6-[3-fluoro-4-(trifluoromethyl)benzyl]-3,4,5,6-tetrahydro-1H-2,5-ethanoazepino[4,3-b]indole A solution of 1-(3-fluoro-4-trifluoromethylbenzyl)-1-(4-fluorophenyl)hydrazine (500 mg, 1.65 mmol; Example 170A) and 1-azabicyclo[3.2.2]nonan-4-one (392 mg, 2.82 mmol; Example 2A) in 7% sulfuric acid in dioxane (10 mL) was heated at 80° C. overnight. Water (20 mL) was added and the solution was basified (~pH 10) by the addition of 4M NaOH$_{(aq)}$. The aqueous solution was extracted with dichloromethane (2×10 mL) and the combined extracts were concentrated in vacuo and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, methanol-d$_4$) δ ppm 1.77-1.95 (m, 2H), 1.94-2.13 (m, 2H), 2.95-3.15 (m, 3H), 3.19-3.42 (m, 2H), 4.25 (s, 2H), 5.50 (s, 2H), 6.76-6.99 (m, 3H), 7.08 (dd, J=9.5, 2.4 Hz, 1H), 7.19-7.41 (m, 1H), 7.59 (t, J=7.9 Hz, 1H); MS (DCI/NH$_3$) m/z 407 (M+H)$^+$.

Example 171

9-fluoro-6-[4-(5-methyl-1,2,4-oxadiazol-3-yl)benzyl]-3,4,5,6-tetrahydro-1H-2,5-ethanoazepino[4,3-b]indole Example 171A 3-(4-((1-fluorophenyl)hydrazinyl)methyl)phenyl)-5-1,2,4-oxadiazole A flask containing tetrahydrofuran (2.0 mL) was charged with sodium amide (152 mg, 3.69 mmol; Aldrich) and chilled to 0° C. (4-Fluorophenyl)hydrazine hydrochloride (400 mg, 2.46 mmol; Aldrich) was added in portions. After 5 minutes, the solid had completely dissolved and the ice bath was removed. Stirring was continued for 1 hour, then the solution was chilled again in an ice bath and 3-(4-(bromomethyl)phenyl)-5-methyl-1,2,4-oxadiazole (623 mg, 2.46 mmol; Alfa Aesar) was added dropwise. After 30 minutes, the ice bath was removed and the reaction was heated to 50° C. overnight. The mixture was diluted with water (5 mL) and extracted with dichloromethane (2×10 mL). The combined organic extracts were dried over magnesium sulfate, filtered, and concentrated in vacuo to afford the title product which was carried on without further purification: LC/MS (DCI/NH$_3$) m/z 282 (M+H-NH$_3$)$^+$.

Example 171B 9-fluoro-6-[4-(5-methyl-1,2,4-oxadiazol-3-yl)benzyl]-3,4,5,6-tetrahydro-1H-2,5-ethanoazepino[4,3-b]indole A solution of 3-(4-((1-fluorophenyl)hydrazinyl)methyl)phenyl)-5-1,2,4-oxadiazole (500 mg, 1.67 mmol; Example 171A) and 1-azabicyclo[3.2.2]nonan-4-one (392 mg, 2.82 mmol; Example 2A) in 7% sulfuric acid in dioxane (10 mL) was heated at 80° C. overnight. Water (20 mL) was added and the solution was basified (~pH 10) by the addition of 4 M NaOH. The aqueous solution was extracted with dichloromethane (2×10 mL) and the combined extracts were concentrated in vacuo and purified by reverse-phase HPLC (Phenomenex® Luna® C8(2) 5 μm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, CDCl$_3$) δ ppm 1.82-2.08 (m, 4H), 2.64 (s, 3H), 2.95-3.17 (m, 3H), 3.18-3.38 (m, 2H), 4.28 (s, 2H), 5.30 (s, 2H), 6.96-7.07 (m, 2H), 7.64-7.72 (m, 1H), 7.82-7.91 (m, 1H), 7.98 (d, J=8.1 Hz, 1H), 8.04-8.14 (m, 1H), 8.22 (d, J=5.4 Hz, 1H); MS (ESI)+ m/z 403 (M+H)+.

Example 172

9-fluoro-6-[(2-methyl-1,3-thiazol-4-yl)methyl]-3,4,5,6-tetrahydro-1H-2,5-ethanoazepino[4,3-b]indole Example 172A 4-((1-(4-fluorophenyl)hydrazinyl)methyl)-2-methylthiazole A flask containing tetrahydrofuran (2.0 mL) was charged with sodium amide (152 mg, 3.69 mmol; Aldrich) and chilled to 0° C. (4-Fluorophenyl)hydrazine hydrochloride (400 mg, 2.46 mmol; Aldrich) was added in portions. After 5 minutes, the solid had completely dissolved and the ice bath was removed. Stirring was continued for 1 hour, then the solution was chilled again in an ice bath and 4-(bromomethyl)-2-methylthiazole (473 mg, 2.46 mmol; Aldrich) was added dropwise. After 30 minutes, the ice bath was removed and the reaction was heated to 50° C. overnight. The mixture was diluted with water (5 mL) and extracted with dichloromethane (2×10 mL). The combined organic extracts were dried over magnesium sulfate, filtered, and concentrated in vacuo to afford the title product which was carried on without further purification: LC/MS (DCI/NH$_3$) m/z 221 (M+H-NH$_3$)+.

Example 172B 9-fluoro-6-[(2-methyl-1,3-thiazol-4-yl)methyl]-3,4,5,6-tetrahydro-1H-2,5-ethanoazepino[4,3-b]indole A solution of 4-((1-(4-fluorophenyl)hydrazinyl)methyl)-2-methylthiazole (500 mg, 2.10 mmol; Example 172A) and 1-azabicyclo[3.2.2]nonan-4-one (392 mg, 2.82 mmol; Example 2A) in 7% sulfuric acid in dioxane (10 mL) was heated at 80° C. overnight. Water (20 mL) was added and the solution was basified (~pH 10) by the addition of 4M NaOH$_{(aq)}$. The aqueous solution was extracted with dichloromethane (2×10 mL) and the combined extracts were concentrated in vacuo and purified by reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (300 MHz, methanol-d$_4$) δ ppm 1.77-1.95 (m, 2H), 1.94-2.13 (m, 2H), 2.65 (s, 3H), 2.95-3.15 (m, 3H), 3.19-3.42 (m, 2H), 4.25 (s, 2H), 5.50 (s, 2H), 6.67 (s, 1H), 6.79-6.90 (m, 1H), 7.02 (dd, J=9.5, 2.4 Hz, 1H), 7.31 (dd, J=9.0, 4.2 Hz, 1H); MS (DCI/NH$_3$) m/z 343 (M+H)+.

Example 173

9-fluoro-6-[(2-phenyl-1,3-oxazol-4-yl)methyl]-3,4,5,6-tetrahydro-1H-2,5-ethanoazepino[4,3-b]indole Example 173A 4-((1-(4-fluorophenyl)hydrazinyl)methyl)-2-phenyloxazole A flask containing tetrahydrofuran (2.0 mL) was charged with sodium amide (152 mg, 3.69 mmol; Aldrich) and chilled to 0° C. (4-Fluorophenyl)hydrazine hydrochloride (400 mg, 2.46 mmol; Aldrich) was added in portions. After 5 minutes, the solid had completely dissolved and the ice bath was removed. Stirring was continued for 1 hour, then the solution was chilled again in an ice bath and 4-(bromomethyl)-2-phenyloxazole (586 mg, 2.46 mmol; Anichem) was added dropwise. After 30 minutes, the ice bath was removed and the reaction was heated to 50° C. overnight. The mixture was diluted with water (5 mL) and extracted with dichloromethane (2×10 mL). The combined organic extracts were dried over magnesium sulfate, filtered, and concentrated in vacuo to afford the title product which was carried on without further purification: LC/MS (DCI/NH$_3$) m/z 267 (M+H-NH$_3$)+.

Example 173B 9-fluoro-6-[(2-phenyl-1,3-oxazol-4-yl)methyl]-3,4,5,6-tetrahydro-1H-2,5-ethanoazepino[4,3-b]indole A solution of 4-((1-(4-fluorophenyl)hydrazinyl)methyl)-2-phenyloxazole (500 mg, 1.67 mmol; Example 173A) and 1-azabicyclo[3.2.2]nonan-4-one (392 mg, 2.82 mmol; Example 2A) in 7% sulfuric acid in dioxane (10 mL) was heated at 80° C. overnight. Water (20 mL) was added and the solution was basified (~pH 10) by the addition of 4 M aqueous NaOH. The aqueous solution was extracted with dichloromethane (2×10 mL) and the combined extracts were concentrated in vacuo and purified by reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: LC/MS (DCI/NH$_3$) m/z 388 (M+H)+.

Example 174

9-bromo-6-[2-(4-chlorophenyl)ethyl]-3,4,5,6-tetrahydro-1H-2,5-ethanoazepino[4,3-b]indole Example 174A 9-bromo-3,4,5,6-tetrahydro-1H-2,5-ethanoazepino[4,3-b]indole A solution of HCl in acetic acid (1 M, 30 mL) was added under nitrogen to a mixture of 4-bromophenylhydrazine hydrochloride (4.33 g, 19.37 mmol; Aldrich) and 1-azabicyclo[3.2.2]nonan-4-one (2.70 g, 19.37 mmol; Example 2A). The mixture was stirred at room temperature for 16 hours, then heated at 75° C. for 3 hours. The mixture was cooled to room temperature and concentrated under vacuum to remove most of the acetic acid. Anhydrous ethanol (100 mL) was added to the residue, and the mixture was heated at reflux for 10 minutes, then cooled to room temperature. The precipitate was collected by filtration, washed with ethanol (25 mL) and dried under vacuum to provide the title compound as its HCl salt (3.02 g). A portion of this salt (400 mg) was partitioned between 20% NaOH (25 mL) and chloroform (50 mL) and the organic phase was dried (sodium sulfate) and concentrated. The residue was crystallized from ethyl acetate-ethanol (5:1) to provide the free base of title compound: $^1$H NMR (300 MHz, methanol-d$_4$) δ ppm 2.14-2.36 (m, 4H), 3.17-3.25 (m, 1H), 3.33-3.45 (m, 2H), 3.45-3.65 (m, 2H), 4.54 (s, 2H), 7.18 (dd, J=8.8, 1.8 Hz, 1H), 7.24 (d, J=9.1 Hz, 1H), 7.51 (d, J=2.4 Hz, 1H); MS (DCI) m/z 291/293 (M+H)+.

Example 174B 9-bromo-6-[2-(4-chlorophenyl)ethyl]-3,4,5,6-tetra-hydro-1H-2,5-ethanoazepino[4,3-b]indole Sodium dispersion in paraffin (30%; 162 mg, 2.11 mmol; Aldrich) was combined with 9-bromo-3,4,5,6-tetrahydro-1H-2,5-ethanoazepino[4,3-b]indole (290 mg, 0.996 mmol; Example 174A) in a 20 mL vial with stir bar and septum cap. Dimethyl sulfoxide (4.0 mL) was added, and the vial was evacuated and purged with nitrogen (10 cycles). The mixture was stirred at room temperature for 30 minutes, and a solution of 4-chlorostyrene (213 mg, 1.54 mmol; Aldrich) and hydroquinone (53 mg, 0.48 mmol; Aldrich) in dimethyl sulfoxide (2 mL) was added. The vial was evacuated and purged with nitrogen (5 cycles) and the mixture was stirred with heating at 105° C. for 110 hours. The mixture was cooled to room temperature, diluted with water (100 mL) and 25% NaOH (2 mL) and extracted with chloroform (3×50 mL). The combined organic phase was concentrated and the residue was purified by flash chromatography (silica, eluted with $CHCl_3$—$CH_3OH$-14.8 M aqueous $NH_4OH$ (90:10:1). The product-containing fractions were combined and concentrated under vacuum to provide a residue (140 mg), which was further purified by reverse-phase HPLC [Waters XBridge™ RP18 column, 5 μm, 30×100 mm, flow rate 40 mL/minute, 40-99% gradient of methanol in buffer (0.1 M aqueous ammonium bicarbonate, adjusted to pH 10 with ammonium hydroxide) over 20 minutes] to provide the title compound: $^1$H NMR (300 MHz, $CDCl_3$) δ ppm 1.60-1.74 (m, 2H), 1.81-1.97 (m, 2H), 2.80-2.88 (m, 1H), 2.97 (t, J=6.8 Hz, 2H), 3.00-3.08 (m, 2H), 3.25 (ddd, J=14.1, 9.0, 5.4 Hz, 2H), 4.20-4.31 (m, 2H), 4.24 (s, 2H), 6.88-6.94 (m, 2H), 7.09 (d, J=7.8 Hz, 1H), 7.21 (d, J=7.1 Hz, 1H), 7.20-7.25 (m, 2H), 7.50 (d, J=1.7 Hz, 1H); MS (DCI) m/z 429/431/433 (M+H)$^+$.

Example 175

9-(trifluoromethoxy)-3,4,5,6-tetrahydro-1H-2,5-etha-noazepino[4,3-b]indole

In a 30 mL microwave reaction tube were combined 4-(trifluoromethoxy)phenylhydrazine hydrochloride (1143 mg, 5.0 mmol; Alfa Aesar), 1-azabicyclo[3.2.2]nonan-4-one (696 mg, 5.0 mmol; Example 2A), 4 N HCl in dioxane (2.5 mL, 10.0 mmol; Aldrich), and acetic acid (15 mL). The reaction mixture was heated in a microwave to 150° C. (Biotage Personal Chemistry, maximum 300 W) for 15 minutes, then cooled to room temperature. The solvent was removed, and the residue was basified with 5 N sodium hydroxide and extracted with ethyl acetate (3×50 mL). The combined organic phases were concentrated in vacuo and purified by reverse-phase HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide) over 20 minutes] to afford the title compound: $^1$H NMR (300 MHz, methanol-$d_4$) δ ppm 2.08 (td, J=7, 4 Hz, 4H), 2.99-3.13 (m, 3H), 3.23 (dd, J=14, 7 Hz, 2H), 4.21 (s, 2H), 6.92 (ddd, J=9, 2, 1 Hz, 1H), 7.16 (d, J=1 Hz, 1H), 7.28 (d, J=8 Hz, 1H); MS (DCI/$NH_3$) m/z 297 (M+H)$^+$.

Example 176

6-[(E)-2-pyridin-3-ylvinyl]-9-(trifluoromethoxy)-3,4,5,6-tetrahydro-1H-2,5-ethanoazepino[4,3-b]indole The coupling of 9-(trifluoromethoxy)-3,4,5,6-tetrahydro-1H-2,5-ethanoazepino[4,3-b]indole (140 mg, 0.473 mmol; Example 175) and 3-ethynylpyridine (97 mg, 0.945 mmol; Aldrich) was performed according to the procedure described in Example 20 to afford the title compound: $^1$H NMR (300 MHz, methanol-$d_4$) δ ppm 2.09-2.18 (m, 4H), 3.03-3.16 (m, 2H), 3.19-3.29 (m, 2H), 3.42-3.49 (m, 1H), 4.25 (s, 2H), 6.86 (d, J=14 Hz, 1H), 7.10 (ddd, J=9, 2, 1 Hz, 1H), 7.28 (d, J=1 Hz, 1H), 7.45 (dd, J=8, 5 Hz, 1H), 7.72 (d, J=9 Hz, 1H), 7.79 (d, J=15 Hz, 1H), 8.10 (dt, J=8, 2 Hz, 1H), 8.43 (dd, J=5, 2 Hz, 1H), 8.71 (d, J=2 Hz, 1H); MS (DCI/$NH_3$) m/z 400 (M+H)$^+$.

Example 177

6-[(Z)-2-(6-methylpyridin-3-yl)vinyl]-9-(trifluoromethoxy)-3,4,5,6-tetrahydro-1H-2,5-ethanoazepino[4,3-b]indole The coupling of 9-(trifluoromethoxy)-3,4,5,6-tetrahydro-1H-2,5-ethanoazepino[4,3-b]indole (140 mg, 0.473 mmol; Example 175) and 5-ethynyl-2-methylpyridine (111 mg, 0.945 mmol; prepared as described in International Publication No. WO2005090333) was performed according to the procedure described in Example 20 to afford the title compound: $^1$H NMR (300 MHz, methanol-$d_4$) δ ppm 1.66-1.80 (m, 2H), 1.84-1.98 (m, 2H), 2.40 (s, 3H), 2.95-3.23 (m, 5H), 4.24 (s, 2H), 6.83 (d, J=8 Hz, 1H), 6.92-6.99 (m, 2H), 7.06-7.16 (m, 3H), 7.28 (s, 1H), 7.85 (s, 1H); MS (DCI/$NH_3$) m/z 414 (M+H)$^+$.

Example 178

6-[2-(6-methylpyridin-3-yl)ethyl]-9-(trifluoromethoxy)-3,4,5,6-tetrahydro-1H-2,5-ethanoazepino[4,3-b]indole A solution of 6-[(Z)-2-(6-methylpyridin-3-yl)vinyl]-9-(trifluoromethoxy)-3,4,5,6-tetrahydro-1H-2,5-ethanoazepino[4,3-b]indole (65 mg, 0.157 mmol; Example 177) in methanol was treated with platinum oxide under a hydrogen atmosphere (1 atm) at 40° C. for 16 hours to afford the title compound as the major product: $^1$H NMR (300 MHz, methanol-$d_4$) δ ppm 1.57-1.71 (m, 2H), 1.86-2.00 (m, 2H), 2.40 (s, 3H), 2.89-3.21 (m, 7H), 4.16 (s, 2H), 4.42 (t, J=6 Hz, 2H), 6.93 (ddd, J=9, 2, 1 Hz, 1H), 7.11 (d, J=8 Hz, 1H), 7.18 (d, J=1 Hz, 1H), 7.25 (d, J=9 Hz, 1H), 7.31 (dd, J=8, 2 Hz, 1H), 7.82 (d, J=2 Hz, 1H); MS (DCI/$NH_3$) m/z 416 (M+H)$^+$.

Example 179

6-[2-(6-methylpiperidin-3-yl)ethyl]-9-(trifluoromethoxy)-3,4,5,6-tetrahydro-1H-2,5-ethanoazepino[4,3-b]indole A solution of 6-[(Z)-2-(6-methylpyridin-3-yl)vinyl]-9-(trifluoromethoxy)-3,4,5,6-tetrahydro-1H-2,5-ethanoazepino[4,3-b]indole (65 mg, 0.157 mmol; Example 177) in methanol was treated with platinum oxide under a hydrogen atmosphere (1 atm) at 40° C. for 16 hours to afford the title compound as the minor product: $^1$H NMR (300 MHz, methanol-$d_4$) δ ppm 1.02-1.14 (m, 3H), 1.46-1.86 (m, 4H), 1.98-2.21 (m, 4H), 2.64-2.79 (m, 2H), 2.96-3.12 (m, 3H), 3.17-3.28 (m, 3H), 4.15-4.25 (m, 4H), 6.99 (ddd, J=9, 2, 1 Hz, 1H), 7.19 (s, 1H), 7.33-7.40 (m, 1H); MS (DCI/$NH_3$) m/z 422 (M+H)$^+$.

Example 180

9-(methylsulfonyl)-3,4,5,6-tetrahydro-H-2,5-ethanoazepino[4,3-b]indole

A mixture of (4-(methylsulfonyl)phenyl)hydrazine hydrochloride (1105 mg, 5.0 mmol; Acros), 1-azabicyclo[3.2.2]nonan-4-one (696 mg, 5.0 mmol; Example 2A), 4 N HCl in dioxane (2.5 mL, 10.0 mmol; Aldrich), and acetic acid (15 mL) was heated to 80° C. overnight (16 hours), then cooled to room temperature. The solvent was removed, and the residue was basified with 5 N aqueous sodium hydroxide and extracted with ethyl acetate (3×50 mL). The combined organic phases were concentrated in vacuo and purified by reverse-phase HPLC [Waters XBridge™ RP18 column, 5 µm, 30×100 mm, flow rate 40 mL/minute, 20-99% gradient of methanol in buffer (0.1 M aqueous ammonium bicarbonate, adjusted to pH 10 with ammonium hydroxide) over 20 minutes] to afford the title compound: $^1$H NMR (300 MHz, methanol-$d_4$) δ ppm 2.05-2.14 (m, 4H), 3.02-3.15 (m, 6H), 3.20-3.28 (m, 2H), 4.29 (s, 2H), 7.47 (d, J=8 Hz, 1H), 7.57-7.62 (m, 1H), 7.95 (d, J=1 Hz, 1H); MS (DCI/NH$_3$) m/z 291 (M+H)$^+$.

Example 181

6-[(Z)-2-(6-methylpyridin-3-yl)vinyl]-9-(methylsulfonyl)-3,4,5,6-tetrahydro-1H-2,5-ethanoazepino[4,3-b]indole The coupling of 9-(methylsulfonyl)-3,4,5,6-tetrahydro-1H-2,5-ethanoazepino[4,3-b]indole (150 mg, 0.517 mmol; Example 180) and 5-ethynyl-2-methylpyridine (182 mg, 1.55 mmol; prepared as described in International Publication No. WO2005090333) was performed according to the procedure described in Example 20 to afford the title compound as the major product: $^1$H NMR (300 MHz, methanol-$d_4$) δ ppm 1.70-1.82 (m, 2H), 1.88-2.01 (m, 2H), 2.40 (s, 3H), 2.96-3.24 (m, 5H), 3.10 (s, 3H), 4.32 (s, 2H), 6.91 (d, J=8 Hz, 1H), 7.00 (d, J=8 Hz, 1H), 7.09 (s, 2H), 7.32 (d, J=9 Hz, 1H), 7.61 (dd, J=9, 2 Hz, 1H), 7.87 (s, 1H), 8.04 (d, J=2 Hz, 1H); MS (DCI/NH$_3$) m/z 408 (M+H)$^+$.

Example 182

6-[2-(6-methylpyridin-3-yl)ethyl]-9-(methylsulfonyl)-3,4,5,6-tetrahydro-1H-2,5-ethanoazepino[4,3-b]indole A solution of 6-[(Z)-2-(6-methylpyridin-3-yl)vinyl]-9-(methylsulfonyl)-3,4,5,6-tetrahydro-1H-2,5-ethanoazepino[4,3-b]indole (20 mg, 0.049 mmol; Example 181) in methanol was treated with platinum oxide under a hydrogen atmosphere (1 atm) at 40° C. for 16 hours to afford the title compound: $^1$H NMR (300 MHz, methanol-$d_4$) δ ppm 1.62-1.76 (m, 2H), 1.90-2.05 (m, 2H), 2.40 (s, 3H), 2.91-3.24 (m, 10H), 4.26 (s, 2H), 4.49 (t, J=6 Hz, 2H), 7.11 (d, J=8 Hz, 1H), 7.34 (dd, J=8, 2 Hz, 1H), 7.42 (d, J=9 Hz, 1H), 7.59 (dd, J=9, 2 Hz, 1H), 7.84 (d, J=2 Hz, 1H), 7.95 (d, J=2 Hz, 1H); MS (DCI/NH$_3$) m/z 410 (M+H)$^+$.

Example 183

9-fluoro-6-{[6-(trifluoromethyl)pyridin-3-yl]methyl}-3,4,5,6-tetrahydro-1H-2,5-ethanoazepino[4,3-b]indole

Example 183A

9-fluoro-6-{[6-(trifluoromethyl)pyridin-3-yl]methyl}-3,4,5,6-tetrahydro-1H-2,5-ethanoazepino[4,3-b]indole N-borane complex To a solution of 9-fluoro-3,4,5,6-tetrahydro-1H-2,5-ethanoazepino[4,3-b]indole N-borane complex (452 mg, 1.85 mmol; Example 164A) in tetrahydrofuran (5.0 mL) was added sodium amide (120 mg, 3.09 mmol; Aldrich) in portions. After 30 minutes, 5-(chloromethyl)-2-(trifluoromethyl)pyridine (250 mg, 1.278 mmol; Aldrich) was added and the solution was heated to 55° C. overnight. The reaction was cooled to room temperature and quenched with water (5.0 mL), then extracted with dichloromethane (2×10 mL). The combined organic extracts were dried over magnesium sulfate, filtered, and concentrated under reduced pressure to provide the titled compound. The resulting material was carried on to the next step without further purification: LC/MS (DCI/NH$_3$) m/z 390 (M+H-BH$_3$)$^+$.

Example 183B

9-fluoro-6-{[6-(trifluoromethyl)pyridin-3-yl]methyl}-3,4,5,6-tetrahydro-1H-2,5-ethanoazepino[4,3-b]indole A solution of 9-fluoro-6-{[6-(trifluoromethyl)pyridin-3-yl]methyl}-3,4,5,6-tetrahydro-1H-2,5-ethanoazepino[4,3-b]indole N-borane complex (515 mg, 1.278 mmol; Example 183B) in ethyl acetate (5.0 mL) was treated with HCl (4 M in dioxane; 2 mL, 65.8 mmol; Aldrich) and the mixture was stirred at room temperature overnight. The reaction mixture was concentrated in vacuo, and the residue dissolved in water (5 mL) and then basified (pH 10) with 4 M aqueous sodium hydroxide. The mixture was concentrated in vacuo and the resulting material was purified by flash chromatography [12 g silica gel, 0-100% gradient of CH$_3$OH-14.8 M aqueous NH$_4$OH (9:1) in CH$_2$Cl$_2$] to afford the title compound: $^1$H NMR (300 MHz, CDCl$_3$) δ ppm 1.86-2.20 (m, 4H), 3.05 (s, 1H), 3.08-3.27 (m, 2H), 3.30-3.55 (m, 2H), 4.40 (s, 2H), 5.41 (s, 2H), 6.88-6.99 (m, 1H), 7.05-7.15 (m, 2H), 7.30 (d, J=6.7 Hz, 1H), 7.59 (d, J=7.5 Hz, 1H), 8.49 (s, 1H); MS (ESI+) m/z 390 (M+H)$^+$.

Example 184

9-fluoro-6-(pyridin-2-ylmethyl)-3,4,5,6-tetrahydro-1H-2,5-ethanoazepino[4,3-b]indole To a solution of 9-fluoro-3,4,5,6-tetrahydro-1H-2,5-ethanoazepino[4,3-b]indole N-borane complex (244 mg, 1.0 mmol; Example 164A) in tetrahydrofuran (5.0 mL) was added sodium hydride (60% dispersion in mineral oil; 80 mg, 2.0 mmol; Aldrich) in one portion. After stirring for 30 minutes, 2-(chloromethyl)pyridine hydrochloride (197 mg, 1.2 mmol; Aldrich) was added and the solution was heated to 55° C. overnight. After the solvent was removed, the residue was treated with HCl in acetone/water (1 N, acetone:water=3:1, 5 mL) and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, methanol-$d_4$) δ ppm 1.82-2.06 (m, 4H), 2.98-3.26 (m, 5H), 4.23 (s, 2H), 5.47 (s, 2H), 6.67 (d, J=8 Hz, 1H), 6.85 (td, J=9, 3 Hz, 1H), 7.05 (dd, J=9, 2 Hz, 1H), 7.27 (dd, J=9, 4 Hz, 2H), 7.67 (td, J=8, 2 Hz, 1H), 8.51 (ddd, J=5, 2, 1 Hz, 1H); MS (DCI/NH$_3$) m/z 322 (M+H)$^+$.

Example 185

9-fluoro-6-(pyridin-3-ylmethyl)-3,4,5,6-tetrahydro-1H-2,5-ethanoazepino[4,3-b]indole To a solution of 9-fluoro-3,4,5,6-tetrahydro-1H-2,5-ethanoazepino[4,3-b]indole N-borane complex (244 mg, 1.0 mmol; Example 164A) in tetrahydrofuran (5.0 mL) was added sodium hydride (60% dispersion in mineral oil; 80 mg, 2.0 mmol; Aldrich) in one portion. After stirring for 30 minutes, 3-(chloromethyl)pyridine hydrochloride (197 mg, 1.2 mmol; Alfa Aesar) was added and the solution was heated to 55° C. overnight. After the solvent was removed, the residue was treated with HCl in acetone/water (1 N, acetone:water=3:1, 5 mL) and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, methanol-$d_4$) δ ppm 1.79-1.92 (m, 2H), 1.94-2.08 (m, 2H), 2.98-3.10 (m, 2H), 3.12-3.25 (m, 3H), 4.23 (s, 2H), 5.48 (s, 2H), 6.87 (td, J=9, 2 Hz, 1H), 7.06 (dd, J=9, 2 Hz, 1H), 7.27-7.40 (m, 3H), 8.21 (d, J=1 Hz, 1H), 8.40 (dd, J=5, 2 Hz, 1H); MS (DCI/NH$_3$) m/z 322 (M+H)$^+$.

Example 186

9-fluoro-6-(pyridin-4-ylmethyl)-3,4,5,6-tetrahydro-1H-2,5-ethanoazepino[4,3-b]indole To a solution of 9-fluoro-3,4,5,6-tetrahydro-1H-2,5-ethanoazepino[4,3-b]indole N-borane complex (244 mg, 1.0 mmol; Example 164A) in tetrahydrofuran (5.0 mL) was added sodium hydride (60% dispersion in mineral oil; 80 mg, 2.0 mmol; Aldrich) in one portion. After stirring for 30 minutes, 4-(chloromethyl)pyridine hydrochloride (197 mg, 1.2 mmol; Aldrich) was added and the solution was heated to 55° C. overnight. After the solvent was removed, the residue was treated with HCl in acetone/water (1 N, acetone:water=3:1, 5 mL) and the mixture was stirred at room for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, methanol-$d_4$) δ ppm 1.83-2.06 (m, 4H), 2.99-3.11 (m, 3H), 3.15-3.25 (m, 2H), 4.24 (s, 2H), 5.48 (s, 2H), 6.85 (td, J=9, 2 Hz, 1H), 6.97 (d, J=6 Hz, 2H), 7.07 (dd, J=10, 2 Hz, 1H), 7.23 (dd, J=9, 4 Hz, 1H), 8.39-8.43 (m, 2H). MS (DCI/NH$_3$) m/z=322 (M+H)$^+$.

Example 187

6-[(pyridin-2-yl)methyl]-3,4,5,6-tetrahydro-1H-2,5-ethanoazepino[4,3-b]indole

Example 187A 3,4,5,6-tetrahydro-1H-2,5-ethanoazepino[4,3-b]indole

Phenylhydrazine hydrochloride (10.0 g, 69.2 mmol) and 1-azabicyclo[3.2.2]nonan-4-one (9.63 g, 69.2 mmol; Example 2A) were dissolved in 7% (v/v) concentrated H$_2$SO$_4$ in dioxane (150 mL). The reaction mixture was heated to 80° C. overnight. H$_2$O (250 mL) was added. The reaction mixture was made basic (pH 12) by the addition of 4 M aqueous NaOH. The resulting precipitate was filtered then washed with H$_2$O (50 mL) followed by hexanes (50 mL) to give the titled compound: $^1$H NMR (300 MHz, CDCl$_3$) δ ppm 1.88-2.22 (m, 4H), 2.93 (s, 1H), 2.99-3.20 (m, 2H), 3.21-3.43 (m, 2H), 4.29 (s, 2H), 7.04-7.17 (m, 2H), 7.28-7.33 (m, 1H), 7.38 (d, J=8.3 Hz, 1H); MS (DCI/NH$_3$) m/z 213 (M+H)$^+$.

Example 187B 3,4,5,6-tetrahydro-1H-2,5-ethanoazepino[4,3-b]indole N-borane complex A suspension of 3,4,5,6-tetrahydro-1H-2,5-ethanoazepino[4,3-b]indole (2.4 g, 11.45 mmol) in tetrahydrofuran (20 mL) was treated with 1 M BH$_3$ in tetrahydrofuran (14.8 mL; Aldrich), which was added dropwise over 15 minutes. After 3 hours, the reaction mixture was concentrated in vacuo and purified by silica gel chromatography (eluting with CH$_2$Cl$_2$) to afford the title compound: $^1$H NMR (300 MHz, CDCl$_3$) δ ppm 2.16 (m, 3H), 3.05 (m, 1H), 3.30 (m, 2H), 3.49 (m, 2H), 3.72 (m, 1H), 4.45 (s, 2H), 7.15 (m, 2H), 7.33 (m, 2H), 7.84 (br s, 1H); MS (ESI) m/z 225 (M−H)$^-$, 453 (2M+H)$^+$.

Example 187C

6-[(pyridin-2-yl)methyl]-3,4,5,6-tetrahydro-1H-2,5-ethanoazepino[4,3-b]indole

To a solution of 3,4,5,6-tetrahydro-1H-2,5-ethanoazepino[4,3-b]indole N-borane complex (113 mg, 0.5 mmol; Example 187B) in tetrahydrofuran (3.0 mL) was added sodium hydride (60% dispersion in mineral oil; 40 mg, 1.0 mmol; Aldrich) in one portion. After stirring for 30 minutes, 2-(chloromethyl)pyridine hydrochloride (99 mg, 0.6 mmol; Aldrich) was added and the solution was heated to 55° C. overnight. After the solvent was removed, the residue was treated with HCl in acetone/water (1 N, acetone:water=3:1, 5 mL) and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, methanol-$d_4$) δ ppm 1.82-2.05 (m, 4H), 2.99-3.25 (m, 5H), 4.28 (s, 2H), 5.48 (s, 2H), 6.63 (d, J=8 Hz, 1H), 7.00-7.13 (m, 2H), 7.23-7.32 (m, 2H), 7.38 (d, J=7 Hz, 1H), 7.65 (td, J=8, 2 Hz, 1H), 8.51 (ddd, J=5, 2, 1 Hz, 1H); MS (DCI/NH$_3$) m/z 304 (M+H)$^+$.

Example 188

6-(pyridin-3-ylmethyl)-3,4,5,6-tetrahydro-1H-2,5-ethanoazepino[4,3-b]indole

To a solution of 3,4,5,6-tetrahydro-1H-2,5-ethanoazepino[4,3-b]indole N-borane complex (113 mg, 0.5 mmol; Example 187B) in tetrahydrofuran (3.0 mL) was added sodium hydride (60% dispersion in mineral oil; 40 mg, 1.0 mmol; Aldrich) in one portion. After stirring for 30 minutes, 3-(chloromethyl)pyridine hydrochloride (99 mg, 0.6 mmol; Alfa Aesar) was added and the solution was heated to 55° C. overnight. After the solvent was removed, the residue was treated with HCl in acetone/water (1 N, acetone:water=3:1, 5 mL) and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes]. This material was purified further by reverse-phase HPLC (Waters XBridge™ C18 5 μm OBD column, 30×100 mm, flow rate 40 mL/minute, 5-95% gradient of methanol in 0.1% aqueous trifluoroacetic acid over 20 minutes) to afford the title compound as the bistrifluoroacetic acid salt: $^1$H NMR (500 MHz, pyridine-$d_5$) δ ppm 1.83-1.92 (m, 2H), 1.97-2.08 (m, 2H), 3.30-3.45 (m, 3H), 3.71 (ddd, J=14, 9, 5 Hz, 2H), 4.87 (s, 2H), 5.50 (s, 2H), 7.17 (dd, J=8, 5 Hz, 1H), 7.25-7.30 (m, 2H), 7.33 (t, J=8 Hz, 1H), 7.49 (d, J=8 Hz, 1H), 7.54 (d, J=8 Hz, 1H), 8.62 (d, J=2 Hz, 1H), 8.66 (d, J=4 Hz, 1H); MS (DCI/NH$_3$) m/z 304 (M+H)$^+$.

Example 189

6-[(pyridin-4-yl)methyl]-3,4,5,6-tetrahydro-1H-2,5-ethanoazepino[4,3-b]indole To a solution of 3,4,5,6-tetrahydro-1H-2,5-ethanoazepino[4,3-b]indole N-borane complex (113 mg, 0.5 mmol; Example 187B) in tetrahydrofuran (3.0 mL) was added sodium hydride (60% dispersion in mineral oil; 40 mg, 1.0 mmol; Aldrich) in one portion. After stirring for 30 minutes, 4-(chloromethyl)pyridine hydrochloride (99 mg, 0.6 mmol; Aldrich) was added and the solution was heated to 55° C. overnight. After the solvent was removed, the residue was treated with HCl in acetone/water (1 N, acetone:water=3:1, 5 mL) and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, methanol-$d_4$) δ ppm 1.83-2.06 (m, 4H), 3.00-3.13 (m, 3H), 3.14-3.25 (m, 2H), 4.29 (s, 2H), 5.49 (s, 2H), 6.98 (d, J=6 Hz, 2H), 7.01-7.14 (m, 2H), 7.26 (d, J=8 Hz, 1H), 7.39 (d, J=7 Hz, 1H), 8.37-8.43 (m, 2H); MS (DCI/NH$_3$) m/z 304 (M+H)$^+$.

Example 190

8-[(6-chloropyridin-3-yl)methyl]-1-fluoro-1,4,5,6,7,8-hexahydro-2H-1,5:3,7-dimethanoazonino[5,4-b]indole

Example 190A

2-chloro-5-{[1-(4-fluorophenyl)hydrazino]methyl}pyridine

A mixture of (4-fluorophenyl)hydrazine hydrochloride (2.52 g, 20 mmol; Aldrich) and 2-chloro-5-(chloromethyl)pyridine (3.24 g, 20.00 mmol; Aldrich) in ethanol (120 mL) was treated with triethylamine (9.76 mL, 70.0 mmol; Aldrich), and the mixture was heated at 80° C. with stirring for 16 hours. The solvent was removed and the residue was purified by flash chromatography (silica gel, 10:1 CH$_2$Cl$_2$—CH$_3$OH) to afford the title compound: $^1$H NMR (300 MHz, methanol-$d_4$) δ ppm 4.53 (s, 2H), 6.93-6.99 (m, 2H), 7.02-7.10 (m, 2H), 7.40 (d, J=8 Hz, 1H), 7.77 (dd, J=8, 3 Hz, 1H), 8.30 (d, J=3 Hz, 1H); MS (DCI/NH$_3$) m/z 252 (M+H)$^+$.

Example 190B

1-azatricyclo[4.3.1.1$^{3,8}$]undecan-4-one

To an ice-cooled solution of trimethylsilyldiazomethane (2 N in hexanes, 9.00 mL, 18.00 mmol; Aldrich) was added a solution of 1-azaadamantan-4-one (2.268 g, 15 mmol; Becker, D. P.; Flynn, D. L. *Synthesis* 1992, 1080) in tetrahydrofuran (12 mL) dropwise over 20 minutes. Anhydrous methanol (6 mL) was added and the mixture was allowed to warm to room temperature. After 18 hours, glacial acetic acid was added dropwise until the mixture was colorless (about 1 mL). The reaction mixture was shaken with saturated sodium carbonate (4 mL), the tetrahydrofuran layer was separated, and the aqueous portion was extracted with dichloromethane (3×12 mL). The combined organic phases were dried over magnesium sulfate, filtered, and concentrated to give the title compound: $^1$H NMR (300 MHz, CDCl$_3$) δ ppm 1.72 (m, 1H), 1.78 (dddd, J=13.6, 4.0, 2.4, 2.1 Hz, 1H), 1.88 (m, 1H), 1.90 (dddd, J=14.6, 4.0, 2.4, 2.1 Hz, 1H), 2.14 (dddd, J=14.4, 6.5, 4.4, 1.9 Hz, 1H), 2.27 (m, 1H), 2.59 (t, J=5.8 Hz, 1H), 2.63-2.68 (m, 2H), 2.96 (m, 1H), 3.01 (dd, J=4.4, 2.0 Hz, 1H), 3.07 (m, 1H), 3.14 (m, 1H), 3.25 (ddd, J=14.6, 4.9, 1.2 Hz, 1H), 3.43 (dd, J=14.2, 5.1 Hz, 1H); MS (DCI/NH$_3$) m/z 166 (M+H)$^+$.

Example 190C

8-[(6-chloropyridin-3-yl)methyl]-1-fluoro-1,4,5,6,7,8-hexahydro-2H-1,5:3,7-dimethanoazonino[5,4-b]indole A solution of 2-chloro-5-{[1-(4-fluorophenyl)hydrazino]methyl}pyridine (252 mg, 1.0 mmol; Example 190A) and 1-azatricyclo[4.3.1.1$^{3,8}$]undecan-4-one (165 mg, 1.0 mmol; Example 190B) in dry dioxane (8 mL) was treated with concentrated sulfuric acid (0.107 mL, 2.0 mmol; J. T. Baker), and the mixture was heated to 100° C. with stirring for 16 hours. The mixture was cooled, concentrated, basified with 1 N aqueous sodium hydroxide, and extracted with dichloromethane (3×50 mL). The combined organic phase was concentrated in vacuo and then purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, methanol-d$_4$) δ ppm 1.81-2.03 (m, 3H), 2.19 (dt, J=13, 5 Hz, 1H), 2.26-2.36 (m, 1H), 2.95 (ddd, J=16, 5, 5 Hz, 2H), 3.09-3.27 (m, 4H), 3.30-3.38 (m, 1H), 3.43 (dd, J=13, 4 Hz, 1H), 5.43 (s, 2H), 6.82 (td, J=9, 3 Hz, 1H), 7.08 (dd, J=10, 2 Hz, 1H), 7.26 (dd, J=9, 4 Hz, 1H), 7.29-7.39 (m, 2H), 8.00 (d, J=1 Hz, 1H). MS (DCI/NH$_3$) m/z=382/384 (M+H)$^+$.

Example 191

9-fluoro-6-[(2-fluoropyridin-4-yl)methyl]-3,4,5,6-tetrahydro-1H-2,5-ethanoazepino[4,3-b]indole

Example 191A 9-fluoro-6-[(2-fluoropyridin-4-yl)methyl]-3,4,5,6-tetrahydro-1H-2,5-ethanoazepino[4,3-b]indole N-borane complex To a solution of 9-fluoro-3,4,5,6-tetrahydro-1H-2,5-ethanoazepino[4,3-b]indole N-borane complex (385 mg, 1.579 mmol; Example 164A) in tetrahydrofuran (5.0 mL) was added sodium amide (103 mg, 2.63 mmol; Aldrich) in portions. After 30 minutes, 4-(bromomethyl)-2-fluoropyridine (250 mg, 1.316 mmol; Biogene Organics) was added and the solution was heated to 55° C. overnight. The reaction was cooled to room temperature and quenched with water (5.0 mL), then extracted with dichloromethane (2×10 mL). The combined organic extracts were dried over magnesium sulfate, filtered, and concentrated under reduced pressure to provide the titled compound. The resulting material was carried on to the next step without further purification: LC/MS (DCI/NH$_3$) m/z 340 (M+H-BH$_3$)$^+$.

Example 191B 9-fluoro-6-[(2-fluoropyridin-4-yl)methyl]-3,4,5,6-tetrahydro-1H-2,5-ethanoazepino[4,3-b]indole A solution of 9-fluoro-6-[(2-fluoropyridin-4-yl)methyl]-3,4,5,6-tetrahydro-1H-2,5-ethanoazepino[4,3-b]indole N-borane complex (447 mg, 1.316 mmol; Example 191A) in ethyl acetate (5.0 mL) was treated with HCl (4 M in dioxane; 2 mL, 65.8 mmol; Aldrich) and the mixture was stirred at room temperature overnight. The reaction mixture was concentrated in vacuo, and the residue dissolved in water (5 mL) and then basified (pH 10) with 4 M aqueous sodium hydroxide. The mixture was concentrated in vacuo and the resulting material was purified by flash chromatography [12 g silica gel, 0-100% gradient of CH$_3$OH-14.8 M aqueous NH$_4$OH (9:1) in CH$_2$Cl$_2$] to afford the title compound: $^1$H NMR (300 MHz, CDCl$_3$) δ ppm 1.78-2.08 (m, 4H), 2.82-2.97 (m, 1H), 3.00-3.18 (m, 2H), 3.20-3.36 (m, 2H), 4.28 (s, 2H), 5.30 (s, 2H), 6.47 (s, 1H), 6.77 (d, J=5.2 Hz, 1H), 6.84-6.95 (m, 1H), 7.00-7.13 (m, 2H), 8.14 (d, J=5.6 Hz, 1H); MS (ESI+) m/z=340 (M+H)$^+$.

Example 192

11-methyl-1,4,5,6,7,8-hexahydro-2H-1,5:3,7-dimethanoazonino[5,4-b]indole

In a 50 mL round-bottom flask were combined p-tolylhydrazine hydrochloride (0.753 g, 4.74 mmol; Aldrich), and 1-azatricyclo[4.3.1.1$^{3,8}$]undecan-4-one (0.784 g, 4.74 mmol; Example 190B) in dioxane (18 mL). After 10 minutes, the suspension cleared. Concentrated sulfuric acid (1.265 mL, 23.72 mmol) was added and the mixture was heated at 80° C. After 1.5 hours, the mixture was cooled and concentrated to about 3 mL. The residue was dissolved in water (75 mL), basified with concentrated sodium hydroxide (30 mmol), extracted with chloroform (4×25 mL), dried over magnesium sulfate, and concentrated. The resulting material was purified by flash chromatography (Analogix 15 mm 12 g silica gel column, eluted with a 10-30% gradient of methanol in chloroform) to afford the title compound: $^1$H NMR (300 MHz, methanol-d$_4$) δ ppm 1.97 (d, J=13.2 Hz, 1H), 2.03-2.13 (m, 2H), 2.21-2.34 (m, 2H), 2.37 (s, 3H), 2.86 (t, J=5.1 Hz, 1H), 3.06 (t, J=5.1 Hz, 1H), 3.22 (d, J=13.2 Hz, 1H), 3.28-3.34 (m, 3H), 3.48 (td, J=13.0, 4.6 Hz, 2H), 6.82 (ddd, J=8.1, 1.2 Hz, 1H), 7.11 (dd, J=1.2, 0.7 Hz, 1H), 7.12 (d, J=8.1 Hz 1H); MS (DCI/NH$_3$) m/z 253 (M+H)$^+$.

Example 193

11-methyl-8-[2-(6-methylpyridin-3-yl)ethyl]-1,4,5,6,7,8-hexahydro-2H-1,5:3,7-dimethanoazonino[5,4-b]indole

Example 193A 11-methyl-8-[2-(6-methylpyridin-3-yl)ethyl]-1,4,5,6,7,8-hexahydro-2H-1,5:3,7-dimethanoazonino[5,4-b]indole A reaction flask with a septum cap was charged with 30% sodium metal dispersion in paraffin wax (0.14 g, 1.86 mmol; Aldrich) and a solution of 11-methyl-1,4,5,6,7,8-hexahydro-2H-1,5:3,7-dimethanoazonino[5,4-b]indole (0.30 g, 1.33 mmol; Example 192) in dimethyl sulfoxide (6 mL). The vessel was sealed, flushed with nitrogen, and stirred for 10 minutes. A solution of 2-methyl-5-vinylpyridine (0.24 g, 1.99 mmol; prepared as described in International Publication No. WO 2001017968) and hydroquinone (0.036 g, 0.33 mmol; Aldrich) in anhydrous dimethyl sulfoxide (1.5 mL) was added and the reaction mixture was heated at 100° C. for 72 hours. After cooling the reaction mixture to room temperature, it was poured into water and extracted with ethyl acetate (4×25 mL). The combined organic extracts were washed with brine, concentrated, and purified by reverse-phase HPLC [Waters XBridge™ C18 5 µm OBD column, 30×100 mm, flow rate 40 mL/minute, 5-95% gradient of acetonitrile in buffer (0.1 M aqueous ammonium bicarbonate, adjusted to pH 10 with ammonium hydroxide) over 15 minutes] to afford the title compound.

Example 193B 11-methyl-8-[2-(6-methylpyridin-3-yl)ethyl]-1,4,5,6,7,8-hexahydro-2H-1,5:3,7-dimethanoazonino[5,4-b]indole hydrochloride A solution of 11-methyl-8-[2-(6-methylpyridin-3-yl)ethyl]-1,4,5,6,7,8-hexahydro-2H-1,5:3,7-dimethanoazonino[5,4-b]indole (93 mg, 0.25 mmol; Example 193A) in ethyl acetate (1.5 mL) was treated with a solution of HCl in dioxane (4 M, 0.063 mL, 0.25 mmol; Aldrich), added dropwise. After stirring for 20 minutes, the solid was collected by filtration, rinsed with ethyl acetate, and dried for 10 hours at 75° C. under high vacuum to afford the title compound: $^1$H NMR (300 MHz, methanol-d$_4$) δ ppm 1.49 (d, J=13.9 Hz, 1H), 1.88 (d, J=13.6 Hz, 1H), 2.10 (dt, J=13.6, 5.3 Hz, 1H), 2.28 (dt, J=13.6, 4.9 Hz, 1H), 2.38 (m, 1H), 2.41 (s, 3H), 2.44 (s, 3H), 2.86 (d, J=12.5 Hz, 1H), 3.05 (t, J=6.4 Hz, 2H), 3.20 (t, J=5.6 Hz, 1H), 3.33 (d, J=12.5 Hz, 1H), 3.46 (t, J=5.1 Hz, 1H), 3.51-3.62 (m, 4H), 3.77 (dd, J=12.7, 4.6 Hz, 1H), 4.40 (td, J=6.4, 3.1 Hz, 2H), 6.97 (dd, J=8.3, 1.5 Hz, 1H), 7.16 (d, J=7.8 Hz, 1H), 7.20 (d, J=8.4 Hz, 1H), 7.22 (d, J=1.3 Hz, 1H), 7.34 (dd, J=7.8, 2.4 Hz, 1H), 7.78 (d, J=2.4 Hz, 1H); MS (DCI/NH$_3$) m/z 372.2 (M+H)$^+$.

Example 194

(1R*,7R*,7aS*,12bR*)-11-methyl-8-[2-(6-methyl-pyridin-3-yl)ethyl]-1,4,5,6,7,7a,8,12b-octahydro-2H-1,5:3,7-dimethanoazonino[5,4-b]indole A solution of the product of Example 193 (94 mg, 0.253 mmol) in trifluoroacetic acid (0.8 mL) was cooled to 4° C. and was treated with a solution of sodium cyanoborohydride (80 mg, 1.265 mmol) in anhydrous methanol (0.2 mL). The mixture was warmed to room temperature for 1 hour, then concentrated. The residue was taken up in water (1 mL) and stirred for 45 minutes. The mixture was purified by reverse-phase HPLC [Waters XBridge™ C18 5 µm OBD column, 30×100 mm, flow rate 40 mL/minute, 5-95% gradient of acetonitrile in buffer (0.1 M aqueous ammonium bicarbonate, adjusted to pH 10 with ammonium hydroxide) over 15 minutes] to provide a mixture of diastereomers (45 mg). The diastereomers were separated by flash chromatography (Analogix 10 mm 4 g silica gel column, eluted with 5-10% 14.8 M aqueous NH$_4$OH—CH$_3$OH (1:20) in CHCl$_3$) to afford the title compound (Rf thin-layer chromatography 0.44 (20% CH$_3$OH/1% 14.8 M aqueous NH$_4$OH/79% CH$_2$Cl$_2$): $^1$H NMR (500 MHz, methanol-d$_4$) δ ppm 1.67 (br d, J=14.0 Hz, 1H), 1.78 (br d, J=14.0 Hz, 1H), 1.79 (m, 1H), 2.14 (m, 1H), 2.19 (s, 3H), 2.20 (m, 1H), 2.25 (m, 1H), 2.28 (m, 1H), 2.48 (s, 3H), 2.52 (br d, J=14.0 Hz, 1H), 2.76 (ddd, J=14.5, 8.9, 6.1 Hz, 1H), 2.87 (ddd, J=15.1, 9.2, 6.3 Hz, 1H), 2.90 (br d, J=14.0 Hz, 1H), 2.95 (m, 3H), 3.05 (d, J=13.7 Hz, 1H), 3.21 (ddd, J=14.8, 8.9, 6.0 Hz, 1H), 3.46 (ddd, J=14.8, 9.1, 6.0 Hz, 1H), 3.67 (dd, J=11.4, 2.6 Hz, 1H), 3.88 (dd, J=11.4, 4.7 Hz, 1H), 6.32 (d, J=7.9 Hz, 1H), 6.72 (s, 1H), 6.82 (d, J=7.9 Hz, 1H), 7.20 (d, J=8.0 Hz, 1H), 7.60 (dd, J=8.0, 2.3 Hz, 1H), 8.24 (d, J=1.8 Hz, 1H); MS (DCI/NH$_3$) m/z 374.3 (M+H)$^+$.

Example 195

(1R*,7R*,7aR*,12bS*)-11-methyl-8-[2-(6-methyl-pyridin-3-yl)ethyl]-1,4,5,6,7,7a,8,12b-octahydro-2H-1,5:3,7-dimethanoazonino[5,4-b]indole Purification of the mixture of Example 194 by flash chromatography as described in Example 194 afforded the title compound (Rf thin-layer chromatography 0.57 (20% CH$_3$OH/1% 14.8 M aqueous NH$_4$OH/79% CH$_2$Cl$_2$): $^1$H NMR (500 MHz, methanol-d$_4$) δ ppm 1.39 (br d, J=13.8 Hz, 1H), 1.50 (m, 1H), 1.75 (m, 1H), 1.79 (m, 1H), 1.91 (br d, J=13.8 Hz, 1H), 2.14 (m, 1H), 2.16 (m, 1H), 2.18 (s, 3H), 2.47 (s, 3H), 2.76 (ddd, J=14.6, 8.9, 6.1 Hz, 1H), 2.86 (ddd, J=15.0, 9.1, 6.3 Hz, 1H), 2.88 (d, J=14.0 Hz, 1H), 2.93 (m, 3H), 3.19 (ddd, J=14.8, 8.8, 6.1 Hz, 1H), 3.34 (ddd, J=14.5, 9.8, 5.5 Hz, 1H), 3.36 (ddd, J=14.5, 9.8, 5.5 Hz, 1H), 3.45 (ddd, J=14.8, 9.0, 6.0 Hz, 1H), 3.73 (dd, J=11.5, 3.1 Hz, 1H), 3.95 (dd, J=11.6, 5.0 Hz, 1H), 6.25 (d, J=8.0 Hz, 1H), 6.70 (s, 1H), 6.79 (d, J=7.9 Hz, 1H), 7.20 (d, J=7.9 Hz, 1H), 7.60 (dd, J=7.9, 2.3 Hz, 1H), 8.24 (d, J=1.8 Hz, 1H); MS (DCI/NH$_3$) m/z 374.3 (M+H)$^+$.

Example 196

8-[2-(6-chloropyridin-3-yl)ethyl]-11-methyl-1,4,5,6,7,8-hexahydro-2H-1,5:3,7-dimethanoazonino[5,4-b]indole In a 50 mL round-bottom flask were combined 2-chloro-5-(2-(1-p-tolylhydrazinyl)-ethyl)pyridine (0.237 g, 0.905 mmol; Example 117D) and 1-azatricyclo[4.3.1.1$^{3,8}$]unde-can-4-one (0.194 g, 1.177 mmol; Example 190B) in dioxane (2 mL). After warming to 50° C. for 10 minutes, the suspension cleared. Concentrated sulfuric acid (0.241 mL, 4.53 mmol) was added and the mixture was heated at 80° C. After 1.5 hours, the flask contained two phases. The mixture was cooled and the upper layer was decanted from the solid lower phase. The residue was dissolved in water (75 mL), basified with concentrated sodium hydroxide (30 mmol), extracted with chloroform (4×25 mL), dried over magnesium sulfate, and concentrated to give a crude solid. This material was purified by reverse-phase HPLC [Waters XBridge™ C18 5 µm OBD column, 30×100 mm, flow rate 40 mL/minute, 5-95% gradient of acetonitrile in buffer (0.1 M aqueous ammonium bicarbonate, adjusted to pH 10 with ammonium hydroxide) over 15 minutes] to afford the title compound: $^1$H NMR (300 MHz, methanol-d$_4$) δ ppm 1.62 (br d, J=13.2 Hz, 1H), 1.89 (br d, J=13.2 Hz, 1H), 1.89-1.93 (m, 1H), 2.12 (dt, J=12.9, 5.1 Hz, 1H), 2.24 (ddd, J=13.7, 5.3, 5.1 Hz, 1H), 2.38 (s, 3H), 2.73 (t, J=4.9 Hz, 1H), 2.76 (d, J=13.6 Hz, 1H), 2.94 (t, J=4.9 Hz, 1H), 3.04 (t, J=6.4 Hz, 2H), 3.09 (d, J=13.6 Hz, 1H), 3.15-3.21 (m, 2H), 3.22 (dd, J=13.5, 4.7 Hz, 1H), 3.38 (dd, J=13.4, 4.6 Hz, 1H), 4.34 (t, J=6.4 Hz, 1H), 4.35 (t, J=6.4 Hz, 1H), 6.86 (dd, J=8.2, 1.4 Hz, 1H), 7.08 (d, J=8.1 Hz, 1H), 7.12 (br s, 1H), 7.25 (dd, J=8.1, 0.7 Hz, 1H), 7.34 (dd, J=8.1, 2.4 Hz, 1H), 7.80 (d, J=2.0 Hz, 1H); MS (DCI/NH$_3$) m/z 392.3 (M+H)$^+$.

Example 197

11-methyl-8-[2-(2-methylphenyl)ethyl]-1,4,5,6,7,8-hexahydro-2H-1,5:3,7-dimethanoazonino[5,4-b]indole Sodium dispersion in paraffin (30%, 75 mg, 0.98 mmol) was combined with 11-methyl-1,4,5,6,7,8-hexahydro-2H-1,5:3,7-dimethanoazonino[5,4-b]indole (120 mg, 0.48 mmol; Example 192) in a 20 mL vial with stir bar and septum cap. Dimethyl sulfoxide (2.0 mL) was added, and the vial was evacuated and purged with nitrogen (10 cycles). The mixture was stirred at room temperature for 30 minutes, and a solution of 2-methylstyrene (116 mg, 0.97 mmol; Aldrich) and hydroquinone (16 mg, 0.15 mmol; Aldrich) in dimethyl sulfoxide (0.5 mL) was added. The vial was evacuated and purged with nitrogen (5 cycles) and the mixture was stirred with heating at 105° C. for 114 hours. The resulting mixture was cooled to room temperature, applied directly to a column of silica gel and eluted with chloroform, then CHCl$_3$—CH$_3$OH-14.8 M aqueous NH$_4$OH (90:10:1). The product-containing fractions were combined and concentrated under vacuum and the residue was further purified by reverse-phase HPLC [Waters XBridge™ C18 5 µm OBD column, 30×100 mm, flow rate 40 mL/minute, 20-90% gradient of acetonitrile in buffer (0.1 M aqueous ammonium bicarbonate, adjusted to pH 10 with ammonium hydroxide) over 20 minutes] to provide the free base of the title compound. This material was dissolved in ethyl acetate (3 mL) and ethanol (0.5 mL) and a solution of HCl in dioxane (4 M; 0.1 mL; Aldrich) was added. The pale solution was stirred at room temperature for 2 hours, then concentrated under vacuum to leave a solid. This was triturated with ethyl acetate (4 mL) and dried under vacuum to provide the title compound as the HCl salt: $^1$H NMR (300 MHz, methanol-$d_4$) δ ppm 1.48 (d, J=13.9 Hz, 1H), 1.84 (d, J=13.6 Hz, 1H), 1.95 (s, 3H), 1.97-2.05 (m, 1H), 2.18-2.41 (m, 3H), 2.42 (s, 3H), 2.98 (t, J=4.9 Hz, 1H), 3.04-3.14 (m, 2H), 3.16-3.25 (m, 1H), 3.32-3.39 (m, 1H), 3.39-3.57 (m, 3H), 3.73 (dd, J=12.6, 4.8 Hz, 1H), 4.30-4.53 (m, 2H), 6.74 (d, J=7.1 Hz, 1H), 6.96-7.04 (m, 2H), 7.07 (d, J=3.7 Hz, 1H), 7.07 (s, 1H), 7.22 (s, 1H), 7.32 (d, J=8.5 Hz, 1H); MS (DCI) m/z 371 (M+H)$^+$.

Example 198

5-[2-(6-chloropyridin-3-yl)ethyl]-2,11-dimethyl-5,6,7,8,9,10-hexahydro-6,10-epiminocyclohepta[b]indole Example 198A 8-methyl-8-azabicyclo[3.2.1]octan-6-one A suspension of exo-6-hydroxy-8-methyl-8-azabicyclo[3.2.1]octane (1.95 g, 13.8 mmol; *J. Heterocycl. Chem.* 1968, 5, 423) and 2-iodoxybenzoic acid (4.83 g, 17.2 mmol; Aldrich) in ethyl acetate (90 mL) was heated at 80° C. for 2.2 hours. The liquid phase was cooled and decanted. The remaining residue was heated briefly at 80° C. with additional ethyl acetate (30 mL), then cooled before the liquid phase was removed. The combined solutions were cooled to 10° C. and filtered. The filtrate was partially concentrated, allowed to stand overnight, filtered again, concentrated and purified by flash chromatography (silica, acetonitrile/ethyl acetate then 2% 14.8 M aqueous ammonium hydroxide in acetonitrile) to afford the title compound: MS (DCI/NH$_3$) m/z 140 (M+H)$^+$.

Example 198B

5-[2-(6-chloropyridin-3-yl)ethyl]-2,11-dimethyl-5,6,7,8,9,10-hexahydro-6,10-epiminocyclohepta[b]indole A suspension of 2-chloro-5-(2-(1-p-tolylhydrazinyl)ethyl)pyridine (393 mg, 1.5 mmol; Example 117D), 8-methyl-8-azabicyclo[3.2.1]octan-6-one (283 mg, 2.0 mmol; Example 198A), and KHSO$_4$ (272 mg, 2.0 mmol) in dioxane (5 mL) was heated at 50° C. for 60 minutes. More dioxane (2 mL) was added, and the suspension was heated at 75° C. for 100 minutes. Concentrated sulfuric acid (0.25 mL) was added and heating was continued overnight. After cooling the reaction mixture to room temperature, the dioxane phase was removed and the gummy residue was dissolved in methanol and added to concentrated aqueous ammonium hydroxide (5 mL). The mixture was extracted with ethyl acetate (3×), and the combined organic phases were concentrated. This was extracted back into ethyl acetate, and the extracts were dried (sodium sulfate), concentrated, and purified by flash chromatography (silica, 0-100% gradient of acetonitrile-ethyl acetate, then 2% 14.8 M aqueous ammonium hydroxide in acetonitrile) to afford the title compound: $^1$H NMR (300 MHz, methanol-$d_4$) δ ppm 0.15-0.36 (m, 1H), 1.13-1.33 (m, 2H), 1.41-1.53 (m, 1H), 1.68-1.89 (m, 2H), 2.20 (s, 3H), 2.40 (s, 3H), 3.07-3.22 (m, 2H), 3.56 (dd, J=2.7, 2.7 Hz, 1H), 3.92 (dd, J=2.7, 2.7 Hz, 1H), 4.20 (ddd, J=14.4, 8.4, 8.4 Hz, 1H), 4.48 (ddd, J=14.4, 5.7, 5.7 Hz, 1H), 6.95 (dd, J=8.5, 1.6 Hz, 1H), 7.12-7.19 (m, 1H), 7.23 (d, J=8.4 Hz, 1H), 7.27 (d, J=8.2 Hz, 1H), 7.47 (dd, J=8.2, 2.4 Hz, 1H), 7.90 (d, J=2.4 Hz, 1H); MS (ESI) m/z 366 (M+H)$^+$.

Example 199

(6R,10S)-5-[2-(6-chloropyridin-3-yl)ethyl]-2,11-dimethyl-5,6,7,8,9,10-hexahydro-6,10-epiminocyclohepta[b]indole The individual enantiomers of the racemic mixture of Example 198B were separated by preparative chiral supercritical fluid chromatography (ChiralPak® OD-H 5 μm column, 21×250 mm, 35° C., 20% CH$_3$OH—CO$_2$ containing 0.1% diethylamine, flow rate 40 mL/minute) to afford the title compound as the first-eluting enantiomer (retention time 10.01 minutes).

Example 200

(6S,10R)-5-[2-(6-chloropyridin-3-yl)ethyl]-2,11-dimethyl-5,6,7,8,9,10-hexahydro-6,10-epiminocyclohepta[b]indole The individual enantiomers of the racemic mixture of Example 198B were separated by preparative chiral supercritical fluid chromatography (ChiralPak® OD-H 5 μm column, 21×250 mm, 35° C., 20% CH$_3$OH—CO$_2$ containing 0.1% diethylamine, flow rate 40 mL/minute) to afford the title compound as the second-eluting enantiomer (retention time 11.61 minutes).

Example 201

10-methyl-1,3,4,5,6,7-hexahydro-2,6-methanoazocino[4,3-b]indole

Example 201A ethyl 1-(3-ethoxy-3-oxopropyl)piperidine-3-carboxylate

A 25 mL round-bottom flask was charged with ethyl nipecotate (4.0 mL, 25.7 mmol, Aldrich) and ethyl acrylate (3.4 mL, 31.4 mmol; Aldrich). The flask was purged with nitrogen and the mixture was heated to 80° C. for 20 hours, then purified by silica gel chromatography (ethyl acetate-dichloromethane-triethylamine 50:50:1; Rf=0.28) to afford the title compound: $^1$H NMR (300 MHz, CDCl$_3$) δ ppm 1.23-1.28 (m, 6H), 1.42-1.59 (m, 2H), 1.68-1.74 (m, 1H), 1.89-1.95 (m, 1H), 2.01-2.08 (m, 1H), 2.17-2.24 (m, 1H), 2.46-2.56 (m, 3H), 2.68-2.76 (m, 3H), 2.94-2.99 (m, 1H), 4.09-4.17 (m, 4H); MS (DCI/NH$_3$) m/z 258 (M+H)$^+$.

Example 201B 1-azabicyclo[3.3.1]nonan-4-one

A suspension of potassium tert-butoxide (8.15 g, 72.6 mmol; Aldrich) in toluene (200 mL) was heated to reflux for 15 minutes, then a solution of ethyl 1-(3-ethoxy-3-oxopropyl)-piperidine-3-carboxylate (6.16 g, 23.9 mmol) in toluene (50 mL) was added dropwise over 1 hour to the refluxing reaction mixture. After the addition was complete, the reaction was heated to reflux for an additional 5 hours, cooled to ambient temperature, and extracted with water (3×50 mL). The combined aqueous layers were acidified with concentrated hydrochloric acid (40 mL), then heated to reflux for 22 hours. The reaction was basified with 45 weight % potassium hydroxide (~35 mL) and extracted with chloroform (3×100 mL). The combined organic extracts were dried over sodium sulfate, filtered and concentrated in vacuo to afford the title compound: $^1$H NMR (300 MHz, CDCl$_3$) δ ppm 1.50-1.81 (m, 2H), 1.90-1.96 (m, 2H), 2.39-2.43 (m, 1H), 2.49-2.54 (m, 2H), 3.08-3.41 (m, 6H); MS (DCI/NH$_3$) m/z 140 (M+H)$^+$.

Example 201C 10-methyl-1,3,4,5,6,7-hexahydro-2,6-methanoazocino[4,3-b]indole

A solution of 1-azabicyclo[3.3.1]nonan-4-one (2.05 g, 14.73 mmol; Example 201B) and p-tolylhydrazine hydrochloride (2.46 g, 15.51 mmol; Aldrich) in ethanol (50 mL) was treated with 4 M HCl in dioxane (4 mL, 16 mmol; Aldrich) and the reaction mixture was heated to reflux for 16 hours. The reaction was allowed to cool to ambient temperature affording a precipitate that was isolated by filtration and washed with additional ethanol (10×2 mL) to provide a solid (3.03 g). This material was dissolved in 1 M aqueous NaOH (50 mL) and extracted with chloroform (3×50 mL). The combined organic layers were dried over sodium sulfate, filtered and concentrated in vacuo to afford the title compound: $^1$H NMR (300 MHz, CDCl$_3$) δ ppm 1.23-1.28 (m, 1H), 1.40-1.53 (m, 1H), 1.79-1.98 (m, 2H), 2.39 (s, 3H), 2.89 (br s, 1H), 2.99-3.10 (m, 3H), 3.20-3.24 (m, 1H), 3.87 (d, J=16.3 Hz, 1H), 4.32 (d, J=16.3 Hz, 1H), 6.88 (dd, J=8.1, 1.4 Hz, 1H), 7.14-7.18 (m, 2H); MS (DCI/NH$_3$) m/z 227 (M+H)$^+$. Anal. Calcd. for C$_{15}$H$_{18}$N$_2$.0.1H$_2$O: C, 78.98; H, 8.04; N, 12.28. Found: C, 78.98; H, 8.04; N, 12.28.

Example 202

10-methyl-7-[2-(6-methylpyridin-3-yl)ethyl]-1,3,4,5,6,7-hexahydro-2,6-methanoazocino[4,3-b]indole A solution of 10-methyl-1,3,4,5,6,7-hexahydro-2,6-methanoazocino[4,3-b]indole (173.8 mg, 0.768 mmol; Example 201) in dimethyl sulfoxide (3 mL) was treated with sodium (30% dispersion in paraffin; 87.7 mg, 1.144 mmol; Aldrich), 2-methyl-5-vinylpyridine (204.6 mg, 1.717 mmol; prepared as described in International Publication No. WO 2001017968) and hydroquinone (28.6 mg, 0.260 mmol; Aldrich). The reaction was purged with nitrogen for 15 minutes, then heated to 100° C. for 17 hours. After cooling, the reaction was partitioned between 1 M aqueous K$_2$CO$_3$ (35 mL) and chloroform (3×35 mL). The combined organic layers were washed with brine (35 mL), dried over sodium sulfate, filtered and concentrated. Methanol (10 mL) was added to the residue and the resulting suspension was filtered through diatomaceous earth, then purified by preparative HPLC (Phenomenex® Luna® Combi-HTS™ C8(2) 5 μm 100 Å AXIA™ 30×75 mm column, gradient of 10-100% acetonitrile in 0.1% trifluoroacetic acid, flow rate 50 mL/minute) to afford the title compound as the bis trifluoroacetic acid salt: $^1$H NMR (300 MHz, methanol-d$_4$) δ ppm 1.54-1.78 (m, 3H), 1.95-2.05 (m, 1H), 2.41 (s, 3H), 2.67 (s, 3H), 3.42-3.55 (m, 4H), 3.68-3.72 (m, 1H), 4.34-4.41 (m, 1H), 4.48-4.57 (m, 2H), 7.01 (d, J=8.3 Hz, 1H), 7.17 (d, J=8.3 Hz, 1H), 7.27 (s, 1H), 7.69 (d, J=8.3 Hz, 1H), 8.03 (dd, J=8.3, 2.0 Hz, 1H), 8.22 (d, J=2.0 Hz, 1H); MS (DCI/NH$_3$) m/z 347 (M+H)$^+$.

Example 203

10-methyl-7-[2-(2-methylphenyl)ethyl]-1,3,4,5,6,7-hexahydro-2,6-methanoazocino[4,3-b]indole The coupling of 10-methyl-1,3,4,5,6,7-hexahydro-2,6-methanoazocino[4,3-b]indole (226.0 mg, 0.999 mmol; Example 201) and 2-methylstyrene (209.0 mg, 176.9 mmol, Alfa Aesar) was performed as described in Example 202, except that the material was purified by reverse-phase HPLC [Waters XBridge™ C18 5 μm OBD column, 30×100 mm, flow rate 40 mL/minute, 20-95% gradient of acetonitrile in buffer (0.1 M aqueous ammonium bicarbonate, adjusted to pH 10 with ammonium hydroxide) over 20 minutes] to afford the title compound: $^1$H NMR (300 MHz, methanol-d$_4$) δ ppm 1.09-1.17 (m, 1H), 1.29-1.47 (m, 2H), 1.65-1.74 (m, 1H), 1.97 (s, 3H), 2.18-2.24 (m, 1H), 2.42 (s, 3H), 2.60-2.65 (m, 1H), 2.94-3.08 (m, 5H), 3.81 (d, J=16.3 Hz, 1H), 4.05-4.15 (m, 1H), 4.23 (d, J=16.3 Hz, 1H), 4.36-4.45 (m, 1H), 6.78 (d, J=7.1 Hz, 1H), 6.95-7.06 (m, 4H), 7.16-7.18 (m, 1H), 7.27 (d, J=8.1 Hz, 1H); MS (DCI/NH$_3$) m/z 345 (M+H)$^+$.

Example 204

7-[2-(4-chlorophenyl)ethyl]-10-methyl-1,3,4,5,6,7-hexahydro-2,6-methanoazocino[4,3-b]indole The coupling of 10-methyl-1,3,4,5,6,7-hexahydro-2,6-methanoazocino[4,3-b]indole (245.1 mg, 1.083 mmol; Example 201) and 4-chlorostyrene (256.3 mg, 1.709 mmol, Aldrich) was performed as described in Example 202, except that the material was purified by reverse-phase HPLC [Waters XBridge™ C18 5 μm OBD column, 30×100 mm, flow rate 40 mL/minute, 20-95% gradient of acetonitrile in buffer (0.1 M aqueous ammonium bicarbonate, adjusted to pH 10 with ammonium hydroxide) over 20 minutes] to afford the title compound: $^1$H NMR (300 MHz, methanol-d$_4$) δ ppm 1.13-1.45 (m, 3H), 1.67-1.79 (m, 1H), 2.31-2.35 (m, 1H), 2.42 (s, 3H), 2.63-2.69 (m, 1H), 2.96-3.11 (m, 5H), 3.82 (d, J=16.3 Hz, 1H), 4.07-4.15 (m, 1H), 4.24 (d, J=16.3 Hz, 1H), 4.34-4.42 (m, 1H), 6.78-6.83 (m, 2H), 6.97-7.00 (m, 1H), 7.12-7.19 (m, 3H), 7.27-7.31 (m, 1H); MS (DCI/NH$_3$) m/z 365 (M+H)$^+$.

Example 205

5-[2-(6-methylpyridin-3-yl)ethyl]-2,3,4,5-tetrahydro-1,4-ethanopyrido[3,2-b]indole Example 205A 2,3,4,5-tetrahydro-1,4-ethanopyrido[3,2-b]indole A mixture of 2-iodoaniline (1.00 g, 4.57 mmol; Aldrich), quinuclidin-3-one hydrochloride (1.24 g, 7.67 mmol; Aldrich), palladium(II) acetate (51 mg, 0.23 mmol; Aldrich), 1,4-diazabicyclo[2.2.2]octane (DABCO; 1.79 g, 15.98 mmol; Aldrich) and magnesium sulfate (0.88 g, 7.31 mmol; Aldrich) in dry N,N-dimethylformamide (14 mL) was evacuated and purged with nitrogen (three cycles) and stirred at 110° C. for 18 hours. The reaction mixture was cooled to ambient temperature and filtered through a microfiber frit. The filtrate was concentrated in vacuo, dissolved in methanol (10 mL) and purified by preparative HPLC [Waters XBridge™ RP18 column, 5 μm, 30×100 mm, flow rate 40 mL/minute, 10-99% gradient of methanol in buffer (0.1 M aqueous ammonium bicarbonate, adjusted to pH 10 with ammonium hydroxide)] to afford the title compound: $^1$H NMR (500 MHz, methanol-$d_4$) δ ppm 1.52-1.66 (m, 2H), 1.97-2.06 (m, 2H), 2.58-2.71 (m, 2H), 3.24-3.31 (m, 2H), 3.40-3.45 (quintet, J=2.9 Hz, 1H), 6.94-7.05 (m, 2H), 7.31-7.35 (m, 1H), 7.52-7.57 (m, 1H); MS (APCI) m/z 199 (M+H)$^+$.

Example 205B

5-[2-(6-methylpyridin-3-yl)ethyl]-2,3,4,5-tetrahydro-1,4-ethanopyrido[3,2-b]indole The coupling of 2,3,4,5-tetrahydro-1,4-ethanopyrido[3,2-b]indole (110 mg, 0.56 mmol; Example 205A) and 2-methyl-5-vinylpyridine (99 mg, 0.83 mmol; prepared as described in International Publication No. WO 2001017968) was performed according to the procedure described in Example 106A to provide the title compound: $^1$H NMR (500 MHz, methanol-$d_4$) δ ppm 0.91-1.05 (m, 2H), 1.75-1.85 (m, 2H), 2.38 (s, 3H), 2.42-2.51 (m, 2H), 3.09-3.21 (m, 5H), 4.44-4.50 (m, 2H), 7.02-7.12 (m, 3H), 7.27 (dd, J=7.9, 2.1 Hz, 1H), 7.41 (d, J=8.2 Hz, 1H), 7.56 (d, J=7.3 Hz, 1H), 7.77 (d, J=2.1 Hz, 1H); MS (ESI) m/z 476 (M+H)$^+$.

Example 206

(4aR*,9bR*)-5-[2-(6-methylpyridin-3-yl)ethyl]-2,3,4,4a,5,9b-hexahydro-1,4-ethanopyrido[3,2-b]indole A solution of 5-[2-(6-methylpyridin-3-yl)ethyl]-2,3,4,5-tetrahydro-1,4-ethanopyrido[3,2-b]indole (45 mg, 0.14 mmol; Example 205B) in trifluoroacetic acid (1.0 mL) was cooled to −30° C. and a solution of sodium cyanoborohydride (66 mg, 0.99 mmol) in methanol (0.5 mL) was added dropwise over a period of 30 minutes. The reaction mixture was allowed to slowly warm up to ambient temperature over a period of 30 minutes. The mixture was concentrated on the rotavap and then twice azeotroped with methanol (30 mL). The residue was purified by preparative HPLC (Waters XBridge™ RP18 column, 5 μm, 30×100 mm, flow rate 40 mL/minute, 20-99% gradient of methanol in 0.1% aqueous trifluoroacetic acid) to afford the title compound as the trifluoroacetic acid salt: $^1$H NMR (500 MHz, methanol-$d_4$) δ ppm 1.75-1.86 (m, 1H), 1.96-2.10 (m, 2H), 2.14-2.25 (m, 1H), 2.48-2.54 (m, 1H), 2.74 (s, 3H), 2.86-2.95 (m, 1H), 3.04-3.15 (m, 3H), 3.42-3.57 (m, 3H), 3.71 (dt, J=15.3, 7.6 Hz, 1H), 4.21 (dd, J=10.4, 4.3 Hz, 1H), 5.21 (d, J=10.4 Hz, 1H), 6.64 (d, J=7.9 Hz, 1H), 6.74 (t, J=7.5 Hz, 1H), 7.22-7.30 (m, 2H), 7.82 (d, J=8.2 Hz, 1H), 8.44 (dd, J=8.2, 2.1 Hz, 1H), 8.65 (d, J=1.5 Hz, 1H); MS (ESI) m/z 320 (M+H)$^+$.

Example 207

5-[2-(2-methylphenyl)ethyl]-2,3,4,5-tetrahydro-1,4-ethanopyrido[3,2-b]indole

The coupling of 2,3,4,5-tetrahydro-1,4-ethanopyrido[3,2-b]indole (30 mg, 0.15 mmol; Example 205A) and 2-methylstyrene (27 mg, 0.23 mmol; Aldrich) was performed according to the procedure described in Example 106A except that the product was purified by reverse-phase HPLC (Waters XBridge™ RP18 column, 5 μm, 30×100 mm, flow rate 40 mL/minute, 20-99% gradient of methanol in 0.1% aqueous trifluoroacetic acid) to afford the title compound as a trifluoroacetic acid salt: $^1$H NMR (500 MHz, methanol-$d_4$) δ ppm 1.03-1.12 (m, 2H), 1.93-2.00 (m, 2H), 2.01 (s, 3H), 2.90-2.99 (m, 2H), 3.16-3.22 (m, 2H), 3.33 (quintet, J=3.1 Hz, 1H), 3.70 (ddd, J=11.1, 9.5, 4.4 Hz, 2H), 4.57-4.64 (m, 2H), 6.67 (d, J=7.6 Hz, 1H), 6.95 (td, J=7.2, 1.7 Hz, 1H), 7.02-7.09 (m, 2H), 7.20-7.26 (m, 1H), 7.29-7.34 (m, 1H), 7.61-7.69 (m, 2H); MS (APCI) m/z 317 (M+H)$^+$.

Example 208

7-methyl-2,3,4,5-tetrahydro-1,4-ethanopyrido[3,2-b]indole

2-Iodo-5-methylaniline (1.0 g, 4.29 mmol; Amfinecom), quinuclidin-3-one hydrochloride (1.24 g, 7.67 mmol; Aldrich), palladium(II) acetate (48 mg, 0.22 mmol; Aldrich), 1,4-diazabicyclo[2.2.2]octane (DABCO; 1.73 g, 15.4 mmol; Aldrich) and magnesium sulfate (0.88 g, 7.31 mmol) were processed as described in Example 205A to provide the title compound: $^1$H NMR (500 MHz, methanol-$d_4$) δ ppm 1.52-1.63 (m, 2H), 1.94-2.05 (m, 2H), 2.40 (s, 3H), 2.59-2.71 (m, 2H), 3.26 (ddd, J=12.2, 8.5, 4.3 Hz, 2H), 3.40 (quintet, J=2.9 Hz, 1H), 6.85 (d, J=7.3, 0.7 Hz, 1H), 7.14 (s, 1H), 7.42 (d, J=7.9 Hz, 1H); MS (DCI) m/z 213 (M+H)$^+$.

Example 209

7-methyl-5-[2-(6-methylpyridin-3-yl)ethyl]-2,3,4,5-tetrahydro-1,4-ethanopyrido[3,2-b]indole The coupling of 7-methyl-2,3,4,5-tetrahydro-1,4-ethanopyrido[3,2-b]indole (110 mg, 0.52 mmol; Example 217) and 2-methyl-5-vinylpyridine (93 mg, 0.78 mmol; prepared as described in International Publication No. WO 2001017968) was performed according to the procedure described in Example 106A to provide the title compound: $^1$H NMR (500 MHz, methanol-$d_4$) δ ppm 0.88-1.03 (m, 2H), 1.71-1.82 (m, 2H), 2.38 (s, 3H), 2.41-2.48 (m, 2H), 2.44 (s, 3H), 3.07-3.17 (m, 5H), 4.42 (t, J=6.3 Hz, 2H), 6.89 (d, J=8.2 Hz, 1H), 7.07 (d, J=7.9 Hz, 1H), 7.16 (s, 1H), 7.25 (dd, J=7.9, 2.1 Hz, 1H), 7.44 (d, J=7.9 Hz, 1H), 7.77 (d, J=1.8 Hz, 1H); MS (DCI) m/z 332 (M+H)$^+$.

Example 210

(4aR*,9bR*)-7-methyl-5-[2-(6-methylpyridin-3-yl)ethyl]-2,3,4,4a,5,9b-hexahydro-1,4-ethanopyrido[3,2-b]indole The product of Example 209 (33 mg, 0.10 mmol) was processed as described in Example 206 except that the product was purified by reverse-phase HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (500 MHz, methanol-$d_4$) δ ppm 1.30-1.41 (m, 1H), 1.58-1.69 (m, 2H), 1.76-1.87 (m, 1H), 2.00-2.05 (m, 1H), 2.23 (s, 3H), 2.48 (s, 3H), 2.49-2.57 (m, 1H), 2.59-2.67 (m, 1H), 2.80-2.92 (m, 1H), 2.95-3.04 (m, 2H), 3.28-3.36 (m, 1H), 3.51 (ddd, J=14.6, 7.8, 6.6 Hz, 1H), 3.62 (dd, J=10.1, 4.0 Hz, 1H), 4.42 (d, J=10.1 Hz, 1H), 6.16 (s, 1H), 6.38 (d, J=7.3 Hz, 1H), 6.97 (d, J=7.6 Hz, 1H), 7.21 (d, J=8.2 Hz, 1H), 7.63 (dd, J=8.1, 2.3 Hz, 1H), 8.26 (d, J=2.1 Hz, 1H); MS (APCI) m/z 334 (M+H)+.

Example 211

8-methyl-2,3,4,5-tetrahydro-1,4-ethanopyrido[3,2-b]indole

2-Iodo-4-methylaniline (2.0 g, 8.58 mmol; prepared as described in J. Org. Chem. 1999, 64, 9650), quinuclidin-3-one hydrochloride (2.36 g, 14.6 mmol; Aldrich), palladium (II) acetate (145 mg, 0.646 mmol; Aldrich), 1,4-diazabicyclo [2.2.2]octane (DABCO; 3.47 g, 30.9 mmol; Aldrich) and magnesium sulfate (1.65 g, 13.7 mmol) were processed as described in Example 205A to provide the title compound: $^1$H NMR (500 MHz, methanol-$d_4$) δ ppm 1.52-1.62 (m, 2H), 1.92-2.05 (m, 2H), 2.39 (s, 3H), 2.55-2.69 (m, 2H), 3.22-3.29 (m, 2H), 3.40 (quintet, J=2.9 Hz, 1H), 6.85 (dd, J=8.2, 1.5 Hz, 1H), 7.21 (d, J=8.2 Hz, 1H), 7.34 (s, 1H); MS (APCI) m/z 213 (M+H)+.

Example 212

8-methyl-5-[2-(6-methylpyridin-3-yl)ethyl]-2,3,4,5-tetrahydro-1,4-ethanopyrido[3,2-b]indole The coupling of 8-methyl-2,3,4,5-tetrahydro-1,4-ethanopyrido[3,2-b]indole (80 mg, 0.38 mmol; Example 211) and 2-methyl-5-vinylpyridine (85 mg, 0.71 mmol; prepared as described in International Publication No. WO 2001017968) was performed according to the procedure described in Example 106A to provide the title compound: $^1$H NMR (400 MHz, methanol-$d_4$) δ ppm 0.87-1.08 (m, 2H), 1.64-1.87 (m, 2H), 2.39 (s, 3H), 2.41 (s, 3H), 2.42-2.52 (m, 2H), 3.07-3.20 (m, 5H), 4.38-4.52 (m, 2H), 6.93 (dd, J=8.2, 1.2 Hz, 1H), 7.09 (d, J=7.9 Hz, 1H), 7.26 (dd, J=5.8, 2.1 Hz, 1H), 7.28 (d, J=8.5 Hz, 1H), 7.36 (s, 1H), 7.77 (d, J=2.1 Hz, 1H); MS (APCI) m/z 332 (M+H)+.

Example 213

(4aR*,9bR*)-8-methyl-5-[2-(6-methylpyridin-3-yl) ethyl]-2,3,4,4a,5,9b-hexahydro-1,4-ethanopyrido[3,2-b]indole The product of Example 212 (27 mg, 0.08 mmol) was processed as described in Example 206 except that the product was purified by reverse-phase HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (500 MHz, methanol-$d_4$) δ ppm 1.26-1.41 (m, 1H), 1.59-1.72 (m, 2H), 1.77-1.89 (m, 1H), 2.00-2.07 (m, 1H), 2.19 (s, 3H), 2.48 (s, 3H), 2.50-2.69 (m, 2H), 2.78-2.93 (m, 2H), 2.99-3.05 (m, 2H), 3.29-3.37 (m, 1H), 3.48 (ddd, J=14.6, 8.2, 6.4 Hz, 1H), 3.61 (dd, J=9.9, 3.8 Hz, 1H), 4.47 (d, J=10.1 Hz, 1H), 6.33 (d, J=8.2 Hz, 1H), 6.91 (d, J=8.2 Hz, 1H), 6.96 (s, 1H), 7.22 (d, J=7.9 Hz, 1H), 7.63 (dd, J=7.9, 2.4 Hz, 1H), 8.26 (d, J=2.1 Hz, 1H); MS (APCI) m/z 334 (M+H)+.

Example 214

8-methyl-5-[2-(2-methylphenyl)ethyl]-2,3,4,5-tetrahydro-1,4-ethanopyrido[3,2-b]indole The coupling of 8-methyl-2,3,4,5-tetrahydro-1,4-ethanopyrido[3,2-b]indole (80 mg, 0.38 mmol; Example 211) and 2-methylstyrene (85 mg, 0.72 mmol; Aldrich) was performed according to the procedure described in Example 106A to provide the title compound: $^1$H NMR (500 MHz, methanol-$d_4$) δ ppm 0.87-1.03 (m, 2H), 1.60-1.76 (m, 2H), 1.97 (s, 3H), 2.38-2.46 (m, 2H), 2.41 (s, 3H), 3.01 (quintet, J=2.9 Hz, 1H), 3.06-3.16 (m, 4H), 4.14-4.55 (m, 2H), 6.77 (d, J=7.3 Hz, 1H), 6.91-6.97 (m, 2H), 6.99-7.03 (m, 2H), 7.32 (d, J=8.2 Hz, 1H), 7.35 (s, 1H); MS (APCI) m/z 331 (M+H)+.

Example 215

5-[(4-chlorophenyl)sulfonyl]-8-methyl-2,3,4,5-tetrahydro-1,4-ethanopyrido[3,2-b]indole The coupling of 8-methyl-2,3,4,5-tetrahydro-1,4-ethanopyrido[3,2-b]indole (20 mg, 0.09 mmol; Example 211) and 4-chlorobenzenesulfonyl chloride (30 mg, 0.14 mmol; Aldrich) was performed according to the procedure described in Example 69, except that the product was purified by reverse-phase HPLC [Waters XBridge™ RP18 column, 5 μm, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-$d_4$) δ ppm 1.42-1.60 (m, 2H), 1.92-2.13 (m, 2H), 2.40 (s, 3H), 2.45-2.61 (m, 2H), 3.13-3.27 (m, 2H), 4.08 (quintet, J=2.9 Hz, 1H), 7.14 (dd, J=8.6, 1.5 Hz, 1H), 7.35 (s, 1H), 7.46-7.55 (m, 2H), 7.76-7.87 (m, 2H), 8.01 (d, J=8.5 Hz, 1H); MS (ESI) m/z 387 (M+H)+.

Example 216

6-isoquinolin-7-yl-9-methyl-3,4,5,6-tetrahydro-1H-2,5-ethanoazepino[4,3-b]indole The reaction of 9-methyl-3,4,5,6-tetrahydro-1H-2,5-ethanoazepino[4,3-b]indole (226 mg, 1.0 mmol; Example 2B) and 7-bromoisoquinoline (312 mg, 1.5 mmol; Frontier) was performed as described in Example 68 to afford the title compound: $^1$H NMR (300 MHz, methanol-$d_4$) δ ppm 1.94-2.20 (m, 4H) 2.42 (s, 3H) 2.91-2.98 (m, 1H) 3.08-3.29 (m, 4H) 4.32 (s, 2H) 6.90-6.96 (m, 1H) 6.98-7.04 (m, 1H) 7.22 (s, 1H) 7.73 (dd, J=8, 2 Hz, 1H) 7.94 (d, J=6 Hz, 1H) 8.09 (d, J=2 Hz, 1H) 8.15 (d, J=9 Hz, 1H) 8.53 (d, J=6 Hz, 1H) 9.33 (s, 1H); MS (DCI/NH$_3$) m/z 354 (M+H)+.

Example 217

9-methyl-6-quinolin-6-yl-3,4,5,6-tetrahydro-1H-2,5-ethanoazepino[4,3-b]indole

The reaction of 9-methyl-3,4,5,6-tetrahydro-1H-2,5-ethanoazepino[4,3-b]indole (136 mg, 0.6 mmol; Example 2B) and 6-bromoquinoline (187 mg, 0.9 mmol; TCI-US) was performed as described in Example 68 to afford the title compound: $^1$H NMR (300 MHz, methanol-$d_4$) δ ppm 1.95-2.20 (m, 4H) 2.42 (s, 3H) 2.92-2.99 (m, 1H) 3.08-3.28 (m, 4H) 4.32 (s, 2H) 6.90-6.96 (m, 1H) 6.98-7.04 (m, 1H) 7.22 (s, 1H) 7.63 (dd, J=8, 4 Hz, 1H) 7.72 (dd, J=9, 2 Hz, 1H) 7.93 (d, J=2 Hz, 1H) 8.21 (d, J=9 Hz, 1H) 8.46 (d, J=7 Hz, 1H) 8.94 (dd, J=4, 2 Hz, 1H); MS (DCI/NH$_3$) m/z 354 (M+H)+.

Example 218

9-methyl-6-(2-methylquinolin-6-yl)-3,4,5,6-tetrahydro-1H-2,5-ethanoazepino[4,3-b]indole The reaction of 9-methyl-3,4,5,6-tetrahydro-1H-2,5-ethanoazepino[4,3-b]indole (136 mg, 0.6 mmol; Example 2B) and 6-bromo-2-methylquinoline (200 mg, 0.9 mmol; Oakwood) was performed as described in Example 68 to afford the title compound: $^1$H NMR (300 MHz, methanol-$d_4$) δ ppm 1.94-2.19 (m, 4H) 2.41 (s, 3H) 2.77 (s, 3H) 2.91-2.98 (m, 1H) 3.08-3.29 (m, 4H) 4.32 (s, 2H) 6.89-6.94 (m, 1H) 6.96-7.01 (m, 1H) 7.21 (s, 1H) 7.52 (d, J=8 Hz, 1H) 7.66 (dd, J=9, 2 Hz, 1H) 7.87 (d, J=2 Hz, 1H) 8.12 (d, J=9 Hz, 1H) 8.32 (d, J=9 Hz, 1H); MS (DCI/NH$_3$) m/z 368 (M+H)$^+$.

Example 219

9-methyl-6-quinazolin-6-yl-3,4,5,6-tetrahydro-1H-2,5-ethanoazepino[4,3-b]indole

The reaction of 9-methyl-3,4,5,6-tetrahydro-1H-2,5-ethanoazepino[4,3-b]indole (136 mg, 0.6 mmol; Example 2B) and 6-bromoquinazoline (188 mg, 0.9 mmol; Parkway Scientific) was performed as described in Example 68 to afford the title compound: $^1$H NMR (300 MHz, methanol-$d_4$) δ ppm 1.94-2.22 (m, 4H) 2.42 (s, 3H) 2.91-3.01 (m, 1H) 3.06-3.32 (m, 4H) 4.33 (s, 2H) 6.92-6.99 (m, 1H) 7.02-7.09 (m, 1H) 7.23 (s, 1H) 7.99 (dd, J=9, 2 Hz, 1H) 8.12 (d, J=2 Hz, 1H) 8.22 (d, J=9 Hz, 1H) 9.33 (s, 1H) 9.63 (s, 1H); MS (DCI/NH$_3$) m/z 355 (M+H)$^+$.

Example 220

6-(9-methyl-1,3,4,5-tetrahydro-6H-2,5-ethanoazepino[4,3-b]indol-6-yl)quinazolin-4-ol The reaction of 9-methyl-3,4,5,6-tetrahydro-1H-2,5-ethanoazepino[4,3-b]indole (136 mg, 0.6 mmol; Example 2B) and 6-bromo-4-methoxyquinazoline (215 mg, 0.9 mmol; ChemBridge) was performed as described in Example 68 to afford the title compound as the major product: $^1$H NMR (300 MHz, methanol-$d_4$) δ ppm 1.95-2.21 (m, 4H) 2.42 (s, 3H) 2.90-2.97 (m, 1H) 3.09-3.41 (m, 4H) 4.33 (s, 2H) 6.91-6.96 (m, 1H) 6.98-7.03 (m, 1H) 7.21 (s, 1H) 7.74-7.81 (m, 1H) 7.86-7.93 (m, 1H) 8.11 (d, J=3 Hz, 1H) 8.17 (s, 1H); MS (DCI/NH$_3$) m/z 371 (M+H)$^+$.

Example 221

6-(4-methoxyquinazolin-6-yl)-9-methyl-3,4,5,6-tetrahydro-1H-2,5-ethanoazepino[4,3-b]indole The reaction of 9-methyl-3,4,5,6-tetrahydro-1H-2,5-ethanoazepino[4,3-b]indole (136 mg, 0.6 mmol; Example 2B) and 6-bromo-4-methoxyquinazoline (215 mg, 0.9 mmol; ChemBridge) was performed as described in Example 68 to afford the title compound as the minor product: $^1$H NMR (300 MHz, methanol-$d_4$) δ ppm 1.95-2.20 (m, 4H) 2.42 (s, 3H) 2.89-2.96 (m, 1H) 3.09-3.30 (m, 4H) 4.23 (s, 3H) 4.33 (s, 2H) 6.91-7.04 (m, 2H) 7.22 (s, 1H) 7.87 (dd, J=9, 2 Hz, 1H) 8.06-8.13 (m, 2H) 8.83 (s, 1H); MS (DCI/NH$_3$) m/z 385 (M+H)$^+$.

Example 222

9-methyl-6-quinolin-2-yl-3,4,5,6-tetrahydro-1H-2,5-ethanoazepino[4,3-b]indole

The reaction of 9-methyl-3,4,5,6-tetrahydro-1H-2,5-ethanoazepino[4,3-b]indole (226 mg, 1.0 mmol; Example 2B) and 7-bromoquinoline (312 mg, 1.5 mmol; Ark Pharm) was performed as described in Example 68 to afford the title compound: $^1$H NMR (300 MHz, methanol-$d_4$) δ ppm 1.97-2.11 (m, 2H) 2.18-2.30 (m, 2H) 2.43 (s, 3H) 3.10-3.29 (m, 5H) 4.32 (s, 2H) 6.96-7.01 (m, 1H) 7.22 (s, 1H) 7.35 (d, J=8 Hz, 1H) 7.57 (d, J=8 Hz, 1H) 7.62-7.69 (m, 1H) 7.82 (ddd, J=8, 7, 1 Hz, 1H) 7.97-8.05 (m, 2H) 8.52 (d, J=8 Hz, 1H); MS (DCI/NH$_3$) m/z 354 (M+H)$^+$.

Example 223

9-fluoro-6-isoquinolin-7-yl-3,4,5,6-tetrahydro-1H-2,5-ethanoazepino[4,3-b]indole The reaction of 9-fluoro-3,4,5,6-tetrahydro-1H-2,5-ethanoazepino[4,3-b]indole (78 mg, 0.34 mmol; Example 161) and 7-bromoisoquinoline (106 mg, 0.51 mmol; Frontier) was performed as described in Example 68 to afford the title compound: $^1$H NMR (300 MHz, methanol-$d_4$) δ ppm 1.94-2.22 (m, 4H) 2.88-2.96 (m, 1H) 3.08-3.29 (m, 4H) 4.31 (s, 2H) 6.85 (td, J=9, 2 Hz, 1H) 7.06 (dd, J=9, 4 Hz, 1H) 7.12 (dd, J=10, 2 Hz, 1H) 7.74 (dd, J=9, 2 Hz, 1H) 7.96 (d, J=6 Hz, 1H) 8.13 (d, J=2 Hz, 1H) 8.17 (d, J=8 Hz, 1H) 8.55 (d, J=6 Hz, 1H) 9.35 (s, 1H); MS (DCI/NH$_3$) m/z 358 (M+H)$^+$.

Example 224

9-fluoro-6-quinolin-2-yl-3,4,5,6-tetrahydro-1H-2,5-ethanoazepino[4,3-b]indole

The reaction of 9-fluoro-3,4,5,6-tetrahydro-1H-2,5-ethanoazepino[4,3-b]indole (230 mg, 1.0 mmol; Example 161) and 2-bromoquinoline (312 mg, 1.5 mmol; Alfa Aesar) was performed as described in Example 68 to afford the title compound: $^1$H NMR (300 MHz, methanol-$d_4$) δ ppm 1.98-2.11 (m, 2H) 2.17-2.31 (m, 2H) 3.09-3.28 (m, 5H) 4.31 (s, 2H) 6.90 (td, J=9, 3 Hz, 1H) 7.13 (dd, J=9, 2 Hz, 1H) 7.42 (dd, J=9, 4 Hz, 1H) 7.57 (d, J=8 Hz, 1H) 7.67 (t, J=8 Hz, 1H) 7.79-7.87 (m, 1H) 7.98-8.08 (m, 2H) 8.55 (d, J=8 Hz, 1H); MS (DCI/NH$_3$) m/z 358 (M+H)$^+$.

Example 225

9-fluoro-6-[6-(1H-pyrazol-1-yl)pyridin-2-yl]-3,4,5,6-tetrahydro-1H-2,5-ethanoazepino[4,3-b]indole The reaction of 9-fluoro-3,4,5,6-tetrahydro-1H-2,5-ethanoazepino[4,3-b]indole (230 mg, 1.0 mmol; Example 161) and 2-bromo-6-(1H-pyrazol-1-yl)pyridine (336 mg, 1.5 mmol; Maybridge) was performed as described in Example 68 to afford the title compound: $^1$H NMR (300 MHz, methanol-$d_4$) δ ppm 1.99-2.14 (m, 2H) 2.15-2.30 (m, 2H) 3.09-3.29 (m, 5H) 4.29 (s, 2H) 6.52-6.57 (m, 1H) 6.90 (td, J=9, 3 Hz, 1H) 7.11 (dd, J=9, 3 Hz, 1H) 7.37 (d, J=8 Hz, 1H) 7.43 (dd, J=9, 4 Hz, 1H) 7.80 (s, 1H) 7.97 (d, J=8 Hz, 1H) 8.16 (t, J=8 Hz, 1H) 8.50 (d, J=3 Hz, 1H); MS (DCI/NH$_3$) m/z 374 (M+H)$^+$.

Example 226

9-fluoro-6-quinolin-7-yl-3,4,5,6-tetrahydro-1H-2,5-ethanoazepino[4,3-b]indole

The reaction of 9-fluoro-3,4,5,6-tetrahydro-1H-2,5-ethanoazepino[4,3-b]indole (230 mg, 1.0 mmol; Example 161) and 7-bromoquinoline (312 mg, 1.5 mmol; Ark Pharm) was performed as described in Example 68 to afford the title compound: $^1$H NMR (300 MHz, methanol-$d_4$) δ ppm 1.95-2.22 (m, 4H) 2.96-3.03 (m, 1H) 3.09-3.29 (m, 4H) 4.32 (s, 2H) 6.86 (td, J=9, 2 Hz, 1H) 7.07-7.17 (m, 2H) 7.58-7.67 (m, 2H) 7.97 (d, J=2 Hz, 1H) 8.18 (d, J=9 Hz, 1H) 8.50 (d, J=8 Hz, 1H) 8.95 (dd, J=4, 2 Hz, 1H); MS (DCI/NH$_3$) m/z 358 (M+H)$^+$.

Example 227

9-fluoro-6-quinazolin-6-yl-3,4,5,6-tetrahydro-1H-2,5-ethanoazepino[4,3-b]indole

The reaction of 9-fluoro-3,4,5,6-tetrahydro-1H-2,5-ethanoazepino[4,3-b]indole (230 mg, 1.0 mmol; Example 161) and 7-bromoquinoline (314 mg, 1.5 mmol; Parkway Scientific) was performed as described in Example 68 to afford the title compound: $^1$H NMR (300 MHz, methanol-$d_4$) δ ppm 1.95-2.22 (m, 4H) 2.91-2.98 (m, 1H) 3.09-3.29 (m, 4H) 4.31 (s, 2H) 6.87 (td, J=9, 2 Hz, 1H) 7.07-7.17 (m, 2H) 7.99 (dd, J=9, 2 Hz, 1H) 8.16 (d, J=2 Hz, 1H) 8.24 (d, J=9 Hz, 1H) 9.34 (s, 1H) 9.64 (s, 1H); MS (DCI/NH$_3$) m/z 359 (M+H)$^+$.

Example 228

9-fluoro-6-quinolin-6-yl-3,4,5,6-tetrahydro-1H-2,5-ethanoazepino[4,3-b]indole

The reaction of 9-fluoro-3,4,5,6-tetrahydro-1H-2,5-ethanoazepino[4,3-b]indole (230 mg, 1.0 mmol; Example 161) and 6-bromoquinoline (312 mg, 1.5 mmol; TCI-US) was performed as described in Example 68 to afford the title compound: $^1$H NMR (300 MHz, methanol-$d_4$) δ ppm 1.94-2.23 (m, 4H) 2.90-2.97 (m, 1H) 3.07-3.30 (m, 4H) 4.31 (s, 2H) 6.85 (td, J=9, 3 Hz, 1H) 7.06 (dd, J=9, 4 Hz, 1H) 7.12 (dd, J=10, 2 Hz, 1H) 7.64 (dd, J=8, 4 Hz, 1H) 7.73 (dd, J=9, 2 Hz, 1H) 7.97 (d, J=2 Hz, 1H) 8.23 (d, J=9 Hz, 1H) 8.47 (d, J=8 Hz, 1H) 8.95 (dd, J=4, 2 Hz, 1H); MS (DCI/NH$_3$) m/z 358 (M+H)$^+$.

Example 229

9-fluoro-6-(2-methylquinolin-6-yl)-3,4,5,6-tetrahydro-1H-2,5-ethanoazepino[4,3-b]indole

The reaction of 9-fluoro-3,4,5,6-tetrahydro-1H-2,5-ethanoazepino[4,3-b]indole (230 mg, 1.0 mmol; Example 161) and 6-bromo-2-methylquinoline (333 mg, 1.5 mmol; Oakwood) was performed as described in Example 68 to afford the title compound: $^1$H NMR (300 MHz, methanol-$d_4$) δ ppm 1.94-2.20 (m, 4H) 2.78 (s, 3H) 2.89-2.96 (m, 1H) 3.08-3.30 (m, 4H) 4.30 (s, 2H) 6.84 (td, J=9, 2 Hz, 1H) 7.04 (dd, J=9, 4 Hz, 1H) 7.11 (dd, J=9, 3 Hz, 1H) 7.54 (d, J=9 Hz, 1H) 7.67 (dd, J=9, 2 Hz, 1H) 7.90 (d, J=2 Hz, 1H) 8.14 (d, J=9 Hz, 1H) 8.33 (d, J=8 Hz, 1H); MS (DCI/NH$_3$) m/z 372 (M+H)$^+$.

Example 230

6-(4-methoxyquinazolin-6-yl)-3,4,5,6-tetrahydro-1H-2,5-ethanoazepino[4,3-b]indole

The reaction of 3,4,5,6-tetrahydro-1H-2,5-ethanoazepino[4,3-b]indole (127 mg, 0.6 mmol; Example 187A) and 6-bromo-4-methoxyquinazoline (215 mg, 0.9 mmol; ChemBridge) was performed as described in Example 68 to afford the title compound as the minor product: $^1$H NMR (300 MHz, methanol-$d_4$) δ ppm 1.95-2.21 (m, 4H) 2.90-2.97 (m, 1H) 3.09-3.30 (m, 4H) 4.23 (s, 3H) 4.35 (s, 2H) 7.08-7.13 (m, 3H) 7.41-7.47 (m, 1H) 7.89 (dd, J=9, 2 Hz, 1H) 8.10 (d, J=9 Hz, 1H) 8.14 (d, J=2 Hz, 1H) 8.85 (s, 1H); MS (DCI/NH$_3$) m/z 371 (M+H)$^+$.

Example 231

6-(1,3,4,5-tetrahydro-6H-2,5-ethanoazepino[4,3-b]indol-6-yl)quinazolin-4-ol

The reaction of 3,4,5,6-tetrahydro-1H-2,5-ethanoazepino[4,3-b]indole (127 mg, 0.6 mmol; Example 187A) and 6-bromo-4-methoxyquinazoline (215 mg, 0.9 mmol; ChemBridge) was performed as described in Example 68 to afford the title compound as the major product: $^1$H NMR (300 MHz, methanol-$d_4$) δ ppm 1.96-2.20 (m, 4H) 2.90-2.97 (m, 1H) 3.08-3.29 (m, 4H) 4.36 (s, 2H) 7.07-7.13 (m, 3H) 7.39-7.46 (m, 1H) 7.75-7.82 (m, 1H) 7.87-7.94 (m, 1H) 8.13 (d, J=2 Hz, 1H) 8.18 (s, 1H); MS (DCI/NH$_3$) m/z 357 (M+H)$^+$.

Example 232

6-(2-methylquinolin-6-yl)-3,4,5,6-tetrahydro-1H-2,5-ethanoazepino[4,3-b]indole

The reaction of 3,4,5,6-tetrahydro-1H-2,5-ethanoazepino[4,3-b]indole (212 mg, 1.0 mmol; Example 187A) and 6-bromo-2-methylquinoline (333 mg, 1.5 mmol; Oakwood) was performed as described in Example 68 to afford the title compound: $^1$H NMR (300 MHz, methanol-$d_4$) δ ppm 1.94-2.20 (m, 4H) 2.78 (s, 3H) 2.91-2.98 (m, 1H) 3.09-3.29 (m, 4H) 4.35 (s, 2H) 7.06-7.11 (m, 3H) 7.39-7.45 (m, 1H) 7.53 (d, J=8 Hz, 1H) 7.67 (dd, J=9, 2 Hz, 1H) 7.89 (d, J=2 Hz, 1H) 8.13 (d, J=9 Hz, 1H) 8.33 (d, J=8 Hz, 1H); MS (DCI/NH$_3$) m/z 354 (M+H)$^+$.

Example 233

6-quinolin-6-yl-3,4,5,6-tetrahydro-1H-2,5-ethanoazepino[4,3-b]indole

The reaction of 3,4,5,6-tetrahydro-1H-2,5-ethanoazepino[4,3-b]indole (212 mg, 1.0 mmol; Example 187A) and 6-bromoquinoline (312 mg, 1.5 mmol; TCI-US) was performed as described in Example 68 to afford the title compound: $^1$H NMR (300 MHz, methanol-$d_4$) δ ppm 1.95-2.22 (m, 4H) 2.94-2.99 (m, 1H) 3.09-3.28 (m, 4H) 4.36 (s, 2H) 7.06-7.13 (m, 3H) 7.39-7.47 (m, 1H) 7.64 (dd, J=8, 4 Hz, 1H) 7.74 (dd, J=9, 2 Hz, 1H) 7.96 (d, J=2 Hz, 1H) 8.23 (d, J=9 Hz, 1H) 8.47 (d, J=8 Hz, 1H) 8.95 (dd, J=4, 2 Hz, 1H); MS (DCI/NH$_3$) m/z 340 (M+H)$^+$.

Example 234

6-quinolin-7-yl-3,4,5,6-tetrahydro-1H-2,5-ethano-azepino[4,3-b]indole

The reaction of 3,4,5,6-tetrahydro-1H-2,5-ethanoazepino[4,3-b]indole (212 mg, 1.0 mmol; Example 187A) and 7-bromoquinoline (312 mg, 1.5 mmol; Ark Pharm) was performed as described in Example 68 to afford the title compound: $^1$H NMR (300 MHz, methanol-$d_4$) δ ppm 1.96-2.23 (m, 4H) 2.99-3.05 (m, 1H) 3.10-3.30 (m, 4H) 4.37 (s, 2H) 7.07-7.21 (m, 3H) 7.40-7.49 (m, 1H) 7.59-7.69 (m, 2H) 7.97 (d, J=2 Hz, 1H) 8.17 (d, J=9 Hz, 1H) 8.50 (d, J=7 Hz, 1H) 8.95 (dd, J=4, 2 Hz, 1H); MS (DCI/NH$_3$) m/z 340 (M+H)$^+$.

Example 235

6-quinolin-2-yl-3,4,5,6-tetrahydro-1H-2,5-ethano-azepino[4,3-b]indole

The reaction of 3,4,5,6-tetrahydro-1H-2,5-ethanoazepino[4,3-b]indole (212 mg, 1.0 mmol; Example 187A) and 2-bromoquinoline (312 mg, 1.5 mmol; Alfa Aesar) was performed as described in Example 68 to afford the title compound: $^1$H NMR (300 MHz, methanol-$d_4$) δ ppm 1.97-2.12 (m, 2H) 2.19-2.32 (m, 2H) 3.11-3.29 (m, 5H) 4.36 (s, 2H) 7.11-7.19 (m, 2H) 7.40-7.48 (m, 2H) 7.60 (d, J=9 Hz, 1H) 7.66 (t, J=8 Hz, 1H) 7.79-7.87 (m, 1H) 8.03 (t, J=7 Hz, 2H) 8.55 (d, J=8 Hz, 1H); MS (DCI/NH$_3$) m/z 340 (M+H)$^+$.

Example 236

6-[6-(1H-pyrazol-1-yl)pyridin-2-yl]-3,4,5,6-tetrahydro-1H-2,5-ethanoazepino[4,3-b]indole The reaction of 3,4,5,6-tetrahydro-1H-2,5-ethanoazepino[4,3-b]indole (212 mg, 1.0 mmol; Example 187A) and 2-bromo-6-(1H-pyrazol-1-yl)pyridine (336 mg, 1.5 mmol; Maybridge) was performed as described in Example 68 to afford the title compound: $^1$H NMR (300 MHz, methanol-$d_4$) δ ppm 1.99-2.12 (m, 2H) 2.17-2.30 (m, 2H) 3.09-3.30 (m, 5H) 4.33 (s, 2H) 6.52-6.57 (m, 1H) 7.09-7.19 (m, 2H) 7.36-7.50 (m, 3H) 7.79 (s, 1H) 7.96 (d, J=7 Hz, 1H) 8.12-8.22 (m, 1H) 8.50 (d, J=2 Hz, 1H); MS (DCI/NH$_3$) m/z 356 (M+H)$^+$.

Example 237

6-[4-(4-methylpiperazin-1-yl)phenyl]-3,4,5,6-tetrahydro-1H-2,5-ethanoazepino[4,3-b]indole The reaction of 3,4,5,6-tetrahydro-1H-2,5-ethanoazepino[4,3-b]indole (212 mg, 1.0 mmol; Example 187A) and 1-(4-bromophenyl)-4-methylpiperazine (255 mg, 1.0 mmol; Accela Chembio) was performed as described in Example 68 to afford the title compound: $^1$H NMR (300 MHz, methanol-$d_4$) δ ppm 1.92-2.11 (m, 4H) 2.37 (s, 3H) 2.61-2.71 (m, 4H) 2.86-2.92 (m, 1H) 3.03-3.28 (m, 8H) 4.31 (s, 2H) 6.95-7.06 (m, 3H) 7.10-7.21 (m, 4H) 7.32-7.40 (m, 1H); MS (DCI/NH$_3$) m/z 387 (M+H)$^+$.

Example 238

2-[2-(9-fluoro-1,3,4,5-tetrahydro-6H-2,5-ethanoazepino[4,3-b]indol-6-yl)ethyl]pyridazin-3(2H)-one

Example 238A

[6-(2-{[tert-butyl(dimethyl)silyl]oxy}ethyl)-9-fluoro-3,4,5,6-tetrahydro-1H-2,5-ethanoazepino[4,3-b]indole-κN$^2$](trihydrido)boron To a stirred solution of KOH (0.030 g, 0.541 mmol) in dimethyl sulfoxide (2 mL) at 25° C. was added dropwise a solution of 9-fluoro-3,4,5,6-tetrahydro-1H-2,5-ethanoazepino[4,3-b]indole N-borane complex (120 mg, 0.492 mmol, Example 164A) in 1 mL dimethyl sulfoxide. The mixture was stirred for 30 minutes, cooled to 0° C., and then (2-bromoethoxy)(tert-butyl)dimethylsilane (0.105 mL, 0.492 mmol, Aldrich) was added dropwise. A gradual warmup to room temperature was allowed with continued stirring for 6 hours. The reaction was quenched in water and extracted with ethyl acetate (3×5 mL). The combined organic phases were dried over sodium sulfate and concentrated in vacuo. The resulting residue was purified by flash chromatography over silica gel (40 g) eluting with 10-50% ethyl acetate-hexane, to give the title compound: MS (DCI/NH$_3$) m/z 389 (M+H-BH$_3$)$^+$.

Example 238B

2-(9-fluoro-1,3,4,5-tetrahydro-6H-2,5-ethanoazepino[4,3-b]indol-6-yl)ethanol The product of Experiment 238A (0.14 g, 0.348 mmol) was treated with HCl in acetone/water (3 N, acetone:water=3:1, 10 mL), and the mixture was stirred at room temperature for 2 hours. The reaction mixture was concentrated in vacuo to give the title compound as the hydrochloride salt: MS (DCI/NH$_3$) m/z 275 (M+H)$^+$.

Experiment 238C

6-(2-bromoethyl)-9-fluoro-3,4,5,6-tetrahydro-1H-2,5-ethanoazepino[4,3-b]indole Dibromotriphenylphosphorane (0.187 g, 0.444 mmol, Aldrich) was stirred in dichloromethane (2.5 mL) at 0° C. A solution of the product of Experiment 238B (0.12 g, 0.386 mmol) in dichloromethane (2 mL) was added, and the resulting mixture was stirred overnight at room temperature. After concentrating in vacuo, the crude product was purified by flash chromatography over silica gel (24 g), eluting with 50-100% ethyl acetate-hexane, then switching to 100-0% ethyl acetate: [10% methanol (+10% 14.8 M aqueous NH$_4$OH):dichloromethane] to yield the title compound: MS (DCI/NH$_3$) m/z 337, 339 (M+H)$^+$.

Experiment 238D

2-[2-(9-fluoro-1,3,4,5-tetrahydro-6H-2,5-ethanoazepino[4,3-b]indol-6-yl)ethyl]pyridazin-3(2H)-one The product of Experiment 238C (0.06 g, 0.178 mmol) and pyridazin-3(2H)-one (0.017 g, 0.178 mmol, Aldrich) were stirred in N,N-dimethylformamide (2 mL) at room temperature. K$_2$CO$_3$ (0.037 g, 0.267 mmol) was added and stirring was continued overnight. The reaction was poured into water and extracted with ethyl acetate (3×3 mL). The combined extracts were washed with brine, dried (MgSO$_4$), concentrated in vacuo, and the residue was purified by flash chromatography over silica gel (12 g), eluting with 0-5% methanol (+10% 14.8 M aqueous NH$_4$OH): dichloromethane to give the title compound: $^1$H NMR (300 MHz, CDCl$_3$) δ ppm 2.23-2.43 (m, 4H) 3.33-3.43 (m, 2H) 3.45-3.50 (m, 1H) 3.67-3.78 (m, 2H) 4.40-4.49 (m, 2H) 4.53 (t, J=6.4 Hz, 2H) 4.60 (s, 2H) 6.83 (d, J=9.5 Hz, 1H) 6.88-7.00 (m, 2H) 7.12 (dd, J=9.5, 3.7 Hz, 1H) 7.21 (dd, J=9.0, 4.1 Hz, 1H) 7.61-7.66 (m, 1H); MS (DCI/NH$_3$) m/z 353 (M+H)$^+$.

Example 239

1-[4-(1,3,4,5-tetrahydro-6H-2,5-ethanoazepino[4,3-b]indol-6-yl)phenyl]pyridin-2(1H)-one Example 239A 6-(4-iodophenyl)-3,4,5,6-tetrahydro-1H-2,5-ethanoazepino[4,3-b]indole 3,4,5,6-Tetrahydro-1H-2,5-ethanoazepino[4,3-b]indole (1.50 g, 7.07 mmol, Example 187A), 1,4-diiodobenzene (3.50 g, 10.6 mmol, Aldrich), copper (I) iodide (0.202 g, 0.150 mmol, Aldrich), and cesium acetate (2.71 g, 14.13 mmol, Aldrich) were combined in dimethyl sulfoxide (25 mL). The reaction vial was sealed and evacuated then back filled with dry N$_2$ (3×). The reaction mixture was heated to 90° C. overnight. The reaction mixture was cooled to room temperature, and then 10% 14.8 M aqueous NH$_4$OH in H$_2$O (40 mL) was added. The aqueous layer was extracted with ethyl acetate (2×25 mL). The combined organic layers were dried over MgSO$_4$, and then the solid was removed by filtration. Volatiles were removed in vacuo. The resulting material was purified by flash chromatography [40 g silica gel column, 5-100% gradient of 14.8 M aqueous NH$_4$OH-methanol-dichloromethane (2:20:78) in dichloromethane] to afford the title compound: $^1$H NMR (300 MHz, CDCl$_3$) δ ppm 1.93-2.25 (m, 4H) 3.02 (s, 1H) 3.16-3.37 (m, 2H) 3.38-3.62 (m, 2H) 4.53 (s, 2H) 7.06 (d, J=8.81 Hz, 2H) 7.09-7.22 (m, 3H) 7.38-7.48 (m, 1H) 7.88 (d, J=8.81 Hz, 2H); MS (ESI+) m/z 415 (M+H)$^+$.

Example 239B

1-[4-(1,3,4,5-tetrahydro-6H-2,5-ethanoazepino[4,3-b]indol-6-yl)phenyl]pyridin-2(1H)-one The product from Example 239A (440 mg, 1.06 mmol), pyridin-2(1H)-one (152 mg, 1.59 mmol, Aldrich), copper (67.5 mg, 1.06 mmol), copper(I) iodide (303 mg, 1.59 mmol, Aldrich), and K$_2$CO$_3$ (440 mg, 3.19 mmol) were combined in pyridine (15 mL). The vial was sealed then evacuated and flushed with dry N$_2$ (2×). N,N'-Dimethylethylenediamine (0.034 ml, 0.319 mmol, Aldrich) was added and the reaction mixture was heated to 117° C. for 72 hours. Volatiles were removed in vacuo. The residue was partitioned between CHCl$_3$ (25 mL) and 14.8 M NH$_4$OH (10 mL). The organic layer was dried over MgSO$_4$, and the solid was removed by filtration. The reaction mixture was concentrated in vacuo, and the residue was purified by reverse-phase HPLC [Waters XBridge™ C18 5 µm OBD column, 30×100 mm, flow rate 40 mL/minute, 20-95% gradient of acetonitrile in buffer (0.1 M aqueous ammonium bicarbonate, adjusted to pH 10 with ammonium hydroxide) over 20 minutes] to afford the title compound: $^1$H NMR (300 MHz, CDCl$_3$) δ ppm 1.82-2.15 (m, 4H) 2.96-3.08 (m, 1H) 3.08-3.26 (m, 2H) 3.23-3.42 (m, 2H) 4.38 (s, 2H) 6.25-6.37 (m, 1H) 6.71 (d, J=9.83 Hz, 1H) 7.10-7.18 (m, 2H) 7.18-7.24 (m, 1H) 7.40-7.51 (m, 5H) 7.60 (s, 2H); MS (ESI+) m/z 382 (M+H)$^+$.

Example 240

9-fluoro-6-{[6-(2-methylpyrrolidin-1-yl)pyridin-3-yl]methyl}-3,4,5,6-tetrahydro-1H-2,5-ethanoazepino[4,3-b]indole 2-Methylpyrrolidine (0.230 mL, 2.248 mmol; Aldrich) and sodium carbonate (238 mg, 2.248 mmol; Aldrich) were added to a solution of 6-[(6-chloropyridin-3-yl)methyl]-9-fluoro-3,4,5,6-tetrahydro-1H-2,5-ethanoazepino[4,3-b]indole (400 mg, 1.124 mmol; Example 164C) in dimethyl sulfoxide (3.0 mL). The reaction mixture was heated to 130° C. overnight. Volatiles were removed in vacuo. The resulting residue was dissolved in CH$_2$Cl$_2$ (25 mL) and then washed with H$_2$O (25 mL). The organic layer was dried over MgSO$_4$. Solid was removed by filtration and volatiles were removed under reduced pressure. The residue was purified by flash chromatography, SiO$_2$ Varian SF-25 12 g column, gradient (0 to 100% CH$_2$Cl$_2$/methanol/14.8 M aqueous NH$_4$OH 78:20:2 in CH$_2$Cl$_2$) over 20 minutes to give the title compound: $^1$H NMR (300 MHz, CHCl$_3$) δ ppm 1.16 (d, J=6.10 Hz, 3H) 1.86-2.25 (m, 8H) 3.19 (s, 4H) 3.48 (d, J=17.29 Hz, 3H) 3.97-4.15 (m, 1H) 4.47 (s, 2H) 5.16 (s, 2H) 6.25 (d, J=8.82 Hz, 1H) 6.81-7.10 (m, 3H) 7.17-7.35 (m, 1H) 7.88 (d, J=2.71 Hz, 1H); MS (ESI) m/z 405 (M+H)$^+$.

Example 241

9-fluoro-6-{[6-(piperidin-1-yl)pyridin-3-yl]methyl}-3,4,5,6-tetrahydro-1H-2,5-ethanoazepino[4,3-b]indole In a 2.5 mL microwave vial, a solution of 6-[(6-chloropyridin-3-yl)methyl]-9-fluoro-3,4,5,6-tetrahydro-1H-2,5-ethanoazepino[4,3-b]indole (20 mg, 1 equivalent, Example 164C) dissolved in N-methylpyrrolidine (0.25 mL) was added, followed by the addition of piperidine (0.6 mmol, 51 mg, 10.5 equivalents) dissolved in N-methylpyrrolidine (2 mL), and K$_2$CO$_3$ as a solid (3 equivalents). The vial was capped and heated at 220° C. for 30 minutes. The reaction was checked by LC/MS and concentrated to dryness. The residue was dissolved in 1:1 dimethyl sulfoxide/methanol and then purified by preparative HPLC on a Phenomenex Luna C8(2) 5 µm 100 Å AXIA column (30 mm×75 mm) to provide the title compound as the trifluoroacetic acid salt. A gradient of acetonitrile (A) and 0.1% trifluoroacetic acid in water (B) was used, at a flow rate of 50 mL/minute (0-0.5 minutes 10% A, 0.5-6.0 minutes linear gradient 10-100% A, 6.0-7.0 minutes 100% A, 7.0-8.0 minutes linear gradient 100-10% A). Samples were injected in 1.5 mL dimethyl sulfoxide:methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/auto sampler. The make-up pump for the mass spectrometer used 3:1 CH$_3$OH/H$_2$O with 0.1% formic acid at a flow rate of 1 mL/minute. Fraction collection was automatically triggered when the extracted ion chromatogram (EIC) for the target mass exceeded the threshold specified in the method.

The system was controlled using Agilent Chemstation (Rev B. 10.03), Agilent A2Prep, and Leap FractPal software, with custom Chemstation macros for data export. $^1$H NMR (400 MHz, pyridine-d$_5$) δ ppm 1.20-1.43 (m, 4H) 1.87-2.13 (m, 4H) 3.08-3.32 (m, 2H) 3.35-3.63 (m, 7H) 3.64-3.77 (m, 2H) 4.82 (s, 2H) 5.31 (s, 2H) 6.55-6.77 (m, 1H) 7.11-7.20 (m, 1H) 7.28 (t, J=7.78 Hz, 2H) 7.56 (d, J=8.85 Hz, 1H) 8.23 (s, 1H); MS (ESI) m/z 405 (M+H)$^+$.

Example 242

5-[(9-fluoro-1,3,4,5-tetrahydro-6H-2,5-ethanoazepino[4,3-b]indol-6-yl)methyl]-N-isopropyl-N-methylpyridin-2-amine In a 2.5 mL microwave vial, a solution of 6-[(6-chloropyridin-3-yl)methyl]-9-fluoro-3,4,5,6-tetrahydro-1H-2,5-ethanoazepino[4,3-b]indole (20 mg, 1 equivalent, Example 164C) dissolved in N-methylpyrrolidine (0.25 mL) was added, followed by the addition of N-methylpropan-2-amine (0.6 mmol, 44 mg, 10.5 equivalents) dissolved in N-methylpyrrolidine (2 mL), and K$_2$CO$_3$ as a solid (3 equivalents). The vial was capped and heated at 220° C. for 30 minutes. The reaction was checked by LC/MS and concentrated to dryness. The residue was dissolved in 1:1 dimethyl sulfoxide/methanol and then purified by preparative HPLC on a Phenomenex Luna C8(2) 5 μm 100 Å AXIA column (30 mm×75 mm) to provide the title compound as the trifluoroacetic acid salt. A gradient of acetonitrile (A) and 0.1% trifluoroacetic acid in water (B) was used, at a flow rate of 50 mL/minute (0-0.5 minutes 10% A, 0.5-6.0 minutes linear gradient 10-100% A, 6.0-7.0 minutes 100% A, 7.0-8.0 minutes linear gradient 100-10% A). Samples were injected in 1.5 mL dimethyl sulfoxide:methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 CH$_3$OH:H$_2$O with 0.1% formic acid at a flow rate of 1 mL/minute. Fraction collection was automatically triggered when the extracted ion chromatogram (EIC) for the target mass exceeded the threshold specified in the method. The system was controlled using Agilent Chemstation (Rev B. 10.03), Agilent A2Prep, and Leap FractPal software, with custom Chemstation macros for data export. $^1$H NMR (400 MHz, pyridine-d$_5$) δ ppm 1.04 (s, 6H) 1.84-2.18 (m, 4H) 2.50 (s, 1H) 2.72-2.85 (m, 3H) 3.18-3.49 (m, 3H) 3.70 (d, J=42.42 Hz, 2H) 4.82 (s, 2H) 5.31 (s, 2H) 6.55-6.77 (m, 1H) 7.11-7.20 (m, 1H) 7.28 (t, J=7.78 Hz, 2H) 7.56 (d, J=8.85 Hz, 1H) 8.23 (s, 1H); MS (ESI) m/z 393 (M+H)$^+$.

Example 243

N-(1,3-dioxolan-2-ylmethyl)-5-[(9-fluoro-1,3,4,5-tetrahydro-6H-2,5-ethanoazepino[4,3-b]indol-6-yl)methyl]-N-methylpyridin-2-amine In a 2.5 mL microwave vial, a solution of 6-[(6-chloropyridin-3-yl)methyl]-9-fluoro-3,4,5,6-tetrahydro-1H-2,5-ethanoazepino[4,3-b]indole (20 mg, 1 equivalent, Example 164C) dissolved in N-methylpyrrolidine (0.25 mL) was added, followed by the addition of 1-(1,3-dioxolan-2-yl)-N-methylmethanamine (0.6 mmol, 70 mg, 10.5 equivalents) dissolved in N-methylpyrrolidine (2 mL), and potassium K$_2$CO$_3$ as a solid (3 equivalents). The vial was capped and heated at 220° C. for 30 minutes. The reaction was checked by LC/MS and concentrated to dryness. The residue was dissolved in 1:1 dimethyl sulfoxide/methanol and then purified by preparative HPLC on a Phenomenex Luna C8(2) 5 μm 100 Å AXIA column (30 mm×75 mm) to provide the title compound as the trifluoroacetic acid salt. A gradient of acetonitrile (A) and 0.1% trifluoroacetic acid in water (B) was used, at a flow rate of 50 mL/minute (0-0.5 minutes 10% A, 0.5-6.0 minutes linear gradient 10-100% A, 6.0-7.0 minutes 100% A, 7.0-8.0 minutes linear gradient 100-10% A). Samples were injected in 1.5 mL dimethyl sulfoxide: methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/auto sampler. The make-up pump for the mass spectrometer used 3:1 methanol:H$_2$O with 0.1% formic acid at a flow rate of 1 mL/minute. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (400 MHz, pyridine-d$_5$) δ ppm 2.50 (s, 1H) 2.74-3.05 (m, 5H) 3.10 (s, 3H) 3.25-3.45 (m, 3H) 3.50-3.66 (m, 2H) 3.68-3.78 (m, 2H) 3.83-3.97 (m, 2H) 4.73 (s, 2H) 5.31 (s, 2H) 6.55-6.77 (m, 1H) 7.11-7.20 (m, 1H) 7.28 (t, J=7.78 Hz, 2H) 7.56 (d, J=8.85 Hz, 1H) 8.23 (s, 1H); MS (ESI) m/z 437 (M+H)$^+$.

Example 244

9-fluoro-6-{[6-(pyrrolidin-1-yl)pyridin-3-yl]methyl}-3,4,5,6-tetrahydro-1H-2,5-ethanoazepino[4,3-b]indole In a 2.5 mL microwave vial, a solution of 6-[(6-chloropyridin-3-yl)methyl]-9-fluoro-3,4,5,6-tetrahydro-1H-2,5-ethanoazepino[4,3-b]indole (20 mg, 1 equivalent, Example 164C) dissolved in N-methylpyrrolidine (0.25 mL) was added, followed by the addition of pyrrolidine (0.6 mmol, 42 mg, 10.5 equivalents) dissolved in N-methylpyrrolidine (2 mL), and K$_2$CO$_3$ as a solid (3 equivalents). The vial was capped and heated at 220° C. for 30 minutes. The reaction was checked by LC/MS and concentrated to dryness. The residue was dissolved in 1:1 dimethyl sulfoxide/methanol and then purified by preparative HPLC on a Phenomenex Luna C8(2) 5 μm 100 Å AXIA column (30 mm×75 mm) to provide the title compound as the trifluoroacetic acid salt. A gradient of acetonitrile (A) and 0.1% trifluoroacetic acid in water (B) was used, at a flow rate of 50 mL/minute (0-0.5 minutes 10% A, 0.5-6.0 minutes linear gradient 10-100% A, 6.0-7.0 minutes 100% A, 7.0-8.0 minutes linear gradient 100-10% A). Samples were injected in 1.5 mL dimethyl sulfoxide:methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/ auto sampler. The make-up pump for the mass spectrometer used 3:1 CH₃OH:H₂O with 0.1% formic acid at a flow rate of 1 mL/minute. Fraction collection was automatically triggered when the extracted ion chromatogram (EIC) for the target mass exceeded the threshold specified in the method. The system was controlled using Agilent Chemstation (Rev B. 10.03), Agilent A2Prep, and Leap FractPal software, with custom Chemstation macros for data export. $^1$H NMR (400 MHz, pyridine-$d_5$) δ ppm 1.43-1.54 (m, 2H) 1.53-1.64 (m, 2H) 1.90-2.01 (m, 2H) 2.01-2.15 (m, 2H) 3.29-3.51 (m, 7H) 3.63-3.76 (m, 2H) 4.73 (s, 2H) 5.31 (s, 2H) 6.55-6.77 (m, 1H) 7.11-7.20 (m, 1H) 7.28 (t, J=7.78 Hz, 2H) 7.56 (d, J=8.85 Hz, 1H) 8.23 (s, 1H); MS (ESI) m/z 391 (M+H)$^+$.

Example 245

5-[(9-fluoro-1,3,4,5-tetrahydro-6H-2,5-ethanoazepino[4,3-b]indol-6-yl)methyl]-N-(2-methoxyethyl)-N-methylpyridin-2-amine In a 2.5 mL microwave vial, a solution of 6-[(6-chloropyridin-3-yl)methyl]-9-fluoro-3,4,5,6-tetrahydro-1H-2,5-ethanoazepino[4,3-b]indole (20 mg, 1 equivalent, Example 164C) dissolved in N-methylpyrrolidine (0.25 mL) was added, followed by the addition of 2-methoxy-N-methylethanamine (0.6 mmol, 53 mg, 10.5 equivalents) dissolved in N-methylpyrrolidine (2 mL), and K₂CO₃ as a solid (3 equivalents). The vial was capped and heated at 220° C. for 30 minutes. The reaction was checked by LC/MS and concentrated to dryness. The residue was dissolved in 1:1 dimethyl sulfoxide/methanol and then purified by preparative HPLC on a Phenomenex Luna C8(2) 5 μm 100 Å AXIA column (30 mm×75 mm) to provide the title compound as the trifluoroacetic acid salt. A gradient of acetonitrile (A) and 0.1% trifluoroacetic acid in water (B) was used, at a flow rate of 50 mL/minute (0-0.5 minutes 10% A, 0.5-6.0 minutes linear gradient 10-100% A, 6.0-7.0 minutes 100% A, 7.0-8.0 minutes linear gradient 100-10% A). Samples were injected in 1.5 mL dimethyl sulfoxide:methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/auto sampler. The make-up pump for the mass spectrometer used 3:1 CH₃OH:H₂O with 0.1% formic acid at a flow rate of 1 mL/minute. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (400 MHz, pyridine-$d_5$) δ ppm 1.86-2.07 (m, 4H) 3.04 (s, 3H) 3.21 (s, 3H) 3.25-3.35 (m, 3H) 3.35-3.41 (m, 2H) 3.48-3.60 (m, 2H) 3.73-3.82 (m, 2H) 4.73 (s, 2H) 5.31 (s, 2H) 6.55-6.77 (m, 1H) 7.11-7.20 (m, 1H) 7.28 (t, J=7.78 Hz, 2H) 7.56 (d, J=8.85 Hz, 1H) 8.23 (s, 1H); MS (ESI) m/z 409 (M+H)$^+$.

Example 246

9-fluoro-6-[(5-fluoropyridin-3-yl)methyl]-3,4,5,6-tetrahydro-1H-2,5-ethanoazepino[4,3-b]indole Example 246A 3-fluoro-5-{[1-(4-fluorophenyl)hydrazino]methyl}pyridine Triethylamine (2.57 mL, 18.45 mmol) was added to a suspension of (4-fluorophenyl)hydrazine hydrochloride (500 mg, 3.08 mmol; Aldrich) in ethanol (12 mL), 3-(bromomethy)-5-fluoropyridine (701 mg, 3.69 mmol; Biogene Organics) was added to this solution. The reaction mixture was heated to 70° C. for 3 hours. Volatiles were removed in vacuo. Ethanol (5 mL) was added to dissolve the solid. 4 M Aqueous HCl (2 mL) was added to make the solution acidic (pH 1). Volatiles were removed under in vacuo. The resulting residue was carried on to the next step without further purification.

Example 246B 9-fluoro-6-[(5-fluoropyridin-3-yl)methyl]-3,4,5,6-tetrahydro-1H-2,5-ethanoazepino[4,3-b]indole The product from Example 246A (290 mg, 1.2 mmol) and 1-azabicyclo[3.2.2]nonan-4-one (172 mg, 1.233 mmol, Example 2A) were dissolved in 7% sulfuric acid in dioxane (v/v, 10 mL). The reaction mixture was stirred at 80° C. for 24 hours. The reaction mixture was cooled to room temperature then made basic by the addition of 4 M NaOH$_{aq}$. The aqueous layer was extracted with CH₂Cl₂. The organic layer was dried over MgSO₄, and then solid was removed by filtration. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in 0.1% trifluoroacetic acid in water over 20 minutes] to afford the title compound as the trifluoroacetic acid salt: $^1$H NMR (300 MHz, methanol-$d_4$) δ ppm 2.00-2.18 (m, 2H) 2.24-2.41 (m, 2H) 3.40-3.58 (m, 3H) 3.57-3.71 (m, 2H) 4.76 (s, 2H) 5.60 (s, 2H) 6.89-7.08 (m, 1H) 7.14-7.32 (m, 2H) 7.44 (dd, J=8.98, 4.24 Hz, 1H) 8.07 (s, 1H) 8.38 (d, J=2.71 Hz, 1H); MS (DCI) m/z 340 (M+H)$^+$.

Example 247

9-fluoro-6-{[6-(1H-pyrazol-1-yl)pyridin-3-yl]methyl}-3,4,5,6-tetrahydro-1H-2,5-ethanoazepino[4,3-b]indole Example 247A 5-{[1-(4-fluorophenyl)hydrazino]methyl}-2-(1H-pyrazol-1-yl)pyridine Triethylamine (2.57 mL, 18.45 mmol) was added to a suspension of (4-fluorophenyl)hydrazine hydrochloride (500 mg, 3.08 mmol; Aldrich) in ethanol (12 mL), 5-(chloromethyl)-2-(1H-pyrazol-1-yl)pyridine (715 mg, 3.69 mmol; ABCHEM-Inc) was added to this solution. The reaction mixture was heated to 70° C. for 3 hours. Volatiles were removed in vacuo. Ethanol (5 mL) was added to dissolve the solid. 4 M Aqueous HCl (2 mL) was added to make the solution acidic (pH 1). Volatiles were removed in vacuo. The resulting residue was carried on to the next step without further purification.

Example 247B 9-fluoro-6-{[6-(1H-pyrazol-1-yl)pyridin-3-yl]methyl}-3,4,5,6-tetrahydro-1H-2,5-ethanoazepino[4,3-b]indole The product from Example 247A (290 mg, 1.02 mmol) and 1-azabicyclo[3.2.2]nonan-4-one (142 mg, 1.02 mmol, Example 2A) were dissolved in 7% sulfuric acid in dioxane (v/v, 10 mL). The reaction mixture was stirred at 80° C. for 24 hours. The reaction mixture was cooled to room temperature then made basic by the addition of 4 M NaOH$_{aq}$. The aqueous layer was extracted with CH$_2$Cl$_2$. The organic layer was dried over MgSO$_4$ and then the solid was removed by filtration. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in 0.1% trifluoroacetic acid in water over 20 minutes] to afford the title compound as the trifluoroacetic acid salt: $^1$H NMR (300 MHz, methanol-d$_4$) δ ppm 1.84-2.04 (m, 2H) 2.04-2.24 (m, 2H) 3.10-3.28 (m, 2H) 3.32-3.46 (m, 3H) 4.39 (s, 2H) 5.54 (s, 2H) 6.49 (s, 1H) 6.87-6.98 (m, 1H) 7.11 (dd, J=9.49, 2.37 Hz, 1H) 7.41 (dd, J=8.98, 4.24 Hz, 1H) 7.50 (dd, J=8.82, 2.37 Hz, 1H) 7.72 (s, 1H) 7.83 (d, J=8.48 Hz, 1H) 8.09 (s, 1H) 8.52 (d, J=3.05 Hz, 1H); MS (ESI) m/z 388 (M+H)$^+$.

Example 248

2-{5-[(9-fluoro-1,3,4,5-tetrahydro-6H-2,5-ethanoazepino[4,3-b]indol-6-yl)methyl]pyridin-2-yl}pyridazin-3(2H)-one A sealed tube was charged with 6-[(6-chloropyridin-3-yl)methyl]-9-fluoro-3,4,5,6-tetrahydro-1H-2,5-ethanoazepino[4,3-b]indole (150 mg, 0.422 mmol, Example 164C), pyridazin-3(2H)-one (81 mg, 0.843 mmol; Fluka), copper (26.8 mg, 0.422 mmol; Aldrich), copper (I) iodide (120 mg, 0.632 mmol; Aldrich), and pyridine (3.5 mL). The tube was flushed with nitrogen (2×). N,N'-Dimethyl-ethylenediamine (0.014 mL, 0.126 mmol) was added to the tube, and the mixture was heated to 117° C. for 72 hours. Volatiles were removed under reduced pressure. The residue was partitioned between CHCl$_3$ and 14.8M NH$_4$OH$_{aq}$. The organic layer was dried over MgSO$_4$ and the solid was removed by filtration. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in 0.1% trifluoroacetic acid in water over 20 minutes] to afford the title compound as the trifluoroacetic acid salt: $^1$H NMR (300 MHz, CDCl$_3$) δ ppm 2.03-2.19 (m, J=17.05, 17.05 Hz, 2H) 2.19-2.33 (m, 2H) 3.24-3.43 (m, 3H) 3.57-3.74 (m, 2H) 4.65 (s, 2H) 5.41 (s, 2H) 6.94-7.12 (m, 3H) 7.16-7.42 (m, 3H) 7.62-7.73 (m, 1H) 7.95 (s, 1H) 8.38 (s, 1H); MS (ESI) m/z 416 (M+H)$^+$.

Example 249

9-fluoro-6-[(2-phenylpyrimidin-5-yl)methyl]-3,4,5,6-tetrahydro-1H-2,5-ethanoazepino[4,3-b]indole To a solution of 9-fluoro-3,4,5,6-tetrahydro-1H-2,5-ethanoazepino[4,3-b]indole N-borane complex (200 mg, 0.82 mmol, Example 164A) in tetrahydrofuran (10 mL) was added sodium hydride (60% dispersion in mineral oil; 47 mg, 1.18 mmol; Aldrich) in one portion. After stirring for 30 minutes, 5-(chloromethyl)-2-phenylpyrimidine (168 mg, 0.819 mmol, Anichem Product) was added, and the solution was heated to 60° C. overnight. After the solvent was removed, the residue was treated with HCl in acetone/water (3 N, acetone:water=3:1, 10 mL) and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, CDCl$_3$) δ ppm 1.82-2.05 (m, 4H), 3.15 (m, 3H), 3.35 (m, 2H), 4.30 (s, 2H), 5.35 (s, 2H), 6.85 (td, J=9, 3 Hz, 1H), 7.13 (dd, J=9, 1 Hz, 1H), 7.23 (dd, J=9, 2 Hz, 1H), 7.42 (m, 4H), 8.40 (m, 3H); MS (ESI) m/z 399 (M+H)$^+$.

Example 250

6-(1H-benzimidazol-2-ylmethyl)-9-fluoro-3,4,5,6-tetrahydro-1H-2,5-ethanoazepino[4,3-b]indole To a solution of 9-fluoro-3,4,5,6-tetrahydro-1H-2,5-ethanoazepino[4,3-b]indole N-borane complex (200 mg, 0.82 mmol, Example 164A) in tetrahydrofuran (10 mL) was added sodium hydride (60% dispersion in mineral oil; 47 mg, 1.18 mmol; Aldrich) in one portion. After stirring for 30 minutes, 2-(chloromethyl)-1H-benzo[d]imidazole (136 mg, 0.819 mmol, Aldrich) was added, and the solution was heated to 60° C. overnight. After the solvent was removed, the residue was treated with HCl in acetone/water (3 N, acetone:water=3:1, 10 mL), and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, CDCl$_3$) δ ppm 1.85-2.10 (m, 4H), 3.10-3.35 (m, 5H), 4.35 (s, 2H), 5.25 (s, 2H), 6.85 (td, J=9, 3 Hz, 1H), 7.05 (m, 6H), 11.05 (s, 1H); MS (ESI) m/z 361 (M+H)$^+$.

Example 251

9-fluoro-6-(quinolin-8-ylmethyl)-3,4,5,6-tetrahydro-1H-2,5-ethanoazepino[4,3-b]indole To a solution of 9-fluoro-3,4,5,6-tetrahydro-1H-2,5-ethanoazepino[4,3-b]indole N-borane complex (200 mg, 0.82 mmol, Example 164A) in tetrahydrofuran (10 mL) was added sodium hydride (60% dispersion in mineral oil; 47 mg, 1.18 mmol; Aldrich) in one portion. After stirring for 30 minutes, 8-(bromomethyl)quinoline (182 mg, 0.819 mmol, Aldrich) was added and the solution was heated to 60° C. overnight. After the solvent was removed, the residue was treated with HCl in acetone/water (3 N, acetone:water=3:1, 10 mL) and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: ¹H NMR (300 MHz, CDCl₃) δ ppm 1.89-2.16 (m, 4H), 3.11-3.35 (m, 3H), 3.35-3.56 (m, 2H), 4.50 (s, 2H), 6.03 (s, 2H), 6.67-6.76 (m, 1H), 6.85-6.97 (m, 1H), 7.10 (dd, J=9.3, 2.2 Hz, 1H), 7.15-7.23 (m, 1H), 7.34 (t, J=6.6 Hz, 1H), 7.52 (dd, J=8.1, 4.1 Hz, 1H), 7.74 (d, J=9.5 Hz, 1H), 8.22 (dd, J=8.1, 1.7 Hz, 1H), 9.00 (dd, J=4.4, 1.7 Hz, 1H); MS (ESI) m/z 372 (M+H)⁺.

Example 252

9-fluoro-6-[(3-methyl-1,2-oxazol-5-yl)methyl]-3,4,5,6-tetrahydro-1H-2,5-ethanoazepino[4,3-b]indole To a solution of 9-fluoro-3,4,5,6-tetrahydro-1H-2,5-ethanoazepino[4,3-b]indole N-borane complex (160 mg, 0.66 mmol, Example 164A) in tetrahydrofuran (10 mL) was added sodium hydride (60% dispersion in mineral oil; 37 mg, 0.98 mmol; Aldrich) in one portion. After stirring for 30 minutes, 5-(bromomethyl)-3-methylisoxazole (121 mg, 0.66 mmol, Aldrich) was added, and the solution was heated to 60° C. overnight. After the solvent was removed, the residue was treated with HCl in acetone/water (3 N, acetone:water=3:1, 10 mL), and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: ¹H NMR (300 MHz, CDCl₃) δ ppm 1.92-2.13 (m, 4H), 2.21 (s, 3H), 2.99-3.23 (m, 3H), 3.24-3.43 (m, 2H), 4.29 (s, 2H), 5.30 (s, 2H), 5.71 (s, 1H), 6.87-6.98 (m, 1H), 7.04 (dd, J=9.3, 2.5 Hz, 1H), 7.17 (dd, J=8.8, 4.1 Hz, 1H); MS (DCI) m/z 326 (M+H)⁺.

Example 253

6-[(6-chloroimidazo[1,2-b]pyridazin-2-yl)methyl]-9-fluoro-3,4,5,6-tetrahydro-1H-2,5-ethanoazepino[4,3-b]indole To a solution of 9-fluoro-3,4,5,6-tetrahydro-1H-2,5-ethanoazepino[4,3-b]indole N-borane complex (200 mg, 0.82 mmol, Example 164A) in tetrahydrofuran (10 mL) was added sodium hydride (60% dispersion in mineral oil; 47 mg, 1.18 mmol; Aldrich) in one portion. After stirring for 30 minutes, 6-chloro-2-(chloromethyl)imidazo[1,2-b]pyridazine (166 mg, 0.819 mmol, Maybridge) was added, and the solution was heated to 60° C. overnight. After the solvent was removed, the residue was treated with HCl in acetone/water (3 N, acetone:water=3:1, 10 mL), and the mixture was stirred at room temperature for 2 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: ¹H NMR (300 MHz, CDCl₃) δ ppm 2.13-2.41 (m, 4H) 3.20-3.42 (m, 2H) 3.53-3.77 (m, 3H) 4.58 (s, 2H) 5.45 (s, 2H) 6.95-7.05 (m, 2H) 7.07 (d, J=9.52 Hz, 1H) 7.32 (dd, J=8.73, 3.97 Hz, 1H) 7.60 (s, 1H) 7.80 (d, J=9.52 Hz, 1H); MS (ESI) m/z 396 (M+H)⁺.

Example 254

9-fluoro-6-(imidazo[1,2-a]pyrimidin-2-ylmethyl)-3,4,5,6-tetrahydro-1H-2,5-ethanoazepino[4,3-b]indole Example 254A 2-{[1-(4-fluorophenyl)hydrazino]methyl}imidazo[1,2-a]pyrimidine Triethylamine (2.57 mL, 18.45 mmol) was added to a suspension of (4-fluorophenyl)hydrazine hydrochloride (500 mg, 3.08 mmol; Aldrich) in ethanol (12 mL), 2-(chloromethyl)imidazo[1,2-a]pyrimidine (715 mg, 3.69 mmol; Anichem) was added to this solution. The reaction mixture was heated to 70° C. for 3 hours. Volatiles were removed in vacuo. Ethanol (5 mL) was added to dissolve the solid. 4 M Aqueous HCl (2 mL) was added to make the solution acidic (pH 1). Volatiles were removed under reduced pressure. The resulting material was carried on to the next step without further purification.

Example 254B 9-fluoro-6-(imidazo[1,2-a]pyrimidin-2-ylmethyl)-3,4,5,6-tetrahydro-1H-2,5-ethanoazepino[4,3-b]indole The product from Example 254A (290 mg, 1.02 mmol) and 1-azabicyclo[3.2.2]nonan-4-one (157 mg, 1.13 mmol. Example 2A) were dissolved in 7% sulfuric acid in dioxane (v/v, 10 mL). The reaction mixture was stirred at 80° C. for 24 hours. The reaction mixture was cooled to room temperature and then made basic by the addition of 4 M aqueous NaOH. The aqueous layer was extracted with CH₂Cl₂. The organic layer was dried over MgSO₄, and then the solid was removed by filtration. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in 0.1% trifluoroacetic acid in water over 20 minutes] to afford the title compound as the trifluoroacetic acid salt: ¹H NMR (300 MHz, methanol-d₄) δ ppm 2.18-2.50 (m, 4H) 3.41-3.58 (m, 3H) 3.56-3.75 (m, 2H) 4.68 (s, Hz, 2H) 5.60 (s, 2H) 6.85-7.17 (m, 3H) 7.48-7.54 (m, 2H) 8.54 (d, J=6.44 Hz, 1H) 8.68-8.79 (m, 1H); MS (ESI) m/z 362 (M+H)⁺.

Example 255

2-{4-[(9-fluoro-1,3,4,5-tetrahydro-6H-2,5-ethanoazepino[4,3-b]indol-6-yl)methyl]phenyl}pyridazin-3(2H)-one A sealed tube was charged with the product from Example 167B (350 mg, 0.877 mmol), pyridazin-3(2H)-one (84 mg, 0.877 mmol; Fluka), copper (67 mg, 1.05 mmol; Aldrich), copper (I) iodide (250 mg, 1.32 mmol; Aldrich) and pyridine (5.0 mL). The tube was flushed with nitrogen (2×). N,N'-Dimethyl-ethylenediamine (0.028 mL, 0.263 mmol) was added to the tube, and the reaction mixture was heated to 117° C. for 72 hours. Volatiles were removed under reduced pressure. The residue was partitioned between CHCl₃ and 14.8 M aqueous NH₄OH. The organic layer was dried over MgSO₄, and the solid was removed by filtration. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, CD3Cl) δ ppm 1.85-2.10 (m, 4H) 2.95-3.21 (m, 3H) 3.21-3.42 (m, 2H) 4.33 (s, 2H) 5.35 (s, 2H) 6.84-6.94 (m, 1H) 7.00-7.09 (m, 4H) 7.13 (dd, J=8.92, 4.16 Hz, 1H) 7.22 (t, J=3.57 Hz, 1H) 7.54 (d, J=8.33 Hz, 2H) 7.87 (dd, J=3.57, 1.59 Hz, 1H); MS (DCI) m/z 415 (M+H)$^+$.

Example 256

6-{[6-(trifluoromethyl)pyridin-3-yl]methyl}-3,4,5,6-tetrahydro-1H-2,5-ethanoazepino[4,3-b]indole To a solution of 3,4,5,6-tetrahydro-1H-2,5-ethanoazepino[4,3-b]indole N-borane complex (300 mg, 1.32 mmol, Example 187B) in tetrahydrofuran (15 mL) was added sodium hydride (60% dispersion in mineral oil; 66 mg, 1.4 mmol; Aldrich) in one portion. After stirring for 30 minutes, 5-(bromomethyl)-2-(trifluoromethyl)pyridine (318 mg, 1.32 mmol, Anichem Product) was added, and the solution was heated to 60° C. overnight. After the solvent was removed, the residue was treated with HCl in acetone/water (3 N, acetone:water=3:1, 20 mL), and the mixture was stirred at room temperature for 3 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, CDCl$_3$) δ ppm 1.80-1.90 (m, 2H), 1.95-2.05 (m, 2H), 3.30-3.45 (m, 3H), 3.71 (m, 2H), 4.25 (s, 2H), 5.45 (s, 2H), 7.05 (dd, J=8, 2 Hz, 1H), 7.25 (m, 1H), 7.33 (t, J=8 Hz, 1H), 7.40 (dd, J=8, 2 Hz, 1H), 7.49 (dd, J=8, 2 Hz, 1H), 7.54 (d, J=8 Hz, 1H), 8.66 (s, 1H); MS (ESI) m/z 372 (M+H)$^+$.

Example 257

6-[(6-chloroimidazo[1,2-b]pyridazin-2-yl)methyl]-3,4,5,6-tetrahydro-1H-2,5-ethanoazepino[4,3-b]indole To a solution of 3,4,5,6-tetrahydro-1H-2,5-ethanoazepino[4,3-b]indole N-borane complex (200 mg, 0.819 mmol, Example 187B) in tetrahydrofuran (15 mL) was added sodium hydride (60% dispersion in mineral oil; 47 mg, 1.96 mmol; Aldrich) in one portion. After stirring for 30 minutes, 6-chloro-2-(chloromethyl)imidazo[1,2-b]pyridazine (166 mg, 0.819 mmol, Maybridge) was added, and the solution was heated to 60° C. overnight. After the solvent was removed, the residue was treated with HCl in acetone/water (3 N, acetone:water=3:1, 20 mL), and the mixture was stirred at room temperature for 3 hours. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, CDCl$_3$) δ ppm 1.84-2.12 (m, 4H) 2.95-3.16 (m, 2H) 3.16-3.38 (m, 3H) 4.32 (s, 2H) 5.47 (s, 2H) 7.03 (d, J=9.49 Hz, 1H) 7.06-7.20 (m, 2H) 7.28-7.34 (m, 1H) 7.36 (s, 1H) 7.42 (d, J=7.80 Hz, 1H) 7.82 (d, J=10.17 Hz, 1H); MS (ESI)$^+$ m/z 378 (M+H)$^+$.

Example 258

6'-(9-fluoro-1,3,4,5-tetrahydro-6H-2,5-ethanoazepino[4,3-b]indol-6-yl)-2H-1,2'-bipyridin-2-one A 10 mL microwave reaction tube was charged with 9-fluoro-3,4,5,6-tetrahydro-1H-2,5-ethanoazepino[4,3-b]indole (231 mg, 1.0 mmol; Example 161), 1-(6-bromopyridin-2-yl)pyridin-2(1H)-one (252 mg, 1.0 mmol; Combi-phos), bis(tri-t-butylphosphine)palladium(0) (25.6 mg, 0.05 mmol; Aldrich) and anhydrous dioxane (4 mL). The vessel was flushed with nitrogen and sodium tert-butoxide (240 mg, 2.5 mmol; Aldrich) was added. After purging the reaction mixture with nitrogen again, it was sealed and heated to 180° C. in a microwave reactor (Biotage Personal Chemistry™, Maximum 300 Watts) with stirring for 30 minutes. The mixture was cooled and quenched with water, and then extracted with ethyl acetate. The organic phase was concentrated and purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.97-2.24 (m, 4H) 3.05-3.28 (m, 5H) 4.26 (s, 2H) 6.46-6.53 (m, 1H) 6.66 (d, J=9.16 Hz, 1H) 6.90 (td, J=9.16, 2.37 Hz, 1H) 7.09 (dd, J=9.32, 2.20 Hz, 1H) 7.44 (dd, J=9.16, 4.07 Hz, 1H) 7.57 (d, J=7.12 Hz, 1H) 7.59-7.66 (m, 1H) 7.80 (d, J=7.12 Hz, 1H) 7.89 (dd, J=7.46, 1.70 Hz, 1H) 8.17-8.27 (m, 1H); MS (DCI/NH$_3$) m/z 401 (M+H)$^+$.

Example 259

6-(9-fluoro-1,3,4,5-tetrahydro-6H-2,5-ethanoazepino[4,3-b]indol-6-yl)quinazolin-4-ol The reaction of 9-fluoro-3,4,5,6-tetrahydro-1H-2,5-ethanoazepino[4,3-b]indole (231 mg, 1.0 mmol; Example 161) and 6-bromoquinazolin-4-ol (225 mg, 1.0 mmol; Ark Pharm) was performed as described in Example 258. The reaction was purified by reverse-phase HPLC [Waters XBridge™ C18 5 μm OBD column, 30×100 mm, flow rate 40 mL/minute, 20-99% gradient of methanol in buffer (0.1% trifluoroacetic acid)] to afford the title compound as the trifluoroacetic acid salt: $^1$H NMR (300 MHz, methanol-d$_4$) δ ppm 2.28-2.38 (m, 4H) 3.13-3.19 (m, 1H) 3.55-3.76 (m, 4H) 6.97 (td, J=9.16, 2.37 Hz, 1H) 7.13 (dd, J=9.16, 4.41 Hz, 1H) 7.24 (dd, J=9.16, 2.03 Hz, 1H) 7.83-7.89 (m, 1H) 7.94-7.98 (m, 1H) 8.19 (d, J=2.03 Hz, 1H) 8.23 (s, 1H); MS (DCI/NH$_3$) m/z 375 (M+H)$^+$.

Example 260

7-(9-fluoro-1,3,4,5-tetrahydro-6H-2,5-ethanoazepino[4,3-b]indol-6-yl)quinoxalin-2(1H)-one The reaction of 9-fluoro-3,4,5,6-tetrahydro-1H-2,5-ethanoazepino[4,3-b]indole (231 mg, 1.0 mmol; Example 161) and 7-bromoquinoxalin-2(1H)-one (225 mg, 1.0 mmol; Ark Pharm) was performed as described in Example 259 to afford the title compound as the trifluoroacetic acid salt: $^1$H NMR (300 MHz, methanol-d$_4$) δ ppm 2.29-2.39 (m, 4H) 3.21-3.28 (m, 1H) 3.54-3.76 (m, 4H) 6.98 (td, J=9.16, 2.37 Hz, 1H) 7.18-7.26 (m, 2H) 7.32-7.41 (m, 2H) 8.06 (d, J=8.48 Hz, 1H) 8.28 (s, 1H); MS (DCI/NH$_3$) m/z 375 (M+H)$^+$.

Example 261

7-(9-fluoro-1,3,4,5-tetrahydro-6H-2,5-ethanoazepino[4,3-b]indol-6-yl)-4H-pyrido[1,2-a]pyrimidin-4-one Example 261A 5-((5-bromopyridin-2-ylamino)methylene)-2,2-dimethyl-1,3-dioxane-4,6-dione To a suspension of 5-bromopyridin-2-amine (4.97 g, 28.7 mmol; Aldrich) and 2,2-dimethyl-1,3-dioxane-4,6-dione (4.55 g, 31.6 mmol; Aldrich) in ethanol (100 mL) was added trimethoxymethane (3.35 g, 31.6 mmol; Aldrich) and mixture was heated to 100° C. with stirring for 30 minutes. Then the ethanol was blown off with a stream of nitrogen, and the residual solid was permitted to cool to ambient temperature. The solid was recrystallized from acetonitrile to afford the title compound: $^1$H NMR (300 MHz, CDCl$_3$) δ ppm 1.76 (s, 6H) 6.94 (d, J=8.73 Hz, 1H) 7.86 (dd, J=8.72, 2.38 Hz, 1H) 8.47 (d, J=2.38 Hz, 1H) 9.33 (d, J=13.09 Hz, 1H) 11.30 (d, J=13.09 Hz, 1H); MS (DCI/NH$_3$) m/z 344, 346 (M+NH$_4$)$^+$.

Example 261B 7-bromo-4H-pyrido[1,2-a]pyrimidin-4-one 5-((5-Bromopyridin-2-ylamino)methylene)-2,2-dimethyl-1,3-dioxane-4,6-dione (7.4 g, 22.62 mmol; Example 261A) in diphenyl ether (150 mL; Alfa Aesar) was heated to 200° C. with stirring for 3 hours. The mixture was purified on a 340 gram silica gel column and washed with hexane first and then eluted with hexane/ethyl acetate (2:3) to afford the title compound: $^1$H NMR (300 MHz, methanol-d$_4$) δ ppm 6.49 (d, J=6.44 Hz, 1H) 7.62 (d, J=9.49 Hz, 1H) 8.03 (dd, J=9.49, 2.37 Hz, 1H) 8.32 (d, J=6.44 Hz, 1H) 9.18 (d, J=1.70 Hz, 1H); MS (DCI/NH$_3$) m/z 225, 227 (M+H)$^+$.

Example 261C 7-(9-fluoro-1,3,4,5-tetrahydro-6H-2,5-ethanoazepino [4,3-b]indol-6-yl)-4H-pyrido[1,2-a]pyrimidin-4-one A 10 mL microwave reaction tube was charged with 9-fluoro-3,4,5,6-tetrahydro-1H-2,5-ethanoazepino[4,3-b]indole (231 mg, 1.0 mmol; Example 161), 7-bromo-4H-pyrido [1,2-a]pyrimidin-4-one (338 mg, 1.5 mmol; Example 261B), copper(I) iodide (19 mg, 0.1 mmol; Aldrich), trans-(1R, 2R)—N,N'-bismethyl-1,2-cyclohexane-diamine (57 mg, 0.4 mmol, Acros) and dry toluene (3 mL). The vessel was flushed with nitrogen and potassium phosphate tribasic (446 mg, 2.1 mmol; Aldrich) was added. After purging the reaction mixture with nitrogen again, it was sealed and heated to 110° C. with stirring for 20 hours. The mixture was cooled and quenched with water, and then extracted with ethyl acetate. The organic phase was concentrated and purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.96-2.21 (m, 4H) 2.91-3.00 (m, 1H) 3.07-3.28 (m, 4H) 4.29 (s, 2H) 6.54 (d, J=6.44 Hz, 1H) 6.90 (td, J=9.16, 2.71 Hz, 1H) 7.11-7.21 (m, 2H) 7.83-7.89 (m, 1H) 7.92-7.99 (m, 1H) 8.39 (d, J=6.44 Hz, 1H) 9.07 (d, J=1.70 Hz, 1H); MS (DCI/NH$_3$) m/z 375 (M+H)$^+$.

Example 262

2-[6-(9-fluoro-1,3,4,5-tetrahydro-6H-2,5-ethanoazepino[4,3-b]indol-6-yl)pyridin-3-yl]pyridazin-3(2H)-one Example 262A 6-(5-bromopyridin-2-yl)-9-fluoro-3,4,5,6-tetrahydro-1H-2,5-ethanoazepino[4,3-b]indole 9-Fluoro-3,4,5,6-tetrahydro-1H-2,5-ethanoazepino[4,3-b]indole (1.4 g, 6.08 mmol, Example 161), 5-bromo-2-iodopyridine (2.59 g, 9.12 mmol), copper(I) iodide (0.116 g, 0.608 mmol), and cesium acetate (2.334 g, 12.16 mmol) were dissolved in dry dimethyl sulfoxide (30 mL). The reaction vial was evacuated then back-filled with dry N$_2$. The sealed vial was heated at 90° C. overnight. The reaction mixture was cooled to room temperature, and then ethyl acetate (25 mL) and brine/14.8 M aqueous NH$_4$OH (8:2, 20 mL) were added. The solution was stirred for 15 minutes and then filter through a bed of diatomaceous earth. The ethyl acetate was removed, and then the aqueous layer was extracted with more ethyl acetate (2×25 mL). The combined organic extracts were dried over MgSO$_4$, and then the solid was removed by filtration. Volatiles were removed in vacuo. The crude residue was purified by flash chromatography [100% CH$_2$Cl$_2$ for 5 minutes followed by a gradient from 0 to 100% CH$_2$Cl$_2$/methanol/14.8 M aqueous NH$_4$OH (78:20: 2) in CH$_2$Cl$_2$ for 15 minutes and then held at 100% CH$_2$Cl$_2$/methanol/14.8 M aqueous NH$_4$OH (78:20:2) for 5 minutes] to give the title compound: $^1$H NMR (300 MHz, CDCl$_3$) δ ppm 1.89-2.08 (m, 2H) 2.07-2.26 (m, 2H) 3.18 (s, 3H) 3.25-3.46 (m, 2H) 4.34 (s, 2H) 6.84-6.97 (m, 1H) 7.00-7.10 (m, 1H) 7.22 (s, 1H) 7.29-7.38 (m, 1H) 8.00 (d, J=10.85 Hz, 1H) 8.70 (s, 1H); MS (ESI) m/z 287 (M+H)$^+$.

Example 262B

2-[6-(9-fluoro-1,3,4,5-tetrahydro-6H-2,5-ethanoazepino[4,3-b]indol-6-yl)pyridin-3-yl]pyridazin-3(2H)-one A sealed tube was charged with the product from Example 262A (390 mg, 1.01 mmol), pyridazin-3(2H)-one (97 mg, 1.01 mmol; Fluka), copper (64 mg, 1.01 mmol; Aldrich), copper (I) iodide (288 mg, 1.32 mmol; Aldrich), K$_2$CO$_3$ (419 mg, 3.03 mmol; Aldrich) and pyridine (5.0 mL). The tube was flushed with N$_2$ (2×). N,N'-Dimethyl-ethylenediamine (0.033 mL, 0.303 mmol) was added to the tube and it was heated to 117° C. for 72 hours. Volatiles were removed under reduced pressure. The residue was partitioned between CHCl$_3$ and 14.8 M aqueous NH$_4$OH$_{aq}$. The organic layer was dried over MgSO$_4$, and the solid was removed by filtration. The reaction mixture was concentrated in vacuo, and the residue was purified by reverse-phase HPLC [Waters XBridge™ C 18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, CDCl$_3$) δ ppm 1.87-2.10 (m, 2H) 2.08-2.31 (m, 2H) 3.07-3.48 (m, 5H) 4.26-4.47 (m, 2H) 6.78-7.02 (m, 1H) 7.02-7.17 (m, 2H) 7.32 (dd, J=9.49, 4.07 Hz, 1H) 7.38-7.49 (m, 2H) 7.99 (d, J=3.73 Hz, 1H) 8.28 (dd, J=8.48, 2.71 Hz, 1H) 8.98 (d, J=2.71 Hz, 1H); MS (ESI) m/z 402 (M+H)$^+$.

Example 263

9-fluoro-6-(2-methylpyrimidin-5-yl)-3,4,5,6-tetrahydro-1H-2,5-ethanoazepino[4,3-b]indole A sealed tube was charged 9-fluoro-3,4,5,6-tetrahydro-1H-2,5-ethanoazepino[4,3-b]indole (130 mg, 0.565 mmol, Example 161), 5-bromo-2-methylpyrimidine (98 mg, 0.565 mmol; Anichem), copper (36 mg, 0.565 mmol; Aldrich), copper (I) iodide (161 mg, 0.847 mmol; Aldrich), K$_2$CO$_3$ (234 mg, 1.69 mmol; Aldrich), and pyridine (5.0 mL). The tube was flushed with N$_2$ (2×). N,N'-Dimethyl-ethylenediamine (0.033 mL, 0.303 mmol) was added to the tube, and the mixture was heated to 117° C. for 72 hours. Volatiles were removed under reduced pressure. The residue was partitioned between CHCl$_3$ and 14.8 M aqueous NH$_4$OH. The organic layer was dried over MgSO$_4$ and then the solid was removed by filtration. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, CDCl$_3$) δ ppm 1.83-2.16 (m, 4H) 2.71-2.80 (m, 1H) 2.86 (s, 3H) 3.03-3.24 (m, 2H) 3.22-3.41 (m, 2H) 4.29 (s, 2H) 6.83-6.94 (m, 1H) 6.94-7.03 (m, 1H) 7.05-7.15 (m, 1H) 8.63 (s, 2H); MS (ESI) m/z 323 (M+H)$^+$.

Example 264

9-fluoro-6-(pyridin-3-yl)-3,4,5,6-tetrahydro-1H-2,5-ethanoazepino[4,3-b]indole

A sealed tube was charged with 9-fluoro-3,4,5,6-tetrahydro-1H-2,5-ethanoazepino[4,3-b]indole (130 mg, 0.565 mmol, Example 161), 3-bromopyridine (98 mg, 0.565 mmol; Aldrich), copper (36 mg, 0.565 mmol; Aldrich), copper (I) iodide (161 mg, 0.847 mmol; Aldrich), K$_2$CO$_3$ (234 mg, 1.69 mmol; Aldrich) and pyridine (5.0 mL). The tube was flushed with N$_2$ (2×). N,N'-Dimethyl-ethylenediamine (0.018 mL, 0.169 mmol) was added to the tube and the reaction mixture was heated to 117° C. for 72 hours. Volatiles were removed under reduced pressure. The residue was partitioned between CHCl$_3$ and 14.8 M aqueous NH$_4$OH. The organic layer was dried over MgSO$_4$, and then the solid was removed by filtration. The reaction mixture was concentrated in vacuo, and the residue was purified by reverse-phase HPLC [Waters XBridge™ C18 5 μm OBD column, 30×100 mm, flow rate 40 mL/minute, 20-95% gradient of methanol in buffer (0.1 M aqueous ammonium bicarbonate, adjusted to pH 10 with ammonium hydroxide) over 20 minutes] to afford the title compound: $^1$H NMR (300 MHz, CDCl$_3$) δ ppm 1.80-2.17 (m, 4H) 2.74-2.93 (m, 1H) 3.03-3.24 (m, 2H) 3.25-3.46 (m, 2H) 4.32 (s, 2H) 6.80-6.93 (m, 1H) 7.00 (dd, J=8.92, 4.16 Hz, 1H) 7.09 (d, J=9.52 Hz, 1H) 7.51 (dd, J=7.93, 4.76 Hz, 1H) 7.63-7.72 (m, 1H) 8.60 (s, 1H) 8.71 (d, J=1.19 Hz, 1H); MS (ESI) m/z 308 (M+H)$^+$.

Example 265

6-[6-(morpholin-4-yl)pyridin-2-yl]-3,4,5,6-tetrahydro-1H-2,5-ethanoazepino[4,3-b]indole The reaction of 3,4,5,6-tetrahydro-1H-2,5-ethanoazepino[4,3-b]indole (212 mg, 1.0 mmol; Example 187A) and 4-(6-bromopyrid-2-yl)morpholine (243 mg, 1.0 mmol; Combi-Blocks) was performed using the methodology described in Example 258 to afford the title compound: $^1$H NMR (300 MHz, methanol-d$_4$) δ ppm 1.94-2.23 (m, 4H) 3.05-3.29 (m, 5H) 3.50-3.56 (m, 4H) 3.73-3.83 (m, 4H) 4.30 (s, 2H) 6.72 (d, J=7.12 Hz, 1H) 6.80 (d, J=8.48 Hz, 1H) 7.03-7.13 (m, 2H) 7.33-7.42 (m, 2H) 7.72-7.80 (m, 1H); MS (DCI/NH$_3$) m/z 375 (M+H)$^+$.

Example 266

6-(1,3,4,5-tetrahydro-6H-2,5-ethanoazepino[4,3-b]indol-6-yl)nicotinamide

The reaction of 3,4,5,6-tetrahydro-1H-2,5-ethanoazepino[4,3-b]indole (212 mg, 1.0 mmol; Example 187A) and 6-bromonicotinonitrile (183 mg, 1.0 mmol; Aldrich) was performed using the methodology described in Example 258 to afford the title compound: $^1$H NMR (300 MHz, methanol-d$_4$) δ ppm 1.97-2.25 (m, 4H) 3.04-3.29 (m, 5H) 4.32 (s, 2H) 7.10-7.19 (m, 2H) 7.38-7.47 (m, 2H) 7.55 (d, J=9.16 Hz, 1H) 8.45 (dd, J=8.31, 2.54 Hz, 1H) 9.08 (d, J=1.70 Hz, 1H); MS (DCI/NH$_3$) m/z 333 (M+H)$^+$.

Example 267

6-(1,2,3,4-tetrahydroisoquinolin-6-yl)-3,4,5,6-tetrahydro-1H-2,5-ethanoazepino[4,3-b]indole The reaction of 3,4,5,6-tetrahydro-1H-2,5-ethanoazepino[4,3-b]indole (162 mg, 0.76 mmol; Example 187A) and tert-butyl 6-bromo-3,4-dihydroisoquinoline-2(1H)-carboxylate (238 mg, 0.76 mmol; Anthem Biosciences) was performed using the methodology described in Example 258 to afford tert-butyl 6-(1,3,4,5-tetrahydro-6H-2,5-ethanoazepino[4,3-b]indol-6-yl)-3,4-dihydroisoquinoline-2(1H)-carboxylate. This compound was treated with trifluoroacetic acid (1 mL) in CH$_2$Cl$_2$ (4 mL) at room temperature with stirring for 16 hours. After concentration, the mixture was purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.92-2.13 (m, 4H) 2.91 (t, J=5.16 Hz, 3H) 3.06-3.29 (m, 6H) 4.06 (s, 2H) 4.32 (s, 2H) 6.98-7.11 (m, 5H) 7.23-7.28 (m, 1H) 7.34-7.40 (m, 1H); MS (DCI/NH$_3$) m/z 344 (M+H)$^+$.

Example 268

6-(2-methyl-1,2,3,4-tetrahydroisoquinolin-6-yl)-3,4,5,6-tetrahydro-1H-2,5-ethanoazepino[4,3-b]indole 6-(1,2,3,4-Tetrahydroisoquinolin-6-yl)-3,4,5,6-tetrahydro-1H-2,5-ethanoazepino[4,3-b]indole (70 mg, 0.20 mmol; Example 267), 37% formaldehyde (50 mg, 0.62 mmol; J. T. Baker) and sodium triacetoxyborohydride (130 mg, 0.61 mmol; Aldrich) were mixed in acetonitrile (4 mL) at room temperature with stirring for 4 hours. The mixture was purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.92-2.13 (m, 4H) 2.51 (s, 3H) 2.80 (t, J=5.95 Hz, 2H) 2.86-2.93 (m, 1H) 2.99-3.28 (m, 6H) 3.71 (s, 2H) 4.31 (s, 2H) 6.97-7.13 (m, 5H) 7.27 (d, J=7.54 Hz, 1H) 7.34-7.40 (m, 1H); MS (DCI/NH$_3$) m/z 358 (M+H)$^+$.

Example 269

6-(quinazolin-6-yl)-3,4,5,6-tetrahydro-1H-2,5-ethanoazepino[4,3-b]indole

The reaction of 3,4,5,6-tetrahydro-1H-2,5-ethanoazepino[4,3-b]indole (110 mg, 0.52 mmol; Example 187A) and 6-bromoquinazoline (162 mg, 0.78 mmol; Parkway) was performed using the methodology described in Example 258 to afford the title compound: $^1$H NMR (300 MHz, methanol-d$_4$) δ ppm 1.95-2.24 (m, 4H) 2.93-3.02 (m, 1H) 3.08-3.29 (m, 4H) 4.36 (s, 2H) 7.07-7.21 (m, 3H) 7.38-7.49 (m, 1H)

8.00 (dd, J=8.73, 2.38 Hz, 1H) 8.15 (d, J=2.38 Hz, 1H) 8.24 (d, J=8.73 Hz, 1H) 9.34 (s, 1H) 9.64 (s, 1H); MS (DCI/NH$_3$) m/z 341 (M+H)$^+$.

Example 270

6-(isoquinolin-7-yl)-3,4,5,6-tetrahydro-1H-2,5-ethanoazepino[4,3-b]indole

The reaction of 3,4,5,6-tetrahydro-1H-2,5-ethanoazepino[4,3-b]indole (112 mg, 0.53 mmol; Example 187A) and 7-bromoisoquinoline (165 mg, 0.79 mmol; Frontier) was performed using the methodology described in Example 258 to afford the title compound: $^1$H NMR (300 MHz, methanol-d$_4$) δ ppm 1.94-2.22 (m, 4H) 2.91-3.00 (m, 1H) 3.09-3.29 (m, 4H) 4.36 (s, 2H) 7.06-7.15 (m, 3H) 7.40-7.46 (m, 1H) 7.75 (dd, J=8.48, 2.03 Hz, 1H) 7.95 (d, J=5.76 Hz, 1H) 8.11 (d, J=2.03 Hz, 1H) 8.16 (d, J=8.82 Hz, 1H) 8.54 (d, J=5.76 Hz, 1H) 9.34 (s, 1H); MS (DCI/NH$_3$) m/z 340 (M+H)$^+$.

Example 271

6-(isoquinolin-6-yl)-3,4,5,6-tetrahydro-1H-2,5-ethanoazepino[4,3-b]indole

The reaction of 3,4,5,6-tetrahydro-1H-2,5-ethanoazepino[4,3-b]indole (112 mg, 0.53 mmol; Example 187A) and 6-bromoisoquinoline (165 mg, 0.79 mmol; Accela ChemBio) was performed using the methodology described in Example 258 to afford the title compound: $^1$H NMR (300 MHz, methanol-d$_4$) δ ppm 1.96-2.22 (m, 4H) 2.99 (ddd, J=7.38, 5.00, 2.20 Hz, 1H) 3.09-3.29 (m, 4H) 4.35 (s, 2H) 7.06-7.20 (m, 3H) 7.39-7.47 (m, 1H) 7.65 (dd, J=8.48, 2.03 Hz, 1H) 7.89-7.97 (m, 2H) 8.32 (d, J=8.48 Hz, 1H) 8.52 (d, J=5.76 Hz, 1H) 9.35 (s, 1H); MS (DCI/NH$_3$) m/z 340 (M+H)$^+$.

Example 272

6-[4-(1H-imidazol-1-yl)pyridin-2-yl]-3,4,5,6-tetrahydro-1H-2,5-ethanoazepino[4,3-b]indole The reaction of 3,4,5,6-tetrahydro-1H-2,5-ethanoazepino[4,3-b]indole (112 mg, 0.53 mmol; Example 187A) and 2-bromo-4-(1H-imidazol-1-yl)pyridine (118 mg, 0.53 mmol; Combi-Phos) was performed using the procedure described in Example 258 to afford the title compound: $^1$H NMR (300 MHz, methanol-d$_4$) δ ppm 1.97-2.10 (m, 2H) 2.14-2.31 (m, 2H) 3.07-3.29 (m, 5H) 4.32 (s, 2H) 7.09-7.19 (m, 2H) 7.23 (s, 1H) 7.36-7.45 (m, 2H) 7.72-7.77 (m, 1H) 7.77-7.80 (m, 1H) 7.85 (t, J=1.53 Hz, 1H) 8.50 (s, 1H) 8.71 (d, J=5.09 Hz, 1H); MS (DCI/NH$_3$) m/z 356 (M+H)$^+$.

Example 273

6'-(1,3,4,5-tetrahydro-6H-2,5-ethanoazepino[4,3-b]indol-6-yl)-2H-1,2'-bipyridin-2-one The reaction of 3,4,5,6-tetrahydro-1H-2,5-ethanoazepino[4,3-b]indole (112 mg, 0.53 mmol; Example 187A) and 1-(6-bromopyridin-2-yl)pyridin-2(1H)-one (132 mg, 0.53 mmol; Combi-Phos) was performed using the procedure described in Example 258 to afford the title compound: $^1$H NMR (300 MHz, methanol-d$_4$) δ ppm 2.02-2.29 (m, 4H) 3.15-3.40 (m, 5H) 4.41 (s, 2H) 6.50 (t, J=6.74 Hz, 1H) 6.66 (d, J=9.12 Hz, 1H) 7.11-7.21 (m, 2H) 7.39-7.52 (m, 2H) 7.59-7.67 (m, 2H) 7.80 (d, J=7.93 Hz, 1H) 7.90 (dd, J=6.74, 1.98 Hz, 1H) 8.23 (t, J=7.93 Hz, 1H); MS (DCI/NH$_3$) m/z 383 (M+H)$^+$.

Example 274

7-(1,3,4,5-tetrahydro-6H-2,5-ethanoazepino[4,3-b]indol-6-yl)quinoxalin-2(1H)-one The reaction of 3,4,5,6-tetrahydro-1H-2,5-ethanoazepino[4,3-b]indole (127 mg, 0.60 mmol; Example 187A) and 7-bromoquinoxalin-2(1H)-one (203 mg, 0.90 mmol; Ark Pharm) was performed using the procedure described in Example 258 to afford the title compound: $^1$H NMR (300 MHz, methanol-d$_4$) δ ppm 1.98-2.20 (m, 4H) 3.03 (ddd, J=7.29, 4.92, 2.37 Hz, 1H) 3.10-3.30 (m, 4H) 4.35 (s, 2H) 7.07-7.14 (m, 2H) 7.15-7.21 (m, 1H) 7.27-7.34 (m, 2H) 7.38-7.45 (m, 1H) 8.00 (d, J=8.48 Hz, 1H) 8.23 (s, 1H); MS (DCI/NH$_3$) m/z 357 (M+H)$^+$.

Example 275

7-(1,3,4,5-tetrahydro-6H-2,5-ethanoazepino[4,3-b]indol-6-yl)-2H-1,4-benzoxazin-3(4H)-one The reaction of 3,4,5,6-tetrahydro-1H-2,5-ethanoazepino[4,3-b]indole (212 mg, 1.0 mmol; Example 187A) and 7-bromo-2H-benzo[b][1,4]oxazin-3(4H)-one (228 mg, 1.0 mmol; Biogene) was performed using the procedure described in Example 258 to afford the title compound: $^1$H NMR (300 MHz, methanol-d$_4$) δ ppm 1.95-2.12 (m, 4H) 2.92 (ddd, J=7.29, 4.75, 2.54 Hz, 1H) 3.05-3.28 (m, 4H) 4.31 (s, 2H) 4.66 (s, 2H) 6.90-6.95 (m, 2H) 7.02-7.09 (m, 4H) 7.35-7.40 (m, 1H); MS (DCI/NH$_3$) m/z 360 (M+H)$^+$.

Example 276

2-amino-5-(3,4,5,6-tetrahydro-1H-2,5-ethanoazepino[4,3-b]indol-6(1H)-yl)benzamide Example 276A 6-(3-cyano-4-nitrophenyl)-3,4,5,6-tetrahydro-1H-2,5-ethanoazepino[4,3-b]indole 3,4,5,6-Tetrahydro-1H-2,5-ethanoazepino[4,3-b]indole (425 mg, 2.0 mmol; Example 187A) in N,N-dimethylformamide (10 mL) was treated with 60% dispersion in oil of NaH (101 mg, 4.2 mmol; Aldrich) at room temperature. The mixture was stirred for 30 minutes, and then 5-fluoro-2-nitrobenzonitrile (415 mg, 2.5 mmol; Oakwood) was added. The mixture was stirred for 3 more hours before being quenched with methanol. The mixture was purified by flash chromatography (200 silica gel, CH$_2$Cl$_2$/methanol 10:1) to afford the title compound: $^1$H NMR (300 MHz, methanol-d$_4$) δ ppm 2.08-2.29 (m, 4H) 3.02-3.10 (m, 1H) 3.21-3.49 (m, 4H) 4.50 (s, 2H) 7.17-7.29 (m, 3H) 7.44-7.49 (m, 1H) 7.91 (dd, J=8.82, 2.37 Hz, 1H) 8.08 (d, J=2.37 Hz, 1H) 8.59 (d, J=8.82 Hz, 1H); MS (DCI/NH$_3$) m/z 359 (M+H)$^+$.

Example 276B 2-amino-5-(3,4,5,6-tetrahydro-1H-2,5-ethanoazepino[4,3-b]indol-6(1H)-yl)benzamide 6-(3-Cyano-4-nitrophenyl)-3,4,5,6-tetrahydro-1H-2,5-ethanoazepino[4,3-b]indole (500 mg, 1.395 mmol; Example 276A) and 10% Pd/C (100 mg; Aldrich) were mixed in methanol (15 mL). The mixture was subjected to hydrogenation under a balloon of hydrogen at room temperature with stirring for 1.5 hours. After the catalyst was removed by filtration, the filtrate was concentrated, and the residue was purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-$d_4$) δ ppm 1.96-2.15 (m, 4H) 2.87-2.93 (m, 1H) 3.06-3.29 (m, 4H) 4.33 (s, 2H) 6.90 (d, J=8.48 Hz, 1H) 6.98-7.07 (m, 3H) 7.11 (dd, J=8.48, 2.37 Hz, 1H) 7.34-7.39 (m, 1H) 7.51 (d, J=2.37 Hz, 1H); MS (DCI/NH$_3$) m/z 347 (M+H)$^+$.

Example 277

7-(1,3,4,5-tetrahydro-6H-2,5-ethanoazepino[4,3-b] indol-6-yl)-4H-pyrido[1,2-a]pyrimidin-4-one The reaction of 3,4,5,6-tetrahydro-1H-2,5-ethanoazepino[4,3-b]indole (212 mg, 1.0 mmol; Example 187A) and 7-bromo-4H-pyrido[1,2-a]pyrimidin-4-one (341 mg, 1.5 mmol; Example 261B) was performed using the procedure described in Example 261C to afford the title compound: $^1$H NMR (300 MHz, methanol-$d_4$) δ ppm 1.98-2.22 (m, 4H) 2.95-3.02 (m, 1H) 3.08-3.29 (m, 4H) 4.34 (s, 2H) 6.54 (d, J=6.44 Hz, 1H) 7.11-7.26 (m, 3H) 7.41-7.49 (m, 1H) 7.82-7.92 (m, 1H) 7.93-8.01 (m, 1H) 8.37-8.41 (m, 1H) 9.07 (d, J=1.70 Hz, 1H); MS (DCI/NH$_3$) m/z 357 (M+H)$^+$.

Example 278

(7S,10R)-5-(quinolin-6-yl)-5,6,7,8,9,10-hexahydro-7,10-epiminocyclohepta[b]indole Example 278A 5,6,7,8,9,10-hexahydro-7,10-epiminocyclohepta[b] indole In a 30 mL round-bottomed microwave reaction tube were combined phenylhydrazine hydrochloride (3.51 g, 24.4 mmol; Aldrich), tert-butyl 3-oxo-6-azabicyclo[3.1.1]heptane-6-carboxylate (5.5 g, 24.4 mmol; Chireach) and 1 N HCl in acetic acid (15 mL; Aldrich). The reaction mixture was heated to 150° C. with stirring for 15 minutes in a microwave reactor (Biotage Personal Chemistry™, maximum 300 Watts), and then cooled to room temperature. The reaction mixture was concentrated, and the residue was purified by flash chromatography (silica gel, eluted with CH$_2$Cl$_2$/methanol 10:1) to afford the title compound: $^1$H NMR (300 MHz, methanol-$d_4$) δ ppm 1.59-1.70 (m, 1H) 1.94-2.22 (m, 3H) 2.54 (dd, J=16.28, 1.36 Hz, 1H) 3.25 (dd, J=16.28, 4.41 Hz, 1H) 3.90-3.98 (m, 1H) 4.50 (d, J=4.75 Hz, 1H) 6.91-7.02 (m, 2H) 7.21-7.25 (m, 1H) 7.36-7.42 (m, 1H); MS (DCI/NH$_3$) m/z 199 (M+H)$^+$.

Example 278B tert-butyl 5,6,7,8,9,10-hexahydro-7,10-epiminocyclohepta[b]indole-11-carboxylate 5,6,7,8,9,10-hexahydro-7,10-epiminocyclohepta[b]indole (4.8 g, 24.21 mmol; Example 276A), di-tert-butyl dicarbonate (5.81 g, 26.6 mmol; Fluka) and triethylamine (10.12 mL, 72.6 mmol; Aldrich) were mixed in dichloromethane (60 mL; Aldrich), and the mixture was stirred at room temperature for 16 hours. After being concentrated, the residue was purified on a flash chromatography (silica gel, eluted with hexane/ethyl acetate 3:2) to afford the title compound: $^1$H NMR (300 MHz, methanol-$d_4$) δ ppm 1.28-1.49 (m, 9H) 1.64-1.77 (m, 1H) 1.86-1.97 (m, 1H) 2.10-2.40 (m, 2H) 2.54 (d, J=16.26 Hz, 1H) 3.34-3.50 (m, 1H) 4.56 (dd, J=7.93, 4.36 Hz, 1H) 5.19 (d, J=5.16 Hz, 1H) 6.92-7.08 (m, 2H) 7.25 (d, J=6.74 Hz, 1H) 7.41 (d, J=7.54 Hz, 1H); MS (DCI/NH$_3$) m/z 299 (M+H)$^+$.

Example 278C tert-butyl 5-(quinolin-6-yl)-5,6,7,8,9,10-hexahydro-7,10-epiminocyclohepta[b]indole-11-carboxylate The reaction of tert-butyl 5,6,7,8,9,10-hexahydro-7,10-epiminocyclohepta[b]indole-11-carboxylate (597 mg, 2.0 mmol; Example 278B) and 6-bromoquinoline (624 mg, 3.0 mmol; Aldrich) was performed as described in Example 261C to afford the title compound: $^1$H NMR (300 MHz, methanol-$d_4$) δ ppm 1.35-1.50 (m, 9H) 1.67-1.82 (m, 1H) 2.01-2.09 (m, 1H) 2.15-2.54 (m, 3H) 3.34-3.49 (m, 1H) 4.61 (dd, J=7.46, 4.41 Hz, 1H) 5.33 (d, J=4.75 Hz, 1H) 7.08-7.18 (m, 2H) 7.22-7.30 (m, 1H) 7.55-7.66 (m, 2H) 7.79 (dd, J=8.82, 2.37 Hz, 1H) 7.97 (d, J=2.37 Hz, 1H) 8.22 (d, J=8.82 Hz, 1H) 8.46 (d, J=8.48 Hz, 1H) 8.93 (dd, J=4.07, 1.70 Hz, 1H); MS (DCI/NH$_3$) m/z 426 (M+H)$^+$.

Example 278D 5-(quinolin-6-yl)-5,6,7,8,9,10-hexahydro-7,10-epiminocyclohepta[b]indole tert-Butyl 5-(quinolin-6-yl)-5,6,7,8,9,10-hexahydro-7,10-epiminocyclohepta[b]indole-11-carboxylate (440 mg, 1.03 mmol; Example 278C) was dissolved in dichloromethane (8 mL; Aldrich) and treated with trifluoroacetic acid (1.5 mL; Aldrich) at room temperature with stirring for 16 hours. The mixture was concentrated and purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-$d_4$) δ ppm 1.64-1.80 (m, 1H) 2.09-2.28 (m, 3H) 2.50 (d, J=16.66 Hz, 1H) 3.31-3.38 (m, 1H) 4.05 (t, J=4.96 Hz, 1H) 4.72 (t, J=4.36 Hz, 1H) 7.07-7.17 (m, 2H) 7.23-7.31 (m, 1H) 7.53-7.59 (m, 1H) 7.62 (dd, J=8.33, 4.36 Hz, 1H) 7.83 (dd, J=8.72, 2.38 Hz, 1H) 7.99 (d, J=1.98 Hz, 1H) 8.21 (d, J=8.72 Hz, 1H) 8.45 (d, J=8.33 Hz, 1H) 8.92 (dd, J=4.36, 1.98 Hz, 1H); MS (DCI/NH$_3$) m/z 326 (M+H)$^+$.

Example 278E (7S,10R)-5-(quinolin-6-yl)-5,6,7,8,9,10-hexahydro-7,10-epiminocyclohepta[b]indole The individual enantiomers from the mixture of 5-(quinolin-6-yl)-5,6,7,8,9,10-hexahydro-7,10-epiminocyclohepta[b]indole (240 mg, 0.74 mmol; Example 278D) were separated by preparative chiral supercritical fluid chromatography (ChiralPak® OD-H 5 μm column, 21×250 mm, 35° C., 10-30% gradient of CH$_3$OH—CO$_2$ containing 0.1% diethylamine) to obtain the title compound as the second eluting peak (retention time=14.7 minutes): $^1$H NMR (300 MHz, methanol-d$_4$) δ ppm 1.60-1.77 (m, 1H) 2.06-2.25 (m, 3H) 2.41-2.52 (m, 1H) 3.26-3.36 (m, 1H) 4.00 (t, J=4.92 Hz, 1H) 4.66 (d, J=3.39 Hz, 1H) 7.05-7.16 (m, 2H) 7.22-7.30 (m, 1H) 7.51-7.59 (m, 1H) 7.59-7.66 (m, 1H) 7.83 (dd, J=8.82, 2.37 Hz, 1H) 7.98 (d, J=2.37 Hz, 1H) 8.21 (d, J=8.82 Hz, 1H) 8.42-8.48 (m, 1H) 8.92 (dd, J=4.41, 1.70 Hz, 1H); MS (DCI/NH$_3$) m/z 326 (M+H)$^+$.

Example 279

(7R,10S)-5-(isoquinolin-7-yl)-6,7,8,9,10-pentahydro-7,10-epiminocyclohepta[b]indole Example 279A tert-butyl 5-(isoquinolin-7-yl)-5,6,7,8,9,10-hexahydro-7,10-epiminocyclohepta[b]indole-11-carboxylate The reaction of tert-butyl 5,6,7,8,9,10-hexahydro-7,10-epiminocyclohepta[b]indole-11-carboxylate (597 mg, 2.0 mmol; Example 278B) and 7-bromoisoquinoline (624 mg, 3.0 mmol; Aldrich) was performed as described in Example 261C to afford the title compound: $^1$H NMR (300 MHz, methanol-d$_4$) δ ppm 1.35-1.50 (m, 9H) 1.69-1.82 (m, 1H) 2.00-2.08 (m, 1H) 2.17-2.40 (m, 2H) 2.46 (d, J=16.28 Hz, 1H) 3.36-3.49 (m, 1H) 4.61 (dd, J=7.12, 4.41 Hz, 1H) 5.33 (d, J=5.09 Hz, 1H) 7.09-7.19 (m, 2H) 7.22-7.31 (m, 1H) 7.54-7.63 (m, 1H) 7.78-7.83 (m, 1H) 7.93 (d, J=5.76 Hz, 1H) 8.11-8.18 (m, 2H) 8.52 (d, J=6.10 Hz, 1H) 9.33 (s, 1H); MS (DCI/NH$_3$) m/z 426 (M+H)$^+$.

Example 279B 5-(isoquinolin-7-yl)-5,6,7,8,9,10-hexahydro-7,10-epiminocyclohepta[b]indole tert-Butyl 5-(isoquinolin-7-yl)-5,6,7,8,9,10-hexahydro-7,10-epiminocyclohepta[b]indole-11-carboxylate (624 mg, 1.47 mmol; Example 279A) was dissolved in dichloromethane (10 mL) and treated with trifluoroacetic acid (2.0 mL; Aldrich) at room temperature with stirring for 16 hours. The mixture was concentrated and purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.63-1.78 (m, 1H) 2.07-2.27 (m, 3H) 2.48 (d, J=16.66 Hz, 1H) 3.27-3.36 (m, 1H) 4.03 (t, J=5.16 Hz, 1H) 4.69 (d, J=3.57 Hz, 1H) 7.07-7.17 (m, 2H) 7.23-7.31 (m, 1H) 7.52-7.62 (m, 1H) 7.84 (dd, J=8.73, 1.98 Hz, 1H) 7.93 (d, J=5.95 Hz, 1H) 8.11-8.19 (m, 2H) 8.52 (d, J=5.55 Hz, 1H) 9.33 (s, 1H); MS (DCI/NH$_3$) m/z 326 (M+H)$^+$.

Example 279C (7R,10S)-5-(isoquinolin-7-yl)-6,7,8,9,10-pentahydro-7,10-epiminocyclohepta[b]indole The individual enantiomers from the mixture of 5-(isoquinolin-7-yl)-5,6,7,8,9,10-hexahydro-7,10-epiminocyclohepta[b]indole (350 mg, 1.07 mmol; Example 279B) were separated by preparative chiral supercritical fluid chromatography (ChiralPak® OD-H 5 μm column, 21×250 mm, 35° C., 10-30% gradient of CH$_3$OH—CO$_2$ containing 0.1% diethylamine) to obtain the title compound as the first eluting peak (retention time=12.2 minutes): $^1$H NMR (300 MHz, methanol-d$_4$) δ ppm 1.64-1.76 (m, 1H) 2.06-2.28 (m, 3H) 2.47 (dd, J=16.62, 1.36 Hz, 1H) 3.25-3.34 (m, 1H) 4.02 (t, J=5.09 Hz, 1H) 4.68 (d, J=3.39 Hz, 1H) 7.06-7.16 (m, 2H) 7.22-7.30 (m, 1H) 7.53-7.62 (m, 1H) 7.84 (dd, J=8.82, 2.03 Hz, 1H) 7.93 (d, J=5.76 Hz, 1H) 8.12-8.18 (m, 2H) 8.51 (d, J=6.10 Hz, 1H) 9.33 (s, 1H); MS (DCI/NH$_3$) m/z 326 (M+H)$^+$.

Example 280

(7S,10R)-5-(isoquinolin-7-yl)-5,6,7,8,9,10-hexahydro-7,10-epiminocyclohepta[b]indole The individual enantiomers from the mixture of 5-(isoquinolin-7-yl)-5,6,7,8,9,10-hexahydro-7,10-epiminocyclohepta[b]indole (350 mg, 1.07 mmol; Example 279B) were separated by preparative chiral supercritical fluid chromatography (ChiralPak® OD-H 5 μm column, 21×250 mm, 35° C., 10-30% gradient of CH$_3$OH—CO$_2$ containing 0.1% diethylamine) to obtain the title compound as the second eluting peak (retention time=14.3 minutes): $^1$H NMR (300 MHz, methanol-d$_4$) δ ppm 1.60-1.76 (m, 1H) 2.04-2.25 (m, 3H) 2.45 (d, J=16.66 Hz, 1H) 3.25-3.34 (m, 1H) 3.99 (t, J=4.96 Hz, 1H) 4.65 (d, J=3.57 Hz, 1H) 7.06-7.17 (m, 2H) 7.22-7.30 (m, 1H) 7.52-7.60 (m, 1H) 7.84 (dd, J=8.72, 1.98 Hz, 1H) 7.93 (d, J=5.55 Hz, 1H) 8.11-8.17 (m, 2H) 8.51 (d, J=5.95 Hz, 1H) 9.32 (s, 1H); MS (DCI/NH$_3$) m/z 326 (M+H)$^+$.

Example 281

(7S,10R)-11-methyl-5-(quinolin-6-yl)-5,6,7,8,9,10-hexahydro-7,10-epiminocyclohepta[b]indole (7S,10R)-5-(Quinolin-6-yl)-5,6,7,8,9,10-hexahydro-7,10-epiminocyclohepta[b]indole (110 mg, 0.338 mmol; Example 278E) in acetonitrile (2 mL) and water (2 mL) was treated with a 37% aqueous solution of formaldehyde (0.4 mL; J. T. Baker) and then sodium triacetoxyborohydride (179 mg, 0.845 mmol; Aldrich). The mixture was stirred at room temperature for 2 hours. After being concentrated, the residue was purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.62-1.78 (m, 1H) 1.96-2.06 (m, 1H) 2.22-2.52 (m, 6H) 3.22-3.29 (m, 1H) 3.56-3.63 (m, 1H) 4.33 (d, J=5.16 Hz, 1H) 7.06-7.16 (m, 2H) 7.22-7.35 (m, 1H) 7.50-7.59 (m, 1H) 7.62 (dd, J=8.72, 4.36 Hz, 1H) 7.84 (dd, J=9.12, 2.38 Hz, 1H) 8.00 (d, J=2.38 Hz, 1H) 8.21 (d, J=8.73 Hz, 1H) 8.46 (d, J=8.33 Hz, 1H) 8.92 (dd, J=4.36, 1.59 Hz, 1H); MS (DCI/NH$_3$) m/z 340 (M+H)$^+$.

Example 282

(7R,10S)-5-(quinolin-6-yl)-5,6,7,8,9,1-hexahydro-7,10-epiminocyclohepta[b]indole The individual enantiomers from the mixture of 5-(quinolin-6-yl)-5,6,7,8,9,10-hexahydro-7,10-epiminocyclohepta[b]indole (240 mg, 0.74 mmol; Example 278D) were separated by preparative chiral supercritical fluid chromatography (ChiralPak® OD-H 5 μm column, 21×250 mm, 35° C., 10-30% gradient of CH$_3$OH—CO$_2$ containing 0.1% diethylamine) to obtain the title compound as the first eluting peak (retention time=11.7 minutes): $^1$H NMR (300 MHz, methanol-$d_4$) δ ppm 1.59-1.77 (m, 1H) 2.05-2.25 (m, 3H) 2.40-2.50 (m, 1H) 3.25-3.31 (m, 1H) 3.99 (t, J=5.09 Hz, 1H) 4.64 (d, J=3.39 Hz, 1H) 7.06-7.15 (m, 2H) 7.21-7.30 (m, 1H) 7.51-7.59 (m, 1H) 7.62 (dd, J=8.31, 4.24 Hz, 1H) 7.78-7.88 (m, 1H) 7.98 (d, J=2.37 Hz, 1H) 8.20 (d, J=9.16 Hz, 1H) 8.45 (d, J=7.46 Hz, 1H) 8.92 (dd, J=4.07, 1.70 Hz, 1H); MS (DCI/NH$_3$) m/z 326 (M+H)$^+$.

Example 283

7-[(7S,10R)-7,8,9,10-tetrahydro-7,10-epiminocyclohepta[b]indol-5(6H)-yl]-4H-pyrido[1,2-a]pyrimidin-4-one Example 283A t-butyl-5-(4-oxo-4H-pyrido[1,2-a]pyrimidin-7-yl)-5,6,7,8,9,10-hexahydro-7,10-epiminocyclohepta[b]indole-11-carboxylate The reaction of tert-butyl 5,6,7,8,9,10-hexahydro-7,10-epiminocyclohepta[b]indole-11-carboxylate (448 mg, 1.5 mmol; Example 278B) and 7-bromo-4H-pyrido[1,2-a]pyrimidin-4-one (506 mg, 2.25 mmol; Example 261B) was performed as described in Example 261C to afford the title compound: $^1$H NMR (300 MHz, methanol-$d_4$) δ ppm 1.40 (s, 9H) 1.69-1.82 (m, 1H) 2.04 (t, J=9.16 Hz, 1H) 2.16-2.41 (m, 2H) 2.50 (d, J=16.28 Hz, 1H) 3.42 (d, J=13.90 Hz, 1H) 4.63 (dd, J=7.63, 4.58 Hz, 1H) 5.31 (d, J=5.09 Hz, 1H) 6.53 (d, J=6.44 Hz, 1H) 7.14-7.23 (m, 2H) 7.29-7.37 (m, 1H) 7.60 (dd, J=5.59, 3.22 Hz, 1H) 7.87 (d, J=9.49 Hz, 1H) 8.05 (d, J=9.16 Hz, 1H) 8.38 (d, J=6.44 Hz, 1H) 9.09 (d, J=2.37 Hz, 1H); MS (DCI/NH$_3$) m/z 443 (M+H)$^+$.

Example 283B 7-(7,8,9,10-tetrahydro-7,10-epiminocyclohepta[b]indol-5(6H)-yl)-4H-pyrido[1,2-a]pyrimidin-4-one The reaction of t-butyl-5-(4-oxo-4H-pyrido[1,2-a]pyrimidin-7-yl)-5,6,7,8,9,10-hexahydro-7,10-epiminocyclohepta[b]indole-11-carboxylate (350 mg, 0.79 mmol; Example 283A) and trifluoroacetic acid (2 mL; Aldrich) was performed as described in Example 278D to afford the title compound: $^1$H NMR (300 MHz, methanol-$d_4$) δ ppm 1.65-1.81 (m, 1H) 2.05-2.28 (m, 3H) 2.53 (d, J=16.62 Hz, 1H) 3.23-3.36 (m, 1H) 4.04-4.13 (m, 1H) 4.70 (s, 1H) 6.53 (d, J=6.44 Hz, 1H) 7.13-7.20 (m, 2H) 7.29-7.37 (m, 1H) 7.54-7.62 (m, 1H) 7.86 (d, J=9.49 Hz, 1H) 8.07 (dd, J=9.16, 2.37 Hz, 1H) 8.38 (d, J=6.44 Hz, 1H) 9.12 (d, J=1.70 Hz, 1H); MS (DCI/NH$_3$) m/z 343 (M+H)$^+$.

Example 283C

7-[(7S,10R)-7,8,9,10-tetrahydro-7,10-epiminocyclohepta[b]indol-5(6H)-yl]-4H-pyrido[1,2-a]pyrimidin-4-one The individual enantiomers from the mixture of 7-(7,8,9,10-tetrahydro-7,10-epiminocyclohepta[b]indol-5(6H)-yl)-4H-pyrido[1,2-a]pyrimidin-4-one (250 mg, 0.73 mmol; Example 283B) were separated by preparative chiral supercritical fluid chromatography (ChiralPak® OD-H 5 μm column, 21×250 mm, 35° C., 10-30% gradient of CH$_3$OH—CO$_2$ containing 0.1% diethylamine) to obtain the title compound as the second eluting peak (retention time=15.2 minutes): $^1$H NMR (300 MHz, methanol-$d_4$) δ ppm 1.63-1.77 (m, 1H) 2.03-2.26 (m, 3H) 2.45-2.56 (m, 1H) 3.24-3.33 (m, 1H) 3.95-4.09 (m, 1H) 4.63 (d, J=3.73 Hz, 1H) 6.53 (d, J=6.10 Hz, 1H) 7.12-7.20 (m, 2H) 7.28-7.38 (m, 1H) 7.52-7.62 (m, 1H) 7.86 (d, J=9.49 Hz, 1H) 8.08 (dd, J=9.49, 2.37 Hz, 1H) 8.38 (d, J=6.44 Hz, 1H) 9.12 (d, J=2.37 Hz, 1H); MS (DCI/NH$_3$) m/z 343 (M+H)$^+$.

Example 284

7-[(7R,10S)-7,8,9,10-tetrahydro-7,10-epiminocyclohepta[b]indol-5(6H)-yl]-4H-pyrido[1,2-a]pyrimidin-4-one The individual enantiomers from the mixture of 5-(4-oxo-4H-pyrido[1,2-a]pyrimidin-7-yl)-5,6,7,8,9,10-hexahydro-7,10-epiminocyclohepta[b]indole (250 mg, 0.73 mmol; Example 283B) were separated by preparative chiral supercritical fluid chromatography (ChiralPak® OD-H 5 μm column, 21×250 mm, 35° C., 10-30% gradient of CH$_3$OH—CO$_2$ containing 0.1% diethylamine) to obtain the title compound as the first eluting peak (retention time=12.7 minutes): $^1$H NMR (300 MHz, methanol-$d_4$) δ ppm 1.62-1.76 (m, 1H) 2.02-2.28 (m, 3H) 2.48 (dd, J=16.28, 1.36 Hz, 1H) 3.23-3.32 (m, 1H) 3.98-4.08 (m, 1H) 4.63 (d, J=4.07 Hz, 1H) 6.52 (d, J=6.44 Hz, 1H) 7.10-7.21 (m, 2H) 7.28-7.38 (m, 1H) 7.53-7.61 (m, 1H) 7.86 (d, J=9.49 Hz, 1H) 8.07 (dd, J=9.32, 2.54 Hz, 1H) 8.38 (d, J=6.10 Hz, 1H) 9.12 (d, J=2.03 Hz, 1H); MS (DCI/NH$_3$) m/z 343 (M+H)$^+$.

Example 285

6-[(6-chloropyridin-3-yl)methyl]-9-fluoro-1,2,3,4,5,6-hexahydro-1,4-methanoazepino[4,3-b]indole Example 285A 2-chloro-5-((1-(4-fluorophenyl)hydrazinyl)methyl)pyridine (4-Fluorophenyl)hydrazine hydrochloride (3.24 g, 20 mmol; Maybridge) and 2-chloro-5-(chloromethyl)pyridine (3.24 g, 20.00 mmol; Aldrich) were mixed in ethanol (120 mL) and then treated with triethylamine (9.76 mL, 70.0 mmol; Aldrich). The mixture was heated to 80° C. with stirring for 16 hours. Then the solvent was removed and the residue was purified by flash chromatography (silica gel, CH$_2$Cl$_2$:methanol=10:1) to afford the title compound: $^1$H NMR (300 MHz, methanol-$d_4$) δ ppm 4.51-4.58 (m, 2H) 6.82-7.10 (m, 4H) 7.40 (d, J=8.14 Hz, 1H) 7.77 (dd, J=8.31, 2.54 Hz, 1H) 8.30 (d, J=2.71 Hz, 1H); MS (DCI/NH$_3$) m/z 237 (M+H)$^+$.

Example 285B

6-[(6-chloropyridin-3-yl)methyl]-9-fluoro-1,2,3,4,5,6-hexahydro-1,4-methanoazepino[4,3-b]indole 2-Chloro-5-((1-(4-fluorophenyl)hydrazinyl)methyl)pyridine (252 mg, 1.0 mmol; Example 285A) and 6-azabicyclo[3.2.1]octan-3-one (125 mg, 1.0 mmol; GLSyntech, LLC) were mixed in dioxane (8 mL) and then treated with sulfuric acid (0.107 mL, 2.000 mmol; J. T. Baker). The mixture was heated to 85° C. with stirring for 16 hours. The mixture was washed with 1 N aqueous NaOH and extracted with methylene chloride, the organic phase was concentrated, and the residue was purified by reverse-phase HPLC [Waters XBridge™ C18 5 μm OBD column, 30×100 mm, flow rate 40 mL/minute, 20-99% gradient of methanol in buffer (0.1% trifluoroacetic acid)] to afford the title compound as the trifluoroacetic acid salt: $^1$H NMR (300 MHz, methanol-d$_4$) δ ppm 2.18-2.37 (m, 2H) 3.07-3.17 (m, 1H) 3.21-3.29 (m, 1H) 3.42-3.55 (m, 2H) 3.79 (s, 1H) 4.49-4.55 (m, 1H) 5.36 (q, J=17.05 Hz, 2H) 6.91 (td, J=9.12, 2.78 Hz, 1H) 7.24-7.34 (m, 2H) 7.36-7.41 (m, 1H) 7.44-7.52 (m, 1H) 8.13 (d, J=2.38 Hz, 1H); MS (DCI/NH$_3$) m/z 342 (M+H)$^+$.

Example 286

(7R,10S)-11-methyl-5-(quinolin-6-yl)-5,6,7,8,9,10-hexahydro-7,10-epiminocyclohepta[b]indole (7R,10S)-5-(Quinolin-6-yl)-5,6,7,8,9,10-hexahydro-7,10-epiminocyclohepta[b]indole (90 mg, 0.277 mmol; Example 282) in acetonitrile (2 mL) and water (2 mL) was treated with a 37% aqueous solution of formaldehyde (0.4 mL; J. T. Baker) and then sodium triacetoxyborohydride (147 mg, 0.69 mmol; Aldrich). The mixture was stirred at room temperature for 2 hours. After being concentrated, the residue was purified by reverse-phase HPLC [Waters XBridge™ C18 5 μm OBD column, 30×100 mm, flow rate 40 mL/minute, 20-99% gradient of methanol in buffer (0.1 M aqueous ammonium bicarbonate, adjusted to pH 10 with ammonium hydroxide)] to afford the title compound: $^1$H NMR (300 MHz, methanol-d$_4$) δ ppm 1.62-1.78 (m, 1H) 1.96-2.07 (m, 1H) 2.21-2.52 (m, 6H) 3.24 (m, 1H) 3.56-3.63 (m, 1H) 4.33 (d, J=5.09 Hz, 1H) 7.06-7.16 (m, 2H) 7.24-7.33 (m, 1H) 7.50-7.57 (m, 1H) 7.62 (dd, J=8.48, 4.41 Hz, 1H) 7.84 (dd, J=9.16, 2.37 Hz, 1H) 8.00 (d, J=2.37 Hz, 1H) 8.21 (d, J=8.82 Hz, 1H) 8.46 (d, J=7.80 Hz, 1H) 8.92 (dd, J=4.41, 1.70 Hz, 1H); MS (DCI/NH$_3$) m/z 340 (M+H)$^+$.

Example 287

2-[4-(1,3,4,5-tetrahydro-6H-2,5-ethanoazepino[4,3-b]indol-6-yl)phenyl]pyridazin-3(2H)-one The reaction of 6-(4-iodophenyl)-3,4,5,6-tetrahydro-1H-2,5-ethanoazepino[4,3-b]indole (235 mg, 0.567 mmol; Example 239A) and pyridazin-3(2H)-one (82.0 mg, 0.851 mmol; Fluka) was performed as described in Example 239B to afford the title compound: $^1$H NMR (300 MHz, CDCl$_3$) δ ppm 1.83-2.19 (m, 4H) 2.96-3.10 (m, 1H) 3.11-3.28 (m, 2H) 3.27-3.52 (m, 2H) 4.42 (s, 2H) 7.11-7.19 (m, 3H) 7.21 (t, J=3.73 Hz, 1H) 7.28-7.35 (m, 1H) 7.38-7.48 (m, 3H) 7.83 (d, J=8.82 Hz, 2H) 7.95 (d, J=1.70 Hz, 1H); MS (DCI) m/z 383 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A compound, or a pharmaceutically acceptable salt thereof, selected from the group consisting of:
2,11-dimethyl-5-[2-(6-methylpyridin-3-yl)ethyl]-5,6,7,8,9,10-hexahydro-7,10-epiminocyclohepta[b]indole;
5-[6-(4-iodophenyl)pyridazin-3-yl]-2,11-dimethyl-5,6,7,8,9,10-hexahydro-7,10-epiminocyclohepta[b]indole;
9-methyl-6-[2-(6-methylpyridin-3-yl)ethyl]-3,4,5,6-tetrahydro-1H-2,5-methanoazepino[4,3-b]indole;
2,8-dimethyl-5-[2-(6-methylpyridin-3-yl)ethyl]-2,3,4,5-tetrahydro-1H-1,4-methanopyrido[4,3-b]indole;
6,10-dimethyl-9-[2-(6-methylpyridin-3-yl)ethyl]-2,3,4,9-tetrahydro-1H-4,1-(epiminomethano)carbazole;
2,6-dimethyl-9-[2-(6-methylpyridin-3-yl)ethyl]-2,3,4,9-tetrahydro-1H-1,4-methano-β-carboline;
6,11-dimethyl-9-[2-(6-methylpyridin-3-yl)ethyl]-2,3,4,9-tetrahydro-1H-1,4-(epiminomethano)carbazole;
2,11-dimethyl-5-[2-(6-methylpyridin-3-yl)ethyl]-5,6,7,8,9,10-hexahydro-6,9-epiminocyclohepta[b]indole;
2,12-dimethyl-5-[2-(6-methylpyridin-3-yl)ethyl]-6,7,8,9,10,11-hexahydro-5H-6,10-epiminocycloocta[b]indole;
6,10-dimethyl-9-[2-(6-methylpyridin-3-yl)ethyl]-2,3,4,9-tetrahydro-1H-1,4-epiminocarbazole;
2,9-dimethyl-6-[2-(6-methylpyridin-3-yl)ethyl]-1,2,3,4,5,6-hexahydro-1,5-methanoazepino[4,3-b]indole;
2,9-dimethyl-6-[2-(6-methylpyridin-3-yl)ethyl]-1,2,3,4,5,6-hexahydro-1,4-methanoazepino[4,3-b]indole;
2,11-dimethyl-5-[2-(6-methylpyridin-3-yl)ethyl]-5,6,7,8,9,10-hexahydro-6,10-epiminocyclohepta[b]indole;
(5aS*,7S*,10R*,10aR*)-2,11-dimethyl-5-[2-(6-methylpyridin-3-yl)ethyl]-5,5a,6,7,8,9,10,10a-octahydro-7,10-epiminocyclohepta[b]indole;
(5aR*,7S*,10R*,10aS*)-2,11-dimethyl-5-[2-(6-methylpyridin-3-yl)ethyl]-5,5a,6,7,8,9,10,10a-octahydro-7,10-epiminocyclohepta[b]indole;
(5aS*,7S*,11R*,11aR*)-2,12-dimethyl-5-[2-(6-methylpyridin-3-yl)ethyl]-5a,6,7,8,9,10,11,11a-octahydro-5H-7,11-epiminocycloocta[b]indole;
(5aR*,7S*,11R*,11aS*)-2,12-dimethyl-5-[2-(6-methylpyridin-3-yl)ethyl]-5a,6,7,8,9,10,11,11a-octahydro-5H-7,11-epiminocycloocta[b]indole;
(5R*,5aS*,10bR*)-9-methyl-6-[2-(6-methylpyridin-3-yl)ethyl]-3,4,5,5a,6,10b-hexahydro-1H-2,5-methanoazepino[4,3-b]indole;
(5R*,5aR*,10bS*)-9-methyl-6-[2-(6-methylpyridin-3-yl)ethyl]-3,4,5,5a,6,10b-hexahydro-1H-2,5-methanoazepino[4,3-b]indole;
(1R*,4R*,4aS*,9bR*)-2,8-dimethyl-5-[2-(6-methylpyridin-3-yl)ethyl]-2,3,4,4a,5,9b-hexahydro-1H-1,4-methanopyrido[4,3-b]indole;
(1R*,4R*,4aR*,9bS*)-2,8-dimethyl-5-[2-(6-methylpyridin-3-yl)ethyl]-2,3,4,4a,5,9b-hexahydro-1H-1,4-methanopyrido[4,3-b]indole;
(1R*,4R*,4aR*,9aS*)-6,10-dimethyl-9-[2-(6-methylpyridin-3-yl)ethyl]-2,3,4,4a,9,9a-hexahydro-1H-4,1-(epiminomethano)carbazole;
(1R*,4R*,4aS*,9aR*)-6,10-dimethyl-9-[2-(6-methylpyridin-3-yl)ethyl]-2,3,4,4a,9,9a-hexahydro-1H-4,1-(epiminomethano)carbazole;
(1S*,4R*,4aS*,9aR*)-2,6-dimethyl-9-[2-(6-methylpyridin-3-yl)ethyl]-2,3,4,4a,9,9a-hexahydro-1H-1,4-methano-β-carboline;
(1S*,4R*,4aR*,9aS*)-2,6-dimethyl-9-[2-(6-methylpyridin-3-yl)ethyl]-2,3,4,4a,9,9a-hexahydro-1H-1,4-methano-β-carboline;
(1S*,4R*,4aS*,9aR*)-6,11-dimethyl-9-[2-(6-methylpyridin-3-yl)ethyl]-2,3,4,4a,9,9a-hexahydro-1H-1,4-(epiminomethano)carbazole;
(1S*,4R*,4aR*,9aS*)-6,11-dimethyl-9-[2-(6-methylpyridin-3-yl)ethyl]-2,3,4,4a,9,9a-hexahydro-1H-1,4-(epiminomethano)carbazole;

(5aR*,6S*,9R*,10aS*)-2,11-dimethyl-5-[2-(6-methyl-pyridin-3-yl)ethyl]-5,5a,6,7,8,9,10,10a-octahydro-6,9-epiminocyclohepta[b]indole;
(5aS*,6S*,9R*,10aR*)-2,11-dimethyl-5-[2-(6-methyl-pyridin-3-yl)ethyl]-5,5a,6,7,8,9,10,10a-octahydro-6,9-epiminocyclohepta[b]indole;
(5aR*,6S*,10R*,11aS*)-2,12-dimethyl-5-[2-(6-methyl-pyridin-3-yl)ethyl]-5a,6,7,8,9,10,11,11a-octahydro-5H-6,10-epiminocycloocta[b]indole;
(5aS*,6S*,10R*,11aR*)-2,12-dimethyl-5-[2-(6-methyl-pyridin-3-yl)ethyl]-5a,6,7,8,9,10,11,11a-octahydro-5H-6,10-epiminocycloocta[b]indole;
(1R*,4S*,4aR*,9aR*)-6,10-dimethyl-9-[2-(6-methyl-pyridin-3-yl)ethyl]-2,3,4,4a,9,9a-hexahydro-1H-1,4-epiminocarbazole;
(1R*,4S*,4aS*,9aS*)-6,10-dimethyl-9-[2-(6-methylpyri-din-3-yl)ethyl]-2,3,4,4a,9,9a-hexahydro-1H-1,4-epimi-nocarbazole;
(1R*,5S*,5aS*,10bR*)-2,9-dimethyl-6-[2-(6-methylpyri-din-3-yl)ethyl]-1,2,3,4,5,5a,6,10b-octahydro-1,5-methanoazepino[4,3-b]indole;
(1R*,5S*,5aR*,10bS*)-2,9-dimethyl-6-[2-(6-methylpyri-din-3-yl)ethyl]-1,2,3,4,5,5a,6,10b-octahydro-1,5-methanoazepino[4,3-b]indole;
(1R*,4S*,5aS*,10bR*)-2,9-dimethyl-6-[2-(6-methylpyri-din-3-yl)ethyl]-1,2,3,4,5,5a,6,10b-octahydro-1,4-methanoazepino[4,3-b]indole;
(1R*,4S*,5aR*,10bS*)-2,9-dimethyl-6-[2-(6-methylpyri-din-3-yl)ethyl]-1,2,3,4,5,5a,6,10b-octahydro-1,4-methanoazepino[4,3-b]indole;
(5aR*,6R*,10S*,10aR*)-2,11-dimethyl-5-[2-(6-methyl-pyridin-3-yl)ethyl]-5,5a,6,7,8,9,10,10a-octahydro-6,10-epiminocyclohepta[b]indole;
(5aS*,6R*,10S*,10aS*)-2,11-dimethyl-5-[2-(6-methyl-pyridin-3-yl)ethyl]-5,5a,6,7,8,9,10,10a-octahydro-6,10-epiminocyclohepta[b]indole;
1',5-dimethyl-1-[2-(6-methylpyridin-3-yl)ethyl]-1,2-di-hydrospiro[indole-3,3'-pyrrolidine];
1',5-dimethyl-1-[2-(6-methylpyridin-3-yl)ethyl]-1,2-di-hydrospiro[indole-3,3'-piperidine];
2-methyl-5-[2-(6-methylpyridin-3-yl)ethyl]-5,6,7,8,9,10-hexahydro-7,10-epiminocyclohepta[b]indole;
(7S,10R)-2-methyl-5-[2-(6-methylpyridin-3-yl)ethyl]-5,6,7,8,9,10-hexahydro-7,10-epiminocyclohepta[b]in-dole;
(7R,10S)-2-methyl-5-[2-(6-methylpyridin-3-yl)ethyl]-5,6,7,8,9,10-hexahydro-7,10-epiminocyclohepta[b]in-dole;
(7R,10S)-2,11-dimethyl-5-[2-(6-methylpyridin-3-yl)ethyl]-5,6,7,8,9,10-hexahydro-7,10-epiminocyclohepta[b]indole;
(7S,10R)-2,11-dimethyl-5-[2-(6-methylpyridin-3-yl)ethyl]-5,6,7,8,9,10-hexahydro-7,10-epiminocyclohepta[b]indole;
5-[2-(6-chloropyridin-3-yl)ethyl]-2,11-dimethyl-5,6,7,8,9,10-hexahydro-7,10-epiminocyclohepta[b]indole;
(7R,10S)-5-[2-(6-chloropyridin-3-yl)ethyl]-2,11-dim-ethyl-5,6,7,8,9,10-hexahydro-7,10-epiminocyclohepta[b]indole;
(7S,10R)-5-[2-(6-chloropyridin-3-yl)ethyl]-2,11-dim-ethyl-5,6,7,8,9,10-hexahydro-7,10-epiminocyclohepta[b]indole;
11-ethyl-2-methyl-5-[2-(6-methylpyridin-3-yl)ethyl]-5,6,7,8,9,10-hexahydro-7,10-epiminocyclohepta[b]indole;
11-(2-fluoroethyl)-2-methyl-5-[2-(6-methylpyridin-3-yl)ethyl]-5,6,7,8,9,10-hexahydro-7,10-epiminocyclohepta[b]indole;
2-methyl-5-[2-(6-methylpyridin-3-yl)ethyl]-11-(2,2,2-tri-fluoroethyl)-5,6,7,8,9,10-hexahydro-7,10-epiminocy-clohepta[b]indole;
ethyl (7R,10S)-2-methyl-5-[2-(6-methylpyridin-3-yl)ethyl]-5,6,7,8,9,10-hexahydro-7,10-epiminocyclohepta[b]indole-11-carboxylate;
ethyl (7S,10R)-2-methyl-5-[2-(6-methylpyridin-3-yl)ethyl]-5,6,7,8,9,10-hexahydro-7,10-epiminocyclohepta[b]indole-11-carboxylate;
11-(4-chlorobenzoyl)-2-methyl-5-[2-(6-methylpyridin-3-yl)ethyl]-5,6,7,8,9,10-hexahydro-7,10-epiminocyclo-hepta[b]indole;
2-methyl-5-[2-(6-methylpyridin-3-yl)ethyl]-11-{[4-(trif-luoromethyl)phenyl]sulfonyl})-5,6,7,8,9,10-hexa-hydro-7,10-epiminocyclohepta[b]indole;
(7R,10S)-2,11-dimethyl-5-[2-(2-methylpyridin-3-yl)ethyl]-5,6,7,8,9,10-hexahydro-7,10-epiminocyclohepta[b]indole;
2,11-dimethyl-5-[(Z)-2-pyridin-3-ylvinyl]-5,6,7,8,9,10-hexahydro-7,10-epiminocyclohepta[b]indole;
(7R,10S)-2,11-dimethyl-5-[(E)-2-pyridin-3-ylvinyl]-5,6,7,8,9,10-hexahydro-7,10-epiminocyclohepta[b]indole;
(7S,10R)-2,11-dimethyl-5-[(E)-2-pyridin-3-ylvinyl]-5,6,7,8,9,10-hexahydro-7,10-epiminocyclohepta[b]indole;
(7S,10R)-2,11-dimethyl-5-[(E)-2-(6-methylpyridin-3-yl)vinyl]-5,6,7,8,9,10-hexahydro-7,10-epiminocyclo-hepta[b]indole;
(7S,10R)-2,11-dimethyl-5-[(Z)-2-(6-methylpyridin-3-yl)vinyl]-5,6,7,8,9,10-hexahydro-7,10-epiminocyclo-hepta[b]indole;
(7R,10S)-2-methyl-5-[(Z)-2-(6-methylpyridin-3-yl)vi-nyl]-5,6,7,8,9,10-hexahydro-7,10-epiminocyclohepta[b]indole;
(7S,10R)-2-methyl-5-[(Z)-2-(6-methylpyridin-3-yl)vi-nyl]-5,6,7,8,9,10-hexahydro-7,10-epiminocyclohepta[b]indole;
(7S,10R)-2,11-dimethyl-5-(2-pyridin-2-yl ethyl)-5,6,7,8,9,10-hexahydro-7,10-epiminocyclohepta[b]indole;
(7S,10R)-5-[2-(5-ethylpyridin-2-yl)ethyl]-2,11-dimethyl-5,6,7,8,9,10-hexahydro-7,10-epiminocyclohepta[b]in-dole;
(7R,10S)-2,11-dimethyl-5-(2-pyridin-4-yl ethyl)-5,6,7,8,9,10-hexahydro-7,10-epiminocyclohepta[b]indole;
2,11-dimethyl-5-(2-pyrimidin-5-ylethyl)-5,6,7,8,9,10-hexahydro-7,10-epiminocyclohepta[b]indole;
(7R,10S)-2,11-dimethyl-5-[2-(2-methylpyrimidin-5-yl)ethyl]-5,6,7,8,9,10-hexahydro-7,10-epiminocyclohepta[b]indole;
(7S,10R)-2,11-dimethyl-5-[2-(2-methylpyrimidin-5-yl)ethyl]-5,6,7,8,9,10-hexahydro-7,10-epiminocyclohepta[b]indole;
(7R,10S)-2,11-dimethyl-5-[2-(6-methylpyridazin-3-yl)ethyl]-5,6,7,8,9,10-hexahydro-7,10-epiminocyclohepta[b]indole;
(7R,10S)-2,11-dimethyl-5-[2-(5-methylpyrazin-2-yl)ethyl]-5,6,7,8,9,10-hexahydro-7,10-epiminocyclohepta[b]indole;
2,11-dimethyl-5-[2-(4-methyl-1,3-thiazol-5-yl)ethyl]-5,6,7,8,9,10-hexahydro-7,10-epiminocyclohepta[b]indole;
2,11-dimethyl-5-(2-phenylethyl)-5,6,7,8,9,10-hexahydro-7,10-epiminocyclohepta[b]indole;
2,11-dimethyl-5-[2-(2-methylphenyl)ethyl]-5,6,7,8,9,10-hexahydro-7,10-epiminocyclohepta[b]indole;
(7R,10S)-2,11-dimethyl-5-[2-(2-methylphenyl)ethyl]-5,6,7,8,9,10-hexahydro-7,10-epiminocyclohepta[b]in-dole;

(7S,10R)-2,11-dimethyl-5-[2-(2-methylphenyl)ethyl]-5,6,7,8,9,10-hexahydro-7,10-epiminocyclohepta[b]indole;
2,11-dimethyl-5-[2-(4-methylphenyl)ethyl]-5,6,7,8,9,10-hexahydro-7,10-epiminocyclohepta[b]indole;
5-[2-(4-fluorophenyl)ethyl]-2,11-dimethyl-5,6,7,8,9,10-hexahydro-7,10-epiminocyclohepta[b]indole;
5-[2-(3-fluorophenyl)ethyl]-2,11-dimethyl-5,6,7,8,9,10-hexahydro-7,10-epiminocyclohepta[b]indole;
5-[2-(2-fluorophenyl)ethyl]-2,11-dimethyl-5,6,7,8,9,10-hexahydro-7,10-epiminocyclohepta[b]indole;
(7R,10S)-5-[2-(4-chlorophenyl)ethyl]-2,11-dimethyl-5,6,7,8,9,10-hexahydro-7,10-epiminocyclohepta[b]indole;
(7S,10R)-5-[2-(4-chlorophenyl)ethyl]-2,11-dimethyl-5,6,7,8,9,10-hexahydro-7,10-epiminocyclohepta[b]indole;
(7S,10R)-5-[2-(2-chlorophenyl)ethyl]-2,11-dimethyl-5,6,7,8,9,10-hexahydro-7,10-epiminocyclohepta[b]indole;
5-[2-(4-bromophenyl)ethyl]-2,11-dimethyl-5,6,7,8,9,10-hexahydro-7,10-epiminocyclohepta[b]indole;
5-[2-(3-bromophenyl)ethyl]-2,11-dimethyl-5,6,7,8,9,10-hexahydro-7,10-epiminocyclohepta[b]indole;
2,11-dimethyl-5-{2-[4-(trifluoromethyl)phenyl]ethyl}-5,6,7,8,9,10-hexahydro-7,10-epiminocyclohepta[b]indole;
2,11-dimethyl-5-{2-[3-(trifluoromethyl)phenyl]ethyl}-5,6,7,8,9,10-hexahydro-7,10-epiminocyclohepta[b]indole;
(7R,10S)-2,11-dimethyl-5-{2-[3-(trifluoromethyl)phenyl]ethyl}-5,6,7,8,9,10-hexahydro-7,10-epiminocyclohepta[b]indole;
(7S,10R)-2,11-dimethyl-5-{2-[3-(trifluoromethyl)phenyl]ethyl}-5,6,7,8,9,10-hexahydro-7,10-epiminocyclohepta[b]indole;
2,11-dimethyl-5-{2-[2-(trifluoromethyl)phenyl]ethyl}-5,6,7,8,9,10-hexahydro-7,10-epiminocyclohepta[b]indole;
(7R,10S)-2,11-dimethyl-5-{2-[2-(trifluoromethyl)phenyl]ethyl}-5,6,7,8,9,10-hexahydro-7,10-epiminocyclohepta[b]indole;
(7S,10R)-2,11-dimethyl-5-{2-[2-(trifluoromethyl)phenyl]ethyl}-5,6,7,8,9,10-hexahydro-7,10-epiminocyclohepta[b]indole;
5-[2-(4-methoxyphenyl)ethyl]-2,11-dimethyl-5,6,7,8,9,10-hexahydro-7,10-epiminocyclohepta[b]indole;
(7R,10S)-2,11-dimethyl-5-[(E)-2-phenylvinyl]-5,6,7,8,9,10-hexahydro-7,10-epiminocyclohepta[b]indole;
2,11-dimethyl-5-[(E)-2-(4-methylphenyl)vinyl]-5,6,7,8,9,10-hexahydro-7,10-epiminocyclohepta[b]indole;
(7R,10S)-2,11-dimethyl-5-[(E)-2-(4-methylphenyl)vinyl]-5,6,7,8,9,10-hexahydro-7,10-epiminocyclohepta[b]indole;
2,11-dimethyl-5-[(Z)-2-(4-methylphenyl)vinyl]-5,6,7,8,9,10-hexahydro-7,10-epiminocyclohepta[b]indole;
(7R,10S)-2,11-dimethyl-5-[(Z)-2-(4-methylphenyl)vinyl]-5,6,7,8,9,10-hexahydro-7,10-epiminocyclohepta[b]indole;
(7R,10S)-5-[(E)-2-(2,4-dimethylphenyl)vinyl]-2,11-dimethyl-5,6,7,8,9,10-hexahydro-7,10-epiminocyclohepta[b]indole;
5-[(4-chlorophenyl)acetyl]-2,11-dimethyl-5,6,7,8,9,10-hexahydro-7,10-epiminocyclohepta[b]indole;
5-[2-(4-chlorophenyl)propyl]-2,11-dimethyl-5,6,7,8,9,10-hexahydro-7,10-epiminocyclohepta[b]indole;
5-(4-isopropenylphenyl)-2,11-dimethyl-5,6,7,8,9,10-hexahydro-7,10-epiminocyclohepta[b]indole;
2,11-dimethyl-5-(3-phenylpropyl)-5,6,7,8,9,10-hexahydro-7,10-epiminocyclohepta[b]indole;
5-[2-(4-fluorophenoxy)ethyl]-2,11-dimethyl-5,6,7,8,9,10-hexahydro-7,10-epiminocyclohepta[b]indole;
(7S,10R)-5-isoquinolin-7-yl-2,11-dimethyl-5,6,7,8,9,10-hexahydro-7,10-epiminocyclohepta[b]indole;
2,11-dimethyl-5-(phenylsulfonyl)-5,6,7,8,9,10-hexahydro-7,10-epiminocyclohepta[b]indole;
(7R,10S)-2,11-dimethyl-5-[(4-methylphenyl)sulfonyl]-5,6,7,8,9,10-hexahydro-7,10-epiminocyclohepta[b]indole;
(7S,10R)-2,11-dimethyl-5-[(4-methylphenyl)sulfonyl]-5,6,7,8,9,10-hexahydro-7,10-epiminocyclohepta[b]indole;
5-[(4-fluorophenyl)sulfonyl]-2,11-dimethyl-5,6,7,8,9,10-hexahydro-7,10-epiminocyclohepta[b]indole;
5-[(4-chlorophenyl)sulfonyl]-2,11-dimethyl-5,6,7,8,9,10-hexahydro-7,10-epiminocyclohepta[b]indole;
2,11-dimethyl-5-{[4-(trifluoromethyl)phenyl]sulfonyl}-5,6,7,8,9,10-hexahydro-7,10-epiminocyclohepta[b]indole;
5-[(4-methoxyphenyl)sulfonyl]-2,11-dimethyl-5,6,7,8,9,10-hexahydro-7,10-epiminocyclohepta[b]indole;
2,11-dimethyl-5-{[4-(trifluoromethoxy)phenyl]sulfonyl})-5,6,7,8,9,10-hexahydro-7,10-epiminocyclohepta[b]indole;
2,11-dimethyl-5-(pyridin-3-ylsulfonyl)-5,6,7,8,9,10-hexahydro-7,10-epiminocyclohepta[b]indole;
11-methyl-5-[2-(6-methylpyridin-3-yl)ethyl]-5,6,7,8,9,10-hexahydro-7,10-epiminocyclohepta[b]indole;
11-methyl-5-(2-phenylethyl)-5,6,7,8,9,10-hexahydro-7,10-epiminocyclohepta[b]indole;
11-methyl-5-[2-(2-methylphenyl)ethyl]-5,6,7,8,9,10-hexahydro-7,10-epiminocyclohepta[b]indole;
5-[2-(4-chlorophenyl)ethyl]-11-methyl-5,6,7,8,9,10-hexahydro-7,10-epiminocyclohepta[b]indole;
11-methyl-5-[2-(2-methyl-1,4,5,6-tetrahydropyrimidin-5-yl)ethyl]-5,6,7,8,9,10-hexahydro-7,10-epiminocyclohepta[b]indole;
11-methyl-5-{[4-(trifluoromethyl)phenyl]sulfonyl}-5,6,7,8,9,10-hexahydro-7,10-epiminocyclohepta[b]indole;
2-fluoro-11-methyl-5-[2-(4-methylphenyl)ethyl]-5,6,7,8,9,10-hexahydro-7,10-epiminocyclohepta[b]indole;
2-fluoro-5-[2-(4-fluorophenyl)ethyl]-11-methyl-5,6,7,8,9,10-hexahydro-7,10-epiminocyclohepta[b]indole;
2-fluoro-5-[2-(3-fluorophenyl)ethyl]-11-methyl-5,6,7,8,9,10-hexahydro-7,10-epiminocyclohepta[b]indole;
2-bromo-5-[2-(4-chlorophenyl)ethyl]-11-methyl-5,6,7,8,9,10-hexahydro-7,10-epiminocyclohepta[b]indole;
(7R,10S)-2-bromo-5-[2-(4-chlorophenyl)ethyl]-11-methyl-5,6,7,8,9,10-hexahydro-7,10-epiminocyclohepta[b]indole;
(7S,10R)-2-bromo-5-[2-(4-chlorophenyl)ethyl]-11-methyl-5,6,7,8,9,10-hexahydro-7,10-epiminocyclohepta[b]indole;
2-bromo-11-methyl-5-[(4-methylphenyl)sulfonyl]-5,6,7,8,9,10-hexahydro-7,10-epiminocyclohepta[b]indole;
2-methoxy-11-methyl-5-[2-(6-methylpyridin-3-yl)ethyl]-5,6,7,8,9,10-hexahydro-7,10-epiminocyclohepta[b]indole;
(7R,10S)-5-[2-(4-chlorophenyl)ethyl]-2-methoxy-11-methyl-5,6,7,8,9,10-hexahydro-7,10-epiminocyclohepta[b]indole;
(7S,10R)-5-[2-(4-chlorophenyl)ethyl]-2-methoxy-11-methyl-5,6,7,8,9,10-hexahydro-7,10-epiminocyclohepta[b]indole;
(7R,10S)-2-methoxy-11-methyl-5-{2-[3-(trifluoromethyl)phenyl]ethyl}-5,6,7,8,9,10-hexahydro-7,10-epiminocyclohepta[b]indole;

(7S,10R)-2-methoxy-11-methyl-5-{2-[3-(trifluoromethyl)phenyl]ethyl}-5,6,7,8,9,10-hexahydro-7,10-epiminocyclohepta[b]indole;
5-[2-(4-chlorophenyl)ethyl]-4-methoxy-11-methyl-5,6,7,8,9,10-hexahydro-7,10-epiminocyclohepta[b]indole;
5-[2-(4-chlorophenyl)ethyl]-11-methyl-2-(trifluoromethoxy)-5,6,7,8,9,10-hexahydro-7,10-epiminocyclohepta[b]indole;
5-[2-(4-chlorophenyl)ethyl]-11-methyl-2-(trifluoromethyl)-5,6,7,8,9,10-hexahydro-7,10-epiminocyclohepta[b]indole;
2-isopropyl-11-methyl-5-[2-(6-methylpyridin-3-yl)ethyl]-5,6,7,8,9,10-hexahydro-7,10-epiminocyclohepta[b]indole;
(7R,10S)-5-[2-(4-chlorophenyl)ethyl]-2-isopropyl-11-methyl-5,6,7,8,9,10-hexahydro-7,10-epiminocyclohepta[b]indole;
(7S,10R)-5-[2-(4-chlorophenyl)ethyl]-2-isopropyl-11-methyl-5,6,7,8,9,10-hexahydro-7,10-epiminocyclohepta[b]indole;
2-cyclopropyl-11-methyl-5-[(4-methylphenyl)sulfonyl]-5,6,7,8,9,10-hexahydro-7,10-epiminocyclohepta[b]indole;
2-cyclopropyl-11-methyl-5-[2-(6-methylpyridin-3-yl)ethyl]-5,6,7,8,9,10-hexahydro-7,10-epiminocyclohepta[b]indole;
2-tert-butyl-11-methyl-5-[2-(6-methylpyridin-3-yl)ethyl]-5,6,7,8,9,10-hexahydro-7,10-epiminocyclohepta[b]indole;
2-tert-butyl-5-[2-(4-chlorophenyl)ethyl]-11-methyl-5,6,7,8,9,10-hexahydro-7,10-epiminocyclohepta[b]indole;
2-(4-chlorophenyl)-11-methyl-5-[2-(6-methylpyridin-3-yl)ethyl]-5,6,7,8,9,10-hexahydro-7,10-epiminocyclohepta[b]indole;
2-bromo-11-methyl-5-[2-(6-methylpyridin-3-yl)ethyl]-5,6,7,8,9,10-hexahydro-7,10-epiminocyclohepta[b]indole;
2-(4-chlorophenyl)-5-[2-(4-chlorophenyl)ethyl]-11-methyl-5,6,7,8,9,10-hexahydro-7,10-epiminocyclohepta[b]indole;
11-methyl-5-[2-(6-methylpyridin-3-yl)ethyl]-2-[3-(trifluoromethyl)phenyl]-5,6,7,8,9,10-hexahydro-7,10-epiminocyclohepta[b]indole;
5-[2-(4-chlorophenyl)ethyl]-11-methyl-2-[3-(trifluoromethyl)phenyl]-5,6,7,8,9,10-hexahydro-7,10-epiminocyclohepta[b]indole;
11-methyl-5-[2-(6-methylpyridin-3-yl)ethyl]-2-pyridin-3-yl-5,6,7,8,9,10-hexahydro-7,10-epiminocyclohepta[b]indole;
5-[2-(4-chlorophenyl)ethyl]-11-methyl-2-pyridin-3-yl-5,6,7,8,9,10-hexahydro-7,10-epiminocyclohepta[b]indole;
11-methyl-5-[2-(6-methylpyridin-3-yl)ethyl]-2-(1H-pyrazol-4-yl)-5,6,7,8,9,10-hexahydro-7,10-epiminocyclohepta[b]indole;
(5aS,7S,10R,10aR)-2,11-dimethyl-5-[2-(6-methylpyridin-3-yl)ethyl]-5,5a,6,7,8,9,10,10a-octahydro-7,10-epiminocyclohepta[b]indole;
2,12-dimethyl-5-[2-(6-methylpyridin-3-yl)ethyl]-6,7,8,9,10,11-hexahydro-5H-7,11-epiminocycloocta[b]indole;
(7R,11S)-2,12-dimethyl-5-[2-(6-methylpyridin-3-yl)ethyl]-6,7,8,9,10,11-hexahydro-5H-7,11-epiminocycloocta[b]indole;
(7S,11R)-2,12-dimethyl-5-[2-(6-methylpyridin-3-yl)ethyl]-6,7,8,9,10,11-hexahydro-5H-7,11-epiminocycloocta[b]indole;
5-[2-(6-chloropyridin-3-yl)ethyl]-2,12-dimethyl-6,7,8,9,10,11-hexahydro-5H-7,11-epiminocycloocta[b]indole;
(7R,11S)-2-methyl-5-[(Z)-2-(6-methylpyridin-3-yl)vinyl]-6,7,8,9,10,11-hexahydro-5H-7,11-epiminocycloocta[b]indole;
(7S,11R)-2-methyl-5-[(Z)-2-(6-methylpyridin-3-yl)vinyl]-6,7,8,9,10,11-hexahydro-5H-7,11-epiminocycloocta[b]indole;
(7R,11S)-2-methyl-5-[2-(6-methylpyridin-3-yl)ethyl]-6,7,8,9,10,11-hexahydro-5H-7,11-epiminocycloocta[b]indole;
(7S,11R)-2-methyl-5-[2-(6-methylpyridin-3-yl)ethyl]-6,7,8,9,10,11-hexahydro-5H-7,11-epiminocycloocta[b]indole;
2,12-dimethyl-5-[(E)-2-(6-methylpyridin-3-yl)vinyl]-6,7,8,9,10,11-hexahydro-5H-7,11-epiminocycloocta[b]indole;
(7R,11S)-2,12-dimethyl-5-[(Z)-2-(6-methylpyridin-3-yl)vinyl]-6,7,8,9,10,11-hexahydro-5H-7,11-epiminocycloocta[b]indole;
(7S,11R)-2,12-dimethyl-5-[(Z)-2-(6-methylpyridin-3-yl)vinyl]-6,7,8,9,10,11-hexahydro-5H-7,11-epiminocycloocta[b]indole;
(7R,11S)-2-methyl-5-[(E)-2-(6-methylpyridin-3-yl)vinyl]-6,7,8,9,10,11-hexahydro-5H-7,11-epiminocycloocta[b]indole;
(7S,11R)-2-methyl-5-[(E)-2-(6-methylpyridin-3-yl)vinyl]-6,7,8,9,10,11-hexahydro-5H-7,11-epiminocycloocta[b]indole;
(7R,11S)-2-methyl-5-[2-(2-methylphenyl)ethyl]-6,7,8,9,10,11-hexahydro-5H-7,11-epiminocycloocta[b]indole;
(7S,11R)-2-methyl-5-[2-(2-methylphenyl)ethyl]-6,7,8,9,10,11-hexahydro-5H-7,11-epiminocycloocta[b]indole;
(7R,11S)-5-[2-(2,5-dimethylphenyl)ethyl]-2-methyl-6,7,8,9,10,11-hexahydro-5H-7,11-epiminocycloocta[b]indole;
(7S,11R)-5-[2-(2,5-dimethylphenyl)ethyl]-2-methyl-6,7,8,9,10,11-hexahydro-5H-7,11-epiminocycloocta[b]indole;
(7R,11S)-5-[2-(4-chlorophenyl)ethyl]-2-methyl-6,7,8,9,10,11-hexahydro-5H-7,11-epiminocycloocta[b]indole;
(7S,11R)-5-[2-(4-chlorophenyl)ethyl]-2-methyl-6,7,8,9,10,11-hexahydro-5H-7,11-epiminocycloocta[b]indole;
(7R,11S)-2-methyl-5-{2-[3-(trifluoromethyl)phenyl]ethyl}-6,7,8,9,10,11-hexahydro-5H-7,11-epiminocycloocta[b]indole;
2-methyl-5-{(E)-2-[3-(trifluoromethyl)phenyl]vinyl}-6,7,8,9,10,11-hexahydro-5H-7,11-epiminocycloocta[b]indole;
(7S,11R)-2-methyl-5-{2-[3-(trifluoromethyl)phenyl]ethyl}-6,7,8,9,10,11-hexahydro-5H-7,11-epiminocycloocta[b]indole;
12-ethyl-2-methyl-5-{2-[3-(trifluoromethyl)phenyl]ethyl}-6,7,8,9,10,11-hexahydro-5H-7,11-epiminocycloocta[b]indole;
(7R,11S)-2-methyl-5-{(E)-2-[3-(trifluoromethyl)phenyl]vinyl}-6,7,8,9,10,11-hexahydro-5H-7,11-epiminocycloocta[b]indole;
(7S,11R)-2-methyl-5-{(E)-2-[3-(trifluoromethyl)phenyl]vinyl}-6,7,8,9,10,11-hexahydro-5H-7,11-epiminocycloocta[b]indole;
2-methyl-5-{(Z)-2-[3-(trifluoromethyl)phenyl]vinyl}-6,7,8,9,10,11-hexahydro-5H-7,11-epiminocycloocta[b]indole;
5-[2-(6-methylpyridin-3-yl)ethyl]-2-(trifluoromethoxy)-6,7,8,9,10,11-hexahydro-5H-7,11-epiminocycloocta[b]indole;

5-[2-(2-methylphenyl)ethyl]-2-(trifluoromethoxy)-6,7,8,9,10,11-hexahydro-5H-7,11-epiminocycloocta[b]indole;
ethyl (9-methyl-1,3,4,5-tetrahydro-6H-2,5-ethanoazepino[4,3-b]indol-6-yl)acetate;
N-(4-chlorophenyl)-2-(9-methyl-1,3,4,5-tetrahydro-6H-2,5-ethanoazepino[4,3-b]indol-6-yl)acetamide;
2-(9-methyl-1,3,4,5-tetrahydro-6H-2,5-ethanoazepino[4,3-b]indol-6-yl)-N-[4-(trifluoromethoxy)phenyl]acetamide;
9-fluoro-6-[(2-methyl-1,3-thiazol-4-yl)methyl]-3,4,5,6-tetrahydro-1H-2,5-ethanoazepino[4,3-b]indole;
9-fluoro-6-[(2-phenyl-1,3-oxazol-4-yl)methyl]-3,4,5,6-tetrahydro-1H-2,5-ethanoazepino[4,3-b]indole;
8-[(6-chloropyridin-3-yl)methyl]-11-fluoro-1,4,5,6,7,8-hexahydro-2H-1,5:3,7-dimethanoazonino[5,4-b]indole;
5-[2-(6-chloropyridin-3-yl)ethyl]-2,11-dimethyl-5,6,7,8,9,10-hexahydro-6,10-epiminocyclohepta[b]indole;
(6R,10S)-5-[2-(6-chloropyridin-3-yl)ethyl]-2,11-dimethyl-5,6,7,8,9,10-hexahydro-6,10-epiminocyclohepta[b]indole;
(6S,10R)-5-[2-(6-chloropyridin-3-yl)ethyl]-2,11-dimethyl-5,6,7,8,9,10-hexahydro-6,10-epiminocyclohepta[b]indole;
10-methyl-7-[2-(6-methylpyridin-3-yl)ethyl]-1,3,4,5,6,7-hexahydro-2,6-methanoazocino[4,3-b]indole;
10-methyl-7-[2-(2-methylphenyl)ethyl]-1,3,4,5,6,7-hexahydro-2,6-methanoazocino[4,3-b]indole;
7-[2-(4-chlorophenyl)ethyl]-10-methyl-1,3,4,5,6,7-hexahydro-2,6-methanoazocino[4,3-b]indole;
5-[(4-chlorophenyl)sulfonyl]-8-methyl-2,3,4,5-tetrahydro-1,4-ethanopyrido[3,2-b]indole;
6-isoquinolin-7-yl-9-methyl-3,4,5,6-tetrahydro-1H-2,5-ethanoazepino[4,3-b]indole;
9-methyl-6-quinolin-6-yl-3,4,5,6-tetrahydro-1H-2,5-ethanoazepino[4,3-b]indole;
9-methyl-6-(2-methylquinolin-6-yl)-3,4,5,6-tetrahydro-1H-2,5-ethanoazepino[4,3-b]indole;
9-methyl-6-quinazolin-6-yl-3,4,5,6-tetrahydro-1H-2,5-ethanoazepino[4,3-b]indole;
6-(9-methyl-1,3,4,5-tetrahydro-6H-2,5-ethanoazepino[4,3-b]indol-6-yl)quinazolin-4-ol;
6-(4-methoxyquinazolin-6-yl)-9-methyl-3,4,5,6-tetrahydro-1H-2,5-ethanoazepino[4,3-b]indole;
9-methyl-6-quinolin-2-yl-3,4,5,6-tetrahydro-1H-2,5-ethanoazepino[4,3-b]indole;
9-fluoro-6-isoquinolin-7-yl-3,4,5,6-tetrahydro-1H-2,5-ethanoazepino[4,3-b]indole;
9-fluoro-6-quinolin-2-yl-3,4,5,6-tetrahydro-1H-2,5-ethanoazepino[4,3-b]indole;
9-fluoro-6-[6-(1H-pyrazol-1-yl)pyridin-2-yl]-3,4,5,6-tetrahydro-1H-2,5-ethanoazepino[4,3-b]indole;
9-fluoro-6-quinolin-7-yl-3,4,5,6-tetrahydro-1H-2,5-ethanoazepino[4,3-b]indole;
9-fluoro-6-quinazolin-6-yl-3,4,5,6-tetrahydro-1H-2,5-ethanoazepino[4,3-b]indole;
9-fluoro-6-quinolin-6-yl-3,4,5,6-tetrahydro-1H-2,5-ethanoazepino[4,3-b]indole;
9-fluoro-6-(2-methylquinolin-6-yl)-3,4,5,6-tetrahydro-1H-2,5-ethanoazepino[4,3-b]indole;
6-(4-methoxyquinazolin-6-yl)-3,4,5,6-tetrahydro-1H-2,5-ethanoazepino[4,3-b]indole;
6-(1,3,4,5-tetrahydro-6H-2,5-ethanoazepino[4,3-b]indol-6-yl)quinazolin-4-ol;
6-(2-methylquinolin-6-yl)-3,4,5,6-tetrahydro-1H-2,5-ethanoazepino[4,3-b]indole;
6-quinolin-6-yl-3,4,5,6-tetrahydro-1H-2,5-ethanoazepino[4,3-b]indole;
6-quinolin-7-yl-3,4,5,6-tetrahydro-1H-2,5-ethanoazepino[4,3-b]indole;
6-quinolin-2-yl-3,4,5,6-tetrahydro-1H-2,5-ethanoazepino[4,3-b]indole;
6-[6-(1H-pyrazol-1-yl)pyridin-2-yl]-3,4,5,6-tetrahydro-1H-2,5-ethanoazepino[4,3-b]indole;
6-[4-(4-methylpiperazin-1-yl)phenyl]-3,4,5,6-tetrahydro-1H-2,5-ethanoazepino[4,3-b]indole;
2-[2-(9-fluoro-1,3,4,5-tetrahydro-6H-2,5-ethanoazepino[4,3-b]indol-6-yl)ethyl]pyridazin-3(2H)-one;
1-[4-(1,3,4,5-tetrahydro-6H-2,5-ethanoazepino[4,3-b]indol-6-yl)phenyl]pyridin-2(1H)-one;
9-fluoro-6-[(2-phenylpyrimidin-5-yl)methyl]-3,4,5,6-tetrahydro-1H-2,5-ethanoazepino[4,3-b]indole;
6-(1H-benzimidazol-2-ylmethyl)-9-fluoro-3,4,5,6-tetrahydro-1H-2,5-ethanoazepino[4,3-b]indole;
9-fluoro-6-(quinolin-8-ylmethyl)-3,4,5,6-tetrahydro-1H-2,5-ethanoazepino[4,3-b]indole;
9-fluoro-6-[(3-methyl-1,2-oxazol-5-yl)methyl]-3,4,5,6-tetrahydro-1H-2,5-ethanoazepino[4,3-b]indole;
6-[(6-chloroimidazo[1,2-b]pyridazin-2-yl)methyl]-9-fluoro-3,4,5,6-tetrahydro-1H-2,5-ethanoazepino[4,3-b]indole;
9-fluoro-6-(imidazo[1,2-a]pyrimidin-2-ylmethyl)-3,4,5,6-tetrahydro-1H-2,5-ethanoazepino[4,3-b]indole;
6-[(6-chloroimidazo[1,2-b]pyridazin-2-yl)methyl]-3,4,5,6-tetrahydro-1H-2,5-ethanoazepino[4,3-b]indole;
6'-(9-fluoro-1,3,4,5-tetrahydro-6H-2,5-ethanoazepino[4,3-b]indol-6-yl)-2H-1,2'-bipyridin-2-one;
6-(9-fluoro-1,3,4,5-tetrahydro-6H-2,5-ethanoazepino[4,3-b]indol-6-yl)quinazolin-4-ol;
7-(9-fluoro-1,3,4,5-tetrahydro-6H-2,5-ethanoazepino[4,3-b]indol-6-yl)quinoxalin-2(1H)-one;
7-(9-fluoro-1,3,4,5-tetrahydro-6H-2,5-ethanoazepino[4,3-b]indol-6-yl)-4H-pyrido[1,2-a]pyrimidin-4-one;
2-[6-(9-fluoro-1,3,4,5-tetrahydro-6H-2,5-ethanoazepino[4,3-b]indol-6-yl)pyridin-3-yl]pyridazin-3(2H)-one;
9-fluoro-6-(2-methylpyrimidin-5-yl)-3,4,5,6-tetrahydro-1H-2,5-ethanoazepino[4,3-b]indole;
9-fluoro-6-(pyridin-3-yl)-3,4,5,6-tetrahydro-1H-2,5-ethanoazepino[4,3-b]indole;
6-[6-(morpholin-4-yl)pyridin-2-yl]-3,4,5,6-tetrahydro-1H-2,5-ethanoazepino[4,3-b]indole;
6-(1,3,4,5-tetrahydro-6H-2,5-ethanoazepino[4,3-b]indol-6-yl)nicotinamide;
6-(1,2,3,4-tetrahydroisoquinolin-6-yl)-3,4,5,6-tetrahydro-1H-2,5-ethanoazepino[4,3-b]indole;
6-(2-methyl-1,2,3,4-tetrahydroisoquinolin-6-yl)-3,4,5,6-tetrahydro-1H-2,5-ethanoazepino[4,3-b]indole;
6-(quinazolin-6-yl)-3,4,5,6-tetrahydro-1H-2,5-ethanoazepino[4,3-b]indole;
6-(isoquinolin-7-yl)-3,4,5,6-tetrahydro-1H-2,5-ethanoazepino[4,3-b]indole;
6-(isoquinolin-6-yl)-3,4,5,6-tetrahydro-1H-2,5-ethanoazepino[4,3-b]indole;
6-[4-(1H-imidazol-1-yl)pyridin-2-yl]-3,4,5,6-tetrahydro-1H-2,5-ethanoazepino[4,3-b]indole;
6'-(1,3,4,5-tetrahydro-6H-2,5-ethanoazepino[4,3-b]indol-6-yl)-2H-1,2'-bipyridin-2-one;
7-(1,3,4,5-tetrahydro-6H-2,5-ethanoazepino[4,3-b]indol-6-yl)quinoxalin-2(1H)-one;
7-(1,3,4,5-tetrahydro-6H-2,5-ethanoazepino[4,3-b]indol-6-yl)-2H-1,4-benzoxazin-3(4H)-one;
2-amino-5-(1,3,4,5-tetrahydro-6H-2,5-ethanoazepino[4,3-b]indol-6-yl)benzamide;

7-(1,3,4,5-tetrahydro-6H-2,5-ethanoazepino[4,3-b]indol-6-yl)-4H-pyrido[1,2-a]pyrimidin-4-one;
(7S,10R)-5-(quinolin-6-yl)-5,6,7,8,9,10-hexahydro-7,10-epiminocyclohepta[b]indole;
(7R,10S)-5-(isoquinolin-7-yl)-5,6,7,8,9,10-hexahydro-7,10-epiminocyclohepta[b]indole;
(7S,10R)-5-(isoquinolin-7-yl)-5,6,7,8,9,10-hexahydro-7,10-epiminocyclohepta[b]indole;
(7S,10R)-11-methyl-5-(quinolin-6-yl)-5,6,7,8,9,10-hexahydro-7,10-epiminocyclohepta[b]indole;
(7R,10S)-5-(quinolin-6-yl)-5,6,7,8,9,10-hexahydro-7,10-epiminocyclohepta[b]indole;
7-[(7S,10R)-7,8,9,10-tetrahydro-7,10-epiminocyclohepta[b]indol-5(6H)-yl]-4H-pyrido[1,2-a]pyrimidin-4-one;
7-[(7R,10S)-7,8,9,10-tetrahydro-7,10-epiminocyclohepta[b]indol-5(6H)-yl]-4H-pyrido[1,2-a]pyrimidin-4-one;
6-[(6-chloropyridin-3-yl)methyl]-9-fluoro-1,2,3,4,5,6-hexahydro-1,4-methanoazepino[4,3-b]indole;
(7R,10S)-11-methyl-5-(quinolin-6-yl)-5,6,7,8,9,10-hexahydro-7,10-epiminocyclohepta[b]indole; and
2-[4-(1,3,4,5-tetrahydro-6H-2,5-ethanoazepino[4,3-b]indol-6-yl)phenyl]pyridazin-3 (2H)-one.

2. A compound that is 6-(1,3,4,5-tetrahydro-6H-2,5-ethanoazepino[4,3-b]indol-6-yl)quinazolin-4-ol or a pharmaceutically acceptable salt thereof.

* * * * *